United States Patent
Ogembo et al.

(10) Patent No.: US 10,960,072 B2
(45) Date of Patent: *Mar. 30, 2021

(54) VIRUS-LIKE PARTICLE COMPOSITIONS AND VACCINES AGAINST EPSTEIN-BARR VIRUS INFECTION AND DISEASE

(71) Applicant: THE UNIVERSITY OF MASSACHUSETTS, Boston, MA (US)

(72) Inventors: Javier Gordon Ogembo, North Grafton, MA (US); Trudy Morrison, Northborough, MA (US)

(73) Assignee: The University of Massachusetts, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/389,701

(22) Filed: Apr. 19, 2019

(65) Prior Publication Data

US 2020/0038505 A1 Feb. 6, 2020

Related U.S. Application Data

(63) Continuation of application No. 15/558,942, filed as application No. PCT/US2016/022663 on Mar. 16, 2016, now Pat. No. 10,314,906.

(60) Provisional application No. 62/134,785, filed on Mar. 18, 2015.

(51) Int. Cl.
| | | |
|---|---|---|
| C12N 7/00 | (2006.01) | |
| A61K 39/245 | (2006.01) | |
| A61K 39/12 | (2006.01) | |
| G01N 33/574 | (2006.01) | |
| A61K 39/00 | (2006.01) | |

(52) U.S. Cl.
CPC ............ *A61K 39/245* (2013.01); *A61K 39/12* (2013.01); *C12N 7/00* (2013.01); *G01N 33/574* (2013.01); *A61K 2039/5256* (2013.01); *A61K 2039/5258* (2013.01); *A61K 2039/575* (2013.01); *A61K 2039/585* (2013.01); *A61K 2039/70* (2013.01); *C12N 2710/16222* (2013.01); *C12N 2710/16223* (2013.01); *C12N 2710/16234* (2013.01); *C12N 2710/16271* (2013.01); *C12N 2710/20022* (2013.01); *C12N 2710/20023* (2013.01); *C12N 2710/20034* (2013.01); *C12N 2710/20071* (2013.01); *C12N 2760/18122* (2013.01); *C12N 2760/18123* (2013.01); *C12N 2760/18134* (2013.01); *C12N 2760/18171* (2013.01); *G01N 2333/05* (2013.01)

(58) Field of Classification Search
None
See application file for complete search history.

(56) References Cited

U.S. PATENT DOCUMENTS

| | | | |
|---|---|---|---|
| 7,951,384 B2 | 5/2011 | Morrison et al. | 424/214.1 |
| 8,974,797 B2 | 3/2015 | Morrison | 424/193.1 |
| 2009/0252761 A1 | 10/2009 | Frazer et al. | 424/204.1 |
| 2014/0227305 A1 | 8/2014 | Lange-Ruiss et al. | 424/186.1 |

FOREIGN PATENT DOCUMENTS

WO WO/2014/018858 1/1914

OTHER PUBLICATIONS

Pantua et al. J. Virol. 2006, 80: 11062-11073.*
Adhikary, D. et al. (2008) "Standardized and Highly Efficient Expansion of Epstein-Ban Virus-Specific CD4(+) T Cells by Using Virus-Like Particles," *Journal of Virology* 82(8), 3903-3911.
Apcher, S. et al. (2010) "Epstein Barr Virus-Encoded EBNA1 Interference with MHC Class I Antigen Presentation Reveals a Close Correlation between mRNA Translation Initiation and Antigen Presentation," *PLoS Pathogens* 6(10), e1001151.
Babcock, G. J. et al. (1998) "EBV Persistence in Memory B Cells In Vivo," *Immunity* 9(3), 395-404.
Balfour, H. H. (2014) "Progress, Prospects, and Problems in Epstein-Barr Virus Vaccine Development," *Current opinion in virology* 0, 1-5.
Battisti, A. J. et al. (2012) "Structure and assembly of a paramyxovirus matrix protein," *Proceedings of the National Academy of Sciences of the United States of America* 109(35), 13996-14000.
Biggar, R. J. et al. (1978) "Primary epstein-barr virus infections in African infants. II. Clinical and serological observations during seroconversion," *International Journal of Cancer* 22(3), 244-250.
Biggar, R. J. et al. (1978) "Primary epstein-barr virus infections in african infants. I. Decline of maternal antibodies and time of infection," *International Journal of Cancer* 22(3), 239-243.
Biggin, M. et al. (1987) "Epstein-Barr virus gene expression in P3HR1-superinfected Raji cells," *Journal of Virology* 61(10), 3120-3132.
Borza, C. M. et al. (2002) "Alternate replication in B cells and epithelial cells switches tropism of Epstein-Barr virus," *Nature Medicine* 8, 594.
Braciale, T. J. et al. (1987) "Antigen Presentation Pathways to Class I and Class II MHC-Restricted T Lymphocytes," *Immunological Reviews* 98(1), 95-114.
Chatterjee, B. et al. (2014) "Animal models of Epstein Barr virus infection," *Journal of Immunological Methods* 410(Supplement C), 80-87.

(Continued)

*Primary Examiner* — Nianxiang Zou
(74) *Attorney, Agent, or Firm* — Medlen & Carroll, LLP

(57) ABSTRACT

The present invention relates to prophylactic and/or therapeutic vaccines that contain Newcastle disease Virus (NDV) virus-like particles (VLPs) comprising one or more Epstein-Barr Virus (EBV) antigens. In one embodiment, the invention provides a recombinant virus-like particle (VLP) comprising, in operable combination, a) Newcastle disease virus (NDV) matrix (M) protein, and b) one or more Epstein-Barr Virus (BBV) antigens. The invention's prophylactic and/or therapeutic vaccines are useful for preventing and/or treating infection with EBV and/or disease associated Epstein-Barr Virus, such as cancer.

23 Claims, 113 Drawing Sheets

Specification includes a Sequence Listing.

(56) References Cited

OTHER PUBLICATIONS

Chesnokova, L. S. et al. (2011) "Fusion of Epstein-Barr Virus with Epithelial Cells Can Be Triggered by $\alpha v \beta 5$ in Addition to $\alpha v \beta 6$ and $\alpha v \beta 8$, and Integrin Binding Triggers a Conformational Change in Glycoproteins gHgL," *Journal of Virology* 85(24), 13214-13223.
Chia, W. K. et al. (2012) "A phase II study evaluating the safety and efficacy of an adenovirus-$\Delta$LMP1-LMP2 transduced dendritic cell vaccine in patients with advanced metastatic nasophary ngeal carcinoma," *Annals of Oncology* 23(4), 997-1005.
Civoli, F. et al. (2012) "Development and optimization of neutralizing antibody assays to monitor clinical immunogenicity," *Bioanalysis* 4(22), 2725-2735.
Cohen, J. I. (2015) "Epstein-barr virus vaccines," *Clinical & Translational Immunology* 4(1), e32.
Cohen, J. I. et al. (2011) "Epstein-Barr Virus: An Important Vaccine Target for Cancer Prevention," *Science Translational Medicine* 3(107), 107fs107-107fs107.
Coté, T. R. et al. (1997) "Non-Hodgkin's lymphoma among people with AIDS: Incidence, presentation and public health burden," *International Journal of Cancer* 73(5), 645-650.
Eisenberg, R. J. et al. (2012) "Herpes Virus Fusion and Entry: A Story with Many Characters," *Viruses* 4(5), 800-832.
Fingeroth, J. D. et al. (1984) "Epstein-Barr virus receptor of human B lymphocytes is the C3d receptor CR2," *Proceedings of the National Academy of Sciences of the United States of America* 81(14), 4510-4514.
Fogg, M. H. et al. (2009) "Decreased EBNA-1-specific CD8+ T cells in patients with Epstein-Barr virus-associated nasopharyngeal carcinoma," *Proceedings of the National Academy of Sciences of the United States of America* 106(9), 3318-3323.
Fuller, A. O. et al. (1989) "Neutralizing antibodies specific for glycoprotein H of herpes simplex virus permit viral attachment to cells but prevent penetration," *Journal of Virology* 63(8), 3435-3443.
Gallot, G. et al. (2014) "T-cell therapy using a bank of EBV-specific cytotoxic T cells: lessons from a phase I/II feasibility and safety study," *Journal of Immunotherapy* 37(3), 170-179.
Ghiran, I. et al. (2008) "Ligation of erythrocyte CR1 induces its clustering in complex with scaffolding protein FAP-1," *Blood* 112(8), 3465-3473.
Goedert, J. J. et al. "Spectrum of AIDS-associated malignant disorders," *The Lancet* 351(9119), 1833-1839.
Gompels, U. A. et al. (1991) "Characterization and sequence analyses of antibody-selected antigenic variants of herpes simplex virus show a conformationally complex epitope on glycoprotein H," *Journal of Virology* 65(5), 2393-2401.
Gottschalk, S. et al. (2005) "Post-Transplant Lymphoproliferative Disorders," *Annual Review of Medicine* 56(1), 29-44.
Gu, S. Y. et al. (1995) "First EBV vaccine trial in humans using recombinant vaccinia virus expressing the major membrane antigen," *Developments in Biological Standardization* 84, 171-177.
Gujer, C. et al. (2015) "Animal models of Epstein Barr virus infection," *Current Opinion in Virology* 13(Supplement C), 6-10.
Heslop, H. E. et al. (1996) "Long-term restoration of immunity against Epstein-Barr virus infection by adoptive transfer of gene-modified virus-specific T lymphocytes," *Nature Medicine* 2(5), 551-555.
Hjalgrim, H. et al. (2007) "The epidemiology of EBV and its association with malignant disease," in *Human Herpesviruses: Biology, Therapy, and Immunoprophylaxis* (Arvin, A., et al., Eds.), Cambridge.
Hui, E. P. et al. (2013) "Phase I Trial of Recombinant Modified Vaccinia Ankara Encoding Epstein-Barr Viral Tumor Antigens in Nasopharyngeal Carcinoma Patients," *Cancer Research* 73(6), 1676.
Icheva, V. et al. (2013) "Adoptive Transfer of Epstein-Barr Virus (EBV) Nuclear Antigen 1—Specific T Cells As Treatment for EBV Reactivation and Lymphoproliferative Disorders After Allogeneic Stem-Cell Transplantation," *Journal of Clinical Oncology* 31(1), 39-48.
Jackman, W. T. et al. (1999) "Expression of Epstein-Barr virus gp350 as a single chain glycoprotein for an EBV subunit vaccine," *Vaccine* 17(7), 660-668.
Janz, A. et al. (2000) "Infectious Epstein-Barr Virus Lacking Major Glycoprotein BLLF1 (gp350/220) Demonstrates the Existence of Additional Viral Ligands," *Journal of Virology* 74(21), 10142-10152.
Kirschner, A. N. et al. (2006) "Soluble Epstein-Barr Virus Glycoproteins gH, gL, and gp42 Form a 1:1:1 Stable Complex That Acts Like Soluble gp42 in B-Cell Fusion but Not in Epithelial Cell Fusion," *Journal of Virology* 80(19), 9444-9454.
Kohrt, H. et al. (2009) "Dynamic CD8 T-cell responses to tumor-associated Epstein-Barr virus antigens in patients with Epstein-Barr virus-negative Hodgkin's disease," *Oncology Research* 18(5-6), 287-292.
Kutok, J. L. et al. (2006) "Spectrum of Epstein-Barr Virus—Associated Diseases," *Annual Review of Pathology: Mechanisms of Disease* 1(1), 375-404.
Laliberte, J. P. et al. (2006) "Integrity of Membrane Lipid Rafts Is Necessary for the Ordered Assembly and Release of Infectious Newcastle Disease Virus Particles," *Journal of Virology* 80(21), 10652-10662.
Lee, S. P. et al. (2004) "CD8 T Cell Recognition of Endogenously Expressed Epstein-Barr Virus Nuclear Antigen 1," *Journal of Experimental Medicine* 199(10), 1409-1420.
Li, Q. et al. (1997) "Epstein-Barr virus uses HLA class II as a cofactor for infection of B lymphocytes," *Journal of Virology* 71(6), 4657-4662.
Li, Q. et al. (1995) "The Epstein-Barr virus (EBV) BZLF2 gene product associates with the gH and gL homologs of EBV and carries an epitope critical to infection of B cells but not of epithelial cells," *Journal of Virology* 69(7), 3987-3994.
Lin, X. et al. (2008) "CD4 and CD8 T cell responses to tumour-associated Epstein-Barr virus antigens in nasopharyngeal carcinoma patients," *Cancer Immunology Immunotherapy* 57(7), 963-975.
Long, H. M. et al. (2013) "MHC II tetramers visualize human CD4(+) T cell responses to Epstein-Barr virus infection and demonstrate atypical kinetics of the nuclear antigen EBNA1 response," *Journal of Experimental Medicine* 210(5), 933-949.
Louis, C. U. et al. (2010) "Adoptive transfer of EBV-specific T cells results in sustained clinical responses in patients with locoregional nasopharyngeal carcinoma," *Journal of immunotherapy* (Hagerstown, Md.: 1997) 33(9), 983-990.
Luzuriaga, K. et al. (2010) "Infectious Mononucleosis," *New England Journal of Medicine* 362(21), 1993-2000.
McGinnes, L. W. et al. (2013) "Newcastle Disease Virus-Like Particles: Preparation, Purification, Quantification, and Incorporation of Foreign Glycoproteins," *Current protocols in microbiology* 30, Unit-18.12.
McGinnes, L. W. et al. (2003) "Evidence for Mixed Membrane Topology of the Newcastle Disease Virus Fusion Protein," *Journal of Virology* 77(3), 1951-1963.
Miller, N. et al. (1988) "A monoclonal antibody to glycoprotein gp85 inhibits fusion but not attachment of Epstein-Barr virus," *Journal of Virology* 62(7), 2366-2372.
Molesworth, S. J. et al. (2000) "Epstein-Barr Virus gH Is Essential for Penetration of B Cells but Also Plays a Role in Attachment of Virus to Epithelial Cells," *Journal of Virology* 74(14), 6324-6332.
Moutschen, M. et al. (2007) "Phase I/II studies to evaluate safety and immunogenicity of a recombinant gp350 Epstein-Barr virus vaccine in healthy adults," *Vaccine* 25(24), 4697-4705.
Murawski, M. R. et al. (2010) "Newcastle Disease Virus-Like Particles Containing Respiratory Syncytial Virus G Protein Induced Protection in BALB/c Mice, with No Evidence of Immunopathology," *Journal of Virology* 84(2), 1110-1123.
Naranatt, P. P. et al. (2002) "Characterization of gamma2-human herpesvirus-8 glycoproteins gH and gL," *Archives of Virology* 147(7), 1349-1370.

(56) References Cited

OTHER PUBLICATIONS

Nemerow, G. R. et al. (1984) "Early events in the infection of human B lymphocytes by Epstein-Barr virus: The internalization process," *Virology* 132(1), 186-198.
Nemerow, G. R. et al. (1989) "Identification of an epitope in the major envelope protein of Epstein-Barr virus that mediates viral binding to the B lymphocyte EBV receptor (CR2)," *Cell* 56(3), 369-377.
Nokta, M. et al. (1994) "Human monoclonal anti-cytomegalovirus (CMV) antibody (MSL 109): enhancement of in vitro foscarnet- and ganciclovir-induced inhibition of CMV replication," *Antiviral Research* 24(1), 17-26.
Ogembo, Javier G. et al. (2013) "Human Complement Receptor Type 1/CD35 Is an Epstein-Ban Virus Receptor," *Cell Reports* 3(2), 371-385.
Ogembo, J. G. et al. (2015) "A chimeric EBV 350/220-based VLP replicates the virion B-cell attachment mechanism and elicits long-lasting neutralizing antibodies in mice," *Journal of Translational Medicine* 13(1), 50.
Paliard, X. et al. (2000) "Priming of Strong, Broad, and Long-Lived HIV Type 1 p55gag-Specific CD8+ Cytotoxic T Cells after Administration of a Virus-Like Particle Vaccine in Rhesus Macaques," *AIDS Research and Human Retroviruses* 16(3), 273-282.
Pantua, H. et al. (2005) "Characterization of an Alternate Form of Newcastle Disease Virus Fusion Protein," *Journal of Virology* 79(18), 11660-11670.
Pantua, H. D. et al. (2006) "Requirements for the Assembly and Release of Newcastle Disease Virus-Like Particles," *Journal of Virology* 80(22), 11062-11073.
Paramita, D. K. et al. (2011) "Humoral immune responses to Epstein-Barr virus encoded tumor associated proteins and their putative extracellular domains in nasopharyngeal carcinoma patients and regional controls," *Journal of Medical Virology* 83(4), 665-678.
Pavlova, S. et al. (2013) "An Epstein-Barr Virus Mutant Produces Immunogenic Defective Particles Devoid of Viral DNA," *Journal of Virology* 87(4), 2011-2022.
Rees, L. et al. (2009) "A phase I trial of epstein-barr virus gp350 vaccine for children with chronic kidney disease awaiting transplantation," *Transplantation* 88(8), 1025-1029.
Rickinson, A. B. et al. (2007) "Epstein-Barr Virus," in *Fields Virology* (Knipe, D., et al., Eds.) Fifth ed., pp. 2680-2700, Lippincott Wilkins and Williams, Philadelphia.
Roche, P. A. et al. (2015) "The ins and outs of MHC class II-mediated antigen processing and presentation," *Nature Reviews Immunology* 15, 203.
Rowe, C. L. et al. (2013) "A soluble form of Epstein-Barr virus gH/gL inhibits EBV-induced membrane fusion and does not function in fusion," *Virology* 436(1), 118-126.
Ruiss, R. et al. (2011) "A Virus-Like Particle-Based Epstein-Barr Virus Vaccine," *Journal of Virology* 85(24), 13105-13113.
Sashihara, J. et al. (2009) "Human Antibody Titers to Epstein-Barr Virus (EBV) gp350 Correlate with Neutralization of Infectivity Better than Antibody Titers to EBV gp42 Using a Rapid Flow Cytometry-Based EBV Neutralization Assay," *Virology* 391(2), 249-256.
Schirmbeck, R. et al. (1996) "Virus-like particles induce MHC class I-restricted T-cell responses. Lessons learned from the hepatitis B small surface antigen," *Intervirology* 39(1-2), 111-119.
Smith, C. et al. (2012) "A new approach for cellular immunotherapy of nasopharyngeal carcinoma," *Oncoimmunology* 1(8), 1440-1442.
Sokal, E. M. et al. (2007) "Recombinant gp350 vaccine for infectious mononucleosis: a phase 2, randomized, double-blind, placebo-controlled trial to evaluate the safety, immunogenicity, and efficacy of an Epstein-Barr virus vaccine in healthy young adults," *Journal of Infectious Diseases* 196(12), 1749-1753.
Speck, P. et al. (1999) "Epstein-Barr virus (EBV) infection visualized by EGFP expression demonstrates dependence on known mediators of EBV entry," *Archives of Virology* 144(6), 1123-1137.
Tanner, J. et al. (1987) "Epstein-barr-virus gp350/220 binding to the B lymphocyte C3d receptor mediates adsorption, capping, and endocytosis," *Cell* 50(2), 203-213.
Tanner, J. et al. (1988) "Soluble 350/220 and deletion mutant glycoproteins block Epstein-Barr virus adsorption to lymphocytes," *Journal of Virology* 62(12), 4452-4464.
Taylor, G. S. et al. (2004) "Dual Stimulation of Epstein-Barr Virus (EBV)-Specific CD4+- and CD8+-T-Cell Responses by a Chimeric Antigen Construct: Potential Therapeutic Vaccine for EBV-Positive Nasopharyngeal Carcinoma," *Journal of Virology* 78(2), 768-778.
Taylor, G. S. et al. (2014) "A recombinant modified vaccinia Ankara vaccine encoding Epstein-Barr virus (EBV) target antigens: a phase I trial in UK patients with EBV-positive cancer," *Clinical Cancer Research* 20(19), 5009-5022.
Wang, H.-B. et al. (2015) Neuropilin 1 is an entry factor that promotes EBV infection of nasopharyngeal epithelial cells, in *Nature Communications*, p. 6240.
Wang, X. et al. (1998) "Epstein-Barr Virus Lacking Glycoprotein gp42 Can Bind to B Cells but Is Not Able to Infect," *Journal of Virology* 72(1), 158-163.
Wu, L. et al. (2005) "Mutations of Epstein-Ban Virus gH That Are Differentially Able to Support Fusion with B Cells or Epithelial Cells," *Journal of Virology* 79(17), 10923-10930.
Wussow, F. et al. (2014) "Human cytomegalovirus vaccine based on the envelope gH/gL pentamer complex," *PLoS Pathogens* 10(11), e1004524.
Yajima, M. et al. (2008) "A New Humanized Mouse Model of Epstein-Barr Virus Infection That Reproduces Persistent Infection, Lymphoproliferative Disorder, and Cell-Mediated and Humoral Immune Responses," *Journal of Infectious Diseases* 198(5), 673-682.
PCT International Search Report of International Application No. PCT/US2016/022663 dated Jul. 22, 2016.

\* cited by examiner

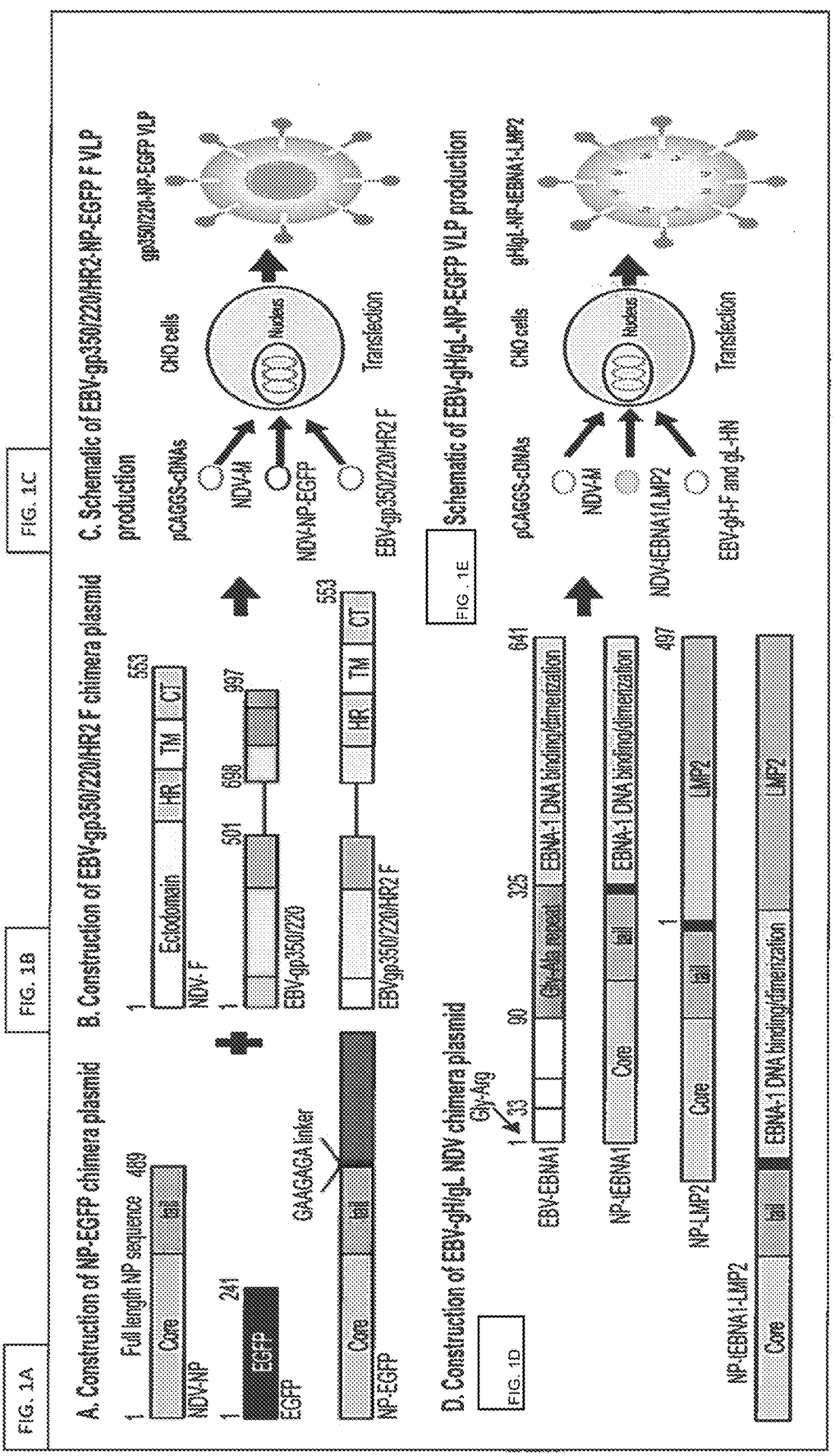

FIG. 2A
FIG. 2B
A. Expression of NP-EGFP in CHO cells
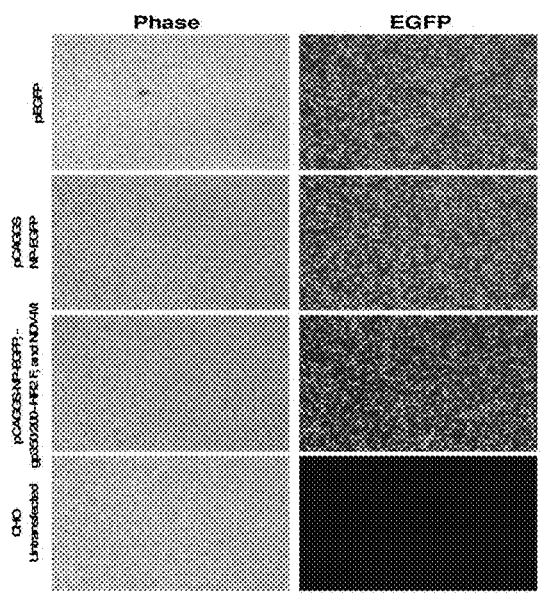
B. Immunoblot of gp350/220 in purified VLPs
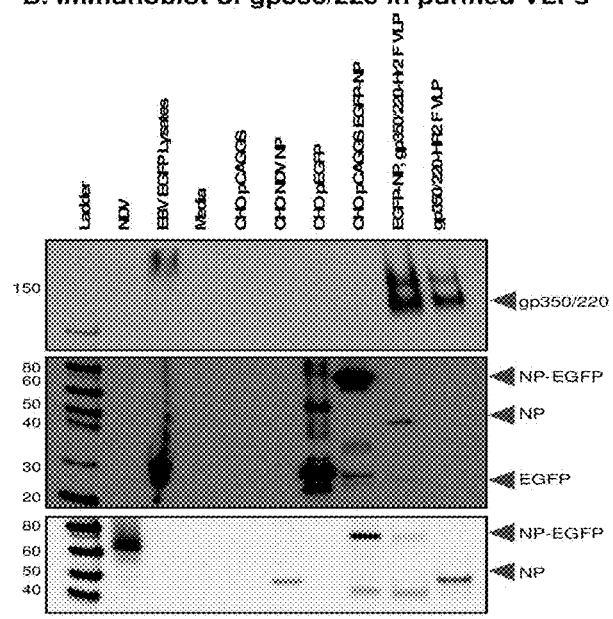

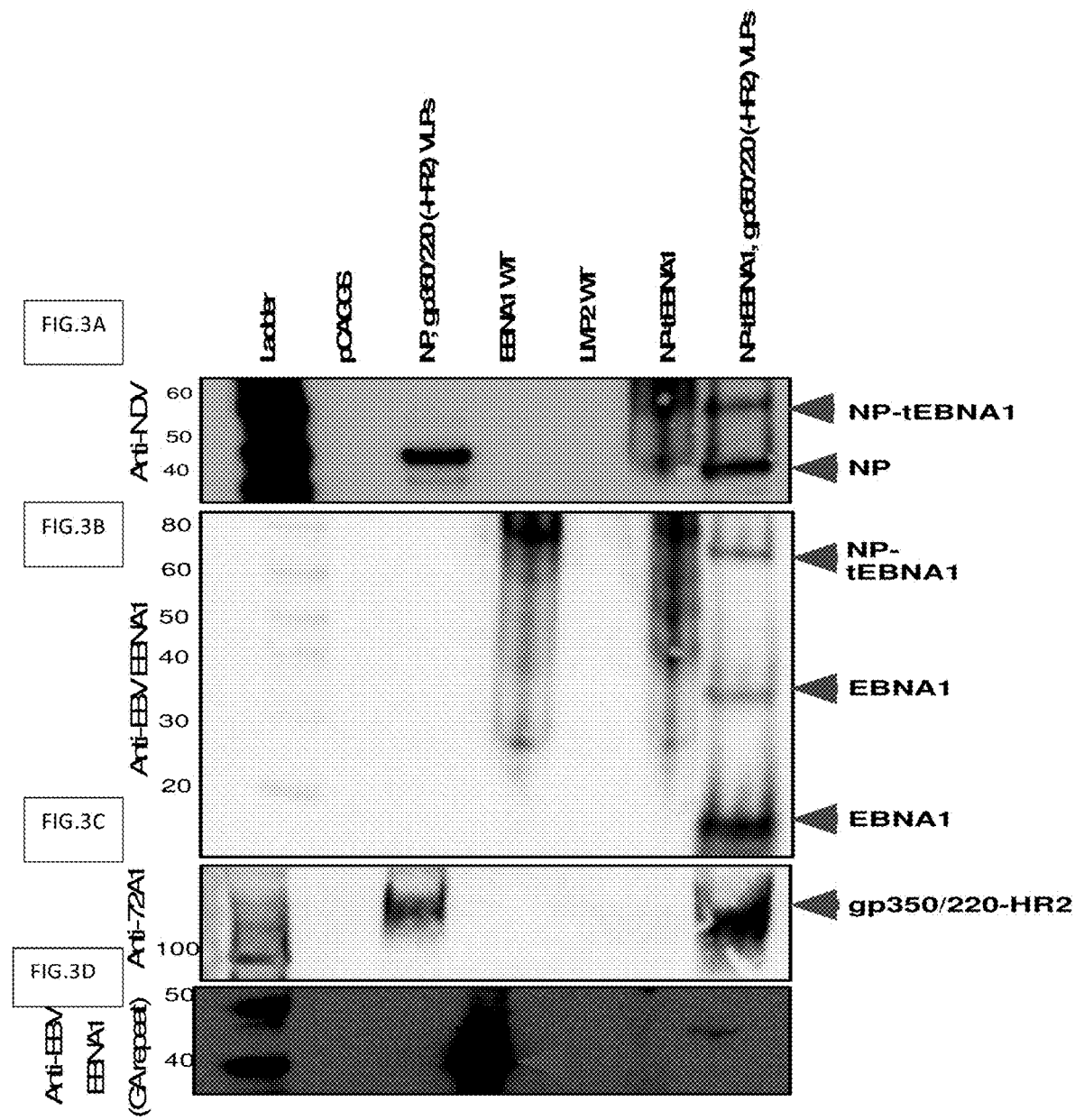

EM Immunogold stain of EBV-gp350/220/HR2 F VLPs

Why are we not achieving sterility with EBV-gp350/220 immunization?

Goal 2: Development of a novel gH/gL VLPs
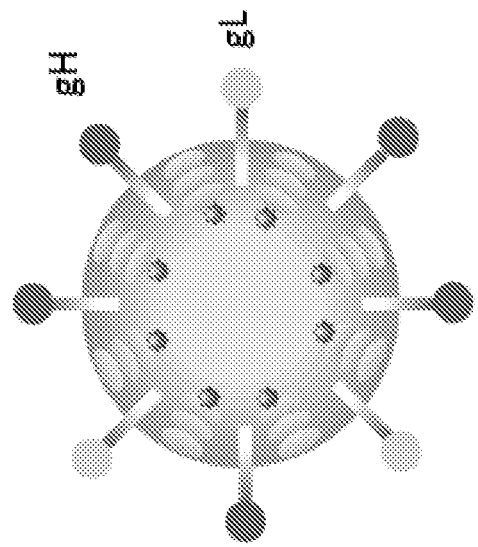
Specific Aims:
① Construct and determine the role of the gH/gL protein complex in generating EBV-specific neutralizing antibody responses in BALB/c mice.
FIGURE 12

Summary 1

(1) We have shown that EBV-gp350/220 VLP-based vaccine can be generated using NDV platform.

(1) These gp350/220 VLPs were functionally active
- Bound CD21 and CD35
- Reactive to anti-gp350/220 mAbs (1) gp350/220 VLPs generated nAbs in BALB/c mice comparable to EBV
- gp350/220 (-)HR2 F VLPs
- gp350/220/HR2 F (2) Despite generation of anti-gp350/220 neutralizing mAbs, as in the cases of clinical trials, EBV infection was not completely neutralized.

(3) We now aim to explore other glycoproteins as alternative vaccine candidates that can be used independently or together with gp350/220 VLPs to neutralize EBV infection.

FIGURE 13

Key Questions: Development of EBV vaccine candidates

- Is the EBV-glycoproteins VLP based vaccine candidates optimal as immunogens for preventing EBV infection and EBV-associated diseases?

- Can other viral antigens such as EBNA1-3, LMP1 and LMP2 be incorporated into VLPs to develop effective vaccine capable of inducing both humoral and cellular responses?

FIGURE 14

EBV Latency Genes Expression and Associated Diseases

① Epstein-Barr Virus-gp350/220, gH/gL and gB: Are attractive vaccine targets for cancer prevention ① EBV intracellular proteins EBNA1 is expressed in all EBV cancers Latency I
Burkitt's Lymphoma Latency II
Hodgkin Lymphoma
T/NK Cell Lymphoma Latency III
Post-transplant
Lymphoproliferative
Disorder (PTLD)

Goal 2: Development of a novel gH/gL-EBNA1-LMP2 VLPs

1. NDV-M (?)
2. NDV-NP (EBNA1/LMP2)
3. NDV-F/HN (gH/gL)

FIGURE 17

Rationale

- Despite strong evidence indicating that antibodies to gH/gL are capable of neutralizing EBV infection (*and also in other herpesviruses*), to my knowledge, no vaccine candidate has exploited the use of these proteins against EBV infection.

- Adoptive transfer of PBMCs for treatment of PTLDs and NPCs targeting LMP2 and EBNA1 is currently used in several clinical settings.
  1. Louis et al, 2009, 2010, Heslop et al 1996 T cells adoptive transfer
  2. Chia et al, 2012 Phase 1 targeting NPC patients in China. Dendritic cells are transduced with adenovirus vector expressing LMP1/LMP2.

- DNA Vaccine: MVA-vector expressing EBNA1 and LMP1 or LMP2
  - Taylor et al, 2004 & Hui et al, 2013: EBNA1/LMP2 (Phase I targeting NPC patients in China)
  - Taylor et al, 2014 (Phase I clinical trials in England)

- Safety is a major concern with this strategies
  - Can VLPs be used as a carrier for both virus glycoproteins and viral antigens expressed by infected or transformed cells?

FIGURE 18

Proof of principle: Can we generate EBVgp350/220 F VLPs expressing EGFP?

FIGURE 19

Summary 2

① We have shown that NDV NP protein can be used as a carrier for EGFP

① The chimera NP-EGFP can be incorporated into gp350/220 VLPs which are functionally active
  - Bound CD21 and CD35
  - Reactive to anti-gp350/220 mAbs

FIGURE 29

NDV NP as a Carrier for EBNA1-LMP2 in EBVgp350/220 or gH/gL VLPs gp350/220

FIGURE 30

Generating NP-tEBNA1 Chimera Protein

FIGURE 31 gH/gL-NP-EBNA1-LMP2 VLPs

1. NDV-M (?)
2. NDV-NP (EBNA1/LMP2)
3. NDV-F/HN (gH/gL)

FIGURE 35

Summary 3

① We have shown that generation of EBNA1-gp350/220 VLP-based vaccine using NDV platform is feasible.

① We will now use the same platform to generate LMP2-gp350/220 VLPs.

① As indicated earlier, despite generation of anti-gp350/220 neutralizing mAbs, as in the cases of clinical trials, EBV infection was not completely neutralized, thus we aim to generate a second generation EBNA1-LMP2gH/gL VLPs ② These EBV-VLP vaccine candidates will be used in Balb/c mice to test their efficacy in generation of humoral and cellular responses against EBV infection.

③ Our study, is the first to show that viral intracellular protein can be packaged inside a VLP, with a potential to be used as a therapeutic vaccine.

④ Can we use the same strategy to make candidate vaccines against other oncogenic viruses such as HPV, KSHV, HCV, HBV, HTLV1, Merckel Cell polyomervirus etc?

FIGURE 38

CHO Transfected with NP-EGFP and EGFP VLP stained with 72A1 (1:100; anti-mouse 1:2500) 12/2/14

Generating NP-tEBNA1 Chimera Protein
FIGURE 50
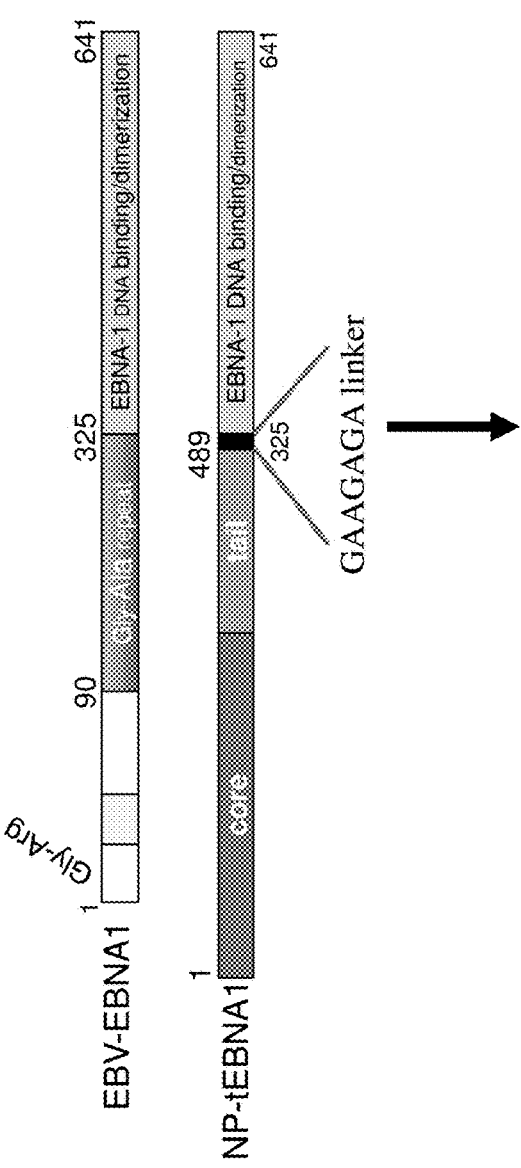
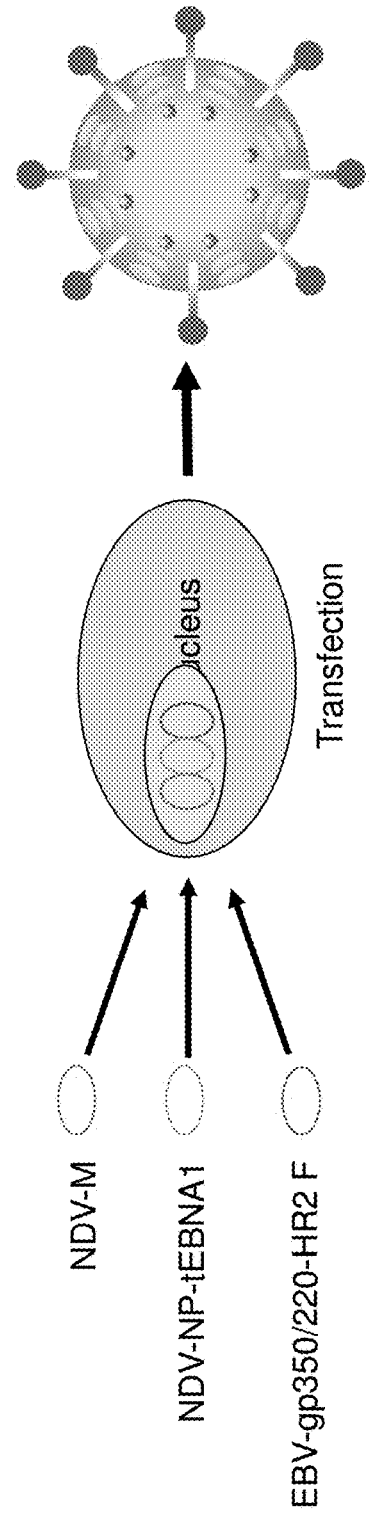

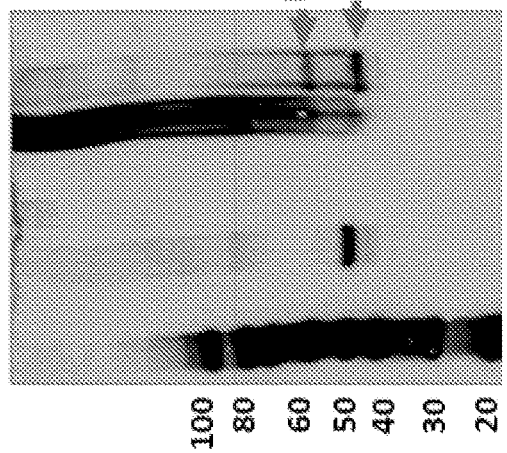
FIGURE 51

Terminal protein LMP2A [Human herpesvirus 4] (SEQ ID NO:01)

NCBI Reference Sequence: YP_401631.1

```
MGSLEMVPMGAGPPSPGGDPDGYDGGNNSQYPSASGSSGNTPTPPNDEERESNEEPPPPYEDPYWGNGDR
HSDYQPLGTQDQSLYLGLQHDGNDGLPPPPYSPRDDSSQHIYEEAGRGSMNPVCLPVIVAPYLFWLAAIA
ASCFTASVSTVVTATGLALSLLLLAAVASSYAAAQRKLLTPVTVLTAVVTFFAICLTWRIEDPPFNSLLF
ALLAAAGGLQGIYVLVMLVLLILAYRRRWRRLTVCGGIMFLACVLVLIVDAVLQLSPLLGAVTVVSMTLL
LLAFVLWLSSPGGLGTLGAALLTLAAALALLASLILGTLNLTTMFLLMLLWTLVVLLICSSCSSCPLSKI
LLARLFLYALALLLLASALIAGGSILQTNFKSLSSTEFIPNLFCMLLLIVAGILFILAILTEWGSGNRTY
GPVFMCLGGLLTMVAGAVWLTVMSNTLLSAWILTAGFLIFLIGFALFGVIRCCRYCCYYCLTLESEERPP
TPYRNTV
```

Figure 54

Glycoprotein gp110 precursor [Human herpesvirus 4] (SEQ ID NO:02)

NCBI Reference Sequence: YP_401713.1

```
  1 mtrrrvlsvv vllaalacrl gaqtpeqpap pattvqptat rqqtsfpfrv celsshgdlf
 61 rfssdiqcps fgtrenhteg llmvfkdnii pysfkvrsyt kivtniliyn gwyadsvtnr
121 heekfsvdsy etdqmdtiyq cynavkmtkd gltrvyvdrd gvnitvnlkp tgglangvrr
181 yasqtelyda pgwliwtyrt rttvnclitd mmaksnspfd ffvtttgqtv emspfydgkn
241 ketfherads fhvrtnykiv dydnrgtnpq gerrafldkg tytlswklen rtaycplqhw
301 qtfdstiate tgksihfvtd egtssfvtnt tvgielpdaf kcieeqvnkt mhekyeavqd
361 rytkgqeait yfitsgglll awlpltprsl atvknltelt tptssppssp sppapsaarg
421 stpaavlrrr rrdagnattp vpptapgksl gtlnnpatvq iqfaydslrr qinrmlgdla
481 rawcleqkrq nmvlreltki npttvmssiy gkavaakrlg dvisvsqcvp vnqatvtlrk
541 smrvpgsetm cysrplvsfs findtktyeg qlgtdneifl tkkmtevcqa tsqyyfqsgn
601 eihvyndyhh fktieldgia tlqtfislnt slienidfas lelysrdeqr asnvfdlegi
661 freynfqaqn iaglrkdldn avsngrnqfv dglgelmdsl gsvgqsitnl vstvgglfss
721 lvsgfisffk npfggmlilv lvagvvilvi sltrrtrqms qqpvqmlypg idelaqqhas
781 gegpginpis ktelqaimla lheqnqeqkr aaqraagpsv asralqaard rfpglrrrry
841 hdpetaaall geaetef
```

Figure 55

Glycoprotein gp85 precursor [Human herpesvirus 4] (SEQ ID NO:03)

NCBI Reference Sequence: YP_401700.1

```
  1 mqllcvfclv llwevgaasl sevklhldie ghashytipw telmakvpgl spealwrean
 61 vtedlasmln rykliyktsg tlgialaepv dipavsegsm qvdaskvhpg visglnspac
121 mlsaplekql fyyigtmlpn trphsyvfyq lrchlsyval singdkfqyt gamtskflmg
181 tykrvtekgd ehvlslvfgk tkdlpdlrgp fsypsltsaq sgdyslvivt tfvhyanfhn
241 yfvpnlkdmf sravtmtaas yaryvlqklv llemkggcre peldtetltt mfevsvaffk
301 vghavgetgn gcvdlrwlak sffeltvlkd iigicygatv kgmqsygler laamlmatvk
361 meelghltte kqeyalrlat vgypkagvys gliggatsvl lsaynrhplf qplhtvmret
421 lfigshvvlr elrlnvttqg pnlalyqlls talcsaleig evlrglalgt esglfspcyl
481 slrfdltrdk llsmapqeat ldqaavsnav dgflgrlsle redrdawhlp aykcvdrldk
541 vlmiiplinv tfiissdrev rgsalyeast tylssslfls pvimnkcsqg avageprqip
601 kiqnftrtqk scifcgfall sydekeglet ttyitsqevq nsilssnyfd fdnlhvhyll
661 lttngtvmei aglyeerahv vlaiilyfia falgiflvhk ivmffl
```

Figure 56 gL (BKRF2) [Human herpesvirus 4 type 2] (SEQ ID NO:04)

NCBI Reference Sequence: YP_001129472.1

```
  1 mrtvgvflat clvtifvlpt wgnwaypcch vtqlraqhll alenisdiyl vsnqtcdgfs
 61 laslnspkng snqlvisrca nglnvvsffi silkrsssal tghlrelltt letlygsfsv
121 edlfganlnr yawhrgg
```

Figure 57

L1 [Human papillomavirus type 16] (SEQ ID NO:05)

GenBank: AAD33259.1

```
  1 mqvtfiyilv itcyendvnv yhiffqmslw lpseatvylp pvpvskvvst deyvartniy
 61 yhagtsrlla vghpyfpikk pnnnkilvpk vsglqyrvfr ihlpdpnkfg fpdtsfynpd
121 tqrlvwacvg vevgrgqplg vgisghplln klddtenasa yaanagvdnr ecismdykqt
181 qlcligckpp igehwgkgsp ctnvavnpgd cpplelintv iqdgdmvdtg fgamdfttlq
241 anksevpldi ctsickypdy ikmvsepygd slffylrreq mfvrhlfnra gavgenvpdd
301 lyikgsgsta nlassnyfpt psgsmvtsda qifnkpywlq raqghnngic wgnqlfvtvv
361 dttrstnmsl caaistsett ykntnfkeyl rhgeeydlqf ifqlckitlt advmtyihsm
421 nstiledwnf glqpppggtl edtyrfvtsq aiacqkhtpp apkedplkky tfwevnlkek
481 fsadldqfpl grkfllqagl kakpkftlgk rkatpttsst sttakrkkrk l
```

Figure 58

L2 [Human papillomavirus type 16] (SEQ ID NO:06)

GenBank: AAD33258.1

```
  1 mrhkrsakrt krasatqlyk tckqagtcpp diipkvegkt iadqilqygs mgvffgglgi
 61 gtgsgtggrt gyiplgtrpp tatdtlapvr ppltvdpvgp sdpsivslve etsfidagap
121 tsvpsippdv sgfsittstd ttpaildinn tvttvtthnn ptftdpsvlq pptpaetggh
181 ftlssstist hnyeeipmdt fivstnpntv tsstpipgsr pvarlglysr ttqqvkvvdp
241 afittptkli tydnpayegi dvdntlyfss ndnsiniapd pdfldivalh rpaltsrrtg
301 irysrignkq tlrtrsgksi gakvhyyydf stidsaeeie lqtitpstyt ttshaalpts
361 innglydiya ddfitdtstt pvpsvpstsl sgyipantti pfggaynipl vsgpdipini
421 tdqapslipi vpgspqytii adagdfylhp syymlrkrrk rlpyffsdvs laa
```

Figure 59

L2 protein [Human papillomavirus type 18] (SEQ ID NO:07)

GenBank: AGG40790.1

```
  1 mvshraarrk rasvtdlykt ckqsgtcppd vvpkvegttl adkilqwssl giflgglgig
 61 tgsgtggrtg yiplggrsnt vvdvgptrpp vviepvgptd psivtlieds svvtsgaprp
121 tftgtsgfdi tsagtttpav lditpsstsv sisttnftnp afsdpsiiev pqtgevagnv
181 fvgtptsgth gyeeiplqtf assgtgeepi sstplptvrr vagprlysra yqqvsvanpe
241 fltrpsslit ydnpafepvd ttltfdprsd vpdsdfmdii rlhrpaltsr rgtvrfsrlg
301 qratmftrsg tqigarvhfy hdispiapsp eyielqplvs atedndlfdi yaddmdpavp
361 vpsrsttsfa ffkysptiss assysnvtvp ltsswdvpvy tgpditlpst tsvwpivspt
421 apastqyigi hgthyylwpl yyfipkkrkr vpyffadgfv aa
```

Figure 60

EBNA-1 protein [Human herpesvirus 4] (SEQ ID NO:08)

NCBI Reference Sequence: YP_401677.1

```
  1 msdegpgtgp gnglgekgdt sgpegsggsg pqrrggdnhg rgrgrgrgrg ggrpgapggs
 61 gsgprhrdgv rrpqkrpsci gckgthggtg agagaggaga ggagagggag agggaggagg
121 aggagaggga gagggaggag gagagggaga gggaggagag ggaggaggag agggagaggg
181 aggagaggga ggaggagagg gagaggagga ggagaggaga gggaggagga gaggagagga
241 gaggagagga ggagaggagg agaggaggag agggaggaga gggaggagag gaggagagga
301 ggagaggagg agagggagag gagagggrg rggsggrgrg gsggrgrggs ggrrgrgrer
361 arggsrerar grgrgrgekr prspssqsss sgspprrppp grrpffhpvg eadyfeyhqe
421 ggpdgepdvp pgaieqgpad dpgegpstgp rgqgdggrrk kggwfgkhrg qggsnpkfen
481 iaeglralla rshverttde gtwvagvfvy ggsktslynl rrgtalaipq crltplsrlp
541 fgmapgpgpq pgplresivc yfmvflqthi faevlkdaik dlvmtkpapt cnirvtvcsf
601 ddgvdlppwf ppmvegaaae gddgddgdeg gdgdegeegq e
```

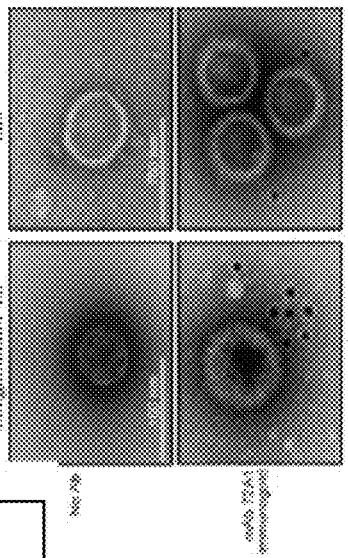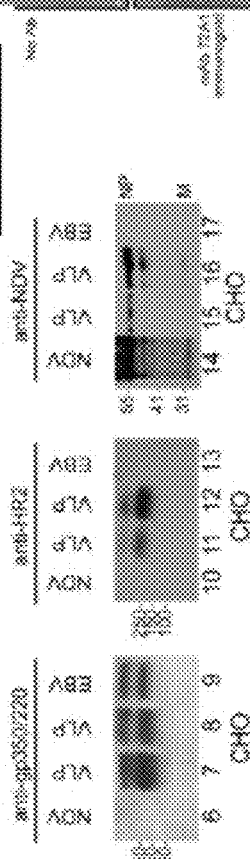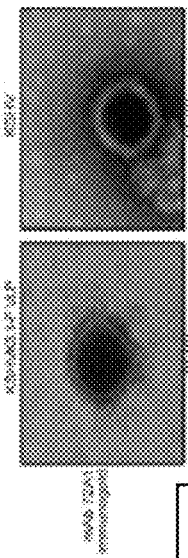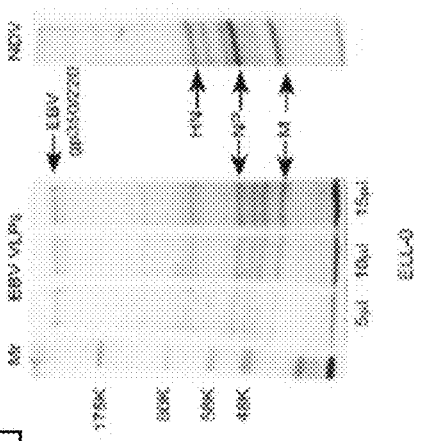
FIGURE 75A - D

FIGURE 78A - B

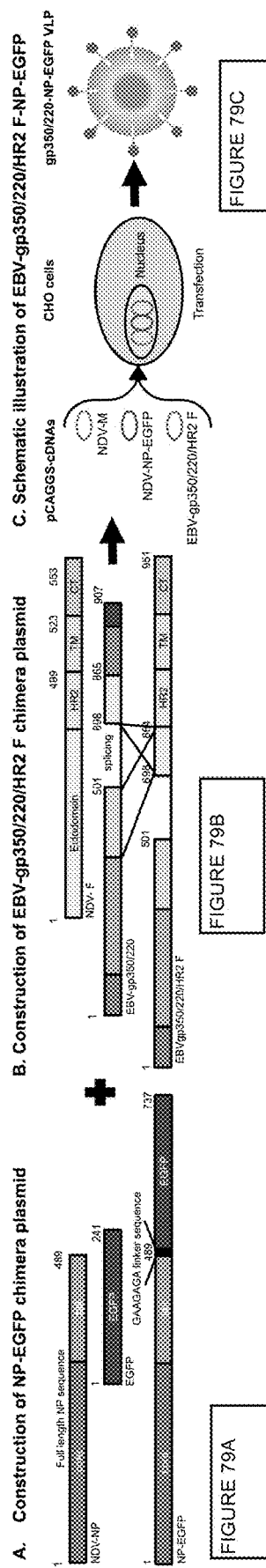

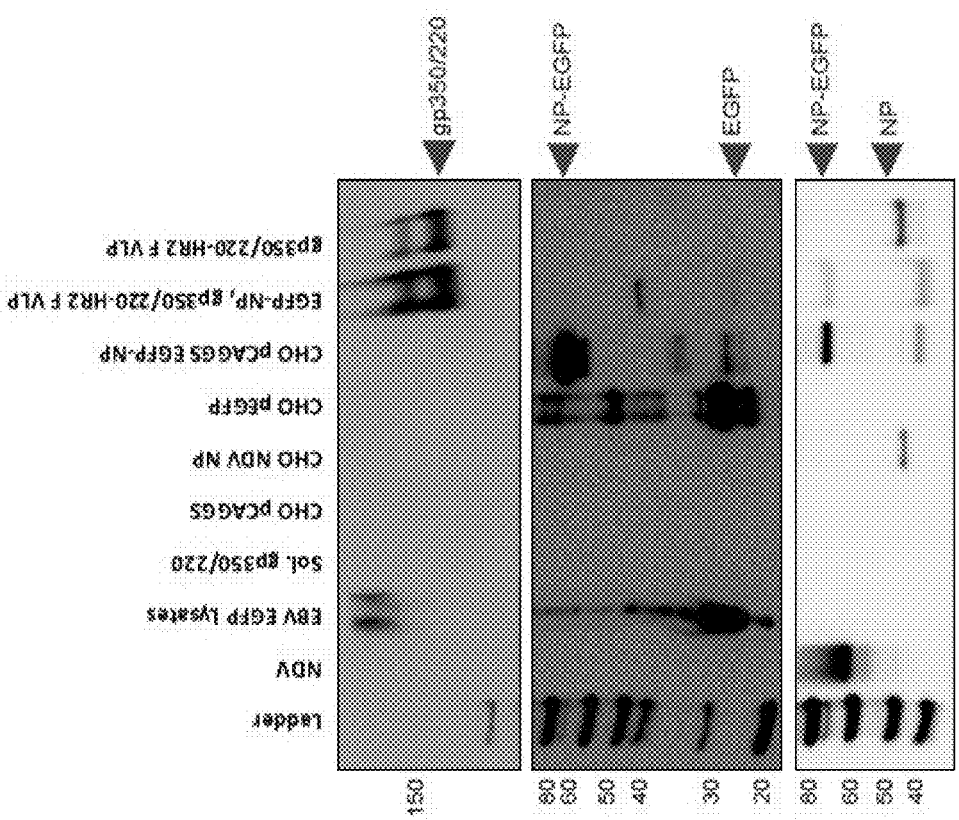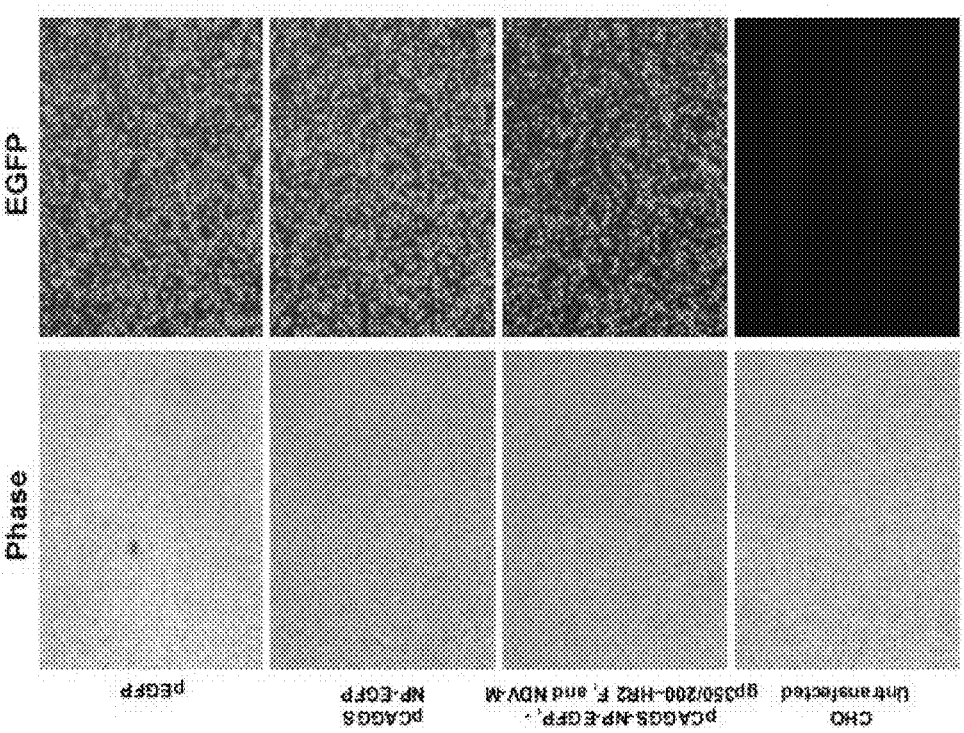
FIGURE 80A - B

A. gp350/220

B. Anti-EBNA1

C. Anti-NDV

D. Anti-EBNA1 Gly-Arg

FIGURE 82A - D

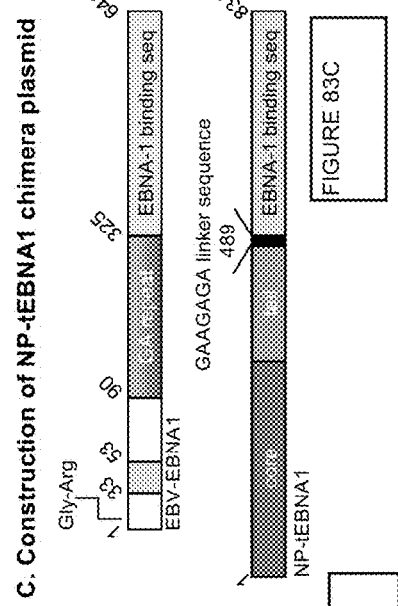
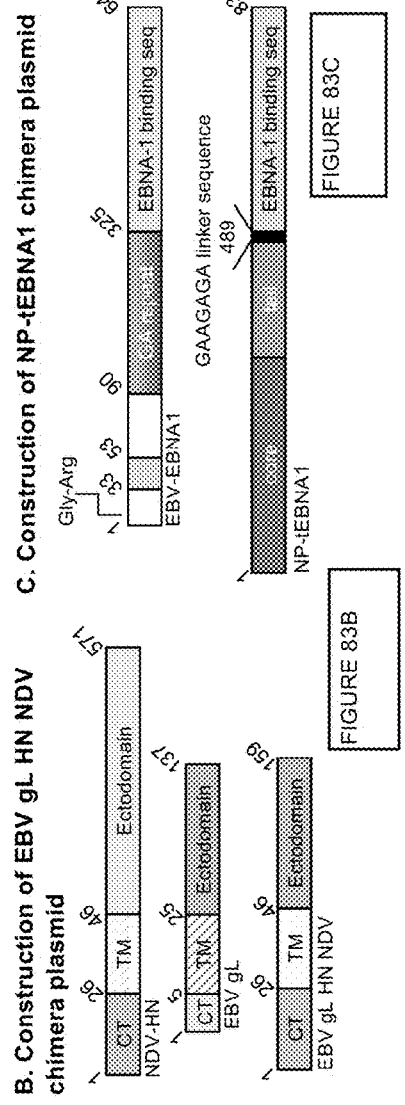
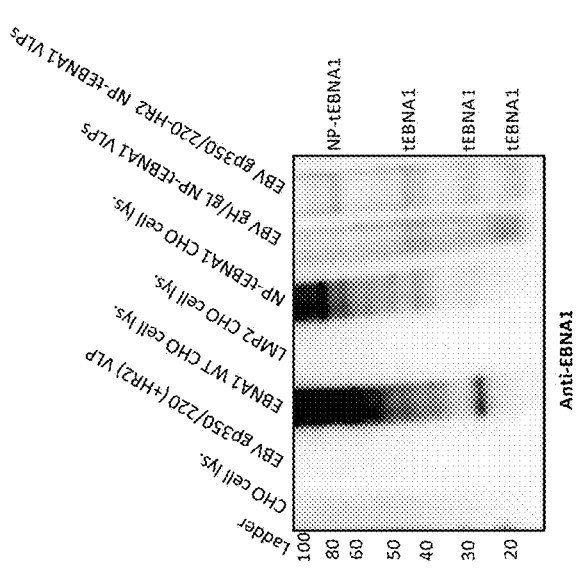
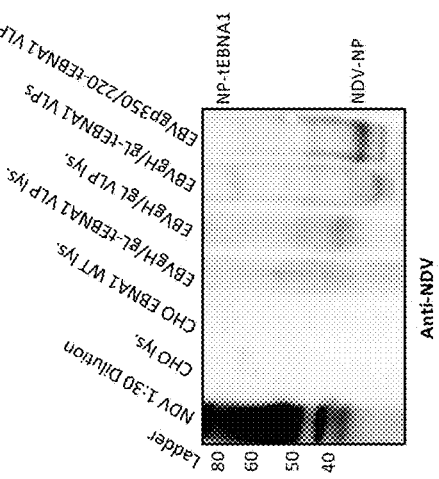
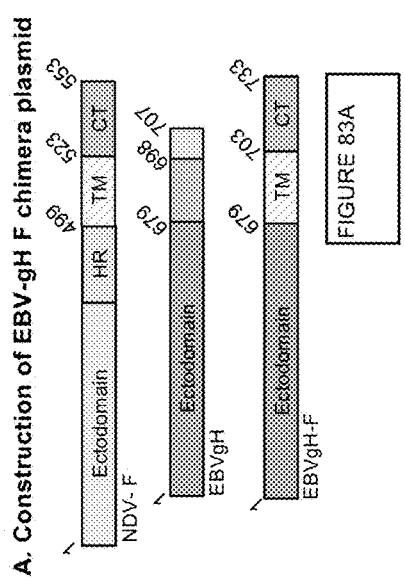
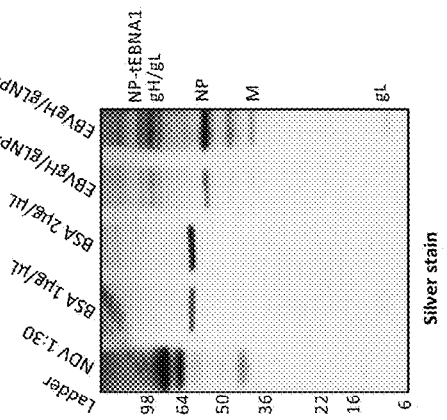
A. Construction of EBV-gH F chimera plasmid
B. Construction of EBV gL HN NDV chimera plasmid
C. Construction of NP-tEBNA1 chimera plasmid
D. Silver Stain
E.

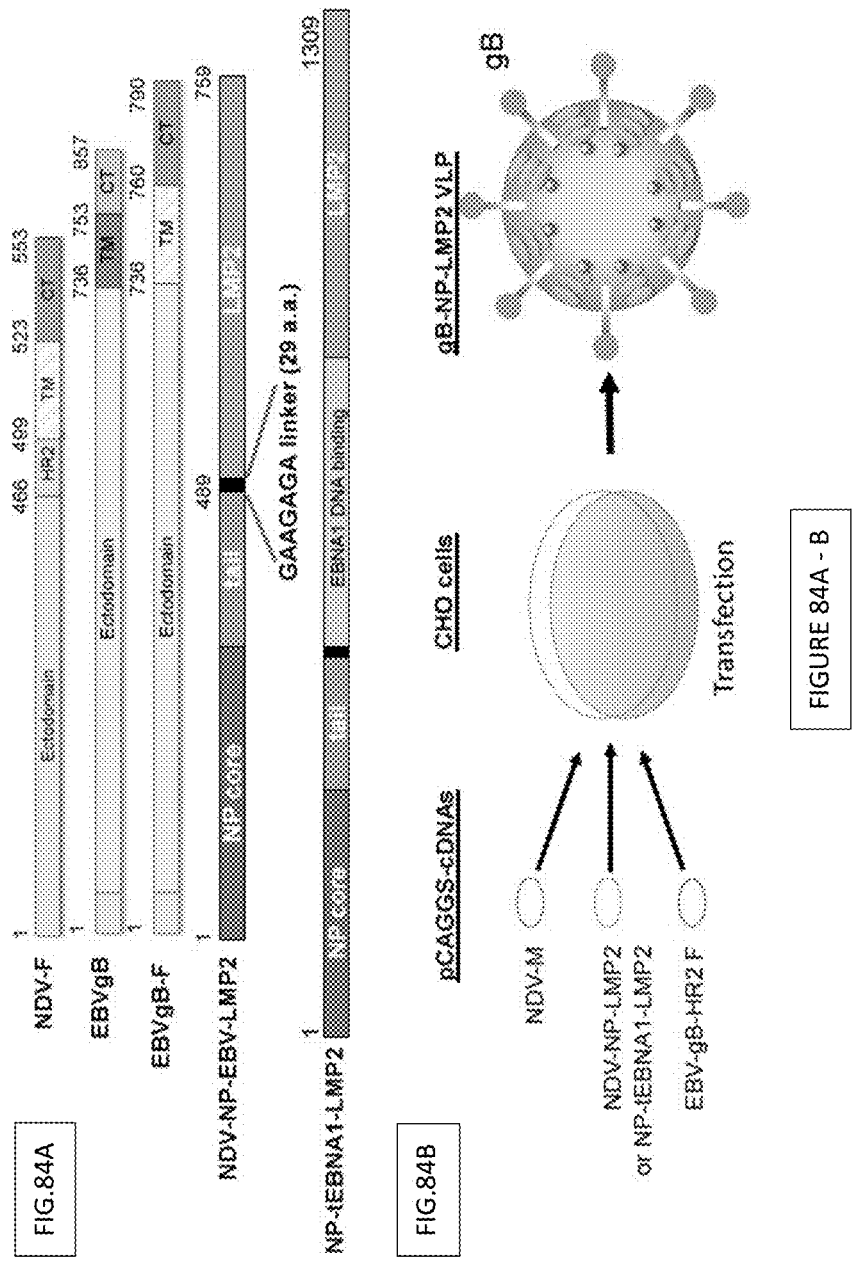

SEQUENCE LISTING

```
<160> NUMBER OF SEQ ID NOS: 577

<210> SEQ ID NO 1
<211> LENGTH: 497
<212> TYPE: PRT
<213> ORGANISM: Human herpesvirus 4

<400> SEQUENCE: 1

Met Gly Ser Leu Glu Met Val Pro Met Gly Ala Gly Pro Pro Ser Pro
1               5                   10                  15
```

```
Gly Gly Asp Pro Asp Gly Tyr Asp Gly Asn Asn Ser Gln Tyr Pro
             20                  25                  30

Ser Ala Ser Gly Ser Ser Gly Asn Thr Pro Thr Pro Pro Asn Asp Glu
         35                  40                  45

Glu Arg Glu Ser Asn Glu Glu Pro Pro Pro Tyr Glu Asp Pro Tyr
         50                  55                  60

Trp Gly Asn Gly Asp Arg His Ser Asp Tyr Gln Pro Leu Gly Thr Gln
 65              70                  75                  80

Asp Gln Ser Leu Tyr Leu Gly Leu Gln His Asp Gly Asn Asp Gly Leu
             85                  90                  95

Pro Pro Pro Pro Tyr Ser Pro Arg Asp Asp Ser Ser Gln His Ile Tyr
            100                 105                 110

Glu Glu Ala Gly Arg Gly Ser Met Asn Pro Val Cys Leu Pro Val Ile
            115                 120                 125

Val Ala Pro Tyr Leu Phe Trp Leu Ala Ala Ile Ala Ala Ser Cys Phe
            130                 135                 140

Thr Ala Ser Val Ser Thr Val Val Thr Ala Thr Gly Leu Ala Leu Ser
145                 150                 155                 160

Leu Leu Leu Leu Ala Ala Val Ala Ser Ser Tyr Ala Ala Ala Gln Arg
                165                 170                 175

Lys Leu Leu Thr Pro Val Thr Val Leu Thr Ala Val Val Thr Phe Phe
            180                 185                 190

Ala Ile Cys Leu Thr Trp Arg Ile Glu Asp Pro Pro Phe Asn Ser Leu
            195                 200                 205

Leu Phe Ala Leu Leu Ala Ala Ala Gly Gly Leu Gln Gly Ile Tyr Val
            210                 215                 220

Leu Val Met Leu Val Leu Leu Ile Leu Ala Tyr Arg Arg Arg Trp Arg
225                 230                 235                 240

Arg Leu Thr Val Cys Gly Gly Ile Met Phe Leu Ala Cys Val Leu Val
                245                 250                 255

Leu Ile Val Asp Ala Val Leu Gln Leu Ser Pro Leu Leu Gly Ala Val
            260                 265                 270

Thr Val Val Ser Met Thr Leu Leu Leu Ala Phe Val Leu Trp Leu
            275                 280                 285

Ser Ser Pro Gly Gly Leu Gly Thr Leu Gly Ala Ala Leu Leu Thr Leu
290                 295                 300

Ala Ala Ala Leu Ala Leu Leu Ala Ser Leu Ile Leu Gly Thr Leu Asn
305                 310                 315                 320

Leu Thr Thr Met Phe Leu Leu Met Leu Leu Trp Thr Leu Val Val Leu
            325                 330                 335

Leu Ile Cys Ser Ser Cys Ser Ser Cys Pro Leu Ser Lys Ile Leu Leu
            340                 345                 350

Ala Arg Leu Phe Leu Tyr Ala Leu Ala Leu Leu Leu Ala Ser Ala
            355                 360                 365

Leu Ile Ala Gly Gly Ser Ile Leu Gln Thr Asn Phe Lys Ser Leu Ser
            370                 375                 380

Ser Thr Glu Phe Ile Pro Asn Leu Phe Cys Met Leu Leu Ile Val
385                 390                 395                 400

Ala Gly Ile Leu Phe Ile Leu Ala Ile Leu Thr Glu Trp Gly Ser Gly
                405                 410                 415

Asn Arg Thr Tyr Gly Pro Val Phe Met Cys Leu Gly Gly Leu Leu Thr
            420                 425                 430

Met Val Ala Gly Ala Val Trp Leu Thr Val Met Ser Asn Thr Leu Leu
```

-continued

```
                435                 440                 445
Ser Ala Trp Ile Leu Thr Ala Gly Phe Leu Ile Phe Leu Ile Gly Phe
450                 455                 460

Ala Leu Phe Gly Val Ile Arg Cys Cys Arg Tyr Cys Cys Tyr Tyr Cys
465                 470                 475                 480

Leu Thr Leu Glu Ser Glu Glu Arg Pro Pro Thr Pro Tyr Arg Asn Thr
                485                 490                 495

Val

<210> SEQ ID NO 2
<211> LENGTH: 857
<212> TYPE: PRT
<213> ORGANISM: Human herpesvirus 4

<400> SEQUENCE: 2

Met Thr Arg Arg Arg Val Leu Ser Val Val Leu Leu Ala Ala Leu
1               5                   10                  15

Ala Cys Arg Leu Gly Ala Gln Thr Pro Glu Gln Pro Ala Pro Ala
            20                  25                  30

Thr Thr Val Gln Pro Thr Ala Thr Arg Gln Gln Thr Ser Phe Pro Phe
                35                  40                  45

Arg Val Cys Glu Leu Ser Ser His Gly Asp Leu Phe Arg Phe Ser Ser
            50                  55                  60

Asp Ile Gln Cys Pro Ser Phe Gly Thr Arg Glu Asn His Thr Glu Gly
65                  70                  75                  80

Leu Leu Met Val Phe Lys Asp Asn Ile Ile Pro Tyr Ser Phe Lys Val
                85                  90                  95

Arg Ser Tyr Thr Lys Ile Val Thr Asn Ile Leu Ile Tyr Asn Gly Trp
            100                 105                 110

Tyr Ala Asp Ser Val Thr Asn Arg His Glu Glu Lys Phe Ser Val Asp
        115                 120                 125

Ser Tyr Glu Thr Asp Gln Met Asp Thr Ile Tyr Gln Cys Tyr Asn Ala
    130                 135                 140

Val Lys Met Thr Lys Asp Gly Leu Thr Arg Val Tyr Val Asp Arg Asp
145                 150                 155                 160

Gly Val Asn Ile Thr Val Asn Leu Lys Pro Thr Gly Gly Leu Ala Asn
                165                 170                 175

Gly Val Arg Arg Tyr Ala Ser Gln Thr Glu Leu Tyr Asp Ala Pro Gly
            180                 185                 190

Trp Leu Ile Trp Thr Tyr Arg Thr Arg Thr Thr Val Asn Cys Leu Ile
        195                 200                 205

Thr Asp Met Met Ala Lys Ser Asn Ser Pro Phe Asp Phe Phe Val Thr
    210                 215                 220

Thr Thr Gly Gln Thr Val Glu Met Ser Pro Phe Tyr Asp Gly Lys Asn
225                 230                 235                 240

Lys Glu Thr Phe His Glu Arg Ala Asp Ser Phe His Val Arg Thr Asn
                245                 250                 255

Tyr Lys Ile Val Asp Tyr Asp Asn Arg Gly Thr Asn Pro Gln Gly Glu
            260                 265                 270

Arg Arg Ala Phe Leu Asp Lys Gly Thr Tyr Thr Leu Ser Trp Lys Leu
        275                 280                 285

Glu Asn Arg Thr Ala Tyr Cys Pro Leu Gln His Trp Gln Thr Phe Asp
    290                 295                 300

Ser Thr Ile Ala Thr Glu Thr Gly Lys Ser Ile His Phe Val Thr Asp
```

```
305                 310                 315                 320
Glu Gly Thr Ser Ser Phe Val Thr Asn Thr Thr Val Gly Ile Glu Leu
                325                 330                 335
Pro Asp Ala Phe Lys Cys Ile Glu Glu Gln Val Asn Lys Thr Met His
                340                 345                 350
Glu Lys Tyr Glu Ala Val Gln Asp Arg Tyr Thr Lys Gly Gln Glu Ala
                355                 360                 365
Ile Thr Tyr Phe Ile Thr Ser Gly Gly Leu Leu Leu Ala Trp Leu Pro
        370                 375                 380
Leu Thr Pro Arg Ser Leu Ala Thr Val Lys Asn Leu Thr Glu Leu Thr
385                 390                 395                 400
Thr Pro Thr Ser Ser Pro Pro Ser Ser Pro Ser Pro Ala Pro Ser
                405                 410                 415
Ala Ala Arg Gly Ser Thr Pro Ala Ala Val Leu Arg Arg Arg Arg
                420                 425                 430
Asp Ala Gly Asn Ala Thr Thr Pro Val Pro Thr Ala Pro Gly Lys
                435                 440                 445
Ser Leu Gly Thr Leu Asn Asn Pro Ala Thr Val Gln Ile Gln Phe Ala
        450                 455                 460
Tyr Asp Ser Leu Arg Arg Gln Ile Asn Arg Met Leu Gly Asp Leu Ala
465                 470                 475                 480
Arg Ala Trp Cys Leu Glu Gln Lys Arg Gln Asn Met Val Leu Arg Glu
                485                 490                 495
Leu Thr Lys Ile Asn Pro Thr Thr Val Met Ser Ser Ile Tyr Gly Lys
                500                 505                 510
Ala Val Ala Ala Lys Arg Leu Gly Asp Val Ile Ser Val Ser Gln Cys
        515                 520                 525
Val Pro Val Asn Gln Ala Thr Val Thr Leu Arg Lys Ser Met Arg Val
                530                 535                 540
Pro Gly Ser Glu Thr Met Cys Tyr Ser Arg Pro Leu Val Ser Phe Ser
545                 550                 555                 560
Phe Ile Asn Asp Thr Lys Thr Tyr Glu Gly Gln Leu Gly Thr Asp Asn
                565                 570                 575
Glu Ile Phe Leu Thr Lys Lys Met Thr Glu Val Cys Gln Ala Thr Ser
                580                 585                 590
Gln Tyr Tyr Phe Gln Ser Gly Asn Glu Ile His Val Tyr Asn Asp Tyr
        595                 600                 605
His His Phe Lys Thr Ile Glu Leu Asp Gly Ile Ala Thr Leu Gln Thr
        610                 615                 620
Phe Ile Ser Leu Asn Thr Ser Leu Ile Glu Asn Ile Asp Phe Ala Ser
625                 630                 635                 640
Leu Glu Leu Tyr Ser Arg Asp Glu Gln Arg Ala Ser Asn Val Phe Asp
                645                 650                 655
Leu Glu Gly Ile Phe Arg Glu Tyr Asn Phe Gln Ala Gln Asn Ile Ala
                660                 665                 670
Gly Leu Arg Lys Asp Leu Asp Asn Ala Val Ser Asn Gly Arg Asn Gln
                675                 680                 685
Phe Val Asp Gly Leu Gly Glu Leu Met Asp Ser Leu Gly Ser Val Gly
        690                 695                 700
Gln Ser Ile Thr Asn Leu Val Ser Thr Val Gly Gly Leu Phe Ser Ser
705                 710                 715                 720
Leu Val Ser Gly Phe Ile Ser Phe Phe Lys Asn Pro Phe Gly Gly Met
                725                 730                 735
```

```
Leu Ile Leu Val Leu Val Ala Gly Val Val Ile Leu Val Ile Ser Leu
                740                 745                 750

Thr Arg Arg Thr Arg Gln Met Ser Gln Gln Pro Val Gln Met Leu Tyr
            755                 760                 765

Pro Gly Ile Asp Glu Leu Ala Gln Gln His Ala Ser Gly Glu Gly Pro
        770                 775                 780

Gly Ile Asn Pro Ile Ser Lys Thr Glu Leu Gln Ala Ile Met Leu Ala
785                 790                 795                 800

Leu His Glu Gln Asn Gln Glu Gln Lys Arg Ala Ala Gln Arg Ala Ala
                805                 810                 815

Gly Pro Ser Val Ala Ser Arg Ala Leu Gln Ala Ala Arg Asp Arg Phe
                820                 825                 830

Pro Gly Leu Arg Arg Arg Arg Tyr His Asp Pro Glu Thr Ala Ala Ala
        835                 840                 845

Leu Leu Gly Glu Ala Glu Thr Glu Phe
        850                 855

<210> SEQ ID NO 3
<211> LENGTH: 706
<212> TYPE: PRT
<213> ORGANISM: Human herpesvirus 4

<400> SEQUENCE: 3

Met Gln Leu Leu Cys Val Phe Cys Leu Val Leu Leu Trp Glu Val Gly
1               5                   10                  15

Ala Ala Ser Leu Ser Glu Val Lys Leu His Leu Asp Ile Glu Gly His
                20                  25                  30

Ala Ser His Tyr Thr Ile Pro Trp Thr Glu Leu Met Ala Lys Val Pro
            35                  40                  45

Gly Leu Ser Pro Glu Ala Leu Trp Arg Glu Ala Asn Val Thr Glu Asp
        50                  55                  60

Leu Ala Ser Met Leu Asn Arg Tyr Lys Leu Ile Tyr Lys Thr Ser Gly
65                  70                  75                  80

Thr Leu Gly Ile Ala Leu Ala Glu Pro Val Asp Ile Pro Ala Val Ser
                85                  90                  95

Glu Gly Ser Met Gln Val Asp Ala Ser Lys Val His Pro Gly Val Ile
                100                 105                 110

Ser Gly Leu Asn Ser Pro Ala Cys Met Leu Ser Ala Pro Leu Glu Lys
            115                 120                 125

Gln Leu Phe Tyr Tyr Ile Gly Thr Met Leu Pro Asn Thr Arg Pro His
        130                 135                 140

Ser Tyr Val Phe Tyr Gln Leu Arg Cys His Leu Ser Tyr Val Ala Leu
145                 150                 155                 160

Ser Ile Asn Gly Asp Lys Phe Gln Tyr Thr Gly Ala Met Thr Ser Lys
                165                 170                 175

Phe Leu Met Gly Thr Tyr Lys Arg Val Thr Glu Lys Gly Asp Glu His
            180                 185                 190

Val Leu Ser Leu Val Phe Gly Lys Thr Lys Asp Leu Pro Asp Leu Arg
        195                 200                 205

Gly Pro Phe Ser Tyr Pro Ser Leu Thr Ser Ala Gln Ser Gly Asp Tyr
        210                 215                 220

Ser Leu Val Ile Val Thr Thr Phe Val His Tyr Ala Asn Phe His Asn
225                 230                 235                 240

Tyr Phe Val Pro Asn Leu Lys Asp Met Phe Ser Arg Ala Val Thr Met
```

```
                  245                 250                 255
Thr Ala Ala Ser Tyr Ala Arg Tyr Val Leu Gln Lys Leu Val Leu Leu
                260                 265                 270

Glu Met Lys Gly Gly Cys Arg Glu Pro Glu Leu Asp Thr Glu Thr Leu
            275                 280                 285

Thr Thr Met Phe Glu Val Ser Val Ala Phe Phe Lys Val Gly His Ala
        290                 295                 300

Val Gly Glu Thr Gly Asn Gly Cys Val Asp Leu Arg Trp Leu Ala Lys
305                 310                 315                 320

Ser Phe Phe Glu Leu Thr Val Leu Lys Asp Ile Ile Gly Ile Cys Tyr
                325                 330                 335

Gly Ala Thr Val Lys Gly Met Gln Ser Tyr Gly Leu Glu Arg Leu Ala
            340                 345                 350

Ala Met Leu Met Ala Thr Val Lys Met Glu Glu Leu Gly His Leu Thr
        355                 360                 365

Thr Glu Lys Gln Glu Tyr Ala Leu Arg Leu Ala Thr Val Gly Tyr Pro
    370                 375                 380

Lys Ala Gly Val Tyr Ser Gly Leu Ile Gly Gly Ala Thr Ser Val Leu
385                 390                 395                 400

Leu Ser Ala Tyr Asn Arg His Pro Leu Phe Gln Pro Leu His Thr Val
                405                 410                 415

Met Arg Glu Thr Leu Phe Ile Gly Ser His Val Val Leu Arg Glu Leu
            420                 425                 430

Arg Leu Asn Val Thr Thr Gln Gly Pro Asn Leu Ala Leu Tyr Gln Leu
        435                 440                 445

Leu Ser Thr Ala Leu Cys Ser Ala Leu Glu Ile Gly Glu Val Leu Arg
    450                 455                 460

Gly Leu Ala Leu Gly Thr Glu Ser Gly Leu Phe Ser Pro Cys Tyr Leu
465                 470                 475                 480

Ser Leu Arg Phe Asp Leu Thr Arg Asp Lys Leu Leu Ser Met Ala Pro
                485                 490                 495

Gln Glu Ala Thr Leu Asp Gln Ala Ala Val Ser Asn Ala Val Asp Gly
            500                 505                 510

Phe Leu Gly Arg Leu Ser Leu Glu Arg Glu Asp Arg Asp Ala Trp His
        515                 520                 525

Leu Pro Ala Tyr Lys Cys Val Asp Arg Leu Asp Lys Val Leu Met Ile
    530                 535                 540

Ile Pro Leu Ile Asn Val Thr Phe Ile Ile Ser Ser Asp Arg Glu Val
545                 550                 555                 560

Arg Gly Ser Ala Leu Tyr Glu Ala Ser Thr Thr Tyr Leu Ser Ser Ser
                565                 570                 575

Leu Phe Leu Ser Pro Val Ile Met Asn Lys Cys Ser Gln Gly Ala Val
            580                 585                 590

Ala Gly Glu Pro Arg Gln Ile Pro Lys Ile Gln Asn Phe Thr Arg Thr
        595                 600                 605

Gln Lys Ser Cys Ile Phe Cys Gly Phe Ala Leu Leu Ser Tyr Asp Glu
    610                 615                 620

Lys Glu Gly Leu Glu Thr Thr Thr Tyr Ile Thr Ser Gln Glu Val Gln
625                 630                 635                 640

Asn Ser Ile Leu Ser Ser Asn Tyr Phe Asp Phe Asp Asn Leu His Val
                645                 650                 655

His Tyr Leu Leu Leu Thr Thr Asn Gly Thr Val Met Glu Ile Ala Gly
            660                 665                 670
```

```
Leu Tyr Glu Glu Arg Ala His Val Val Leu Ala Ile Ile Leu Tyr Phe
            675                 680                 685

Ile Ala Phe Ala Leu Gly Ile Phe Leu Val His Lys Ile Val Met Phe
        690                 695                 700

Phe Leu
705

<210> SEQ ID NO 4
<211> LENGTH: 137
<212> TYPE: PRT
<213> ORGANISM: Human herpesvirus 4

<400> SEQUENCE: 4

Met Arg Thr Val Gly Val Phe Leu Ala Thr Cys Leu Val Thr Ile Phe
1               5                   10                  15

Val Leu Pro Thr Trp Gly Asn Trp Ala Tyr Pro Cys Cys His Val Thr
            20                  25                  30

Gln Leu Arg Ala Gln His Leu Leu Ala Leu Glu Asn Ile Ser Asp Ile
        35                  40                  45

Tyr Leu Val Ser Asn Gln Thr Cys Asp Gly Phe Ser Leu Ala Ser Leu
    50                  55                  60

Asn Ser Pro Lys Asn Gly Ser Asn Gln Leu Val Ile Ser Arg Cys Ala
65                  70                  75                  80

Asn Gly Leu Asn Val Ser Phe Phe Ile Ser Leu Lys Arg Ser
                85                  90                  95

Ser Ser Ala Leu Thr Gly His Leu Arg Glu Leu Leu Thr Thr Leu Glu
            100                 105                 110

Thr Leu Tyr Gly Ser Phe Ser Val Glu Asp Leu Phe Gly Ala Asn Leu
        115                 120                 125

Asn Arg Tyr Ala Trp His Arg Gly Gly
    130                 135

<210> SEQ ID NO 5
<211> LENGTH: 531
<212> TYPE: PRT
<213> ORGANISM: Human papillomavirus type 16

<400> SEQUENCE: 5

Met Gln Val Thr Phe Ile Tyr Ile Leu Val Ile Thr Cys Tyr Glu Asn
1               5                   10                  15

Asp Val Asn Val Tyr His Ile Phe Phe Gln Met Ser Leu Trp Leu Pro
            20                  25                  30

Ser Glu Ala Thr Val Tyr Leu Pro Pro Val Pro Val Ser Lys Val Val
        35                  40                  45

Ser Thr Asp Glu Tyr Val Ala Arg Thr Asn Ile Tyr Tyr His Ala Gly
    50                  55                  60

Thr Ser Arg Leu Leu Ala Val Gly His Pro Tyr Phe Pro Ile Lys Lys
65                  70                  75                  80

Pro Asn Asn Asn Lys Ile Leu Val Pro Lys Val Ser Gly Leu Gln Tyr
                85                  90                  95

Arg Val Phe Arg Ile His Leu Pro Asp Pro Asn Lys Phe Gly Phe Pro
            100                 105                 110

Asp Thr Ser Phe Tyr Asn Pro Asp Thr Gln Arg Leu Val Trp Ala Cys
        115                 120                 125

Val Gly Val Glu Val Gly Arg Gly Gln Pro Leu Gly Val Gly Ile Ser
    130                 135                 140
```

Gly His Pro Leu Leu Asn Lys Leu Asp Asp Thr Glu Asn Ala Ser Ala
145                 150                 155                 160

Tyr Ala Asn Ala Gly Val Asp Asn Arg Glu Cys Ile Ser Met Asp
                165                 170                 175

Tyr Lys Gln Thr Gln Leu Cys Leu Ile Gly Cys Lys Pro Pro Ile Gly
            180                 185                 190

Glu His Trp Gly Lys Gly Ser Pro Cys Thr Asn Val Ala Val Asn Pro
        195                 200                 205

Gly Asp Cys Pro Pro Leu Glu Leu Ile Asn Thr Val Ile Gln Asp Gly
    210                 215                 220

Asp Met Val Asp Thr Gly Phe Gly Ala Met Asp Phe Thr Thr Leu Gln
225                 230                 235                 240

Ala Asn Lys Ser Glu Val Pro Leu Asp Ile Cys Thr Ser Ile Cys Lys
                245                 250                 255

Tyr Pro Asp Tyr Ile Lys Met Val Ser Glu Pro Tyr Gly Asp Ser Leu
            260                 265                 270

Phe Phe Tyr Leu Arg Arg Glu Gln Met Phe Val Arg His Leu Phe Asn
        275                 280                 285

Arg Ala Gly Ala Val Gly Glu Asn Val Pro Asp Asp Leu Tyr Ile Lys
    290                 295                 300

Gly Ser Gly Ser Thr Ala Asn Leu Ala Ser Ser Asn Tyr Phe Pro Thr
305                 310                 315                 320

Pro Ser Gly Ser Met Val Thr Ser Asp Ala Gln Ile Phe Asn Lys Pro
                325                 330                 335

Tyr Trp Leu Gln Arg Ala Gln Gly His Asn Asn Gly Ile Cys Trp Gly
            340                 345                 350

Asn Gln Leu Phe Val Thr Val Val Asp Thr Thr Arg Ser Thr Asn Met
        355                 360                 365

Ser Leu Cys Ala Ala Ile Ser Thr Ser Glu Thr Thr Tyr Lys Asn Thr
370                 375                 380

Asn Phe Lys Glu Tyr Leu Arg His Gly Glu Glu Tyr Asp Leu Gln Phe
385                 390                 395                 400

Ile Phe Gln Leu Cys Lys Ile Thr Leu Thr Ala Asp Val Met Thr Tyr
                405                 410                 415

Ile His Ser Met Asn Ser Thr Ile Leu Glu Asp Trp Asn Phe Gly Leu
            420                 425                 430

Gln Pro Pro Pro Gly Gly Thr Leu Glu Asp Thr Tyr Arg Phe Val Thr
        435                 440                 445

Ser Gln Ala Ile Ala Cys Gln Lys His Thr Pro Pro Ala Pro Lys Glu
450                 455                 460

Asp Pro Leu Lys Lys Tyr Thr Phe Trp Glu Val Asn Leu Lys Glu Lys
465                 470                 475                 480

Phe Ser Ala Asp Leu Asp Gln Phe Pro Leu Gly Arg Lys Phe Leu Leu
                485                 490                 495

Gln Ala Gly Leu Lys Ala Lys Pro Lys Phe Thr Leu Gly Lys Arg Lys
            500                 505                 510

Ala Thr Pro Thr Thr Ser Ser Thr Ser Thr Thr Ala Lys Arg Lys Lys
        515                 520                 525

Arg Lys Leu
    530

<210> SEQ ID NO 6
<211> LENGTH: 473

<212> TYPE: PRT
<213> ORGANISM: Human papillomavirus type 16

<400> SEQUENCE: 6

```
Met Arg His Lys Arg Ser Ala Lys Arg Thr Lys Arg Ala Ser Ala Thr
1               5                   10                  15

Gln Leu Tyr Lys Thr Cys Lys Gln Ala Gly Thr Cys Pro Pro Asp Ile
            20                  25                  30

Ile Pro Lys Val Glu Gly Lys Thr Ile Ala Asp Gln Ile Leu Gln Tyr
        35                  40                  45

Gly Ser Met Gly Val Phe Phe Gly Gly Leu Gly Ile Gly Thr Gly Ser
    50                  55                  60

Gly Thr Gly Gly Arg Thr Gly Tyr Ile Pro Leu Gly Thr Arg Pro Pro
65                  70                  75                  80

Thr Ala Thr Asp Thr Leu Ala Pro Val Arg Pro Pro Leu Thr Val Asp
                85                  90                  95

Pro Val Gly Pro Ser Asp Pro Ser Ile Val Ser Leu Val Glu Glu Thr
            100                 105                 110

Ser Phe Ile Asp Ala Gly Ala Pro Thr Ser Val Pro Ser Ile Pro Pro
        115                 120                 125

Asp Val Ser Gly Phe Ser Ile Thr Thr Ser Thr Asp Thr Thr Pro Ala
130                 135                 140

Ile Leu Asp Ile Asn Asn Thr Val Thr Thr Val Thr Thr His Asn Asn
145                 150                 155                 160

Pro Thr Phe Thr Asp Pro Ser Val Leu Gln Pro Pro Thr Pro Ala Glu
                165                 170                 175

Thr Gly Gly His Phe Thr Leu Ser Ser Ser Thr Ile Ser Thr His Asn
            180                 185                 190

Tyr Glu Glu Ile Pro Met Asp Thr Phe Ile Val Ser Thr Asn Pro Asn
        195                 200                 205

Thr Val Thr Ser Ser Thr Pro Ile Pro Gly Ser Arg Pro Val Ala Arg
210                 215                 220

Leu Gly Leu Tyr Ser Arg Thr Thr Gln Gln Val Lys Val Val Asp Pro
225                 230                 235                 240

Ala Phe Ile Thr Thr Pro Thr Lys Leu Ile Thr Tyr Asp Asn Pro Ala
                245                 250                 255

Tyr Glu Gly Ile Asp Val Asp Asn Thr Leu Tyr Phe Ser Ser Asn Asp
            260                 265                 270

Asn Ser Ile Asn Ile Ala Pro Asp Pro Asp Phe Leu Asp Ile Val Ala
        275                 280                 285

Leu His Arg Pro Ala Leu Thr Ser Arg Arg Thr Gly Ile Arg Tyr Ser
290                 295                 300

Arg Ile Gly Asn Lys Gln Thr Leu Arg Thr Arg Ser Gly Lys Ser Ile
305                 310                 315                 320

Gly Ala Lys Val His Tyr Tyr Tyr Asp Phe Ser Thr Ile Asp Ser Ala
                325                 330                 335

Glu Glu Ile Glu Leu Gln Thr Ile Thr Pro Ser Thr Tyr Thr Thr Thr
            340                 345                 350

Ser His Ala Ala Leu Pro Thr Ser Ile Asn Asn Gly Leu Tyr Asp Ile
        355                 360                 365

Tyr Ala Asp Asp Phe Ile Thr Asp Thr Ser Thr Thr Pro Val Pro Ser
370                 375                 380

Val Pro Ser Thr Ser Leu Ser Gly Tyr Ile Pro Ala Asn Thr Thr Ile
385                 390                 395                 400
```

```
Pro Phe Gly Gly Ala Tyr Asn Ile Pro Leu Val Ser Gly Pro Asp Ile
                405                 410                 415

Pro Ile Asn Ile Thr Asp Gln Ala Pro Ser Leu Ile Pro Ile Val Pro
            420                 425                 430

Gly Ser Pro Gln Tyr Thr Ile Ile Ala Asp Ala Gly Asp Phe Tyr Leu
        435                 440                 445

His Pro Ser Tyr Tyr Met Leu Arg Lys Arg Arg Lys Arg Leu Pro Tyr
    450                 455                 460

Phe Phe Ser Asp Val Ser Leu Ala Ala
465                 470

<210> SEQ ID NO 7
<211> LENGTH: 462
<212> TYPE: PRT
<213> ORGANISM: Human papillomavirus type 18

<400> SEQUENCE: 7

Met Val Ser His Arg Ala Ala Arg Arg Lys Arg Ala Ser Val Thr Asp
1               5                   10                  15

Leu Tyr Lys Thr Cys Lys Gln Ser Gly Thr Cys Pro Pro Asp Val Val
            20                  25                  30

Pro Lys Val Glu Gly Thr Thr Leu Ala Asp Lys Ile Leu Gln Trp Ser
        35                  40                  45

Ser Leu Gly Ile Phe Leu Gly Gly Leu Gly Ile Gly Thr Gly Ser Gly
    50                  55                  60

Thr Gly Gly Arg Thr Gly Tyr Ile Pro Leu Gly Gly Arg Ser Asn Thr
65                  70                  75                  80

Val Val Asp Val Gly Pro Thr Arg Pro Pro Val Val Ile Glu Pro Val
                85                  90                  95

Gly Pro Thr Asp Pro Ser Ile Val Thr Leu Ile Glu Asp Ser Ser Val
            100                 105                 110

Val Thr Ser Gly Ala Pro Arg Pro Thr Phe Thr Gly Thr Ser Gly Phe
        115                 120                 125

Asp Ile Thr Ser Ala Gly Thr Thr Thr Pro Ala Val Leu Asp Ile Thr
130                 135                 140

Pro Ser Ser Thr Ser Val Ser Ile Ser Thr Thr Asn Phe Thr Asn Pro
145                 150                 155                 160

Ala Phe Ser Asp Pro Ser Ile Ile Glu Val Pro Gln Thr Gly Glu Val
                165                 170                 175

Ala Gly Asn Val Phe Val Gly Thr Pro Thr Ser Gly Thr His Gly Tyr
            180                 185                 190

Glu Glu Ile Pro Leu Gln Thr Phe Ala Ser Ser Gly Thr Gly Glu Glu
        195                 200                 205

Pro Ile Ser Ser Thr Pro Leu Pro Thr Val Arg Arg Val Ala Gly Pro
210                 215                 220

Arg Leu Tyr Ser Arg Ala Tyr Gln Gln Val Ser Val Ala Asn Pro Glu
225                 230                 235                 240

Phe Leu Thr Arg Pro Ser Ser Leu Ile Thr Tyr Asp Asn Pro Ala Phe
                245                 250                 255

Glu Pro Val Asp Thr Thr Leu Thr Phe Asp Pro Arg Ser Asp Val Pro
            260                 265                 270

Asp Ser Asp Phe Met Asp Ile Ile Arg Leu His Arg Pro Ala Leu Thr
        275                 280                 285

Ser Arg Arg Gly Thr Val Arg Phe Ser Arg Leu Gly Gln Arg Ala Thr
```

-continued

```
                290                 295                 300
Met Phe Thr Arg Ser Gly Thr Gln Ile Gly Ala Arg Val His Phe Tyr
305                 310                 315                 320

His Asp Ile Ser Pro Ile Ala Pro Ser Pro Glu Tyr Ile Glu Leu Gln
                325                 330                 335

Pro Leu Val Ser Ala Thr Glu Asp Asn Asp Leu Phe Asp Ile Tyr Ala
                340                 345                 350

Asp Asp Met Asp Pro Ala Val Pro Val Pro Ser Arg Ser Thr Thr Ser
                355                 360                 365

Phe Ala Phe Phe Lys Tyr Ser Pro Thr Ile Ser Ser Ala Ser Ser Tyr
                370                 375                 380

Ser Asn Val Thr Val Pro Leu Thr Ser Ser Trp Asp Val Pro Val Tyr
385                 390                 395                 400

Thr Gly Pro Asp Ile Thr Leu Pro Ser Thr Thr Ser Val Trp Pro Ile
                405                 410                 415

Val Ser Pro Thr Ala Pro Ala Ser Thr Gln Tyr Ile Gly Ile His Gly
                420                 425                 430

Thr His Tyr Tyr Leu Trp Pro Leu Tyr Tyr Phe Ile Pro Lys Lys Arg
                435                 440                 445

Lys Arg Val Pro Tyr Phe Phe Ala Asp Gly Phe Val Ala Ala
                450                 455                 460

<210> SEQ ID NO 8
<211> LENGTH: 641
<212> TYPE: PRT
<213> ORGANISM: Human herpesvirus 4

<400> SEQUENCE: 8

Met Ser Asp Glu Gly Pro Gly Thr Gly Pro Gly Asn Gly Leu Gly Glu
1               5                   10                  15

Lys Gly Asp Thr Ser Gly Pro Glu Gly Ser Gly Gly Ser Gly Pro Gln
                20                  25                  30

Arg Arg Gly Gly Asp Asn His Gly Arg Gly Arg Gly Arg Gly Arg Gly
                35                  40                  45

Arg Gly Gly Gly Arg Pro Gly Ala Pro Gly Gly Ser Gly Ser Gly Pro
                50                  55                  60

Arg His Arg Asp Gly Val Arg Arg Pro Gln Lys Arg Pro Ser Cys Ile
65              70                  75                  80

Gly Cys Lys Gly Thr His Gly Gly Thr Gly Ala Gly Ala Gly Ala Gly
                85                  90                  95

Gly Ala Gly Ala Gly Gly Ala Gly Ala Gly Gly Gly Ala Gly Ala Gly
                100                 105                 110

Gly Gly Ala Gly Gly Ala Gly Gly Ala Gly Gly Ala Gly Ala Gly Gly
                115                 120                 125

Gly Ala Gly Ala Gly Gly Gly Ala Gly Gly Ala Gly Gly Ala Gly Ala
                130                 135                 140

Gly Gly Gly Ala Gly Ala Gly Gly Gly Ala Gly Gly Ala Gly Ala Gly
145                 150                 155                 160

Gly Gly Ala Gly Gly Ala Gly Gly Ala Gly Gly Ala Gly Gly Ala Gly
                165                 170                 175

Ala Gly Gly Ala Gly Gly Ala Gly Ala Gly Gly Ala Gly Gly Ala Gly
                180                 185                 190

Ala Gly Gly Ala Gly Ala Gly Gly Gly Ala Gly Ala Gly Gly Ala Gly
                195                 200                 205
```

-continued

```
Gly Ala Gly Gly Ala Gly Ala Gly Gly Ala Gly Ala Gly Gly Ala
    210                 215                 220
Gly Gly Ala Gly Gly Ala Gly Ala Gly Gly Ala Gly Ala Gly Ala
225                 230                 235                 240
Gly Ala Gly Gly Ala Gly Ala Gly Gly Ala Gly Gly Ala Gly Ala Gly
                245                 250                 255
Gly Ala Gly Gly Ala Gly Ala Gly Gly Ala Gly Gly Ala Gly Ala Gly
                260                 265                 270
Gly Gly Ala Gly Gly Ala Gly Ala Gly Gly Gly Ala Gly Ala Gly
                275                 280                 285
Ala Gly Gly Ala Gly Gly Ala Gly Ala Gly Gly Ala Gly Gly Ala Gly
    290                 295                 300
Ala Gly Gly Ala Gly Gly Ala Gly Ala Gly Gly Ala Gly Ala Gly
    305                 310                 315                 320
Gly Ala Gly Ala Gly Gly Gly Arg Gly Arg Gly Gly Ser Gly Gly
                325                 330                 335
Arg Gly Arg Gly Gly Ser Gly Gly Arg Gly Arg Gly Gly Ser Gly Gly
                340                 345                 350
Arg Arg Gly Arg Gly Arg Glu Arg Ala Arg Gly Gly Ser Arg Glu Arg
    355                 360                 365
Ala Arg Gly Arg Gly Arg Gly Arg Gly Glu Lys Arg Pro Arg Ser Pro
    370                 375                 380
Ser Ser Gln Ser Ser Ser Ser Gly Ser Pro Pro Arg Arg Pro Pro Pro
385                 390                 395                 400
Gly Arg Arg Pro Phe Phe His Pro Val Gly Glu Ala Asp Tyr Phe Glu
                405                 410                 415
Tyr His Gln Glu Gly Gly Pro Asp Gly Glu Pro Asp Val Pro Pro Gly
            420                 425                 430
Ala Ile Glu Gln Gly Pro Ala Asp Asp Pro Gly Glu Gly Pro Ser Thr
            435                 440                 445
Gly Pro Arg Gly Gln Gly Asp Gly Gly Arg Arg Lys Lys Gly Gly Trp
    450                 455                 460
Phe Gly Lys His Arg Gly Gln Gly Gly Ser Asn Pro Lys Phe Glu Asn
465                 470                 475                 480
Ile Ala Glu Gly Leu Arg Ala Leu Leu Ala Arg Ser His Val Glu Arg
                485                 490                 495
Thr Thr Asp Glu Gly Thr Trp Val Ala Gly Val Phe Val Tyr Gly Gly
            500                 505                 510
Ser Lys Thr Ser Leu Tyr Asn Leu Arg Arg Gly Thr Ala Leu Ala Ile
    515                 520                 525
Pro Gln Cys Arg Leu Thr Pro Leu Ser Arg Leu Pro Phe Gly Met Ala
    530                 535                 540
Pro Gly Pro Gly Pro Gln Pro Gly Pro Leu Arg Glu Ser Ile Val Cys
545                 550                 555                 560
Tyr Phe Met Val Phe Leu Gln Thr His Ile Phe Ala Glu Val Leu Lys
                565                 570                 575
Asp Ala Ile Lys Asp Leu Val Met Thr Lys Pro Ala Pro Thr Cys Asn
            580                 585                 590
Ile Arg Val Thr Val Cys Ser Phe Asp Asp Gly Val Asp Leu Pro Pro
                595                 600                 605
Trp Phe Pro Pro Met Val Glu Gly Ala Ala Glu Gly Asp Asp Gly
    610                 615                 620
Asp Asp Gly Asp Glu Gly Gly Asp Gly Asp Glu Gly Glu Glu Gly Gln
```

```
                    625                 630                 635                 640
Glu

<210> SEQ ID NO 9
<211> LENGTH: 1356
<212> TYPE: PRT
<213> ORGANISM: Artificial Sequence
<220> FEATURE:
<223> OTHER INFORMATION: Synthethic

<400> SEQUENCE: 9

Phe Leu Glu Thr Gly Arg Thr Cys Lys Ser Arg Val Arg Asp Arg Ser
1               5                   10                  15

Ser Asn Ser Arg Glu Pro Ser Ala Asn Met Ser Ser Val Phe Asp Glu
            20                  25                  30

Tyr Glu Gln Leu Leu Ala Ala Gln Thr Arg Pro Asn Gly Ala His Gly
        35                  40                  45

Gly Gly Glu Lys Gly Ser Thr Leu Lys Val Glu Val Pro Val Phe Thr
    50                  55                  60

Leu Asn Ser Asp Asp Pro Glu Asp Arg Trp Asn Phe Val Val Phe Cys
65                  70                  75                  80

Leu Arg Ile Ala Val Ser Glu Asp Ala Asn Lys Pro Leu Arg Gln Gly
                85                  90                  95

Ala Leu Ile Ser Leu Leu Cys Ser His Ser Gln Val Met Arg Asn His
            100                 105                 110

Val Ala Leu Ala Gly Lys Gln Asn Glu Ala Thr Leu Ala Val Leu Glu
        115                 120                 125

Ile Asp Gly Phe Thr Asn Ser Val Pro Gln Phe Asn Asn Thr Ser Gly
    130                 135                 140

Val Ser Glu Glu Arg Ala Gln Arg Phe Met Met Ile Ala Gly Ser Leu
145                 150                 155                 160

Pro Arg Ala Cys Ser Asn Gly Thr Pro Phe Ile Thr Ala Gly Val Glu
                165                 170                 175

Asp Asp Ala Pro Glu Asp Ile Ile Asp Thr Leu Glu Arg Ile Leu Ser
            180                 185                 190

Ile Gln Ala Gln Val Trp Val Thr Val Ala Lys Ala Met Thr Ala Tyr
        195                 200                 205

Glu Thr Ala Asp Glu Ser Glu Thr Arg Arg Ile Asn Lys Tyr Met Gln
    210                 215                 220

Gln Gly Arg Val Gln Lys Lys Tyr Ile Leu His Pro Val Cys Arg Ser
225                 230                 235                 240

Ala Ile Gln Leu Thr Ile Arg Gln Ser Leu Ala Val Arg Ile Phe Leu
                245                 250                 255

Val Ser Glu Leu Lys Arg Gly Arg Asn His Ala Gly Gly Ser Ser Thr
            260                 265                 270

Tyr Tyr Asn Leu Val Gly Asp Val Asp Ser Tyr Ile Arg Asn Thr Gly
        275                 280                 285

Leu Thr Ala Phe Phe Leu Thr Leu Lys Tyr Gly Ile Asn Thr Lys Thr
    290                 295                 300

Ser Ala Leu Ala Leu Ser Ser Leu Ala Gly Asp Ile Gln Lys Met Lys
305                 310                 315                 320

Gln Leu Met Arg Leu Tyr Arg Met Lys Gly Asp Asn Ala Pro Tyr Met
                325                 330                 335

Thr Leu Leu Gly Asp Ser Asp Gln Met Ser Phe Ala Pro Ala Glu Tyr
            340                 345                 350
```

```
Ala Gln Leu Tyr Ser Phe Ala Met Ala Met Ala Ser Val Leu Asp Lys
            355                 360                 365

Gly Thr Gly Lys Tyr Gln Phe Ala Arg Asp Phe Met Ser Thr Ser Phe
        370                 375                 380

Trp Arg Leu Gly Val Glu Tyr Ala Gln Ala Gln Gly Ser Ser Ile Asn
385                 390                 395                 400

Glu Asp Met Ala Ala Glu Leu Lys Leu Thr Pro Ala Ala Arg Arg Gly
                405                 410                 415

Leu Ala Ala Ala Gln Arg Val Ser Glu Glu Thr Ser Ser Met Asp
                420                 425                 430

Ile Pro Thr Gln Gln Ala Gly Val Leu Thr Gly Leu Ser Asp Gly Gly
            435                 440                 445

Pro Gln Ala Pro Gln Gly Gly Ser Asn Arg Ser Gln Gly Arg Pro Asp
        450                 455                 460

Ala Gly Asp Gly Glu Thr Gln Phe Leu Asp Leu Met Arg Ala Val Ala
465                 470                 475                 480

Asn Ser Met Arg Glu Ala Pro Asn Ser Val Gln Ser Thr Thr Gln Pro
                485                 490                 495

Glu Pro Pro Pro Thr Pro Gly Pro Ser Gln Asp Asn Asp Thr Asp Trp
            500                 505                 510

Gly Tyr Pro Ala Thr Leu Ser Leu Pro Pro Asp His Pro Asn Ser Ser
        515                 520                 525

Ala Arg Ser Pro Pro Asp Pro Gly Ala Ala Gly Ala Gly
        530                 535                 540

Gly Gly Arg Gly Arg Gly Gly Ser Gly Gly Arg Gly Arg Gly Gly Ser
545                 550                 555                 560

Gly Gly Arg Gly Arg Gly Gly Ser Gly Gly Arg Arg Gly Arg Gly Arg
                565                 570                 575

Glu Arg Ala Arg Gly Gly Ser Arg Glu Arg Ala Arg Gly Arg Gly Arg
            580                 585                 590

Gly Arg Gly Glu Lys Arg Pro Arg Ser Pro Ser Ser Gln Ser Ser Ser
        595                 600                 605

Ser Gly Ser Pro Pro Arg Arg Pro Pro Gly Arg Arg Pro Phe Phe
610                 615                 620

His Pro Val Gly Glu Ala Asp Tyr Phe Glu Tyr His Gln Glu Gly Gly
625                 630                 635                 640

Pro Asp Gly Glu Pro Asp Val Pro Gly Ala Ile Glu Gln Gly Pro
                645                 650                 655

Ala Asp Asp Pro Gly Glu Gly Pro Ser Thr Gly Pro Arg Gly Gln Gly
                660                 665                 670

Asp Gly Gly Arg Arg Lys Lys Gly Gly Trp Phe Gly Lys His Arg Gly
            675                 680                 685

Gln Gly Gly Ser Asn Pro Lys Phe Glu Asn Ile Ala Glu Gly Leu Arg
        690                 695                 700

Ala Leu Leu Ala Arg Ser His Val Glu Arg Thr Thr Asp Glu Gly Thr
705                 710                 715                 720

Trp Val Ala Gly Val Phe Val Tyr Gly Gly Ser Lys Thr Ser Leu Tyr
                725                 730                 735

Asn Leu Arg Arg Gly Thr Ala Leu Ala Ile Pro Gln Cys Arg Leu Thr
            740                 745                 750

Pro Leu Ser Arg Leu Pro Phe Gly Met Ala Pro Gly Pro Gly Pro Gln
        755                 760                 765
```

```
Pro Gly Pro Leu Arg Glu Ser Ile Val Cys Tyr Phe Met Val Phe Leu
770                 775                 780

Gln Thr His Ile Phe Ala Glu Val Leu Lys Asp Ala Ile Lys Asp Leu
785                 790                 795                 800

Val Met Thr Lys Pro Ala Pro Thr Cys Asn Ile Arg Val Thr Val Cys
                805                 810                 815

Ser Phe Asp Asp Gly Val Asp Leu Pro Pro Trp Phe Pro Pro Met Val
            820                 825                 830

Glu Gly Ala Ala Ala Glu Gly Asp Asp Gly Asp Asp Gly Asp Glu Gly
835                 840                 845

Gly Asp Gly Asp Glu Gly Glu Glu Gly Gln Glu Met Gly Ser Leu Glu
850                 855                 860

Met Val Pro Met Gly Ala Gly Pro Pro Ser Pro Gly Gly Asp Pro Asp
865                 870                 875                 880

Gly Tyr Asp Gly Gly Asn Asn Ser Gln Tyr Pro Ser Ala Ser Gly Ser
                885                 890                 895

Ser Gly Asn Thr Pro Thr Pro Pro Asn Asp Glu Glu Arg Glu Ser Asn
            900                 905                 910

Glu Glu Pro Pro Pro Pro Tyr Glu Asp Pro Tyr Trp Gly Asn Gly Asp
        915                 920                 925

Arg His Ser Asp Tyr Gln Pro Leu Gly Thr Gln Asp Gln Ser Leu Tyr
930                 935                 940

Leu Gly Leu Gln His Asp Gly Asn Asp Gly Leu Pro Pro Pro Pro Tyr
945                 950                 955                 960

Ser Pro Arg Asp Asp Ser Ser Gln His Ile Tyr Glu Glu Ala Gly Arg
                965                 970                 975

Gly Ser Met Asn Pro Val Cys Leu Pro Val Ile Val Ala Pro Tyr Leu
            980                 985                 990

Phe Trp Leu Ala Ala Ile Ala Ala Ser Cys Phe Thr Ala Ser Val Ser
        995                 1000                1005

Thr Val Val Thr Ala Thr Gly Leu Ala Leu Ser Leu Leu Leu Leu
    1010                1015                1020

Ala Ala Val Ala Ser Ser Tyr Ala Ala Ala Gln Arg Lys Leu Leu
    1025                1030                1035

Thr Pro Val Thr Val Leu Thr Ala Val Val Thr Phe Phe Ala Ile
    1040                1045                1050

Cys Leu Thr Trp Arg Ile Glu Asp Pro Pro Phe Asn Ser Leu Leu
    1055                1060                1065

Phe Ala Leu Leu Ala Ala Ala Gly Gly Leu Gln Gly Ile Tyr Val
    1070                1075                1080

Leu Val Met Leu Val Leu Ile Leu Ala Tyr Arg Arg Arg Trp
    1085                1090                1095

Arg Arg Leu Thr Val Cys Gly Gly Ile Met Phe Leu Ala Cys Val
    1100                1105                1110

Leu Val Leu Ile Val Asp Ala Val Leu Gln Leu Ser Pro Leu Leu
    1115                1120                1125

Gly Ala Val Thr Val Val Ser Met Thr Leu Leu Leu Leu Ala Phe
    1130                1135                1140

Val Leu Trp Leu Ser Ser Pro Gly Gly Leu Gly Thr Leu Gly Ala
    1145                1150                1155

Ala Leu Leu Thr Leu Ala Ala Ala Leu Ala Leu Leu Ala Ser Leu
    1160                1165                1170

Ile Leu Gly Thr Leu Asn Leu Thr Thr Met Phe Leu Leu Met Leu
```

-continued

```
            1175                1180                1185

Leu Trp Thr Leu Val Val Leu Leu Ile Cys Ser Ser Cys Ser Ser
    1190                1195                1200

Cys Pro Leu Ser Lys Ile Leu Leu Ala Arg Leu Phe Leu Tyr Ala
    1205                1210                1215

Leu Ala Leu Leu Leu Leu Ala Ser Ala Leu Ile Ala Gly Gly Ser
    1220                1225                1230

Ile Leu Gln Thr Asn Phe Lys Ser Leu Ser Ser Thr Glu Phe Ile
    1235                1240                1245

Pro Asn Leu Phe Cys Met Leu Leu Leu Ile Val Ala Gly Ile Leu
    1250                1255                1260

Phe Ile Leu Ala Ile Leu Thr Glu Trp Gly Ser Gly Asn Arg Thr
    1265                1270                1275

Tyr Gly Pro Val Phe Met Cys Leu Gly Gly Leu Leu Thr Met Val
    1280                1285                1290

Ala Gly Ala Val Trp Leu Thr Val Met Ser Asn Thr Leu Leu Ser
    1295                1300                1305

Ala Trp Ile Leu Thr Ala Gly Phe Leu Ile Phe Leu Ile Gly Phe
    1310                1315                1320

Ala Leu Phe Gly Val Ile Arg Cys Cys Arg Tyr Cys Cys Tyr Tyr
    1325                1330                1335

Cys Leu Thr Leu Glu Ser Glu Glu Arg Pro Pro Thr Pro Tyr Arg
    1340                1345                1350

Asn Thr Val
    1355

<210> SEQ ID NO 10
<211> LENGTH: 23
<212> TYPE: PRT
<213> ORGANISM: Artificial Sequence
<220> FEATURE:
<223> OTHER INFORMATION: Synthethic

<400> SEQUENCE: 10

Trp Pro Met Pro Trp Leu Thr Asn Thr Thr Glu Ile Phe Phe Pro Leu
1               5                   10                  15

Pro Lys Ile Met Gly Thr Ser
            20

<210> SEQ ID NO 11
<211> LENGTH: 5
<212> TYPE: PRT
<213> ORGANISM: Artificial Sequence
<220> FEATURE:
<223> OTHER INFORMATION: Synthethic

<400> SEQUENCE: 11

Ser Pro Leu Ser Ile
1               5

<210> SEQ ID NO 12
<211> LENGTH: 12
<212> TYPE: PRT
<213> ORGANISM: Artificial Sequence
<220> FEATURE:
<223> OTHER INFORMATION: Synthethic

<400> SEQUENCE: 12

Leu Leu Ala Asn Lys Gly Asn Leu Phe Ser Leu Gln
1               5                   10
```

<210> SEQ ID NO 13
<211> LENGTH: 19
<212> TYPE: PRT
<213> ORGANISM: Artificial Sequence
<220> FEATURE:
<223> OTHER INFORMATION: Synthethic

<400> SEQUENCE: 13

Cys Val Gly Ile Phe Cys Val Ser His Ser Glu Gly His Met Gly Gly
1               5                   10                  15

Gln Ile Ile

<210> SEQ ID NO 14
<211> LENGTH: 20
<212> TYPE: PRT
<213> ORGANISM: Artificial Sequence
<220> FEATURE:
<223> OTHER INFORMATION: Synthethic

<400> SEQUENCE: 14

Asn Ile Arg Met Ser Ile Trp Phe Arg Val Trp Gln His Met Pro Ile
1               5                   10                  15

Cys Trp Leu Pro
            20

<210> SEQ ID NO 15
<211> LENGTH: 11
<212> TYPE: PRT
<213> ORGANISM: Artificial Sequence
<220> FEATURE:
<223> OTHER INFORMATION: Synthethic

<400> SEQUENCE: 15

Thr Lys Val Gly Tyr Lys Glu Val Ile Ser Ile
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Synthethic

<400> SEQUENCE: 16

Asn Ser Pro Leu Leu Ser Ile Pro Tyr Ser Ile Glu Lys Pro
1               5                   10

<210> SEQ ID NO 17
<211> LENGTH: 16
<212> TYPE: PRT
<213> ORGANISM: Artificial Sequence
<220> FEATURE:
<223> OTHER INFORMATION: Synthethic

<400> SEQUENCE: 17

Leu Glu Val Arg Phe Phe Leu Tyr Phe Val Leu Cys Tyr Phe Phe Leu
1               5                   10                  15

<210> SEQ ID NO 18
<211> LENGTH: 2
<212> TYPE: PRT
<213> ORGANISM: Artificial Sequence
<220> FEATURE:
<223> OTHER INFORMATION: Synthethic

```
<400> SEQUENCE: 18

His Pro
1

<210> SEQ ID NO 19
<211> LENGTH: 7
<212> TYPE: PRT
<213> ORGANISM: Artificial Sequence
<220> FEATURE:
<223> OTHER INFORMATION: Synthethic

<400> SEQUENCE: 19

Asn Phe Pro Tyr Met Phe Tyr
1               5

<210> SEQ ID NO 20
<211> LENGTH: 12
<212> TYPE: PRT
<213> ORGANISM: Artificial Sequence
<220> FEATURE:
<223> OTHER INFORMATION: Synthethic

<400> SEQUENCE: 20

Pro Asp Phe Ser Ser Ser Pro Asp Tyr Ser Gln Ser
1               5                   10

<210> SEQ ID NO 21
<211> LENGTH: 17
<212> TYPE: PRT
<213> ORGANISM: Artificial Sequence
<220> FEATURE:
<223> OTHER INFORMATION: Synthethic

<400> SEQUENCE: 21

Leu Ser Leu Phe Ser Tyr Gly Asp Pro Ser Thr Cys Ser Pro Ser Leu
1               5                   10                  15

Ala

<210> SEQ ID NO 22
<211> LENGTH: 3
<212> TYPE: PRT
<213> ORGANISM: Artificial Sequence
<220> FEATURE:
<223> OTHER INFORMATION: Synthethic

<400> SEQUENCE: 22

Ser Trp Ser
1

<210> SEQ ID NO 23
<211> LENGTH: 4
<212> TYPE: PRT
<213> ORGANISM: Artificial Sequence
<220> FEATURE:
<223> OTHER INFORMATION: Synthethic

<400> SEQUENCE: 23

Leu Phe Pro Val
1

<210> SEQ ID NO 24
<211> LENGTH: 25
<212> TYPE: PRT
<213> ORGANISM: Artificial Sequence
<220> FEATURE:
<223> OTHER INFORMATION: Synthethic
```

<400> SEQUENCE: 24

Asn Cys Tyr Pro Leu Thr Ile Pro His Asn Ile Arg Ala Gly Ser Ile
1               5                   10                  15

Lys Cys Lys Ala Trp Val Pro Asn Glu
            20                  25

<210> SEQ ID NO 25
<211> LENGTH: 4
<212> TYPE: PRT
<213> ORGANISM: Artificial Sequence
<220> FEATURE:
<223> OTHER INFORMATION: Synthethic

<400> SEQUENCE: 25

Ala Asn Ser His
1

<210> SEQ ID NO 26
<211> LENGTH: 66
<212> TYPE: PRT
<213> ORGANISM: Artificial Sequence
<220> FEATURE:
<223> OTHER INFORMATION: Synthethic

<400> SEQUENCE: 26

Leu Arg Cys Ala His Cys Pro Leu Ser Ser Arg Glu Thr Cys Arg Ala
1               5                   10                  15

Ser Gly Ser Ala Ser Gln Leu Val Ser Asn His Ser Pro Ala Pro Asn
            20                  25                  30

Ser Ala His Pro Ala Pro Asn Ser Ala Gln Phe Arg Pro Phe Ser Ala
        35                  40                  45

Pro Trp Leu Thr Asn Phe Phe Tyr Leu Cys Arg Gly Arg Gly Arg Leu
    50                  55                  60

Gly Leu
65

<210> SEQ ID NO 27
<211> LENGTH: 30
<212> TYPE: PRT
<213> ORGANISM: Artificial Sequence
<220> FEATURE:
<223> OTHER INFORMATION: Synthethic

<400> SEQUENCE: 27

Ala Ile Pro Glu Val Val Arg Arg Leu Phe Trp Arg Pro Arg Leu Leu
1               5                   10                  15

Gln Lys Ala Asn Leu Phe Ile Ala Ala Tyr Asn Gly Tyr Lys
            20                  25                  30

<210> SEQ ID NO 28
<211> LENGTH: 78
<212> TYPE: PRT
<213> ORGANISM: Artificial Sequence
<220> FEATURE:
<223> OTHER INFORMATION: Synthethic

<400> SEQUENCE: 28

Ser Asn Ser Ile Thr Asn Phe Thr Asn Lys Ala Phe Phe Ser Leu His
1               5                   10                  15

Ser Ser Cys Gly Leu Ser Lys Leu Ile Asn Val Ser Tyr His Val Trp
            20                  25                  30

```
Ile Arg Cys Ile Asn Glu Ser Ala Asn Ala Arg Gly Glu Ala Val Cys
            35                  40                  45

Val Leu Gly Ala Leu Pro Leu Pro Arg Ser Leu Thr Arg Cys Ala Arg
 50                  55                  60

Ser Phe Gly Cys Gly Glu Arg Tyr Gln Leu Thr Gln Arg Arg
 65                  70                  75
```

<210> SEQ ID NO 29
<211> LENGTH: 8
<212> TYPE: PRT
<213> ORGANISM: Artificial Sequence
<220> FEATURE:
<223> OTHER INFORMATION: Synthethic

<400> SEQUENCE: 29

```
Tyr Gly Tyr Pro Gln Asn Gln Gly
 1               5
```

<210> SEQ ID NO 30
<211> LENGTH: 16
<212> TYPE: PRT
<213> ORGANISM: Artificial Sequence
<220> FEATURE:
<223> OTHER INFORMATION: Synthethic

<400> SEQUENCE: 30

```
Arg Arg Lys Glu His Val Ser Lys Arg Pro Ala Lys Gly Gln Glu Pro
 1               5                  10                  15
```

<210> SEQ ID NO 31
<211> LENGTH: 9
<212> TYPE: PRT
<213> ORGANISM: Artificial Sequence
<220> FEATURE:
<223> OTHER INFORMATION: Synthethic

<400> SEQUENCE: 31

```
Lys Gly Arg Val Ala Gly Val Phe Pro
 1               5
```

<210> SEQ ID NO 32
<211> LENGTH: 4
<212> TYPE: PRT
<213> ORGANISM: Artificial Sequence
<220> FEATURE:
<223> OTHER INFORMATION: Synthethic

<400> SEQUENCE: 32

```
Ala Pro Pro Pro
 1
```

<210> SEQ ID NO 33
<211> LENGTH: 57
<212> TYPE: PRT
<213> ORGANISM: Artificial Sequence
<220> FEATURE:
<223> OTHER INFORMATION: Synthethic

<400> SEQUENCE: 33

```
Arg Ala Ser Gln Lys Ser Thr Leu Lys Ser Glu Val Ala Lys Pro Asp
 1               5                  10                  15

Arg Thr Ile Lys Ile Pro Gly Val Ser Pro Trp Lys Leu Pro Arg Ala
            20                  25                  30

Leu Ser Cys Ser Asp Pro Ala Ala Tyr Arg Ile Pro Val Arg Leu Ser
            35                  40                  45
```

```
Pro Phe Gly Lys Arg Gly Ala Phe Ser
    50                  55
```

<210> SEQ ID NO 34
<211> LENGTH: 3
<212> TYPE: PRT
<213> ORGANISM: Artificial Sequence
<220> FEATURE:
<223> OTHER INFORMATION: Synthethic

<400> SEQUENCE: 34

```
Leu Thr Leu
1
```

<210> SEQ ID NO 35
<211> LENGTH: 29
<212> TYPE: PRT
<213> ORGANISM: Artificial Sequence
<220> FEATURE:
<223> OTHER INFORMATION: Synthethic

<400> SEQUENCE: 35

```
Val Ser Gln Phe Gly Val Gly Arg Ser Leu Gln Ala Gly Leu Cys Ala
1               5                   10                  15

Arg Thr Pro Arg Ser Ala Arg Pro Leu Arg Leu Ile Arg
            20                  25
```

<210> SEQ ID NO 36
<211> LENGTH: 3
<212> TYPE: PRT
<213> ORGANISM: Artificial Sequence
<220> FEATURE:
<223> OTHER INFORMATION: Synthethic

<400> SEQUENCE: 36

```
Leu Ser Ser
1
```

<210> SEQ ID NO 37
<211> LENGTH: 16
<212> TYPE: PRT
<213> ORGANISM: Artificial Sequence
<220> FEATURE:
<223> OTHER INFORMATION: Synthethic

<400> SEQUENCE: 37

```
Val Gln Pro Gly Lys Thr Arg Leu Ile Ala Thr Gly Ser Ser His Trp
1               5                   10                  15
```

<210> SEQ ID NO 38
<211> LENGTH: 2
<212> TYPE: PRT
<213> ORGANISM: Artificial Sequence
<220> FEATURE:
<223> OTHER INFORMATION: Synthethic

<400> SEQUENCE: 38

```
Gln Asp
1
```

<210> SEQ ID NO 39
<211> LENGTH: 16
<212> TYPE: PRT
<213> ORGANISM: Artificial Sequence
<220> FEATURE:
<223> OTHER INFORMATION: Synthethic

<400> SEQUENCE: 39

Gln Ser Glu Val Cys Arg Arg Cys Tyr Arg Val Leu Glu Val Val Ala
1               5                   10                  15

<210> SEQ ID NO 40
<211> LENGTH: 4
<212> TYPE: PRT
<213> ORGANISM: Artificial Sequence
<220> FEATURE:
<223> OTHER INFORMATION: Synthethic

<400> SEQUENCE: 40

Leu Arg Leu His
1

<210> SEQ ID NO 41
<211> LENGTH: 20
<212> TYPE: PRT
<213> ORGANISM: Artificial Sequence
<220> FEATURE:
<223> OTHER INFORMATION: Synthethic

<400> SEQUENCE: 41

Lys Asn Ser Ile Trp Tyr Leu Arg Ser Ala Glu Ala Ser Tyr Leu Arg
1               5                   10                  15

Lys Lys Ser Trp
            20

<210> SEQ ID NO 42
<211> LENGTH: 10
<212> TYPE: PRT
<213> ORGANISM: Artificial Sequence
<220> FEATURE:
<223> OTHER INFORMATION: Synthethic

<400> SEQUENCE: 42

Leu Leu Ile Arg Gln Thr Asn His Arg Trp
1               5                   10

<210> SEQ ID NO 43
<211> LENGTH: 28
<212> TYPE: PRT
<213> ORGANISM: Artificial Sequence
<220> FEATURE:
<223> OTHER INFORMATION: Synthethic

<400> SEQUENCE: 43

Arg Trp Phe Phe Cys Leu Gln Ala Ala Asp Tyr Ala Gln Lys Lys Arg
1               5                   10                  15

Ile Ser Arg Arg Ser Phe Asp Leu Phe Tyr Gly Val
            20                  25

<210> SEQ ID NO 44
<211> LENGTH: 32
<212> TYPE: PRT
<213> ORGANISM: Artificial Sequence
<220> FEATURE:
<223> OTHER INFORMATION: Synthethic

<400> SEQUENCE: 44

Arg Ser Val Glu Arg Lys Leu Thr Leu Arg Asp Phe Gly His Glu Ile
1               5                   10                  15

Ile Lys Lys Asp Leu His Leu Asp Pro Phe Lys Leu Lys Met Lys Phe
            20                  25                  30

```
<210> SEQ ID NO 45
<211> LENGTH: 6
<212> TYPE: PRT
<213> ORGANISM: Artificial Sequence
<220> FEATURE:
<223> OTHER INFORMATION: Synthethic

<400> SEQUENCE: 45

Ile Asn Leu Lys Tyr Ile
1               5

<210> SEQ ID NO 46
<211> LENGTH: 4
<212> TYPE: PRT
<213> ORGANISM: Artificial Sequence
<220> FEATURE:
<223> OTHER INFORMATION: Synthethic

<400> SEQUENCE: 46

Val Asn Leu Val
1

<210> SEQ ID NO 47
<211> LENGTH: 7
<212> TYPE: PRT
<213> ORGANISM: Artificial Sequence
<220> FEATURE:
<223> OTHER INFORMATION: Synthethic

<400> SEQUENCE: 47

Gln Leu Pro Met Leu Asn Gln
1               5

<210> SEQ ID NO 48
<211> LENGTH: 75
<212> TYPE: PRT
<213> ORGANISM: Artificial Sequence
<220> FEATURE:
<223> OTHER INFORMATION: Synthethic

<400> SEQUENCE: 48

Gly Thr Tyr Leu Ser Asp Leu Ser Ile Ser Phe Ile His Ser Cys Leu
1               5                   10                  15

Thr Pro Arg Arg Val Asp Asn Tyr Asp Thr Gly Gly Leu Thr Ile Trp
            20                  25                  30

Pro Gln Cys Cys Asn Asp Thr Ala Arg Pro Thr Leu Thr Gly Ser Arg
        35                  40                  45

Phe Ile Ser Asn Lys Pro Ala Ser Arg Lys Gly Arg Ala Gln Lys Trp
    50                  55                  60

Ser Cys Asn Phe Ile Arg Leu His Pro Val Tyr
65                  70                  75

<210> SEQ ID NO 49
<211> LENGTH: 5
<212> TYPE: PRT
<213> ORGANISM: Artificial Sequence
<220> FEATURE:
<223> OTHER INFORMATION: Synthethic

<400> SEQUENCE: 49

Leu Leu Pro Gly Ser
1               5
```

```
<210> SEQ ID NO 50
<211> LENGTH: 2
<212> TYPE: PRT
<213> ORGANISM: Artificial Sequence
<220> FEATURE:
<223> OTHER INFORMATION: Synthethic

<400> SEQUENCE: 50

Ser Lys
1

<210> SEQ ID NO 51
<211> LENGTH: 3
<212> TYPE: PRT
<213> ORGANISM: Artificial Sequence
<220> FEATURE:
<223> OTHER INFORMATION: Synthethic

<400> SEQUENCE: 51

Phe Ala Ser
1

<210> SEQ ID NO 52
<211> LENGTH: 44
<212> TYPE: PRT
<213> ORGANISM: Artificial Sequence
<220> FEATURE:
<223> OTHER INFORMATION: Synthethic

<400> SEQUENCE: 52

Phe Ala Gln Arg Cys Cys His Cys Tyr Arg His Arg Gly Val Thr Leu
1               5                   10                  15

Val Val Trp Tyr Gly Phe Ile Gln Leu Arg Phe Pro Thr Ile Lys Ala
            20                  25                  30

Ser Tyr Met Ile Pro His Val Val Gln Lys Ser Gly
        35                  40

<210> SEQ ID NO 53
<211> LENGTH: 10
<212> TYPE: PRT
<213> ORGANISM: Artificial Sequence
<220> FEATURE:
<223> OTHER INFORMATION: Synthethic

<400> SEQUENCE: 53

Leu Leu Arg Ser Ser Asp Arg Cys Gln Lys
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Synthethic

<400> SEQUENCE: 54

Val Gly Arg Ser Val Ile Thr His Gly Tyr Gly Ser Thr Ala
1               5                   10

<210> SEQ ID NO 55
<211> LENGTH: 15
<212> TYPE: PRT
<213> ORGANISM: Artificial Sequence
<220> FEATURE:
<223> OTHER INFORMATION: Synthethic

<400> SEQUENCE: 55
```

```
Phe Ser Tyr Cys His Ala Ile Arg Lys Met Leu Phe Cys Asp Trp
1               5                  10                  15
```

<210> SEQ ID NO 56
<211> LENGTH: 24
<212> TYPE: PRT
<213> ORGANISM: Artificial Sequence
<220> FEATURE:
<223> OTHER INFORMATION: Synthethic

<400> SEQUENCE: 56

```
Val Leu Asn Gln Val Ile Leu Arg Ile Val Tyr Ala Ala Thr Glu Leu
1               5                  10                  15

Leu Leu Pro Gly Val Asn Thr Gly
            20
```

<210> SEQ ID NO 57
<211> LENGTH: 4
<212> TYPE: PRT
<213> ORGANISM: Artificial Sequence
<220> FEATURE:
<223> OTHER INFORMATION: Synthethic

<400> SEQUENCE: 57

```
Tyr Arg Ala Thr
1
```

<210> SEQ ID NO 58
<211> LENGTH: 95
<212> TYPE: PRT
<213> ORGANISM: Artificial Sequence
<220> FEATURE:
<223> OTHER INFORMATION: Synthethic

<400> SEQUENCE: 58

```
Gln Asn Phe Lys Ser Ala His His Trp Lys Thr Phe Phe Gly Ala Lys
1               5                  10                  15

Thr Leu Lys Asp Leu Thr Ala Val Glu Ile Gln Phe Asp Val Thr His
            20                  25                  30

Ser Cys Thr Gln Leu Ile Phe Ser Ile Phe Tyr Phe His Gln Arg Phe
        35                  40                  45

Trp Val Ser Lys Asn Arg Lys Ala Lys Cys Arg Lys Lys Gly Asn Lys
    50                  55                  60

Gly Asp Thr Glu Met Leu Asn Thr His Thr Leu Pro Phe Ser Ile Leu
65                  70                  75                  80

Leu Lys His Leu Ser Gly Leu Leu Ser His Glu Arg Ile His Ile
                85                  90                  95
```

<210> SEQ ID NO 59
<211> LENGTH: 5
<212> TYPE: PRT
<213> ORGANISM: Artificial Sequence
<220> FEATURE:
<223> OTHER INFORMATION: Synthethic

<400> SEQUENCE: 59

```
Met Tyr Leu Glu Lys
1               5
```

<210> SEQ ID NO 60
<211> LENGTH: 20
<212> TYPE: PRT
<213> ORGANISM: Artificial Sequence

```
<220> FEATURE:
<223> OTHER INFORMATION: Synthethic

<400> SEQUENCE: 60

Thr Asn Arg Gly Ser Ala His Ile Ser Pro Lys Ser Ala Thr Trp Val
1               5                   10                  15

Asp Ile Asp Tyr
            20

<210> SEQ ID NO 61
<211> LENGTH: 11
<212> TYPE: PRT
<213> ORGANISM: Artificial Sequence
<220> FEATURE:
<223> OTHER INFORMATION: Synthethic

<400> SEQUENCE: 61

Leu Val Ile Asn Ser Asn Gln Leu Arg Gly His
1               5                   10

<210> SEQ ID NO 62
<211> LENGTH: 14
<212> TYPE: PRT
<213> ORGANISM: Artificial Sequence
<220> FEATURE:
<223> OTHER INFORMATION: Synthethic

<400> SEQUENCE: 62

Phe Ile Ala His Ile Trp Ser Ser Ala Leu His Asn Leu Arg
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Synthethic

<400> SEQUENCE: 63

Met Ala Arg Leu Ala Asp Arg Pro Thr Thr Pro Ala His
1               5                   10

<210> SEQ ID NO 64
<211> LENGTH: 2
<212> TYPE: PRT
<213> ORGANISM: Artificial Sequence
<220> FEATURE:
<223> OTHER INFORMATION: Synthethic

<400> SEQUENCE: 64

Arg Gln
1

<210> SEQ ID NO 65
<211> LENGTH: 4
<212> TYPE: PRT
<213> ORGANISM: Artificial Sequence
<220> FEATURE:
<223> OTHER INFORMATION: Synthethic

<400> SEQUENCE: 65

Arg Met Phe Pro
1

<210> SEQ ID NO 66
<211> LENGTH: 2
```

<212> TYPE: PRT
<213> ORGANISM: Artificial Sequence
<220> FEATURE:
<223> OTHER INFORMATION: Synthethic

<400> SEQUENCE: 66

Arg Gln
1

<210> SEQ ID NO 67
<211> LENGTH: 47
<212> TYPE: PRT
<213> ORGANISM: Artificial Sequence
<220> FEATURE:
<223> OTHER INFORMATION: Synthethic

<400> SEQUENCE: 67

Gly Leu Ser Ile Asp Val Asn Gly Trp Ser Ile Tyr Gly Lys Leu Pro
1               5                   10                  15

Thr Trp Gln Tyr Ile Lys Cys Ile Ile Cys Gln Val Arg Pro Leu Leu
            20                  25                  30

Thr Ser Met Thr Val Asn Gly Pro Pro Gly Ile Met Pro Ser Thr
        35                  40                  45

<210> SEQ ID NO 68
<211> LENGTH: 13
<212> TYPE: PRT
<213> ORGANISM: Artificial Sequence
<220> FEATURE:
<223> OTHER INFORMATION: Synthethic

<400> SEQUENCE: 68

Pro Tyr Gly Thr Phe Leu Leu Gly Ser Thr Ser Thr Tyr
1               5                   10

<210> SEQ ID NO 69
<211> LENGTH: 8
<212> TYPE: PRT
<213> ORGANISM: Artificial Sequence
<220> FEATURE:
<223> OTHER INFORMATION: Synthethic

<400> SEQUENCE: 69

Ser Ser Leu Leu Pro Trp Ser Arg
1               5

<210> SEQ ID NO 70
<211> LENGTH: 114
<212> TYPE: PRT
<213> ORGANISM: Artificial Sequence
<220> FEATURE:
<223> OTHER INFORMATION: Synthethic

<400> SEQUENCE: 70

Ala Pro Arg Ser Ala Ser Leu Ser Pro Ser Pro Pro Pro His Pro
1               5                   10                  15

Gln Phe Cys Ile Tyr Leu Phe Phe Asn Tyr Phe Val Gln Arg Trp Gly
            20                  25                  30

Arg Gly Gly Gly Gly Pro Pro Gln Ala Arg Gly Gly Ala Arg
        35                  40                  45

Gly Gly Ala Gly Arg Gly Gly Lys Val Arg Arg Gln Pro Ile Arg Ala
    50                  55                  60

Ala Arg Ser Glu Ser Phe Leu Leu Trp Arg Gly Gly Gly Gly Gly
65                  70                  75                  80

```
Pro Ile Lys Ser Glu Ala Arg Gly Gly Arg Glu Ser Leu Arg Ala Ala
                85                  90                  95

Phe Pro Pro Cys Pro Ala Pro Pro Pro Arg Ala Ala Arg Pro Gly
            100                 105                 110

Ser Asp
```

<210> SEQ ID NO 71
<211> LENGTH: 6
<212> TYPE: PRT
<213> ORGANISM: Artificial Sequence
<220> FEATURE:
<223> OTHER INFORMATION: Synthethic

<400> SEQUENCE: 71

```
Pro Arg Tyr Ser His Arg
1               5
```

<210> SEQ ID NO 72
<211> LENGTH: 202
<212> TYPE: PRT
<213> ORGANISM: Artificial Sequence
<220> FEATURE:
<223> OTHER INFORMATION: Synthethic

<400> SEQUENCE: 72

```
Ala Gly Gly Thr Ala Leu Leu Leu Arg Ala Val Ile Ser Ala Trp Phe
1               5                   10                  15

Asn Asp Gly Leu Phe Leu Phe Cys Gly Cys Val Lys Ala Leu Arg Gly
                20                  25                  30

Ser Gly Arg Ala Leu Cys Ala Gly Gly Ala Arg Gly Val Arg Ala
            35                  40                  45

Cys Val Cys Ala Trp Gly Ala Pro Arg Ala Pro Arg Cys Pro Ala
50                  55                  60

Ala Val Ser Ala Ala Gly Ala Ala Arg Gly Phe Val Arg Ser Ala Val
65                  70                  75                  80

Cys Ala Arg Gly Ala Arg Pro Gly Ala Val Pro Arg Gly Ala Gly Gly
                85                  90                  95

Ala Ala Arg Gly Thr Lys Ala Ala Cys Gly Val Cys Ala Trp Gly Gly
                100                 105                 110

Glu Gln Gly Val Trp Ala Arg Arg Ser Gly Cys Asn Pro Pro Cys Thr
            115                 120                 125

Pro Leu Pro Glu Leu Leu Ser Thr Ala Arg Leu Arg Val Arg Gly Ser
            130                 135                 140

Val Arg Gly Val Ala Arg Gly Ser Pro Cys Arg Ala Gly Gly Gly
145                 150                 155                 160

Arg Trp Gly Cys Arg Ala Gly Arg Gly Leu Gly Pro Gly Arg Ala
                165                 170                 175

Arg Gly Lys Gly Arg Gly Gly Pro Arg Ser Ala Gly Gly Cys Arg Gly
            180                 185                 190

Ala Ala Ser Arg Ser His Cys Leu Leu Trp
            195                 200
```

<210> SEQ ID NO 73
<211> LENGTH: 121
<212> TYPE: PRT
<213> ORGANISM: Artificial Sequence
<220> FEATURE:
<223> OTHER INFORMATION: Synthethic

<400> SEQUENCE: 73

```
Ser Cys Glu Arg Ala Gln Gly Leu Pro Leu Ser Gln Ile Cys Ala Glu
1               5                   10                  15
Pro Lys Ser Gly Arg Arg Arg Thr Pro Ser Ser Gly Arg Gly Ala
            20                  25                  30
Lys Arg Cys Gly Ala Gly Arg Lys Glu Met Gly Gly Glu Gly Leu Arg
        35                  40                  45
Ala Ser Pro Arg Arg Pro Leu Leu Pro Leu Gln Pro Arg Gly Cys
    50                  55                  60
Pro Arg Gly Asp Gly Cys Leu Arg Gly Arg Gly Arg Ala Gly Phe
65              70                  75                  80
Gly Phe Trp Arg Val Thr Gly Gly Ser Arg Ala Ser Ala Asn His Val
            85                  90                  95
His Ala Phe Phe Phe Phe Leu Gln Leu Leu Gly Asn Val Leu Val Ile
            100                 105                 110
Val Leu Ser His His Phe Gly Lys Glu
        115                 120
```

<210> SEQ ID NO 74
<211> LENGTH: 8817
<212> TYPE: DNA
<213> ORGANISM: Artificial Sequence
<220> FEATURE:
<223> OTHER INFORMATION: Synthethic

<400> SEQUENCE: 74

| | | | |
|---|---|---|---|
| ttcctcgaga cgggtagaac gtgtaaatct cgagtgcgag accgaagctc aaactcgaga | 60 |
| gagccttctg ccaacatgtc ttccgtattc gacgagtacg agcagctcct cgcagctcag | 120 |
| actcgcccta atggagctca tggaggagga gagaagggga gcaccttaaa ggttgaagtc | 180 |
| ccggtattca ctcttaacag tgacgaccca aagatagat ggaactttgt ggtattctgt | 240 |
| cttcggattg ctgttagcga ggatgccaac aaaccactca gcaaggtgc tctcatatct | 300 |
| ctcttatgct cccactctca agtgatgagg aaccatgttg ccctcgcagg gaaacagaat | 360 |
| gaggccacac tggctgttct tgagatcgat gggtttacca cagcgtgcc ccagttcaac | 420 |
| aacacgagtg gagtgtctga ggagagagca cagaggttca tgatgatagc agggtctctc | 480 |
| cctcgggcat gcagcaacgg taccccgttc atcacagctg gggttgaaga tgatgcacca | 540 |
| gaagacatca tcgatactct ggaaagaatc ctctctatcc aggctcaagt atgggtcacg | 600 |
| gtagcaaagg ccatgactgc atatgagaca gcggatgagt cggaaacgag aagaatcaat | 660 |
| aagtatatgc agcaaggcag agtccagaag aagtatatcc tccacccgt atgcaggagc | 720 |
| gcaattcaac tcacgatcag acagtctctg gcagtccgca ttttcttggt tagcgagctt | 780 |
| aagagaggcc gcaaccacgc aggtgggagc tccacctatt acaacttggt aggggatgta | 840 |
| gactcataca tcaggaacac tgggctcacc gcattcttcc tgacactcaa gtatggaatt | 900 |
| aacaccaaga catcagccct tgcactcagc agcctcgcag gcgatatcca aaaaatgaag | 960 |
| cagctcatgc gtttatatcg gatgaaagga gataatgcgc cgtacatgac attgctaggt | 1020 |
| gacagcgacc agatgagctt tgcaccagct gagtatgcac aactttactc ttttgccatg | 1080 |
| gctatggcat cagtcctaga taaggaact ggcaaatacc aatttgccag agactttatg | 1140 |
| agcacatcat tctggagact tggagtagag tatgctcagg ctcagggaag tagcatcaat | 1200 |
| gaagatatgg ctgccgagct aaagctaacc ccagcagcaa ggagaggcct ggcagctgct | 1260 |
| gcccaacgag tgtctgagga gaccagcagc atggatattc ccacgcaaca agccggggtc | 1320 |

```
ctcactgggc tcagcgacgg aggccccaa gccccacaag gtggatcgaa caggtcgcaa    1380
gggcggccgg acgccggga tggggagacc caatttttgg atttgatgag agcggtggca    1440
aatagtatga gagaagcgcc aaactccgtg cagagcacca ctcaaccaga gcctccccca    1500
actcctgggc atctcaaga caacgacacc gactgggggt acccggcaac actcagcctg    1560
cctccagatc atcccaactc ttctgcccga agcccacccc ccgatcctgg cgccgccggc    1620
gccggcgccg gtggtggaag aggcagaggc ggaagcggag gaaggggcag aggaggaagc    1680
ggaggaagag gcagaggcgg ctccggagga aggagaggca gaggcaggga gagagccaga    1740
ggcggaagca gggagagggc caggaggaagg ggaagaggca gggagagaa gaggcctagg    1800 tcccctagca gccaaagcag cagctccggc agccctccta aaggcctcc tcctggcagg    1860 agacccttct tccaccccgt cggcgaggcc gactacttcg aataccacca ggagggaggc    1920
cccgatggcg aacctgatgt gcctcctggc gccattgagc agggccctgc cgatgaccct    1980
ggcgaaggac ctagcaccgg acccagaggc caggagatg gaggcagaag gaagaaggga    2040
ggctggtttg gcaagcatag aggccagggc ggcagcaacc ccaagttcga aatatcgcc    2100 gagggcctga gagctctgct ggctaggagc acgtggaga gaaccaccga cgagggaacc    2160
tgggtggctg gcgtgttcgt gtacggcggc agcaagacaa gcctgtacaa cctgaggaga    2220
ggcaccgccc tggctattcc ccagtgtagg ctcaccccc tgagcaggct cccttttggc    2280
atggctcctg gacctggacc ccagcctgga cctctgaggg agagcatcgt gtgctacttc    2340
atggtgttcc tgcagaccca catcttcgcc gaggtgctga aggacgccat caaggacctg    2400
gtgatgacca agcccgcccc tacctgcaac attagggtga ccgtgtgctc cttcgacgac    2460
ggagtggacc tgcctcctg gttccctcct atggtggaag agctgctgc cgagggagac    2520 gacggcgatg atggcgatga gggcggcgat ggcgatgaag gagaggaggg acaggagatg    2580
ggcagcctgg aaatggtccc catgggcgcc ggccctccca gccctggagg cgaccctgac    2640
ggctatgacg gcggcaacaa cagccagtac cccagcgcca gcggatccag cggaaacacc    2700
cctacacccc ccaacgacga ggagagggag agcaatgagg aaccccctcc cccttacgag    2760
gacccctact gggggcaatgg cgacaggcac agcgactacc agcccctcgg cacccaggat    2820
cagtccctct acctcggcct gcagcacgac ggcaatgatg gcctgccccc tcctccctat    2880
agccctaggg atgacagctc ccagcacatt tacgaggagg ccggcagggg ctccatgaat    2940
cccgtgtgcc tgcccgtgat cgtcgcccct tacctgttct ggctggccgc cattgccgcc    3000
tcctgcttca gcctccgt gtccaccgtg gtgaccgcca caggactggc tctctccctg    3060
ctcctgctgg ctgccgtggc tagctcctac gctgccgccc aaagaaagct gctgaccccc    3120
gtgaccgtgt gaccgctgt ggtgaccttc tttgctattt gcctgacctg gagaatcgag    3180
gaccctcctt tcaacagcct gctgttcgct ctgctggctg ctgctggcgg cctccaagga    3240
atctacgtgc tggtgatgct ggtgctgctg attctcgcct atagaaggag gtggaggaga    3300
ctgaccgtgt gtggaggcat catgttcctg gcttgtgtgc tggtgctgat cgtcgatgct    3360
gtgctgcaac tgtcccctct gctgggagcc gtgaccgtgg tctccatgac cctgctgctg    3420
ctcgccttcg tgctgtggct cagctcccct ggaggactgg gaaccctggg agctgctctc    3480
ctgacactcg ccgccgccct ggccctgctg gcttccctga ttctgggaac cctgaacctg    3540
accaccatgt tcctgctgat gctgctgtgg accctggtgg tgctgctgat ctgctccagc    3600
tgttccagct gccccctcag caagatcctg ctagcgaggc tgttcctgta cgccctggcc    3660
```

```
ctgctgctcc tggcttccgc cctgattgct ggcggaagca tcctgcaaac caacttcaag    3720
agcctgagca gcaccgagtt catccccaat ctgttctgca tgctcctcct gatcgtggcc    3780
ggaatcctgt tcattctggc tatcctgacc gagtggggct ccggcaacag aacctacggc    3840
cctgtgttca tgtgtctggg cggactgctg accatggtgg ccggagctgt gtggctgacc    3900
gtgatgtcca acaccctgct cagcgcctgg attctgaccg ccggattcct gatcttcctg    3960
attggcttcg ccctgttcgg cgtgattagg tgctgcaggt actgctgcta ctactgcctc    4020
accctggaga gcgaggaaag gcctcccaca ccctacagaa ataccgtgtg atgatggcca    4080
atgccctggc tcacaaatac cactgagatc ttttcccctc tgccaaaaat tatggggaca    4140
tcatgaagcc ccttgagcat ctgacttctg gctaataaag gaaatttatt ttcattgcaa    4200
tagtgtgttg gaatttttg tgtctctcac tcggaaggac atatgggagg gcaaatcatt    4260
taaaacatca gaatgagtat ttggtttaga gtttggcaac atatgccat atgctggctg    4320 ccatgaacaa aggttggcta taagagggtc atcagtatat gaaacagccc cctgctgtcc    4380
attccttatt ccatagaaaa gccttgactt gaggttagat ttttttata ttttgttttg    4440 tgttattttt ttcttttaaca tccctaaaat tttccttaca tgttttacta gccagatttt    4500
tcctcctctc ctgactactc ccagtcatag ctgtccctct tctcttatgg agatccctcg    4560
acctgcagcc caagcttggc gtaatcatgg tcatagctgt ttcctgtgtg aaattgttat    4620
ccgctcacaa ttccacacaa catacgagcc ggaagcataa agtgtaaagc ctgggtgcct    4680
aatgagtgag ctaactcaca ttaattgcgt tgcgctcact gcccgctttc cagtcgggaa    4740
acctgtcgtg ccagcggatc cgcatctcaa ttagtcagca accatagtcc cgcccctaac    4800
tccgcccatc ccgcccctaa ctccgcccag ttccgcccat tctccgcccc atggctgact    4860
aatttttttt atttatgcag aggccgaggc cgcctcggcc tctgagctat tccagaagta    4920
gtgaggaggc ttttttggag gcctaggctt ttgcaaaaag ctaacttgtt tattgcagct    4980
tataatggtt acaaataaag caatagcatc acaaatttca caataaagc atttttttca    5040 ctgcattcta gttgtggttt gtccaaactc atcaatgtat cttatcatgt ctggatccgc    5100
tgcattaatg aatcggccaa cgcgcgggga gaggcggttt gcgtattggg cgctcttccg    5160
cttcctcgct cactgactcg ctgcgctcgg tcgttcggct gcggcgagcg gtatcagctc    5220
actcaaaggc ggtaatacgg ttatccacag aatcagggga acgcaggaa agaacatgtg    5280 agcaaaaggc cagcaaaagg ccaggaaccg taaaaaggcc gcgttgctgg cgttttttcca    5340 taggctccgc cccctgacg agcatcacaa aaatcgacgc tcaagtcaga ggtggcgaaa    5400
cccgacagga ctataaagat accaggcgtt tccccctgga agctccctcg tgcgctctcc    5460
tgttccgacc ctgccgctta ccggatacct gtccgccttt ctcccttcgg gaagcgtggc    5520
gctttctcat agctcacgct gtaggtatct cagttcggtg taggtcgttc gctccaagct    5580
gggctgtgtg cacgaacccc ccgttcagcc cgaccgctgc gccttatccg gtaactatcg    5640
tcttgagtcc aacccggtaa gacacgactt atcgccactg gcagcagcca ctggtaacag    5700
gattagcaga gcgaggtatg taggcggtgc tacagagttc ttgaagtggt ggcctaacta    5760
cggctacact agaagaacag tatttggtat ctgcgctctg ctgaagccag ttaccttcgg    5820
aaaaagagtt ggtagctctt gatccggcaa acaaaccacc gctggtagcg tggtttttt    5880 tgtttgcaag cagcagatta cgcgcagaaa aaaaggatct caagaagatc ctttgatctt    5940
ttctacgggg tctgacgctc agtggaacga aaactcacgt taagggattt tggtcatgag    6000
attatcaaaa aggatcttca cctagatcct tttaaattaa aaatgaagtt ttaaatcaat    6060
```

```
ctaaagtata tatgagtaaa cttggtctga cagttaccaa tgcttaatca gtgaggcacc   6120
tatctcagcg atctgtctat ttcgttcatc catagttgcc tgactcccg tcgtgtagat    6180 aactacgata cgggagggct taccatctgg ccccagtgct gcaatgatac cgcgagaccc   6240
acgctcaccg gctccagatt tatcagcaat aaaccagcca gccggaaggg ccgagcgcag   6300
aagtggtcct gcaactttat ccgcctccat ccagtctatt aattgttgcc gggaagctag   6360
agtaagtagt tcgccagtta atagtttgcg caacgttgtt gccattgcta caggcatcgt   6420
ggtgtcacgc tcgtcgtttg gtatggcttc attcagctcc ggttcccaac gatcaaggcg   6480
agttacatga tcccccatgt tgtgcaaaaa agcggttagc tccttcggtc ctccgatcgt   6540
tgtcagaagt aagttggccg cagtgttatc actcatggtt atggcagcac tgcataattc   6600
tcttactgtc atgccatccg taagatgctt ttctgtgact ggtgagtact caaccaagtc   6660
attctgagaa tagtgtatgc ggcgaccgag ttgctcttgc ccggcgtcaa tacgggataa   6720
taccgcgcca catagcagaa ctttaaaagt gctcatcatt ggaaaacgtt cttcggggcg   6780
aaaactctca aggatcttac cgctgttgag atccagttcg atgtaaccca ctcgtgcacc   6840
caactgatct tcagcatctt ttactttcac cagcgtttct gggtgagcaa aaacaggaag   6900
gcaaaatgcc gcaaaaaagg gaataagggc gacacggaaa tgttgaatac tcatactctt   6960
cctttttcaa tattattgaa gcatttatca gggttattgt ctcatgagcg gatacatatt   7020
tgaatgtatt tagaaaaata aacaaatagg ggttccgcgc acatttcccc gaaaagtgcc   7080
acctgggtcg acattgatta ttgactagtt attaatagta atcaattacg ggtcattag    7140 ttcatagccc atatatggag ttccgcgtta cataacttac ggtaaatggc ccgcctggct   7200
gaccgcccaa cgacccccgc ccattgacgt caataatgac gtatgttccc atagtaacgc   7260
caatagggac tttccattga cgtcaatggg tggagtattt acggtaaact gcccacttgg   7320
cagtacatca agtgtatcat atgccaagta cgccccctat tgacgtcaat gacggtaaat   7380
ggcccgcctg gcattatgcc cagtacatga ccttatggga ctttcctact ggcagtaca    7440 tctacgtatt agtcatcgct attaccatgg tcgaggtgag ccccacgttc tgcttcactc   7500
tccccatctc cccccctcc ccaccccaa ttttgtattt atttattttt taattatttt     7560
gtgcagcgat gggggcgggg gggggggggg ggcccccccc aggcggggcg gggcggggcg   7620
aggggcgggg cggggcgagg cggaaaggtg cggcggcagc caatcagagc ggcgcgctcc   7680
gaaagtttcc ttttatggcg aggcggcggc ggcggcggcc ctataaaaag cgaagcgcgc   7740
ggcgggcggg agtcgttgcg cgctgccttc cccccgtgcc ccgctccgcc gccgcctcgc   7800
gccgcccgcc ccggctctga ctgaccgcgt tactcccaca ggtgagcggg cgggacggcc   7860
cttctcctcc gggctgtaat tagcgcttgg tttaatgacg gcttgtttct ttctgtggc    7920 tgcgtgaaag ccttgagggg ctccgggagg gcccttgtg cggggggagc ggctcggggg   7980
gtgcgtgcgt gtgtgtgtgc gtggggagcg ccgcgtgcgg ctccgcgctg cccggcggct   8040
gtgagcgctg cgggcgcggc gcgggctttt gtgcgctccg cagtgtgcgc gaggggagcg   8100
cggccggggg cggtgccccg cggtgcgggg gggctgcga ggggaacaaa ggctgcgtgc    8160
ggggtgtgtg cgtgggggg tgagcagggg gtgtgggcgc gtcggtcggg ctgcaacccc    8220
ccctgcaccc ccctccccga gttgctgagc acggcccggc ttcgggtgcg ggctccgta    8280 cggggcgtgg cgcggggctc gccgtgccgg cggggggtg gcgcaggtg gggtgccgg     8340 gcggggcggg gccgcctcgg gccggggagg gctcggggga aggggcgcgg cggccccgg   8400
```

```
agcgccggcg gctgtcgagg cgcggcgagc cgcagccatt gccttttatg gtaatcgtgc    8460
gagagggcgc agggacttcc tttgtcccaa atctgtgcgg agccgaaatc tgggaggcgc    8520
cgccgcaccc cctctagcgg gcgcggggcg aagcggtgcg gcgccggcag gaaggaaatg    8580
ggcggggagg gccttcgtgc gtcgccgcgc cgccgtcccc ttctccctct ccagcctcgg    8640
ggctgtccgc gggggacgg ctgccttcgg ggggacggg gcagggcggg gttcggcttc     8700
tggcgtgtga ccggcggctc tagagcctct gctaaccatg ttcatgcctt cttcttttttc   8760 ctacagctcc tgggcaacgt gctggttatt gtgctgtctc atcattttgg caaagaa       8817
```

<210> SEQ ID NO 75
<211> LENGTH: 500
<212> TYPE: PRT
<213> ORGANISM: Artificial Sequence
<220> FEATURE:
<223> OTHER INFORMATION: Synthethic

<400> SEQUENCE: 75

```
Phe Leu Glu Met Gly Ser Leu Glu Met Val Pro Met Gly Ala Gly Pro
1               5                   10                  15

Pro Ser Pro Gly Gly Asp Pro Asp Gly Tyr Asp Gly Gly Asn Asn Ser
            20                  25                  30

Gln Tyr Pro Ser Ala Ser Gly Ser Ser Gly Asn Thr Pro Thr Pro Pro
        35                  40                  45

Asn Asp Glu Glu Arg Glu Ser Asn Glu Glu Pro Pro Pro Pro Tyr Glu
50                  55                  60

Asp Pro Tyr Trp Gly Asn Gly Asp Arg His Ser Asp Tyr Gln Pro Leu
65                  70                  75                  80

Gly Thr Gln Asp Gln Ser Leu Tyr Leu Gly Leu Gln His Asp Gly Asn
                85                  90                  95

Asp Gly Leu Pro Pro Pro Pro Tyr Ser Pro Arg Asp Asp Ser Ser Gln
            100                 105                 110

His Ile Tyr Glu Glu Ala Gly Arg Gly Ser Met Asn Pro Val Cys Leu
        115                 120                 125

Pro Val Ile Val Ala Pro Tyr Leu Phe Trp Leu Ala Ala Ile Ala Ala
130                 135                 140

Ser Cys Phe Thr Ala Ser Val Ser Thr Val Val Thr Ala Thr Gly Leu
145                 150                 155                 160

Ala Leu Ser Leu Leu Leu Leu Ala Ala Val Ala Ser Ser Tyr Ala Ala
                165                 170                 175

Ala Gln Arg Lys Leu Leu Thr Pro Val Thr Val Leu Thr Ala Val Val
            180                 185                 190

Thr Phe Phe Ala Ile Cys Leu Thr Trp Arg Ile Glu Asp Pro Pro Phe
        195                 200                 205

Asn Ser Leu Leu Phe Ala Leu Leu Ala Ala Ala Gly Gly Leu Gln Gly
210                 215                 220

Ile Tyr Val Leu Val Met Leu Val Leu Leu Ile Leu Ala Tyr Arg Arg
225                 230                 235                 240

Arg Trp Arg Arg Leu Thr Val Cys Gly Gly Ile Met Phe Leu Ala Cys
                245                 250                 255

Val Leu Val Leu Ile Val Asp Ala Val Leu Gln Leu Ser Pro Leu Leu
            260                 265                 270

Gly Ala Val Thr Val Val Ser Met Thr Leu Leu Leu Ala Phe Val
        275                 280                 285

Leu Trp Leu Ser Ser Pro Gly Gly Leu Gly Thr Leu Gly Ala Ala Leu
```

```
                290                 295                 300
Leu Thr Leu Ala Ala Ala Leu Ala Leu Leu Ala Ser Leu Ile Leu Gly
305                 310                 315                 320

Thr Leu Asn Leu Thr Thr Met Phe Leu Leu Met Leu Leu Trp Thr Leu
                325                 330                 335

Val Val Leu Leu Ile Cys Ser Ser Ser Ser Cys Pro Leu Ser Lys
            340                 345                 350

Ile Leu Leu Ala Arg Leu Phe Leu Tyr Ala Leu Ala Leu Leu Leu
        355                 360                 365

Ala Ser Ala Leu Ile Ala Gly Gly Ser Ile Leu Gln Thr Asn Phe Lys
        370                 375                 380

Ser Leu Ser Ser Thr Glu Phe Ile Pro Asn Leu Phe Cys Met Leu Leu
385                 390                 395                 400

Leu Ile Val Ala Gly Ile Leu Phe Ile Leu Ala Ile Leu Thr Glu Trp
                405                 410                 415

Gly Ser Gly Asn Arg Thr Tyr Gly Pro Val Phe Met Cys Leu Gly Gly
                420                 425                 430

Leu Leu Thr Met Val Ala Gly Ala Val Trp Leu Thr Val Met Ser Asn
            435                 440                 445

Thr Leu Leu Ser Ala Trp Ile Leu Thr Ala Gly Phe Leu Ile Phe Leu
        450                 455                 460

Ile Gly Phe Ala Leu Phe Gly Val Ile Arg Cys Cys Arg Tyr Cys Cys
465                 470                 475                 480

Tyr Tyr Cys Leu Thr Leu Glu Ser Glu Arg Pro Thr Pro Tyr
                485                 490                 495

Arg Asn Thr Val
            500

<210> SEQ ID NO 76
<211> LENGTH: 23
<212> TYPE: PRT
<213> ORGANISM: Artificial Sequence
<220> FEATURE:
<223> OTHER INFORMATION: Synthethic

<400> SEQUENCE: 76

Trp Pro Met Pro Trp Leu Thr Asn Thr Thr Glu Ile Phe Phe Pro Leu
1               5                   10                  15

Pro Lys Ile Met Gly Thr Ser
            20

<210> SEQ ID NO 77
<211> LENGTH: 5
<212> TYPE: PRT
<213> ORGANISM: Artificial Sequence
<220> FEATURE:
<223> OTHER INFORMATION: Synthethic

<400> SEQUENCE: 77

Ser Pro Leu Ser Ile
1               5

<210> SEQ ID NO 78
<211> LENGTH: 12
<212> TYPE: PRT
<213> ORGANISM: Artificial Sequence
<220> FEATURE:
<223> OTHER INFORMATION: Synthethic

<400> SEQUENCE: 78
```

```
Leu Leu Ala Asn Lys Gly Asn Leu Phe Ser Leu Gln
1               5                   10
```

<210> SEQ ID NO 79
<211> LENGTH: 19
<212> TYPE: PRT
<213> ORGANISM: Artificial Sequence
<220> FEATURE:
<223> OTHER INFORMATION: Synthethic

<400> SEQUENCE: 79

```
Cys Val Gly Ile Phe Cys Val Ser His Ser Glu Gly His Met Gly Gly
1               5                   10                  15

Gln Ile Ile
```

<210> SEQ ID NO 80
<211> LENGTH: 20
<212> TYPE: PRT
<213> ORGANISM: Artificial Sequence
<220> FEATURE:
<223> OTHER INFORMATION: Synthethic

<400> SEQUENCE: 80

```
Asn Ile Arg Met Ser Ile Trp Phe Arg Val Trp Gln His Met Pro Ile
1               5                   10                  15

Cys Trp Leu Pro
            20
```

<210> SEQ ID NO 81
<211> LENGTH: 11
<212> TYPE: PRT
<213> ORGANISM: Artificial Sequence
<220> FEATURE:
<223> OTHER INFORMATION: Synthethic

<400> SEQUENCE: 81

```
Thr Lys Val Gly Tyr Lys Glu Val Ile Ser Ile
1               5                   10
```

<210> SEQ ID NO 82
<211> LENGTH: 14
<212> TYPE: PRT
<213> ORGANISM: Artificial Sequence
<220> FEATURE:
<223> OTHER INFORMATION: Synthethic

<400> SEQUENCE: 82

```
Asn Ser Pro Leu Leu Ser Ile Pro Tyr Ser Ile Glu Lys Pro
1               5                   10
```

<210> SEQ ID NO 83
<211> LENGTH: 16
<212> TYPE: PRT
<213> ORGANISM: Artificial Sequence
<220> FEATURE:
<223> OTHER INFORMATION: Synthethic

<400> SEQUENCE: 83

```
Leu Glu Val Arg Phe Phe Leu Tyr Phe Val Leu Cys Tyr Phe Phe Leu
1               5                   10                  15
```

<210> SEQ ID NO 84
<211> LENGTH: 2
<212> TYPE: PRT
<213> ORGANISM: Artificial Sequence

```
<220> FEATURE:
<223> OTHER INFORMATION: Synthethic

<400> SEQUENCE: 84

His Pro
1

<210> SEQ ID NO 85
<211> LENGTH: 7
<212> TYPE: PRT
<213> ORGANISM: Artificial Sequence
<220> FEATURE:
<223> OTHER INFORMATION: Synthethic

<400> SEQUENCE: 85

Asn Phe Pro Tyr Met Phe Tyr
1               5

<210> SEQ ID NO 86
<211> LENGTH: 12
<212> TYPE: PRT
<213> ORGANISM: Artificial Sequence
<220> FEATURE:
<223> OTHER INFORMATION: Synthethic

<400> SEQUENCE: 86

Pro Asp Phe Ser Ser Ser Pro Asp Tyr Ser Gln Ser
1               5                   10

<210> SEQ ID NO 87
<211> LENGTH: 17
<212> TYPE: PRT
<213> ORGANISM: Artificial Sequence
<220> FEATURE:
<223> OTHER INFORMATION: Synthethic

<400> SEQUENCE: 87

Leu Ser Leu Phe Ser Tyr Gly Asp Pro Ser Thr Cys Ser Pro Ser Leu
1               5                   10                  15

Ala

<210> SEQ ID NO 88
<211> LENGTH: 3
<212> TYPE: PRT
<213> ORGANISM: Artificial Sequence
<220> FEATURE:
<223> OTHER INFORMATION: Synthethic

<400> SEQUENCE: 88

Ser Trp Ser
1

<210> SEQ ID NO 89
<211> LENGTH: 4
<212> TYPE: PRT
<213> ORGANISM: Artificial Sequence
<220> FEATURE:
<223> OTHER INFORMATION: Synthethic

<400> SEQUENCE: 89

Leu Phe Pro Val
1

<210> SEQ ID NO 90
<211> LENGTH: 25
<212> TYPE: PRT
```

<213> ORGANISM: Artificial Sequence
<220> FEATURE:
<223> OTHER INFORMATION: Synthethic

<400> SEQUENCE: 90

Asn Cys Tyr Pro Leu Thr Ile Pro His Asn Ile Arg Ala Gly Ser Ile
1 5 10 15

Lys Cys Lys Ala Trp Val Pro Asn Glu
20 25

<210> SEQ ID NO 91
<211> LENGTH: 4
<212> TYPE: PRT
<213> ORGANISM: Artificial Sequence
<220> FEATURE:
<223> OTHER INFORMATION: Synthethic

<400> SEQUENCE: 91

Ala Asn Ser His
1

<210> SEQ ID NO 92
<211> LENGTH: 66
<212> TYPE: PRT
<213> ORGANISM: Artificial Sequence
<220> FEATURE:
<223> OTHER INFORMATION: Synthethic

<400> SEQUENCE: 92

Leu Arg Cys Ala His Cys Pro Leu Ser Ser Arg Glu Thr Cys Arg Ala
1 5 10 15

Ser Gly Ser Ala Ser Gln Leu Val Ser Asn His Ser Pro Ala Pro Asn
20 25 30

Ser Ala His Pro Ala Pro Asn Ser Ala Gln Phe Arg Pro Phe Ser Ala
35 40 45

Pro Trp Leu Thr Asn Phe Phe Tyr Leu Cys Arg Gly Arg Gly Arg Leu
50 55 60

Gly Leu
65

<210> SEQ ID NO 93
<211> LENGTH: 30
<212> TYPE: PRT
<213> ORGANISM: Artificial Sequence
<220> FEATURE:
<223> OTHER INFORMATION: Synthethic

<400> SEQUENCE: 93

Ala Ile Pro Glu Val Val Arg Arg Leu Phe Trp Arg Pro Arg Leu Leu
1 5 10 15

Gln Lys Ala Asn Leu Phe Ile Ala Ala Tyr Asn Gly Tyr Lys
20 25 30

<210> SEQ ID NO 94
<211> LENGTH: 78
<212> TYPE: PRT
<213> ORGANISM: Artificial Sequence
<220> FEATURE:
<223> OTHER INFORMATION: Synthethic

<400> SEQUENCE: 94

Ser Asn Ser Ile Thr Asn Phe Thr Asn Lys Ala Phe Phe Ser Leu His
1 5 10 15

```
Ser Ser Cys Gly Leu Ser Lys Leu Ile Asn Val Ser Tyr His Val Trp
            20                  25                  30

Ile Arg Cys Ile Asn Glu Ser Ala Asn Ala Arg Gly Glu Ala Val Cys
        35                  40                  45

Val Leu Gly Ala Leu Pro Leu Pro Arg Ser Leu Thr Arg Cys Ala Arg
    50                  55                  60

Ser Phe Gly Cys Gly Glu Arg Tyr Gln Leu Thr Gln Arg Arg
65                  70                  75
```

<210> SEQ ID NO 95
<211> LENGTH: 8
<212> TYPE: PRT
<213> ORGANISM: Artificial Sequence
<220> FEATURE:
<223> OTHER INFORMATION: Synthethic

<400> SEQUENCE: 95

```
Tyr Gly Tyr Pro Gln Asn Gln Gly
1               5
```

<210> SEQ ID NO 96
<211> LENGTH: 16
<212> TYPE: PRT
<213> ORGANISM: Artificial Sequence
<220> FEATURE:
<223> OTHER INFORMATION: Synthethic

<400> SEQUENCE: 96

```
Arg Arg Lys Glu His Val Ser Lys Arg Pro Ala Lys Gly Gln Glu Pro
1               5                   10                  15
```

<210> SEQ ID NO 97
<211> LENGTH: 9
<212> TYPE: PRT
<213> ORGANISM: Artificial Sequence
<220> FEATURE:
<223> OTHER INFORMATION: Synthethic

<400> SEQUENCE: 97

```
Lys Gly Arg Val Ala Gly Val Phe Pro
1               5
```

<210> SEQ ID NO 98
<211> LENGTH: 4
<212> TYPE: PRT
<213> ORGANISM: Artificial Sequence
<220> FEATURE:
<223> OTHER INFORMATION: Synthethic

<400> SEQUENCE: 98

```
Ala Pro Pro Pro
1
```

<210> SEQ ID NO 99
<211> LENGTH: 57
<212> TYPE: PRT
<213> ORGANISM: Artificial Sequence
<220> FEATURE:
<223> OTHER INFORMATION: Synthethic

<400> SEQUENCE: 99

```
Arg Ala Ser Gln Lys Ser Thr Leu Lys Ser Glu Val Ala Lys Pro Asp
1               5                   10                  15

Arg Thr Ile Lys Ile Pro Gly Val Ser Pro Trp Lys Leu Pro Arg Ala
            20                  25                  30
```

```
Leu Ser Cys Ser Asp Pro Ala Ala Tyr Arg Ile Pro Val Arg Leu Ser
        35                  40                  45

Pro Phe Gly Lys Arg Gly Ala Phe Ser
    50                  55

<210> SEQ ID NO 100
<211> LENGTH: 3
<212> TYPE: PRT
<213> ORGANISM: Artificial Sequence
<220> FEATURE:
<223> OTHER INFORMATION: Synthethic

<400> SEQUENCE: 100

Leu Thr Leu
1

<210> SEQ ID NO 101
<211> LENGTH: 29
<212> TYPE: PRT
<213> ORGANISM: Artificial Sequence
<220> FEATURE:
<223> OTHER INFORMATION: Synthethic

<400> SEQUENCE: 101

Val Ser Gln Phe Gly Val Gly Arg Ser Leu Gln Ala Gly Leu Cys Ala
1               5                   10                  15

Arg Thr Pro Arg Ser Ala Arg Pro Leu Arg Leu Ile Arg
            20                  25

<210> SEQ ID NO 102
<211> LENGTH: 3
<212> TYPE: PRT
<213> ORGANISM: Artificial Sequence
<220> FEATURE:
<223> OTHER INFORMATION: Synthethic

<400> SEQUENCE: 102

Leu Ser Ser
1

<210> SEQ ID NO 103
<211> LENGTH: 16
<212> TYPE: PRT
<213> ORGANISM: Artificial Sequence
<220> FEATURE:
<223> OTHER INFORMATION: Synthethic

<400> SEQUENCE: 103

Val Gln Pro Gly Lys Thr Arg Leu Ile Ala Thr Gly Ser Ser His Trp
1               5                   10                  15

<210> SEQ ID NO 104
<211> LENGTH: 2
<212> TYPE: PRT
<213> ORGANISM: Artificial Sequence
<220> FEATURE:
<223> OTHER INFORMATION: Synthethic

<400> SEQUENCE: 104

Gln Asp
1

<210> SEQ ID NO 105
<211> LENGTH: 16
<212> TYPE: PRT
```

```
<213> ORGANISM: Artificial Sequence
<220> FEATURE:
<223> OTHER INFORMATION: Synthethic

<400> SEQUENCE: 105

Gln Ser Glu Val Cys Arg Arg Cys Tyr Arg Val Leu Glu Val Val Ala
1               5                   10                  15

<210> SEQ ID NO 106
<211> LENGTH: 4
<212> TYPE: PRT
<213> ORGANISM: Artificial Sequence
<220> FEATURE:
<223> OTHER INFORMATION: Synthethic

<400> SEQUENCE: 106

Leu Arg Leu His
1

<210> SEQ ID NO 107
<211> LENGTH: 20
<212> TYPE: PRT
<213> ORGANISM: Artificial Sequence
<220> FEATURE:
<223> OTHER INFORMATION: Synthethic

<400> SEQUENCE: 107

Lys Asn Ser Ile Trp Tyr Leu Arg Ser Ala Glu Ala Ser Tyr Leu Arg
1               5                   10                  15

Lys Lys Ser Trp
            20

<210> SEQ ID NO 108
<211> LENGTH: 10
<212> TYPE: PRT
<213> ORGANISM: Artificial Sequence
<220> FEATURE:
<223> OTHER INFORMATION: Synthethic

<400> SEQUENCE: 108

Leu Leu Ile Arg Gln Thr Asn His Arg Trp
1               5                   10

<210> SEQ ID NO 109
<211> LENGTH: 28
<212> TYPE: PRT
<213> ORGANISM: Artificial Sequence
<220> FEATURE:
<223> OTHER INFORMATION: Synthethic

<400> SEQUENCE: 109

Arg Trp Phe Phe Cys Leu Gln Ala Ala Asp Tyr Ala Gln Lys Lys Arg
1               5                   10                  15

Ile Ser Arg Arg Ser Phe Asp Leu Phe Tyr Gly Val
            20                  25

<210> SEQ ID NO 110
<211> LENGTH: 32
<212> TYPE: PRT
<213> ORGANISM: Artificial Sequence
<220> FEATURE:
<223> OTHER INFORMATION: Synthethic

<400> SEQUENCE: 110

Arg Ser Val Glu Arg Lys Leu Thr Leu Arg Asp Phe Gly His Glu Ile
1               5                   10                  15
```

Ile Lys Lys Asp Leu His Leu Asp Pro Phe Lys Leu Lys Met Lys Phe
            20                  25                  30

<210> SEQ ID NO 111
<211> LENGTH: 6
<212> TYPE: PRT
<213> ORGANISM: Artificial Sequence
<220> FEATURE:
<223> OTHER INFORMATION: Synthethic

<400> SEQUENCE: 111

Ile Asn Leu Lys Tyr Ile
1               5

<210> SEQ ID NO 112
<211> LENGTH: 4
<212> TYPE: PRT
<213> ORGANISM: Artificial Sequence
<220> FEATURE:
<223> OTHER INFORMATION: Synthethic

<400> SEQUENCE: 112

Val Asn Leu Val
1

<210> SEQ ID NO 113
<211> LENGTH: 7
<212> TYPE: PRT
<213> ORGANISM: Artificial Sequence
<220> FEATURE:
<223> OTHER INFORMATION: Synthethic

<400> SEQUENCE: 113

Gln Leu Pro Met Leu Asn Gln
1               5

<210> SEQ ID NO 114
<211> LENGTH: 75
<212> TYPE: PRT
<213> ORGANISM: Artificial Sequence
<220> FEATURE:
<223> OTHER INFORMATION: Synthethic

<400> SEQUENCE: 114

Gly Thr Tyr Leu Ser Asp Leu Ser Ile Ser Phe Ile His Ser Cys Leu
1               5                   10                  15

Thr Pro Arg Arg Val Asp Asn Tyr Asp Thr Gly Gly Leu Thr Ile Trp
            20                  25                  30

Pro Gln Cys Cys Asn Asp Thr Ala Arg Pro Thr Leu Thr Gly Ser Arg
        35                  40                  45

Phe Ile Ser Asn Lys Pro Ala Ser Arg Lys Gly Arg Ala Gln Lys Trp
    50                  55                  60

Ser Cys Asn Phe Ile Arg Leu His Pro Val Tyr
65                  70                  75

<210> SEQ ID NO 115
<211> LENGTH: 5
<212> TYPE: PRT
<213> ORGANISM: Artificial Sequence
<220> FEATURE:
<223> OTHER INFORMATION: Synthethic

<400> SEQUENCE: 115

Leu Leu Pro Gly Ser

```
1               5

<210> SEQ ID NO 116
<211> LENGTH: 2
<212> TYPE: PRT
<213> ORGANISM: Artificial Sequence
<220> FEATURE:
<223> OTHER INFORMATION: Synthethic

<400> SEQUENCE: 116

Ser Lys
1

<210> SEQ ID NO 117
<211> LENGTH: 3
<212> TYPE: PRT
<213> ORGANISM: Artificial Sequence
<220> FEATURE:
<223> OTHER INFORMATION: Synthethic

<400> SEQUENCE: 117

Phe Ala Ser
1

<210> SEQ ID NO 118
<211> LENGTH: 44
<212> TYPE: PRT
<213> ORGANISM: Artificial Sequence
<220> FEATURE:
<223> OTHER INFORMATION: Synthethic

<400> SEQUENCE: 118

Phe Ala Gln Arg Cys Cys His Cys Tyr Arg His Arg Gly Val Thr Leu
1               5                   10                  15

Val Val Trp Tyr Gly Phe Ile Gln Leu Arg Phe Pro Thr Ile Lys Ala
            20                  25                  30

Ser Tyr Met Ile Pro His Val Val Gln Lys Ser Gly
        35                  40

<210> SEQ ID NO 119
<211> LENGTH: 10
<212> TYPE: PRT
<213> ORGANISM: Artificial Sequence
<220> FEATURE:
<223> OTHER INFORMATION: Synthethic

<400> SEQUENCE: 119

Leu Leu Arg Ser Ser Asp Arg Cys Gln Lys
1               5                   10

<210> SEQ ID NO 120
<211> LENGTH: 14
<212> TYPE: PRT
<213> ORGANISM: Artificial Sequence
<220> FEATURE:
<223> OTHER INFORMATION: Synthethic

<400> SEQUENCE: 120

Val Gly Arg Ser Val Ile Thr His Gly Tyr Gly Ser Thr Ala
1               5                   10

<210> SEQ ID NO 121
<211> LENGTH: 15
<212> TYPE: PRT
<213> ORGANISM: Artificial Sequence
<220> FEATURE:
```

<223> OTHER INFORMATION: Synthethic

<400> SEQUENCE: 121

Phe Ser Tyr Cys His Ala Ile Arg Lys Met Leu Phe Cys Asp Trp
1               5                   10                  15

<210> SEQ ID NO 122
<211> LENGTH: 24
<212> TYPE: PRT
<213> ORGANISM: Artificial Sequence
<220> FEATURE:
<223> OTHER INFORMATION: Synthethic

<400> SEQUENCE: 122

Val Leu Asn Gln Val Ile Leu Arg Ile Val Tyr Ala Ala Thr Glu Leu
1               5                   10                  15

Leu Leu Pro Gly Val Asn Thr Gly
            20

<210> SEQ ID NO 123
<211> LENGTH: 4
<212> TYPE: PRT
<213> ORGANISM: Artificial Sequence
<220> FEATURE:
<223> OTHER INFORMATION: Synthethic

<400> SEQUENCE: 123

Tyr Arg Ala Thr
1

<210> SEQ ID NO 124
<211> LENGTH: 95
<212> TYPE: PRT
<213> ORGANISM: Artificial Sequence
<220> FEATURE:
<223> OTHER INFORMATION: Synthethic

<400> SEQUENCE: 124

Gln Asn Phe Lys Ser Ala His His Trp Lys Thr Phe Phe Gly Ala Lys
1               5                   10                  15

Thr Leu Lys Asp Leu Thr Ala Val Glu Ile Gln Phe Asp Val Thr His
            20                  25                  30

Ser Cys Thr Gln Leu Ile Phe Ser Ile Phe Tyr Phe His Gln Arg Phe
        35                  40                  45

Trp Val Ser Lys Asn Arg Lys Ala Lys Cys Arg Lys Lys Gly Asn Lys
    50                  55                  60

Gly Asp Thr Glu Met Leu Asn Thr His Thr Leu Pro Phe Ser Ile Leu
65                  70                  75                  80

Leu Lys His Leu Ser Gly Leu Leu Ser His Glu Arg Ile His Ile
                85                  90                  95

<210> SEQ ID NO 125
<211> LENGTH: 5
<212> TYPE: PRT
<213> ORGANISM: Artificial Sequence
<220> FEATURE:
<223> OTHER INFORMATION: Synthethic

<400> SEQUENCE: 125

Met Tyr Leu Glu Lys
1               5

<210> SEQ ID NO 126

```
<211> LENGTH: 20
<212> TYPE: PRT
<213> ORGANISM: Artificial Sequence
<220> FEATURE:
<223> OTHER INFORMATION: Synthethic

<400> SEQUENCE: 126

Thr Asn Arg Gly Ser Ala His Ile Ser Pro Lys Ser Ala Thr Trp Val
1               5                   10                  15
Asp Ile Asp Tyr
            20

<210> SEQ ID NO 127
<211> LENGTH: 11
<212> TYPE: PRT
<213> ORGANISM: Artificial Sequence
<220> FEATURE:
<223> OTHER INFORMATION: Synthethic

<400> SEQUENCE: 127

Leu Val Ile Asn Ser Asn Gln Leu Arg Gly His
1               5                   10

<210> SEQ ID NO 128
<211> LENGTH: 14
<212> TYPE: PRT
<213> ORGANISM: Artificial Sequence
<220> FEATURE:
<223> OTHER INFORMATION: Synthethic

<400> SEQUENCE: 128

Phe Ile Ala His Ile Trp Ser Ser Ala Leu His Asn Leu Arg
1               5                   10

<210> SEQ ID NO 129
<211> LENGTH: 13
<212> TYPE: PRT
<213> ORGANISM: Artificial Sequence
<220> FEATURE:
<223> OTHER INFORMATION: Synthethic

<400> SEQUENCE: 129

Met Ala Arg Leu Ala Asp Arg Pro Thr Thr Pro Ala His
1               5                   10

<210> SEQ ID NO 130
<211> LENGTH: 2
<212> TYPE: PRT
<213> ORGANISM: Artificial Sequence
<220> FEATURE:
<223> OTHER INFORMATION: Synthethic

<400> SEQUENCE: 130

Arg Gln
1

<210> SEQ ID NO 131
<211> LENGTH: 4
<212> TYPE: PRT
<213> ORGANISM: Artificial Sequence
<220> FEATURE:
<223> OTHER INFORMATION: Synthethic

<400> SEQUENCE: 131

Arg Met Phe Pro
1
```

```
<210> SEQ ID NO 132
<211> LENGTH: 2
<212> TYPE: PRT
<213> ORGANISM: Artificial Sequence
<220> FEATURE:
<223> OTHER INFORMATION: Synthethic

<400> SEQUENCE: 132

Arg Gln
1

<210> SEQ ID NO 133
<211> LENGTH: 47
<212> TYPE: PRT
<213> ORGANISM: Artificial Sequence
<220> FEATURE:
<223> OTHER INFORMATION: Synthethic

<400> SEQUENCE: 133

Gly Leu Ser Ile Asp Val Asn Gly Trp Ser Ile Tyr Gly Lys Leu Pro
1               5                   10                  15

Thr Trp Gln Tyr Ile Lys Cys Ile Ile Cys Gln Val Arg Pro Leu Leu
            20                  25                  30

Thr Ser Met Thr Val Asn Gly Pro Pro Gly Ile Met Pro Ser Thr
        35                  40                  45

<210> SEQ ID NO 134
<211> LENGTH: 13
<212> TYPE: PRT
<213> ORGANISM: Artificial Sequence
<220> FEATURE:
<223> OTHER INFORMATION: Synthethic

<400> SEQUENCE: 134

Pro Tyr Gly Thr Phe Leu Leu Gly Ser Thr Ser Thr Tyr
1               5                   10

<210> SEQ ID NO 135
<211> LENGTH: 8
<212> TYPE: PRT
<213> ORGANISM: Artificial Sequence
<220> FEATURE:
<223> OTHER INFORMATION: Synthethic

<400> SEQUENCE: 135

Ser Ser Leu Leu Pro Trp Ser Arg
1               5

<210> SEQ ID NO 136
<211> LENGTH: 114
<212> TYPE: PRT
<213> ORGANISM: Artificial Sequence
<220> FEATURE:
<223> OTHER INFORMATION: Synthethic

<400> SEQUENCE: 136

Ala Pro Arg Ser Ala Ser Leu Ser Pro Ser Pro Pro Pro His Pro
1               5                   10                  15

Gln Phe Cys Ile Tyr Leu Phe Phe Asn Tyr Phe Val Gln Arg Trp Gly
            20                  25                  30

Arg Gly Gly Gly Gly Pro Pro Gln Ala Gly Arg Gly Gly Ala Arg
        35                  40                  45

Gly Gly Ala Gly Arg Gly Gly Lys Val Arg Arg Gln Pro Ile Arg Ala
    50                  55                  60
```

Ala Arg Ser Glu Ser Phe Leu Leu Trp Arg Gly Gly Gly Gly
65                  70                  75                  80

Pro Ile Lys Ser Glu Ala Arg Gly Gly Arg Glu Ser Leu Arg Ala Ala
                85                  90                  95

Phe Pro Pro Cys Pro Ala Pro Pro Pro Arg Ala Ala Arg Pro Gly
                100                 105                 110

Ser Asp

<210> SEQ ID NO 137
<211> LENGTH: 6
<212> TYPE: PRT
<213> ORGANISM: Artificial Sequence
<220> FEATURE:
<223> OTHER INFORMATION: Synthethic

<400> SEQUENCE: 137

Pro Arg Tyr Ser His Arg
1               5

<210> SEQ ID NO 138
<211> LENGTH: 202
<212> TYPE: PRT
<213> ORGANISM: Artificial Sequence
<220> FEATURE:
<223> OTHER INFORMATION: Synthethic

<400> SEQUENCE: 138

Ala Gly Gly Thr Ala Leu Leu Leu Arg Ala Val Ile Ser Ala Trp Phe
1               5                   10                  15

Asn Asp Gly Leu Phe Leu Phe Cys Gly Cys Val Lys Ala Leu Arg Gly
                20                  25                  30

Ser Gly Arg Ala Leu Cys Ala Gly Gly Ala Ala Arg Gly Val Arg Ala
                35                  40                  45

Cys Val Cys Ala Trp Gly Ala Pro Arg Ala Ala Pro Arg Cys Pro Ala
            50                  55                  60

Ala Val Ser Ala Ala Gly Ala Ala Arg Gly Phe Val Arg Ser Ala Val
65                  70                  75                  80

Cys Ala Arg Gly Ala Arg Pro Gly Ala Val Pro Arg Gly Ala Gly Gly
                85                  90                  95

Ala Ala Arg Gly Thr Lys Ala Ala Cys Gly Val Cys Ala Trp Gly Gly
                100                 105                 110

Glu Gln Gly Val Trp Ala Arg Arg Ser Gly Cys Asn Pro Pro Cys Thr
            115                 120                 125

Pro Leu Pro Glu Leu Leu Ser Thr Ala Arg Leu Arg Val Arg Gly Ser
130                 135                 140

Val Arg Gly Val Ala Arg Gly Ser Pro Cys Arg Ala Gly Gly Gly
145                 150                 155                 160

Arg Trp Gly Cys Arg Ala Gly Arg Gly Arg Leu Gly Pro Gly Arg Ala
                165                 170                 175

Arg Gly Lys Gly Arg Gly Gly Pro Arg Ser Ala Gly Gly Cys Arg Gly
                180                 185                 190

Ala Ala Ser Arg Ser His Cys Leu Leu Trp
                195                 200

<210> SEQ ID NO 139
<211> LENGTH: 121
<212> TYPE: PRT
<213> ORGANISM: Artificial Sequence
<220> FEATURE:
<223> OTHER INFORMATION: Synthethic

<400> SEQUENCE: 139

Ser Cys Glu Arg Ala Gln Gly Leu Pro Leu Ser Gln Ile Cys Ala Glu
1               5                   10                  15

Pro Lys Ser Gly Arg Arg Arg Thr Pro Ser Ser Gly Arg Gly Ala
            20                  25                  30

Lys Arg Cys Gly Ala Gly Arg Lys Glu Met Gly Gly Glu Gly Leu Arg
            35                  40                  45

Ala Ser Pro Arg Arg Pro Leu Leu Pro Leu Gln Pro Arg Gly Cys
        50                  55                  60

Pro Arg Gly Asp Gly Cys Leu Arg Gly Arg Gly Arg Ala Gly Phe
65                  70                  75                  80

Gly Phe Trp Arg Val Thr Gly Gly Ser Arg Ala Ser Ala Asn His Val
                85                  90                  95

His Ala Phe Phe Phe Phe Leu Gln Leu Leu Gly Asn Val Leu Val Ile
                100                 105                 110

Val Leu Ser His His Phe Gly Lys Glu
        115                 120

<210> SEQ ID NO 140
<211> LENGTH: 6249
<212> TYPE: DNA
<213> ORGANISM: Artificial Sequence
<220> FEATURE:
<223> OTHER INFORMATION: Synthethic

<400> SEQUENCE: 140
ttcctcgaga tgggcagcct ggaaatggtc cccatgggcg ccggccctcc cagccctgga      60
ggcgaccctg acggctatga cggcggcaac aacagccagt accccagcgc cagcggatcc     120
agcggaaaca cccctacacc ccccaacgac gaggagaggg agagcaatga ggaaccccct     180
cccccttacg aggaccccta ctgggcaat ggcgacaggc acagcgacta ccagcccctc     240
ggcacccagg atcagtccct ctacctcggc ctgcagcacg acggcaatga tggcctgccc     300
cctcctccct atagccctag ggatgacagc tcccagcaca tttacgagga ggccggcagg     360
ggctccatga atcccgtgtg cctgcccgtg atcgtcgccc cttacctgtt ctggctggcc     420
gccattgccg cctcctgctt cacagcctcc gtgtccaccg tggtgaccgc cacaggactg     480
gctctctccc tgctcctgct ggctgccgtg ctagctcct acgctgccgc ccaaagaaag     540
ctgctgaccc ccgtgaccgt gctgaccgct gtggtgacct tctttgctat ttgcctgacc     600
tggagaatcg aggaccctcc tttcaacagc ctgctgttcg ctctgctggc tgctgctggc     660
ggcctccaag gaatctacgt gctggtgatg ctggtgctgc tgattctcgc ctatagaagg     720
aggtggagga gactgaccgt gtgtggaggc atcatgttcc tggcttgtgt gctggtgctg     780
atcgtcgatg ctgtgctgca actgtcccct ctgctgggag ccgtgaccgt ggtctccatg     840
accctgctgc tgctcgccct cgtgctgtgg ctcagctccc ctggaggact gggaaccctg     900
ggagctgctc tcctgacact cgccgccgcc ctggccctgc tggcttccct gattctggga     960
accctgaacc tgaccaccat gttcctgctg atgctgctgt ggaccctggt ggtgctgctg    1020
atctgctcca gctgttccag ctgccccctc agcaagatcc tgctagcgag gctgttcctg    1080
tacgccctgg ccctgctgct cctggcttcc gccctgattg ctggcggaag catcctgcaa    1140
accaacttca gagcctgag cagcaccgag ttcatcccca atctgttctg catgctcctc    1200

```
ctgatcgtgg ccggaatcct gttcattctg gctatcctga ccgagtgggg ctccggcaac    1260
agaacctacg gccctgtgtt catgtgtctg ggcggactgc tgaccatggt ggccggagct    1320
gtgtggctga ccgtgatgtc caacaccctg ctcagcgcct ggattctgac cgccggattc    1380
ctgatcttcc tgattggctt cgccctgttc ggcgtgatta ggtgctgcag gtactgctgc    1440
tactactgcc tcaccctgga gagcgaggaa aggcctccca caccctacag aaataccgtg    1500
tgatgatggc caatgccctg ctcacaaat accactgaga tcttttttccc tctgccaaaa    1560
attatgggga catcatgaag ccccttgagc atctgacttc tggctaataa aggaaattta    1620
ttttcattgc aatagtgtgt tggaattttt tgtgtctctc actcggaagg acatatggga    1680
gggcaaatca tttaaaacat cagaatgagt atttggttta gagtttggca acatatgccc    1740
atatgctggc tgccatgaac aaaggttggc tataaagagg tcatcagtat atgaaacagc    1800
cccctgctgt ccattcctta ttccatagaa aagccttgac ttgaggttag atttttttta    1860
tattttgttt tgtgttattt ttttctttaa catccctaaa attttcctta catgttttac    1920
tagccagatt tttcctcctc tcctgactac tcccagtcat agctgtccct cttctcttat    1980
ggagatccct cgacctgcag cccaagcttg gcgtaatcat ggtcatagct gtttcctgtg    2040
tgaaattgtt atccgctcac aattccacac aacatacgag ccggaagcat aaagtgtaaa    2100
gcctgggtgc ctaatgagtg agctaactca cattaattgc gttgcgctca ctgcccgctt    2160
tccagtcggg aaacctgtcg tgccagcgga tccgcatctc aattagtcag caaccatagt    2220
cccgccccta actccgccca tcccgcccct aactccgccc agttccgccc attctccgcc    2280
ccatggctga ctaatttttt ttatttatgc agaggccgag gccgcctcgg cctctgagct    2340
attccagaag tagtgaggag gcttttttgg aggcctaggc ttttgcaaaa agctaacttg    2400
tttattgcag cttataatgg ttacaaataa agcaatagca tcacaaattt cacaaataaa    2460
gcatttttt cactgcattc tagttgtggt ttgtccaaac tcatcaatgt atcttatcat    2520
gtctggatcc gctgcattaa tgaatcggcc aacgcgcggg gagaggcggt ttgcgtattg    2580
ggcgctcttc cgcttcctcg ctcactgact cgctgcgctc ggtcgttcgg ctgcggcgag    2640
cggtatcagc tcactcaaag gcggtaatac ggttatccac agaatcaggg ataacgcagg    2700
aaagaacatg tgagcaaaag gccagcaaaa ggccaggaac cgtaaaaagg ccgcgttgct    2760
ggcgtttttc cataggctcc gcccccctga cgagcatcac aaaaatcgac gctcaagtca    2820
gaggtggcga aacccgacag gactataaag ataccaggcg tttccccctg gaagctccct    2880
cgtgcgctct cctgttccga ccctgccgct taccggatac ctgtccgcct ttctcccttc    2940
gggaagcgtg gcgctttctc atagctcacg ctgtaggtat ctcagttcgg tgtaggtcgt    3000
tcgctccaag ctgggctgtg tgcacgaacc ccccgttcag cccgaccgct gcgccttatc    3060
cggtaactat cgtcttgagt ccaacccggt aagacacgac ttatcgccac tggcagcagc    3120
cactggtaac aggattagca gagcgaggta tgtaggcggt gctacagagt tcttgaagtg    3180
gtggcctaac tacggctaca ctagaagaac agtatttggt atctgcgctc tgctgaagcc    3240
agttaccttc ggaaaaagag ttggtagctc ttgatccggc aaacaaacca ccgctggtag    3300
cggtggtttt tttgtttgca agcagcagat tacgcgcaga aaaaaaggat ctcaagaaga    3360
tcctttgatc ttttctacgg ggtctgacgc tcagtggaac gaaaactcac gttaagggat    3420
tttggtcatg agattatcaa aaaggatctt cacctagatc cttttaaatt aaaaatgaag    3480
ttttaaatca atctaaagta tatatgagta aacttggtct gacagttacc aatgcttaat    3540
cagtgaggca cctatctcag cgatctgtct atttcgttca tccatagttg cctgactccc    3600
```

```
cgtcgtgtag ataactacga tacgggaggg cttaccatct ggccccagtg ctgcaatgat   3660
accgcgagac ccacgctcac cggctccaga tttatcagca ataaaccagc cagccggaag   3720
ggccgagcgc agaagtggtc ctgcaacttt atccgcctcc atccagtcta ttaattgttg   3780
ccgggaagct agagtaagta gttcgccagt taatagtttg cgcaacgttg ttgccattgc   3840
tacaggcatc gtggtgtcac gctcgtcgtt tggtatggct tcattcagct ccggttccca   3900
acgatcaagg cgagttacat gatcccccat gttgtgcaaa aaagcggtta gctccttcgg   3960
tcctccgatc gttgtcagaa gtaagttggc cgcagtgtta tcactcatgg ttatggcagc   4020
actgcataat tctcttactg tcatgccatc cgtaagatgc ttttctgtga ctggtgagta   4080
ctcaaccaag tcattctgag aatagtgtat gcggcgaccg agttgctctt gcccggcgtc   4140
aatacgggat aataccgcgc cacatagcag aactttaaaa gtgctcatca ttggaaaacg   4200
ttcttcgggg cgaaaactct caaggatctt accgctgttg agatccagtt cgatgtaacc   4260
cactcgtgca cccaactgat cttcagcatc ttttactttc accagcgttt ctgggtgagc   4320
aaaaacagga aggcaaaatg ccgcaaaaaa gggaataagg gcgacacgga aatgttgaat   4380
actcatactc ttcctttttc aatattattg aagcatttat cagggttatt gtctcatgag   4440
cggatacata tttgaatgta tttagaaaaa taaacaaata ggggttccgc gcacatttcc   4500
ccgaaaagtg ccacctgggt cgacattgat tattgactag ttattaatag taatcaatta   4560
cggggtcatt agttcatagc ccatatatgg agttccgcgt tacataactt acggtaaatg   4620
gcccgcctgg ctgaccgccc aacgaccccc gcccattgac gtcaataatg acgtatgttc   4680
ccatagtaac gccaataggg actttccatt gacgtcaatg ggtggagtat ttacggtaaa   4740
ctgcccactt ggcagtacat caagtgtatc atatgccaag tacgccccct attgacgtca   4800
atgacggtaa atggcccgcc tggcattatg cccagtacat gaccttatgg gactttccta   4860
cttggcagta catctacgta ttagtcatcg ctattaccat ggtcgaggtg agccccacgt   4920
tctgcttcac tctccccatc tcccccccct ccccaccccc aattttgtat ttatttattt   4980
tttaattatt ttgtgcagcg atggggggcgg ggggggggggg gggcccccc ccaggcgggg   5040 cggggcgggg cgaggggcgg ggcggggcga ggcgaaagg tgcggcggca gccaatcaga   5100
gcggcgcgct ccgaaagttt cctttatgg cgaggcggcg gcggcggcgg ccctataaaa   5160
agcgaagcgc gcggcgggcg ggagtcgttg cgcgctgcct tcccccgtg cccgctccg   5220 ccgccgcctc gcgccgcccg ccccggctct gactgaccgc gttactccca caggtgagcg   5280
ggcgggacgg cccttctcct ccgggctgta attagcgctt ggtttaatga cggcttgttt   5340
cttttctgtg gctgcgtgaa agccttgagg ggctccggga gggccctttg tgcgggggga   5400
gcggctcggg gggtgcgtgc gtgtgtgtgt gcgtggggag cgccgcgtgc ggctccgcgc   5460
tgcccggcgg ctgtgagcgc tgcgggcgcg gcgcggggct tgtgcgctc cgcagtgtgc   5520 gcgaggggag cgcggccggg ggcggtgccc cgcggtgcgg ggggggctgc gaggggaaca   5580
aaggctgcgt gcggggtgtg tgcgtggggg ggtgagcagg gggtgtgggc gcgtcggtcg   5640
ggctgcaacc cccctgcac ccccctcccc gagttgctga gcacggcccg gcttcgggtg   5700
cggggctccg tacgggggcgt ggcgcggggc tcgccgtgcc gggcgggggg tggcggcagg   5760 tggggggtgcc gggcggggcg gggccgcctc gggccgggga gggctcgggg gaaggggcgc   5820
ggcggccccc ggagcgccgg cggctgtcga ggcgcggcga ccgcagcca ttgccttta   5880 tggtaatcgt gcgagagggc gcagggactt cctttgtccc aaatctgtgc ggagccgaaa   5940
```

-continued

```
tctgggaggc gccgccgcac ccctctagc gggcgcgggg cgaagcggtg cggcgccggc    6000
aggaaggaaa tgggcgggga gggccttcgt gcgtcgccgc gccgccgtcc ccttctccct    6060
ctccagcctc ggggctgtcc gcgggggggac ggctgccttc gggggggacg gggcagggcg    6120
gggttcggct tctggcgtgt gaccggcggc tctagagcct ctgctaacca tgttcatgcc    6180 ttcttcttt tcctacagct cctgggcaac gtgctggtta ttgtgctgtc tcatcatttt    6240
ggcaaagaa                                                             6249
```

<210> SEQ ID NO 141
<211> LENGTH: 644
<212> TYPE: PRT
<213> ORGANISM: Artificial Sequence
<220> FEATURE:
<223> OTHER INFORMATION: Synthethic

<400> SEQUENCE: 141

```
Phe Leu Glu Met Ser Asp Glu Gly Pro Gly Thr Gly Pro Gly Asn Gly
1               5                   10                  15

Leu Gly Glu Lys Gly Asp Thr Ser Gly Pro Glu Gly Ser Gly Gly Ser
            20                  25                  30

Gly Pro Gln Arg Arg Gly Gly Asp Asn His Gly Arg Gly Arg Gly Arg
        35                  40                  45

Gly Arg Gly Arg Gly Gly Arg Pro Gly Ala Pro Gly Gly Ser Gly
    50                  55                  60

Ser Gly Pro Arg His Arg Asp Gly Val Arg Arg Pro Gln Lys Arg Pro
65                  70                  75                  80

Ser Cys Ile Gly Cys Lys Gly Thr His Gly Gly Thr Gly Ala Gly Ala
                85                  90                  95

Gly Ala Gly Gly Ala Gly Ala Gly Gly Ala Gly Ala Gly Gly Gly Ala
            100                 105                 110

Gly Ala Gly Gly Gly Ala Gly Gly Ala Gly Gly Ala Gly Gly Ala Gly
        115                 120                 125

Ala Gly Gly Gly Ala Gly Ala Gly Gly Gly Ala Gly Gly Ala Gly Gly
    130                 135                 140

Ala Gly Ala Gly Gly Ala Gly Ala Gly Gly Ala Gly Gly Ala Gly Ala
145                 150                 155                 160

Gly Ala Gly Gly Gly Ala Gly Ala Gly Gly Ala Gly Ala Gly Gly Gly
                165                 170                 175

Gly Ala Gly Ala Gly Gly Ala Gly Gly Ala Gly Ala Gly Gly Gly
            180                 185                 190

Ala Gly Gly Ala Gly Ala Gly Ala Gly Gly Gly Ala Gly Ala Gly Gly
        195                 200                 205

Gly Ala Gly Gly Ala Gly Gly Ala Gly Gly Ala Gly Ala Gly
    210                 215                 220

Gly Gly Ala Gly Gly Ala Gly Ala Gly Gly Ala Gly Ala
225                 230                 235                 240

Gly Gly Ala Gly Ala Gly Gly Ala Gly Ala Gly Gly Ala Gly Gly Ala
                245                 250                 255

Gly Ala Gly Gly Ala Gly Gly Ala Gly Ala Gly Gly Ala Gly Gly Ala
            260                 265                 270

Gly Ala Gly Gly Gly Ala Gly Gly Ala Gly Ala Gly Gly Ala Gly
        275                 280                 285

Gly Ala Gly Ala Gly Gly Ala Gly Gly Ala Gly Ala Gly Gly Ala Gly
    290                 295                 300
```

Gly Ala Gly Ala Gly Ala Gly Gly Ala Gly Gly Gly Ala
305                 310                 315                 320

Gly Ala Gly Gly Ala Gly Gly Gly Arg Gly Arg Gly
            325                 330                 335

Ser Gly Gly Arg Gly Arg Gly Ser Gly Arg Gly Arg Gly Gly
            340                 345                 350

Ser Gly Gly Arg Arg Gly Arg Gly Arg Glu Arg Ala Arg Gly Gly Ser
            355                 360                 365

Arg Glu Arg Ala Arg Gly Arg Gly Arg Gly Glu Lys Arg Pro
        370                 375                 380

Arg Ser Pro Ser Ser Gln Ser Ser Ser Gly Ser Pro Pro Arg Arg
385                 390                 395                 400

Pro Pro Pro Gly Arg Arg Pro Phe Phe His Pro Val Gly Glu Ala Asp
                405                 410                 415

Tyr Phe Glu Tyr His Gln Gly Gly Pro Asp Gly Glu Pro Asp Val
                420                 425                 430

Pro Pro Gly Ala Ile Glu Gln Gly Pro Ala Asp Asp Pro Gly Glu Gly
                435                 440                 445

Pro Ser Thr Gly Pro Arg Gly Gln Gly Asp Gly Arg Arg Lys Lys
        450                 455                 460

Gly Gly Trp Phe Gly Lys His Arg Gly Gln Gly Gly Ser Asn Pro Lys
465                 470                 475                 480

Phe Glu Asn Ile Ala Glu Gly Leu Arg Ala Leu Leu Ala Arg Ser His
                485                 490                 495

Val Glu Arg Thr Thr Asp Glu Gly Thr Trp Val Ala Gly Val Phe Val
                500                 505                 510

Tyr Gly Gly Ser Lys Thr Ser Leu Tyr Asn Leu Arg Arg Gly Thr Ala
                515                 520                 525

Leu Ala Ile Pro Gln Cys Arg Leu Thr Pro Leu Ser Arg Leu Pro Phe
                530                 535                 540

Gly Met Ala Pro Gly Pro Gly Pro Gln Pro Gly Pro Leu Arg Glu Ser
545                 550                 555                 560

Ile Val Cys Tyr Phe Met Val Phe Leu Gln Thr His Ile Phe Ala Glu
                565                 570                 575

Val Leu Lys Asp Ala Ile Lys Asp Leu Val Met Thr Lys Pro Ala Pro
                580                 585                 590

Thr Cys Asn Ile Arg Val Thr Val Cys Ser Phe Asp Gly Val Asp
                595                 600                 605

Leu Pro Pro Trp Phe Pro Met Val Glu Gly Ala Ala Glu Gly
        610                 615                 620

Asp Asp Gly Asp Asp Gly Asp Glu Gly Gly Asp Gly Asp Glu Gly Glu
625                 630                 635                 640

Glu Gly Gln Glu

<210> SEQ ID NO 142
<211> LENGTH: 23
<212> TYPE: PRT
<213> ORGANISM: Artificial Sequence
<220> FEATURE:
<223> OTHER INFORMATION: Synthethic

<400> SEQUENCE: 142

Trp Pro Met Pro Trp Leu Thr Asn Thr Thr Glu Ile Phe Phe Pro Leu
1               5                   10                  15

Pro Lys Ile Met Gly Thr Ser

20

<210> SEQ ID NO 143
<211> LENGTH: 5
<212> TYPE: PRT
<213> ORGANISM: Artificial Sequence
<220> FEATURE:
<223> OTHER INFORMATION: Synthethic

<400> SEQUENCE: 143

Ser Pro Leu Ser Ile
1               5

<210> SEQ ID NO 144
<211> LENGTH: 12
<212> TYPE: PRT
<213> ORGANISM: Artificial Sequence
<220> FEATURE:
<223> OTHER INFORMATION: Synthethic

<400> SEQUENCE: 144

Leu Leu Ala Asn Lys Gly Asn Leu Phe Ser Leu Gln
1               5                   10

<210> SEQ ID NO 145
<211> LENGTH: 19
<212> TYPE: PRT
<213> ORGANISM: Artificial Sequence
<220> FEATURE:
<223> OTHER INFORMATION: Synthethic

<400> SEQUENCE: 145

Cys Val Gly Ile Phe Cys Val Ser His Ser Glu Gly His Met Gly Gly
1               5                   10                  15

Gln Ile Ile

<210> SEQ ID NO 146
<211> LENGTH: 20
<212> TYPE: PRT
<213> ORGANISM: Artificial Sequence
<220> FEATURE:
<223> OTHER INFORMATION: Synthethic

<400> SEQUENCE: 146

Asn Ile Arg Met Ser Ile Trp Phe Arg Val Trp Gln His Met Pro Ile
1               5                   10                  15

Cys Trp Leu Pro
            20

<210> SEQ ID NO 147
<211> LENGTH: 11
<212> TYPE: PRT
<213> ORGANISM: Artificial Sequence
<220> FEATURE:
<223> OTHER INFORMATION: Synthethic

<400> SEQUENCE: 147

Thr Lys Val Gly Tyr Lys Glu Val Ile Ser Ile
1               5                   10

<210> SEQ ID NO 148
<211> LENGTH: 14
<212> TYPE: PRT
<213> ORGANISM: Artificial Sequence
<220> FEATURE:
<223> OTHER INFORMATION: Synthethic

<400> SEQUENCE: 148

Asn Ser Pro Leu Leu Ser Ile Pro Tyr Ser Ile Glu Lys Pro
1               5                   10

<210> SEQ ID NO 149
<211> LENGTH: 16
<212> TYPE: PRT
<213> ORGANISM: Artificial Sequence
<220> FEATURE:
<223> OTHER INFORMATION: Synthethic

<400> SEQUENCE: 149

Leu Glu Val Arg Phe Phe Leu Tyr Phe Val Leu Cys Tyr Phe Phe Leu
1               5                   10                  15

<210> SEQ ID NO 150
<211> LENGTH: 2
<212> TYPE: PRT
<213> ORGANISM: Artificial Sequence
<220> FEATURE:
<223> OTHER INFORMATION: Synthethic

<400> SEQUENCE: 150

His Pro
1

<210> SEQ ID NO 151
<211> LENGTH: 7
<212> TYPE: PRT
<213> ORGANISM: Artificial Sequence
<220> FEATURE:
<223> OTHER INFORMATION: Synthethic

<400> SEQUENCE: 151

Asn Phe Pro Tyr Met Phe Tyr
1               5

<210> SEQ ID NO 152
<211> LENGTH: 12
<212> TYPE: PRT
<213> ORGANISM: Artificial Sequence
<220> FEATURE:
<223> OTHER INFORMATION: Synthethic

<400> SEQUENCE: 152

Pro Asp Phe Ser Ser Ser Pro Asp Tyr Ser Gln Ser
1               5                   10

<210> SEQ ID NO 153
<211> LENGTH: 17
<212> TYPE: PRT
<213> ORGANISM: Artificial Sequence
<220> FEATURE:
<223> OTHER INFORMATION: Synthethic

<400> SEQUENCE: 153

Leu Ser Leu Phe Ser Tyr Gly Asp Pro Ser Thr Cys Ser Pro Ser Leu
1               5                   10                  15
Ala

<210> SEQ ID NO 154
<211> LENGTH: 3
<212> TYPE: PRT
<213> ORGANISM: Artificial Sequence
<220> FEATURE:

```
<223> OTHER INFORMATION: Synthethic

<400> SEQUENCE: 154

Ser Trp Ser
1

<210> SEQ ID NO 155
<211> LENGTH: 4
<212> TYPE: PRT
<213> ORGANISM: Artificial Sequence
<220> FEATURE:
<223> OTHER INFORMATION: Synthethic

<400> SEQUENCE: 155

Leu Phe Pro Val
1

<210> SEQ ID NO 156
<211> LENGTH: 25
<212> TYPE: PRT
<213> ORGANISM: Artificial Sequence
<220> FEATURE:
<223> OTHER INFORMATION: Synthethic

<400> SEQUENCE: 156

Asn Cys Tyr Pro Leu Thr Ile Pro His Asn Ile Arg Ala Gly Ser Ile
1               5                   10                  15

Lys Cys Lys Ala Trp Val Pro Asn Glu
            20                  25

<210> SEQ ID NO 157
<211> LENGTH: 4
<212> TYPE: PRT
<213> ORGANISM: Artificial Sequence
<220> FEATURE:
<223> OTHER INFORMATION: Synthethic

<400> SEQUENCE: 157

Ala Asn Ser His
1

<210> SEQ ID NO 158
<211> LENGTH: 66
<212> TYPE: PRT
<213> ORGANISM: Artificial Sequence
<220> FEATURE:
<223> OTHER INFORMATION: Synthethic

<400> SEQUENCE: 158

Leu Arg Cys Ala His Cys Pro Leu Ser Arg Glu Thr Cys Arg Ala
1               5                   10                  15

Ser Gly Ser Ala Ser Gln Leu Val Ser Asn His Ser Pro Ala Pro Asn
            20                  25                  30

Ser Ala His Pro Ala Pro Asn Ser Ala Gln Phe Arg Pro Phe Ser Ala
                35                  40                  45

Pro Trp Leu Thr Asn Phe Phe Tyr Leu Cys Arg Gly Arg Gly Arg Leu
    50                  55                  60

Gly Leu
65

<210> SEQ ID NO 159
<211> LENGTH: 30
<212> TYPE: PRT
<213> ORGANISM: Artificial Sequence
```

<220> FEATURE:
<223> OTHER INFORMATION: Synthethic

<400> SEQUENCE: 159

Ala Ile Pro Glu Val Val Arg Arg Leu Phe Trp Arg Pro Arg Leu Leu
1               5                   10                  15

Gln Lys Ala Asn Leu Phe Ile Ala Ala Tyr Asn Gly Tyr Lys
            20                  25                  30

<210> SEQ ID NO 160
<211> LENGTH: 78
<212> TYPE: PRT
<213> ORGANISM: Artificial Sequence
<220> FEATURE:
<223> OTHER INFORMATION: Synthethic

<400> SEQUENCE: 160

Ser Asn Ser Ile Thr Asn Phe Thr Asn Lys Ala Phe Phe Ser Leu His
1               5                   10                  15

Ser Ser Cys Gly Leu Ser Lys Leu Ile Asn Val Ser Tyr His Val Trp
            20                  25                  30

Ile Arg Cys Ile Asn Glu Ser Ala Asn Ala Arg Gly Glu Ala Val Cys
        35                  40                  45

Val Leu Gly Ala Leu Pro Leu Pro Arg Ser Leu Thr Arg Cys Ala Arg
    50                  55                  60

Ser Phe Gly Cys Gly Glu Arg Tyr Gln Leu Thr Gln Arg Arg
65                  70                  75

<210> SEQ ID NO 161
<211> LENGTH: 8
<212> TYPE: PRT
<213> ORGANISM: Artificial Sequence
<220> FEATURE:
<223> OTHER INFORMATION: Synthethic

<400> SEQUENCE: 161

Tyr Gly Tyr Pro Gln Asn Gln Gly
1               5

<210> SEQ ID NO 162
<211> LENGTH: 16
<212> TYPE: PRT
<213> ORGANISM: Artificial Sequence
<220> FEATURE:
<223> OTHER INFORMATION: Synthethic

<400> SEQUENCE: 162

Arg Arg Lys Glu His Val Ser Lys Arg Pro Ala Lys Gly Gln Glu Pro
1               5                   10                  15

<210> SEQ ID NO 163
<211> LENGTH: 9
<212> TYPE: PRT
<213> ORGANISM: Artificial Sequence
<220> FEATURE:
<223> OTHER INFORMATION: Synthethic

<400> SEQUENCE: 163

Lys Gly Arg Val Ala Gly Val Phe Pro
1               5

<210> SEQ ID NO 164
<211> LENGTH: 4
<212> TYPE: PRT

```
<213> ORGANISM: Artificial Sequence
<220> FEATURE:
<223> OTHER INFORMATION: Synthethic

<400> SEQUENCE: 164

Ala Pro Pro Pro
1

<210> SEQ ID NO 165
<211> LENGTH: 57
<212> TYPE: PRT
<213> ORGANISM: Artificial Sequence
<220> FEATURE:
<223> OTHER INFORMATION: Synthethic

<400> SEQUENCE: 165

Arg Ala Ser Gln Lys Ser Thr Leu Lys Ser Glu Val Ala Lys Pro Asp
1               5                   10                  15

Arg Thr Ile Lys Ile Pro Gly Val Ser Pro Trp Lys Leu Pro Arg Ala
            20                  25                  30

Leu Ser Cys Ser Asp Pro Ala Ala Tyr Arg Ile Pro Val Arg Leu Ser
        35                  40                  45

Pro Phe Gly Lys Arg Gly Ala Phe Ser
    50                  55

<210> SEQ ID NO 166
<211> LENGTH: 3
<212> TYPE: PRT
<213> ORGANISM: Artificial Sequence
<220> FEATURE:
<223> OTHER INFORMATION: Synthethic

<400> SEQUENCE: 166

Leu Thr Leu
1

<210> SEQ ID NO 167
<211> LENGTH: 29
<212> TYPE: PRT
<213> ORGANISM: Artificial Sequence
<220> FEATURE:
<223> OTHER INFORMATION: Synthethic

<400> SEQUENCE: 167

Val Ser Gln Phe Gly Val Gly Arg Ser Leu Gln Ala Gly Leu Cys Ala
1               5                   10                  15

Arg Thr Pro Arg Ser Ala Arg Pro Leu Arg Leu Ile Arg
            20                  25

<210> SEQ ID NO 168
<211> LENGTH: 3
<212> TYPE: PRT
<213> ORGANISM: Artificial Sequence
<220> FEATURE:
<223> OTHER INFORMATION: Synthethic

<400> SEQUENCE: 168

Leu Ser Ser
1

<210> SEQ ID NO 169
<211> LENGTH: 16
<212> TYPE: PRT
<213> ORGANISM: Artificial Sequence
<220> FEATURE:
```

<223> OTHER INFORMATION: Synthethic

<400> SEQUENCE: 169

Val Gln Pro Gly Lys Thr Arg Leu Ile Ala Thr Gly Ser Ser His Trp
1               5                   10                  15

<210> SEQ ID NO 170
<211> LENGTH: 2
<212> TYPE: PRT
<213> ORGANISM: Artificial Sequence
<220> FEATURE:
<223> OTHER INFORMATION: Synthethic

<400> SEQUENCE: 170

Gln Asp
1

<210> SEQ ID NO 171
<211> LENGTH: 16
<212> TYPE: PRT
<213> ORGANISM: Artificial Sequence
<220> FEATURE:
<223> OTHER INFORMATION: Synthethic

<400> SEQUENCE: 171

Gln Ser Glu Val Cys Arg Arg Cys Tyr Arg Val Leu Glu Val Val Ala
1               5                   10                  15

<210> SEQ ID NO 172
<211> LENGTH: 4
<212> TYPE: PRT
<213> ORGANISM: Artificial Sequence
<220> FEATURE:
<223> OTHER INFORMATION: Synthethic

<400> SEQUENCE: 172

Leu Arg Leu His
1

<210> SEQ ID NO 173
<211> LENGTH: 20
<212> TYPE: PRT
<213> ORGANISM: Artificial Sequence
<220> FEATURE:
<223> OTHER INFORMATION: Synthethic

<400> SEQUENCE: 173

Lys Asn Ser Ile Trp Tyr Leu Arg Ser Ala Glu Ala Ser Tyr Leu Arg
1               5                   10                  15

Lys Lys Ser Trp
            20

<210> SEQ ID NO 174
<211> LENGTH: 10
<212> TYPE: PRT
<213> ORGANISM: Artificial Sequence
<220> FEATURE:
<223> OTHER INFORMATION: Synthethic

<400> SEQUENCE: 174

Leu Leu Ile Arg Gln Thr Asn His Arg Trp
1               5                   10

<210> SEQ ID NO 175
<211> LENGTH: 28
<212> TYPE: PRT

<213> ORGANISM: Artificial Sequence
<220> FEATURE:
<223> OTHER INFORMATION: Synthethic

<400> SEQUENCE: 175

Arg Trp Phe Phe Cys Leu Gln Ala Ala Asp Tyr Ala Gln Lys Lys Arg
1               5                   10                  15

Ile Ser Arg Arg Ser Phe Asp Leu Phe Tyr Gly Val
            20                  25

<210> SEQ ID NO 176
<211> LENGTH: 32
<212> TYPE: PRT
<213> ORGANISM: Artificial Sequence
<220> FEATURE:
<223> OTHER INFORMATION: Synthethic

<400> SEQUENCE: 176

Arg Ser Val Glu Arg Lys Leu Thr Leu Arg Asp Phe Gly His Glu Ile
1               5                   10                  15

Ile Lys Lys Asp Leu His Leu Asp Pro Phe Lys Leu Lys Met Lys Phe
            20                  25                  30

<210> SEQ ID NO 177
<211> LENGTH: 6
<212> TYPE: PRT
<213> ORGANISM: Artificial Sequence
<220> FEATURE:
<223> OTHER INFORMATION: Synthethic

<400> SEQUENCE: 177

Ile Asn Leu Lys Tyr Ile
1               5

<210> SEQ ID NO 178
<211> LENGTH: 4
<212> TYPE: PRT
<213> ORGANISM: Artificial Sequence
<220> FEATURE:
<223> OTHER INFORMATION: Synthethic

<400> SEQUENCE: 178

Val Asn Leu Val
1

<210> SEQ ID NO 179
<211> LENGTH: 7
<212> TYPE: PRT
<213> ORGANISM: Artificial Sequence
<220> FEATURE:
<223> OTHER INFORMATION: Synthethic

<400> SEQUENCE: 179

Gln Leu Pro Met Leu Asn Gln
1               5

<210> SEQ ID NO 180
<211> LENGTH: 75
<212> TYPE: PRT
<213> ORGANISM: Artificial Sequence
<220> FEATURE:
<223> OTHER INFORMATION: Synthethic

<400> SEQUENCE: 180

Gly Thr Tyr Leu Ser Asp Leu Ser Ile Ser Phe Ile His Ser Cys Leu
1               5                   10                  15

```
Thr Pro Arg Arg Val Asp Asn Tyr Asp Thr Gly Gly Leu Thr Ile Trp
            20                  25                  30

Pro Gln Cys Cys Asn Asp Thr Ala Arg Pro Thr Leu Thr Gly Ser Arg
            35                  40                  45

Phe Ile Ser Asn Lys Pro Ala Ser Arg Lys Gly Arg Ala Gln Lys Trp
50                  55                  60

Ser Cys Asn Phe Ile Arg Leu His Pro Val Tyr
65                  70                  75
```

<210> SEQ ID NO 181
<211> LENGTH: 5
<212> TYPE: PRT
<213> ORGANISM: Artificial Sequence
<220> FEATURE:
<223> OTHER INFORMATION: Synthethic

<400> SEQUENCE: 181

```
Leu Leu Pro Gly Ser
1               5
```

<210> SEQ ID NO 182
<211> LENGTH: 2
<212> TYPE: PRT
<213> ORGANISM: Artificial Sequence
<220> FEATURE:
<223> OTHER INFORMATION: Synthethic

<400> SEQUENCE: 182

```
Ser Lys
1
```

<210> SEQ ID NO 183
<211> LENGTH: 3
<212> TYPE: PRT
<213> ORGANISM: Artificial Sequence
<220> FEATURE:
<223> OTHER INFORMATION: Synthethic

<400> SEQUENCE: 183

```
Phe Ala Ser
1
```

<210> SEQ ID NO 184
<211> LENGTH: 44
<212> TYPE: PRT
<213> ORGANISM: Artificial Sequence
<220> FEATURE:
<223> OTHER INFORMATION: Synthethic

<400> SEQUENCE: 184

```
Phe Ala Gln Arg Cys Cys His Cys Tyr Arg His Arg Gly Val Thr Leu
1               5                   10                  15

Val Val Trp Tyr Gly Phe Ile Gln Leu Arg Phe Pro Thr Ile Lys Ala
            20                  25                  30

Ser Tyr Met Ile Pro His Val Val Gln Lys Ser Gly
            35                  40
```

<210> SEQ ID NO 185
<211> LENGTH: 10
<212> TYPE: PRT
<213> ORGANISM: Artificial Sequence
<220> FEATURE:
<223> OTHER INFORMATION: Synthethic

```
<400> SEQUENCE: 185

Leu Leu Arg Ser Ser Asp Arg Cys Gln Lys
1               5                   10

<210> SEQ ID NO 186
<211> LENGTH: 14
<212> TYPE: PRT
<213> ORGANISM: Artificial Sequence
<220> FEATURE:
<223> OTHER INFORMATION: Synthethic

<400> SEQUENCE: 186

Val Gly Arg Ser Val Ile Thr His Gly Tyr Gly Ser Thr Ala
1               5                   10

<210> SEQ ID NO 187
<211> LENGTH: 15
<212> TYPE: PRT
<213> ORGANISM: Artificial Sequence
<220> FEATURE:
<223> OTHER INFORMATION: Synthethic

<400> SEQUENCE: 187

Phe Ser Tyr Cys His Ala Ile Arg Lys Met Leu Phe Cys Asp Trp
1               5                   10                  15

<210> SEQ ID NO 188
<211> LENGTH: 24
<212> TYPE: PRT
<213> ORGANISM: Artificial Sequence
<220> FEATURE:
<223> OTHER INFORMATION: Synthethic

<400> SEQUENCE: 188

Val Leu Asn Gln Val Ile Leu Arg Ile Val Tyr Ala Ala Thr Glu Leu
1               5                   10                  15

Leu Leu Pro Gly Val Asn Thr Gly
            20

<210> SEQ ID NO 189
<211> LENGTH: 4
<212> TYPE: PRT
<213> ORGANISM: Artificial Sequence
<220> FEATURE:
<223> OTHER INFORMATION: Synthethic

<400> SEQUENCE: 189

Tyr Arg Ala Thr
1

<210> SEQ ID NO 190
<211> LENGTH: 95
<212> TYPE: PRT
<213> ORGANISM: Artificial Sequence
<220> FEATURE:
<223> OTHER INFORMATION: Synthethic

<400> SEQUENCE: 190

Gln Asn Phe Lys Ser Ala His His Trp Lys Thr Phe Phe Gly Ala Lys
1               5                   10                  15

Thr Leu Lys Asp Leu Thr Ala Val Glu Ile Gln Phe Asp Val Thr His
            20                  25                  30

Ser Cys Thr Gln Leu Ile Phe Ser Ile Phe Tyr Phe His Gln Arg Phe
        35                  40                  45
```

```
Trp Val Ser Lys Asn Arg Lys Ala Lys Cys Arg Lys Lys Gly Asn Lys
 50                  55                  60

Gly Asp Thr Glu Met Leu Asn Thr His Thr Leu Pro Phe Ser Ile Leu
 65                  70                  75                  80

Leu Lys His Leu Ser Gly Leu Leu Ser His Glu Arg Ile His Ile
                 85                  90                  95
```

<210> SEQ ID NO 191
<211> LENGTH: 5
<212> TYPE: PRT
<213> ORGANISM: Artificial Sequence
<220> FEATURE:
<223> OTHER INFORMATION: Synthethic

<400> SEQUENCE: 191

```
Met Tyr Leu Glu Lys
1               5
```

<210> SEQ ID NO 192
<211> LENGTH: 20
<212> TYPE: PRT
<213> ORGANISM: Artificial Sequence
<220> FEATURE:
<223> OTHER INFORMATION: Synthethic

<400> SEQUENCE: 192

```
Thr Asn Arg Gly Ser Ala His Ile Ser Pro Lys Ser Ala Thr Trp Val
1               5                  10                  15

Asp Ile Asp Tyr
             20
```

<210> SEQ ID NO 193
<211> LENGTH: 11
<212> TYPE: PRT
<213> ORGANISM: Artificial Sequence
<220> FEATURE:
<223> OTHER INFORMATION: Synthethic

<400> SEQUENCE: 193

```
Leu Val Ile Asn Ser Asn Gln Leu Arg Gly His
1               5                  10
```

<210> SEQ ID NO 194
<211> LENGTH: 14
<212> TYPE: PRT
<213> ORGANISM: Artificial Sequence
<220> FEATURE:
<223> OTHER INFORMATION: Synthethic

<400> SEQUENCE: 194

```
Phe Ile Ala His Ile Trp Ser Ser Ala Leu His Asn Leu Arg
1               5                  10
```

<210> SEQ ID NO 195
<211> LENGTH: 13
<212> TYPE: PRT
<213> ORGANISM: Artificial Sequence
<220> FEATURE:
<223> OTHER INFORMATION: Synthethic

<400> SEQUENCE: 195

```
Met Ala Arg Leu Ala Asp Arg Pro Thr Thr Pro Ala His
1               5                  10
```

<210> SEQ ID NO 196

```
<211> LENGTH: 2
<212> TYPE: PRT
<213> ORGANISM: Artificial Sequence
<220> FEATURE:
<223> OTHER INFORMATION: Synthethic

<400> SEQUENCE: 196

Arg Gln
1

<210> SEQ ID NO 197
<211> LENGTH: 4
<212> TYPE: PRT
<213> ORGANISM: Artificial Sequence
<220> FEATURE:
<223> OTHER INFORMATION: Synthethic

<400> SEQUENCE: 197

Arg Met Phe Pro
1

<210> SEQ ID NO 198
<211> LENGTH: 2
<212> TYPE: PRT
<213> ORGANISM: Artificial Sequence
<220> FEATURE:
<223> OTHER INFORMATION: Synthethic

<400> SEQUENCE: 198

Arg Gln
1

<210> SEQ ID NO 199
<211> LENGTH: 47
<212> TYPE: PRT
<213> ORGANISM: Artificial Sequence
<220> FEATURE:
<223> OTHER INFORMATION: Synthethic

<400> SEQUENCE: 199

Gly Leu Ser Ile Asp Val Asn Gly Trp Ser Ile Tyr Gly Lys Leu Pro
1               5                   10                  15

Thr Trp Gln Tyr Ile Lys Cys Ile Ile Cys Gln Val Arg Pro Leu Leu
            20                  25                  30

Thr Ser Met Thr Val Asn Gly Pro Pro Gly Ile Met Pro Ser Thr
        35                  40                  45

<210> SEQ ID NO 200
<211> LENGTH: 13
<212> TYPE: PRT
<213> ORGANISM: Artificial Sequence
<220> FEATURE:
<223> OTHER INFORMATION: Synthethic

<400> SEQUENCE: 200

Pro Tyr Gly Thr Phe Leu Leu Gly Ser Thr Ser Thr Tyr
1               5                   10

<210> SEQ ID NO 201
<211> LENGTH: 8
<212> TYPE: PRT
<213> ORGANISM: Artificial Sequence
<220> FEATURE:
<223> OTHER INFORMATION: Synthethic

<400> SEQUENCE: 201
```

```
Ser Ser Leu Leu Pro Trp Ser Arg
 1               5
```

<210> SEQ ID NO 202
<211> LENGTH: 114
<212> TYPE: PRT
<213> ORGANISM: Artificial Sequence
<220> FEATURE:
<223> OTHER INFORMATION: Synthethic

<400> SEQUENCE: 202

```
Ala Pro Arg Ser Ala Ser Leu Ser Pro Ser Pro Pro Pro His Pro
 1               5                  10                  15

Gln Phe Cys Ile Tyr Leu Phe Phe Asn Tyr Phe Val Gln Arg Trp Gly
                20                  25                  30

Arg Gly Gly Gly Gly Gly Pro Pro Gln Ala Gly Arg Gly Gly Ala Arg
            35                  40                  45

Gly Gly Ala Gly Arg Gly Gly Lys Val Arg Arg Gln Pro Ile Arg Ala
        50                  55                  60

Ala Arg Ser Glu Ser Phe Leu Leu Trp Arg Gly Gly Gly Gly Gly
65                  70                  75                  80

Pro Ile Lys Ser Glu Ala Arg Gly Gly Arg Glu Ser Leu Arg Ala Ala
                85                  90                  95

Phe Pro Pro Cys Pro Ala Pro Pro Pro Arg Ala Ala Arg Pro Gly
            100                 105                 110

Ser Asp
```

<210> SEQ ID NO 203
<211> LENGTH: 6
<212> TYPE: PRT
<213> ORGANISM: Artificial Sequence
<220> FEATURE:
<223> OTHER INFORMATION: Synthethic

<400> SEQUENCE: 203

```
Pro Arg Tyr Ser His Arg
 1               5
```

<210> SEQ ID NO 204
<211> LENGTH: 202
<212> TYPE: PRT
<213> ORGANISM: Artificial Sequence
<220> FEATURE:
<223> OTHER INFORMATION: Synthethic

<400> SEQUENCE: 204

```
Ala Gly Gly Thr Ala Leu Leu Leu Arg Ala Val Ile Ser Ala Trp Phe
 1               5                  10                  15

Asn Asp Gly Leu Phe Leu Phe Cys Gly Cys Val Lys Ala Leu Arg Gly
                20                  25                  30

Ser Gly Arg Ala Leu Cys Ala Gly Gly Ala Ala Arg Gly Val Arg Ala
            35                  40                  45

Cys Val Cys Ala Trp Gly Ala Pro Arg Ala Ala Pro Arg Cys Pro Ala
        50                  55                  60

Ala Val Ser Ala Ala Gly Ala Ala Arg Gly Phe Val Arg Ser Ala Val
65                  70                  75                  80

Cys Ala Arg Gly Ala Arg Pro Gly Ala Val Pro Arg Gly Ala Gly Gly
                85                  90                  95

Ala Ala Arg Gly Thr Lys Ala Ala Cys Gly Val Cys Ala Trp Gly Gly
            100                 105                 110
```

```
Glu Gln Gly Val Trp Ala Arg Arg Ser Gly Cys Asn Pro Pro Cys Thr
            115                 120                 125

Pro Leu Pro Glu Leu Leu Ser Thr Ala Arg Leu Arg Val Arg Gly Ser
    130                 135                 140

Val Arg Gly Val Ala Arg Gly Ser Pro Cys Arg Ala Gly Gly Gly Gly
145                 150                 155                 160

Arg Trp Gly Cys Arg Ala Gly Arg Gly Arg Leu Gly Pro Gly Arg Ala
                165                 170                 175

Arg Gly Lys Gly Arg Gly Pro Arg Ser Ala Gly Gly Cys Arg Gly
            180                 185                 190

Ala Ala Ser Arg Ser His Cys Leu Leu Trp
        195                 200

<210> SEQ ID NO 205
<211> LENGTH: 121
<212> TYPE: PRT
<213> ORGANISM: Artificial Sequence
<220> FEATURE:
<223> OTHER INFORMATION: Synthethic

<400> SEQUENCE: 205

Ser Cys Glu Arg Ala Gln Gly Leu Pro Leu Ser Gln Ile Cys Ala Glu
1               5                   10                  15

Pro Lys Ser Gly Arg Arg Arg Thr Pro Ser Ser Gly Arg Gly Ala
            20                  25                  30

Lys Arg Cys Gly Ala Gly Arg Lys Glu Met Gly Gly Glu Gly Leu Arg
            35                  40                  45

Ala Ser Pro Arg Arg Arg Pro Leu Leu Pro Leu Gln Pro Arg Gly Cys
    50                  55                  60

Pro Arg Gly Asp Gly Cys Leu Arg Gly Gly Arg Gly Arg Ala Gly Phe
65                  70                  75                  80

Gly Phe Trp Arg Val Thr Gly Gly Ser Arg Ala Ser Ala Asn His Val
                85                  90                  95

His Ala Phe Phe Phe Phe Leu Gln Leu Leu Gly Asn Val Leu Val Ile
            100                 105                 110

Val Leu Ser His His Phe Gly Lys Glu
        115                 120

<210> SEQ ID NO 206
<211> LENGTH: 6681
<212> TYPE: DNA
<213> ORGANISM: Artificial Sequence
<220> FEATURE:
<223> OTHER INFORMATION: Synthethic

<400> SEQUENCE: 206
ttcctcgaga tgagcgacga gggacctggc accggacccg gcaatggact gggcgagaag      60
ggcgatacct ccggccctga aggatccgga ggatccggac cccagagaag ggaggcgac     120 aaccacggca gaggaagagg tagaggtaga ggcagaggcg aggaagacc tggagctcct     180 ggaggaagcg gcagcggacc taggcatagg gatggcgtga ggaggcccca gaagaggcct     240
agctgcatcg gctgcaaggg aacacatgga ggaacaggac tgggagctgg agctggcgga     300
gccggagccg gcggagctgg cgctggcgga ggcgctggcg ctggcggagg cgctggaggc     360
gctggcggag ctgaggagc tggcgctggc ggcggcccg gcgccggcgg cggcgctgga     420
ggagccggag gcgctggagc tggaggcgga gctggcgctg gcggaggcgc aggaggtgct     480
```

-continued

| | |
|---|---|
| ggagctggcg gcggagctgg aggtgctgga ggagcaggag ctggaggagg agctggagca | 540 |
| ggtggtggtg caggaggcgc cggcgccggc ggcggcgctg gaggtgctgg aggtgctggt | 600 |
| gcaggtggag gtgcaggagc tggcggcgcc ggcggagctg gaggagctgg agctggaggc | 660 |
| gctggagctg gaggaggagc tggaggagct ggaggtgctg gagctggcgg agccggagct | 720 |
| ggaggcgccg gcgccggcgg cgctggagca ggaggtgcag gaggagcagg tgctggaggt | 780 |
| gctggaggag ctggtgcagg aggagctgga ggtgcaggtg caggaggcgg tgcaggaggt | 840 |
| gcaggtgctg gaggaggagc aggtggagca ggtgcaggag gtgcaggagg agctggagct | 900 |
| ggaggcgcag gaggagcagg tgctggaggt gctggaggtg caggagctgg aggtggagca | 960 |
| ggtgcaggtg gagctggagc aggaggtggt ggaagaggca gaggcggaag cggaggaagg | 1020 |
| ggcagaggag gaagcggagg aagaggcaga ggcggctccg gaggaaggag aggcagaggc | 1080 |
| agggagagag ccagaggcgg aagcagggag agggccagag gaaggggaag aggcagggga | 1140 |
| gagaagaggc ctaggtcccc tagcagccaa agcagcagct ccggcagccc tcctagaagg | 1200 |
| cctcctcctg gcaggagacc cttcttccac cccgtcggcg aggccgacta cttcgaatac | 1260 |
| caccaggagg gaggccccga tggcgaacct gatgtgcctc ctggcgccat tgagcagggc | 1320 |
| cctgccgatg accctggcga aggacctagc accggaccca gaggccaggg agatggaggc | 1380 |
| agaaggaaga agggaggctg gtttggcaag catagaggcc agggcggcag caaccccaag | 1440 |
| ttcgagaata tcgccgaggg cctgagagct ctgctggcta ggagccacgt ggagagaacc | 1500 |
| accgacgagg gaacctgggt ggctggcgtg ttcgtgtacg gcggcagcaa gacaagcctg | 1560 |
| tacaacctga ggagaggcac cgccctggct attccccagt gtaggctcac ccccctgagc | 1620 |
| aggctcccctt ttggcatggc tcctggacct ggaccccagc ctggacctct gagggagagc | 1680 |
| atcgtgtgct acttcatggt gttcctgcag acccacatct tcgccgaggt gctgaaggac | 1740 |
| gccatcaagg acctggtgat gaccaagccc gcccctacct gcaacattag ggtgaccgtg | 1800 |
| tgctccttcg acgacggagt ggacctgcct ccctggttcc ctcctatggt ggaaggagct | 1860 |
| gctgccgagg gagacgacgg cgatgatggc gatgagggcg gcgatggcga tgaaggagag | 1920 |
| gagggacagg agtgatgatg gccaatgccc tggctcacaa ataccactga gatcttttc | 1980 |
| cctctgccaa aaattatggg gacatcatga agccccttga gcatctgact tctggctaat | 2040 |
| aaaggaaatt tattttcatt gcaatagtgt gttggaattt tttgtgtctc tcactcggaa | 2100 |
| ggacatatgg gagggcaaat catttaaaac atcagaatga gtatttggtt tagagtttgg | 2160 |
| caacatatgc ccatatgctg gctgccatga caaaggttg gctataaaga ggtcatcagt | 2220 |
| atatgaaaca gccccctgct gtccattcct tattccatag aaaagccttg acttgaggtt | 2280 |
| agatttttt tatattttgt tttgtgttat ttttttcttt aacatcccta aaattttcct | 2340 |
| tacatgtttt actagccaga ttttcctcc tctcctgact actcccagtc atagctgtcc | 2400 |
| ctcttctctt atgagatcc ctcgacctgc agcccaagct ggcgtaatc atggtcatag | 2460 |
| ctgtttcctg tgtgaaattg ttatccgctc acaattccac acaacatacg agccggaagc | 2520 |
| ataaagtgta aagcctgggt gcctaatgag tgagctaact cacattaatt gcgttgcgct | 2580 |
| cactgcccgc tttccagtcg ggaaacctgt cgtgccagcg gatccgcatc tcaattagtc | 2640 |
| agcaaccata gtcccgcccc taactccgcc catcccgccc taactccgcc cagttccgc | 2700 |
| ccattctccg cccatggct gactaatttt tttatttat gcagaggccg aggccgcctc | 2760 |
| ggcctctgag ctattccaga agtagtgagg aggcttttt ggaggcctag cttttgcaa | 2820 |
| aaagctaact tgtttattgc agcttataat ggttacaaat aaagcaatag catcacaaat | 2880 |

```
ttcacaaata aagcattttt ttcactgcat tctagttgtg gtttgtccaa actcatcaat    2940
gtatcttatc atgtctggat ccgctgcatt aatgaatcgg ccaacgcgcg gggagaggcg    3000
gtttgcgtat tgggcgctct tccgcttcct cgctcactga ctcgctgcgc tcggtcgttc    3060
ggctgcggcg agcggtatca gctcactcaa aggcggtaat acggttatcc acagaatcag    3120
ggataacgca ggaaagaaca tgtgagcaaa aggccagcaa aaggccagga accgtaaaaa    3180
ggccgcgttg ctggcgtttt tccataggct ccgcccccct gacgagcatc acaaaaatcg    3240
acgctcaagt cagaggtggc gaaacccgac aggactataa agataccagg cgtttccccc    3300
tggaagctcc ctcgtgcgct ctcctgttcc gaccctgccg cttaccggat acctgtccgc    3360
ctttctccct tcgggaagcg tggcgctttc tcatagctca cgctgtaggt atctcagttc    3420
ggtgtaggtc gttcgctcca agctgggctg tgtgcacgaa ccccccgttc agcccgaccg    3480
ctgcgcctta tccggtaact atcgtcttga gtccaacccg gtaagacacg acttatcgcc    3540
actggcagca gccactggta acaggattag cagagcgagg tatgtaggcg gtgctacaga    3600
gttcttgaag tggtggccta actacggcta cactagaaga acagtatttg gtatctgcgc    3660
tctgctgaag ccagttacct tcggaaaaag agttggtagc tcttgatccg gcaaacaaac    3720
caccgctggt agcggtggtt tttttgtttg caagcagcag attacgcgca gaaaaaaagg    3780
atctcaagaa gatcctttga tcttttctac ggggtctgac gctcagtgga acgaaaactc    3840
acgttaaggg attttggtca tgagattatc aaaaaggatc ttcacctaga tccttttaaa    3900
ttaaaaatga agttttaaat caatctaaag tatatatgag taaacttggt ctgacagtta    3960
ccaatgctta atcagtgagg cacctatctc agcgatctgt ctatttcgtt catccatagt    4020
tgcctgactc cccgtcgtgt agataactac gatacgggag ggcttaccat ctggccccag    4080
tgctgcaatg ataccgcgag acccacgctc accggctcca gatttatcag caataaacca    4140
gccagccgga agggccgagc gcagaagtgg tcctgcaact ttatccgcct ccatccagtc    4200
tattaattgt tgccgggaag ctagagtaag tagttcgcca gttaatagtt tgcgcaacgt    4260
tgttgccatt gctacaggca tcgtggtgtc acgctcgtcg tttggtatgg cttcattcag    4320
ctccggttcc caacgatcaa ggcgagttac atgatccccc atgttgtgca aaaaagcggt    4380
tagctccttc ggtcctccga tcgttgtcag aagtaagttg gccgcagtgt tatcactcat    4440
ggttatggca gcactgcata attctcttac tgtcatgcca tccgtaagat gcttttctgt    4500
gactggtgag tactcaacca agtcattctg agaatagtgt atgcggcgac cgagttgctc    4560
ttgcccggcg tcaatacggg ataataccgc gccacatagc agaactttaa aagtgctcat    4620
cattggaaaa cgttcttcgg ggcgaaaact ctcaaggatc ttaccgctgt tgagatccag    4680
ttcgatgtaa cccactcgtg cacccaactg atcttcagca tcttttactt tcaccagcgt    4740
ttctgggtga gcaaaaacag gaaggcaaaa tgccgcaaaa aagggaataa gggcgacacg    4800
gaaatgttga atactcatac tcttcctttt tcaatattat tgaagcattt atcagggtta    4860
ttgtctcatg agcggataca tatttgaatg tatttagaaa aataaacaaa tagggg ttcc    4920
gcgcacattt ccccgaaaag tgccacctgg gtcgacattg attattgact agttattaat    4980
agtaatcaat tacggggtca ttagttcata gcccatatat ggagttccgc gttacataac    5040
ttacggtaaa tggcccgcct ggctgaccgc ccaacgaccc ccgcccattg acgtcaataa    5100
tgacgtatgt tcccatagta acgccaatag ggactttcca ttgacgtcaa tgggtggagt    5160
atttacggta aactgcccac ttggcagtac atcaagtgta tcatatgcca agtacgcccc    5220
```

-continued

```
ctattgacgt caatgacggt aaatggcccg cctggcatta tgcccagtac atgaccttat    5280
gggactttcc tacttggcag tacatctacg tattagtcat cgctattacc atggtcgagg    5340
tgagccccac gttctgcttc actctcccca tctccccccc ctccccaccc ccaattttgt    5400
atttatttat tttttaatta ttttgtgcag cgatggggc gggggggggg gggggccccc    5460
ccccaggcgg ggcggggcgg ggcgagggc ggggcgggc gaggcggaaa ggtgcggcgg    5520
cagccaatca gagcggcgcg ctccgaaagt ttccttttat ggcgaggcgg cggcggcggc    5580
ggccctataa aaagcgaagc gcgcggcggg cgggagtcgt tgcgcgctgc cttcccccg     5640 tgccccgctc cgccgccgcc tcgcgccgcc cgccccggct ctgactgacc gcgttactcc    5700
cacaggtgag cgggcgggac ggcccttctc ctccgggctg taattagcgc ttggtttaat    5760
gacggcttgt ttcttttctg tggctgcgtg aaagccttga ggggctccgg gagggccctt    5820
tgtgcggggg gagcggctcg gggggtgcgt gcgtgtgtgt gtgcgtgggg agcgccgcgt    5880
gcggctccgc gctgcccggc ggctgtgagc gctgcgggcg cggcgcgggg ctttgtgcgc    5940
tccgcagtgt gcgcgagggg agcgcggccg ggggcggtgc cccgcggtgc gggggggggct   6000 gcgagggggaa caaaggctgc gtgcggggtg tgtgcgtggg ggggtgagca ggggtgtgg    6060 gcgcgtcggt cgggctgcaa ccccccctgc accccctcc ccgagttgct gagcacggcc    6120
cggcttcggg tgcggggctc cgtacggggc gtggcgcggg gctcgccgtg ccgggcgggg    6180
ggtggcggca ggtgggggtg ccgggcgggg cggggccgcc tcgggccggg gagggctcgg    6240
gggaaggggc gcggcggccc ccggagcgcc ggcggctgtc gaggcgcggc gagccgcagc    6300
cattgccttt tatggtaatc gtgcgagagg gcgcaggac ttcctttgtc ccaaatctgt     6360
gcggagccga aatctgggag gcgccgccgc accccctcta gcgggcgcgg ggcgaagcgg    6420
tgcggcgccg gcaggaagga aatgggcggg gagggccttc gtgcgtcgcc gcgccgccgt    6480
ccccttctcc ctctccagcc tcggggctgt ccgcgggggg acggctgcct tcgggggga    6540 cggggcaggg cggggttcgg cttctggcgt gtgaccggcg gctctagagc ctctgctaac    6600
catgttcatg ccttcttctt tttcctacag ctcctgggca acgtgctggt tattgtgctg    6660
tctcatcatt ttggcaaaga a                                              6681
```

<210> SEQ ID NO 207
<211> LENGTH: 456
<212> TYPE: PRT
<213> ORGANISM: Artificial Sequence
<220> FEATURE:
<223> OTHER INFORMATION: Synthethic

<400> SEQUENCE: 207

```
Glu Phe Leu Glu Thr Gly Arg Thr Cys Lys Ser Arg Val Arg Asp Arg
1               5                   10                  15

Ser Ser Asn Ser Arg Glu Pro Ser Ala Asn Asp Ala Thr Met Asn Arg
            20                  25                  30

Ala Val Cys Gln Val Ala Leu Glu Asn Asp Arg Glu Ala Lys Asn
        35                  40                  45

Thr Trp Arg Leu Val Phe Arg Ile Ala Ile Leu Leu Thr Val Met
    50                  55                  60

Thr Leu Ala Ile Ser Ala Ala Leu Ala Tyr Ser Tyr Pro Cys Cys
65                  70                  75                  80

His Val Thr Gln Leu Arg Ala Gln His Leu Leu Ala Leu Glu Asn Ile
                85                  90                  95

Ser Asp Ile Tyr Leu Val Ser Asn Gln Thr Cys Asp Gly Phe Ser Leu
```

```
                100             105             110
Ala Ser Leu Asn Ser Pro Lys Asn Gly Ser Asn Gln Leu Val Ile Ser
            115                 120                 125

Arg Cys Ala Asn Gly Leu Asn Val Val Ser Phe Phe Ile Ser Ile Leu
130                 135                 140

Lys Arg Ser Ser Ser Ala Leu Thr Gly His Leu Arg Glu Leu Leu Thr
145                 150                 155                 160

Thr Leu Glu Thr Leu Tyr Gly Ser Phe Ser Val Glu Asp Leu Phe Gly
                165                 170                 175

Ala Asn Leu Asn Arg Tyr Ala Trp His Arg Gly Gly Pro Ala Thr Leu
            180                 185                 190

Ser Leu Pro Pro Asp His Pro Asn Ser Ser Ala Arg Ser Pro Pro Pro
        195                 200                 205

Asp Pro Gly Ala Ala Gly Ala Gly Ala Met Val Ser Lys Gly Glu Glu
210                 215                 220

Leu Phe Thr Gly Val Val Pro Ile Leu Val Glu Leu Asp Gly Asp Val
225                 230                 235                 240

Asn Gly His Lys Phe Ser Val Ser Gly Glu Gly Glu Gly Asp Ala Thr
                245                 250                 255

Tyr Gly Lys Leu Thr Leu Lys Phe Ile Cys Thr Thr Gly Lys Leu Pro
            260                 265                 270

Val Pro Trp Pro Thr Leu Val Thr Thr Leu Thr Tyr Gly Val Gln Cys
        275                 280                 285

Phe Ser Arg Tyr Pro Asp His Met Lys Gln His Asp Phe Phe Lys Ser
290                 295                 300

Ala Met Pro Glu Gly Tyr Val Gln Glu Arg Thr Ile Phe Phe Lys Asp
305                 310                 315                 320

Asp Gly Asn Tyr Lys Thr Arg Ala Glu Val Lys Phe Glu Gly Asp Thr
                325                 330                 335

Leu Val Asn Arg Ile Glu Leu Lys Gly Ile Asp Phe Lys Glu Asp Gly
            340                 345                 350

Asn Ile Leu Gly His Lys Leu Glu Tyr Asn Tyr Asn Ser His Asn Val
        355                 360                 365

Tyr Ile Met Ala Asp Lys Gln Lys Asn Gly Ile Lys Ala Asn Phe Lys
370                 375                 380

Ile Arg His Asn Ile Glu Asp Gly Ser Val Gln Leu Ala Asp His Tyr
385                 390                 395                 400

Gln Gln Asn Thr Pro Ile Gly Asp Gly Pro Val Leu Leu Pro Asp Asn
                405                 410                 415

His Tyr Leu Ser Thr Gln Ser Ala Leu Ser Lys Asp Pro Asn Glu Lys
            420                 425                 430

Arg Asp His Met Val Leu Leu Glu Phe Val Thr Ala Ala Gly Ile Thr
        435                 440                 445

Leu Gly Met Asp Glu Leu Tyr Lys
    450                 455

<210> SEQ ID NO 208
<211> LENGTH: 12
<212> TYPE: PRT
<213> ORGANISM: Artificial Sequence
<220> FEATURE:
<223> OTHER INFORMATION: Synthethic

<400> SEQUENCE: 208

Trp Pro Met Pro Trp Leu Thr Asn Thr Thr Glu Ile
```

<210> SEQ ID NO 209
<211> LENGTH: 28
<212> TYPE: PRT
<213> ORGANISM: Artificial Sequence
<220> FEATURE:
<223> OTHER INFORMATION: Synthethic

<400> SEQUENCE: 209

Ala Trp Arg Asn His Gly His Ser Cys Phe Leu Cys Glu Ile Val Ile
1               5                   10                  15

Arg Ser Gln Phe His Thr Thr Tyr Glu Pro Glu Ala
            20                  25

<210> SEQ ID NO 210
<211> LENGTH: 37
<212> TYPE: PRT
<213> ORGANISM: Artificial Sequence
<220> FEATURE:
<223> OTHER INFORMATION: Synthethic

<400> SEQUENCE: 210

Ser Val Lys Pro Gly Cys Leu Met Ser Glu Leu Thr His Ile Asn Cys
1               5                   10                  15

Val Ala Leu Thr Ala Arg Phe Pro Val Gly Lys Pro Val Val Pro Ala
            20                  25                  30

Asp Pro His Leu Asn
        35

<210> SEQ ID NO 211
<211> LENGTH: 27
<212> TYPE: PRT
<213> ORGANISM: Artificial Sequence
<220> FEATURE:
<223> OTHER INFORMATION: Synthethic

<400> SEQUENCE: 211

Ser Ala Thr Ile Val Pro Pro Leu Thr Pro Ile Pro Pro Leu Thr
1               5                   10                  15

Pro Pro Ser Ser Ala His Ser Pro Pro His Gly
            20                  25

<210> SEQ ID NO 212
<211> LENGTH: 20
<212> TYPE: PRT
<213> ORGANISM: Artificial Sequence
<220> FEATURE:
<223> OTHER INFORMATION: Synthethic

<400> SEQUENCE: 212

Leu Ile Phe Phe Ile Tyr Ala Glu Ala Glu Ala Ala Ser Ala Ser Glu
1               5                   10                  15

Leu Phe Gln Lys
        20

<210> SEQ ID NO 213
<211> LENGTH: 83
<212> TYPE: PRT
<213> ORGANISM: Artificial Sequence
<220> FEATURE:
<223> OTHER INFORMATION: Synthethic

<400> SEQUENCE: 213

-continued

Gly Gly Phe Phe Gly Leu Gly Phe Cys Lys Lys Leu Thr Cys Leu
1               5                   10                  15

Leu Gln Leu Ile Met Val Thr Asn Lys Ala Ile Ala Ser Gln Ile Ser
                20                  25                  30

Gln Ile Lys His Phe Phe His Cys Ile Leu Val Val Val Cys Pro Asn
            35                  40                  45

Ser Ser Met Tyr Leu Ile Met Ser Gly Ser Ala Ala Leu Met Asn Arg
        50                  55                  60

Pro Thr Arg Gly Glu Arg Phe Ala Tyr Trp Ala Leu Phe Arg Phe
65                  70                  75                  80

Leu Ala His

<210> SEQ ID NO 214
<211> LENGTH: 34
<212> TYPE: PRT
<213> ORGANISM: Artificial Sequence
<220> FEATURE:
<223> OTHER INFORMATION: Synthethic

<400> SEQUENCE: 214

Leu Ala Ala Leu Gly Arg Ser Ala Ala Ser Gly Ile Ser Ser Leu
1               5                   10                  15

Lys Gly Gly Asn Thr Val Ile His Arg Ile Arg Asp Asn Ala Gly Lys
                20                  25                  30

Asn Met

<210> SEQ ID NO 215
<211> LENGTH: 44
<212> TYPE: PRT
<213> ORGANISM: Artificial Sequence
<220> FEATURE:
<223> OTHER INFORMATION: Synthethic

<400> SEQUENCE: 215

Ala Lys Gly Gln Gln Lys Ala Arg Asn Arg Lys Lys Ala Ala Leu Leu
1               5                   10                  15

Ala Phe Phe His Arg Leu Arg Pro Pro Asp Glu His His Lys Asn Arg
                20                  25                  30

Arg Ser Ser Gln Arg Trp Arg Asn Pro Thr Gly Leu
            35                  40

<210> SEQ ID NO 216
<211> LENGTH: 48
<212> TYPE: PRT
<213> ORGANISM: Artificial Sequence
<220> FEATURE:
<223> OTHER INFORMATION: Synthethic

<400> SEQUENCE: 216

Arg Tyr Gln Ala Phe Pro Pro Gly Ser Ser Leu Val Arg Ser Pro Val
1               5                   10                  15

Pro Thr Leu Pro Leu Thr Gly Tyr Leu Ser Ala Phe Leu Pro Ser Gly
                20                  25                  30

Ser Val Ala Leu Ser His Ser Ser Arg Cys Arg Tyr Leu Ser Ser Val
            35                  40                  45

<210> SEQ ID NO 217
<211> LENGTH: 92
<212> TYPE: PRT
<213> ORGANISM: Artificial Sequence
<220> FEATURE:

<223> OTHER INFORMATION: Synthethic

<400> SEQUENCE: 217

Val Val Arg Ser Lys Leu Gly Cys Val His Glu Pro Pro Val Gln Pro
1               5                   10                  15

Asp Arg Cys Ala Leu Ser Gly Asn Tyr Arg Leu Glu Ser Asn Pro Val
            20                  25                  30

Arg His Asp Leu Ser Pro Leu Ala Ala Ala Thr Gly Asn Arg Ile Ser
        35                  40                  45

Arg Ala Arg Tyr Val Gly Gly Ala Thr Glu Phe Leu Lys Trp Trp Pro
    50                  55                  60

Asn Tyr Gly Tyr Thr Arg Arg Thr Val Phe Gly Ile Cys Ala Leu Leu
65                  70                  75                  80

Lys Pro Val Thr Phe Gly Lys Arg Val Gly Ser Ser
                85                  90

<210> SEQ ID NO 218
<211> LENGTH: 46
<212> TYPE: PRT
<213> ORGANISM: Artificial Sequence
<220> FEATURE:
<223> OTHER INFORMATION: Synthethic

<400> SEQUENCE: 218

Ser Gly Lys Gln Thr Thr Ala Gly Ser Gly Phe Phe Val Cys Lys
1               5                   10                  15

Gln Gln Ile Thr Arg Arg Lys Lys Gly Ser Gln Glu Asp Pro Leu Ile
            20                  25                  30

Phe Ser Thr Gly Ser Asp Ala Gln Trp Asn Glu Asn Ser Arg
        35                  40                  45

<210> SEQ ID NO 219
<211> LENGTH: 13
<212> TYPE: PRT
<213> ORGANISM: Artificial Sequence
<220> FEATURE:
<223> OTHER INFORMATION: Synthethic

<400> SEQUENCE: 219

Gly Ile Leu Val Met Arg Leu Ser Lys Arg Ile Phe Thr
1               5                   10

<210> SEQ ID NO 220
<211> LENGTH: 4
<212> TYPE: PRT
<213> ORGANISM: Artificial Sequence
<220> FEATURE:
<223> OTHER INFORMATION: Synthethic

<400> SEQUENCE: 220

Ile Leu Leu Asn
1

<210> SEQ ID NO 221
<211> LENGTH: 1
<212> TYPE: PRT
<213> ORGANISM: Artificial Sequence
<220> FEATURE:
<223> OTHER INFORMATION: Synthethic

<400> SEQUENCE: 221

Lys
1

<210> SEQ ID NO 222
<211> LENGTH: 5
<212> TYPE: PRT
<213> ORGANISM: Artificial Sequence
<220> FEATURE:
<223> OTHER INFORMATION: Synthethic

<400> SEQUENCE: 222

Ser Phe Lys Ser Ile
1               5

<210> SEQ ID NO 223
<211> LENGTH: 4
<212> TYPE: PRT
<213> ORGANISM: Artificial Sequence
<220> FEATURE:
<223> OTHER INFORMATION: Synthethic

<400> SEQUENCE: 223

Ser Ile Tyr Glu
1

<210> SEQ ID NO 224
<211> LENGTH: 27
<212> TYPE: PRT
<213> ORGANISM: Artificial Sequence
<220> FEATURE:
<223> OTHER INFORMATION: Synthethic

<400> SEQUENCE: 224

Thr Trp Ser Asp Ser Tyr Gln Cys Leu Ile Ser Glu Ala Pro Ile Ser
1               5                   10                  15

Ala Ile Cys Leu Phe Arg Ser Ser Ile Val Ala
            20                  25

<210> SEQ ID NO 225
<211> LENGTH: 4
<212> TYPE: PRT
<213> ORGANISM: Artificial Sequence
<220> FEATURE:
<223> OTHER INFORMATION: Synthethic

<400> SEQUENCE: 225

Leu Pro Val Val
1

<210> SEQ ID NO 226
<211> LENGTH: 103
<212> TYPE: PRT
<213> ORGANISM: Artificial Sequence
<220> FEATURE:
<223> OTHER INFORMATION: Synthethic

<400> SEQUENCE: 226

Ile Thr Thr Ile Arg Glu Gly Leu Pro Ser Gly Pro Ser Ala Ala Met
1               5                   10                  15

Ile Pro Arg Asp Pro Arg Ser Pro Ala Pro Asp Leu Ser Ala Ile Asn
            20                  25                  30

Gln Pro Ala Gly Arg Ala Glu Arg Ser Gly Pro Ala Thr Leu Ser
        35                  40                  45

Ala Ser Ile Gln Ser Ile Asn Cys Cys Arg Glu Ala Arg Val Ser Ser
    50                  55                  60

Ser Pro Val Asn Ser Leu Arg Asn Val Val Ala Ile Ala Thr Gly Ile

```
                65                  70                  75                  80
Val Val Ser Arg Ser Ser Phe Gly Met Ala Ser Phe Ser Ser Gly Ser
                    85                  90                  95

Gln Arg Ser Arg Arg Val Thr
            100

<210> SEQ ID NO 227
<211> LENGTH: 58
<212> TYPE: PRT
<213> ORGANISM: Artificial Sequence
<220> FEATURE:
<223> OTHER INFORMATION: Synthethic

<400> SEQUENCE: 227

Ser Pro Met Leu Cys Lys Lys Ala Val Ser Phe Gly Pro Pro Ile
1               5                   10                  15

Val Val Arg Ser Lys Leu Ala Ala Val Leu Ser Leu Met Val Met Ala
                    20                  25                  30

Ala Leu His Asn Ser Leu Thr Val Met Pro Ser Val Arg Cys Phe Ser
            35                  40                  45

Val Thr Gly Glu Tyr Ser Thr Lys Ser Phe
        50                  55

<210> SEQ ID NO 228
<211> LENGTH: 1
<212> TYPE: PRT
<213> ORGANISM: Artificial Sequence
<220> FEATURE:
<223> OTHER INFORMATION: Synthethic

<400> SEQUENCE: 228

Glu
1

<210> SEQ ID NO 229
<211> LENGTH: 50
<212> TYPE: PRT
<213> ORGANISM: Artificial Sequence
<220> FEATURE:
<223> OTHER INFORMATION: Synthethic

<400> SEQUENCE: 229

Cys Met Arg Arg Pro Ser Cys Ser Cys Pro Ala Ser Ile Arg Asp Asn
1               5                   10                  15

Thr Ala Pro His Ser Arg Thr Leu Lys Val Leu Ile Ile Gly Lys Arg
                    20                  25                  30

Ser Ser Gly Arg Lys Leu Ser Arg Ile Leu Pro Leu Leu Arg Ser Ser
            35                  40                  45

Ser Met
    50

<210> SEQ ID NO 230
<211> LENGTH: 6
<212> TYPE: PRT
<213> ORGANISM: Artificial Sequence
<220> FEATURE:
<223> OTHER INFORMATION: Synthethic

<400> SEQUENCE: 230

Pro Thr Arg Ala Pro Asn
1               5
```

```
<210> SEQ ID NO 231
<211> LENGTH: 12
<212> TYPE: PRT
<213> ORGANISM: Artificial Sequence
<220> FEATURE:
<223> OTHER INFORMATION: Synthethic

<400> SEQUENCE: 231

Ser Ser Ala Ser Phe Thr Phe Thr Ser Val Ser Gly
1               5                   10

<210> SEQ ID NO 232
<211> LENGTH: 19
<212> TYPE: PRT
<213> ORGANISM: Artificial Sequence
<220> FEATURE:
<223> OTHER INFORMATION: Synthethic

<400> SEQUENCE: 232

Ala Lys Thr Gly Arg Gln Asn Ala Ala Lys Lys Gly Ile Arg Ala Thr
1               5                   10                  15

Arg Lys Cys

<210> SEQ ID NO 233
<211> LENGTH: 10
<212> TYPE: PRT
<213> ORGANISM: Artificial Sequence
<220> FEATURE:
<223> OTHER INFORMATION: Synthethic

<400> SEQUENCE: 233

Ile Leu Ile Leu Phe Leu Phe Gln Tyr Tyr
1               5                   10

<210> SEQ ID NO 234
<211> LENGTH: 17
<212> TYPE: PRT
<213> ORGANISM: Artificial Sequence
<220> FEATURE:
<223> OTHER INFORMATION: Synthethic

<400> SEQUENCE: 234

Ser Ile Tyr Gln Gly Tyr Cys Leu Met Ser Gly Tyr Ile Phe Glu Cys
1               5                   10                  15

Ile

<210> SEQ ID NO 235
<211> LENGTH: 24
<212> TYPE: PRT
<213> ORGANISM: Artificial Sequence
<220> FEATURE:
<223> OTHER INFORMATION: Synthethic

<400> SEQUENCE: 235

Lys Asn Lys Gln Ile Gly Val Pro Arg Thr Phe Pro Arg Lys Val Pro
1               5                   10                  15

Pro Gly Ser Thr Leu Ile Ile Asp
            20

<210> SEQ ID NO 236
<211> LENGTH: 12
<212> TYPE: PRT
<213> ORGANISM: Artificial Sequence
<220> FEATURE:
<223> OTHER INFORMATION: Synthethic
```

<400> SEQUENCE: 236

Leu Leu Ile Val Ile Asn Tyr Gly Val Ile Ser Ser
1               5                   10

<210> SEQ ID NO 237
<211> LENGTH: 71
<212> TYPE: PRT
<213> ORGANISM: Artificial Sequence
<220> FEATURE:
<223> OTHER INFORMATION: Synthethic

<400> SEQUENCE: 237

Pro Ile Tyr Gly Val Pro Arg Tyr Ile Thr Tyr Gly Lys Trp Pro Ala
1               5                   10                  15

Trp Leu Thr Ala Gln Arg Pro Pro Ile Asp Val Asn Asn Asp Val
            20                  25                  30

Cys Ser His Ser Asn Ala Asn Arg Asp Phe Pro Leu Thr Ser Met Gly
        35                  40                  45

Gly Val Phe Thr Val Asn Cys Pro Leu Gly Ser Thr Ser Ser Val Ser
    50                  55                  60

Tyr Ala Lys Tyr Ala Pro Tyr
65                  70

<210> SEQ ID NO 238
<211> LENGTH: 2
<212> TYPE: PRT
<213> ORGANISM: Artificial Sequence
<220> FEATURE:
<223> OTHER INFORMATION: Synthethic

<400> SEQUENCE: 238

Arg Gln
1

<210> SEQ ID NO 239
<211> LENGTH: 1
<212> TYPE: PRT
<213> ORGANISM: Artificial Sequence
<220> FEATURE:
<223> OTHER INFORMATION: Synthethic

<400> SEQUENCE: 239

Arg
1

<210> SEQ ID NO 240
<211> LENGTH: 115
<212> TYPE: PRT
<213> ORGANISM: Artificial Sequence
<220> FEATURE:
<223> OTHER INFORMATION: Synthethic

<400> SEQUENCE: 240

Met Ala Arg Leu Ala Leu Cys Pro Val His Asp Leu Met Gly Leu Ser
1               5                   10                  15

Tyr Leu Ala Val His Leu Arg Ile Ser His Arg Tyr Tyr His Gly Arg
            20                  25                  30

Gly Glu Pro His Val Leu Leu His Ser Pro His Leu Pro Pro Leu Pro
        35                  40                  45

Thr Pro Asn Phe Val Phe Ile Tyr Phe Leu Ile Ile Leu Cys Ser Asp
    50                  55                  60

Gly Gly Gly Gly Gly Gly Gly Ala Pro Pro Arg Arg Gly Gly Ala Gly

```
                65                  70                  75                  80
Arg Gly Ala Gly Arg Gly Glu Ala Glu Arg Cys Gly Gly Ser Gln Ser
                    85                  90                  95

Glu Arg Arg Ala Pro Lys Val Ser Phe Tyr Gly Glu Ala Ala Ala
            100                 105                 110

Ala Ala Leu
        115
```

<210> SEQ ID NO 241
<211> LENGTH: 50
<212> TYPE: PRT
<213> ORGANISM: Artificial Sequence
<220> FEATURE:
<223> OTHER INFORMATION: Synthethic

<400> SEQUENCE: 241

```
Lys Ala Lys Arg Ala Ala Gly Gly Ser Arg Cys Ala Leu Pro Ser Pro
1               5                   10                  15

Arg Ala Pro Leu Arg Arg Arg Leu Ala Pro Pro Ala Pro Ala Leu Thr
            20                  25                  30

Asp Arg Val Thr Pro Thr Gly Glu Arg Ala Gly Arg Pro Phe Ser Ser
        35                  40                  45

Gly Leu
     50
```

<210> SEQ ID NO 242
<211> LENGTH: 15
<212> TYPE: PRT
<213> ORGANISM: Artificial Sequence
<220> FEATURE:
<223> OTHER INFORMATION: Synthethic

<400> SEQUENCE: 242

```
Leu Ala Leu Gly Leu Met Thr Ala Cys Phe Phe Ser Val Ala Ala
1               5                   10                  15
```

<210> SEQ ID NO 243
<211> LENGTH: 2
<212> TYPE: PRT
<213> ORGANISM: Artificial Sequence
<220> FEATURE:
<223> OTHER INFORMATION: Synthethic

<400> SEQUENCE: 243

```
Lys Pro
1
```

<210> SEQ ID NO 244
<211> LENGTH: 35
<212> TYPE: PRT
<213> ORGANISM: Artificial Sequence
<220> FEATURE:
<223> OTHER INFORMATION: Synthethic

<400> SEQUENCE: 244

```
Gly Ala Pro Gly Gly Pro Phe Val Arg Gly Glu Arg Leu Gly Gly Cys
1               5                   10                  15

Val Arg Val Cys Val Arg Gly Glu Arg Val Arg Leu Arg Ala Ala
            20                  25                  30

Arg Arg Leu
        35
```

-continued

```
<210> SEQ ID NO 245
<211> LENGTH: 67
<212> TYPE: PRT
<213> ORGANISM: Artificial Sequence
<220> FEATURE:
<223> OTHER INFORMATION: Synthethic

<400> SEQUENCE: 245

Ala Leu Arg Ala Arg Arg Gly Ala Leu Cys Ala Pro Gln Cys Ala Arg
1               5                   10                  15

Gly Glu Arg Gly Arg Gly Arg Cys Pro Ala Val Arg Gly Gly Leu Arg
            20                  25                  30

Gly Glu Gln Arg Leu Arg Ala Gly Cys Val Arg Gly Gly Val Ser Arg
        35                  40                  45

Gly Cys Gly Arg Val Gly Arg Ala Ala Thr Pro Pro Ala Pro Pro Ser
    50                  55                  60

Pro Ser Cys
65

<210> SEQ ID NO 246
<211> LENGTH: 153
<212> TYPE: PRT
<213> ORGANISM: Artificial Sequence
<220> FEATURE:
<223> OTHER INFORMATION: Synthethic

<400> SEQUENCE: 246

Ala Arg Pro Gly Phe Gly Cys Gly Ala Pro Tyr Gly Ala Trp Arg Gly
1               5                   10                  15

Ala Arg Arg Ala Gly Arg Gly Val Ala Gly Gly Ala Gly Ala Gly Arg
            20                  25                  30

Gly Gly Ala Ala Ser Gly Arg Gly Gly Leu Gly Gly Arg Gly Ala Ala
        35                  40                  45

Ala Pro Gly Ala Pro Ala Ala Val Glu Ala Arg Arg Ala Ala Ala Ile
    50                  55                  60

Ala Phe Tyr Gly Asn Arg Ala Arg Gly Arg Arg Asp Phe Leu Cys Pro
65                  70                  75                  80

Lys Ser Val Arg Ser Arg Asn Leu Gly Ala Ala Pro Pro Leu
                85                  90                  95

Ala Gly Ala Gly Arg Ser Gly Ala Ala Pro Ala Gly Arg Lys Trp Ala
            100                 105                 110

Gly Arg Ala Phe Val Arg Arg Ala Ala Val Pro Phe Ser Leu Ser
        115                 120                 125

Ser Leu Gly Ala Val Arg Gly Gly Thr Ala Ala Phe Gly Gly Asp Gly
    130                 135                 140

Ala Gly Arg Gly Ser Ala Ser Gly Val
145                 150

<210> SEQ ID NO 247
<211> LENGTH: 34
<212> TYPE: PRT
<213> ORGANISM: Artificial Sequence
<220> FEATURE:
<223> OTHER INFORMATION: Synthethic

<400> SEQUENCE: 247

Pro Ala Ala Leu Glu Pro Leu Leu Thr Met Phe Met Pro Ser Ser Phe
1               5                   10                  15

Ser Tyr Ser Ser Trp Ala Thr Cys Trp Leu Leu Cys Cys Leu Ile Ile
            20                  25                  30
```

Leu Ala

<210> SEQ ID NO 248
<211> LENGTH: 5652
<212> TYPE: DNA
<213> ORGANISM: Artificial Sequence
<220> FEATURE:
<223> OTHER INFORMATION: Synthethic

<400> SEQUENCE: 248

```
gaattcctcg agacgggtag aacgtgtaaa tctcgagtgc gagaccgaag ctcaaactcg      60
agagagcctt ctgccaacga cgccaccatg aaccgcgcag tttgccaagt tgcgctagag     120
aatgatgaaa gggaagcgaa gaatacatgg cgcttggtat tccggatcgc aatcttactt     180
ttaacagtaa tgaccttagc catctctgca gccgccctgg catatagtta cccatgttgt     240
cacgtcactc agctccgcgc tcaacacctt ctcgcgttgg aaaacattag cgacatttac     300
ctggtgagca atcagacatg cgacggcttt agcctggcct ccttaaattc acctaagaat     360
gggagcaacc agctggtcat cagccgctgc gcaaacggac tcaacgtggt ctccttcttt     420
atctccatcc tgaagcgaag cagctccgcc ctcacgggcc atctccgtga gttgttaacc     480
accctggaga ctctttacgg ttcattctca gtggaagacc tgtttggtgc aacttaaac     540
agatacgcat ggcatcgcgg gggcccggca cactcagcc tgcctccaga tcatcccaac     600
tcttctgccc gaagcccacc ccccgatcct ggcgccgccg gcgccggcgc catggtgagc     660
aagggcgagg agctgttcac cggggtggtg cccatcctgg tcgagctgga cggcgacgta     720
aacggccaca gttcagcgt gtctggcgag ggcgagggcg atgccaccta cggcaagctg     780
accctgaagt tcatctgcac caccggcaag ctgcccgtgc cctggcccac cctcgtgacc     840
accctgacct acggcgtgca gtgcttcagc cgctaccccg accacatgaa gcagcacgac     900
ttcttcaagt ccgccatgcc cgaaggctac gtccaggagc gcaccatctt cttcaaggac     960
gacggcaact acaagacccg cgccgaggtg aagttcgagg gcgacaccct ggtgaaccgc    1020
atcgagctga agggcatcga cttcaaggag gacggcaaca tcctgggca caagctggag    1080
tacaactaca acagccacaa cgtctatatc atggccgaca agcagaagaa cggcatcaag    1140
gcgaacttca agatccgcca caacatcgag gacggcagcg tgcagctcgc cgaccactac    1200
cagcagaaca cccccatcgg cgacggcccc gtgctgctgc ccgacaacca ctacctgagc    1260
acccagtccg ccctgagcaa agaccccaac gagaagcgcg atcacatggt cctgctggag    1320
ttcgtgaccg ccgccgggat cactctcggc atggacgagc tgtacaagta ataatggcca    1380
atgccctggc tcacaaatac cactgagatc taagcttggc gtaatcatgg tcatagctgt    1440
ttcctgtgtg aaattgttat ccgctcacaa ttccacacaa catacgagcc ggaagcataa    1500
agtgtaaagc ctgggtgcct aatgagtgag ctaactcaca ttaattgcgt tgcgctcact    1560
gcccgctttc cagtcgggaa acctgtcgtg ccagcggatc cgcatctcaa ttagtcagca    1620
accatagtcc cgcccctaac tccgcccatc ccgcccctaa ctccgcccag ttccgcccat    1680
tctccgcccc atggctgact aatttttttt atttatgcag aggccgaggc cgcctcggcc    1740
tctgagctat tccagaagta gtgaggaggc ttttttggag gcctaggctt ttgcaaaaag    1800
ctaacttgtt tattgcagct tataatggtt acaaataaag caatagcatc acaaatttca    1860
caaataaagc atttttttca ctgcattcta gttgtggttt gtccaaactc atcaatgtat    1920
cttatcatgt ctggatccgc tgcattaatg aatcggccaa cgcgcgggga gaggcggttt    1980
```

```
gcgtattggg cgctcttccg cttcctcgct cactgactcg ctgcgctcgg tcgttcggct      2040
gcggcgagcg gtatcagctc actcaaaggc ggtaatacgg ttatccacag aatcagggat      2100
aacgcaggaa agaacatgtg agcaaaaggc cagcaaaagg ccaggaaccg taaaaaggcc      2160
gcgttgctgg cgttttttcca taggctccgc cccctgacg agcatcacaa aaatcgacgc      2220
tcaagtcaga ggtggcgaaa cccgacagga ctataaagat accaggcgtt ccccctgga      2280 agctccctcg tgcgctctcc tgttccgacc ctgccgctta ccggatacct gtccgccttt      2340
ctcccttcgg gaagcgtggc gctttctcat agctcacgct gtaggtatct cagttcggtg      2400
taggtcgttc gctccaagct gggctgtgtg cacgaacccc ccgttcagcc cgaccgctgc      2460
gccttatccg gtaactatcg tcttgagtcc aacccggtaa gacacgactt atcgccactg      2520
gcagcagcca ctggtaacag gattagcaga gcgaggtatg taggcggtgc tacagagttc      2580
ttgaagtggt ggcctaacta cggctacact agaagaacag tatttggtat ctgcgctctg      2640
ctgaagccag ttaccttcgg aaaaagagtt ggtagctctt gatccggcaa acaaaccacc      2700
gctggtagcg gtggtttttt tgtttgcaag cagcagatta cgcgcagaaa aaaggatct      2760 caagaagatc ctttgatctt ttctacgggg tctgacgctc agtggaacga aaactcacgt      2820
taagggattt tggtcatgag attatcaaaa aggatcttca cctagatcct tttaaattaa      2880
aaatgaagtt ttaaatcaat ctaaagtata tgagtaaa cttggtctga cagttaccaa      2940
tgcttaatca gtgaggcacc tatctcagcg atctgtctat ttcgttcatc catagttgcc      3000
tgactccccg tcgtgtagat aactacgata cgggagggct taccatctgg ccccagtgct      3060
gcaatgatac cgcgagaccc acgctcaccg gctccagatt tatcagcaat aaaccagcca      3120
gccggaaggg ccgagcgcag aagtggtcct gcaactttat ccgcctccat ccagtctatt      3180
aattgttgcc gggaagctag agtaagtagt tcgccagtta atagtttgcg caacgttgtt      3240
gccattgcta caggcatcgt ggtgtcacgc tcgtcgtttg gtatggcttc attcagctcc      3300
ggttcccaac gatcaaggcg agttacatga tcccccatgt tgtgcaaaaa agcggttagc      3360
tccttcggtc ctccgatcgt tgtcagaagt aagttggccg cagtgttatc actcatggtt      3420
atggcagcac tgcataattc tcttactgtc atgccatccg taagatgctt ttctgtgact      3480
ggtgagtact caaccaagtc attctgagaa tagtgtatgc ggcgaccgag ttgctcttgc      3540
ccggcgtcaa tacgggataa taccgcgcca catagcagaa ctttaaaagt gctcatcatt      3600
ggaaaacgtt cttcggggcg aaaactctca aggatcttac cgctgttgag atccagttcg      3660
atgtaaccca ctcgtgcacc caactgatct tcagcatctt ttactttcac cagcgtttct      3720
gggtgagcaa aaacaggaag gcaaaatgcc gcaaaaaagg gaataagggc gacacggaaa      3780
tgttgaatac tcatactctt cctttttcaa tattattgaa gcatttatca gggttattgt      3840
ctcatgagcg gatacatatt tgaatgtatt tagaaaaata aacaaatagg ggttccgcgc      3900
acatttcccc gaaaagtgcc acctgggtcg acattgatta ttgactagtt attaatagta      3960
atcaattacg gggtcattag ttcatagccc atatatggag ttccgcgtta cataacttac      4020
ggtaaatggc ccgcctggct gaccgcccaa cgacccccgc ccattgacgt caataatgac      4080
gtatgttccc atagtaacgc caatagggac tttccattga cgtcaatggg tggagtattt      4140
acggtaaact gcccacttgg cagtacatca agtgtatcat atgccaagta cgccccctat      4200
tgacgtcaat gacggtaaat ggcccgcctg gcattatgcc cagtacatga ccttatggga      4260
ctttcctact tggcagtaca tctacgtatt agtcatcgct attaccatgg tcgaggtgag      4320
ccccacgttc tgcttcactc tccccatctc ccccccctcc ccacccccaa ttttgtattt      4380
```

```
atttatttttt taattatttt gtgcagcgat gggggcgggg gggggggggg ggcccccccc    4440
aggcggggcg gggcggggcg aggggcgggg cgggcgagg cggaaaggtg cggcggcagc      4500
caatcagagc ggcgcgctcc gaaagtttcc ttttatggcg aggcggcggc ggcggcggcc     4560
ctataaaaag cgaagcgcgc ggcggcgggg agtcgttgcg cgctgccttc cccccgtgcc     4620
ccgctccgcc gccgcctcgc gccgcccgcc ccggctctga ctgaccgcgt tactcccaca     4680
ggtgagcggg cgggacggcc cttctcctcc gggctgtaat tagcgcttgg tttaatgacg     4740
gcttgtttct tttctgtggc tgcgtgaaag ccttgagggg ctccgggagg gcctttgtg     4800 cggggggagc ggctcggggg gtgcgtgcgt gtgtgtgtgc gtggggagcg ccgcgtgcgg    4860
ctccgcgctg cccggcggct gtgagcgctg cgggcgcggc gcgggctttt gtgcgctccg    4920
cagtgtgcgc gaggggagcg cggccggggg cggtgccccg cggtgcgggg ggggctgcga    4980
ggggaacaaa ggctgcgtgc ggggtgtgtg cgtggggggg tgagcagggg gtgtgggcgc    5040
gtcggtcggg ctgcaacccc ccctgcaccc ccctccccga gttgctgagc acggccggc     5100 ttcgggtgcg gggctccgta cggggcgtgg cgcggggctc gccgtgccgg gcgggggtg     5160 gcggcaggtg ggggtgccgg gcggggcggg gccgcctcgg gccggggagg gctcggggga    5220
aggggcgcgg cggcccccgg agcgccggcg gctgtcgagg gcgcggcgagc cgcagccatt   5280 gcctttatg gtaatcgtgc gagagggcgc agggacttcc tttgtcccaa atctgtgcgg    5340
agccgaaatc tgggaggcgc cgccgcaccc cctctagcgg gcgcgggggcg aagcggtgcg   5400 gcgccggcag gaaggaaatg ggcggggagg gccttcgtgc gtcgccgcgc cgccgtcccc    5460
ttctccctct ccagcctcgg ggctgtccgc gggggacgg ctgccttcgg gggggacggg    5520
gcagggcggg gttcggcttc tggcgtgtga ccggcggctc tagagcctct gctaaccatg   5580
ttcatgcctt cttcttttc ctacagctcc tgggcaacgt gctggttatt gtgctgtctc    5640
atcattttgg ca                                                        5652

<210> SEQ ID NO 249
<211> LENGTH: 57
<212> TYPE: PRT
<213> ORGANISM: Artificial Sequence
<220> FEATURE:
<223> OTHER INFORMATION: Synthethic

<400> SEQUENCE: 249

Ser Arg Val Ser Val Met Thr Val Lys Thr Ser Asp Thr Cys Ser Ser
1               5                   10                  15

Arg Arg Arg Ser Gln Leu Val Cys Lys Arg Met Pro Gly Ala Asp Lys
            20                  25                  30

Pro Val Arg Ala Arg Gln Arg Val Leu Ala Gly Val Gly Ala Gly Leu
        35                  40                  45

Thr Met Arg His Gln Ser Arg Leu Tyr
    50                  55

<210> SEQ ID NO 250
<211> LENGTH: 13
<212> TYPE: PRT
<213> ORGANISM: Artificial Sequence
<220> FEATURE:
<223> OTHER INFORMATION: Synthethic

<400> SEQUENCE: 250

Glu Cys Thr Ile Cys Gly Val Lys Tyr Arg Thr Asp Ala
1               5                   10
```

<210> SEQ ID NO 251
<211> LENGTH: 41
<212> TYPE: PRT
<213> ORGANISM: Artificial Sequence
<220> FEATURE:
<223> OTHER INFORMATION: Synthethic

<400> SEQUENCE: 251

Gly Glu Asn Thr Ala Ser Gly Ala Ile Arg His Ser Gly Cys Ala Thr
1               5                   10                  15

Val Gly Lys Gly Asp Arg Cys Gly Pro Leu Arg Tyr Tyr Ala Ser Trp
            20                  25                  30

Arg Lys Gly Asp Val Leu Gln Gly Asp
        35                  40

<210> SEQ ID NO 252
<211> LENGTH: 2
<212> TYPE: PRT
<213> ORGANISM: Artificial Sequence
<220> FEATURE:
<223> OTHER INFORMATION: Synthethic

<400> SEQUENCE: 252

Val Gly
1

<210> SEQ ID NO 253
<211> LENGTH: 25
<212> TYPE: PRT
<213> ORGANISM: Artificial Sequence
<220> FEATURE:
<223> OTHER INFORMATION: Synthethic

<400> SEQUENCE: 253

Arg Gln Gly Phe Pro Ser His Asp Val Val Lys Arg Arg Pro Val Asn
1               5                   10                  15

Ser Ser Ser Val Pro Arg Glu Cys Ile
            20                  25

<210> SEQ ID NO 254
<211> LENGTH: 746
<212> TYPE: PRT
<213> ORGANISM: Artificial Sequence
<220> FEATURE:
<223> OTHER INFORMATION: Synthethic

<400> SEQUENCE: 254

Ile Ser Asp Pro Gly Pro Val Asp Cys Ser Asp Ala Thr Met Gln Leu
1               5                   10                  15

Leu Cys Val Phe Cys Leu Val Leu Leu Trp Glu Val Gly Ala Ala Ser
            20                  25                  30

Leu Ser Glu Val Lys Leu His Leu Asp Ile Glu Gly His Ala Ser His
        35                  40                  45

Tyr Thr Ile Pro Trp Thr Glu Leu Met Ala Lys Val Pro Gly Leu Ser
    50                  55                  60

Pro Glu Ala Leu Trp Arg Glu Ala Asn Val Thr Glu Asp Leu Ala Ser
65                  70                  75                  80

Met Leu Asn Arg Tyr Lys Leu Ile Tyr Lys Thr Ser Gly Thr Leu Gly
                85                  90                  95

Ile Ala Leu Ala Glu Pro Val Asp Ile Pro Ala Val Ser Glu Gly Ser
            100                 105                 110

```
Met Gln Val Asp Ala Ser Lys Val His Pro Gly Val Ile Ser Gly Leu
        115                 120                 125

Asn Ser Pro Ala Cys Met Leu Ser Ala Pro Leu Glu Lys Gln Leu Phe
        130                 135                 140

Tyr Tyr Ile Gly Thr Met Leu Pro Asn Thr Arg Pro His Ser Tyr Val
145                 150                 155                 160

Phe Tyr Gln Leu Arg Cys His Leu Ser Tyr Val Ala Leu Ser Ile Asn
                165                 170                 175

Gly Asp Lys Phe Gln Tyr Thr Gly Ala Met Thr Ser Lys Phe Leu Met
                180                 185                 190

Gly Thr Tyr Lys Arg Val Thr Glu Lys Gly Asp Glu His Val Leu Ser
            195                 200                 205

Leu Val Phe Gly Lys Thr Lys Asp Leu Pro Asp Leu Arg Gly Pro Phe
        210                 215                 220

Ser Tyr Pro Ser Leu Thr Ser Ala Gln Ser Gly Asp Tyr Ser Leu Val
225                 230                 235                 240

Ile Val Thr Thr Phe Val His Tyr Ala Asn Phe His Asn Tyr Phe Val
                245                 250                 255

Pro Asn Leu Lys Asp Met Phe Ser Arg Ala Val Thr Met Thr Ala Ala
                260                 265                 270

Ser Tyr Ala Arg Tyr Val Leu Gln Lys Leu Val Leu Leu Glu Met Lys
            275                 280                 285

Gly Gly Cys Arg Glu Pro Glu Leu Asp Thr Glu Thr Leu Thr Thr Met
        290                 295                 300

Phe Glu Val Ser Val Ala Phe Phe Lys Val His Ala Val Gly Glu
305                 310                 315                 320

Thr Gly Asn Gly Cys Val Asp Leu Arg Trp Leu Ala Lys Ser Phe Phe
                325                 330                 335

Glu Leu Thr Val Leu Lys Asp Ile Ile Gly Ile Cys Tyr Gly Ala Thr
                340                 345                 350

Val Lys Gly Met Gln Ser Tyr Gly Leu Glu Arg Leu Ala Ala Met Leu
            355                 360                 365

Met Ala Thr Val Lys Met Glu Glu Leu Gly His Leu Thr Thr Glu Lys
        370                 375                 380

Gln Glu Tyr Ala Leu Arg Leu Ala Thr Val Gly Tyr Pro Lys Ala Gly
385                 390                 395                 400

Val Tyr Ser Gly Leu Ile Gly Gly Ala Thr Ser Val Leu Leu Ser Ala
                405                 410                 415

Tyr Asn Arg His Pro Leu Phe Gln Pro Leu His Thr Val Met Arg Glu
                420                 425                 430

Thr Leu Phe Ile Gly Ser His Val Val Leu Arg Glu Leu Arg Leu Asn
            435                 440                 445

Val Thr Thr Gln Gly Pro Asn Leu Ala Leu Tyr Gln Leu Leu Ser Thr
        450                 455                 460

Ala Leu Cys Ser Ala Leu Glu Ile Gly Glu Val Leu Arg Gly Leu Ala
465                 470                 475                 480

Leu Gly Thr Glu Ser Gly Leu Phe Ser Pro Cys Tyr Leu Ser Leu Arg
                485                 490                 495

Phe Asp Leu Thr Arg Asp Lys Leu Leu Ser Met Ala Pro Gln Glu Ala
                500                 505                 510

Thr Leu Asp Gln Ala Ala Val Ser Asn Ala Val Asp Gly Phe Leu Gly
            515                 520                 525
```

```
Arg Leu Ser Leu Glu Arg Glu Asp Arg Asp Ala Trp His Leu Pro Ala
        530                 535                 540

Tyr Lys Cys Val Asp Arg Leu Asp Lys Val Leu Met Ile Ile Pro Leu
545                 550                 555                 560

Ile Asn Val Thr Phe Ile Ile Ser Ser Asp Arg Glu Val Arg Gly Ser
                565                 570                 575

Ala Leu Tyr Glu Ala Ser Thr Thr Tyr Leu Ser Ser Ser Leu Phe Leu
        580                 585                 590

Ser Pro Val Ile Met Asn Lys Cys Ser Gln Gly Ala Val Ala Gly Glu
        595                 600                 605

Pro Arg Gln Ile Pro Lys Ile Gln Asn Phe Thr Arg Thr Gln Lys Ser
610                 615                 620

Cys Ile Phe Cys Gly Phe Ala Leu Leu Ser Tyr Asp Glu Lys Glu Gly
625                 630                 635                 640

Leu Glu Thr Thr Thr Tyr Ile Thr Ser Gln Glu Val Gln Asn Ser Ile
                645                 650                 655

Leu Ser Ser Asn Tyr Phe Asp Phe Asp Asn Leu His Val His Tyr Leu
            660                 665                 670

Leu Leu Thr Thr Asn Gly Thr Val Met Glu Ile Ala Gly Leu Tyr Glu
        675                 680                 685

Glu Arg Ala His Ala Leu Ile Thr Tyr Ile Ala Leu Thr Ala Ile Ser
690                 695                 700

Leu Val Cys Gly Ile Leu Ser Leu Val Leu Ala Cys Tyr Leu Met Tyr
705                 710                 715                 720

Lys Gln Lys Ala Gln Gln Lys Thr Leu Leu Trp Leu Gly Asn Asn Thr
                725                 730                 735

Leu Gly Gln Met Arg Ala Thr Thr Lys Met
            740                 745

<210> SEQ ID NO 255
<211> LENGTH: 32
<212> TYPE: PRT
<213> ORGANISM: Artificial Sequence
<220> FEATURE:
<223> OTHER INFORMATION: Synthethic

<400> SEQUENCE: 255

Pro Lys Leu Gly Val Ile Met Val Ile Ala Val Ser Cys Val Lys Leu
1               5                   10                  15

Leu Ser Ala His Asn Ser Thr Gln His Thr Ser Arg Lys His Lys Val
            20                  25                  30

<210> SEQ ID NO 256
<211> LENGTH: 54
<212> TYPE: PRT
<213> ORGANISM: Artificial Sequence
<220> FEATURE:
<223> OTHER INFORMATION: Synthethic

<400> SEQUENCE: 256

Ser Leu Gly Cys Leu Met Ser Glu Leu Thr His Ile Asn Cys Val Ala
1               5                   10                  15

Leu Thr Ala Arg Phe Pro Val Gly Lys Pro Val Val Pro Ala Ala Leu
            20                  25                  30

Met Asn Arg Pro Thr Arg Gly Glu Arg Phe Ala Tyr Trp Ala Leu
        35                  40                  45

Phe Arg Phe Leu Ala His
        50
```

```
<210> SEQ ID NO 257
<211> LENGTH: 28
<212> TYPE: PRT
<213> ORGANISM: Artificial Sequence
<220> FEATURE:
<223> OTHER INFORMATION: Synthethic

<400> SEQUENCE: 257

Leu Ala Ala Leu Gly Arg Ser Ala Ala Ala Ser Gly Ile Ser Ser Leu
1               5                   10                  15

Lys Gly Gly Asn Thr Val Ile His Arg Ile Arg Gly
            20                  25

<210> SEQ ID NO 258
<211> LENGTH: 16
<212> TYPE: PRT
<213> ORGANISM: Artificial Sequence
<220> FEATURE:
<223> OTHER INFORMATION: Synthethic

<400> SEQUENCE: 258

Arg Arg Lys Glu His Val Ser Lys Arg Pro Ala Lys Gly Gln Glu Pro
1               5                   10                  15

<210> SEQ ID NO 259
<211> LENGTH: 9
<212> TYPE: PRT
<213> ORGANISM: Artificial Sequence
<220> FEATURE:
<223> OTHER INFORMATION: Synthethic

<400> SEQUENCE: 259

Lys Gly Arg Val Ala Gly Val Phe Pro
1               5

<210> SEQ ID NO 260
<211> LENGTH: 4
<212> TYPE: PRT
<213> ORGANISM: Artificial Sequence
<220> FEATURE:
<223> OTHER INFORMATION: Synthethic

<400> SEQUENCE: 260

Ala Pro Pro Pro
1

<210> SEQ ID NO 261
<211> LENGTH: 57
<212> TYPE: PRT
<213> ORGANISM: Artificial Sequence
<220> FEATURE:
<223> OTHER INFORMATION: Synthethic

<400> SEQUENCE: 261

Arg Ala Ser Gln Lys Ser Thr Leu Lys Ser Glu Val Ala Lys Pro Asp
1               5                   10                  15

Arg Thr Ile Lys Ile Pro Gly Val Ser Pro Trp Lys Leu Pro Arg Ala
            20                  25                  30

Leu Ser Cys Ser Asp Pro Ala Ala Tyr Arg Ile Pro Val Arg Leu Ser
        35                  40                  45

Pro Phe Gly Lys Arg Gly Ala Phe Ser
    50                  55
```

```
<210> SEQ ID NO 262
<211> LENGTH: 3
<212> TYPE: PRT
<213> ORGANISM: Artificial Sequence
<220> FEATURE:
<223> OTHER INFORMATION: Synthethic

<400> SEQUENCE: 262

Leu Thr Leu
1

<210> SEQ ID NO 263
<211> LENGTH: 29
<212> TYPE: PRT
<213> ORGANISM: Artificial Sequence
<220> FEATURE:
<223> OTHER INFORMATION: Synthethic

<400> SEQUENCE: 263

Val Ser Gln Phe Gly Val Gly Arg Ser Leu Gln Ala Gly Leu Cys Ala
1               5                   10                  15

Arg Thr Pro Arg Ser Ala Arg Pro Leu Arg Leu Ile Arg
            20                  25

<210> SEQ ID NO 264
<211> LENGTH: 3
<212> TYPE: PRT
<213> ORGANISM: Artificial Sequence
<220> FEATURE:
<223> OTHER INFORMATION: Synthethic

<400> SEQUENCE: 264

Leu Ser Ser
1

<210> SEQ ID NO 265
<211> LENGTH: 16
<212> TYPE: PRT
<213> ORGANISM: Artificial Sequence
<220> FEATURE:
<223> OTHER INFORMATION: Synthethic

<400> SEQUENCE: 265

Val Gln Pro Gly Lys Thr Arg Leu Ile Ala Thr Gly Ser Ser His Trp
1               5                   10                  15

<210> SEQ ID NO 266
<211> LENGTH: 2
<212> TYPE: PRT
<213> ORGANISM: Artificial Sequence
<220> FEATURE:
<223> OTHER INFORMATION: Synthethic

<400> SEQUENCE: 266

Gln Asp
1

<210> SEQ ID NO 267
<211> LENGTH: 16
<212> TYPE: PRT
<213> ORGANISM: Artificial Sequence
<220> FEATURE:
<223> OTHER INFORMATION: Synthethic

<400> SEQUENCE: 267

Gln Ser Glu Val Cys Arg Arg Cys Tyr Arg Val Leu Glu Val Val Ala
1               5                   10                  15
```

<210> SEQ ID NO 268
<211> LENGTH: 4
<212> TYPE: PRT
<213> ORGANISM: Artificial Sequence
<220> FEATURE:
<223> OTHER INFORMATION: Synthethic

<400> SEQUENCE: 268

Leu Arg Leu His
1

<210> SEQ ID NO 269
<211> LENGTH: 20
<212> TYPE: PRT
<213> ORGANISM: Artificial Sequence
<220> FEATURE:
<223> OTHER INFORMATION: Synthethic

<400> SEQUENCE: 269

Lys Asn Ser Ile Trp Tyr Leu Arg Ser Ala Glu Ala Ser Tyr Leu Arg
1               5                   10                  15

Lys Lys Ser Trp
            20

<210> SEQ ID NO 270
<211> LENGTH: 10
<212> TYPE: PRT
<213> ORGANISM: Artificial Sequence
<220> FEATURE:
<223> OTHER INFORMATION: Synthethic

<400> SEQUENCE: 270

Leu Leu Ile Arg Gln Thr Asn His Arg Trp
1               5                   10

<210> SEQ ID NO 271
<211> LENGTH: 28
<212> TYPE: PRT
<213> ORGANISM: Artificial Sequence
<220> FEATURE:
<223> OTHER INFORMATION: Synthethic

<400> SEQUENCE: 271

Arg Trp Phe Phe Cys Leu Gln Ala Ala Asp Tyr Ala Gln Lys Lys Arg
1               5                   10                  15

Ile Ser Arg Arg Ser Phe Asp Leu Phe Tyr Gly Val
            20                  25

<210> SEQ ID NO 272
<211> LENGTH: 32
<212> TYPE: PRT
<213> ORGANISM: Artificial Sequence
<220> FEATURE:
<223> OTHER INFORMATION: Synthethic

<400> SEQUENCE: 272

Arg Ser Val Glu Arg Lys Leu Thr Leu Arg Asp Phe Gly His Glu Ile
1               5                   10                  15

Ile Lys Lys Asp Leu His Leu Asp Pro Phe Lys Leu Lys Met Lys Phe
            20                  25                  30

<210> SEQ ID NO 273
<211> LENGTH: 6
<212> TYPE: PRT

```
<213> ORGANISM: Artificial Sequence
<220> FEATURE:
<223> OTHER INFORMATION: Synthethic

<400> SEQUENCE: 273

Ile Asn Leu Lys Tyr Ile
1               5

<210> SEQ ID NO 274
<211> LENGTH: 4
<212> TYPE: PRT
<213> ORGANISM: Artificial Sequence
<220> FEATURE:
<223> OTHER INFORMATION: Synthethic

<400> SEQUENCE: 274

Val Asn Leu Val
1

<210> SEQ ID NO 275
<211> LENGTH: 7
<212> TYPE: PRT
<213> ORGANISM: Artificial Sequence
<220> FEATURE:
<223> OTHER INFORMATION: Synthethic

<400> SEQUENCE: 275

Gln Leu Pro Met Leu Asn Gln
1               5

<210> SEQ ID NO 276
<211> LENGTH: 75
<212> TYPE: PRT
<213> ORGANISM: Artificial Sequence
<220> FEATURE:
<223> OTHER INFORMATION: Synthethic

<400> SEQUENCE: 276

Gly Thr Tyr Leu Ser Asp Leu Ser Ile Ser Phe Ile His Ser Cys Leu
1               5                   10                  15

Thr Pro Arg Arg Val Asp Asn Tyr Asp Thr Gly Gly Leu Thr Ile Trp
            20                  25                  30

Pro Gln Cys Cys Asn Asp Thr Ala Arg Pro Thr Leu Thr Gly Ser Arg
        35                  40                  45

Phe Ile Ser Asn Lys Pro Ala Ser Arg Lys Gly Arg Ala Gln Lys Trp
    50                  55                  60

Ser Cys Asn Phe Ile Arg Leu His Pro Val Tyr
65                  70                  75

<210> SEQ ID NO 277
<211> LENGTH: 5
<212> TYPE: PRT
<213> ORGANISM: Artificial Sequence
<220> FEATURE:
<223> OTHER INFORMATION: Synthethic

<400> SEQUENCE: 277

Leu Leu Pro Gly Ser
1               5

<210> SEQ ID NO 278
<211> LENGTH: 2
<212> TYPE: PRT
<213> ORGANISM: Artificial Sequence
<220> FEATURE:
```

<223> OTHER INFORMATION: Synthethic

<400> SEQUENCE: 278

Ser Lys
1

<210> SEQ ID NO 279
<211> LENGTH: 3
<212> TYPE: PRT
<213> ORGANISM: Artificial Sequence
<220> FEATURE:
<223> OTHER INFORMATION: Synthethic

<400> SEQUENCE: 279

Phe Ala Ser
1

<210> SEQ ID NO 280
<211> LENGTH: 44
<212> TYPE: PRT
<213> ORGANISM: Artificial Sequence
<220> FEATURE:
<223> OTHER INFORMATION: Synthethic

<400> SEQUENCE: 280

Phe Ala Gln Arg Cys Cys His Cys Tyr Arg His Arg Gly Val Thr Leu
1               5                   10                  15

Val Val Trp Tyr Gly Phe Ile Gln Leu Arg Phe Pro Thr Ile Lys Ala
            20                  25                  30

Ser Tyr Met Ile Pro His Val Val Gln Lys Ser Gly
        35                  40

<210> SEQ ID NO 281
<211> LENGTH: 10
<212> TYPE: PRT
<213> ORGANISM: Artificial Sequence
<220> FEATURE:
<223> OTHER INFORMATION: Synthethic

<400> SEQUENCE: 281

Leu Leu Arg Ser Ser Asp Arg Cys Gln Lys
1               5                   10

<210> SEQ ID NO 282
<211> LENGTH: 14
<212> TYPE: PRT
<213> ORGANISM: Artificial Sequence
<220> FEATURE:
<223> OTHER INFORMATION: Synthethic

<400> SEQUENCE: 282

Val Gly Arg Ser Val Ile Thr His Gly Tyr Gly Ser Thr Ala
1               5                   10

<210> SEQ ID NO 283
<211> LENGTH: 15
<212> TYPE: PRT
<213> ORGANISM: Artificial Sequence
<220> FEATURE:
<223> OTHER INFORMATION: Synthethic

<400> SEQUENCE: 283

Phe Ser Tyr Cys His Ala Ile Arg Lys Met Leu Phe Cys Asp Trp
1               5                   10                  15

-continued

```
<210> SEQ ID NO 284
<211> LENGTH: 24
<212> TYPE: PRT
<213> ORGANISM: Artificial Sequence
<220> FEATURE:
<223> OTHER INFORMATION: Synthethic

<400> SEQUENCE: 284

Val Leu Asn Gln Val Ile Leu Arg Ile Val Tyr Ala Ala Thr Glu Leu
1               5                   10                  15

Leu Leu Pro Gly Val Asn Thr Gly
            20

<210> SEQ ID NO 285
<211> LENGTH: 4
<212> TYPE: PRT
<213> ORGANISM: Artificial Sequence
<220> FEATURE:
<223> OTHER INFORMATION: Synthethic

<400> SEQUENCE: 285

Tyr Arg Ala Thr
1

<210> SEQ ID NO 286
<211> LENGTH: 95
<212> TYPE: PRT
<213> ORGANISM: Artificial Sequence
<220> FEATURE:
<223> OTHER INFORMATION: Synthethic

<400> SEQUENCE: 286

Gln Asn Phe Lys Ser Ala His His Trp Lys Thr Phe Phe Gly Ala Lys
1               5                   10                  15

Thr Leu Lys Asp Leu Thr Ala Val Glu Ile Gln Phe Asp Val Thr His
            20                  25                  30

Ser Cys Thr Gln Leu Ile Phe Ser Ile Phe Tyr Phe His Gln Arg Phe
        35                  40                  45

Trp Val Ser Lys Asn Arg Lys Ala Lys Cys Arg Lys Lys Gly Asn Lys
    50                  55                  60

Gly Asp Thr Glu Met Leu Asn Thr His Thr Leu Pro Phe Ser Ile Leu
65                  70                  75                  80

Leu Lys His Leu Ser Gly Leu Leu Ser His Glu Arg Ile His Ile
                85                  90                  95

<210> SEQ ID NO 287
<211> LENGTH: 5
<212> TYPE: PRT
<213> ORGANISM: Artificial Sequence
<220> FEATURE:
<223> OTHER INFORMATION: Synthethic

<400> SEQUENCE: 287

Met Tyr Leu Glu Lys
1               5

<210> SEQ ID NO 288
<211> LENGTH: 14
<212> TYPE: PRT
<213> ORGANISM: Artificial Sequence
<220> FEATURE:
<223> OTHER INFORMATION: Synthethic

<400> SEQUENCE: 288
```

-continued

```
Thr Asn Arg Gly Ser Ala His Ile Ser Pro Lys Ser Ala Thr
1               5                   10
```

<210> SEQ ID NO 289
<211> LENGTH: 12
<212> TYPE: PRT
<213> ORGANISM: Artificial Sequence
<220> FEATURE:
<223> OTHER INFORMATION: Synthethic

<400> SEQUENCE: 289

```
Arg Leu Arg Asn His Tyr Tyr His Asp Ile Asn Leu
1               5                   10
```

<210> SEQ ID NO 290
<211> LENGTH: 1
<212> TYPE: PRT
<213> ORGANISM: Artificial Sequence
<220> FEATURE:
<223> OTHER INFORMATION: Synthethic

<400> SEQUENCE: 290

```
Lys
1
```

<210> SEQ ID NO 291
<211> LENGTH: 7
<212> TYPE: PRT
<213> ORGANISM: Artificial Sequence
<220> FEATURE:
<223> OTHER INFORMATION: Synthethic

<400> SEQUENCE: 291

```
Ala Tyr His Glu Ala Leu Ser
1               5
```

<210> SEQ ID NO 292
<211> LENGTH: 4911
<212> TYPE: PRT
<213> ORGANISM: Artificial Sequence
<220> FEATURE:
<223> OTHER INFORMATION: Synthethic

<400> SEQUENCE: 292

```
Thr Cys Gly Cys Gly Cys Gly Thr Thr Cys Gly Thr Gly Ala
1               5                   10                  15

Thr Gly Ala Cys Gly Gly Thr Gly Ala Ala Ala Cys Cys Thr Cys
                20                  25                  30

Thr Gly Ala Cys Ala Cys Ala Thr Gly Cys Ala Gly Cys Thr Cys Cys
            35                  40                  45

Cys Gly Gly Ala Gly Ala Cys Gly Gly Thr Cys Ala Cys Ala Gly Cys
        50                  55                  60

Thr Thr Gly Thr Cys Thr Gly Thr Ala Ala Gly Cys Gly Gly Ala Thr
65                  70                  75                  80

Gly Cys Cys Gly Gly Gly Ala Gly Cys Ala Gly Ala Cys Ala Ala Gly
                85                  90                  95

Cys Cys Cys Gly Thr Cys Ala Gly Gly Gly Cys Gly Cys Gly Thr Cys
                100                 105                 110

Ala Gly Cys Gly Gly Gly Thr Gly Thr Thr Gly Gly Cys Gly Gly Gly
            115                 120                 125

Thr Gly Thr Cys Gly Gly Gly Gly Cys Thr Gly Gly Cys Thr Thr Ala
        130                 135                 140
```

```
Ala Cys Thr Ala Thr Gly Cys Gly Gly Cys Ala Thr Cys Ala Gly Ala
145                 150                 155                 160

Gly Cys Ala Gly Ala Thr Thr Gly Thr Ala Cys Thr Gly Ala Gly Ala
                165                 170                 175

Gly Thr Gly Cys Ala Cys Cys Ala Thr Ala Gly Cys Gly Gly Thr
                180                 185                 190

Gly Thr Gly Ala Ala Ala Thr Ala Cys Cys Gly Cys Ala Cys Ala Gly
                195                 200                 205

Ala Thr Gly Cys Gly Thr Ala Ala Gly Gly Ala Gly Ala Ala Ala Ala
210                 215                 220

Thr Ala Cys Cys Gly Cys Ala Thr Cys Ala Gly Gly Cys Gly Cys Cys
225                 230                 235                 240

Ala Thr Thr Cys Gly Cys Cys Ala Thr Thr Cys Ala Gly Gly Cys Thr
                245                 250                 255

Gly Cys Gly Cys Ala Ala Cys Thr Gly Thr Thr Gly Gly Gly Ala Ala
                260                 265                 270

Gly Gly Gly Cys Gly Ala Thr Cys Gly Gly Thr Gly Cys Gly Gly Gly
                275                 280                 285

Cys Cys Thr Cys Thr Thr Cys Gly Cys Thr Ala Thr Thr Ala Cys Gly
290                 295                 300

Cys Cys Ala Gly Cys Thr Gly Gly Cys Gly Ala Ala Ala Gly Gly Gly
305                 310                 315                 320

Gly Gly Ala Thr Gly Thr Gly Cys Thr Gly Cys Ala Ala Gly Gly Cys
                325                 330                 335

Gly Ala Thr Thr Ala Ala Gly Thr Thr Gly Gly Gly Thr Ala Ala Cys
                340                 345                 350

Gly Cys Cys Ala Gly Gly Gly Thr Thr Thr Thr Cys Cys Cys Ala Gly
                355                 360                 365

Thr Cys Ala Cys Gly Ala Cys Gly Thr Thr Gly Thr Ala Ala Ala Ala
                370                 375                 380

Cys Gly Ala Cys Gly Gly Cys Cys Ala Gly Thr Gly Ala Ala Thr Thr
385                 390                 395                 400

Cys Gly Ala Gly Cys Thr Cys Gly Gly Thr Ala Cys Cys Thr Cys Gly
                405                 410                 415

Cys Gly Ala Ala Thr Gly Cys Ala Thr Cys Thr Ala Gly Ala Thr Ala
                420                 425                 430

Thr Cys Gly Gly Ala Thr Cys Cys Cys Gly Gly Gly Cys Cys Cys Gly
                435                 440                 445

Thr Cys Gly Ala Cys Thr Gly Cys Ala Gly Cys Ala Cys Gly Cys Gly
                450                 455                 460

Cys Ala Cys Cys Ala Thr Gly Cys Ala Gly Thr Thr Gly Cys Thr Cys
465                 470                 475                 480

Thr Gly Thr Gly Thr Thr Thr Thr Thr Gly Cys Cys Thr Gly Thr Gly
                485                 490                 495

Thr Gly Thr Thr Gly Cys Thr Ala Thr Gly Gly Ala Gly Gly Thr
                500                 505                 510

Gly Gly Gly Gly Gly Cys Thr Gly Cys Cys Ala Gly Cys Cys Thr Cys
                515                 520                 525

Ala Gly Cys Gly Ala Gly Gly Thr Thr Ala Ala Cys Thr Gly Cys
                530                 535                 540

Ala Cys Cys Thr Gly Gly Ala Cys Ala Thr Gly Ala Gly Gly Gly
545                 550                 555                 560

Gly Cys Ala Thr Gly Cys Thr Thr Cys Gly Cys Ala Thr Thr Ala Cys
```

```
                565                 570                 575

Ala Cys Cys Ala Thr Cys Cys Cys Ala Thr Gly Gly Ala Cys Cys Gly
            580                 585                 590

Ala Ala Cys Thr Gly Ala Thr Gly Gly Cys Ala Ala Ala Gly Gly Thr
        595                 600                 605

Cys Cys Cys Ala Gly Gly Cys Cys Thr Thr Ala Gly Cys Cys Cys Ala
    610                 615                 620

Gly Ala Gly Gly Cys Gly Cys Thr Gly Thr Gly Gly Ala Gly Ala Gly
625                 630                 635                 640

Ala Gly Gly Cys Ala Ala Ala Thr Gly Thr Cys Ala Cys Cys Gly Ala
                645                 650                 655

Ala Gly Ala Thr Thr Thr Gly Gly Cys Gly Thr Cys Thr Ala Thr Gly
            660                 665                 670

Cys Thr Thr Ala Ala Cys Cys Gly Cys Thr Ala Cys Ala Ala Gly Thr
        675                 680                 685

Thr Ala Ala Thr Thr Thr Ala Cys Ala Ala Gly Ala Cys Gly Thr Cys
    690                 695                 700

Thr Gly Gly Thr Ala Cys Cys Cys Thr Thr Gly Gly Thr Ala Thr Thr
705                 710                 715                 720

Gly Cys Gly Cys Thr Gly Gly Cys Cys Gly Ala Gly Cys Cys Thr Gly
                725                 730                 735

Thr Cys Gly Ala Thr Ala Thr Cys Cys Cys Thr Gly Cys Thr Gly Thr
            740                 745                 750

Cys Thr Cys Thr Gly Ala Ala Gly Gly Ala Thr Cys Cys Ala Thr Gly
        755                 760                 765

Cys Ala Ala Gly Thr Gly Gly Ala Thr Gly Cys Ala Thr Cys Thr Ala
    770                 775                 780

Ala Gly Gly Thr Cys Cys Ala Thr Cys Cys Cys Gly Gly Ala Gly Thr
785                 790                 795                 800

Cys Ala Thr Thr Ala Gly Cys Gly Gly Cys Cys Thr Gly Ala Ala Thr
                805                 810                 815

Thr Cys Cys Cys Cys Thr Gly Cys Cys Thr Gly Cys Ala Thr Gly Cys
            820                 825                 830

Thr Thr Ala Gly Thr Gly Cys Cys Cys Cys Cys Cys Thr Thr Gly Ala
        835                 840                 845

Gly Ala Ala Gly Cys Ala Gly Cys Thr Cys Thr Thr Cys Thr Ala Cys
    850                 855                 860

Thr Ala Thr Ala Thr Thr Gly Gly Cys Ala Cys Cys Ala Thr Gly Cys
865                 870                 875                 880

Thr Gly Cys Cys Cys Ala Ala Cys Ala Cys Gly Cys Gly Gly Cys Cys
                885                 890                 895

Ala Cys Ala Cys Ala Gly Cys Thr Ala Thr Gly Thr Cys Thr Thr Thr
            900                 905                 910

Thr Ala Thr Cys Ala Gly Cys Thr Gly Cys Gly Cys Thr Gly Thr Cys
        915                 920                 925

Ala Cys Thr Thr Gly Thr Cys Thr Thr Ala Thr Gly Thr Gly Gly Cys
    930                 935                 940

Cys Cys Thr Gly Thr Cys Cys Ala Thr Cys Ala Ala Cys Gly Gly Gly
945                 950                 955                 960

Gly Ala Cys Ala Ala Gly Thr Thr Thr Cys Ala Gly Thr Ala Cys Ala
                965                 970                 975

Cys Gly Gly Gly Gly Gly Cys Cys Ala Thr Gly Ala Cys Thr Thr Cys
            980                 985                 990
```

```
Thr Ala Ala Ala Thr Thr Thr Cys  Thr Gly Ala Thr Gly  Gly Gly Cys
        995                 1000                 1005

Ala Cys Cys Thr Ala Cys Ala  Ala Gly Cys Gly Ala  Gly Thr Gly
    1010                1015                 1020

Ala Cys Cys Gly Ala Gly Ala  Ala Gly Gly Gly Ala  Gly Ala Thr
    1025                1030                 1035

Gly Ala Gly Cys Ala Thr Gly  Thr Gly Thr Thr Gly  Ala Gly Cys
    1040                1045                 1050

Cys Thr Gly Gly Thr Cys Thr  Thr Thr Gly Gly Cys  Ala Ala Gly
    1055                1060                 1065

Ala Cys Gly Ala Ala Gly Gly  Ala Cys Cys Thr Gly  Cys Cys Gly
    1070                1075                 1080

Gly Ala Thr Cys Thr Gly Ala  Gly Gly Gly Gly Cys  Cys Thr
    1085                1090                 1095

Thr Thr Thr Ala Gly Thr Thr  Ala Cys Cys Cys Ala  Thr Cys Cys
    1100                1105                 1110

Thr Thr Ala Ala Cys Cys Ala  Gly Thr Gly Cys Cys  Cys Ala Ala
    1115                1120                 1125

Ala Gly Cys Gly Gly Gly Gly  Ala Cys Thr Ala Thr  Thr Cys Cys
    1130                1135                 1140

Cys Thr Gly Gly Thr Gly Ala  Thr Thr Gly Thr Thr  Ala Cys Ala
    1145                1150                 1155

Ala Cys Cys Thr Thr Thr Gly  Thr Gly Cys Ala Thr  Thr Ala Thr
    1160                1165                 1170

Gly Cys Cys Ala Ala Cys Thr  Thr Thr Cys Ala Cys  Ala Ala Cys
    1175                1180                 1185

Thr Ala Cys Thr Thr Thr Gly  Thr Ala Cys Cys Cys  Ala Ala Cys
    1190                1195                 1200

Cys Thr Gly Ala Ala Gly Gly  Ala Thr Ala Thr Gly  Thr Thr Thr
    1205                1210                 1215

Thr Cys Cys Cys Gly Ala Gly  Cys Cys Gly Thr Cys  Ala Cys Cys
    1220                1225                 1230

Ala Thr Gly Ala Cys Ala Gly  Cys Cys Gly Cys Cys  Ala Gly Cys
    1235                1240                 1245

Thr Ala Cys Gly Cys Thr Cys  Gly Cys Thr Ala Cys  Gly Thr Thr
    1250                1255                 1260

Cys Thr Cys Cys Ala Gly Ala  Ala Ala Cys Thr Gly  Gly Thr Cys
    1265                1270                 1275

Cys Thr Gly Cys Thr Gly Gly  Ala Gly Ala Thr Gly  Ala Ala Gly
    1280                1285                 1290

Gly Gly Ala Gly Gly Cys Thr  Gly Cys Cys Gly Gly  Gly Ala Gly
    1295                1300                 1305

Cys Cys Gly Gly Ala Ala Cys  Thr Gly Gly Ala Cys  Ala Cys Gly
    1310                1315                 1320

Gly Ala Ala Ala Cys Gly Cys  Thr Gly Ala Cys Thr  Ala Cys Cys
    1325                1330                 1335

Ala Thr Gly Thr Thr Thr Gly  Ala Gly Gly Thr Thr  Thr Cys Thr
    1340                1345                 1350

Gly Thr Gly Gly Cys Cys Thr  Thr Cys Thr Thr Thr  Ala Ala Gly
    1355                1360                 1365

Gly Thr Gly Gly Gly Thr Cys  Ala Thr Gly Cys Thr  Gly Thr Gly
    1370                1375                 1380
```

```
Gly Gly Thr Gly Ala Gly Ala Cys Thr Gly Gly Cys Ala Ala Thr
    1385            1390            1395

Gly Gly Cys Thr Gly Cys Gly Thr Gly Gly Ala Cys Cys Thr Cys
    1400            1405            1410

Cys Gly Cys Thr Gly Gly Thr Thr Gly Gly Cys Cys Ala Ala Gly
    1415            1420            1425

Ala Gly Cys Thr Thr Cys Thr Thr Thr Gly Ala Gly Cys Thr Gly
    1430            1435            1440

Ala Cys Thr Gly Thr Cys Cys Thr Gly Ala Ala Ala Gly Ala Cys
    1445            1450            1455

Ala Thr Cys Ala Thr Cys Gly Gly Cys Ala Thr Ala Thr Gly Thr
    1460            1465            1470

Thr Ala Thr Gly Gly Gly Gly Cys Cys Ala Cys Thr Gly Thr Cys
    1475            1480            1485

Ala Ala Gly Gly Gly Cys Ala Thr Gly Cys Ala Ala Thr Cys Cys
    1490            1495            1500

Thr Ala Cys Gly Gly Gly Cys Thr Gly Gly Ala Gly Cys Gly Cys
    1505            1510            1515

Thr Thr Gly Gly Cys Cys Gly Cys Cys Ala Thr Gly Cys Thr Gly
    1520            1525            1530

Ala Thr Gly Gly Cys Cys Ala Cys Gly Gly Thr Cys Ala Ala Gly
    1535            1540            1545

Ala Thr Gly Gly Ala Gly Gly Ala Gly Cys Thr Gly Gly Gly Thr
    1550            1555            1560

Cys Ala Cys Cys Thr Gly Ala Cys Thr Ala Cys Thr Gly Ala Gly
    1565            1570            1575

Ala Ala Ala Cys Ala Gly Gly Ala Gly Thr Ala Cys Gly Cys Gly
    1580            1585            1590

Cys Thr Gly Ala Gly Gly Thr Thr Ala Gly Cys Cys Ala Cys Cys
    1595            1600            1605

Gly Thr Cys Gly Gly Cys Thr Ala Cys Cys Cys Ala Ala Gly
    1610            1615            1620

Gly Cys Cys Gly Gly Gly Gly Thr Thr Thr Ala Cys Ala Gly Thr
    1625            1630            1635

Gly Gly Cys Cys Thr Cys Ala Thr Thr Gly Gly Ala Gly Gly Cys
    1640            1645            1650

Gly Cys Cys Ala Cys Ala Thr Cys Thr Gly Thr Gly Cys Thr Thr
    1655            1660            1665

Cys Thr Cys Thr Cys Gly Gly Cys Cys Thr Ala Cys Ala Ala Cys
    1670            1675            1680

Cys Gly Cys Cys Ala Cys Cys Cys Cys Thr Thr Thr Cys
    1685            1690            1695

Cys Ala Gly Cys Cys Cys Thr Gly Cys Ala Thr Ala Cys Cys
    1700            1705            1710

Gly Thr Gly Ala Thr Gly Ala Gly Ala Gly Ala Cys Cys
    1715            1720            1725

Cys Thr Gly Thr Thr Ala Thr Cys Gly Gly Cys Ala Gly Cys
    1730            1735            1740

Cys Ala Cys Gly Thr Gly Gly Thr Gly Cys Thr Ala Cys Gly Cys
    1745            1750            1755

Gly Ala Gly Thr Thr Gly Cys Gly Gly Cys Thr Gly Ala Ala Cys
    1760            1765            1770

Gly Thr Gly Ala Cys Thr Ala Cys Cys Cys Ala Gly Gly Gly Gly
```

```
                 1775                1780                1785
Cys  Cys  Cys  Ala  Ala  Cys  Cys  Thr  Thr  Gly  Cys  Cys  Cys  Thr  Ala
     1790                1795                1800

Thr  Ala  Cys  Cys  Ala  Ala  Cys  Thr  Gly  Cys  Thr  Gly  Thr  Cys  Cys
     1805                1810                1815

Ala  Cys  Cys  Gly  Cys  Cys  Thr  Gly  Thr  Gly  Cys  Thr  Cys  Gly
     1820                1825                1830

Gly  Cys  Cys  Cys  Thr  Ala  Gly  Ala  Gly  Ala  Thr  Thr  Gly  Gly  Gly
     1835                1840                1845

Gly  Ala  Gly  Gly  Thr  Thr  Thr  Thr  Gly  Cys  Gly  Gly  Gly  Gly  Gly
     1850                1855                1860

Cys  Thr  Ala  Gly  Cys  Cys  Cys  Thr  Gly  Gly  Gly  Ala  Cys  Ala
     1865                1870                1875

Gly  Ala  Gly  Ala  Gly  Cys  Gly  Gly  Gly  Cys  Thr  Cys  Thr  Thr  Cys
     1880                1885                1890

Thr  Cys  Ala  Cys  Cys  Gly  Thr  Gly  Cys  Thr  Ala  Cys  Cys  Thr  Cys
     1895                1900                1905

Ala  Gly  Cys  Cys  Thr  Ala  Cys  Gly  Ala  Thr  Thr  Gly  Ala  Cys
     1910                1915                1920

Cys  Thr  Cys  Ala  Cys  Ala  Cys  Gly  Ala  Gly  Ala  Cys  Ala  Ala  Gly
     1925                1930                1935

Cys  Thr  Gly  Cys  Thr  Gly  Ala  Gly  Cys  Ala  Thr  Gly  Gly  Cys  Cys
     1940                1945                1950

Cys  Cys  Cys  Cys  Ala  Gly  Gly  Ala  Gly  Gly  Cys  Ala  Ala  Cys  Gly
     1955                1960                1965

Cys  Thr  Gly  Gly  Ala  Cys  Cys  Ala  Gly  Cys  Gly  Gly  Cys  Cys  Cys
     1970                1975                1980

Gly  Thr  Thr  Thr  Cys  Ala  Ala  Ala  Thr  Gly  Cys  Thr  Gly  Thr  Gly
     1985                1990                1995

Gly  Ala  Thr  Gly  Gly  Gly  Thr  Thr  Thr  Cys  Thr  Gly  Gly  Gly
     2000                2005                2010

Cys  Gly  Gly  Cys  Thr  Cys  Thr  Cys  Thr  Thr  Thr  Gly  Gly  Ala  Gly
     2015                2020                2025

Cys  Gly  Ala  Gly  Ala  Ala  Gly  Ala  Cys  Ala  Gly  Gly  Gly  Ala  Thr
     2030                2035                2040

Gly  Cys  Gly  Thr  Gly  Gly  Cys  Ala  Thr  Cys  Thr  Cys  Cys  Cys  Cys
     2045                2050                2055

Gly  Cys  Cys  Thr  Ala  Cys  Ala  Ala  Ala  Thr  Gly  Cys  Gly  Thr  Gly
     2060                2065                2070

Gly  Ala  Cys  Ala  Gly  Gly  Cys  Thr  Cys  Gly  Ala  Cys  Ala  Ala  Ala
     2075                2080                2085

Gly  Thr  Thr  Cys  Thr  Gly  Ala  Thr  Gly  Ala  Thr  Thr  Ala  Thr  Cys
     2090                2095                2100

Cys  Cys  Gly  Cys  Thr  Cys  Ala  Thr  Cys  Ala  Ala  Thr  Gly  Thr  Gly
     2105                2110                2115

Ala  Cys  Ala  Thr  Thr  Cys  Ala  Thr  Ala  Ala  Thr  Cys  Thr  Cys  Thr
     2120                2125                2130

Ala  Gly  Thr  Gly  Ala  Cys  Cys  Gly  Thr  Gly  Ala  Gly  Gly  Thr  Cys
     2135                2140                2145

Cys  Gly  Ala  Gly  Gly  Cys  Thr  Cys  Gly  Gly  Cys  Gly  Cys  Thr  Ala
     2150                2155                2160

Thr  Ala  Cys  Gly  Ala  Gly  Gly  Cys  Cys  Ala  Gly  Cys  Ala  Cys  Cys
     2165                2170                2175
```

-continued

```
Ala Cys Cys Thr Ala Thr Cys Thr Cys Ala Gly Cys Ala Gly Cys
    2180            2185            2190
Thr Cys Thr Cys Thr Cys Thr Thr Thr Cys Thr Cys Thr Cys Cys
    2195            2200            2205
Cys Cys Cys Gly Thr Thr Ala Thr Ala Ala Thr Gly Ala Ala Thr
    2210            2215            2220
Ala Ala Ala Thr Gly Thr Thr Cys Gly Cys Ala Gly Gly Gly Thr
    2225            2230            2235
Gly Cys Thr Gly Thr Gly Gly Cys Thr Gly Gly Gly Ala Gly
    2240            2245            2250
Cys Cys Cys Cys Gly Cys Cys Ala Gly Ala Thr Thr Cys Cys Ala
    2255            2260            2265
Ala Ala Gly Ala Thr Cys Cys Ala Gly Ala Ala Thr Thr Thr Thr
    2270            2275            2280
Ala Cys Cys Ala Gly Gly Ala Cys Gly Cys Ala Gly Ala Ala Ala
    2285            2290            2295
Thr Cys Cys Thr Gly Cys Ala Thr Thr Thr Thr Thr Thr Gly Thr
    2300            2305            2310
Gly Gly Cys Thr Thr Thr Gly Cys Cys Cys Thr Gly Cys Thr Cys
    2315            2320            2325
Ala Gly Thr Thr Ala Thr Gly Ala Thr Gly Ala Ala Ala Ala Gly
    2330            2335            2340
Gly Ala Ala Gly Gly Cys Cys Thr Gly Gly Ala Ala Ala Cys Thr
    2345            2350            2355
Ala Cys Ala Ala Cys Cys Thr Ala Cys Ala Thr Cys Ala Cys Cys
    2360            2365            2370
Thr Cys Cys Cys Ala Gly Gly Ala Ala Gly Thr Cys Cys Ala Ala
    2375            2380            2385
Ala Ala Cys Thr Cys Cys Ala Thr Cys Thr Thr Gly Ala Gly Cys
    2390            2395            2400
Thr Cys Cys Ala Ala Cys Thr Ala Cys Thr Thr Thr Gly Ala Thr
    2405            2410            2415
Thr Thr Thr Gly Ala Cys Ala Ala Cys Cys Thr Cys Cys Ala Cys
    2420            2425            2430
Gly Thr Thr Cys Ala Cys Thr Ala Thr Cys Thr Gly Cys Thr Gly
    2435            2440            2445
Cys Thr Gly Ala Cys Cys Ala Cys Cys Ala Ala Cys Gly Gly Gly
    2450            2455            2460
Ala Cys Thr Gly Thr Cys Ala Thr Gly Gly Ala Ala Ala Thr Thr
    2465            2470            2475
Gly Cys Gly Gly Gly Cys Cys Thr Gly Thr Ala Thr Gly Ala Ala
    2480            2485            2490
Gly Ala Ala Ala Gly Ala Gly Cys Ala Cys Ala Gly Cys Cys Thr
    2495            2500            2505
Cys Thr Cys Ala Thr Thr Ala Cys Cys Thr Ala Thr Ala Thr Cys
    2510            2515            2520
Gly Cys Thr Thr Thr Ala Ala Cys Thr Gly Cys Cys Ala Thr Ala
    2525            2530            2535
Thr Cys Thr Cys Thr Thr Gly Thr Thr Gly Cys Gly Gly Thr
    2540            2545            2550
Ala Thr Ala Cys Thr Thr Ala Gly Thr Cys Thr Gly Gly Thr Thr
    2555            2560            2565
```

Cys Thr Ala Gly Cys Ala Thr Gly Cys Thr Ala Cys Cys Thr Ala
         2570            2575            2580

Ala Thr Gly Thr Ala Cys Ala Ala Gly Cys Ala Ala Ala Ala Gly
         2585            2590            2595

Gly Cys Gly Cys Ala Ala Cys Ala Ala Ala Gly Ala Cys Cys
         2600            2605            2610

Thr Thr Gly Thr Thr Ala Thr Gly Gly Cys Thr Thr Gly Gly Gly
         2615            2620            2625

Ala Ala Thr Ala Ala Thr Ala Cys Cys Cys Thr Gly Gly Gly Thr
         2630            2635            2640

Cys Ala Gly Ala Thr Gly Ala Gly Ala Gly Cys Cys Ala Cys Thr
         2645            2650            2655

Ala Cys Ala Ala Ala Ala Ala Thr Gly Thr Gly Ala Cys Cys Cys
         2660            2665            2670

Ala Ala Gly Cys Thr Thr Gly Gly Cys Gly Thr Ala Ala Thr Cys
         2675            2680            2685

Ala Thr Gly Gly Thr Cys Ala Thr Ala Gly Cys Thr Gly Thr Thr
         2690            2695            2700

Thr Cys Cys Thr Gly Thr Gly Thr Gly Ala Ala Ala Thr Thr Gly
         2705            2710            2715

Thr Thr Ala Thr Cys Cys Gly Cys Thr Cys Ala Cys Ala Ala Thr
         2720            2725            2730

Thr Cys Cys Ala Cys Ala Cys Ala Ala Cys Ala Thr Ala Cys Gly
         2735            2740            2745

Ala Gly Cys Cys Gly Gly Ala Ala Gly Cys Ala Thr Ala Ala Ala
         2750            2755            2760

Gly Thr Gly Thr Ala Ala Gly Cys Cys Thr Gly Gly Gly Gly
         2765            2770            2775

Thr Gly Cys Cys Thr Ala Ala Thr Gly Ala Gly Thr Gly Ala Gly
         2780            2785            2790

Cys Thr Ala Ala Cys Thr Cys Ala Cys Ala Thr Thr Ala Ala Thr
         2795            2800            2805

Thr Gly Cys Gly Thr Thr Gly Cys Gly Cys Thr Cys Ala Cys Thr
         2810            2815            2820

Gly Cys Cys Cys Gly Cys Thr Thr Thr Cys Cys Ala Gly Thr Cys
         2825            2830            2835

Gly Gly Gly Ala Ala Ala Cys Cys Thr Gly Thr Cys Gly Thr Gly
         2840            2845            2850

Cys Cys Ala Gly Cys Thr Gly Cys Ala Thr Thr Ala Ala Thr Gly
         2855            2860            2865

Ala Ala Thr Cys Gly Gly Cys Cys Ala Ala Cys Gly Cys Gly Cys
         2870            2875            2880

Gly Gly Gly Gly Ala Gly Ala Gly Gly Cys Gly Gly Thr Thr Thr
         2885            2890            2895

Gly Cys Gly Thr Ala Thr Thr Gly Gly Gly Cys Gly Cys Thr Cys
         2900            2905            2910

Thr Thr Cys Cys Gly Cys Thr Thr Cys Cys Thr Cys Gly Cys Thr
         2915            2920            2925

Cys Ala Cys Thr Gly Ala Cys Thr Cys Gly Cys Thr Gly Cys Gly
         2930            2935            2940

Cys Thr Cys Gly Gly Thr Cys Gly Thr Thr Cys Gly Gly Cys Thr
         2945            2950            2955

Gly Cys Gly Gly Cys Gly Ala Gly Cys Gly Gly Thr Ala Thr Cys

-continued

```
                    2960                2965                2970

Ala  Gly  Cys  Thr  Cys  Ala  Cys  Thr  Cys  Ala  Ala  Gly  Gly  Cys
          2975                2980                2985

Gly  Gly  Thr  Ala  Ala  Thr  Ala  Cys  Gly  Gly  Thr  Thr  Ala  Thr  Cys
          2990                2995                3000

Cys  Ala  Cys  Ala  Gly  Ala  Ala  Thr  Cys  Ala  Gly  Gly  Gly  Gly  Ala
          3005                3010                3015

Thr  Ala  Ala  Cys  Gly  Cys  Ala  Gly  Gly  Ala  Ala  Gly  Ala  Ala
          3020                3025                3030

Cys  Ala  Thr  Gly  Thr  Gly  Ala  Gly  Cys  Ala  Ala  Ala  Gly  Gly
          3035                3040                3045

Cys  Cys  Ala  Gly  Cys  Ala  Ala  Ala  Gly  Gly  Cys  Cys  Ala  Gly
          3050                3055                3060

Gly  Ala  Ala  Cys  Cys  Gly  Thr  Ala  Ala  Ala  Ala  Gly  Gly  Cys
          3065                3070                3075

Cys  Gly  Cys  Gly  Thr  Thr  Gly  Cys  Thr  Gly  Gly  Cys  Gly  Thr  Thr
          3080                3085                3090

Thr  Thr  Thr  Cys  Cys  Ala  Thr  Ala  Gly  Gly  Cys  Thr  Cys  Cys  Gly
          3095                3100                3105

Cys  Cys  Cys  Cys  Cys  Thr  Gly  Ala  Cys  Gly  Ala  Gly  Cys  Ala
          3110                3115                3120

Thr  Cys  Ala  Cys  Ala  Ala  Ala  Ala  Thr  Cys  Gly  Ala  Cys  Gly
          3125                3130                3135

Cys  Thr  Cys  Ala  Ala  Gly  Thr  Cys  Ala  Gly  Ala  Gly  Gly  Thr  Gly
          3140                3145                3150

Gly  Cys  Gly  Ala  Ala  Ala  Cys  Cys  Cys  Gly  Ala  Cys  Ala  Gly  Gly
          3155                3160                3165

Ala  Cys  Thr  Ala  Thr  Ala  Ala  Ala  Gly  Ala  Thr  Ala  Cys  Cys  Ala
          3170                3175                3180

Gly  Gly  Cys  Gly  Thr  Thr  Thr  Cys  Cys  Cys  Cys  Cys  Thr  Gly  Gly
          3185                3190                3195

Ala  Ala  Gly  Cys  Thr  Cys  Cys  Cys  Thr  Cys  Gly  Thr  Gly  Cys  Gly
          3200                3205                3210

Cys  Thr  Cys  Thr  Cys  Cys  Thr  Gly  Thr  Thr  Cys  Cys  Gly  Ala  Cys
          3215                3220                3225

Cys  Cys  Thr  Gly  Cys  Cys  Gly  Cys  Thr  Thr  Ala  Cys  Cys  Gly  Gly
          3230                3235                3240

Ala  Thr  Ala  Cys  Cys  Thr  Gly  Thr  Cys  Cys  Gly  Cys  Cys  Thr  Thr
          3245                3250                3255

Thr  Cys  Thr  Cys  Cys  Cys  Thr  Thr  Cys  Gly  Gly  Gly  Ala  Ala  Gly
          3260                3265                3270

Cys  Gly  Thr  Gly  Gly  Cys  Gly  Cys  Thr  Thr  Thr  Cys  Thr  Cys  Ala
          3275                3280                3285

Thr  Ala  Gly  Cys  Thr  Cys  Ala  Cys  Gly  Cys  Thr  Gly  Thr  Ala  Gly
          3290                3295                3300

Gly  Thr  Ala  Thr  Cys  Thr  Cys  Ala  Gly  Thr  Thr  Cys  Gly  Gly  Thr
          3305                3310                3315

Gly  Thr  Ala  Gly  Gly  Thr  Cys  Gly  Thr  Thr  Cys  Gly  Cys  Thr  Cys
          3320                3325                3330

Cys  Ala  Ala  Gly  Cys  Thr  Gly  Gly  Gly  Cys  Thr  Gly  Thr  Gly  Thr
          3335                3340                3345

Gly  Cys  Ala  Cys  Gly  Ala  Ala  Cys  Cys  Cys  Cys  Cys  Gly  Thr
          3350                3355                3360
```

```
Thr Cys Ala Gly Cys Cys Cys Gly Ala Cys Cys Gly Cys Thr Gly
    3365                3370                3375

Cys Gly Cys Cys Thr Thr Ala Thr Cys Cys Gly Gly Thr Ala Ala
    3380                3385                3390

Cys Thr Ala Thr Cys Gly Thr Cys Thr Gly Ala Gly Thr Cys
    3395                3400                3405

Cys Ala Ala Cys Cys Gly Gly Thr Ala Ala Gly Ala Cys Ala
    3410                3415                3420

Cys Gly Ala Cys Thr Thr Ala Thr Cys Gly Cys Cys Ala Cys Thr
    3425                3430                3435

Gly Gly Cys Ala Gly Cys Ala Gly Cys Cys Ala Cys Thr Gly Gly
    3440                3445                3450

Thr Ala Ala Cys Ala Gly Gly Ala Thr Thr Ala Gly Cys Ala Gly
    3455                3460                3465

Ala Gly Cys Gly Ala Gly Gly Thr Ala Thr Gly Thr Ala Gly Gly
    3470                3475                3480

Cys Gly Gly Thr Gly Cys Thr Ala Cys Ala Gly Ala Gly Thr Thr
    3485                3490                3495

Cys Thr Thr Gly Ala Ala Gly Thr Gly Gly Thr Gly Gly Cys Cys
    3500                3505                3510

Thr Ala Ala Cys Thr Ala Cys Gly Gly Cys Thr Ala Cys Ala Cys
    3515                3520                3525

Thr Ala Gly Ala Ala Gly Ala Ala Cys Ala Gly Thr Ala Thr Thr
    3530                3535                3540

Thr Gly Gly Thr Ala Thr Cys Thr Gly Cys Gly Cys Thr Cys Thr
    3545                3550                3555

Gly Cys Thr Gly Ala Ala Gly Cys Cys Ala Gly Thr Thr Ala Cys
    3560                3565                3570

Cys Thr Thr Cys Gly Gly Ala Ala Ala Ala Gly Ala Gly Thr
    3575                3580                3585

Thr Gly Gly Thr Ala Gly Cys Thr Cys Thr Thr Gly Ala Thr Cys
    3590                3595                3600

Cys Gly Gly Cys Ala Ala Ala Cys Ala Ala Ala Cys Cys Ala Cys
    3605                3610                3615

Cys Gly Cys Thr Gly Gly Thr Ala Gly Cys Gly Gly Thr Gly Gly
    3620                3625                3630

Thr Thr Thr Thr Thr Thr Thr Gly Thr Thr Thr Gly Cys Ala Ala
    3635                3640                3645

Gly Cys Ala Gly Cys Ala Gly Ala Thr Thr Ala Cys Gly Cys Gly
    3650                3655                3660

Cys Ala Gly Ala Ala Ala Ala Ala Ala Gly Gly Ala Thr Cys
    3665                3670                3675

Thr Cys Ala Ala Gly Ala Ala Gly Ala Thr Cys Cys Thr Thr Thr
    3680                3685                3690

Gly Ala Thr Cys Thr Thr Thr Thr Cys Thr Ala Cys Gly Gly Gly
    3695                3700                3705

Gly Thr Cys Thr Gly Ala Cys Gly Cys Thr Cys Ala Gly Thr Gly
    3710                3715                3720

Gly Ala Ala Cys Gly Ala Ala Ala Ala Cys Thr Cys Ala Cys Gly
    3725                3730                3735

Thr Thr Ala Ala Gly Gly Gly Ala Thr Thr Thr Gly Gly Thr
    3740                3745                3750
```

```
Cys Ala Thr Gly Ala Gly Ala Thr Thr Ala Thr Cys Ala Ala Ala
    3755                3760                3765
Ala Ala Gly Gly Ala Thr Cys Thr Thr Cys Ala Cys Cys Thr Ala
    3770                3775                3780
Gly Ala Thr Cys Cys Thr Thr Thr Ala Ala Ala Thr Thr Ala
    3785                3790                3795
Ala Ala Ala Ala Thr Gly Ala Ala Gly Thr Thr Thr Ala Ala
    3800                3805                3810
Ala Thr Cys Ala Ala Thr Cys Thr Ala Ala Ala Gly Thr Ala Thr
    3815                3820                3825
Ala Thr Ala Thr Gly Ala Gly Thr Ala Ala Ala Cys Thr Thr Gly
    3830                3835                3840
Gly Thr Cys Thr Gly Ala Cys Ala Gly Thr Thr Ala Cys Cys Ala
    3845                3850                3855
Ala Thr Gly Cys Thr Thr Ala Ala Thr Cys Ala Gly Thr Gly Ala
    3860                3865                3870
Gly Gly Cys Ala Cys Cys Thr Ala Thr Cys Thr Cys Ala Gly Cys
    3875                3880                3885
Gly Ala Thr Cys Thr Gly Thr Cys Thr Ala Thr Thr Cys Gly
    3890                3895                3900
Thr Thr Cys Ala Thr Cys Cys Ala Thr Ala Gly Thr Thr Gly Cys
    3905                3910                3915
Cys Thr Gly Ala Cys Thr Cys Cys Cys Cys Gly Thr Cys Gly Thr
    3920                3925                3930
Gly Thr Ala Gly Ala Thr Ala Ala Cys Thr Ala Cys Gly Ala Thr
    3935                3940                3945
Ala Cys Gly Gly Gly Ala Gly Gly Gly Cys Thr Thr Ala Cys Cys
    3950                3955                3960
Ala Thr Cys Thr Gly Gly Cys Cys Cys Cys Ala Gly Thr Gly Cys
    3965                3970                3975
Thr Gly Cys Ala Ala Thr Gly Ala Thr Ala Cys Cys Gly Cys Gly
    3980                3985                3990
Ala Gly Ala Cys Cys Cys Ala Cys Gly Cys Thr Cys Ala Cys Cys
    3995                4000                4005
Gly Gly Cys Thr Cys Cys Ala Gly Ala Thr Thr Thr Ala Thr Cys
    4010                4015                4020
Ala Gly Cys Ala Ala Thr Ala Ala Ala Cys Cys Ala Gly Cys Cys
    4025                4030                4035
Ala Gly Cys Cys Gly Gly Ala Ala Gly Gly Gly Cys Cys Gly Ala
    4040                4045                4050
Gly Cys Gly Cys Ala Gly Ala Ala Gly Thr Gly Gly Thr Cys Cys
    4055                4060                4065
Thr Gly Cys Ala Ala Cys Thr Thr Thr Ala Thr Cys Cys Gly Cys
    4070                4075                4080
Cys Thr Cys Cys Ala Thr Cys Cys Ala Gly Thr Cys Thr Ala Thr
    4085                4090                4095
Thr Ala Ala Thr Thr Gly Thr Thr Gly Cys Cys Gly Gly Gly Ala
    4100                4105                4110
Ala Gly Cys Thr Ala Gly Ala Gly Thr Ala Ala Gly Thr Ala Gly
    4115                4120                4125
Thr Thr Cys Gly Cys Cys Ala Gly Thr Thr Ala Ala Thr Ala Gly
    4130                4135                4140
Thr Thr Thr Gly Cys Gly Cys Ala Ala Cys Gly Thr Thr Gly Thr
```

-continued 4145 4150 4155

Thr Gly Cys Cys Ala Thr Thr Gly Cys Thr Ala Cys Ala Gly Gly
4160 4165 4170

Cys Ala Thr Cys Gly Thr Gly Gly Thr Gly Thr Cys Ala Cys Gly
4175 4180 4185

Cys Thr Cys Gly Thr Cys Gly Thr Thr Thr Gly Gly Thr Ala Thr
4190 4195 4200

Gly Gly Cys Thr Thr Cys Ala Thr Thr Cys Ala Gly Cys Thr Cys
4205 4210 4215

Cys Gly Gly Thr Thr Cys Cys Cys Ala Ala Cys Gly Ala Thr Cys
4220 4225 4230

Ala Ala Gly Gly Cys Gly Ala Gly Thr Thr Ala Cys Ala Thr Gly
4235 4240 4245

Ala Thr Cys Cys Cys Cys Cys Ala Thr Gly Thr Thr Gly Thr Gly
4250 4255 4260

Cys Ala Ala Ala Ala Ala Ala Gly Cys Gly Gly Thr Thr Ala Gly
4265 4270 4275

Cys Thr Cys Cys Thr Thr Cys Gly Gly Thr Cys Cys Thr Cys Cys
4280 4285 4290

Gly Ala Thr Cys Gly Thr Thr Gly Thr Cys Ala Gly Ala Ala Gly
4295 4300 4305

Thr Ala Ala Gly Thr Thr Gly Gly Cys Cys Gly Cys Ala Gly Thr
4310 4315 4320

Gly Thr Thr Ala Thr Cys Ala Cys Thr Cys Ala Thr Gly Gly Thr
4325 4330 4335

Thr Ala Thr Gly Gly Cys Ala Gly Cys Ala Cys Thr Gly Cys Ala
4340 4345 4350

Thr Ala Ala Thr Thr Cys Thr Cys Thr Thr Ala Cys Thr Gly Thr
4355 4360 4365

Cys Ala Thr Gly Cys Cys Ala Thr Cys Cys Gly Thr Ala Ala Gly
4370 4375 4380

Ala Thr Gly Cys Thr Thr Thr Thr Cys Thr Gly Thr Gly Ala Cys
4385 4390 4395

Thr Gly Gly Thr Gly Ala Gly Thr Ala Cys Thr Cys Ala Ala Cys
4400 4405 4410

Cys Ala Ala Gly Thr Cys Ala Thr Thr Cys Thr Gly Ala Gly Ala
4415 4420 4425

Ala Thr Ala Gly Thr Gly Thr Ala Thr Gly Cys Gly Gly Cys Gly
4430 4435 4440

Ala Cys Cys Gly Ala Gly Thr Thr Gly Cys Thr Cys Thr Thr Gly
4445 4450 4455

Cys Cys Cys Gly Gly Cys Gly Thr Cys Ala Ala Thr Ala Cys Gly
4460 4465 4470

Gly Gly Ala Thr Ala Ala Thr Ala Cys Cys Gly Cys Gly Cys Cys
4475 4480 4485

Ala Cys Ala Thr Ala Gly Cys Ala Gly Ala Ala Cys Thr Thr Thr
4490 4495 4500

Ala Ala Ala Ala Gly Thr Gly Cys Thr Cys Ala Thr Cys Ala Thr
4505 4510 4515

Thr Gly Gly Ala Ala Ala Ala Cys Gly Thr Thr Cys Thr Thr Cys
4520 4525 4530

Gly Gly Gly Gly Cys Gly Ala Ala Ala Ala Cys Thr Cys Thr Cys
4535 4540 4545

-continued

Ala Ala Gly Gly Ala Thr Cys Thr Thr Ala Cys Cys Gly Cys Thr
4550                4555                4560

Gly Thr Thr Gly Ala Gly Ala Thr Cys Cys Ala Gly Thr Thr Cys
    4565                4570                4575

Gly Ala Thr Gly Thr Ala Ala Cys Cys Cys Ala Cys Thr Cys Gly
    4580                4585                4590

Thr Gly Cys Ala Cys Cys Cys Ala Ala Cys Thr Gly Ala Thr Cys
    4595                4600                4605

Thr Thr Cys Ala Gly Cys Ala Thr Cys Thr Thr Thr Ala Cys
    4610                4615                4620

Thr Thr Thr Cys Ala Cys Cys Ala Gly Cys Gly Thr Thr Thr Cys
    4625                4630                4635

Thr Gly Gly Gly Thr Gly Ala Gly Cys Ala Ala Ala Ala Cys
    4640                4645                4650

Ala Gly Gly Ala Ala Gly Gly Cys Ala Ala Ala Thr Gly Cys
    4655                4660                4665

Cys Gly Cys Ala Ala Ala Ala Ala Gly Gly Gly Ala Ala Thr
    4670                4675                4680

Ala Ala Gly Gly Gly Cys Gly Ala Cys Ala Cys Gly Gly Ala Ala
    4685                4690                4695

Ala Thr Gly Thr Thr Gly Ala Ala Thr Ala Cys Thr Cys Ala Thr
    4700                4705                4710

Ala Cys Thr Cys Thr Thr Cys Cys Thr Thr Thr Thr Cys Ala
    4715                4720                4725

Ala Thr Ala Thr Thr Ala Thr Thr Gly Ala Ala Gly Cys Ala Thr
    4730                4735                4740

Thr Thr Ala Thr Cys Ala Gly Gly Gly Thr Thr Ala Thr Thr Gly
    4745                4750                4755

Thr Cys Thr Cys Ala Thr Gly Ala Gly Cys Gly Gly Ala Thr Ala
    4760                4765                4770

Cys Ala Thr Ala Thr Thr Thr Gly Ala Ala Thr Gly Thr Ala Thr
    4775                4780                4785

Thr Thr Ala Gly Ala Ala Ala Ala Ala Thr Ala Ala Ala Cys Ala
    4790                4795                4800

Ala Ala Thr Ala Gly Gly Gly Gly Thr Thr Cys Cys Gly Cys Gly
    4805                4810                4815

Cys Ala Cys Ala Thr Thr Thr Cys Cys Cys Cys Gly Ala Ala Ala
    4820                4825                4830

Ala Gly Thr Gly Cys Cys Ala Cys Cys Thr Gly Ala Cys Gly Thr
    4835                4840                4845

Cys Thr Ala Ala Gly Ala Ala Ala Cys Cys Ala Thr Thr Ala Thr
    4850                4855                4860

Thr Ala Thr Cys Ala Thr Gly Ala Cys Ala Thr Thr Ala Ala Cys
    4865                4870                4875

Cys Thr Ala Thr Ala Ala Ala Ala Thr Ala Gly Gly Cys Gly
    4880                4885                4890

Thr Ala Thr Cys Ala Cys Gly Ala Gly Gly Cys Cys Cys Thr Thr
    4895                4900                4905

Thr Cys Gly
    4910

<210> SEQ ID NO 293
<211> LENGTH: 57

```
<212> TYPE: PRT
<213> ORGANISM: Artificial Sequence
<220> FEATURE:
<223> OTHER INFORMATION: Synthethic

<400> SEQUENCE: 293

Ser Arg Val Ser Val Met Thr Val Lys Thr Ser Asp Thr Cys Ser Ser
1               5                   10                  15

Arg Arg Arg Ser Gln Leu Val Cys Lys Arg Met Pro Gly Ala Asp Lys
            20                  25                  30

Pro Val Arg Ala Arg Gln Arg Val Leu Ala Gly Val Gly Ala Gly Leu
        35                  40                  45

Thr Met Arg His Gln Ser Arg Leu Tyr
    50                  55

<210> SEQ ID NO 294
<211> LENGTH: 13
<212> TYPE: PRT
<213> ORGANISM: Artificial Sequence
<220> FEATURE:
<223> OTHER INFORMATION: Synthethic

<400> SEQUENCE: 294

Glu Cys Thr Ile Cys Gly Val Lys Tyr Arg Thr Asp Ala
1               5                   10

<210> SEQ ID NO 295
<211> LENGTH: 41
<212> TYPE: PRT
<213> ORGANISM: Artificial Sequence
<220> FEATURE:
<223> OTHER INFORMATION: Synthethic

<400> SEQUENCE: 295

Gly Glu Asn Thr Ala Ser Gly Ala Ile Arg His Ser Gly Cys Ala Thr
1               5                   10                  15

Val Gly Lys Gly Asp Arg Cys Gly Pro Leu Arg Tyr Tyr Ala Ser Trp
            20                  25                  30

Arg Lys Gly Asp Val Leu Gln Gly Asp
        35                  40

<210> SEQ ID NO 296
<211> LENGTH: 2
<212> TYPE: PRT
<213> ORGANISM: Artificial Sequence
<220> FEATURE:
<223> OTHER INFORMATION: Synthethic

<400> SEQUENCE: 296

Val Gly
1

<210> SEQ ID NO 297
<211> LENGTH: 70
<212> TYPE: PRT
<213> ORGANISM: Artificial Sequence
<220> FEATURE:
<223> OTHER INFORMATION: Synthethic

<400> SEQUENCE: 297

Arg Gln Gly Phe Pro Ser His Asp Val Val Lys Arg Arg Pro Val Asn
1               5                   10                  15

Ser Thr Pro Pro Cys Val Leu Leu Val Tyr Phe Trp Pro Ser Val Leu
            20                  25                  30
```

Ser Pro Phe Ser Ser Gln His Gly Ala Ile Gly His Thr His Val
         35                  40                  45

Val Thr Ser Leu Ser Ser Ala Leu Asn Thr Phe Ser Arg Trp Lys Thr
 50                  55                  60

Leu Ala Thr Phe Thr Trp
 65                  70

<210> SEQ ID NO 298
<211> LENGTH: 12
<212> TYPE: PRT
<213> ORGANISM: Artificial Sequence
<220> FEATURE:
<223> OTHER INFORMATION: Synthethic

<400> SEQUENCE: 298

Ala Ile Arg His Ala Thr Ala Leu Ala Trp Pro Pro
1               5                   10

<210> SEQ ID NO 299
<211> LENGTH: 28
<212> TYPE: PRT
<213> ORGANISM: Artificial Sequence
<220> FEATURE:
<223> OTHER INFORMATION: Synthethic

<400> SEQUENCE: 299

Ile His Leu Arg Met Gly Ala Thr Ser Trp Ser Ala Ala Ala Gln
1               5                   10                  15

Thr Asp Ser Thr Trp Ser Pro Ser Leu Ser Pro Ser
            20                  25

<210> SEQ ID NO 300
<211> LENGTH: 14
<212> TYPE: PRT
<213> ORGANISM: Artificial Sequence
<220> FEATURE:
<223> OTHER INFORMATION: Synthethic

<400> SEQUENCE: 300

Ser Glu Ala Ala Pro Pro Ser Arg Ala Ile Ser Val Ser Cys
1               5                   10

<210> SEQ ID NO 301
<211> LENGTH: 19
<212> TYPE: PRT
<213> ORGANISM: Artificial Sequence
<220> FEATURE:
<223> OTHER INFORMATION: Synthethic

<400> SEQUENCE: 301

Pro Pro Trp Arg Leu Phe Thr Val His Ser Gln Trp Lys Thr Cys Leu
1               5                   10                  15

Val Pro Thr

<210> SEQ ID NO 302
<211> LENGTH: 12
<212> TYPE: PRT
<213> ORGANISM: Artificial Sequence
<220> FEATURE:
<223> OTHER INFORMATION: Synthethic

<400> SEQUENCE: 302

Thr Asp Thr His Gly Ile Ala Gly Ala Arg Cys Arg
1               5                   10

<210> SEQ ID NO 303
<211> LENGTH: 55
<212> TYPE: PRT
<213> ORGANISM: Artificial Sequence
<220> FEATURE:
<223> OTHER INFORMATION: Synthethic

<400> SEQUENCE: 303

Glu Ala Glu Val Ser Pro Ile Ala Ile Cys Val Gln Ile Leu Cys Pro
1               5                   10                  15

Gly Ser Gln Ile Pro Leu Arg Ser Lys Leu Gly Val Ile Met Val Ile
            20                  25                  30

Ala Val Ser Cys Val Lys Leu Leu Ser Ala His Asn Ser Thr Gln His
        35                  40                  45

Thr Ser Arg Lys His Lys Val
    50                  55

<210> SEQ ID NO 304
<211> LENGTH: 54
<212> TYPE: PRT
<213> ORGANISM: Artificial Sequence
<220> FEATURE:
<223> OTHER INFORMATION: Synthethic

<400> SEQUENCE: 304

Ser Leu Gly Cys Leu Met Ser Glu Leu Thr His Ile Asn Cys Val Ala
1               5                   10                  15

Leu Thr Ala Arg Phe Pro Val Gly Lys Pro Val Val Pro Ala Ala Leu
            20                  25                  30

Met Asn Arg Pro Thr Arg Gly Glu Arg Phe Ala Tyr Trp Ala Leu
        35                  40                  45

Phe Arg Phe Leu Ala His
    50

<210> SEQ ID NO 305
<211> LENGTH: 28
<212> TYPE: PRT
<213> ORGANISM: Artificial Sequence
<220> FEATURE:
<223> OTHER INFORMATION: Synthethic

<400> SEQUENCE: 305

Leu Ala Ala Leu Gly Arg Ser Ala Ala Ser Gly Ile Ser Ser Leu
1               5                   10                  15

Lys Gly Gly Asn Thr Val Ile His Arg Ile Arg Gly
            20                  25

<210> SEQ ID NO 306
<211> LENGTH: 16
<212> TYPE: PRT
<213> ORGANISM: Artificial Sequence
<220> FEATURE:
<223> OTHER INFORMATION: Synthethic

<400> SEQUENCE: 306

Arg Arg Lys Glu His Val Ser Lys Arg Pro Ala Lys Gly Gln Glu Pro
1               5                   10                  15

<210> SEQ ID NO 307
<211> LENGTH: 9
<212> TYPE: PRT
<213> ORGANISM: Artificial Sequence -continued
<220> FEATURE:
<223> OTHER INFORMATION: Synthethic

<400> SEQUENCE: 307

Lys Gly Arg Val Ala Gly Val Phe Pro
1               5

<210> SEQ ID NO 308
<211> LENGTH: 4
<212> TYPE: PRT
<213> ORGANISM: Artificial Sequence
<220> FEATURE:
<223> OTHER INFORMATION: Synthethic

<400> SEQUENCE: 308

Ala Pro Pro Pro
1

<210> SEQ ID NO 309
<211> LENGTH: 57
<212> TYPE: PRT
<213> ORGANISM: Artificial Sequence
<220> FEATURE:
<223> OTHER INFORMATION: Synthethic

<400> SEQUENCE: 309

Arg Ala Ser Gln Lys Ser Thr Leu Lys Ser Glu Val Ala Lys Pro Asp
1               5                   10                  15

Arg Thr Ile Lys Ile Pro Gly Val Ser Pro Trp Lys Leu Pro Arg Ala
                20                  25                  30

Leu Ser Cys Ser Asp Pro Ala Ala Tyr Arg Ile Pro Val Arg Leu Ser
            35                  40                  45

Pro Phe Gly Lys Arg Gly Ala Phe Ser
    50                  55

<210> SEQ ID NO 310
<211> LENGTH: 3
<212> TYPE: PRT
<213> ORGANISM: Artificial Sequence
<220> FEATURE:
<223> OTHER INFORMATION: Synthethic

<400> SEQUENCE: 310

Leu Thr Leu
1

<210> SEQ ID NO 311
<211> LENGTH: 29
<212> TYPE: PRT
<213> ORGANISM: Artificial Sequence
<220> FEATURE:
<223> OTHER INFORMATION: Synthethic

<400> SEQUENCE: 311

Val Ser Gln Phe Gly Val Gly Arg Ser Leu Gln Ala Gly Leu Cys Ala
1               5                   10                  15

Arg Thr Pro Arg Ser Ala Arg Pro Leu Arg Leu Ile Arg
                20                  25

<210> SEQ ID NO 312
<211> LENGTH: 3
<212> TYPE: PRT
<213> ORGANISM: Artificial Sequence
<220> FEATURE:
<223> OTHER INFORMATION: Synthethic

```
<400> SEQUENCE: 312

Leu Ser Ser
1

<210> SEQ ID NO 313
<211> LENGTH: 16
<212> TYPE: PRT
<213> ORGANISM: Artificial Sequence
<220> FEATURE:
<223> OTHER INFORMATION: Synthethic

<400> SEQUENCE: 313

Val Gln Pro Gly Lys Thr Arg Leu Ile Ala Thr Gly Ser Ser His Trp
1               5                   10                  15

<210> SEQ ID NO 314
<211> LENGTH: 2
<212> TYPE: PRT
<213> ORGANISM: Artificial Sequence
<220> FEATURE:
<223> OTHER INFORMATION: Synthethic

<400> SEQUENCE: 314

Gln Asp
1

<210> SEQ ID NO 315
<211> LENGTH: 16
<212> TYPE: PRT
<213> ORGANISM: Artificial Sequence
<220> FEATURE:
<223> OTHER INFORMATION: Synthethic

<400> SEQUENCE: 315

Gln Ser Glu Val Cys Arg Arg Cys Tyr Arg Val Leu Glu Val Val Ala
1               5                   10                  15

<210> SEQ ID NO 316
<211> LENGTH: 4
<212> TYPE: PRT
<213> ORGANISM: Artificial Sequence
<220> FEATURE:
<223> OTHER INFORMATION: Synthethic

<400> SEQUENCE: 316

Leu Arg Leu His
1

<210> SEQ ID NO 317
<211> LENGTH: 20
<212> TYPE: PRT
<213> ORGANISM: Artificial Sequence
<220> FEATURE:
<223> OTHER INFORMATION: Synthethic

<400> SEQUENCE: 317

Lys Asn Ser Ile Trp Tyr Leu Arg Ser Ala Glu Ala Ser Tyr Leu Arg
1               5                   10                  15

Lys Lys Ser Trp
            20

<210> SEQ ID NO 318
<211> LENGTH: 10
<212> TYPE: PRT
<213> ORGANISM: Artificial Sequence
```

```
<220> FEATURE:
<223> OTHER INFORMATION: Synthethic

<400> SEQUENCE: 318

Leu Leu Ile Arg Gln Thr Asn His Arg Trp
1               5                   10

<210> SEQ ID NO 319
<211> LENGTH: 28
<212> TYPE: PRT
<213> ORGANISM: Artificial Sequence
<220> FEATURE:
<223> OTHER INFORMATION: Synthethic

<400> SEQUENCE: 319

Arg Trp Phe Phe Cys Leu Gln Ala Ala Asp Tyr Ala Gln Lys Lys Arg
1               5                   10                  15

Ile Ser Arg Arg Ser Phe Asp Leu Phe Tyr Gly Val
            20                  25

<210> SEQ ID NO 320
<211> LENGTH: 32
<212> TYPE: PRT
<213> ORGANISM: Artificial Sequence
<220> FEATURE:
<223> OTHER INFORMATION: Synthethic

<400> SEQUENCE: 320

Arg Ser Val Glu Arg Lys Leu Thr Leu Arg Asp Phe Gly His Glu Ile
1               5                   10                  15

Ile Lys Lys Asp Leu His Leu Asp Pro Phe Lys Leu Lys Met Lys Phe
            20                  25                  30

<210> SEQ ID NO 321
<211> LENGTH: 6
<212> TYPE: PRT
<213> ORGANISM: Artificial Sequence
<220> FEATURE:
<223> OTHER INFORMATION: Synthethic

<400> SEQUENCE: 321

Ile Asn Leu Lys Tyr Ile
1               5

<210> SEQ ID NO 322
<211> LENGTH: 4
<212> TYPE: PRT
<213> ORGANISM: Artificial Sequence
<220> FEATURE:
<223> OTHER INFORMATION: Synthethic

<400> SEQUENCE: 322

Val Asn Leu Val
1

<210> SEQ ID NO 323
<211> LENGTH: 7
<212> TYPE: PRT
<213> ORGANISM: Artificial Sequence
<220> FEATURE:
<223> OTHER INFORMATION: Synthethic

<400> SEQUENCE: 323

Gln Leu Pro Met Leu Asn Gln
1               5
```

<210> SEQ ID NO 324
<211> LENGTH: 75
<212> TYPE: PRT
<213> ORGANISM: Artificial Sequence
<220> FEATURE:
<223> OTHER INFORMATION: Synthethic

<400> SEQUENCE: 324

Gly Thr Tyr Leu Ser Asp Leu Ser Ile Ser Phe Ile His Ser Cys Leu
1               5                   10                  15

Thr Pro Arg Arg Val Asp Asn Tyr Asp Thr Gly Gly Leu Thr Ile Trp
            20                  25                  30

Pro Gln Cys Cys Asn Asp Thr Ala Arg Pro Thr Leu Thr Gly Ser Arg
        35                  40                  45

Phe Ile Ser Asn Lys Pro Ala Ser Arg Lys Gly Arg Ala Gln Lys Trp
    50                  55                  60

Ser Cys Asn Phe Ile Arg Leu His Pro Val Tyr
65                  70                  75

<210> SEQ ID NO 325
<211> LENGTH: 5
<212> TYPE: PRT
<213> ORGANISM: Artificial Sequence
<220> FEATURE:
<223> OTHER INFORMATION: Synthethic

<400> SEQUENCE: 325

Leu Leu Pro Gly Ser
1               5

<210> SEQ ID NO 326
<211> LENGTH: 2
<212> TYPE: PRT
<213> ORGANISM: Artificial Sequence
<220> FEATURE:
<223> OTHER INFORMATION: Synthethic

<400> SEQUENCE: 326

Ser Lys
1

<210> SEQ ID NO 327
<211> LENGTH: 3
<212> TYPE: PRT
<213> ORGANISM: Artificial Sequence
<220> FEATURE:
<223> OTHER INFORMATION: Synthethic

<400> SEQUENCE: 327

Phe Ala Ser
1

<210> SEQ ID NO 328
<211> LENGTH: 44
<212> TYPE: PRT
<213> ORGANISM: Artificial Sequence
<220> FEATURE:
<223> OTHER INFORMATION: Synthethic

<400> SEQUENCE: 328

Phe Ala Gln Arg Cys Cys His Cys Tyr Arg His Arg Gly Val Thr Leu
1               5                   10                  15

Val Val Trp Tyr Gly Phe Ile Gln Leu Arg Phe Pro Thr Ile Lys Ala
            20                  25                  30

Ser Tyr Met Ile Pro His Val Val Gln Lys Ser Gly
        35                  40

<210> SEQ ID NO 329
<211> LENGTH: 10
<212> TYPE: PRT
<213> ORGANISM: Artificial Sequence
<220> FEATURE:
<223> OTHER INFORMATION: Synthethic

<400> SEQUENCE: 329

Leu Leu Arg Ser Ser Asp Arg Cys Gln Lys
1               5                   10

<210> SEQ ID NO 330
<211> LENGTH: 14
<212> TYPE: PRT
<213> ORGANISM: Artificial Sequence
<220> FEATURE:
<223> OTHER INFORMATION: Synthethic

<400> SEQUENCE: 330

Val Gly Arg Ser Val Ile Thr His Gly Tyr Gly Ser Thr Ala
1               5                   10

<210> SEQ ID NO 331
<211> LENGTH: 15
<212> TYPE: PRT
<213> ORGANISM: Artificial Sequence
<220> FEATURE:
<223> OTHER INFORMATION: Synthethic

<400> SEQUENCE: 331

Phe Ser Tyr Cys His Ala Ile Arg Lys Met Leu Phe Cys Asp Trp
1               5                   10                  15

<210> SEQ ID NO 332
<211> LENGTH: 24
<212> TYPE: PRT
<213> ORGANISM: Artificial Sequence
<220> FEATURE:
<223> OTHER INFORMATION: Synthethic

<400> SEQUENCE: 332

Val Leu Asn Gln Val Ile Leu Arg Ile Val Tyr Ala Ala Thr Glu Leu
1               5                   10                  15

Leu Leu Pro Gly Val Asn Thr Gly
            20

<210> SEQ ID NO 333
<211> LENGTH: 4
<212> TYPE: PRT
<213> ORGANISM: Artificial Sequence
<220> FEATURE:
<223> OTHER INFORMATION: Synthethic

<400> SEQUENCE: 333

Tyr Arg Ala Thr
1

<210> SEQ ID NO 334
<211> LENGTH: 95
<212> TYPE: PRT
<213> ORGANISM: Artificial Sequence
<220> FEATURE:
<223> OTHER INFORMATION: Synthethic

<400> SEQUENCE: 334

Gln Asn Phe Lys Ser Ala His His Trp Lys Thr Phe Gly Ala Lys
1               5                   10                  15

Thr Leu Lys Asp Leu Thr Ala Val Glu Ile Gln Phe Asp Val Thr His
                20                  25                  30

Ser Cys Thr Gln Leu Ile Phe Ser Ile Phe Tyr Phe His Gln Arg Phe
            35                  40                  45

Trp Val Ser Lys Asn Arg Lys Ala Lys Cys Arg Lys Lys Gly Asn Lys
50                  55                  60

Gly Asp Thr Glu Met Leu Asn Thr His Thr Leu Pro Phe Ser Ile Leu
65                  70                  75                  80

Leu Lys His Leu Ser Gly Leu Leu Ser His Glu Arg Ile His Ile
                85                  90                  95

<210> SEQ ID NO 335
<211> LENGTH: 5
<212> TYPE: PRT
<213> ORGANISM: Artificial Sequence
<220> FEATURE:
<223> OTHER INFORMATION: Synthethic

<400> SEQUENCE: 335

Met Tyr Leu Glu Lys
1               5

<210> SEQ ID NO 336
<211> LENGTH: 14
<212> TYPE: PRT
<213> ORGANISM: Artificial Sequence
<220> FEATURE:
<223> OTHER INFORMATION: Synthethic

<400> SEQUENCE: 336

Thr Asn Arg Gly Ser Ala His Ile Ser Pro Lys Ser Ala Thr
1               5                   10

<210> SEQ ID NO 337
<211> LENGTH: 12
<212> TYPE: PRT
<213> ORGANISM: Artificial Sequence
<220> FEATURE:
<223> OTHER INFORMATION: Synthethic

<400> SEQUENCE: 337

Arg Leu Arg Asn His Tyr Tyr His Asp Ile Asn Leu
1               5                   10

<210> SEQ ID NO 338
<211> LENGTH: 1
<212> TYPE: PRT
<213> ORGANISM: Artificial Sequence
<220> FEATURE:
<223> OTHER INFORMATION: Synthethic

<400> SEQUENCE: 338

Lys
1

<210> SEQ ID NO 339
<211> LENGTH: 7
<212> TYPE: PRT
<213> ORGANISM: Artificial Sequence
<220> FEATURE:

<223> OTHER INFORMATION: Synthethic

<400> SEQUENCE: 339

Ala Tyr His Glu Ala Leu Ser
1               5

<210> SEQ ID NO 340
<211> LENGTH: 3144
<212> TYPE: PRT
<213> ORGANISM: Artificial Sequence
<220> FEATURE:
<223> OTHER INFORMATION: Synthethic

<400> SEQUENCE: 340

Thr Cys Gly Cys Gly Cys Gly Thr Thr Cys Gly Thr Gly Ala
1               5                   10                  15

Thr Gly Ala Cys Gly Gly Thr Gly Ala Ala Ala Cys Cys Thr Cys
                20                  25                  30

Thr Gly Ala Cys Ala Cys Ala Thr Gly Cys Ala Gly Cys Thr Cys Cys
                35                  40                      45

Cys Gly Gly Ala Gly Ala Cys Gly Gly Thr Cys Ala Cys Ala Gly Cys
            50                  55                  60

Thr Thr Gly Thr Cys Thr Gly Thr Ala Ala Gly Cys Gly Gly Ala Thr
65                  70                  75                  80

Gly Cys Cys Gly Gly Gly Ala Cys Ala Gly Cys Ala Ala Gly
                85                  90                  95

Cys Cys Cys Gly Thr Cys Ala Gly Gly Gly Cys Gly Cys Gly Thr Cys
                100                 105                 110

Ala Gly Cys Gly Gly Gly Thr Gly Thr Gly Gly Cys Gly Gly Gly
            115                 120                 125

Thr Gly Thr Cys Gly Gly Gly Cys Thr Gly Cys Thr Thr Ala
            130                 135                 140

Ala Cys Thr Ala Thr Gly Cys Gly Gly Cys Ala Thr Cys Ala Gly Ala
145                 150                 155                 160

Gly Cys Ala Gly Ala Thr Thr Gly Thr Ala Cys Thr Gly Ala Gly Ala
                165                 170                 175

Gly Thr Gly Cys Ala Cys Cys Ala Thr Ala Thr Gly Cys Gly Gly Thr
                180                 185                 190

Gly Thr Gly Ala Ala Ala Thr Ala Cys Cys Gly Cys Ala Cys Ala Gly
                195                 200                 205

Ala Thr Gly Cys Gly Thr Ala Ala Gly Gly Ala Gly Ala Ala Ala Ala
            210                 215                 220

Thr Ala Cys Cys Gly Cys Ala Thr Cys Ala Gly Gly Cys Gly Cys Cys
225                 230                 235                 240

Ala Thr Thr Cys Gly Cys Cys Ala Thr Thr Cys Ala Gly Gly Cys Thr
                245                 250                 255

Gly Cys Gly Cys Ala Ala Cys Thr Gly Thr Thr Gly Gly Gly Ala Ala
                260                 265                 270

Gly Gly Gly Cys Gly Ala Thr Cys Gly Gly Thr Gly Cys Gly Gly Gly
            275                 280                 285

Cys Cys Thr Cys Thr Thr Cys Gly Cys Thr Ala Thr Thr Ala Cys Gly
            290                 295                 300

Cys Cys Ala Gly Cys Thr Gly Gly Cys Gly Ala Ala Ala Gly Gly Gly
305                 310                 315                 320

Gly Gly Ala Thr Gly Thr Gly Cys Thr Gly Cys Ala Ala Gly Gly Cys
                325                 330                 335

```
Gly Ala Thr Thr Ala Ala Gly Thr Thr Gly Gly Thr Ala Ala Cys
            340                 345                 350
Gly Cys Cys Ala Gly Gly Thr Thr Thr Cys Cys Cys Ala Gly
            355                 360                 365
Thr Cys Ala Cys Gly Ala Cys Gly Thr Thr Gly Thr Ala Ala Ala
            370                 375                 380
Cys Gly Ala Cys Gly Gly Cys Ala Gly Thr Gly Ala Ala Thr Thr
385                 390                 395                 400
Cys Gly Ala Cys Gly Cys Cys Ala Cys Cys Ala Thr Gly Cys Gly Thr
                405                 410                 415
Gly Cys Thr Gly Thr Thr Gly Gly Thr Gly Thr Ala Thr Thr Thr Cys
            420                 425                 430
Thr Gly Gly Cys Ala Thr Cys Thr Gly Thr Cys Thr Thr Gly Thr
            435                 440                 445
Cys Ala Cys Cys Ala Thr Thr Thr Cys Gly Thr Cys Cys Thr Cys
            450                 455                 460
Cys Cys Ala Ala Cys Ala Thr Gly Gly Gly Cys Ala Ala Thr Thr
465                 470                 475                 480
Gly Gly Gly Cys Ala Thr Ala Cys Cys Ala Thr Gly Thr Thr Gly
                485                 490                 495
Thr Cys Ala Cys Gly Thr Cys Ala Cys Thr Cys Ala Gly Cys Thr Cys
            500                 505                 510
Cys Gly Cys Gly Cys Thr Cys Ala Ala Cys Ala Cys Cys Thr Thr Cys
            515                 520                 525
Thr Cys Gly Cys Gly Thr Thr Gly Gly Ala Ala Ala Cys Ala Thr
            530                 535                 540
Thr Ala Gly Cys Gly Ala Cys Ala Thr Thr Thr Ala Cys Cys Thr Gly
545                 550                 555                 560
Gly Thr Gly Ala Gly Cys Ala Ala Thr Cys Ala Gly Ala Cys Ala Thr
                565                 570                 575
Gly Cys Gly Ala Cys Gly Gly Cys Thr Thr Thr Ala Gly Cys Cys Thr
            580                 585                 590
Gly Gly Cys Cys Thr Cys Thr Thr Ala Ala Ala Thr Thr Cys Ala
            595                 600                 605
Cys Cys Thr Ala Ala Gly Ala Ala Thr Gly Gly Gly Ala Gly Cys Ala
610                 615                 620
Ala Cys Cys Ala Gly Cys Thr Gly Gly Thr Cys Ala Thr Cys Ala Gly
625                 630                 635                 640
Cys Cys Gly Cys Thr Gly Cys Gly Cys Ala Ala Cys Gly Gly Ala
                645                 650                 655
Cys Thr Cys Ala Ala Cys Gly Thr Gly Gly Thr Cys Thr Cys Cys Thr
            660                 665                 670
Thr Cys Thr Thr Thr Ala Thr Cys Thr Cys Ala Thr Cys Cys Thr
            675                 680                 685
Gly Ala Ala Gly Cys Gly Ala Ala Gly Cys Ala Cys Thr Cys Cys
            690                 695                 700
Gly Cys Cys Cys Thr Cys Ala Cys Gly Gly Cys Cys Ala Thr Cys
705                 710                 715                 720
Thr Cys Cys Gly Thr Gly Ala Gly Thr Thr Gly Thr Ala Ala Cys
                725                 730                 735
Cys Ala Cys Cys Cys Thr Gly Gly Ala Gly Ala Cys Thr Cys Thr Thr
            740                 745                 750
```

-continued

```
Thr Ala Cys Gly Gly Thr Thr Cys Ala Thr Thr Cys Thr Cys Ala Gly
        755                 760                 765

Thr Gly Gly Ala Ala Gly Ala Cys Cys Thr Gly Thr Thr Thr Gly Gly
    770                 775                 780

Thr Gly Cys Cys Ala Ala Cys Thr Thr Ala Ala Ala Cys Ala Gly Ala
785                 790                 795                 800

Thr Ala Cys Gly Cys Ala Thr Gly Gly Cys Ala Thr Cys Gly Cys Gly
                805                 810                 815

Gly Gly Gly Gly Cys Thr Ala Gly Ala Thr Gly Cys Ala Gly Ala Thr
            820                 825                 830

Gly Ala Gly Ala Gly Gly Cys Gly Gly Ala Gly Gly Thr Ala Thr Cys
        835                 840                 845

Cys Cys Cys Ala Ala Thr Ala Gly Cys Ala Ala Thr Thr Thr Gly Thr
    850                 855                 860

Gly Thr Gly Cys Ala Ala Ala Thr Thr Cys Thr Ala Thr Gly Cys Cys
865                 870                 875                 880

Cys Thr Gly Gly Cys Thr Cys Ala Cys Ala Ala Ala Thr Ala Cys Cys
                885                 890                 895

Ala Cys Thr Gly Ala Gly Ala Thr Cys Thr Ala Ala Gly Cys Thr Thr
            900                 905                 910

Gly Gly Cys Gly Thr Ala Ala Thr Cys Ala Thr Gly Gly Thr Cys Ala
        915                 920                 925

Thr Ala Gly Cys Thr Gly Thr Thr Thr Cys Cys Thr Gly Thr Gly Thr
    930                 935                 940

Gly Ala Ala Ala Thr Thr Gly Thr Thr Ala Thr Cys Cys Gly Cys Thr
945                 950                 955                 960

Cys Ala Cys Ala Ala Thr Thr Cys Cys Ala Cys Ala Cys Ala Ala Cys
                965                 970                 975

Ala Thr Ala Cys Gly Ala Gly Cys Cys Gly Gly Ala Ala Gly Cys Ala
            980                 985                 990

Thr Ala Ala Ala Gly Thr Gly Thr  Ala Ala Ala Gly Cys  Cys Thr Gly
        995                 1000                1005

Gly Gly  Gly Thr Gly Cys Cys  Thr Ala Ala Thr Gly  Ala Gly Thr
    1010                1015                1020

Gly Ala  Gly Cys Thr Ala Ala  Cys Thr Cys Ala Cys  Ala Thr Thr
    1025                1030                1035

Ala Ala  Thr Thr Gly Cys Gly  Thr Thr Gly Cys Gly  Cys Thr Cys
    1040                1045                1050

Ala Cys  Thr Gly Cys Cys Cys  Gly Cys Thr Thr Thr  Cys Cys Ala
    1055                1060                1065

Gly Thr  Cys Gly Gly Gly Ala  Ala Ala Cys Cys Thr  Gly Thr Cys
    1070                1075                1080

Gly Thr  Gly Cys Cys Ala Gly  Cys Thr Gly Cys Ala  Thr Thr Ala
    1085                1090                1095

Ala Thr  Gly Ala Ala Thr Cys  Gly Gly Cys Cys Ala  Ala Cys Gly
    1100                1105                1110

Cys Gly  Cys Gly Gly Gly Gly  Ala Gly Ala Gly Gly  Cys Gly Gly
    1115                1120                1125

Thr Thr  Thr Gly Cys Gly Thr  Ala Thr Thr Gly Gly  Gly Cys Gly
    1130                1135                1140

Cys Thr  Cys Thr Thr Cys Cys  Gly Cys Thr Thr Cys  Cys Thr Cys
    1145                1150                1155

Gly Cys  Thr Cys Ala Cys Thr  Gly Ala Cys Thr Cys  Gly Cys Thr
```

```
            1160                1165                1170
Gly Cys Gly Cys Thr Cys Gly Gly Thr Cys Gly Thr Thr Cys Gly
            1175                1180                1185
Gly Cys Thr Gly Cys Gly Gly Cys Gly Ala Cys Gly Gly Thr
            1190                1195                1200
Ala Thr Cys Ala Gly Cys Thr Cys Ala Cys Thr Cys Ala Ala Ala
            1205                1210                1215
Gly Gly Cys Gly Gly Thr Ala Ala Thr Ala Cys Gly Gly Thr Thr
            1220                1225                1230
Ala Thr Cys Cys Ala Cys Ala Gly Ala Ala Thr Cys Ala Gly Gly
            1235                1240                1245
Gly Gly Ala Thr Ala Ala Cys Gly Cys Ala Gly Gly Ala Ala Ala
            1250                1255                1260
Gly Ala Ala Cys Ala Thr Gly Thr Gly Ala Gly Cys Ala Ala Ala
            1265                1270                1275
Ala Gly Gly Cys Cys Ala Gly Cys Ala Ala Ala Ala Gly Gly Cys
            1280                1285                1290
Cys Ala Gly Gly Ala Ala Cys Cys Gly Thr Ala Ala Ala Ala Ala
            1295                1300                1305
Gly Gly Cys Cys Gly Cys Gly Thr Thr Gly Cys Thr Gly Gly Cys
            1310                1315                1320
Gly Thr Thr Thr Thr Thr Cys Cys Ala Thr Ala Gly Gly Cys Thr
            1325                1330                1335
Cys Cys Gly Cys Cys Cys Cys Cys Thr Gly Ala Cys Gly Ala
            1340                1345                1350
Gly Cys Ala Thr Cys Ala Cys Ala Ala Ala Ala Ala Thr Cys Gly
            1355                1360                1365
Ala Cys Gly Cys Thr Cys Ala Ala Gly Thr Cys Ala Gly Ala Gly
            1370                1375                1380
Gly Thr Gly Gly Cys Gly Ala Ala Ala Cys Cys Cys Gly Ala Cys
            1385                1390                1395
Ala Gly Gly Ala Cys Thr Ala Thr Ala Ala Ala Gly Ala Thr Ala
            1400                1405                1410
Cys Cys Ala Gly Gly Cys Gly Thr Thr Thr Cys Cys Cys Cys Cys
            1415                1420                1425
Thr Gly Gly Ala Ala Gly Cys Thr Cys Cys Cys Thr Cys Gly Thr
            1430                1435                1440
Gly Cys Gly Cys Thr Cys Thr Cys Cys Thr Gly Thr Thr Cys Cys
            1445                1450                1455
Gly Ala Cys Cys Cys Thr Gly Cys Cys Gly Cys Thr Thr Ala Cys
            1460                1465                1470
Cys Gly Gly Ala Thr Ala Cys Cys Thr Gly Thr Cys Cys Gly Cys
            1475                1480                1485
Cys Thr Thr Thr Cys Thr Cys Cys Cys Thr Thr Cys Gly Gly Gly
            1490                1495                1500
Ala Ala Gly Cys Gly Thr Gly Gly Cys Gly Cys Thr Thr Thr Cys
            1505                1510                1515
Thr Cys Ala Thr Ala Gly Cys Thr Cys Ala Cys Gly Cys Thr Gly
            1520                1525                1530
Thr Ala Gly Gly Thr Ala Thr Cys Thr Cys Ala Gly Thr Thr Cys
            1535                1540                1545
Gly Gly Thr Gly Thr Ala Gly Gly Thr Cys Gly Thr Thr Cys Gly
            1550                1555                1560
```

-continued

```
Cys Thr Cys Cys Ala Ala Gly Cys Thr Gly Gly Cys Thr Gly
    1565                1570            1575

Thr Gly Thr Gly Cys Ala Cys Gly Ala Ala Cys Cys Cys Cys
    1580                1585            1590

Cys Gly Thr Thr Cys Ala Gly Cys Cys Cys Gly Ala Cys Cys Gly
    1595                1600            1605

Cys Thr Gly Cys Gly Cys Cys Thr Thr Ala Thr Cys Cys Gly Gly
    1610                1615            1620

Thr Ala Ala Cys Thr Ala Thr Cys Gly Thr Cys Thr Thr Gly Ala
    1625                1630            1635

Gly Thr Cys Cys Ala Ala Cys Cys Cys Gly Gly Thr Ala Ala Gly
    1640                1645            1650

Ala Cys Ala Cys Gly Ala Cys Thr Thr Ala Thr Cys Gly Cys Cys
    1655                1660            1665

Ala Cys Thr Gly Gly Cys Ala Gly Cys Ala Gly Cys Cys Ala Cys
    1670                1675            1680

Thr Gly Gly Thr Ala Ala Cys Ala Gly Gly Ala Thr Thr Ala Gly
    1685                1690            1695

Cys Ala Gly Ala Gly Cys Gly Ala Gly Gly Thr Ala Thr Gly Thr
    1700                1705            1710

Ala Gly Gly Cys Gly Gly Thr Gly Cys Thr Ala Cys Ala Gly Ala
    1715                1720            1725

Gly Thr Thr Cys Thr Thr Gly Ala Ala Gly Thr Gly Gly Thr Gly
    1730                1735            1740

Gly Cys Cys Thr Ala Ala Cys Thr Ala Cys Gly Gly Cys Thr Ala
    1745                1750            1755

Cys Ala Cys Thr Ala Gly Ala Ala Gly Ala Ala Cys Ala Gly Thr
    1760                1765            1770

Ala Thr Thr Thr Gly Gly Thr Ala Thr Cys Thr Gly Cys Gly Cys
    1775                1780            1785

Thr Cys Thr Gly Cys Thr Gly Ala Ala Gly Cys Cys Ala Gly Thr
    1790                1795            1800

Thr Ala Cys Cys Thr Thr Cys Gly Gly Ala Ala Ala Ala Ala Gly
    1805                1810            1815

Ala Gly Thr Thr Gly Gly Thr Ala Gly Cys Thr Cys Thr Thr Gly
    1820                1825            1830

Ala Thr Cys Cys Gly Gly Cys Ala Ala Ala Cys Ala Ala Ala Cys
    1835                1840            1845

Cys Ala Cys Cys Gly Cys Thr Gly Gly Thr Ala Gly Cys Gly Gly
    1850                1855            1860

Thr Gly Gly Thr Thr Thr Thr Thr Thr Thr Gly Thr Thr Thr Gly
    1865                1870            1875

Cys Ala Ala Gly Cys Ala Gly Cys Ala Gly Ala Thr Thr Ala Cys
    1880                1885            1890

Gly Cys Gly Cys Ala Gly Ala Ala Ala Ala Ala Ala Ala Gly Gly
    1895                1900            1905

Ala Thr Cys Thr Cys Ala Ala Gly Ala Ala Gly Ala Thr Cys Cys
    1910                1915            1920

Thr Thr Thr Gly Ala Thr Cys Thr Thr Thr Thr Cys Thr Ala Cys
    1925                1930            1935

Gly Gly Gly Gly Thr Cys Thr Gly Ala Cys Gly Cys Thr Cys Ala
    1940                1945            1950
```

```
Gly Thr Gly Gly Ala Ala Cys Gly Ala Ala Ala   Cys Thr Cys
    1955            1960            1965

Ala Cys Gly Thr Thr Ala Ala Gly Gly Gly Ala   Thr Thr Thr
    1970            1975            1980

Gly Gly Thr Cys Ala Thr Gly Ala Gly Ala Thr   Ala Thr Cys
    1985            1990            1995

Ala Ala Ala Ala Ala Gly Gly Ala Thr Cys Thr   Cys Ala Cys
    2000            2005            2010

Cys Thr Ala Gly Ala Thr Cys Cys Thr Thr Thr   Ala Ala Ala
    2015            2020            2025

Thr Thr Ala Ala Ala Ala Ala Thr Gly Ala Ala   Gly Thr Thr Thr
    2030            2035            2040

Thr Ala Ala Ala Thr Cys Ala Ala Thr Cys Thr   Ala Ala Gly
    2045            2050            2055

Thr Ala Thr Ala Thr Ala Thr Gly Ala Gly Thr   Ala Ala Ala Cys
    2060            2065            2070

Thr Thr Gly Gly Thr Cys Thr Gly Ala Cys Ala   Gly Thr Thr Ala
    2075            2080            2085

Cys Cys Ala Ala Thr Gly Cys Thr Thr Ala Ala   Thr Cys Ala Gly
    2090            2095            2100

Thr Gly Ala Gly Gly Cys Ala Cys Cys Thr Ala   Thr Cys Thr Cys
    2105            2110            2115

Ala Gly Cys Gly Ala Thr Cys Thr Gly Thr Cys   Thr Ala Thr Thr
    2120            2125            2130

Thr Cys Gly Thr Thr Cys Ala Thr Cys Cys Ala   Thr Ala Gly Thr
    2135            2140            2145

Thr Gly Cys Cys Thr Gly Ala Cys Thr Cys Cys   Cys Cys Gly Thr
    2150            2155            2160

Cys Gly Thr Gly Thr Ala Gly Ala Thr Ala Ala   Cys Thr Ala Cys
    2165            2170            2175

Gly Ala Thr Ala Cys Gly Gly Gly Ala Gly Gly   Gly Cys Thr Thr
    2180            2185            2190

Ala Cys Cys Ala Thr Cys Thr Gly Gly Cys Cys   Cys Cys Ala Gly
    2195            2200            2205

Thr Gly Cys Thr Gly Cys Ala Ala Thr Gly Ala   Thr Ala Cys Cys
    2210            2215            2220

Gly Cys Gly Ala Gly Ala Cys Cys Cys Ala Cys   Gly Cys Thr Cys
    2225            2230            2235

Ala Cys Cys Gly Gly Cys Thr Cys Cys Ala Gly   Ala Thr Thr Thr
    2240            2245            2250

Ala Thr Cys Ala Gly Cys Ala Ala Thr Ala Ala   Ala Cys Cys Ala
    2255            2260            2265

Gly Cys Cys Ala Gly Cys Cys Gly Gly Ala Ala   Gly Gly Gly Cys
    2270            2275            2280

Cys Gly Ala Gly Cys Gly Cys Ala Gly Ala Ala   Gly Thr Gly Gly
    2285            2290            2295

Thr Cys Cys Thr Gly Cys Ala Ala Cys Thr Thr   Thr Ala Thr Cys
    2300            2305            2310

Cys Gly Cys Cys Thr Cys Cys Ala Thr Cys Cys   Ala Gly Thr Cys
    2315            2320            2325

Thr Ala Thr Thr Ala Ala Thr Thr Gly Thr Thr   Gly Cys Cys Gly
    2330            2335            2340

Gly Gly Ala Ala Gly Cys Thr Ala Gly Ala Gly   Thr Ala Ala Gly
```

-continued

```
    2345                2350                2355

Thr Ala  Gly Thr Thr Cys Gly  Cys Cys Ala Gly Thr  Thr Ala Ala
    2360                2365                2370

Thr Ala  Gly Thr Thr Thr Gly  Cys Gly Cys Ala Ala  Cys Gly Thr
    2375                2380                2385

Thr Gly  Thr Thr Gly Cys Cys  Ala Thr Thr Gly Cys  Thr Ala Cys
    2390                2395                2400

Ala Gly  Gly Cys Ala Thr Cys  Gly Thr Gly Gly Thr  Gly Thr Cys
    2405                2410                2415

Ala Cys  Gly Cys Thr Cys Gly  Thr Cys Gly Thr Thr  Thr Gly Gly
    2420                2425                2430

Thr Ala  Thr Gly Gly Cys Thr  Thr Cys Ala Thr Thr  Cys Ala Gly
    2435                2440                2445

Cys Thr  Cys Cys Gly Gly Thr  Thr Cys Cys Cys Ala  Ala Cys Gly
    2450                2455                2460

Ala Thr  Cys Ala Ala Gly Gly  Cys Gly Ala Gly Thr  Thr Ala Cys
    2465                2470                2475

Ala Thr  Gly Ala Thr Cys Cys  Cys Cys Cys Ala Thr  Gly Thr Thr
    2480                2485                2490

Gly Thr  Gly Cys Ala Ala Ala  Ala Ala Ala Gly Cys  Gly Gly Thr
    2495                2500                2505

Thr Ala  Gly Cys Thr Cys Cys  Thr Thr Cys Gly Gly  Thr Cys Cys
    2510                2515                2520

Thr Cys  Cys Gly Ala Thr Cys  Gly Thr Thr Gly Thr  Cys Ala Gly
    2525                2530                2535

Ala Ala  Gly Thr Ala Ala Gly  Thr Thr Gly Gly Cys  Cys Gly Cys
    2540                2545                2550

Ala Gly  Thr Gly Thr Thr Ala  Thr Cys Ala Cys Thr  Cys Ala Thr
    2555                2560                2565

Gly Gly  Thr Thr Ala Thr Gly  Gly Cys Ala Gly Cys  Ala Cys Thr
    2570                2575                2580

Gly Cys  Ala Thr Ala Ala Thr  Thr Cys Thr Cys Thr  Thr Ala Cys
    2585                2590                2595

Thr Gly  Thr Cys Ala Thr Gly  Cys Cys Ala Thr Cys  Cys Gly Thr
    2600                2605                2610

Ala Ala  Gly Ala Thr Gly Cys  Thr Thr Thr Thr Cys  Thr Gly Thr
    2615                2620                2625

Gly Ala  Cys Thr Gly Gly Thr  Gly Ala Gly Thr Ala  Cys Thr Cys
    2630                2635                2640

Ala Ala  Cys Cys Ala Ala Gly  Thr Cys Ala Thr Thr  Cys Thr Gly
    2645                2650                2655

Ala Gly  Ala Ala Thr Ala Gly  Thr Gly Thr Ala Thr  Gly Cys Gly
    2660                2665                2670

Gly Cys  Gly Ala Cys Cys Gly  Ala Gly Thr Thr Gly  Cys Thr Cys
    2675                2680                2685

Thr Thr  Gly Cys Cys Cys Gly  Gly Cys Gly Thr Cys  Ala Ala Thr
    2690                2695                2700

Ala Cys  Gly Gly Gly Ala Thr  Ala Ala Thr Ala Cys  Cys Gly Cys
    2705                2710                2715

Gly Cys  Cys Ala Cys Ala Thr  Ala Gly Cys Ala Gly  Ala Ala Cys
    2720                2725                2730

Thr Thr  Thr Ala Ala Ala Ala  Gly Thr Gly Cys Thr  Cys Ala Thr
    2735                2740                2745
```

```
Cys Ala Thr Thr Gly Gly Ala Ala Ala Cys Gly Thr Thr Cys
    2750                2755                2760

Thr Thr Cys Gly Gly Gly Gly Cys Gly Ala Ala Ala Cys Thr
    2765                2770                2775

Cys Thr Cys Ala Ala Gly Gly Ala Thr Cys Thr Ala Cys Cys
    2780                2785                2790

Gly Cys Thr Gly Thr Thr Gly Ala Gly Ala Thr Cys Ala Gly
    2795                2800                2805

Thr Thr Cys Gly Ala Thr Gly Thr Ala Ala Cys Cys Ala Cys
    2810                2815                2820

Thr Cys Gly Thr Gly Cys Ala Cys Cys Cys Ala Ala Cys Thr Gly
    2825                2830                2835

Ala Thr Cys Thr Thr Cys Ala Gly Cys Ala Thr Cys Thr Thr Thr
    2840                2845                2850

Thr Ala Cys Thr Thr Cys Ala Cys Cys Ala Gly Cys Gly Thr
    2855                2860                2865

Thr Thr Cys Thr Gly Gly Gly Thr Gly Ala Gly Cys Ala Ala Ala
    2870                2875                2880

Ala Ala Cys Ala Gly Gly Ala Ala Gly Gly Cys Ala Ala Ala
    2885                2890                2895

Thr Gly Cys Cys Gly Cys Ala Ala Ala Ala Ala Gly Gly Gly
    2900                2905                2910

Ala Ala Thr Ala Ala Gly Gly Gly Cys Gly Ala Cys Ala Cys Gly
    2915                2920                2925

Gly Ala Ala Ala Thr Gly Thr Thr Gly Ala Ala Thr Ala Cys Thr
    2930                2935                2940

Cys Ala Thr Ala Cys Thr Cys Thr Thr Cys Cys Thr Thr Thr Thr
    2945                2950                2955

Thr Cys Ala Ala Thr Ala Thr Thr Ala Thr Thr Gly Ala Ala Gly
    2960                2965                2970

Cys Ala Thr Thr Thr Ala Thr Cys Ala Gly Gly Gly Thr Thr Ala
    2975                2980                2985

Thr Thr Gly Thr Cys Thr Cys Ala Thr Gly Ala Gly Cys Gly Gly
    2990                2995                3000

Ala Thr Ala Cys Ala Thr Ala Thr Thr Thr Gly Ala Ala Thr Gly
    3005                3010                3015

Thr Ala Thr Thr Thr Ala Gly Ala Ala Ala Ala Ala Thr Ala Ala
    3020                3025                3030

Ala Cys Ala Ala Ala Thr Ala Gly Gly Gly Gly Thr Thr Cys Cys
    3035                3040                3045

Gly Cys Gly Cys Ala Cys Ala Thr Thr Thr Cys Cys Cys Cys Gly
    3050                3055                3060

Ala Ala Ala Ala Gly Thr Gly Cys Cys Ala Cys Cys Thr Gly Ala
    3065                3070                3075

Cys Gly Thr Cys Thr Ala Ala Gly Ala Ala Ala Cys Cys Ala Thr
    3080                3085                3090

Thr Ala Thr Thr Ala Thr Cys Ala Thr Gly Ala Cys Ala Thr Thr
    3095                3100                3105

Ala Ala Cys Cys Thr Ala Thr Ala Ala Ala Ala Ala Thr Ala Gly
    3110                3115                3120

Gly Cys Gly Thr Ala Thr Cys Ala Cys Gly Ala Gly Gly Cys Cys
    3125                3130                3135
```

```
Cys Thr  Thr Thr Cys Gly
    3140
```

<210> SEQ ID NO 341
<211> LENGTH: 57
<212> TYPE: PRT
<213> ORGANISM: Artificial Sequence
<220> FEATURE:
<223> OTHER INFORMATION: Synthethic

<400> SEQUENCE: 341

```
Ser Arg Val Ser Val Met Thr Val Lys Thr Ser Asp Thr Cys Ser Ser
1               5                   10                  15

Arg Arg Arg Ser Gln Leu Val Cys Lys Arg Met Pro Gly Ala Asp Lys
            20                  25                  30

Pro Val Arg Ala Arg Gln Arg Val Leu Ala Gly Val Gly Ala Gly Leu
        35                  40                  45

Thr Met Arg His Gln Ser Arg Leu Tyr
    50                  55
```

<210> SEQ ID NO 342
<211> LENGTH: 13
<212> TYPE: PRT
<213> ORGANISM: Artificial Sequence
<220> FEATURE:
<223> OTHER INFORMATION: Synthethic

<400> SEQUENCE: 342

```
Glu Cys Thr Ile Cys Gly Val Lys Tyr Arg Thr Asp Ala
1               5                   10
```

<210> SEQ ID NO 343
<211> LENGTH: 41
<212> TYPE: PRT
<213> ORGANISM: Artificial Sequence
<220> FEATURE:
<223> OTHER INFORMATION: Synthethic

<400> SEQUENCE: 343

```
Gly Glu Asn Thr Ala Ser Gly Ala Ile Arg His Ser Gly Cys Ala Thr
1               5                   10                  15

Val Gly Lys Gly Asp Arg Cys Gly Pro Leu Arg Tyr Tyr Ala Ser Trp
            20                  25                  30

Arg Lys Gly Asp Val Leu Gln Gly Asp
        35                  40
```

<210> SEQ ID NO 344
<211> LENGTH: 2
<212> TYPE: PRT
<213> ORGANISM: Artificial Sequence
<220> FEATURE:
<223> OTHER INFORMATION: Synthethic

<400> SEQUENCE: 344

```
Val Gly
1
```

<210> SEQ ID NO 345
<211> LENGTH: 21
<212> TYPE: PRT
<213> ORGANISM: Artificial Sequence
<220> FEATURE:
<223> OTHER INFORMATION: Synthethic

<400> SEQUENCE: 345

Arg Gln Gly Phe Pro Ser His Asp Val Val Lys Arg Arg Pro Val Asn
1               5                   10                  15

Ser Ser Arg Pro Pro
            20

<210> SEQ ID NO 346
<211> LENGTH: 5
<212> TYPE: PRT
<213> ORGANISM: Artificial Sequence
<220> FEATURE:
<223> OTHER INFORMATION: Synthethic

<400> SEQUENCE: 346

Leu Gly Val Gly Cys
1               5

<210> SEQ ID NO 347
<211> LENGTH: 5
<212> TYPE: PRT
<213> ORGANISM: Artificial Sequence
<220> FEATURE:
<223> OTHER INFORMATION: Synthethic

<400> SEQUENCE: 347

Ala Trp Ser Cys Cys
1               5

<210> SEQ ID NO 348
<211> LENGTH: 68
<212> TYPE: PRT
<213> ORGANISM: Artificial Sequence
<220> FEATURE:
<223> OTHER INFORMATION: Synthethic

<400> SEQUENCE: 348

Pro Pro Trp Arg Ala Val Ser Val Arg Pro Gln Ser Ser Pro His
1               5                   10                  15

Pro Pro Pro Pro Arg Cys Ser Leu Pro Pro Arg Val Ser Lys Pro Ala
                20                  25                  30

Phe Leu Ser Glu Ser Ala Ser Ser Pro Ala Thr Ala Thr Cys Ser Ala
            35                  40                  45

Ser Pro Arg Thr Ser Ser Val Pro Arg Leu Ala Arg Gly Arg Ile Thr
        50                  55                  60

Arg Arg Ala Cys
65

<210> SEQ ID NO 349
<211> LENGTH: 19
<212> TYPE: PRT
<213> ORGANISM: Artificial Sequence
<220> FEATURE:
<223> OTHER INFORMATION: Synthethic

<400> SEQUENCE: 349

Trp Cys Leu Lys Thr Thr Leu Phe Pro Thr Arg Leu Arg Ser Ala Pro
1               5                   10                  15

Thr Pro Arg

<210> SEQ ID NO 350
<211> LENGTH: 13
<212> TYPE: PRT
<213> ORGANISM: Artificial Sequence
<220> FEATURE:

<223> OTHER INFORMATION: Synthethic

<400> SEQUENCE: 350

Pro Thr Phe Ser Ser Thr Met Ala Gly Thr Arg Thr Pro
1               5                   10

<210> SEQ ID NO 351
<211> LENGTH: 29
<212> TYPE: PRT
<213> ORGANISM: Artificial Sequence
<220> FEATURE:
<223> OTHER INFORMATION: Synthethic

<400> SEQUENCE: 351

Pro Thr Gly Thr Arg Arg Ser Ser Pro Leu Thr Ala Thr Lys Leu Thr
1               5                   10                  15

Arg Trp Ile Pro Ser Thr Ser Ala Thr Thr Arg Ser Arg
            20                  25

<210> SEQ ID NO 352
<211> LENGTH: 4
<212> TYPE: PRT
<213> ORGANISM: Artificial Sequence
<220> FEATURE:
<223> OTHER INFORMATION: Synthethic

<400> SEQUENCE: 352

Gln Lys Met Gly
1

<210> SEQ ID NO 353
<211> LENGTH: 4
<212> TYPE: PRT
<213> ORGANISM: Artificial Sequence
<220> FEATURE:
<223> OTHER INFORMATION: Synthethic

<400> SEQUENCE: 353

Arg Ala Cys Met
1

<210> SEQ ID NO 354
<211> LENGTH: 10
<212> TYPE: PRT
<213> ORGANISM: Artificial Sequence
<220> FEATURE:
<223> OTHER INFORMATION: Synthethic

<400> SEQUENCE: 354

Thr Ala Thr Glu Leu Thr Ser Pro Ser Thr
1               5                   10

<210> SEQ ID NO 355
<211> LENGTH: 25
<212> TYPE: PRT
<213> ORGANISM: Artificial Sequence
<220> FEATURE:
<223> OTHER INFORMATION: Synthethic

<400> SEQUENCE: 355

Ser Pro Pro Gly Ala Trp Pro Thr Gly Cys Ala Ala Thr Pro Ala Arg
1               5                   10                  15

Arg Ser Ser Met Thr Pro Pro Gly Gly
            20                  25

```
<210> SEQ ID NO 356
<211> LENGTH: 12
<212> TYPE: PRT
<213> ORGANISM: Artificial Sequence
<220> FEATURE:
<223> OTHER INFORMATION: Synthethic

<400> SEQUENCE: 356

Tyr Gly Leu Thr Glu Gln Glu Leu Pro Ser Thr Ala
1               5                   10

<210> SEQ ID NO 357
<211> LENGTH: 2
<212> TYPE: PRT
<213> ORGANISM: Artificial Sequence
<220> FEATURE:
<223> OTHER INFORMATION: Synthethic

<400> SEQUENCE: 357

Leu Thr
1

<210> SEQ ID NO 358
<211> LENGTH: 11
<212> TYPE: PRT
<213> ORGANISM: Artificial Sequence
<220> FEATURE:
<223> OTHER INFORMATION: Synthethic

<400> SEQUENCE: 358

Trp Pro Ser Pro Thr Ala Pro Ser Thr Ser Leu
1               5                   10

<210> SEQ ID NO 359
<211> LENGTH: 29
<212> TYPE: PRT
<213> ORGANISM: Artificial Sequence
<220> FEATURE:
<223> OTHER INFORMATION: Synthethic

<400> SEQUENCE: 359

Pro Pro Pro Gly Arg Leu Trp Lys Cys Pro Leu Ser Met Thr Gly Lys
1               5                   10                  15

Ile Arg Lys Pro Ser Met Ser Gly Gln Thr Pro Ser Thr
            20                  25

<210> SEQ ID NO 360
<211> LENGTH: 5
<212> TYPE: PRT
<213> ORGANISM: Artificial Sequence
<220> FEATURE:
<223> OTHER INFORMATION: Synthethic

<400> SEQUENCE: 360

Glu Leu Thr Thr Arg
1               5

<210> SEQ ID NO 361
<211> LENGTH: 58
<212> TYPE: PRT
<213> ORGANISM: Artificial Sequence
<220> FEATURE:
<223> OTHER INFORMATION: Synthethic

<400> SEQUENCE: 361

Trp Thr Thr Thr Thr Glu Gly Arg Thr Arg Lys Ala Asn Ala Glu Pro
1               5                   10                  15
```

Ser Trp Thr Arg Ala Leu Thr Arg Tyr Leu Gly Ser Ser Arg Thr Gly
        20                  25                  30

Gln Pro Thr Ala Arg Phe Asn Thr Gly Lys Pro Leu Thr Arg Pro Ser
    35                  40                  45

Pro Gln Lys Gln Gly Ser Gln Tyr Ile Leu
    50                  55

<210> SEQ ID NO 362
<211> LENGTH: 8
<212> TYPE: PRT
<213> ORGANISM: Artificial Sequence
<220> FEATURE:
<223> OTHER INFORMATION: Synthethic

<400> SEQUENCE: 362

Leu Thr Arg Ala Pro Leu Ala Ser
1               5

<210> SEQ ID NO 363
<211> LENGTH: 6
<212> TYPE: PRT
<213> ORGANISM: Artificial Sequence
<220> FEATURE:
<223> OTHER INFORMATION: Synthethic

<400> SEQUENCE: 363

Pro Thr Gln Pro Trp Ala
1               5

<210> SEQ ID NO 364
<211> LENGTH: 12
<212> TYPE: PRT
<213> ORGANISM: Artificial Sequence
<220> FEATURE:
<223> OTHER INFORMATION: Synthethic

<400> SEQUENCE: 364

Ser Ser Arg Thr Pro Ser Ser Ala Ser Lys Ser Arg
1               5                   10

<210> SEQ ID NO 365
<211> LENGTH: 25
<212> TYPE: PRT
<213> ORGANISM: Artificial Sequence
<220> FEATURE:
<223> OTHER INFORMATION: Synthethic

<400> SEQUENCE: 365

Thr Arg Pro Cys Met Arg Ser Thr Arg Pro Ser Arg Ile Val Thr Arg
1               5                   10                  15

Arg Ala Arg Lys Pro Leu His Ile Leu
        20                  25

<210> SEQ ID NO 366
<211> LENGTH: 6
<212> TYPE: PRT
<213> ORGANISM: Artificial Sequence
<220> FEATURE:
<223> OTHER INFORMATION: Synthethic

<400> SEQUENCE: 366

Arg Ala Glu Asp Cys Tyr
1               5

```
<210> SEQ ID NO 367
<211> LENGTH: 4
<212> TYPE: PRT
<213> ORGANISM: Artificial Sequence
<220> FEATURE:
<223> OTHER INFORMATION: Synthethic

<400> SEQUENCE: 367

Leu Gly Tyr Leu
1

<210> SEQ ID NO 368
<211> LENGTH: 10
<212> TYPE: PRT
<213> ORGANISM: Artificial Sequence
<220> FEATURE:
<223> OTHER INFORMATION: Synthethic

<400> SEQUENCE: 368

Pro Arg Ala Arg Trp Pro Pro Ser Arg Thr
1               5                   10

<210> SEQ ID NO 369
<211> LENGTH: 30
<212> TYPE: PRT
<213> ORGANISM: Artificial Sequence
<220> FEATURE:
<223> OTHER INFORMATION: Synthethic

<400> SEQUENCE: 369

Arg Ser Leu Pro Leu Arg Leu Pro His Pro Pro Ala Val His Arg Pro
1               5                   10                  15

Gln Pro His Pro Arg Pro Ala Gly Ala Pro Pro Pro Pro Phe
            20                  25                  30

<210> SEQ ID NO 370
<211> LENGTH: 66
<212> TYPE: PRT
<213> ORGANISM: Artificial Sequence
<220> FEATURE:
<223> OTHER INFORMATION: Synthethic

<400> SEQUENCE: 370

Gly Val Gly Gly Met Arg Gly Thr Pro Pro His Arg Cys Pro Pro
1               5                   10                  15

Arg Pro Pro Gly Ser Pro Trp Ala Pro Ser Thr Ile Pro Pro Pro Ser
            20                  25                  30

Arg Ser Asn Leu Pro Thr Thr Pro Cys Ala Ala Arg Ser Thr Ala Cys
        35                  40                  45

Trp Glu Thr Leu Arg Gly Pro Gly Ala Trp Ser Arg Arg Gly Arg Thr
    50                  55                  60

Trp Cys
65

<210> SEQ ID NO 371
<211> LENGTH: 2
<212> TYPE: PRT
<213> ORGANISM: Artificial Sequence
<220> FEATURE:
<223> OTHER INFORMATION: Synthethic

<400> SEQUENCE: 371

Glu Asn
1
```

<210> SEQ ID NO 372
<211> LENGTH: 44
<212> TYPE: PRT
<213> ORGANISM: Artificial Sequence
<220> FEATURE:
<223> OTHER INFORMATION: Synthethic

<400> SEQUENCE: 372

```
Pro Arg Leu Ile Gln Pro Pro Ser Cys Pro Ala Ser Thr Val Arg Arg
1               5                   10                  15

Trp Arg Pro Ser Ala Trp Gly Met Ser Ser Gln Ser Pro Ser Ala Cys
            20                  25                  30

Pro Leu Thr Arg Pro Pro Ser Pro Cys Ala Arg Ala
        35                  40
```

<210> SEQ ID NO 373
<211> LENGTH: 41
<212> TYPE: PRT
<213> ORGANISM: Artificial Sequence
<220> FEATURE:
<223> OTHER INFORMATION: Synthethic

<400> SEQUENCE: 373

```
Gly Ser Leu Ala Pro Arg Pro Cys Ala Thr Arg Ala Pro Trp Cys Pro
1               5                   10                  15

Ser Ala Leu Ser Thr Thr Pro Arg Pro Thr Arg Asp Ser Trp Ala Pro
            20                  25                  30

Thr Thr Arg Ser Ser Ser Gln Lys Arg
        35                  40
```

<210> SEQ ID NO 374
<211> LENGTH: 43
<212> TYPE: PRT
<213> ORGANISM: Artificial Sequence
<220> FEATURE:
<223> OTHER INFORMATION: Synthethic

<400> SEQUENCE: 374

```
Arg Arg Cys Ala Arg Arg Pro Ala Ser Thr Thr Ser Ser Pro Ala Thr
1               5                   10                  15

Arg Ser Thr Ser Thr Thr Thr Thr Thr Leu Lys Pro Ser Ser Trp
            20                  25                  30

Thr Ala Leu Pro Pro Cys Arg Pro Ser Ser His
        35                  40
```

<210> SEQ ID NO 375
<211> LENGTH: 81
<212> TYPE: PRT
<213> ORGANISM: Artificial Sequence
<220> FEATURE:
<223> OTHER INFORMATION: Synthethic

<400> SEQUENCE: 375

```
Thr Pro Pro Ser Ser Arg Thr Leu Thr Leu Pro Pro Trp Ser Cys Thr
1               5                   10                  15

His Gly Thr Asn Ser Val Pro Pro Thr Ser Leu Thr Trp Arg Ala Ser
            20                  25                  30

Ser Gly Ser Thr Thr Ser Arg Arg Lys Thr Ser Pro Ala Cys Gly Arg
        35                  40                  45

Ile Trp Thr Met Gln Cys Gln Thr Glu Glu Ile Asn Ser Trp Thr Ala
    50                  55                  60
```

Trp Gly Asn Leu Trp Thr Val Trp Val Ala Trp Val Ser Pro Ser Pro
65                  70                  75                  80

Thr

<210> SEQ ID NO 376
<211> LENGTH: 32
<212> TYPE: PRT
<213> ORGANISM: Artificial Sequence
<220> FEATURE:
<223> OTHER INFORMATION: Synthethic

<400> SEQUENCE: 376

Ser Ala Arg Trp Gly Val Cys Leu Ala Ala Trp Ser Leu Val Ser Ser
1               5                   10                  15

Pro Ser Ser Lys Thr Pro Ser Ala Ala Leu Ser Leu Pro Ile Ser Leu
                20                  25                  30

<210> SEQ ID NO 377
<211> LENGTH: 13
<212> TYPE: PRT
<213> ORGANISM: Artificial Sequence
<220> FEATURE:
<223> OTHER INFORMATION: Synthethic

<400> SEQUENCE: 377

Leu Pro Tyr Leu Leu Phe Ala Val Tyr Leu Val Trp Phe
1               5                   10

<210> SEQ ID NO 378
<211> LENGTH: 3
<212> TYPE: PRT
<213> ORGANISM: Artificial Sequence
<220> FEATURE:
<223> OTHER INFORMATION: Synthethic

<400> SEQUENCE: 378

His Ala Thr
1

<210> SEQ ID NO 379
<211> LENGTH: 21
<212> TYPE: PRT
<213> ORGANISM: Artificial Sequence
<220> FEATURE:
<223> OTHER INFORMATION: Synthethic

<400> SEQUENCE: 379

Cys Thr Ser Lys Arg Arg Asn Lys Arg Pro Cys Tyr Gly Leu Gly Ile
1               5                   10                  15

Ile Pro Trp Val Arg
                20

<210> SEQ ID NO 380
<211> LENGTH: 9
<212> TYPE: PRT
<213> ORGANISM: Artificial Sequence
<220> FEATURE:
<223> OTHER INFORMATION: Synthethic

<400> SEQUENCE: 380

Glu Pro Leu Gln Lys Cys Glu Cys Arg
1               5

<210> SEQ ID NO 381
<211> LENGTH: 38

<212> TYPE: PRT
<213> ORGANISM: Artificial Sequence
<220> FEATURE:
<223> OTHER INFORMATION: Synthethic

<400> SEQUENCE: 381

Glu Ala Glu Val Ser Pro Ile Ala Ile Cys Val Gln Ile Leu Cys Pro
1               5                   10                  15

Gly Ser Gln Ile Pro Leu Arg Ser Phe Ser Leu Cys Gln Lys Leu Trp
            20                  25                  30

Gly His His Glu Ala Pro
            35

<210> SEQ ID NO 382
<211> LENGTH: 39
<212> TYPE: PRT
<213> ORGANISM: Artificial Sequence
<220> FEATURE:
<223> OTHER INFORMATION: Synthethic

<400> SEQUENCE: 382

Ala Ser Asp Phe Trp Leu Ile Lys Glu Ile Tyr Phe His Cys Asn Ser
1               5                   10                  15

Val Leu Glu Phe Phe Val Ser Leu Thr Arg Lys Asp Ile Trp Glu Gly
            20                  25                  30

Lys Ser Phe Lys Thr Ser Glu
            35

<210> SEQ ID NO 383
<211> LENGTH: 39
<212> TYPE: PRT
<213> ORGANISM: Artificial Sequence
<220> FEATURE:
<223> OTHER INFORMATION: Synthethic

<400> SEQUENCE: 383

Val Phe Gly Leu Glu Phe Gly Asn Ile Cys Pro Tyr Ala Gly Cys His
1               5                   10                  15

Glu Gln Arg Leu Ala Ile Lys Arg Ser Ser Val Tyr Glu Thr Ala Pro
            20                  25                  30

Cys Cys Pro Phe Leu Ile Pro
            35

<210> SEQ ID NO 384
<211> LENGTH: 87
<212> TYPE: PRT
<213> ORGANISM: Artificial Sequence
<220> FEATURE:
<223> OTHER INFORMATION: Synthethic

<400> SEQUENCE: 384

Lys Ser Leu Asp Leu Arg Leu Asp Phe Tyr Ile Leu Phe Cys Val
1               5                   10                  15

Ile Phe Phe Phe Asn Ile Pro Lys Ile Phe Leu Thr Cys Phe Thr Ser
            20                  25                  30

Gln Ile Phe Pro Pro Leu Leu Thr Thr Pro Ser His Ser Cys Pro Ser
            35                  40                  45

Ser Leu Met Glu Ile Pro Arg Pro Ala Ala Gln Ala Trp Arg Asn His
    50                  55                  60

Gly His Ser Cys Phe Leu Cys Glu Ile Val Ile Arg Ser Gln Phe His
65                  70                  75                  80

```
Thr Thr Tyr Glu Pro Glu Ala
            85
```

<210> SEQ ID NO 385
<211> LENGTH: 9
<212> TYPE: PRT
<213> ORGANISM: Artificial Sequence
<220> FEATURE:
<223> OTHER INFORMATION: Synthethic

<400> SEQUENCE: 385

```
Ser Val Lys Pro Gly Val Pro Asn Glu
1               5
```

<210> SEQ ID NO 386
<211> LENGTH: 4
<212> TYPE: PRT
<213> ORGANISM: Artificial Sequence
<220> FEATURE:
<223> OTHER INFORMATION: Synthethic

<400> SEQUENCE: 386

```
Ala Asn Ser His
1
```

<210> SEQ ID NO 387
<211> LENGTH: 61
<212> TYPE: PRT
<213> ORGANISM: Artificial Sequence
<220> FEATURE:
<223> OTHER INFORMATION: Synthethic

<400> SEQUENCE: 387

```
Leu Arg Cys Ala His Cys Pro Leu Ser Ser Arg Glu Thr Cys Arg Ala
1               5                   10                  15

Ser Cys Ile Asn Glu Ser Ala Asn Ala Arg Gly Glu Ala Val Cys Val
            20                  25                  30

Leu Gly Ala Leu Pro Leu Pro Arg Ser Leu Thr Arg Cys Ala Arg Ser
        35                  40                  45

Phe Gly Cys Gly Glu Arg Tyr Gln Leu Thr Gln Arg Arg
    50                  55                  60
```

<210> SEQ ID NO 388
<211> LENGTH: 141
<212> TYPE: PRT
<213> ORGANISM: Artificial Sequence
<220> FEATURE:
<223> OTHER INFORMATION: Synthethic

<400> SEQUENCE: 388

```
Tyr Gly Tyr Pro Gln Asn Gln Gly Ile Thr Gln Glu Arg Thr Cys Glu
1               5                   10                  15

Gln Lys Ala Ser Lys Arg Pro Gly Thr Val Lys Arg Pro Arg Cys Trp
            20                  25                  30

Arg Phe Ser Ile Gly Ser Ala Pro Leu Thr Ser Ile Thr Lys Ile Asp
        35                  40                  45

Ala Gln Val Arg Gly Gly Glu Thr Arg Gln Asp Tyr Lys Asp Thr Arg
    50                  55                  60

Arg Phe Pro Leu Glu Ala Pro Ser Cys Ala Leu Leu Phe Arg Pro Cys
65                  70                  75                  80

Arg Leu Pro Asp Thr Cys Pro Pro Phe Ser Leu Arg Glu Ala Trp Arg
            85                  90                  95
```

```
Phe Leu Ile Ala His Ala Val Gly Ile Ser Val Arg Cys Arg Ser Phe
            100                 105                 110

Ala Pro Ser Trp Ala Val Cys Thr Asn Pro Pro Phe Ser Pro Thr Ala
        115                 120                 125

Ala Pro Tyr Pro Val Thr Ile Val Leu Ser Pro Thr Arg
    130                 135                 140

<210> SEQ ID NO 389
<211> LENGTH: 20
<212> TYPE: PRT
<213> ORGANISM: Artificial Sequence
<220> FEATURE:
<223> OTHER INFORMATION: Synthethic

<400> SEQUENCE: 389

Asp Thr Thr Tyr Arg His Trp Gln Gln Pro Leu Val Thr Gly Leu Ala
1               5                   10                  15

Glu Arg Gly Met
            20

<210> SEQ ID NO 390
<211> LENGTH: 6
<212> TYPE: PRT
<213> ORGANISM: Artificial Sequence
<220> FEATURE:
<223> OTHER INFORMATION: Synthethic

<400> SEQUENCE: 390

Ala Val Leu Gln Ser Ser
1               5

<210> SEQ ID NO 391
<211> LENGTH: 19
<212> TYPE: PRT
<213> ORGANISM: Artificial Sequence
<220> FEATURE:
<223> OTHER INFORMATION: Synthethic

<400> SEQUENCE: 391

Ser Gly Gly Leu Thr Thr Ala Thr Leu Glu Glu Gln Tyr Leu Val Ser
1               5                   10                  15

Ala Leu Cys

<210> SEQ ID NO 392
<211> LENGTH: 43
<212> TYPE: PRT
<213> ORGANISM: Artificial Sequence
<220> FEATURE:
<223> OTHER INFORMATION: Synthethic

<400> SEQUENCE: 392

Ser Gln Leu Pro Ser Glu Lys Glu Leu Val Ala Leu Asp Pro Ala Asn
1               5                   10                  15

Lys Pro Pro Leu Val Ala Val Val Phe Leu Phe Ala Ser Ser Arg Leu
            20                  25                  30

Arg Ala Glu Lys Lys Asp Leu Lys Lys Ile Leu
        35                  40

<210> SEQ ID NO 393
<211> LENGTH: 20
<212> TYPE: PRT
<213> ORGANISM: Artificial Sequence
<220> FEATURE:
<223> OTHER INFORMATION: Synthethic
```

<400> SEQUENCE: 393

Ser Phe Leu Arg Gly Leu Thr Leu Ser Gly Thr Lys Thr His Val Lys
1               5                   10                  15

Gly Phe Trp Ser
            20

<210> SEQ ID NO 394
<211> LENGTH: 11
<212> TYPE: PRT
<213> ORGANISM: Artificial Sequence
<220> FEATURE:
<223> OTHER INFORMATION: Synthethic

<400> SEQUENCE: 394

Asp Tyr Gln Lys Gly Ser Ser Pro Arg Ser Phe
1               5                   10

<210> SEQ ID NO 395
<211> LENGTH: 23
<212> TYPE: PRT
<213> ORGANISM: Artificial Sequence
<220> FEATURE:
<223> OTHER INFORMATION: Synthethic

<400> SEQUENCE: 395

Ile Lys Asn Glu Val Leu Asn Gln Ser Lys Val Tyr Met Ser Lys Leu
1               5                   10                  15

Gly Leu Thr Val Thr Asn Ala
            20

<210> SEQ ID NO 396
<211> LENGTH: 15
<212> TYPE: PRT
<213> ORGANISM: Artificial Sequence
<220> FEATURE:
<223> OTHER INFORMATION: Synthethic

<400> SEQUENCE: 396

Ser Val Arg His Leu Ser Gln Arg Ser Val Tyr Phe Val His Pro
1               5                   10                  15

<210> SEQ ID NO 397
<211> LENGTH: 8
<212> TYPE: PRT
<213> ORGANISM: Artificial Sequence
<220> FEATURE:
<223> OTHER INFORMATION: Synthethic

<400> SEQUENCE: 397

Leu Pro Asp Ser Pro Ser Cys Arg
1               5

<210> SEQ ID NO 398
<211> LENGTH: 14
<212> TYPE: PRT
<213> ORGANISM: Artificial Sequence
<220> FEATURE:
<223> OTHER INFORMATION: Synthethic

<400> SEQUENCE: 398

Leu Arg Tyr Gly Arg Ala Tyr His Leu Ala Pro Val Leu Gln
1               5                   10

<210> SEQ ID NO 399

```
<211> LENGTH: 14
<212> TYPE: PRT
<213> ORGANISM: Artificial Sequence
<220> FEATURE:
<223> OTHER INFORMATION: Synthethic

<400> SEQUENCE: 399

Tyr Arg Glu Thr His Ala His Arg Leu Gln Ile Tyr Gln Gln
1               5                   10

<210> SEQ ID NO 400
<211> LENGTH: 30
<212> TYPE: PRT
<213> ORGANISM: Artificial Sequence
<220> FEATURE:
<223> OTHER INFORMATION: Synthethic

<400> SEQUENCE: 400

Thr Ser Gln Pro Glu Gly Pro Ser Ala Glu Val Val Leu Gln Leu Tyr
1               5                   10                  15

Pro Pro Pro Ser Ser Leu Leu Ile Val Ala Gly Lys Leu Glu
            20                  25                  30

<210> SEQ ID NO 401
<211> LENGTH: 85
<212> TYPE: PRT
<213> ORGANISM: Artificial Sequence
<220> FEATURE:
<223> OTHER INFORMATION: Synthethic

<400> SEQUENCE: 401

Val Val Arg Gln Leu Ile Val Cys Ala Thr Leu Leu Pro Leu Leu Gln
1               5                   10                  15

Ala Ser Trp Cys His Ala Arg Arg Leu Val Trp Leu His Ser Ala Pro
            20                  25                  30

Val Pro Asn Asp Gln Gly Glu Leu His Asp Pro Pro Cys Cys Ala Lys
        35                  40                  45

Lys Arg Leu Ala Pro Ser Val Leu Arg Ser Leu Ser Glu Val Ser Trp
    50                  55                  60

Pro Gln Cys Tyr His Ser Trp Leu Trp Gln His Cys Ile Ile Leu Leu
65                  70                  75                  80

Leu Ser Cys His Pro
                85

<210> SEQ ID NO 402
<211> LENGTH: 4
<212> TYPE: PRT
<213> ORGANISM: Artificial Sequence
<220> FEATURE:
<223> OTHER INFORMATION: Synthethic

<400> SEQUENCE: 402

Asp Ala Phe Leu
1

<210> SEQ ID NO 403
<211> LENGTH: 35
<212> TYPE: PRT
<213> ORGANISM: Artificial Sequence
<220> FEATURE:
<223> OTHER INFORMATION: Synthethic

<400> SEQUENCE: 403

Leu Val Ser Thr Gln Pro Ser His Ser Glu Asn Ser Val Cys Gly Asp
```

```
                1               5                  10                  15
Arg Val Ala Leu Ala Arg Arg Gln Tyr Gly Ile Ile Pro Arg His Ile
                20                  25                  30

Ala Glu Leu
        35

<210> SEQ ID NO 404
<211> LENGTH: 20
<212> TYPE: PRT
<213> ORGANISM: Artificial Sequence
<220> FEATURE:
<223> OTHER INFORMATION: Synthethic

<400> SEQUENCE: 404

Lys Cys Ser Ser Leu Glu Asn Val Leu Arg Gly Glu Asn Ser Gln Gly
1               5                   10                  15

Ser Tyr Arg Cys
            20

<210> SEQ ID NO 405
<211> LENGTH: 38
<212> TYPE: PRT
<213> ORGANISM: Artificial Sequence
<220> FEATURE:
<223> OTHER INFORMATION: Synthethic

<400> SEQUENCE: 405

Asp Pro Val Arg Cys Asn Pro Leu Val His Pro Thr Asp Leu Gln His
1               5                   10                  15

Leu Leu Leu Ser Pro Ala Phe Leu Gly Glu Gln Lys Gln Glu Gly Lys
                20                  25                  30

Met Pro Gln Lys Arg Glu
        35

<210> SEQ ID NO 406
<211> LENGTH: 26
<212> TYPE: PRT
<213> ORGANISM: Artificial Sequence
<220> FEATURE:
<223> OTHER INFORMATION: Synthethic

<400> SEQUENCE: 406

Gly Arg His Gly Asn Val Glu Tyr Ser Tyr Ser Ser Phe Phe Asn Ile
1               5                   10                  15

Ile Glu Ala Phe Ile Arg Val Ile Val Ser
                20                  25

<210> SEQ ID NO 407
<211> LENGTH: 13
<212> TYPE: PRT
<213> ORGANISM: Artificial Sequence
<220> FEATURE:
<223> OTHER INFORMATION: Synthethic

<400> SEQUENCE: 407

Ala Asp Thr Tyr Leu Asn Val Phe Arg Lys Ile Asn Lys
1               5                   10

<210> SEQ ID NO 408
<211> LENGTH: 20
<212> TYPE: PRT
<213> ORGANISM: Artificial Sequence
<220> FEATURE:
<223> OTHER INFORMATION: Synthethic
```

<400> SEQUENCE: 408

Gly Phe Arg Ala His Phe Pro Glu Lys Cys His Leu Thr Ser Lys Lys
1               5                   10                  15

Pro Leu Leu Ser
            20

<210> SEQ ID NO 409
<211> LENGTH: 1
<212> TYPE: PRT
<213> ORGANISM: Artificial Sequence
<220> FEATURE:
<223> OTHER INFORMATION: Synthethic

<400> SEQUENCE: 409

His
1

<210> SEQ ID NO 410
<211> LENGTH: 12
<212> TYPE: PRT
<213> ORGANISM: Artificial Sequence
<220> FEATURE:
<223> OTHER INFORMATION: Synthethic

<400> SEQUENCE: 410

Pro Ile Lys Ile Gly Val Ser Arg Gly Pro Phe Val
1               5                   10

<210> SEQ ID NO 411
<211> LENGTH: 5565
<212> TYPE: DNA
<213> ORGANISM: Artificial Sequence
<220> FEATURE:
<223> OTHER INFORMATION: Synthethic

<400> SEQUENCE: 411

```
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg      120
ttggcgggtg tcgggctgg cttaactatg cggcatcaga gcagattgta ctgagagtgc      180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta acgccagggt      360
tttcccagtc acgacgttgt aaaacgacgg ccagtgaatt cctcgaggcc accatgactc      420
ggcgtagggt gctaagcgtg gtcgtgctgc tagccgccct ggcgtgccgt ctcggtgcgc      480
agaccccaga gcagcccgca cccccgccca ccacggtgca gcctaccgcc acgcgtcagc      540
aaaccagctt cctttccgga gtctgcgagc tctccagcca cggcgacctg ttccgcttct      600
cctcggacat ccagtgtccc tcgtttggca cgcgggagaa tcacacggag ggcctgttga      660
tggtgtttaa agacaacatt attccctact cgtttaaggt ccgctcctac accaagatag      720
tgaccaacat tctcatctac aatggctggt acgcggactc cgtgaccaac cggcacgagg      780
agaagttctc cgttgacagc tacgaaactg accagatgga taccatctac cagtgctaca      840
acgcggtcaa gatgacaaaa gatgggctga cgcgcgtgta tgtagaccgc gacggagtta      900
acatcaccgt caacctaaag cccaccgggg gcctggccaa cggggtgcgc cgctacgcca      960
gccagacgga gctctatgac gccccgggg ggttgatatg gacttacaga acaagaacta     1020
```

```
ccgtcaactg cctgataact gacatgatgg ccaagtccaa cagccccttc gacttctttg    1080
tgaccaccac cgggcagact gtggaaatgt cccctttcta tgacgggaaa aataaggaaa    1140
ccttccatga gcgggcagac tccttccacg tgagaactaa ctacaagata gtggactacg    1200
acaaccgagg gacgaacccg caaggcgaac gccgagcctt cctggacaag gcacttaca    1260 cgctatcttg gaagctcgag aacaggacag cctactgccc gcttcaacac tggcaaacct    1320
ttgactcgac catcgccaca gaaacaggga agtcaataca ttttgtgact gacgagggca    1380
cctctagctt cgtgaccaac acaaccgtgg gcatagagct cccggacgcc ttcaagtgca    1440
tcgaagagca ggtgaacaag accatgcatg agaagtacga ggccgtccag gatcgttaca    1500
cgaagggcca ggaagccatt acatatttta taacgagcgg aggattgtta ttagcttggc    1560
tacctctgac cccgcgctcg ttggccaccg tcaagaacct gacggagctt accactccga    1620
cttcctcacc ccccagcagt ccatcgcccc cagccccatc cgcggcccgc gggagcaccc    1680
ccgccgccgt tctgaggcgt cggaggcggg atgcggggaa cgccaccaca ccggtgcccc    1740
ccacggcccc cgggaagtcc ctgggcaccc tcaacaatcc cgccaccgtc cagatccaat    1800
ttgcctacga ctccctgcgc cgccagatca accgcatgct gggagacctt gcgcgggcct    1860
ggtgcctgga gcagaagagg cagaacatgg tgctgagaga actaaccaag attaatccaa    1920
ccaccgtcat gtccagcatc tacggtaagg cggtggcggc caagcgcctg ggggatgtca    1980
tctcagtctc ccagtgcgtg cccgttaacc aggccaccgt caccctgcgc aagagcatga    2040
gggtccctgg ctccgagacc atgtgctact cgcgcccct ggtgtccttc agctttatca    2100
acgacaccaa gacctacgag ggacagctgg gcaccgacaa cgagatcttc ctcacaaaaa    2160
agatgacgga ggtgtgccag gcgaccagcc agtactactt ccagtccggc aacgagatcc    2220
acgtctacaa cgactaccac cacttttaaaa ccatcgagct ggacggcatt gccaccctgc    2280
agaccttcat ctcactaaac acctccctca tcgagaacat tgactttgcc tccctggagc    2340
tgtactcacg ggacgaacag cgtgcctcca acgtctttga cctggagggc atcttccggg    2400
agtacaactt ccaggcgcaa aacatcgccg gcctgcggaa ggatttggac aatgcagtgt    2460
caaacggaag aaatcaattc gtggacggcc tggggaact tatggacagt ctgggtagcg    2520
tgggtcagtc catcaccaac ctagtcagca cggtgggggg tttgtttagc agcctggtct    2580
ctggtttcat ctccttcttc aaaaaccct tcggcggcgc tctcattacc tatatcgctt    2640
taactgccat atctcttgtt tgcggtatac ttagtctggt tctagcatgc tacctaatgt    2700
acaagcaaaa ggcgcaacaa aagaccttgt tatggcttgg gaataatacc ctgggtcaga    2760
tgagagccac tacaaaaatg tgaatgcaga tgagaggcgg aggtatcccc aatagcaatt    2820
tgtgtgcaaa ttctatgccc tggctcacaa ataccactga gatctttttc cctctgccaa    2880
aaattatggg gacatcatga agcccttga gcatctgact tctggctaat aaaggaaatt    2940
tattttcatt gcaatagtgt gttggaattt tttgtgtctc tcactcggaa ggacatatgg    3000
gagggcaaat catttaaaac atcagaatga gtatttggtt tagagtttgg caacatatgc    3060
ccatatgctg gctgccatga acaaaggttg gctataaaga ggtcatcagt atatgaaaca    3120
gccccctgct gtccattcct tattccatag aaaagccttg acttgaggtt agatttttt    3180 tatattttgt tttgtgttat ttttttcttt aacatcccta aaattttcct tacatgtttt    3240
actagccaga ttttccctcc tctcctgact actcccagtc atagctgtcc ctcttctctt    3300
atggagatcc ctcgacctgc agcccaagct tggcgtaatc atggtcatag ctgtttcctg    3360
tgtgaaattg ttatccgctc acaattccac acaacatacg agccggaagc ataaagtgta    3420
```

```
aagcctgggg tgcctaatga gtgagctaac tcacattaat tgcgttgcgc tcactgcccg    3480
ctttccagtc gggaaacctg tcgtgccagc tgcattaatg aatcggccaa cgcgcgggga    3540
gaggcggttt gcgtattggg cgctcttccg cttcctcgct cactgactcg ctgcgctcgg    3600
tcgttcggct gcggcgagcg gtatcagctc actcaaaggc ggtaatacgg ttatccacag    3660
aatcagggga taacgcagga agaacatgt gagcaaaagg ccagcaaaag gccaggaacc    3720
gtaaaaaggc cgcgttgctg gcgtttttcc ataggctccg ccccctgac gagcatcaca    3780 aaaatcgacg ctcaagtcag aggtggcgaa acccgacagg actataaaga taccaggcgt    3840 ttcccctgg aagctccctc gtgcgctctc ctgttccgac cctgccgctt accggatacc    3900
tgtccgcctt tctcccttcg ggaagcgtgg cgctttctca tagctcacgc tgtaggtatc    3960
tcagttcggt gtaggtcgtt cgctccaagc tgggctgtgt gcacgaaccc cccgttcagc    4020
ccgaccgctg cgccttatcc ggtaactatc gtcttgagtc caacccggta agacacgact    4080
tatcgccact ggcagcagcc actggtaaca ggattagcag agcgaggtat gtaggcggtg    4140
ctacagagtt cttgaagtgg tggcctaact acggctacac tagaagaaca gtatttggta    4200
tctgcgctct gctgaagcca gttaccttcg gaaaaagagt tggtagctct tgatccggca    4260
aacaaaccac cgctggtagc ggtggttttt tgtttgcaa gcagcagatt acgcgcagaa    4320
aaaaaggatc tcaagaagat cctttgatct tttctacggg gtctgacgct cagtggaacg    4380
aaaactcacg ttaagggatt ttggtcatga gattatcaaa aaggatcttc acctagatcc    4440
ttttaaatta aaaatgaagt tttaaatcaa tctaaagtat atatgagtaa acttggtctg    4500
acagttacca atgcttaatc agtgaggcac ctatctcagc gatctgtcta tttcgttcat    4560
ccatagttgc ctgactcccc gtcgtgtaga taactacgat acgggagggc ttaccatctg    4620
gccccagtgc tgcaatgata ccgcgagacc cacgctcacc ggctccagat ttatcagcaa    4680
taaaccagcc agccggaagg gccgagcgca gaagtggtcc tgcaacttta tccgcctcca    4740
tccagtctat taattgttgc cgggaagcta gagtaagtag ttcgccagtt aatagtttgc    4800
gcaacgttgt tgccattgct acaggcatcg tggtgtcacg ctcgtcgttt ggtatggctt    4860
cattcagctc cggttcccaa cgatcaaggc gagttacatg atccccatg ttgtgcaaaa    4920 aagcggttag ctccttcggt cctccgatcg ttgtcagaag taagttggcc gcagtgttat    4980
cactcatggt tatggcagca ctgcataatt ctcttactgt catgccatcc gtaagatgct    5040
tttctgtgac tggtgagtac tcaaccaagt cattctgaga atagtgtatg cggcgaccga    5100
gttgctcttg cccggcgtca atacgggata ataccgcgcc acatagcaga actttaaaag    5160
tgctcatcat tggaaaacgt tcttcggggc gaaaactctc aaggatctta ccgctgttga    5220
gatccagttc gatgtaaccc actcgtgcac ccaactgatc ttcagcatct tttactttca    5280
ccagcgtttc tgggtgagca aaaacaggaa ggcaaaatgc cgcaaaaaag gaataaggg    5340 cgacacggaa atgttgaata ctcatactct ccttttttca atattattga agcatttatc    5400
agggttattg tctcatgagc ggatacatat ttgaatgtat ttagaaaaat aaacaaatag    5460
gggttccgcg cacatttccc cgaaaagtgc cacctgacgt ctaagaaacc attattatca    5520
tgacattaac ctataaaaat aggcgtatca cgaggccctt tcgtc              5565
```

<210> SEQ ID NO 412
<211> LENGTH: 57
<212> TYPE: PRT
<213> ORGANISM: Artificial Sequence
<220> FEATURE:

<223> OTHER INFORMATION: Synthethic

<400> SEQUENCE: 412

```
Ser Arg Val Ser Val Met Thr Val Lys Thr Ser Asp Thr Cys Ser Ser
1               5                   10                  15
Arg Arg Arg Ser Gln Leu Val Cys Lys Arg Met Pro Gly Ala Asp Lys
            20                  25                  30
Pro Val Arg Ala Arg Gln Arg Val Leu Ala Gly Val Gly Ala Gly Leu
        35                  40                  45
Thr Met Arg His Gln Ser Arg Leu Tyr
    50                  55
```

<210> SEQ ID NO 413
<211> LENGTH: 13
<212> TYPE: PRT
<213> ORGANISM: Artificial Sequence
<220> FEATURE:
<223> OTHER INFORMATION: Synthethic

<400> SEQUENCE: 413

```
Glu Cys Thr Ile Cys Gly Val Lys Tyr Arg Thr Asp Ala
1               5                   10
```

<210> SEQ ID NO 414
<211> LENGTH: 41
<212> TYPE: PRT
<213> ORGANISM: Artificial Sequence
<220> FEATURE:
<223> OTHER INFORMATION: Synthethic

<400> SEQUENCE: 414

```
Gly Glu Asn Thr Ala Ser Gly Ala Ile Arg His Ser Gly Cys Ala Thr
1               5                   10                  15
Val Gly Lys Gly Asp Arg Cys Gly Pro Leu Arg Tyr Tyr Ala Ser Trp
            20                  25                  30
Arg Lys Gly Asp Val Leu Gln Gly Asp
        35                  40
```

<210> SEQ ID NO 415
<211> LENGTH: 2
<212> TYPE: PRT
<213> ORGANISM: Artificial Sequence
<220> FEATURE:
<223> OTHER INFORMATION: Synthethic

<400> SEQUENCE: 415

```
Val Gly
1
```

<210> SEQ ID NO 416
<211> LENGTH: 25
<212> TYPE: PRT
<213> ORGANISM: Artificial Sequence
<220> FEATURE:
<223> OTHER INFORMATION: Synthethic

<400> SEQUENCE: 416

```
Arg Gln Gly Phe Pro Ser His Asp Val Val Lys Arg Arg Pro Val Asn
1               5                   10                  15
Ser Ser Ser Val Pro Arg Glu Cys Ile
            20                  25
```

<210> SEQ ID NO 417

<211> LENGTH: 720
<212> TYPE: PRT
<213> ORGANISM: Artificial Sequence
<220> FEATURE:
<223> OTHER INFORMATION: Synthethic

<400> SEQUENCE: 417

Ile Ser Asp Pro Gly Pro Val Asp Cys Ser Leu Glu Ala Thr Met Gln
1               5                   10                  15

Leu Leu Cys Val Phe Cys Leu Val Leu Leu Trp Glu Val Gly Ala Ala
            20                  25                  30

Ser Leu Ser Glu Val Lys Leu His Leu Asp Ile Glu Gly His Ala Ser
        35                  40                  45

His Tyr Thr Ile Pro Trp Thr Glu Leu Met Ala Lys Val Pro Gly Leu
    50                  55                  60

Ser Pro Glu Ala Leu Trp Arg Glu Ala Asn Val Thr Glu Asp Leu Ala
65                  70                  75                  80

Ser Met Leu Asn Arg Tyr Lys Leu Ile Tyr Lys Thr Ser Gly Thr Leu
                85                  90                  95

Gly Ile Ala Leu Ala Glu Pro Val Asp Ile Pro Ala Val Ser Glu Gly
            100                 105                 110

Ser Met Gln Val Asp Ala Ser Lys Val His Pro Gly Val Ile Ser Gly
        115                 120                 125

Leu Asn Ser Pro Ala Cys Met Leu Ser Ala Pro Leu Glu Lys Gln Leu
130                 135                 140

Phe Tyr Tyr Ile Gly Thr Met Leu Pro Asn Thr Arg Pro His Ser Tyr
145                 150                 155                 160

Val Phe Tyr Gln Leu Arg Cys His Leu Ser Tyr Val Ala Leu Ser Ile
                165                 170                 175

Asn Gly Asp Lys Phe Gln Tyr Thr Gly Ala Met Thr Ser Lys Phe Leu
            180                 185                 190

Met Gly Thr Tyr Lys Arg Val Thr Glu Lys Gly Asp Glu His Val Leu
        195                 200                 205

Ser Leu Val Phe Gly Lys Thr Lys Asp Leu Pro Asp Leu Arg Gly Pro
210                 215                 220

Phe Ser Tyr Pro Ser Leu Thr Ser Ala Gln Ser Gly Asp Tyr Ser Leu
225                 230                 235                 240

Val Ile Val Thr Thr Phe Val His Tyr Ala Asn Phe His Asn Tyr Phe
                245                 250                 255

Val Pro Asn Leu Lys Asp Met Phe Ser Arg Ala Val Thr Met Thr Ala
            260                 265                 270

Ala Ser Tyr Ala Arg Tyr Val Leu Gln Lys Leu Val Leu Leu Glu Met
        275                 280                 285

Lys Gly Gly Cys Arg Glu Pro Glu Leu Asp Thr Glu Thr Leu Thr Thr
290                 295                 300

Met Phe Glu Val Ser Val Ala Phe Phe Lys Val Gly His Ala Val Gly
305                 310                 315                 320

Glu Thr Gly Asn Gly Cys Val Asp Leu Arg Trp Leu Ala Lys Ser Phe
                325                 330                 335

Phe Glu Leu Thr Val Leu Lys Asp Ile Ile Gly Ile Cys Tyr Gly Ala
            340                 345                 350

Thr Val Lys Gly Met Gln Ser Tyr Gly Leu Glu Arg Leu Ala Ala Met
        355                 360                 365

Leu Met Ala Thr Val Lys Met Glu Glu Leu Gly His Leu Thr Thr Glu
370                 375                 380

```
Lys Gln Glu Tyr Ala Leu Arg Leu Ala Thr Val Gly Tyr Pro Lys Ala
385                 390                 395                 400

Gly Val Tyr Ser Gly Leu Ile Gly Gly Ala Thr Ser Val Leu Leu Ser
            405                 410                 415

Ala Tyr Asn Arg His Pro Leu Phe Gln Pro Leu His Thr Val Met Arg
        420                 425                 430

Glu Thr Leu Phe Ile Gly Ser His Val Val Leu Arg Glu Leu Arg Leu
            435                 440                 445

Asn Val Thr Thr Gln Gly Pro Asn Leu Ala Leu Tyr Gln Leu Leu Ser
        450                 455                 460

Thr Ala Leu Cys Ser Ala Leu Glu Ile Gly Val Leu Arg Gly Leu
465                 470                 475                 480

Ala Leu Gly Thr Glu Ser Gly Leu Phe Ser Pro Cys Tyr Leu Ser Leu
            485                 490                 495

Arg Phe Asp Leu Thr Arg Asp Lys Leu Leu Ser Met Ala Pro Gln Glu
            500                 505                 510

Ala Thr Leu Asp Gln Ala Ala Val Ser Asn Ala Val Asp Gly Phe Leu
        515                 520                 525

Gly Arg Leu Ser Leu Glu Arg Glu Asp Arg Asp Ala Trp His Leu Pro
530                 535                 540

Ala Tyr Lys Cys Val Asp Arg Leu Asp Lys Val Leu Met Ile Ile Pro
545                 550                 555                 560

Leu Ile Asn Val Thr Phe Ile Ile Ser Ser Asp Arg Glu Val Arg Gly
            565                 570                 575

Ser Ala Leu Tyr Glu Ala Ser Thr Thr Tyr Leu Ser Ser Leu Phe
        580                 585                 590

Leu Ser Pro Val Ile Met Asn Lys Cys Ser Gln Gly Ala Val Ala Gly
            595                 600                 605

Glu Pro Arg Gln Ile Pro Lys Ile Gln Asn Phe Thr Arg Thr Gln Lys
        610                 615                 620

Ser Cys Ile Phe Cys Gly Phe Ala Leu Leu Ser Tyr Asp Glu Lys Glu
625                 630                 635                 640

Gly Leu Glu Thr Thr Thr Tyr Ile Thr Ser Gln Glu Val Gln Asn Ser
            645                 650                 655

Ile Leu Ser Ser Asn Tyr Phe Asp Phe Asp Asn Leu His Val His Tyr
        660                 665                 670

Leu Leu Leu Thr Thr Asn Gly Thr Val Met Glu Ile Ala Gly Leu Tyr
            675                 680                 685

Glu Glu Arg Ala His Val Val Leu Ala Ile Ile Leu Tyr Phe Ile Ala
        690                 695                 700

Phe Ala Leu Gly Ile Phe Leu Val His Lys Ile Val Met Phe Phe Leu
705                 710                 715                 720

<210> SEQ ID NO 418
<211> LENGTH: 32
<212> TYPE: PRT
<213> ORGANISM: Artificial Sequence
<220> FEATURE:
<223> OTHER INFORMATION: Synthethic

<400> SEQUENCE: 418

Pro Lys Leu Gly Val Ile Met Val Ile Ala Val Ser Cys Val Lys Leu
1               5                   10                  15

Leu Ser Ala His Asn Ser Thr Gln His Thr Ser Arg Lys His Lys Val
            20                  25                  30
```

<210> SEQ ID NO 419
<211> LENGTH: 54
<212> TYPE: PRT
<213> ORGANISM: Artificial Sequence
<220> FEATURE:
<223> OTHER INFORMATION: Synthethic

<400> SEQUENCE: 419

Ser Leu Gly Cys Leu Met Ser Glu Leu Thr His Ile Asn Cys Val Ala
1               5                   10                  15

Leu Thr Ala Arg Phe Pro Val Gly Lys Pro Val Val Pro Ala Ala Leu
            20                  25                  30

Met Asn Arg Pro Thr Arg Gly Glu Arg Arg Phe Ala Tyr Trp Ala Leu
        35                  40                  45

Phe Arg Phe Leu Ala His
    50

<210> SEQ ID NO 420
<211> LENGTH: 28
<212> TYPE: PRT
<213> ORGANISM: Artificial Sequence
<220> FEATURE:
<223> OTHER INFORMATION: Synthethic

<400> SEQUENCE: 420

Leu Ala Ala Leu Gly Arg Ser Ala Ala Ala Ser Gly Ile Ser Ser Leu
1               5                   10                  15

Lys Gly Gly Asn Thr Val Ile His Arg Ile Arg Gly
            20                  25

<210> SEQ ID NO 421
<211> LENGTH: 16
<212> TYPE: PRT
<213> ORGANISM: Artificial Sequence
<220> FEATURE:
<223> OTHER INFORMATION: Synthethic

<400> SEQUENCE: 421

Arg Arg Lys Glu His Val Ser Lys Arg Pro Ala Lys Gly Gln Glu Pro
1               5                   10                  15

<210> SEQ ID NO 422
<211> LENGTH: 9
<212> TYPE: PRT
<213> ORGANISM: Artificial Sequence
<220> FEATURE:
<223> OTHER INFORMATION: Synthethic

<400> SEQUENCE: 422

Lys Gly Arg Val Ala Gly Val Phe Pro
1               5

<210> SEQ ID NO 423
<211> LENGTH: 4
<212> TYPE: PRT
<213> ORGANISM: Artificial Sequence
<220> FEATURE:
<223> OTHER INFORMATION: Synthethic

<400> SEQUENCE: 423

Ala Pro Pro Pro
1

```
<210> SEQ ID NO 424
<211> LENGTH: 57
<212> TYPE: PRT
<213> ORGANISM: Artificial Sequence
<220> FEATURE:
<223> OTHER INFORMATION: Synthethic

<400> SEQUENCE: 424

Arg Ala Ser Gln Lys Ser Thr Leu Lys Ser Glu Val Ala Lys Pro Asp
1               5                   10                  15

Arg Thr Ile Lys Ile Pro Gly Val Ser Pro Trp Lys Leu Pro Arg Ala
            20                  25                  30

Leu Ser Cys Ser Asp Pro Ala Ala Tyr Arg Ile Pro Val Arg Leu Ser
        35                  40                  45

Pro Phe Gly Lys Arg Gly Ala Phe Ser
    50                  55

<210> SEQ ID NO 425
<211> LENGTH: 3
<212> TYPE: PRT
<213> ORGANISM: Artificial Sequence
<220> FEATURE:
<223> OTHER INFORMATION: Synthethic

<400> SEQUENCE: 425

Leu Thr Leu
1

<210> SEQ ID NO 426
<211> LENGTH: 29
<212> TYPE: PRT
<213> ORGANISM: Artificial Sequence
<220> FEATURE:
<223> OTHER INFORMATION: Synthethic

<400> SEQUENCE: 426

Val Ser Gln Phe Gly Val Gly Arg Ser Leu Gln Ala Gly Leu Cys Ala
1               5                   10                  15

Arg Thr Pro Arg Ser Ala Arg Pro Leu Arg Leu Ile Arg
            20                  25

<210> SEQ ID NO 427
<211> LENGTH: 3
<212> TYPE: PRT
<213> ORGANISM: Artificial Sequence
<220> FEATURE:
<223> OTHER INFORMATION: Synthethic

<400> SEQUENCE: 427

Leu Ser Ser
1

<210> SEQ ID NO 428
<211> LENGTH: 16
<212> TYPE: PRT
<213> ORGANISM: Artificial Sequence
<220> FEATURE:
<223> OTHER INFORMATION: Synthethic

<400> SEQUENCE: 428

Val Gln Pro Gly Lys Thr Arg Leu Ile Ala Thr Gly Ser Ser His Trp
1               5                   10                  15

<210> SEQ ID NO 429
<211> LENGTH: 2
```

```
<212> TYPE: PRT
<213> ORGANISM: Artificial Sequence
<220> FEATURE:
<223> OTHER INFORMATION: Synthethic

<400> SEQUENCE: 429

Gln Asp
1

<210> SEQ ID NO 430
<211> LENGTH: 16
<212> TYPE: PRT
<213> ORGANISM: Artificial Sequence
<220> FEATURE:
<223> OTHER INFORMATION: Synthethic

<400> SEQUENCE: 430

Gln Ser Glu Val Cys Arg Arg Cys Tyr Arg Val Leu Glu Val Val Ala
1               5                   10                  15

<210> SEQ ID NO 431
<211> LENGTH: 4
<212> TYPE: PRT
<213> ORGANISM: Artificial Sequence
<220> FEATURE:
<223> OTHER INFORMATION: Synthethic

<400> SEQUENCE: 431

Leu Arg Leu His
1

<210> SEQ ID NO 432
<211> LENGTH: 20
<212> TYPE: PRT
<213> ORGANISM: Artificial Sequence
<220> FEATURE:
<223> OTHER INFORMATION: Synthethic

<400> SEQUENCE: 432

Lys Asn Ser Ile Trp Tyr Leu Arg Ser Ala Glu Ala Ser Tyr Leu Arg
1               5                   10                  15

Lys Lys Ser Trp
            20

<210> SEQ ID NO 433
<211> LENGTH: 10
<212> TYPE: PRT
<213> ORGANISM: Artificial Sequence
<220> FEATURE:
<223> OTHER INFORMATION: Synthethic

<400> SEQUENCE: 433

Leu Leu Ile Arg Gln Thr Asn His Arg Trp
1               5                   10

<210> SEQ ID NO 434
<211> LENGTH: 28
<212> TYPE: PRT
<213> ORGANISM: Artificial Sequence
<220> FEATURE:
<223> OTHER INFORMATION: Synthethic

<400> SEQUENCE: 434

Arg Trp Phe Phe Cys Leu Gln Ala Ala Asp Tyr Ala Gln Lys Lys Arg
1               5                   10                  15

Ile Ser Arg Arg Ser Phe Asp Leu Phe Tyr Gly Val
```

20                  25

<210> SEQ ID NO 435
<211> LENGTH: 32
<212> TYPE: PRT
<213> ORGANISM: Artificial Sequence
<220> FEATURE:
<223> OTHER INFORMATION: Synthethic

<400> SEQUENCE: 435

Arg Ser Val Glu Arg Lys Leu Thr Leu Arg Asp Phe Gly His Glu Ile
1               5                   10                  15

Ile Lys Lys Asp Leu His Leu Asp Pro Phe Lys Leu Lys Met Lys Phe
            20                  25                  30

<210> SEQ ID NO 436
<211> LENGTH: 6
<212> TYPE: PRT
<213> ORGANISM: Artificial Sequence
<220> FEATURE:
<223> OTHER INFORMATION: Synthethic

<400> SEQUENCE: 436

Ile Asn Leu Lys Tyr Ile
1               5

<210> SEQ ID NO 437
<211> LENGTH: 4
<212> TYPE: PRT
<213> ORGANISM: Artificial Sequence
<220> FEATURE:
<223> OTHER INFORMATION: Synthethic

<400> SEQUENCE: 437

Val Asn Leu Val
1

<210> SEQ ID NO 438
<211> LENGTH: 7
<212> TYPE: PRT
<213> ORGANISM: Artificial Sequence
<220> FEATURE:
<223> OTHER INFORMATION: Synthethic

<400> SEQUENCE: 438

Gln Leu Pro Met Leu Asn Gln
1               5

<210> SEQ ID NO 439
<211> LENGTH: 75
<212> TYPE: PRT
<213> ORGANISM: Artificial Sequence
<220> FEATURE:
<223> OTHER INFORMATION: Synthethic

<400> SEQUENCE: 439

Gly Thr Tyr Leu Ser Asp Leu Ser Ile Ser Phe Ile His Ser Cys Leu
1               5                   10                  15

Thr Pro Arg Arg Val Asp Asn Tyr Asp Thr Gly Gly Leu Thr Ile Trp
            20                  25                  30

Pro Gln Cys Cys Asn Asp Thr Ala Arg Pro Thr Leu Thr Gly Ser Arg
        35                  40                  45

Phe Ile Ser Asn Lys Pro Ala Ser Arg Lys Gly Arg Ala Gln Lys Trp
    50                  55                  60

```
Ser Cys Asn Phe Ile Arg Leu His Pro Val Tyr
 65                  70                  75
```

<210> SEQ ID NO 440
<211> LENGTH: 5
<212> TYPE: PRT
<213> ORGANISM: Artificial Sequence
<220> FEATURE:
<223> OTHER INFORMATION: Synthethic

<400> SEQUENCE: 440

```
Leu Leu Pro Gly Ser
 1               5
```

<210> SEQ ID NO 441
<211> LENGTH: 2
<212> TYPE: PRT
<213> ORGANISM: Artificial Sequence
<220> FEATURE:
<223> OTHER INFORMATION: Synthethic

<400> SEQUENCE: 441

```
Ser Lys
 1
```

<210> SEQ ID NO 442
<211> LENGTH: 3
<212> TYPE: PRT
<213> ORGANISM: Artificial Sequence
<220> FEATURE:
<223> OTHER INFORMATION: Synthethic

<400> SEQUENCE: 442

```
Phe Ala Ser
 1
```

<210> SEQ ID NO 443
<211> LENGTH: 44
<212> TYPE: PRT
<213> ORGANISM: Artificial Sequence
<220> FEATURE:
<223> OTHER INFORMATION: Synthethic

<400> SEQUENCE: 443

```
Phe Ala Gln Arg Cys Cys His Cys Tyr Arg His Arg Gly Val Thr Leu
 1               5                  10                  15

Val Val Trp Tyr Gly Phe Ile Gln Leu Arg Phe Pro Thr Ile Lys Ala
                 20                  25                  30

Ser Tyr Met Ile Pro His Val Val Gln Lys Ser Gly
             35                  40
```

<210> SEQ ID NO 444
<211> LENGTH: 10
<212> TYPE: PRT
<213> ORGANISM: Artificial Sequence
<220> FEATURE:
<223> OTHER INFORMATION: Synthethic

<400> SEQUENCE: 444

```
Leu Leu Arg Ser Ser Asp Arg Cys Gln Lys
 1               5                  10
```

<210> SEQ ID NO 445
<211> LENGTH: 14
<212> TYPE: PRT
<213> ORGANISM: Artificial Sequence

```
<220> FEATURE:
<223> OTHER INFORMATION: Synthethic

<400> SEQUENCE: 445

Val Gly Arg Ser Val Ile Thr His Gly Tyr Gly Ser Thr Ala
1               5                   10

<210> SEQ ID NO 446
<211> LENGTH: 15
<212> TYPE: PRT
<213> ORGANISM: Artificial Sequence
<220> FEATURE:
<223> OTHER INFORMATION: Synthethic

<400> SEQUENCE: 446

Phe Ser Tyr Cys His Ala Ile Arg Lys Met Leu Phe Cys Asp Trp
1               5                   10                  15

<210> SEQ ID NO 447
<211> LENGTH: 24
<212> TYPE: PRT
<213> ORGANISM: Artificial Sequence
<220> FEATURE:
<223> OTHER INFORMATION: Synthethic

<400> SEQUENCE: 447

Val Leu Asn Gln Val Ile Leu Arg Ile Val Tyr Ala Ala Thr Glu Leu
1               5                   10                  15

Leu Leu Pro Gly Val Asn Thr Gly
            20

<210> SEQ ID NO 448
<211> LENGTH: 4
<212> TYPE: PRT
<213> ORGANISM: Artificial Sequence
<220> FEATURE:
<223> OTHER INFORMATION: Synthethic

<400> SEQUENCE: 448

Tyr Arg Ala Thr
1

<210> SEQ ID NO 449
<211> LENGTH: 95
<212> TYPE: PRT
<213> ORGANISM: Artificial Sequence
<220> FEATURE:
<223> OTHER INFORMATION: Synthethic

<400> SEQUENCE: 449

Gln Asn Phe Lys Ser Ala His His Trp Lys Thr Phe Phe Gly Ala Lys
1               5                   10                  15

Thr Leu Lys Asp Leu Thr Ala Val Glu Ile Gln Phe Asp Val Thr His
            20                  25                  30

Ser Cys Thr Gln Leu Ile Phe Ser Ile Phe Tyr Phe His Gln Arg Phe
        35                  40                  45

Trp Val Ser Lys Asn Arg Lys Ala Lys Cys Arg Lys Lys Gly Asn Lys
    50                  55                  60

Gly Asp Thr Glu Met Leu Asn Thr His Thr Leu Pro Phe Ser Ile Leu
65                  70                  75                  80

Leu Lys His Leu Ser Gly Leu Leu Ser His Glu Arg Ile His Ile
                85                  90                  95
```

<210> SEQ ID NO 450
<211> LENGTH: 5
<212> TYPE: PRT
<213> ORGANISM: Artificial Sequence
<220> FEATURE:
<223> OTHER INFORMATION: Synthethic

<400> SEQUENCE: 450

Met Tyr Leu Glu Lys
1               5

<210> SEQ ID NO 451
<211> LENGTH: 14
<212> TYPE: PRT
<213> ORGANISM: Artificial Sequence
<220> FEATURE:
<223> OTHER INFORMATION: Synthethic

<400> SEQUENCE: 451

Thr Asn Arg Gly Ser Ala His Ile Ser Pro Lys Ser Ala Thr
1               5                   10

<210> SEQ ID NO 452
<211> LENGTH: 12
<212> TYPE: PRT
<213> ORGANISM: Artificial Sequence
<220> FEATURE:
<223> OTHER INFORMATION: Synthethic

<400> SEQUENCE: 452

Arg Leu Arg Asn His Tyr Tyr His Asp Ile Asn Leu
1               5                   10

<210> SEQ ID NO 453
<211> LENGTH: 1
<212> TYPE: PRT
<213> ORGANISM: Artificial Sequence
<220> FEATURE:
<223> OTHER INFORMATION: Synthethic

<400> SEQUENCE: 453

Lys
1

<210> SEQ ID NO 454
<211> LENGTH: 7
<212> TYPE: PRT
<213> ORGANISM: Artificial Sequence
<220> FEATURE:
<223> OTHER INFORMATION: Synthethic

<400> SEQUENCE: 454

Ala Tyr His Glu Ala Leu Ser
1               5

<210> SEQ ID NO 455
<211> LENGTH: 4833
<212> TYPE: DNA
<213> ORGANISM: Artificial Sequence
<220> FEATURE:
<223> OTHER INFORMATION: Synthethic

<400> SEQUENCE: 455
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc   180

-continued

| | |
|---|---|
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cgagctcggt acctcgcgaa | 420 |
| tgcatctaga tatcggatcc cgggcccgtc gactgcagcc tcgaggccac catgcagttg | 480 |
| ctctgtgttt tttgcctggt gttgctatgg gaggtgsggg ctgccagcct cagcgaggtt | 540 |
| aagctgcacc tggacataga ggggcatgct tcgcattaca ccatcccatg gaccgaactg | 600 |
| atggcaaagg tcccaggcct tagcccagag gcgctgtgga gagaggcaaa tgtcaccgaa | 660 |
| gatttggcgt ctatgcttaa ccgctacaag ttaatttaca agacgtctgg tacccttggt | 720 |
| attgcgctgg ccgagcctgt cgatatccct gctgtctctg aaggatccat gcaagtggat | 780 |
| gcatctaagg tccatcccgg agtcattagc ggcctgaatt cccctgcctg catgcttagt | 840 |
| gccccccttg agaagcagct cttctactat attggcacca tgctgcccaa cacgcggcca | 900 |
| cacagctatg tcttttatca gctgcgctgt cacttgtctt atgtggccct gtccatcaac | 960 |
| ggggacaagt tcagtacac gggggccatg acttctaaat ttctgatggg cacctacaag | 1020 |
| cgagtgaccg agaagggaga tgagcatgtg ttgagcctgg tctttggcaa gacgaaggac | 1080 |
| ctgccggatc tgaggggggcc ttttagttac ccatccttaa ccagtgccca aagcggggac | 1140 |
| tattccctgg tgattgttac aacctttgtg cattatgcca actttcacaa ctactttgta | 1200 |
| cccaacctga aggatatgtt ttcccgagcc gtcaccatga cagccgccag ctacgctcgc | 1260 |
| tacgttctcc agaaactggt cctgctggag atgaagggag gctgccggga gccggaactg | 1320 |
| gacacggaaa cgctgactac catgtttgag gtttctgtgg ccttctttaa ggtgggtcat | 1380 |
| gctgtgggtg agactggcaa tggctgcgtg gacctccgct ggttggccaa gagcttcttt | 1440 |
| gagctgactg tcctgaaaga catcatcggc atatgttatg gggccactgt caagggcatg | 1500 |
| caatcctacg ggctggagcg cttggccgcc atgctgatgg ccacggtcaa gatggaggag | 1560 |
| ctgggtcacc tgactactga gaaacaggag tacgcgctga ggttagccac cgtcggctac | 1620 |
| cccaaggccg gggtttacag tggcctcatt ggaggcgcca catctgtgct tctctcggcc | 1680 |
| tacaaccgcc accccctttt ccagcccctg cataccgtga tgagagagac cctgtttatc | 1740 |
| ggcagccacg tggtgctacg cgagttgcgg ctgaacgtga ctacccaggg gcccaacctt | 1800 |
| gccctatacc aactgctgtc caccgccctg tgctcggccc tagagattgg ggaggttttg | 1860 |
| cgggggctag ccctgggggac agagagcggg ctcttctcac cgtgctacct cagcctacga | 1920 |
| tttgacctca cacgagacaa gctgctgagc atggccccc aggaggcaac gctggaccag | 1980 |
| gcggccgttt caaatgctgt ggatgggttt cttgggcggc tctctttgga gcgagaagac | 2040 |
| agggatgcgt ggcatctccc cgcctacaaa tgcgtggaca ggctcgacaa agttctgatg | 2100 |
| attatcccgc tcatcaatgt gacattcata atctctagtg accgtgaggt ccgaggctcg | 2160 |
| gcgctatacg aggccagcac cacctatctc agcagctctc tctttctctc cccgttata | 2220 |
| atgaataaat gttcgcaggg tgctgtggct ggggagcccc gccagattcc aaagatccag | 2280 |
| aattttacca ggacgcagaa atcctgcatt ttttgtggct ttgccctgct cagttatgat | 2340 |
| gaaaaggaag gcctggaaac tacaacctac atcacctccc aggaagtcca aaactccatc | 2400 |
| ttgagctcca actactttga ttttgacaac ctccacgttc actatctgct gctgaccacc | 2460 |
| aacgggactg tcatggaaat tgcgggcctg tatgaagaaa gagcacacgt tgttttggca | 2520 |

```
ataatcctgt actttattgc ttttgctctg ggtatctttc tggttcacaa gattgttatg    2580 ttttccttt  agcccaagct tggcgtaatc atggtcatag ctgtttcctg tgtgaaattg    2640
ttatccgctc acaattccac acaacatacg agccggaagc ataaagtgta aagcctgggg    2700
tgcctaatga gtgagctaac tcacattaat tgcgttgcgc tcactgcccg ctttccagtc    2760
gggaaacctg tcgtgccagc tgcattaatg aatcggccaa cgcgcgggga gaggcggttt    2820
gcgtattggg cgctcttccg cttcctcgct cactgactcg ctgcgctcgg tcgttcggct    2880
gcggcgagcg gtatcagctc actcaaaggc ggtaatacgg ttatccacag aatcagggga    2940
taacgcagga aagaacatgt gagcaaaagg ccagcaaaag gccaggaacc gtaaaaaggc    3000
cgcgttgctg gcgttttcc  ataggctccg ccccctgac  gagcatcaca aaaatcgacg    3060
ctcaagtcag aggtggcgaa acccgacagg actataaaga taccaggcgt ttccccctgg    3120
aagctccctc gtgcgctctc ctgttccgac cctgccgctt accggatacc tgtccgcctt    3180
tctcccttcg ggaagcgtgg cgctttctca tagctcacgc tgtaggtatc tcagttcggt    3240
gtaggtcgtt cgctccaagc tgggctgtgt gcacgaaccc cccgttcagc ccgaccgctg    3300
cgccttatcc ggtaactatc gtcttgagtc aacccggta  agacacgact tatcgccact    3360
ggcagcagcc actggtaaca ggattagcag agcgaggtat gtaggcggtg ctacagagtt    3420
cttgaagtgg tggcctaact acggctacac tagaagaaca gtatttggta tctgcgctct    3480
gctgaagcca gttaccttcg gaaaaagagt tggtagctct tgatccggca acaaaccac    3540 cgctggtagc ggtggttttt ttgtttgcaa gcagcagatt acgcgcagaa aaaaggatc    3600 tcaagaagat cctttgatct tttctacggg gtctgacgct cagtggaacg aaaactcacg    3660
ttaagggatt ttggtcatga gattatcaaa aaggatcttc acctagatcc ttttaaatta    3720
aaaatgaagt tttaaatcaa tctaaagtat atatgagtaa acttggtctg acagttacca    3780
atgcttaatc agtgaggcac ctatctcagc gatctgtcta tttcgttcat ccatagttgc    3840
ctgactcccc gtcgtgtaga taactacgat acgggagggc ttaccatctg gccccagtgc    3900
tgcaatgata ccgcgagacc cacgctcacc ggctccagat ttatcagcaa taaaccagcc    3960
agccggaagg gccgagcgca gaagtggtcc tgcaacttta tccgcctcca tccagtctat    4020
taattgttgc cgggaagcta gagtaagtag ttcgccagtt aatagtttgc gcaacgttgt    4080
tgccattgct acaggcatcg tggtgtcacg ctcgtcgttt ggtatggctt cattcagctc    4140
cggttcccaa cgatcaaggc gagttacatg atccccatg  ttgtgcaaaa aagcggttag    4200
ctccttcggt cctccgatcg ttgtcagaag taagttggcc gcagtgttat cactcatggt    4260
tatggcagca ctgcataatt ctcttactgt catgccatcc gtaagatgct tttctgtgac    4320
tggtgagtac tcaaccaagt cattctgaga atagtgtatg cggcgaccga gttgctcttg    4380
cccggcgtca atacgggata ataccgcgcc acatagcaga actttaaaag tgctcatcat    4440
tggaaaacgt tcttcgggc  gaaaactctc aaggatctta ccgctgttga gatccagttc    4500
gatgtaaccc actcgtgcac ccaactgatc ttcagcatct tttactttca ccagcgtttc    4560
tgggtgagca aaaacaggaa ggcaaaatgc cgcaaaaaag gaataagggc gacacggaa    4620 atgttgaata ctcatactct tcctttttca atattattga agcatttatc agggttattg    4680
tctcatgagc ggatacatat ttgaatgtat ttagaaaaat aaacaaatag gggttccgcg    4740
cacatttccc cgaaaagtgc cacctgacgt ctaagaaacc attattatca tgacattaac    4800
ctataaaaat aggcgtatca cgaggccctt tcg                                 4833
```

```
<210> SEQ ID NO 456
<211> LENGTH: 57
<212> TYPE: PRT
<213> ORGANISM: Artificial Sequence
<220> FEATURE:
<223> OTHER INFORMATION: Synthethic

<400> SEQUENCE: 456

Ser Arg Val Ser Val Met Thr Val Lys Thr Ser Asp Thr Cys Ser Ser
1               5                   10                  15

Arg Arg Arg Ser Gln Leu Val Cys Lys Arg Met Pro Gly Ala Asp Lys
            20                  25                  30

Pro Val Arg Ala Arg Gln Arg Val Leu Ala Gly Val Gly Ala Gly Leu
        35                  40                  45

Thr Met Arg His Gln Ser Arg Leu Tyr
    50                  55

<210> SEQ ID NO 457
<211> LENGTH: 13
<212> TYPE: PRT
<213> ORGANISM: Artificial Sequence
<220> FEATURE:
<223> OTHER INFORMATION: Synthethic

<400> SEQUENCE: 457

Glu Cys Thr Ile Cys Gly Val Lys Tyr Arg Thr Asp Ala
1               5                   10

<210> SEQ ID NO 458
<211> LENGTH: 41
<212> TYPE: PRT
<213> ORGANISM: Artificial Sequence
<220> FEATURE:
<223> OTHER INFORMATION: Synthethic

<400> SEQUENCE: 458

Gly Glu Asn Thr Ala Ser Gly Ala Ile Arg His Ser Gly Cys Ala Thr
1               5                   10                  15

Val Gly Lys Gly Asp Arg Cys Gly Pro Leu Arg Tyr Tyr Ala Ser Trp
            20                  25                  30

Arg Lys Gly Asp Val Leu Gln Gly Asp
        35                  40

<210> SEQ ID NO 459
<211> LENGTH: 2
<212> TYPE: PRT
<213> ORGANISM: Artificial Sequence
<220> FEATURE:
<223> OTHER INFORMATION: Synthethic

<400> SEQUENCE: 459

Val Gly
1

<210> SEQ ID NO 460
<211> LENGTH: 20
<212> TYPE: PRT
<213> ORGANISM: Artificial Sequence
<220> FEATURE:
<223> OTHER INFORMATION: Synthethic

<400> SEQUENCE: 460

Arg Gln Gly Phe Pro Ser His Asp Val Val Lys Arg Arg Pro Val Asn
1               5                   10                  15
```

Ser Thr Pro Pro
        20

<210> SEQ ID NO 461
<211> LENGTH: 8
<212> TYPE: PRT
<213> ORGANISM: Artificial Sequence
<220> FEATURE:
<223> OTHER INFORMATION: Synthethic

<400> SEQUENCE: 461

Thr Ala Gln Phe Ala Lys Leu Arg
1               5

<210> SEQ ID NO 462
<211> LENGTH: 21
<212> TYPE: PRT
<213> ORGANISM: Artificial Sequence
<220> FEATURE:
<223> OTHER INFORMATION: Synthethic

<400> SEQUENCE: 462

Arg Met Met Lys Gly Lys Arg Ile His Gly Ala Trp Tyr Ser Gly
1               5                   10                  15

Ser Gln Ser Tyr Phe
        20

<210> SEQ ID NO 463
<211> LENGTH: 1
<212> TYPE: PRT
<213> ORGANISM: Artificial Sequence
<220> FEATURE:
<223> OTHER INFORMATION: Synthethic

<400> SEQUENCE: 463

Gln
1

<210> SEQ ID NO 464
<211> LENGTH: 1
<212> TYPE: PRT
<213> ORGANISM: Artificial Sequence
<220> FEATURE:
<223> OTHER INFORMATION: Synthethic

<400> SEQUENCE: 464

Pro
1

<210> SEQ ID NO 465
<211> LENGTH: 35
<212> TYPE: PRT
<213> ORGANISM: Artificial Sequence
<220> FEATURE:
<223> OTHER INFORMATION: Synthethic

<400> SEQUENCE: 465

Pro Ser Leu Gln Pro Pro Trp His Ile Val Thr His Val Val Thr Ser
1               5                   10                  15

Leu Ser Ser Ala Leu Asn Thr Phe Ser Arg Trp Lys Thr Leu Ala Thr
            20                  25                  30

Phe Thr Trp
        35

<210> SEQ ID NO 466

```
<211> LENGTH: 12
<212> TYPE: PRT
<213> ORGANISM: Artificial Sequence
<220> FEATURE:
<223> OTHER INFORMATION: Synthethic

<400> SEQUENCE: 466

Ala Ile Arg His Ala Thr Ala Leu Ala Trp Pro Pro
1               5                   10

<210> SEQ ID NO 467
<211> LENGTH: 28
<212> TYPE: PRT
<213> ORGANISM: Artificial Sequence
<220> FEATURE:
<223> OTHER INFORMATION: Synthethic

<400> SEQUENCE: 467

Ile His Leu Arg Met Gly Ala Thr Ser Trp Ser Ser Ala Ala Ala Gln
1               5                   10                  15

Thr Asp Ser Thr Trp Ser Pro Ser Leu Ser Pro Ser
            20                  25

<210> SEQ ID NO 468
<211> LENGTH: 14
<212> TYPE: PRT
<213> ORGANISM: Artificial Sequence
<220> FEATURE:
<223> OTHER INFORMATION: Synthethic

<400> SEQUENCE: 468

Ser Glu Ala Ala Pro Pro Ser Arg Ala Ile Ser Val Ser Cys
1               5                   10

<210> SEQ ID NO 469
<211> LENGTH: 19
<212> TYPE: PRT
<213> ORGANISM: Artificial Sequence
<220> FEATURE:
<223> OTHER INFORMATION: Synthethic

<400> SEQUENCE: 469

Pro Pro Trp Arg Leu Phe Thr Val His Ser Gln Trp Lys Thr Cys Leu
1               5                   10                  15

Val Pro Thr

<210> SEQ ID NO 470
<211> LENGTH: 12
<212> TYPE: PRT
<213> ORGANISM: Artificial Sequence
<220> FEATURE:
<223> OTHER INFORMATION: Synthethic

<400> SEQUENCE: 470

Thr Asp Thr His Gly Ile Ala Gly Ala Arg Cys Arg
1               5                   10

<210> SEQ ID NO 471
<211> LENGTH: 55
<212> TYPE: PRT
<213> ORGANISM: Artificial Sequence
<220> FEATURE:
<223> OTHER INFORMATION: Synthethic

<400> SEQUENCE: 471

Glu Ala Glu Val Ser Pro Ile Ala Ile Cys Val Gln Ile Leu Cys Pro
```

```
                    1               5                  10                 15
Gly Ser Gln Ile Pro Leu Arg Ser Lys Leu Gly Val Ile Met Val Ile
                    20                 25                 30

Ala Val Ser Cys Val Lys Leu Leu Ser Ala His Asn Ser Thr Gln His
        35                 40                 45

Thr Ser Arg Lys His Lys Val
        50                 55

<210> SEQ ID NO 472
<211> LENGTH: 54
<212> TYPE: PRT
<213> ORGANISM: Artificial Sequence
<220> FEATURE:
<223> OTHER INFORMATION: Synthethic

<400> SEQUENCE: 472

Ser Leu Gly Cys Leu Met Ser Glu Leu Thr His Ile Asn Cys Val Ala
1               5                   10                  15

Leu Thr Ala Arg Phe Pro Val Gly Lys Pro Val Val Pro Ala Ala Leu
                20                  25                  30

Met Asn Arg Pro Thr Arg Gly Glu Arg Phe Ala Tyr Trp Ala Leu
        35                  40                  45

Phe Arg Phe Leu Ala His
    50

<210> SEQ ID NO 473
<211> LENGTH: 28
<212> TYPE: PRT
<213> ORGANISM: Artificial Sequence
<220> FEATURE:
<223> OTHER INFORMATION: Synthethic

<400> SEQUENCE: 473

Leu Ala Ala Leu Gly Arg Ser Ala Ala Ala Ser Gly Ile Ser Ser Leu
1               5                   10                  15

Lys Gly Gly Asn Thr Val Ile His Arg Ile Arg Gly
            20                  25

<210> SEQ ID NO 474
<211> LENGTH: 16
<212> TYPE: PRT
<213> ORGANISM: Artificial Sequence
<220> FEATURE:
<223> OTHER INFORMATION: Synthethic

<400> SEQUENCE: 474

Arg Arg Lys Glu His Val Ser Lys Arg Pro Ala Lys Gly Gln Glu Pro
1               5                   10                  15

<210> SEQ ID NO 475
<211> LENGTH: 9
<212> TYPE: PRT
<213> ORGANISM: Artificial Sequence
<220> FEATURE:
<223> OTHER INFORMATION: Synthethic

<400> SEQUENCE: 475

Lys Gly Arg Val Ala Gly Val Phe Pro
1               5

<210> SEQ ID NO 476
<211> LENGTH: 4
<212> TYPE: PRT
```

```
<213> ORGANISM: Artificial Sequence
<220> FEATURE:
<223> OTHER INFORMATION: Synthethic

<400> SEQUENCE: 476

Ala Pro Pro Pro
1

<210> SEQ ID NO 477
<211> LENGTH: 57
<212> TYPE: PRT
<213> ORGANISM: Artificial Sequence
<220> FEATURE:
<223> OTHER INFORMATION: Synthethic

<400> SEQUENCE: 477

Arg Ala Ser Gln Lys Ser Thr Leu Lys Ser Glu Val Ala Lys Pro Asp
1               5                   10                  15

Arg Thr Ile Lys Ile Pro Gly Val Ser Pro Trp Lys Leu Pro Arg Ala
            20                  25                  30

Leu Ser Cys Ser Asp Pro Ala Ala Tyr Arg Ile Pro Val Arg Leu Ser
        35                  40                  45

Pro Phe Gly Lys Arg Gly Ala Phe Ser
    50                  55

<210> SEQ ID NO 478
<211> LENGTH: 3
<212> TYPE: PRT
<213> ORGANISM: Artificial Sequence
<220> FEATURE:
<223> OTHER INFORMATION: Synthethic

<400> SEQUENCE: 478

Leu Thr Leu
1

<210> SEQ ID NO 479
<211> LENGTH: 29
<212> TYPE: PRT
<213> ORGANISM: Artificial Sequence
<220> FEATURE:
<223> OTHER INFORMATION: Synthethic

<400> SEQUENCE: 479

Val Ser Gln Phe Gly Val Gly Arg Ser Leu Gln Ala Gly Leu Cys Ala
1               5                   10                  15

Arg Thr Pro Arg Ser Ala Arg Pro Leu Arg Leu Ile Arg
            20                  25

<210> SEQ ID NO 480
<211> LENGTH: 3
<212> TYPE: PRT
<213> ORGANISM: Artificial Sequence
<220> FEATURE:
<223> OTHER INFORMATION: Synthethic

<400> SEQUENCE: 480

Leu Ser Ser
1

<210> SEQ ID NO 481
<211> LENGTH: 16
<212> TYPE: PRT
<213> ORGANISM: Artificial Sequence
<220> FEATURE:
```

```
<223> OTHER INFORMATION: Synthethic

<400> SEQUENCE: 481

Val Gln Pro Gly Lys Thr Arg Leu Ile Ala Thr Gly Ser Ser His Trp
1               5                   10                  15

<210> SEQ ID NO 482
<211> LENGTH: 2
<212> TYPE: PRT
<213> ORGANISM: Artificial Sequence
<220> FEATURE:
<223> OTHER INFORMATION: Synthethic

<400> SEQUENCE: 482

Gln Asp
1

<210> SEQ ID NO 483
<211> LENGTH: 16
<212> TYPE: PRT
<213> ORGANISM: Artificial Sequence
<220> FEATURE:
<223> OTHER INFORMATION: Synthethic

<400> SEQUENCE: 483

Gln Ser Glu Val Cys Arg Arg Cys Tyr Arg Val Leu Glu Val Val Ala
1               5                   10                  15

<210> SEQ ID NO 484
<211> LENGTH: 4
<212> TYPE: PRT
<213> ORGANISM: Artificial Sequence
<220> FEATURE:
<223> OTHER INFORMATION: Synthethic

<400> SEQUENCE: 484

Leu Arg Leu His
1

<210> SEQ ID NO 485
<211> LENGTH: 20
<212> TYPE: PRT
<213> ORGANISM: Artificial Sequence
<220> FEATURE:
<223> OTHER INFORMATION: Synthethic

<400> SEQUENCE: 485

Lys Asn Ser Ile Trp Tyr Leu Arg Ser Ala Glu Ala Ser Tyr Leu Arg
1               5                   10                  15

Lys Lys Ser Trp
            20

<210> SEQ ID NO 486
<211> LENGTH: 10
<212> TYPE: PRT
<213> ORGANISM: Artificial Sequence
<220> FEATURE:
<223> OTHER INFORMATION: Synthethic

<400> SEQUENCE: 486

Leu Leu Ile Arg Gln Thr Asn His Arg Trp
1               5                   10

<210> SEQ ID NO 487
<211> LENGTH: 28
<212> TYPE: PRT
```

```
<213> ORGANISM: Artificial Sequence
<220> FEATURE:
<223> OTHER INFORMATION: Synthethic

<400> SEQUENCE: 487

Arg Trp Phe Phe Cys Leu Gln Ala Ala Asp Tyr Ala Gln Lys Lys Arg
1               5                   10                  15

Ile Ser Arg Arg Ser Phe Asp Leu Phe Tyr Gly Val
            20                  25

<210> SEQ ID NO 488
<211> LENGTH: 32
<212> TYPE: PRT
<213> ORGANISM: Artificial Sequence
<220> FEATURE:
<223> OTHER INFORMATION: Synthethic

<400> SEQUENCE: 488

Arg Ser Val Glu Arg Lys Leu Thr Leu Arg Asp Phe Gly His Glu Ile
1               5                   10                  15

Ile Lys Lys Asp Leu His Leu Asp Pro Phe Lys Leu Lys Met Lys Phe
            20                  25                  30

<210> SEQ ID NO 489
<211> LENGTH: 6
<212> TYPE: PRT
<213> ORGANISM: Artificial Sequence
<220> FEATURE:
<223> OTHER INFORMATION: Synthethic

<400> SEQUENCE: 489

Ile Asn Leu Lys Tyr Ile
1               5

<210> SEQ ID NO 490
<211> LENGTH: 4
<212> TYPE: PRT
<213> ORGANISM: Artificial Sequence
<220> FEATURE:
<223> OTHER INFORMATION: Synthethic

<400> SEQUENCE: 490

Val Asn Leu Val
1

<210> SEQ ID NO 491
<211> LENGTH: 7
<212> TYPE: PRT
<213> ORGANISM: Artificial Sequence
<220> FEATURE:
<223> OTHER INFORMATION: Synthethic

<400> SEQUENCE: 491

Gln Leu Pro Met Leu Asn Gln
1               5

<210> SEQ ID NO 492
<211> LENGTH: 75
<212> TYPE: PRT
<213> ORGANISM: Artificial Sequence
<220> FEATURE:
<223> OTHER INFORMATION: Synthethic

<400> SEQUENCE: 492

Gly Thr Tyr Leu Ser Asp Leu Ser Ile Ser Phe Ile His Ser Cys Leu
1               5                   10                  15
```

```
Thr Pro Arg Arg Val Asp Asn Tyr Asp Thr Gly Gly Leu Thr Ile Trp
            20                  25                  30

Pro Gln Cys Cys Asn Asp Thr Ala Arg Pro Thr Leu Thr Gly Ser Arg
            35                  40                  45

Phe Ile Ser Asn Lys Pro Ala Ser Arg Lys Gly Arg Ala Gln Lys Trp
 50                  55                  60

Ser Cys Asn Phe Ile Arg Leu His Pro Val Tyr
 65                  70                  75
```

<210> SEQ ID NO 493
<211> LENGTH: 5
<212> TYPE: PRT
<213> ORGANISM: Artificial Sequence
<220> FEATURE:
<223> OTHER INFORMATION: Synthethic

<400> SEQUENCE: 493

```
Leu Leu Pro Gly Ser
 1               5
```

<210> SEQ ID NO 494
<211> LENGTH: 2
<212> TYPE: PRT
<213> ORGANISM: Artificial Sequence
<220> FEATURE:
<223> OTHER INFORMATION: Synthethic

<400> SEQUENCE: 494

```
Ser Lys
 1
```

<210> SEQ ID NO 495
<211> LENGTH: 3
<212> TYPE: PRT
<213> ORGANISM: Artificial Sequence
<220> FEATURE:
<223> OTHER INFORMATION: Synthethic

<400> SEQUENCE: 495

```
Phe Ala Ser
 1
```

<210> SEQ ID NO 496
<211> LENGTH: 44
<212> TYPE: PRT
<213> ORGANISM: Artificial Sequence
<220> FEATURE:
<223> OTHER INFORMATION: Synthethic

<400> SEQUENCE: 496

```
Phe Ala Gln Arg Cys Cys His Cys Tyr Arg His Arg Gly Val Thr Leu
 1               5                  10                  15

Val Val Trp Tyr Gly Phe Ile Gln Leu Arg Phe Pro Thr Ile Lys Ala
            20                  25                  30

Ser Tyr Met Ile Pro His Val Val Gln Lys Ser Gly
            35                  40
```

<210> SEQ ID NO 497
<211> LENGTH: 10
<212> TYPE: PRT
<213> ORGANISM: Artificial Sequence
<220> FEATURE:
<223> OTHER INFORMATION: Synthethic

<400> SEQUENCE: 497

Leu Leu Arg Ser Ser Asp Arg Cys Gln Lys
1               5                   10

<210> SEQ ID NO 498
<211> LENGTH: 14
<212> TYPE: PRT
<213> ORGANISM: Artificial Sequence
<220> FEATURE:
<223> OTHER INFORMATION: Synthethic

<400> SEQUENCE: 498

Val Gly Arg Ser Val Ile Thr His Gly Tyr Gly Ser Thr Ala
1               5                   10

<210> SEQ ID NO 499
<211> LENGTH: 15
<212> TYPE: PRT
<213> ORGANISM: Artificial Sequence
<220> FEATURE:
<223> OTHER INFORMATION: Synthethic

<400> SEQUENCE: 499

Phe Ser Tyr Cys His Ala Ile Arg Lys Met Leu Phe Cys Asp Trp
1               5                   10                  15

<210> SEQ ID NO 500
<211> LENGTH: 24
<212> TYPE: PRT
<213> ORGANISM: Artificial Sequence
<220> FEATURE:
<223> OTHER INFORMATION: Synthethic

<400> SEQUENCE: 500

Val Leu Asn Gln Val Ile Leu Arg Ile Val Tyr Ala Ala Thr Glu Leu
1               5                   10                  15

Leu Leu Pro Gly Val Asn Thr Gly
            20

<210> SEQ ID NO 501
<211> LENGTH: 4
<212> TYPE: PRT
<213> ORGANISM: Artificial Sequence
<220> FEATURE:
<223> OTHER INFORMATION: Synthethic

<400> SEQUENCE: 501

Tyr Arg Ala Thr
1

<210> SEQ ID NO 502
<211> LENGTH: 95
<212> TYPE: PRT
<213> ORGANISM: Artificial Sequence
<220> FEATURE:
<223> OTHER INFORMATION: Synthethic

<400> SEQUENCE: 502

Gln Asn Phe Lys Ser Ala His His Trp Lys Thr Phe Phe Gly Ala Lys
1               5                   10                  15

Thr Leu Lys Asp Leu Thr Ala Val Glu Ile Gln Phe Asp Val Thr His
            20                  25                  30

Ser Cys Thr Gln Leu Ile Phe Ser Ile Phe Tyr Phe His Gln Arg Phe
        35                  40                  45

```
Trp Val Ser Lys Asn Arg Lys Ala Lys Cys Arg Lys Lys Gly Asn Lys
        50                  55                  60

Gly Asp Thr Glu Met Leu Asn Thr His Thr Leu Pro Phe Ser Ile Leu
 65              70                  75                  80

Leu Lys His Leu Ser Gly Leu Leu Ser His Glu Arg Ile His Ile
                85                  90                  95

<210> SEQ ID NO 503
<211> LENGTH: 5
<212> TYPE: PRT
<213> ORGANISM: Artificial Sequence
<220> FEATURE:
<223> OTHER INFORMATION: Synthethic

<400> SEQUENCE: 503

Met Tyr Leu Glu Lys
1               5

<210> SEQ ID NO 504
<211> LENGTH: 14
<212> TYPE: PRT
<213> ORGANISM: Artificial Sequence
<220> FEATURE:
<223> OTHER INFORMATION: Synthethic

<400> SEQUENCE: 504

Thr Asn Arg Gly Ser Ala His Ile Ser Pro Lys Ser Ala Thr
1               5                   10

<210> SEQ ID NO 505
<211> LENGTH: 12
<212> TYPE: PRT
<213> ORGANISM: Artificial Sequence
<220> FEATURE:
<223> OTHER INFORMATION: Synthethic

<400> SEQUENCE: 505

Arg Leu Arg Asn His Tyr Tyr His Asp Ile Asn Leu
1               5                   10

<210> SEQ ID NO 506
<211> LENGTH: 1
<212> TYPE: PRT
<213> ORGANISM: Artificial Sequence
<220> FEATURE:
<223> OTHER INFORMATION: Synthethic

<400> SEQUENCE: 506

Lys
1

<210> SEQ ID NO 507
<211> LENGTH: 7
<212> TYPE: PRT
<213> ORGANISM: Artificial Sequence
<220> FEATURE:
<223> OTHER INFORMATION: Synthethic

<400> SEQUENCE: 507

Ala Tyr His Glu Ala Leu Ser
1               5

<210> SEQ ID NO 508
<211> LENGTH: 3210
<212> TYPE: DNA
<213> ORGANISM: Artificial Sequence
```

<220> FEATURE:
<223> OTHER INFORMATION: Synthethic

<400> SEQUENCE: 508

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cgacgccacc atgaaccgcg | 420 |
| cagtttgcca agttgcgcta gagaatgatg aaagggaagc gaagaataca tggcgcttgg | 480 |
| tattccggat cgcaatctta cttttaacag taatgacctt agccatctct gcagccgccc | 540 |
| tggcatatag ttacccatgt tgtcacgtca ctcagctccg cgctcaacac cttctcgcgt | 600 |
| tggaaaacat tagcgacatt tacctggtga gcaatcagac atgcgacggc tttagcctgg | 660 |
| cctccttaaa ttcacctaag aatgggagca accagctggt catcagccgc tgcgcaaacg | 720 |
| gactcaacgt ggtctccttc tttatctcca tcctgaagcg aagcagctcc gccctcacgg | 780 |
| gccatctccg tgagttgtta accaccctgg agactcttta cggttcattc tcagtggaag | 840 |
| acctgtttgg tgccaactta aacagatacg catggcatcg cggggctag atgcagatga | 900 |
| gaggcggagg tatccccaat agcaatttgt gtgcaaattc tatgccctgg ctcacaaata | 960 |
| ccactgagat ctaagcttgg cgtaatcatg gtcatagctg tttcctgtgt gaaattgtta | 1020 |
| tccgctcaca attccacaca acatacgagc cggaagcata aagtgtaaag cctggggtgc | 1080 |
| ctaatgagtg agctaactca cattaattgc gttgcgctca ctgcccgctt ccagtcggg | 1140 |
| aaacctgtcg tgccagctgc attaatgaat cggccaacgc gcgggagag gcggtttgcg | 1200 |
| tattgggcgc tcttccgctt cctcgctcac tgactcgctg cgctcggtcg ttcggctgcg | 1260 |
| gcgagcggta tcagctcact caaaggcggt aatacggtta tccacagaat caggggataa | 1320 |
| cgcaggaaag aacatgtgag caaaaggcca gcaaaaggcc aggaaccgta aaaaggccgc | 1380 |
| gttgctggcg tttttccata ggctccgccc cctgacgag catcacaaaa atcgacgctc | 1440 |
| aagtcagagg tggcgaaacc cgacaggact ataaagatac caggcgtttc ccctggaag | 1500 |
| ctccctcgtg cgctctcctg ttccgaccct gccgcttacc ggatacctgt ccgcctttct | 1560 |
| cccttcggga agcgtggcgc tttctcatag ctcacgctgt aggtatctca gttcggtgta | 1620 |
| ggtcgttcgc tccaagctgg gctgtgtgca cgaacccccc gttcagcccg accgctgcgc | 1680 |
| cttatccggt aactatcgtc ttgagtccaa cccggtaaga cacgacttat cgccactggc | 1740 |
| agcagccact ggtaacagga ttagcagagc gaggtatgta ggcggtgcta cagagttctt | 1800 |
| gaagtggtgg cctaactacg gctacactag aagaacagta tttggtatct gcgctctgct | 1860 |
| gaagccagtt accttcggaa aaagagttgg tagctcttga tccggcaaac aaaccaccgc | 1920 |
| tggtagcggt ggtttttttg tttgcaagca gcagattacg cgcagaaaaa aaggatctca | 1980 |
| agaagatcct ttgatctttt ctacggggtc tgacgctcag tggaacgaaa actcacgtta | 2040 |
| agggattttg gtcatgagat tatcaaaaag gatcttcacc tagatccttt taaattaaaa | 2100 |
| atgaagtttt aaatcaatct aaagtatata tgagtaaact tggtctgaca gttaccaatg | 2160 |
| cttaatcagt gaggcaccta tctcagcgat ctgtctattt cgttcatcca tagttgcctg | 2220 |

```
actccccgtc gtgtagataa ctacgatacg ggagggctta ccatctggcc ccagtgctgc    2280
aatgataccg cgagacccac gctcaccggc tccagattta tcagcaataa accagccagc    2340
cggaagggcc gagcgcagaa gtggtcctgc aactttatcc gcctccatcc agtctattaa    2400
ttgttgccgg gaagctagag taagtagttc gccagttaat agtttgcgca acgttgttgc    2460
cattgctaca ggcatcgtgg tgtcacgctc gtcgtttggt atggcttcat tcagctccgg    2520
ttcccaacga tcaaggcgag ttacatgatc ccccatgttg tgcaaaaaag cggttagctc    2580
cttcggtcct ccgatcgttg tcagaagtaa gttggccgca gtgttatcac tcatggttat    2640
ggcagcactg cataattctc ttactgtcat gccatccgta agatgctttt ctgtgactgg    2700
tgagtactca accaagtcat tctgagaata gtgtatgcgg cgaccgagtt gctcttgccc    2760
ggcgtcaata cgggataata ccgcgccaca tagcagaact ttaaaagtgc tcatcattgg    2820
aaaacgttct cgggcgaa aactctcaag gatcttaccg ctgttgagat ccagttcgat    2880
gtaacccact cgtgcaccca actgatcttc agcatctttt actttcacca gcgtttctgg    2940
gtgagcaaaa acaggaaggc aaaatgccgc aaaaaaggga ataagggcga cacggaaatg    3000
ttgaatactc atactcttcc tttttcaata ttattgaagc atttatcagg gttattgtct    3060
catgagcgga tacatatttg aatgtattta gaaaataaa caaatagggg ttccgcgcac    3120
atttccccga aagtgccac ctgacgtcta agaaaccatt attatcatga cattaaccta    3180
taaaaatagg cgtatcacga ggccctttcg                                     3210
```

<210> SEQ ID NO 509
<211> LENGTH: 57
<212> TYPE: PRT
<213> ORGANISM: Artificial Sequence
<220> FEATURE:
<223> OTHER INFORMATION: Synthethic

<400> SEQUENCE: 509

Ser Arg Val Ser Val Met Thr Val Lys Thr Ser Asp Thr Cys Ser Ser
1               5                   10                  15

Arg Arg Arg Ser Gln Leu Val Cys Lys Arg Met Pro Gly Ala Asp Lys
            20                  25                  30

Pro Val Arg Ala Arg Gln Arg Val Leu Ala Gly Val Gly Ala Gly Leu
        35                  40                  45

Thr Met Arg His Gln Ser Arg Leu Tyr
    50                  55

<210> SEQ ID NO 510
<211> LENGTH: 13
<212> TYPE: PRT
<213> ORGANISM: Artificial Sequence
<220> FEATURE:
<223> OTHER INFORMATION: Synthethic

<400> SEQUENCE: 510

Glu Cys Thr Ile Cys Gly Val Lys Tyr Arg Thr Asp Ala
1               5                   10

<210> SEQ ID NO 511

<400> SEQUENCE: 511

000

<210> SEQ ID NO 512
<211> LENGTH: 2

-continued

```
<212> TYPE: PRT
<213> ORGANISM: Artificial Sequence
<220> FEATURE:
<223> OTHER INFORMATION: Synthethic

<400> SEQUENCE: 512

Val Gly
1

<210> SEQ ID NO 513
<211> LENGTH: 23
<212> TYPE: PRT
<213> ORGANISM: Artificial Sequence
<220> FEATURE:
<223> OTHER INFORMATION: Synthethic

<400> SEQUENCE: 513

Arg Gln Gly Phe Pro Ser His Asp Val Val Lys Arg Arg Pro Val Asn
1               5                   10                  15

Ser Ser Ser Ser Arg Pro Pro
            20

<210> SEQ ID NO 514
<211> LENGTH: 5
<212> TYPE: PRT
<213> ORGANISM: Artificial Sequence
<220> FEATURE:
<223> OTHER INFORMATION: Synthethic

<400> SEQUENCE: 514

Leu Gly Val Gly Cys
1               5

<210> SEQ ID NO 515
<211> LENGTH: 5
<212> TYPE: PRT
<213> ORGANISM: Artificial Sequence
<220> FEATURE:
<223> OTHER INFORMATION: Synthethic

<400> SEQUENCE: 515

Ala Trp Ser Cys Cys
1               5

<210> SEQ ID NO 516
<211> LENGTH: 68
<212> TYPE: PRT
<213> ORGANISM: Artificial Sequence
<220> FEATURE:
<223> OTHER INFORMATION: Synthethic

<400> SEQUENCE: 516

Pro Pro Trp Arg Ala Val Ser Val Arg Arg Pro Gln Ser Ser Pro His
1               5                   10                  15

Pro Pro Pro Pro Arg Cys Ser Leu Pro Pro Arg Val Ser Lys Pro Ala
            20                  25                  30

Phe Leu Ser Glu Ser Ala Ser Ser Pro Ala Thr Ala Thr Cys Ser Ala
        35                  40                  45

Ser Pro Arg Thr Ser Ser Val Pro Arg Leu Ala Arg Gly Arg Ile Thr
    50                  55                  60

Arg Arg Ala Cys
65

<210> SEQ ID NO 517
```

```
<211> LENGTH: 19
<212> TYPE: PRT
<213> ORGANISM: Artificial Sequence
<220> FEATURE:
<223> OTHER INFORMATION: Synthethic

<400> SEQUENCE: 517

Trp Cys Leu Lys Thr Thr Leu Phe Pro Thr Arg Leu Arg Ser Ala Pro
1               5                   10                  15

Thr Pro Arg

<210> SEQ ID NO 518
<211> LENGTH: 13
<212> TYPE: PRT
<213> ORGANISM: Artificial Sequence
<220> FEATURE:
<223> OTHER INFORMATION: Synthethic

<400> SEQUENCE: 518

Pro Thr Phe Ser Ser Thr Met Ala Gly Thr Arg Thr Pro
1               5                   10

<210> SEQ ID NO 519
<211> LENGTH: 29
<212> TYPE: PRT
<213> ORGANISM: Artificial Sequence
<220> FEATURE:
<223> OTHER INFORMATION: Synthethic

<400> SEQUENCE: 519

Pro Thr Gly Thr Arg Arg Ser Ser Pro Leu Thr Ala Thr Lys Leu Thr
1               5                   10                  15

Arg Trp Ile Pro Ser Thr Ser Ala Thr Thr Arg Ser Arg
            20                  25

<210> SEQ ID NO 520
<211> LENGTH: 4
<212> TYPE: PRT
<213> ORGANISM: Artificial Sequence
<220> FEATURE:
<223> OTHER INFORMATION: Synthethic

<400> SEQUENCE: 520

Gln Lys Met Gly
1

<210> SEQ ID NO 521
<211> LENGTH: 4
<212> TYPE: PRT
<213> ORGANISM: Artificial Sequence
<220> FEATURE:
<223> OTHER INFORMATION: Synthethic

<400> SEQUENCE: 521

Arg Ala Cys Met
1

<210> SEQ ID NO 522
<211> LENGTH: 10
<212> TYPE: PRT
<213> ORGANISM: Artificial Sequence
<220> FEATURE:
<223> OTHER INFORMATION: Synthethic

<400> SEQUENCE: 522

Thr Ala Thr Glu Leu Thr Ser Pro Ser Thr
```

```
-continued 1               5                   10

<210> SEQ ID NO 523
<211> LENGTH: 25
<212> TYPE: PRT
<213> ORGANISM: Artificial Sequence
<220> FEATURE:
<223> OTHER INFORMATION: Synthethic

<400> SEQUENCE: 523

Ser Pro Pro Gly Ala Trp Pro Thr Gly Cys Ala Ala Thr Pro Ala Arg
1               5                   10                  15

Arg Ser Ser Met Thr Pro Pro Gly Gly
            20                  25

<210> SEQ ID NO 524
<211> LENGTH: 12
<212> TYPE: PRT
<213> ORGANISM: Artificial Sequence
<220> FEATURE:
<223> OTHER INFORMATION: Synthethic

<400> SEQUENCE: 524

Tyr Gly Leu Thr Glu Gln Glu Leu Pro Ser Thr Ala
1               5                   10

<210> SEQ ID NO 525
<211> LENGTH: 2
<212> TYPE: PRT
<213> ORGANISM: Artificial Sequence
<220> FEATURE:
<223> OTHER INFORMATION: Synthethic

<400> SEQUENCE: 525

Leu Thr
1

<210> SEQ ID NO 526
<211> LENGTH: 11
<212> TYPE: PRT
<213> ORGANISM: Artificial Sequence
<220> FEATURE:
<223> OTHER INFORMATION: Synthethic

<400> SEQUENCE: 526

Trp Pro Ser Pro Thr Ala Pro Ser Thr Ser Leu
1               5                   10

<210> SEQ ID NO 527
<211> LENGTH: 29
<212> TYPE: PRT
<213> ORGANISM: Artificial Sequence
<220> FEATURE:
<223> OTHER INFORMATION: Synthethic

<400> SEQUENCE: 527

Pro Pro Pro Gly Arg Leu Trp Lys Cys Pro Leu Ser Met Thr Gly Lys
1               5                   10                  15

Ile Arg Lys Pro Ser Met Ser Gly Gln Thr Pro Ser Thr
            20                  25

<210> SEQ ID NO 528
<211> LENGTH: 5
<212> TYPE: PRT
<213> ORGANISM: Artificial Sequence
<220> FEATURE:
```

```
<223> OTHER INFORMATION: Synthethic

<400> SEQUENCE: 528

Glu Leu Thr Thr Arg
1               5

<210> SEQ ID NO 529
<211> LENGTH: 58
<212> TYPE: PRT
<213> ORGANISM: Artificial Sequence
<220> FEATURE:
<223> OTHER INFORMATION: Synthethic

<400> SEQUENCE: 529

Trp Thr Thr Thr Thr Glu Gly Arg Thr Arg Lys Ala Asn Ala Glu Pro
1               5                   10                  15

Ser Trp Thr Arg Ala Leu Thr Arg Tyr Leu Gly Ser Ser Arg Thr Gly
            20                  25                  30

Gln Pro Thr Ala Arg Phe Asn Thr Gly Lys Pro Leu Thr Arg Pro Ser
        35                  40                  45

Pro Gln Lys Gln Gly Ser Gln Tyr Ile Leu
    50                  55

<210> SEQ ID NO 530
<211> LENGTH: 8
<212> TYPE: PRT
<213> ORGANISM: Artificial Sequence
<220> FEATURE:
<223> OTHER INFORMATION: Synthethic

<400> SEQUENCE: 530

Leu Thr Arg Ala Pro Leu Ala Ser
1               5

<210> SEQ ID NO 531
<211> LENGTH: 6
<212> TYPE: PRT
<213> ORGANISM: Artificial Sequence
<220> FEATURE:
<223> OTHER INFORMATION: Synthethic

<400> SEQUENCE: 531

Pro Thr Gln Pro Trp Ala
1               5

<210> SEQ ID NO 532
<211> LENGTH: 12
<212> TYPE: PRT
<213> ORGANISM: Artificial Sequence
<220> FEATURE:
<223> OTHER INFORMATION: Synthethic

<400> SEQUENCE: 532

Ser Ser Arg Thr Pro Ser Ser Ala Ser Lys Ser Arg
1               5                   10

<210> SEQ ID NO 533
<211> LENGTH: 25
<212> TYPE: PRT
<213> ORGANISM: Artificial Sequence
<220> FEATURE:
<223> OTHER INFORMATION: Synthethic

<400> SEQUENCE: 533

Thr Arg Pro Cys Met Arg Ser Thr Arg Pro Ser Arg Ile Val Thr Arg
```

```
1               5                   10                  15
Arg Ala Arg Lys Pro Leu His Ile Leu
            20                  25
```

<210> SEQ ID NO 534
<211> LENGTH: 6
<212> TYPE: PRT
<213> ORGANISM: Artificial Sequence
<220> FEATURE:
<223> OTHER INFORMATION: Synthethic

<400> SEQUENCE: 534

```
Arg Ala Glu Asp Cys Tyr
1               5
```

<210> SEQ ID NO 535
<211> LENGTH: 4
<212> TYPE: PRT
<213> ORGANISM: Artificial Sequence
<220> FEATURE:
<223> OTHER INFORMATION: Synthethic

<400> SEQUENCE: 535

```
Leu Gly Tyr Leu
1
```

<210> SEQ ID NO 536
<211> LENGTH: 10
<212> TYPE: PRT
<213> ORGANISM: Artificial Sequence
<220> FEATURE:
<223> OTHER INFORMATION: Synthethic

<400> SEQUENCE: 536

```
Pro Arg Ala Arg Trp Pro Pro Ser Arg Thr
1               5                   10
```

<210> SEQ ID NO 537
<211> LENGTH: 30
<212> TYPE: PRT
<213> ORGANISM: Artificial Sequence
<220> FEATURE:
<223> OTHER INFORMATION: Synthethic

<400> SEQUENCE: 537

```
Arg Ser Leu Pro Leu Arg Leu Pro His Pro Pro Ala Val His Arg Pro
1               5                   10                  15
Gln Pro His Pro Arg Pro Ala Gly Ala Pro Pro Pro Pro Phe
            20                  25                  30
```

<210> SEQ ID NO 538
<211> LENGTH: 66
<212> TYPE: PRT
<213> ORGANISM: Artificial Sequence
<220> FEATURE:
<223> OTHER INFORMATION: Synthethic

<400> SEQUENCE: 538

```
Gly Val Gly Gly Gly Met Arg Gly Thr Pro Pro His Arg Cys Pro Pro
1               5                   10                  15
Arg Pro Pro Gly Ser Pro Trp Ala Pro Ser Thr Ile Pro Pro Pro Ser
            20                  25                  30
Arg Ser Asn Leu Pro Thr Thr Pro Cys Ala Ala Arg Ser Thr Ala Cys
            35                  40                  45
```

Trp Glu Thr Leu Arg Gly Pro Gly Ala Trp Ser Arg Arg Gly Arg Thr
        50                  55                  60

Trp Cys
65

<210> SEQ ID NO 539
<211> LENGTH: 2
<212> TYPE: PRT
<213> ORGANISM: Artificial Sequence
<220> FEATURE:
<223> OTHER INFORMATION: Synthethic

<400> SEQUENCE: 539

Glu Asn
1

<210> SEQ ID NO 540
<211> LENGTH: 44
<212> TYPE: PRT
<213> ORGANISM: Artificial Sequence
<220> FEATURE:
<223> OTHER INFORMATION: Synthethic

<400> SEQUENCE: 540

Pro Arg Leu Ile Gln Pro Pro Ser Cys Pro Ala Ser Thr Val Arg Arg
1               5                   10                  15

Trp Arg Pro Ser Ala Trp Gly Met Ser Ser Gln Ser Pro Ser Ala Cys
            20                  25                  30

Pro Leu Thr Arg Pro Pro Ser Pro Cys Ala Arg Ala
        35                  40

<210> SEQ ID NO 541
<211> LENGTH: 41
<212> TYPE: PRT
<213> ORGANISM: Artificial Sequence
<220> FEATURE:
<223> OTHER INFORMATION: Synthethic

<400> SEQUENCE: 541

Gly Ser Leu Ala Pro Arg Pro Cys Ala Thr Arg Ala Pro Trp Cys Pro
1               5                   10                  15

Ser Ala Leu Ser Thr Thr Pro Arg Pro Thr Arg Asp Ser Trp Ala Pro
            20                  25                  30

Thr Thr Arg Ser Ser Ser Gln Lys Arg
        35                  40

<210> SEQ ID NO 542
<211> LENGTH: 43
<212> TYPE: PRT
<213> ORGANISM: Artificial Sequence
<220> FEATURE:
<223> OTHER INFORMATION: Synthethic

<400> SEQUENCE: 542

Arg Arg Cys Ala Arg Arg Pro Ala Ser Thr Thr Ser Ser Pro Ala Thr
1               5                   10                  15

Arg Ser Thr Ser Thr Thr Thr Thr Thr Thr Leu Lys Pro Ser Ser Trp
            20                  25                  30

Thr Ala Leu Pro Pro Cys Arg Pro Ser Ser His
        35                  40

<210> SEQ ID NO 543
<211> LENGTH: 81

```
<212> TYPE: PRT
<213> ORGANISM: Artificial Sequence
<220> FEATURE:
<223> OTHER INFORMATION: Synthethic

<400> SEQUENCE: 543

Thr Pro Pro Ser Ser Arg Thr Leu Thr Leu Pro Pro Trp Ser Cys Thr
1               5                   10                  15

His Gly Thr Asn Ser Val Pro Pro Thr Ser Leu Thr Trp Arg Ala Ser
            20                  25                  30

Ser Gly Ser Thr Thr Ser Arg Arg Lys Thr Ser Pro Ala Cys Gly Arg
        35                  40                  45

Ile Trp Thr Met Gln Cys Gln Thr Glu Glu Ile Asn Ser Trp Thr Ala
50                  55                  60

Trp Gly Asn Leu Trp Thr Val Trp Val Ala Trp Val Ser Pro Ser Pro
65                  70                  75                  80

Thr

<210> SEQ ID NO 544
<211> LENGTH: 35
<212> TYPE: PRT
<213> ORGANISM: Artificial Sequence
<220> FEATURE:
<223> OTHER INFORMATION: Synthethic

<400> SEQUENCE: 544

Ser Ala Arg Trp Gly Val Cys Leu Ala Ala Trp Ser Leu Val Ser Ser
1               5                   10                  15

Pro Ser Ser Lys Thr Pro Ser Ala Ala Cys Ser Phe Trp Ser Trp Trp
            20                  25                  30

Arg Gly Trp
        35

<210> SEQ ID NO 545
<211> LENGTH: 52
<212> TYPE: PRT
<213> ORGANISM: Artificial Sequence
<220> FEATURE:
<223> OTHER INFORMATION: Synthethic

<400> SEQUENCE: 545

Ser Trp Leu Phe Pro Ser Arg Gly Ala Arg Ala Arg Cys Arg Ser Ser
1               5                   10                  15

Arg Cys Arg Cys Ser Thr Pro Gly Ser Thr Ser Ser Leu Ser Asn Met
            20                  25                  30

Pro Leu Val Arg Val Gln Ala Leu Ile Pro Leu Val Arg Gln Asn Tyr
        35                  40                  45

Lys Pro Ser Cys
    50

<210> SEQ ID NO 546
<211> LENGTH: 61
<212> TYPE: PRT
<213> ORGANISM: Artificial Sequence
<220> FEATURE:
<223> OTHER INFORMATION: Synthethic

<400> SEQUENCE: 546

Arg Cys Met Ser Lys Thr Arg Ser Lys Arg Glu Gln Leu Arg Gly Arg
1               5                   10                  15

Pro Asp Pro Gln Trp Pro Ala Glu His Cys Arg Gln Pro Gly Thr Val
```

```
                    20                  25                  30

Phe Gln Ala Tyr Ala Glu Asp Ala Ile Thr Ile Gln Arg Pro Pro
            35                  40                  45

His Cys Leu Gly Arg Gln Arg Leu Ser Phe Lys Cys Arg
        50                  55                  60

<210> SEQ ID NO 547
<211> LENGTH: 38
<212> TYPE: PRT
<213> ORGANISM: Artificial Sequence
<220> FEATURE:
<223> OTHER INFORMATION: Synthethic

<400> SEQUENCE: 547

Glu Ala Glu Val Ser Pro Ile Ala Ile Cys Val Gln Ile Leu Cys Pro
1               5                   10                  15

Gly Ser Gln Ile Pro Leu Arg Ser Phe Ser Leu Cys Gln Lys Leu Trp
            20                  25                  30

Gly His His Glu Ala Pro
        35

<210> SEQ ID NO 548
<211> LENGTH: 39
<212> TYPE: PRT
<213> ORGANISM: Artificial Sequence
<220> FEATURE:
<223> OTHER INFORMATION: Synthethic

<400> SEQUENCE: 548

Ala Ser Asp Phe Trp Leu Ile Lys Glu Ile Tyr Phe His Cys Asn Ser
1               5                   10                  15

Val Leu Glu Phe Phe Val Ser Leu Thr Arg Lys Asp Ile Trp Glu Gly
            20                  25                  30

Lys Ser Phe Lys Thr Ser Glu
        35

<210> SEQ ID NO 549
<211> LENGTH: 39
<212> TYPE: PRT
<213> ORGANISM: Artificial Sequence
<220> FEATURE:
<223> OTHER INFORMATION: Synthethic

<400> SEQUENCE: 549

Val Phe Gly Leu Glu Phe Gly Asn Ile Cys Pro Tyr Ala Gly Cys His
1               5                   10                  15

Glu Gln Arg Leu Ala Ile Lys Arg Ser Ser Val Tyr Glu Thr Ala Pro
            20                  25                  30

Cys Cys Pro Phe Leu Ile Pro
        35

<210> SEQ ID NO 550
<211> LENGTH: 87
<212> TYPE: PRT
<213> ORGANISM: Artificial Sequence
<220> FEATURE:
<223> OTHER INFORMATION: Synthethic

<400> SEQUENCE: 550

Lys Ser Leu Asp Leu Arg Leu Asp Phe Phe Tyr Ile Leu Phe Cys Val
1               5                   10                  15

Ile Phe Phe Phe Asn Ile Pro Lys Ile Phe Leu Thr Cys Phe Thr Ser
```

```
                    20                  25                  30

Gln Ile Phe Pro Pro Leu Leu Thr Thr Pro Ser His Ser Cys Pro Ser
                35                  40                  45

Ser Leu Met Glu Ile Pro Arg Pro Ala Ala Gln Ala Trp Arg Asn His
            50                  55                  60

Gly His Ser Cys Phe Leu Cys Glu Ile Val Ile Arg Ser Gln Phe His
65                  70                  75                  80

Thr Thr Tyr Glu Pro Glu Ala
                85

<210> SEQ ID NO 551
<211> LENGTH: 9
<212> TYPE: PRT
<213> ORGANISM: Artificial Sequence
<220> FEATURE:
<223> OTHER INFORMATION: Synthethic

<400> SEQUENCE: 551

Ser Val Lys Pro Gly Val Pro Asn Glu
1               5

<210> SEQ ID NO 552
<211> LENGTH: 4
<212> TYPE: PRT
<213> ORGANISM: Artificial Sequence
<220> FEATURE:
<223> OTHER INFORMATION: Synthethic

<400> SEQUENCE: 552

Ala Asn Ser His
1

<210> SEQ ID NO 553
<211> LENGTH: 61
<212> TYPE: PRT
<213> ORGANISM: Artificial Sequence
<220> FEATURE:
<223> OTHER INFORMATION: Synthethic

<400> SEQUENCE: 553

Leu Arg Cys Ala His Cys Pro Leu Ser Ser Arg Glu Thr Cys Arg Ala
1               5                   10                  15

Ser Cys Ile Asn Glu Ser Ala Asn Ala Arg Gly Glu Ala Val Cys Val
                20                  25                  30

Leu Gly Ala Leu Pro Leu Pro Arg Ser Leu Thr Arg Cys Ala Arg Ser
            35                  40                  45

Phe Gly Cys Gly Glu Arg Tyr Gln Leu Thr Gln Arg Arg
        50                  55                  60

<210> SEQ ID NO 554
<211> LENGTH: 141
<212> TYPE: PRT
<213> ORGANISM: Artificial Sequence
<220> FEATURE:
<223> OTHER INFORMATION: Synthethic

<400> SEQUENCE: 554

Tyr Gly Tyr Pro Gln Asn Gln Gly Ile Thr Gln Glu Arg Thr Cys Glu
1               5                   10                  15

Gln Lys Ala Ser Lys Arg Pro Gly Thr Val Lys Arg Pro Arg Cys Trp
                20                  25                  30

Arg Phe Ser Ile Gly Ser Ala Pro Leu Thr Ser Ile Thr Lys Ile Asp
```

```
                35                  40                  45
Ala Gln Val Arg Gly Gly Glu Thr Arg Gln Asp Tyr Lys Asp Thr Arg
         50                  55                  60
Arg Phe Pro Leu Glu Ala Pro Ser Cys Ala Leu Leu Phe Arg Pro Cys
 65                  70                  75                  80
Arg Leu Pro Asp Thr Cys Pro Pro Phe Ser Leu Arg Glu Ala Trp Arg
                 85                  90                  95
Phe Leu Ile Ala His Ala Val Gly Ile Ser Val Arg Cys Arg Ser Phe
            100                 105                 110
Ala Pro Ser Trp Ala Val Cys Thr Asn Pro Pro Phe Ser Pro Thr Ala
        115                 120                 125
Ala Pro Tyr Pro Val Thr Ile Val Leu Ser Pro Thr Arg
    130                 135                 140

<210> SEQ ID NO 555
<211> LENGTH: 20
<212> TYPE: PRT
<213> ORGANISM: Artificial Sequence
<220> FEATURE:
<223> OTHER INFORMATION: Synthethic

<400> SEQUENCE: 555

Asp Thr Thr Tyr Arg His Trp Gln Gln Pro Leu Val Thr Gly Leu Ala
 1               5                  10                  15
Glu Arg Gly Met
            20

<210> SEQ ID NO 556
<211> LENGTH: 6
<212> TYPE: PRT
<213> ORGANISM: Artificial Sequence
<220> FEATURE:
<223> OTHER INFORMATION: Synthethic

<400> SEQUENCE: 556

Ala Val Leu Gln Ser Ser
 1               5

<210> SEQ ID NO 557
<211> LENGTH: 19
<212> TYPE: PRT
<213> ORGANISM: Artificial Sequence
<220> FEATURE:
<223> OTHER INFORMATION: Synthethic

<400> SEQUENCE: 557

Ser Gly Gly Leu Thr Thr Ala Thr Leu Glu Glu Gln Tyr Leu Val Ser
 1               5                  10                  15
Ala Leu Cys

<210> SEQ ID NO 558
<211> LENGTH: 43
<212> TYPE: PRT
<213> ORGANISM: Artificial Sequence
<220> FEATURE:
<223> OTHER INFORMATION: Synthethic

<400> SEQUENCE: 558

Ser Gln Leu Pro Ser Glu Lys Glu Leu Val Ala Leu Asp Pro Ala Asn
 1               5                  10                  15
Lys Pro Pro Leu Val Ala Val Val Phe Leu Phe Ala Ser Ser Arg Leu
                20                  25                  30
```

```
Arg Ala Glu Lys Lys Asp Leu Lys Lys Ile Leu
        35                  40

<210> SEQ ID NO 559
<211> LENGTH: 20
<212> TYPE: PRT
<213> ORGANISM: Artificial Sequence
<220> FEATURE:
<223> OTHER INFORMATION: Synthethic

<400> SEQUENCE: 559

Ser Phe Leu Arg Gly Leu Thr Leu Ser Gly Thr Lys Thr His Val Lys
1               5                   10                  15

Gly Phe Trp Ser
            20

<210> SEQ ID NO 560
<211> LENGTH: 11
<212> TYPE: PRT
<213> ORGANISM: Artificial Sequence
<220> FEATURE:
<223> OTHER INFORMATION: Synthethic

<400> SEQUENCE: 560

Asp Tyr Gln Lys Gly Ser Ser Pro Arg Ser Phe
1               5                   10

<210> SEQ ID NO 561
<211> LENGTH: 23
<212> TYPE: PRT
<213> ORGANISM: Artificial Sequence
<220> FEATURE:
<223> OTHER INFORMATION: Synthethic

<400> SEQUENCE: 561

Ile Lys Asn Glu Val Leu Asn Gln Ser Lys Val Tyr Met Ser Lys Leu
1               5                   10                  15

Gly Leu Thr Val Thr Asn Ala
            20

<210> SEQ ID NO 562
<211> LENGTH: 15
<212> TYPE: PRT
<213> ORGANISM: Artificial Sequence
<220> FEATURE:
<223> OTHER INFORMATION: Synthethic

<400> SEQUENCE: 562

Ser Val Arg His Leu Ser Gln Arg Ser Val Tyr Phe Val His Pro
1               5                   10                  15

<210> SEQ ID NO 563
<211> LENGTH: 8
<212> TYPE: PRT
<213> ORGANISM: Artificial Sequence
<220> FEATURE:
<223> OTHER INFORMATION: Synthethic

<400> SEQUENCE: 563

Leu Pro Asp Ser Pro Ser Cys Arg
1               5

<210> SEQ ID NO 564
<211> LENGTH: 14
<212> TYPE: PRT
```

-continued

```
<213> ORGANISM: Artificial Sequence
<220> FEATURE:
<223> OTHER INFORMATION: Synthethic

<400> SEQUENCE: 564

Leu Arg Tyr Gly Arg Ala Tyr His Leu Ala Pro Val Leu Gln
1               5                   10

<210> SEQ ID NO 565
<211> LENGTH: 14
<212> TYPE: PRT
<213> ORGANISM: Artificial Sequence
<220> FEATURE:
<223> OTHER INFORMATION: Synthethic

<400> SEQUENCE: 565

Tyr Arg Glu Thr His Ala His Arg Leu Gln Ile Tyr Gln Gln
1               5                   10

<210> SEQ ID NO 566
<211> LENGTH: 30
<212> TYPE: PRT
<213> ORGANISM: Artificial Sequence
<220> FEATURE:
<223> OTHER INFORMATION: Synthethic

<400> SEQUENCE: 566

Thr Ser Gln Pro Glu Gly Pro Ser Ala Glu Val Val Leu Gln Leu Tyr
1               5                   10                  15

Pro Pro Pro Ser Ser Leu Leu Ile Val Ala Gly Lys Leu Glu
            20                  25                  30

<210> SEQ ID NO 567
<211> LENGTH: 85
<212> TYPE: PRT
<213> ORGANISM: Artificial Sequence
<220> FEATURE:
<223> OTHER INFORMATION: Synthethic

<400> SEQUENCE: 567

Val Val Arg Gln Leu Ile Val Cys Ala Thr Leu Leu Pro Leu Leu Gln
1               5                   10                  15

Ala Ser Trp Cys His Ala Arg Arg Leu Val Trp Leu His Ser Ala Pro
            20                  25                  30

Val Pro Asn Asp Gln Gly Glu Leu His Asp Pro Pro Cys Cys Ala Lys
        35                  40                  45

Lys Arg Leu Ala Pro Ser Val Leu Arg Ser Leu Ser Glu Val Ser Trp
    50                  55                  60

Pro Gln Cys Tyr His Ser Trp Leu Trp Gln His Cys Ile Ile Leu Leu
65                  70                  75                  80

Leu Ser Cys His Pro
                85

<210> SEQ ID NO 568
<211> LENGTH: 4
<212> TYPE: PRT
<213> ORGANISM: Artificial Sequence
<220> FEATURE:
<223> OTHER INFORMATION: Synthethic

<400> SEQUENCE: 568

Asp Ala Phe Leu
1
```

<210> SEQ ID NO 569
<211> LENGTH: 35
<212> TYPE: PRT
<213> ORGANISM: Artificial Sequence
<220> FEATURE:
<223> OTHER INFORMATION: Synthethic

<400> SEQUENCE: 569

Leu Val Ser Thr Gln Pro Ser His Ser Glu Asn Ser Val Cys Gly Asp
1               5                   10                  15

Arg Val Ala Leu Ala Arg Arg Gln Tyr Gly Ile Ile Pro Arg His Ile
            20                  25                  30

Ala Glu Leu
        35

<210> SEQ ID NO 570
<211> LENGTH: 20
<212> TYPE: PRT
<213> ORGANISM: Artificial Sequence
<220> FEATURE:
<223> OTHER INFORMATION: Synthethic

<400> SEQUENCE: 570

Lys Cys Ser Ser Leu Glu Asn Val Leu Arg Gly Glu Asn Ser Gln Gly
1               5                   10                  15

Ser Tyr Arg Cys
        20

<210> SEQ ID NO 571
<211> LENGTH: 38
<212> TYPE: PRT
<213> ORGANISM: Artificial Sequence
<220> FEATURE:
<223> OTHER INFORMATION: Synthethic

<400> SEQUENCE: 571

Asp Pro Val Arg Cys Asn Pro Leu Val His Pro Thr Asp Leu Gln His
1               5                   10                  15

Leu Leu Leu Ser Pro Ala Phe Leu Gly Glu Gln Lys Gln Glu Gly Lys
            20                  25                  30

Met Pro Gln Lys Arg Glu
        35

<210> SEQ ID NO 572
<211> LENGTH: 26
<212> TYPE: PRT
<213> ORGANISM: Artificial Sequence
<220> FEATURE:
<223> OTHER INFORMATION: Synthethic

<400> SEQUENCE: 572

Gly Arg His Gly Asn Val Glu Tyr Ser Tyr Ser Ser Phe Phe Asn Ile
1               5                   10                  15

Ile Glu Ala Phe Ile Arg Val Ile Val Ser
            20                  25

<210> SEQ ID NO 573
<211> LENGTH: 13
<212> TYPE: PRT
<213> ORGANISM: Artificial Sequence
<220> FEATURE:
<223> OTHER INFORMATION: Synthethic

<400> SEQUENCE: 573

Ala Asp Thr Tyr Leu Asn Val Phe Arg Lys Ile Asn Lys
1               5                   10

<210> SEQ ID NO 574
<211> LENGTH: 20
<212> TYPE: PRT
<213> ORGANISM: Artificial Sequence
<220> FEATURE:
<223> OTHER INFORMATION: Synthethic

<400> SEQUENCE: 574

Gly Phe Arg Ala His Phe Pro Glu Lys Cys His Leu Thr Ser Lys Lys
1               5                   10                  15

Pro Leu Leu Ser
            20

<210> SEQ ID NO 575
<211> LENGTH: 1
<212> TYPE: PRT
<213> ORGANISM: Artificial Sequence
<220> FEATURE:
<223> OTHER INFORMATION: Synthethic

<400> SEQUENCE: 575

His
1

<210> SEQ ID NO 576
<211> LENGTH: 12
<212> TYPE: PRT
<213> ORGANISM: Artificial Sequence
<220> FEATURE:
<223> OTHER INFORMATION: Synthethic

<400> SEQUENCE: 576

Pro Ile Lys Ile Gly Val Ser Arg Gly Pro Phe Val
1               5                   10

<210> SEQ ID NO 577
<211> LENGTH: 5775
<212> TYPE: PRT
<213> ORGANISM: Artificial Sequence
<220> FEATURE:
<223> OTHER INFORMATION: Synthethic

<400> SEQUENCE: 577

Thr Cys Gly Cys Gly Cys Gly Thr Thr Cys Gly Gly Thr Gly Ala
1               5                   10                  15

Thr Gly Ala Cys Gly Gly Thr Gly Ala Ala Ala Cys Cys Thr Cys
                20                  25                  30

Thr Gly Ala Cys Ala Cys Ala Thr Gly Cys Ala Gly Cys Thr Cys
            35                  40                  45

Cys Gly Gly Ala Gly Ala Cys Gly Gly Thr Cys Ala Cys Ala Gly Cys
        50                  55                  60

Thr Thr Gly Thr Cys Thr Gly Thr Ala Ala Gly Cys Gly Gly Ala Thr
65                  70                  75                  80

Gly Cys Cys Gly Gly Gly Ala Gly Cys Ala Gly Ala Cys Ala Ala Gly
                85                  90                  95

Cys Cys Cys Gly Thr Cys Ala Gly Gly Gly Cys Gly Cys Gly Thr Cys
            100                 105                 110

Ala Gly Cys Gly Gly Gly Thr Gly Thr Thr Gly Gly Cys Gly Gly Gly
        115                 120                 125

Thr Gly Thr Cys Gly Gly Gly Cys Thr Gly Cys Thr Thr Ala
    130                 135             140

Ala Cys Thr Ala Thr Gly Cys Gly Gly Cys Ala Thr Cys Ala Gly Ala
145             150             155                 160

Gly Cys Ala Gly Ala Thr Thr Gly Thr Ala Cys Thr Gly Ala Gly Ala
            165             170             175

Gly Thr Gly Cys Ala Cys Cys Ala Thr Ala Thr Gly Cys Gly Gly Thr
            180             185             190

Gly Thr Gly Ala Ala Ala Thr Ala Cys Cys Gly Cys Ala Cys Ala Gly
            195             200             205

Ala Thr Gly Cys Gly Thr Ala Ala Gly Gly Ala Gly Ala Ala Ala Ala
210             215             220

Thr Ala Cys Cys Gly Cys Ala Thr Cys Ala Gly Gly Cys Gly Cys Cys
225             230             235             240

Ala Thr Thr Cys Gly Cys Cys Ala Thr Thr Cys Ala Gly Gly Cys Thr
            245             250             255

Gly Cys Gly Cys Ala Ala Cys Thr Gly Thr Thr Gly Gly Gly Ala Ala
            260             265             270

Gly Gly Gly Cys Gly Ala Thr Cys Gly Gly Thr Gly Cys Gly Gly Gly
            275             280             285

Cys Cys Thr Cys Thr Thr Cys Gly Cys Thr Ala Thr Ala Cys Gly
290             295             300

Cys Cys Ala Gly Cys Thr Gly Gly Cys Gly Ala Ala Ala Gly Gly Gly
305             310             315             320

Gly Gly Ala Thr Gly Thr Gly Cys Thr Gly Cys Ala Ala Gly Gly Cys
            325             330             335

Gly Ala Thr Thr Ala Ala Gly Thr Thr Gly Gly Gly Thr Ala Ala Cys
            340             345             350

Gly Cys Cys Ala Gly Gly Gly Thr Thr Thr Thr Cys Cys Cys Ala Gly
            355             360             365

Thr Cys Ala Cys Gly Ala Cys Gly Thr Thr Gly Thr Ala Ala Ala Ala
            370             375             380

Cys Gly Ala Cys Gly Gly Cys Cys Ala Gly Thr Gly Ala Ala Thr Thr
385             390             395             400

Cys Cys Thr Cys Gly Ala Gly Cys Thr Cys Gly Gly Thr Ala Cys Cys
            405             410             415

Ala Cys Cys Ala Thr Gly Ala Cys Thr Cys Gly Gly Cys Gly Thr Ala
            420             425             430

Gly Gly Gly Thr Gly Cys Thr Ala Ala Gly Gly Thr Gly Gly Gly Thr
            435             440             445

Cys Gly Thr Gly Cys Thr Gly Cys Thr Ala Gly Cys Cys Gly Cys Cys
450             455             460

Cys Thr Gly Gly Cys Gly Thr Gly Cys Cys Gly Thr Cys Thr Cys Gly
465             470             475             480

Gly Thr Gly Cys Gly Cys Ala Gly Ala Cys Cys Cys Ala Gly Gly Ala
            485             490             495

Gly Cys Ala Gly Cys Cys Gly Cys Ala Cys Cys Cys Cys Cys
            500             505             510

Gly Cys Cys Ala Cys Ala Cys Gly Gly Thr Gly Cys Ala Gly Cys
            515             520             525

Cys Thr Ala Cys Cys Gly Cys Ala Cys Gly Cys Gly Thr Cys Ala
            530             535             540

Gly Cys Ala Ala Ala Cys Cys Ala Gly Cys Thr Thr Thr Cys Cys Thr
545 550 555 560

Thr Thr Cys Cys Gly Ala Gly Thr Cys Thr Gly Cys Gly Ala Gly Cys
565 570 575

Thr Cys Thr Cys Cys Ala Gly Cys Cys Ala Cys Gly Gly Cys Gly Ala
580 585 590

Cys Cys Thr Gly Thr Thr Cys Cys Gly Cys Thr Thr Cys Thr Cys Cys
595 600 605

Thr Cys Gly Gly Ala Cys Ala Thr Cys Cys Ala Gly Thr Gly Thr Cys
610 615 620

Cys Cys Thr Cys Gly Thr Thr Thr Gly Gly Cys Ala Cys Gly Cys Gly
625 630 635 640

Gly Gly Ala Gly Ala Ala Thr Cys Ala Cys Ala Cys Gly Gly Ala Gly
645 650 655

Gly Gly Cys Cys Thr Gly Thr Thr Gly Ala Thr Gly Gly Thr Gly Thr
660 665 670

Thr Thr Ala Ala Ala Gly Ala Cys Ala Ala Cys Ala Thr Thr Ala Thr
675 680 685

Thr Cys Cys Cys Thr Ala Cys Thr Cys Gly Thr Thr Thr Ala Ala Gly
690 695 700

Gly Thr Cys Cys Gly Cys Thr Cys Cys Thr Ala Cys Ala Cys Cys Ala
705 710 715 720

Ala Gly Ala Thr Ala Gly Thr Gly Ala Cys Cys Ala Ala Cys Ala Thr
725 730 735

Thr Cys Thr Cys Ala Thr Cys Thr Ala Cys Ala Ala Thr Gly Gly Cys
740 745 750

Thr Gly Gly Thr Ala Cys Gly Cys Gly Gly Ala Cys Thr Cys Cys Gly
755 760 765

Thr Gly Ala Cys Cys Ala Ala Cys Cys Gly Gly Cys Ala Cys Gly Ala
770 775 780

Gly Gly Ala Gly Ala Ala Gly Thr Thr Cys Thr Cys Cys Gly Thr Thr
785 790 795 800

Gly Ala Cys Ala Gly Cys Thr Ala Cys Gly Ala Ala Ala Cys Thr Gly
805 810 815

Ala Cys Cys Ala Gly Ala Thr Gly Gly Ala Thr Ala Cys Cys Ala Thr
820 825 830

Cys Thr Ala Cys Cys Ala Gly Thr Gly Cys Thr Ala Cys Ala Ala Cys
835 840 845

Gly Cys Gly Gly Thr Cys Ala Ala Gly Ala Thr Gly Ala Cys Ala Ala
850 855 860

Ala Ala Gly Ala Thr Gly Gly Gly Cys Thr Gly Ala Cys Gly Cys Gly
865 870 875 880

Cys Gly Thr Gly Thr Ala Thr Gly Thr Ala Gly Ala Cys Cys Gly Cys
885 890 895

Gly Ala Cys Gly Gly Ala Gly Thr Thr Ala Ala Cys Ala Thr Cys Ala
900 905 910

Cys Cys Gly Thr Cys Ala Ala Cys Cys Thr Ala Ala Ala Gly Cys Cys
915 920 925

Cys Ala Cys Cys Gly Gly Gly Gly Gly Cys Cys Thr Gly Gly Cys Cys
930 935 940

Ala Ala Cys Gly Gly Gly Gly Thr Gly Cys Gly Cys Cys Gly Cys Thr
945 950 955 960

Ala Cys Gly Cys Cys Ala Gly Cys Cys Ala Gly Ala Cys Gly Gly Ala

-continued

```
              965                 970                 975
Gly Cys Thr Cys Thr Ala Thr Gly Ala Cys Gly Cys Cys Cys Cys
                980                 985                 990
Gly Gly Gly Thr Gly Thr Thr Gly Ala Thr Ala Thr Gly Gly Ala
            995                 1000                1005
Cys Thr Thr Ala Cys Ala Gly Ala Ala Cys Ala Ala Gly Ala Ala
            1010                1015                1020
Cys Thr Ala Cys Cys Gly Thr Cys Ala Ala Cys Thr Gly Cys Cys
            1025                1030                1035
Thr Gly Ala Thr Ala Ala Cys Thr Gly Ala Cys Ala Thr Gly Ala
            1040                1045                1050
Thr Gly Gly Cys Cys Ala Ala Gly Thr Cys Cys Ala Ala Cys Ala
            1055                1060                1065
Gly Cys Cys Cys Cys Thr Thr Cys Gly Ala Cys Thr Thr Cys Thr
            1070                1075                1080
Thr Thr Gly Thr Gly Ala Cys Ala Cys Cys Ala Cys Cys Gly
            1085                1090                1095
Gly Gly Cys Ala Gly Ala Cys Thr Gly Thr Gly Gly Ala Ala Ala
            1100                1105                1110
Thr Gly Thr Cys Cys Cys Cys Thr Thr Thr Cys Thr Ala Thr Gly
            1115                1120                1125
Ala Cys Gly Gly Gly Ala Ala Ala Ala Ala Thr Ala Ala Gly Gly
            1130                1135                1140
Ala Ala Ala Cys Cys Thr Thr Cys Cys Ala Thr Gly Ala Gly Cys
            1145                1150                1155
Gly Gly Gly Cys Ala Gly Ala Cys Thr Cys Cys Thr Thr Cys Cys
            1160                1165                1170
Ala Cys Gly Thr Gly Ala Gly Ala Ala Cys Thr Ala Ala Cys Thr
            1175                1180                1185
Ala Cys Ala Ala Gly Ala Thr Ala Gly Thr Gly Gly Ala Cys Thr
            1190                1195                1200
Ala Cys Gly Ala Cys Ala Ala Cys Cys Gly Ala Gly Gly Gly Ala
            1205                1210                1215
Cys Gly Ala Ala Cys Cys Gly Cys Ala Ala Gly Gly Cys Gly
            1220                1225                1230
Ala Ala Cys Gly Cys Cys Gly Ala Gly Cys Cys Thr Thr Cys Cys
            1235                1240                1245
Thr Gly Gly Ala Cys Ala Ala Gly Gly Gly Cys Ala Cys Thr Thr
            1250                1255                1260
Ala Cys Ala Cys Gly Cys Thr Ala Thr Cys Thr Thr Gly Gly Ala
            1265                1270                1275
Ala Gly Cys Thr Cys Gly Ala Gly Ala Ala Cys Ala Gly Gly Ala
            1280                1285                1290
Cys Ala Gly Cys Cys Thr Ala Cys Thr Gly Cys Cys Cys Gly Cys
            1295                1300                1305
Thr Thr Cys Ala Ala Cys Ala Cys Thr Gly Gly Cys Ala Ala Ala
            1310                1315                1320
Cys Cys Thr Thr Thr Gly Ala Cys Thr Cys Gly Ala Cys Cys Ala
            1325                1330                1335
Thr Cys Gly Cys Cys Ala Cys Ala Gly Ala Ala Ala Cys Ala Gly
            1340                1345                1350
Gly Gly Ala Ala Gly Thr Cys Ala Ala Thr Ala Cys Ala Thr Thr
            1355                1360                1365
```

-continued

Thr Thr Gly Thr Gly Ala Cys Thr Gly Ala Cys Gly Ala Gly Gly
1370 1375 1380

Gly Cys Ala Cys Cys Thr Cys Thr Ala Gly Cys Thr Thr Cys Gly
1385 1390 1395

Thr Gly Ala Cys Cys Ala Ala Cys Ala Cys Ala Ala Cys Cys Gly
1400 1405 1410

Thr Gly Gly Gly Cys Ala Thr Ala Gly Ala Gly Cys Thr Cys Cys
1415 1420 1425

Cys Gly Gly Ala Cys Gly Cys Cys Thr Thr Cys Ala Ala Gly Thr
1430 1435 1440

Gly Cys Ala Thr Cys Gly Ala Ala Gly Ala Gly Cys Ala Gly Gly
1445 1450 1455

Thr Gly Ala Ala Cys Ala Ala Gly Ala Cys Cys Ala Thr Gly Cys
1460 1465 1470

Ala Thr Gly Ala Gly Ala Ala Gly Thr Ala Cys Gly Ala Gly Gly
1475 1480 1485

Cys Cys Gly Thr Cys Cys Ala Gly Gly Ala Thr Cys Gly Thr Thr
1490 1495 1500

Ala Cys Ala Cys Gly Ala Ala Gly Gly Gly Cys Cys Ala Gly Gly
1505 1510 1515

Ala Ala Gly Cys Cys Ala Thr Thr Ala Cys Ala Thr Ala Thr Thr
1520 1525 1530

Thr Thr Ala Thr Ala Ala Cys Gly Ala Gly Cys Gly Gly Ala Gly
1535 1540 1545

Gly Ala Thr Thr Gly Thr Thr Ala Thr Thr Ala Gly Cys Thr Thr
1550 1555 1560

Gly Gly Cys Thr Ala Cys Cys Thr Cys Thr Gly Ala Cys Cys Cys
1565 1570 1575

Cys Gly Cys Gly Cys Thr Cys Gly Thr Thr Gly Gly Cys Cys Ala
1580 1585 1590

Cys Cys Gly Thr Cys Ala Ala Gly Ala Ala Cys Cys Thr Gly Ala
1595 1600 1605

Cys Gly Gly Ala Gly Cys Thr Thr Ala Cys Cys Ala Cys Thr Cys
1610 1615 1620

Cys Gly Ala Cys Thr Thr Cys Cys Thr Cys Ala Cys Cys Cys Cys
1625 1630 1635

Cys Cys Ala Gly Cys Ala Gly Thr Cys Cys Ala Thr Cys Gly Cys
1640 1645 1650

Cys Cys Cys Cys Ala Gly Cys Cys Cys Cys Ala Thr Cys Cys Gly
1655 1660 1665

Cys Gly Gly Cys Cys Cys Gly Cys Gly Gly Gly Ala Gly Cys Ala
1670 1675 1680

Cys Cys Cys Cys Cys Gly Cys Cys Gly Cys Cys Gly Thr Thr Cys
1685 1690 1695

Thr Gly Ala Gly Gly Cys Gly Thr Cys Gly Gly Ala Gly Gly Cys
1700 1705 1710

Gly Gly Gly Ala Thr Gly Cys Gly Gly Gly Gly Ala Ala Cys Gly
1715 1720 1725

Cys Cys Ala Cys Cys Ala Cys Ala Cys Cys Gly Gly Thr Gly Cys
1730 1735 1740

Cys Cys Cys Cys Cys Ala Cys Gly Gly Cys Cys Cys Cys Cys Gly
1745 1750 1755

-continued

```
Gly Gly  Ala Ala Gly Thr Cys  Cys Cys Thr Gly Gly  Gly Cys Ala
    1760                 1765                 1770

Cys Cys  Cys Thr Cys Ala Ala  Cys Ala Ala Thr Cys  Cys Cys Gly
    1775                 1780                 1785

Cys Cys  Ala Cys Cys Gly Thr  Cys Cys Ala Gly Ala  Thr Cys Cys
    1790                 1795                 1800

Ala Ala  Thr Thr Thr Gly Cys  Cys Thr Ala Cys Gly  Ala Cys Thr
    1805                 1810                 1815

Cys Cys  Cys Thr Gly Cys Gly  Cys Cys Gly Cys Cys  Ala Gly Ala
    1820                 1825                 1830

Thr Cys  Ala Ala Cys Cys Gly  Cys Ala Thr Gly Cys  Thr Gly Gly
    1835                 1840                 1845

Gly Ala  Gly Ala Cys Cys Thr  Thr Gly Cys Gly Cys  Gly Gly Gly
    1850                 1855                 1860

Cys Cys  Thr Gly Gly Thr Gly  Cys Cys Thr Gly Gly  Ala Gly Cys
    1865                 1870                 1875

Ala Gly  Ala Ala Gly Ala Gly  Gly Cys Ala Gly Ala  Ala Cys Ala
    1880                 1885                 1890

Thr Gly  Gly Thr Gly Cys Thr  Gly Ala Gly Ala Gly  Ala Ala Cys
    1895                 1900                 1905

Thr Ala  Ala Cys Cys Ala Ala  Gly Ala Thr Thr Ala  Ala Thr Cys
    1910                 1915                 1920

Cys Ala  Ala Cys Cys Ala Cys  Cys Gly Thr Cys Ala  Thr Gly Thr
    1925                 1930                 1935

Cys Cys  Ala Gly Cys Ala Thr  Cys Thr Ala Cys Gly  Gly Thr Ala
    1940                 1945                 1950

Ala Gly  Gly Cys Gly Gly Thr  Gly Gly Cys Gly Gly  Cys Cys Ala
    1955                 1960                 1965

Ala Gly  Cys Gly Cys Cys Thr  Gly Gly Gly Gly Gly  Ala Thr Gly
    1970                 1975                 1980

Thr Cys  Ala Thr Cys Thr Cys  Ala Gly Thr Cys Thr  Cys Cys Cys
    1985                 1990                 1995

Ala Gly  Thr Gly Cys Gly Thr  Gly Cys Cys Cys Gly  Thr Thr Ala
    2000                 2005                 2010

Ala Cys  Cys Ala Gly Gly Cys  Cys Ala Cys Cys Gly  Thr Cys Ala
    2015                 2020                 2025

Cys Cys  Cys Thr Gly Cys Gly  Cys Ala Ala Gly Ala  Gly Cys Ala
    2030                 2035                 2040

Thr Gly  Ala Gly Gly Gly Thr  Cys Cys Cys Thr Gly  Gly Cys Thr
    2045                 2050                 2055

Cys Cys  Gly Ala Gly Ala Cys  Cys Ala Thr Gly Thr  Gly Cys Thr
    2060                 2065                 2070

Ala Cys  Thr Cys Gly Cys Gly  Cys Cys Cys Cys Cys  Thr Gly Gly
    2075                 2080                 2085

Thr Gly  Thr Cys Cys Thr Thr  Cys Ala Gly Cys Thr  Thr Thr Ala
    2090                 2095                 2100

Thr Cys  Ala Ala Cys Gly Ala  Cys Ala Cys Cys Ala  Ala Gly Ala
    2105                 2110                 2115

Cys Cys  Thr Ala Cys Gly Ala  Gly Gly Gly Ala Cys  Ala Gly Cys
    2120                 2125                 2130

Thr Gly  Gly Gly Cys Ala Cys  Cys Gly Ala Cys Ala  Ala Cys Gly
    2135                 2140                 2145

Ala Gly  Ala Thr Cys Thr Thr  Cys Cys Thr Cys Ala  Cys Ala Ala
```

```
    2150                2155                2160

Ala Ala  Ala Ala Gly Ala Thr  Gly Ala Cys Gly Gly  Ala Gly Gly
    2165                2170                2175

Thr Gly  Thr Gly Cys Cys Ala  Gly Gly Cys Gly Ala  Cys Cys Ala
    2180                2185                2190

Gly Cys  Cys Ala Gly Thr Ala  Cys Thr Ala Cys Thr  Thr Cys Cys
    2195                2200                2205

Ala Gly  Thr Cys Cys Gly Gly  Cys Ala Ala Cys Gly  Ala Gly Ala
    2210                2215                2220

Thr Cys  Cys Ala Cys Gly Thr  Cys Thr Ala Cys Ala  Ala Cys Gly
    2225                2230                2235

Ala Cys  Thr Ala Cys Cys Ala  Cys Cys Ala Cys Thr  Thr Thr Ala
    2240                2245                2250

Ala Ala  Ala Cys Cys Ala Thr  Cys Gly Ala Gly Cys  Thr Gly Gly
    2255                2260                2265

Ala Cys  Gly Gly Cys Ala Thr  Thr Gly Cys Cys Ala  Cys Cys Cys
    2270                2275                2280

Thr Gly  Cys Ala Gly Ala Cys  Cys Thr Thr Cys Ala  Thr Cys Thr
    2285                2290                2295

Cys Ala  Cys Thr Ala Ala Ala  Cys Ala Cys Cys Thr  Cys Cys Cys
    2300                2305                2310

Thr Cys  Ala Thr Cys Gly Ala  Gly Ala Ala Cys Ala  Thr Thr Gly
    2315                2320                2325

Ala Cys  Thr Thr Thr Gly Cys  Cys Thr Cys Cys Cys  Thr Gly Gly
    2330                2335                2340

Ala Gly  Cys Thr Gly Thr Ala  Cys Thr Cys Ala Cys  Gly Gly Gly
    2345                2350                2355

Ala Cys  Gly Ala Ala Cys Ala  Gly Cys Gly Thr Gly  Cys Cys Thr
    2360                2365                2370

Cys Cys  Ala Ala Cys Gly Thr  Cys Thr Thr Thr Gly  Ala Cys Cys
    2375                2380                2385

Thr Gly  Gly Ala Gly Gly Gly  Cys Ala Thr Cys Thr  Thr Cys Cys
    2390                2395                2400

Gly Gly  Gly Ala Gly Thr Ala  Cys Ala Ala Cys Thr  Thr Cys Cys
    2405                2410                2415

Ala Gly  Gly Cys Gly Cys Ala  Ala Ala Ala Cys Ala  Thr Cys Gly
    2420                2425                2430

Cys Cys  Gly Gly Cys Cys Thr  Gly Cys Gly Gly Ala  Ala Gly Gly
    2435                2440                2445

Ala Thr  Thr Thr Gly Gly Ala  Cys Ala Ala Thr Gly  Cys Ala Gly
    2450                2455                2460

Thr Gly  Thr Cys Ala Ala Ala  Cys Gly Gly Ala Ala  Gly Ala Ala
    2465                2470                2475

Ala Thr  Cys Ala Ala Thr Thr  Cys Gly Thr Gly Gly  Ala Cys Gly
    2480                2485                2490

Gly Cys  Cys Thr Gly Gly Gly  Gly Gly Ala Ala Cys  Thr Thr Ala
    2495                2500                2505

Thr Gly  Gly Ala Cys Ala Gly  Thr Cys Thr Gly Gly  Gly Thr Ala
    2510                2515                2520

Gly Cys  Gly Thr Gly Gly Gly  Thr Cys Ala Gly Thr  Cys Cys Ala
    2525                2530                2535

Thr Cys  Ala Cys Cys Ala Ala  Cys Cys Thr Ala Gly  Thr Cys Ala
    2540                2545                2550
```

-continued

Gly Cys Ala Cys Gly Gly Thr Gly Gly Gly Gly Gly Thr Thr
2555                2560                2565

Thr Gly Thr Thr Thr Ala Gly Cys Ala Gly Cys Cys Thr Gly Gly
2570                2575                2580

Thr Cys Thr Cys Thr Gly Gly Thr Thr Thr Cys Ala Thr Cys Thr
2585                2590                2595

Cys Cys Thr Thr Cys Thr Cys Ala Ala Ala Ala Cys Cys
2600                2605                2610

Cys Cys Thr Thr Cys Gly Gly Cys Gly Gly Cys Ala Thr Gly Cys
2615                2620                2625

Thr Cys Ala Thr Thr Cys Thr Gly Gly Thr Cys Cys Thr Gly Gly
2630                2635                2640

Thr Gly Gly Cys Gly Gly Gly Gly Gly Thr Gly Gly Thr Gly Ala
2645                2650                2655

Thr Cys Cys Thr Gly Gly Thr Thr Ala Thr Thr Cys Cys Cys
2660                2665                2670

Thr Cys Ala Cys Gly Ala Gly Gly Cys Gly Cys Ala Cys Gly Cys
2675                2680                2685

Gly Cys Cys Ala Gly Ala Thr Gly Thr Cys Gly Cys Ala Gly Cys
2690                2695                2700

Ala Gly Cys Cys Gly Gly Thr Gly Cys Ala Gly Ala Thr Gly Cys
2705                2710                2715

Thr Cys Thr Ala Cys Cys Cys Gly Gly Ala Thr Cys Gly
2720                2725                2730

Ala Cys Gly Ala Gly Cys Thr Cys Gly Cys Thr Cys Ala Gly Cys
2735                2740                2745

Ala Ala Cys Ala Thr Gly Cys Cys Thr Cys Thr Gly Gly Thr Gly
2750                2755                2760

Ala Gly Gly Gly Thr Cys Cys Ala Gly Gly Cys Ala Thr Thr Ala
2765                2770                2775

Ala Thr Cys Cys Cys Ala Thr Thr Ala Gly Thr Ala Ala Gly Ala
2780                2785                2790

Cys Ala Gly Ala Ala Thr Thr Ala Cys Ala Ala Gly Cys Cys Ala
2795                2800                2805

Thr Cys Ala Thr Gly Thr Thr Ala Gly Cys Gly Cys Thr Gly Cys
2810                2815                2820

Ala Thr Gly Ala Gly Cys Ala Ala Ala Cys Cys Ala Gly Gly
2825                2830                2835

Ala Gly Cys Ala Ala Ala Gly Ala Gly Ala Gly Cys Ala Gly
2840                2845                2850

Cys Thr Cys Ala Gly Ala Gly Gly Gly Cys Gly Cys Cys Gly
2855                2860                2865

Gly Ala Cys Cys Cys Thr Cys Ala Gly Thr Gly Gly Cys Cys Ala
2870                2875                2880

Gly Cys Ala Gly Ala Gly Cys Ala Thr Thr Gly Cys Ala Gly Gly
2885                2890                2895

Cys Ala Gly Cys Cys Ala Gly Gly Ala Cys Cys Gly Thr Thr
2900                2905                2910

Thr Thr Cys Cys Ala Gly Gly Cys Cys Thr Ala Cys Gly Cys Ala
2915                2920                2925

Gly Ala Ala Gly Ala Cys Gly Cys Thr Ala Thr Cys Ala Cys Gly
2930                2935                2940

```
Ala Thr Cys Cys Ala Gly Ala Gly Cys Gly Cys Cys Gly
    2945                2950                2955

Cys Cys Gly Cys Ala Cys Thr Gly Cys Thr Thr Gly Gly Gly
    2960                2965                2970

Ala Gly Gly Cys Ala Gly Ala Gly Ala Cys Thr Gly Ala Gly Thr
    2975                2980                2985

Thr Thr Thr Ala Ala Ala Thr Gly Cys Ala Gly Ala Thr Gly Ala
    2990                2995                3000

Gly Ala Gly Gly Cys Gly Gly Ala Gly Gly Thr Ala Thr Cys Cys
    3005                3010                3015

Cys Cys Ala Ala Thr Ala Gly Cys Ala Ala Thr Thr Thr Gly Thr
    3020                3025                3030

Gly Thr Gly Cys Ala Ala Ala Thr Thr Cys Thr Ala Thr Gly Cys
    3035                3040                3045

Cys Cys Thr Gly Gly Cys Thr Cys Ala Cys Ala Ala Ala Thr Ala
    3050                3055                3060

Cys Cys Ala Cys Thr Gly Ala Gly Ala Thr Cys Thr Thr Thr Thr
    3065                3070                3075

Thr Cys Cys Cys Thr Cys Thr Gly Cys Cys Ala Ala Ala Ala Ala
    3080                3085                3090

Thr Thr Ala Thr Gly Gly Gly Gly Ala Cys Ala Thr Cys Ala Thr
    3095                3100                3105

Gly Ala Ala Gly Cys Cys Cys Cys Thr Thr Gly Ala Gly Cys Ala
    3110                3115                3120

Thr Cys Thr Gly Ala Cys Thr Thr Cys Thr Gly Gly Cys Thr Ala
    3125                3130                3135

Ala Thr Ala Ala Ala Gly Gly Ala Ala Ala Thr Thr Thr Ala Thr
    3140                3145                3150

Thr Thr Thr Cys Ala Thr Thr Gly Cys Ala Ala Thr Ala Gly Thr
    3155                3160                3165

Gly Thr Gly Thr Thr Gly Gly Ala Ala Thr Thr Thr Thr Thr Thr
    3170                3175                3180

Gly Thr Gly Thr Cys Thr Cys Thr Cys Ala Cys Thr Cys Gly Gly
    3185                3190                3195

Ala Ala Gly Gly Ala Cys Ala Thr Ala Thr Gly Gly Gly Ala Gly
    3200                3205                3210

Gly Gly Cys Ala Ala Ala Thr Cys Ala Thr Thr Thr Ala Ala Ala
    3215                3220                3225

Ala Cys Ala Thr Cys Ala Gly Ala Ala Thr Gly Ala Gly Thr Ala
    3230                3235                3240

Thr Thr Thr Gly Gly Thr Thr Thr Ala Gly Ala Gly Thr Thr Thr
    3245                3250                3255

Gly Gly Cys Ala Ala Cys Ala Thr Ala Thr Gly Cys Cys Cys Ala
    3260                3265                3270

Thr Ala Thr Gly Cys Thr Gly Gly Cys Thr Gly Cys Cys Ala Thr
    3275                3280                3285

Gly Ala Ala Cys Ala Ala Ala Gly Gly Thr Thr Gly Gly Cys Thr
    3290                3295                3300

Ala Thr Ala Ala Ala Gly Ala Gly Gly Thr Cys Ala Thr Cys Ala
    3305                3310                3315

Gly Thr Ala Thr Ala Thr Gly Ala Ala Ala Cys Ala Gly Cys Cys
    3320                3325                3330

Cys Cys Cys Thr Gly Cys Thr Gly Thr Cys Cys Ala Thr Thr Cys
```

-continued

Cys Thr Thr Ala Thr Thr Cys Cys Ala Thr Ala Gly Ala Ala Ala
3335          3340          3345
                3350              3355              3360

Ala Gly Cys Cys Thr Thr Gly Ala Cys Thr Thr Gly Ala Gly Gly
3365              3370              3375

Thr Thr Ala Gly Ala Thr Thr Thr Thr Thr Thr Thr Ala Thr
3380              3385              3390

Ala Thr Thr Thr Thr Gly Thr Thr Thr Gly Thr Gly Thr Thr
3395              3400              3405

Ala Thr Thr Thr Thr Thr Thr Cys Thr Thr Thr Ala Ala Cys
3410              3415              3420

Ala Thr Cys Cys Cys Thr Ala Ala Ala Thr Thr Thr Thr Cys
3425              3430              3435

Cys Thr Thr Ala Cys Ala Thr Gly Thr Thr Thr Ala Cys Thr
3440              3445              3450

Ala Gly Cys Cys Ala Gly Ala Thr Thr Thr Thr Cys Cys Thr
3455              3460              3465

Cys Cys Thr Cys Thr Cys Cys Thr Gly Ala Cys Thr Ala Cys Thr
3470              3475              3480

Cys Cys Cys Ala Gly Thr Cys Ala Thr Ala Gly Cys Thr Gly Thr
3485              3490              3495

Cys Cys Cys Thr Cys Thr Thr Cys Thr Cys Thr Thr Ala Thr Gly
3500              3505              3510

Gly Ala Gly Ala Thr Cys Cys Thr Cys Gly Ala Cys Cys Thr
3515              3520              3525

Gly Cys Ala Gly Cys Cys Cys Ala Ala Gly Cys Thr Thr Gly Gly
3530              3535              3540

Cys Gly Thr Ala Ala Thr Cys Ala Thr Gly Gly Thr Cys Ala Thr
3545              3550              3555

Ala Gly Cys Thr Gly Thr Thr Thr Cys Cys Thr Gly Thr Gly Thr
3560              3565              3570

Gly Ala Ala Ala Thr Thr Gly Thr Thr Ala Thr Cys Cys Gly Cys
3575              3580              3585

Thr Cys Ala Cys Ala Ala Thr Thr Cys Cys Ala Cys Ala Cys Ala
3590              3595              3600

Ala Cys Ala Thr Ala Cys Gly Ala Gly Cys Cys Gly Gly Ala Ala
3605              3610              3615

Gly Cys Ala Thr Ala Ala Ala Gly Thr Gly Thr Ala Ala Ala Gly
3620              3625              3630

Cys Cys Thr Gly Gly Gly Gly Thr Gly Cys Cys Thr Ala Ala Thr
3635              3640              3645

Gly Ala Gly Thr Gly Ala Gly Cys Thr Ala Ala Cys Thr Cys Ala
3650              3655              3660

Cys Ala Thr Thr Ala Ala Thr Thr Gly Cys Gly Thr Thr Gly Cys
3665              3670              3675

Gly Cys Thr Cys Ala Cys Thr Gly Cys Cys Cys Gly Cys Thr Thr
3680              3685              3690

Thr Cys Cys Ala Gly Thr Cys Gly Gly Gly Ala Ala Ala Cys Cys
3695              3700              3705

Thr Gly Thr Cys Gly Thr Gly Cys Cys Ala Gly Cys Thr Gly Cys
3710              3715              3720

Ala Thr Thr Ala Ala Thr Gly Ala Ala Thr Cys Gly Gly Cys Cys
3725              3730              3735

```
Ala Ala Cys Gly Cys Gly Cys Gly Gly Gly Ala Gly Ala Gly
    3740            3745                3750

Gly Cys Gly Gly Thr Thr Thr Gly Cys Gly Thr Ala Thr Thr Gly
    3755            3760                3765

Gly Gly Cys Gly Cys Thr Cys Thr Thr Cys Cys Gly Cys Thr Thr
    3770            3775                3780

Cys Cys Thr Cys Gly Cys Thr Cys Ala Cys Thr Gly Ala Cys Thr
    3785            3790                3795

Cys Gly Cys Thr Gly Cys Gly Cys Thr Cys Gly Gly Thr Cys Gly
    3800            3805                3810

Thr Thr Cys Gly Gly Cys Thr Gly Cys Gly Gly Cys Gly Ala Gly
    3815            3820                3825

Cys Gly Gly Thr Ala Thr Cys Ala Gly Cys Thr Cys Ala Cys Thr
    3830            3835                3840

Cys Ala Ala Ala Gly Gly Cys Gly Gly Thr Ala Ala Thr Ala Cys
    3845            3850                3855

Gly Gly Thr Thr Ala Thr Cys Cys Ala Cys Ala Gly Ala Ala Thr
    3860            3865                3870

Cys Ala Gly Gly Gly Gly Ala Thr Ala Ala Cys Gly Cys Ala Gly
    3875            3880                3885

Gly Ala Ala Ala Gly Ala Ala Cys Ala Thr Gly Thr Gly Ala Gly
    3890            3895                3900

Cys Ala Ala Ala Ala Gly Gly Cys Cys Ala Gly Cys Ala Ala Ala
    3905            3910                3915

Ala Gly Gly Cys Cys Ala Gly Gly Ala Ala Cys Cys Gly Thr Ala
    3920            3925                3930

Ala Ala Ala Ala Gly Gly Cys Cys Gly Cys Gly Thr Thr Gly Cys
    3935            3940                3945

Thr Gly Gly Cys Gly Thr Thr Thr Thr Thr Cys Cys Ala Thr Ala
    3950            3955                3960

Gly Gly Cys Thr Cys Cys Gly Cys Cys Cys Cys Cys Cys Thr Gly
    3965            3970                3975

Ala Cys Gly Ala Gly Cys Ala Thr Cys Ala Cys Ala Ala Ala Ala
    3980            3985                3990

Ala Thr Cys Gly Ala Cys Gly Cys Thr Cys Ala Ala Gly Thr Cys
    3995            4000                4005

Ala Gly Ala Gly Gly Thr Gly Gly Cys Gly Ala Ala Ala Cys Cys
    4010            4015                4020

Cys Gly Ala Cys Ala Gly Gly Ala Cys Thr Ala Thr Ala Ala Ala
    4025            4030                4035

Gly Ala Thr Ala Cys Cys Ala Gly Gly Cys Gly Thr Thr Thr Cys
    4040            4045                4050

Cys Cys Cys Cys Thr Gly Gly Ala Ala Gly Cys Thr Cys Cys Cys
    4055            4060                4065

Thr Cys Gly Thr Gly Cys Gly Cys Thr Cys Thr Cys Cys Thr Gly
    4070            4075                4080

Thr Thr Cys Cys Gly Ala Cys Cys Cys Thr Gly Cys Cys Gly Cys
    4085            4090                4095

Thr Thr Ala Cys Cys Gly Gly Ala Thr Ala Cys Cys Thr Gly Thr
    4100            4105                4110

Cys Cys Gly Cys Cys Thr Thr Thr Cys Thr Cys Cys Thr Thr
    4115            4120                4125
```

```
Cys Gly Gly Gly Ala Ala Gly Cys Gly Thr Gly Cys Gly Cys
    4130            4135            4140

Thr Thr Thr Cys Thr Cys Ala Thr Ala Gly Cys Thr Cys Ala Cys
    4145            4150            4155

Gly Cys Thr Gly Thr Ala Gly Gly Thr Ala Thr Cys Thr Cys Ala
    4160            4165            4170

Gly Thr Thr Cys Gly Gly Thr Gly Thr Ala Gly Thr Cys Gly
    4175            4180            4185

Thr Thr Cys Gly Cys Thr Cys Cys Ala Ala Gly Cys Thr Gly Gly
    4190            4195            4200

Gly Cys Thr Gly Thr Gly Thr Gly Cys Ala Cys Gly Ala Ala Cys
    4205            4210            4215

Cys Cys Cys Cys Cys Gly Thr Thr Cys Ala Gly Cys Cys Cys Gly
    4220            4225            4230

Ala Cys Cys Gly Cys Thr Gly Cys Gly Cys Cys Thr Thr Ala Thr
    4235            4240            4245

Cys Cys Gly Gly Thr Ala Ala Cys Thr Ala Thr Cys Gly Thr Cys
    4250            4255            4260

Thr Thr Gly Ala Gly Thr Cys Cys Ala Ala Cys Cys Cys Gly Gly
    4265            4270            4275

Thr Ala Ala Gly Ala Cys Ala Cys Gly Ala Cys Thr Thr Ala Thr
    4280            4285            4290

Cys Gly Cys Cys Ala Cys Thr Gly Gly Cys Ala Gly Cys Ala Gly
    4295            4300            4305

Cys Cys Ala Cys Thr Gly Gly Thr Ala Ala Cys Ala Gly Gly Ala
    4310            4315            4320

Thr Thr Ala Gly Cys Ala Gly Ala Gly Cys Gly Ala Gly Gly Thr
    4325            4330            4335

Ala Thr Gly Thr Ala Gly Gly Cys Gly Gly Thr Gly Cys Thr Ala
    4340            4345            4350

Cys Ala Gly Ala Gly Thr Thr Cys Thr Thr Gly Ala Ala Gly Thr
    4355            4360            4365

Gly Gly Thr Gly Gly Cys Cys Thr Ala Ala Cys Thr Ala Cys Gly
    4370            4375            4380

Gly Cys Thr Ala Cys Ala Cys Thr Ala Gly Ala Ala Gly Ala Ala
    4385            4390            4395

Cys Ala Gly Thr Ala Thr Thr Thr Gly Gly Thr Ala Thr Cys Thr
    4400            4405            4410

Gly Cys Gly Cys Thr Cys Thr Gly Cys Thr Gly Ala Ala Gly Cys
    4415            4420            4425

Cys Ala Gly Thr Thr Ala Cys Cys Thr Thr Cys Gly Gly Ala Ala
    4430            4435            4440

Ala Ala Ala Gly Ala Gly Thr Thr Gly Gly Thr Ala Gly Cys Thr
    4445            4450            4455

Cys Thr Thr Gly Ala Thr Cys Cys Gly Gly Cys Ala Ala Ala Cys
    4460            4465            4470

Ala Ala Ala Cys Cys Ala Cys Cys Gly Cys Thr Gly Gly Thr Ala
    4475            4480            4485

Gly Cys Gly Gly Thr Gly Gly Thr Thr Thr Thr Thr Thr Thr Gly
    4490            4495            4500

Thr Thr Thr Gly Cys Ala Ala Gly Cys Ala Gly Cys Ala Gly Ala
    4505            4510            4515

Thr Thr Ala Cys Gly Cys Gly Cys Ala Gly Ala Ala Ala Ala Ala
```

```
    4520                4525                4530

Ala Ala  Gly Gly Ala Thr Cys  Thr Cys Ala Ala Gly  Ala Ala Gly
    4535                4540                4545

Ala Thr  Cys Cys Thr Thr Thr  Gly Ala Thr Cys Thr  Thr Thr Thr
    4550                4555                4560

Cys Thr  Ala Cys Gly Gly Gly  Gly Thr Cys Thr Gly  Ala Cys Gly
    4565                4570                4575

Cys Thr  Cys Ala Gly Thr Gly  Gly Ala Ala Cys Gly  Ala Ala Ala
    4580                4585                4590

Ala Cys  Thr Cys Ala Cys Gly  Thr Thr Ala Ala Gly  Gly Gly Ala
    4595                4600                4605

Thr Thr  Thr Thr Gly Gly Thr  Cys Ala Thr Gly Ala  Gly Ala Thr
    4610                4615                4620

Thr Ala  Thr Cys Ala Ala Ala  Ala Ala Gly Gly Ala  Thr Cys Thr
    4625                4630                4635

Thr Cys  Ala Cys Cys Thr Ala  Gly Ala Thr Cys Cys  Thr Thr Thr
    4640                4645                4650

Thr Ala  Ala Ala Thr Thr Ala  Ala Ala Ala Ala Thr  Gly Ala Ala
    4655                4660                4665

Gly Thr  Thr Thr Thr Ala Ala  Ala Thr Cys Ala Ala  Thr Cys Thr
    4670                4675                4680

Ala Ala  Ala Gly Thr Ala Thr  Ala Thr Ala Thr Gly  Ala Gly Thr
    4685                4690                4695

Ala Ala  Ala Cys Thr Thr Gly  Gly Thr Cys Thr Gly  Ala Cys Ala
    4700                4705                4710

Gly Thr  Thr Ala Cys Cys Ala  Ala Thr Gly Cys Thr  Thr Ala Ala
    4715                4720                4725

Thr Cys  Ala Gly Thr Gly Ala  Gly Gly Cys Ala Cys  Cys Thr Ala
    4730                4735                4740

Thr Cys  Thr Cys Ala Gly Cys  Gly Ala Thr Cys Thr  Gly Thr Cys
    4745                4750                4755

Thr Ala  Thr Thr Thr Cys Gly  Thr Thr Cys Ala Thr  Cys Cys Ala
    4760                4765                4770

Thr Ala  Gly Thr Thr Gly Cys  Cys Thr Gly Ala Cys  Thr Cys Cys
    4775                4780                4785

Cys Cys  Gly Thr Cys Gly Thr  Gly Thr Ala Gly Ala  Thr Ala Ala
    4790                4795                4800

Cys Thr  Ala Cys Gly Ala Thr  Ala Cys Gly Gly Gly  Ala Gly Gly
    4805                4810                4815

Gly Cys  Thr Thr Ala Cys Cys  Ala Thr Cys Thr Gly  Gly Cys Cys
    4820                4825                4830

Cys Cys  Ala Gly Thr Gly Cys  Thr Gly Cys Ala Ala  Thr Gly Ala
    4835                4840                4845

Thr Ala  Cys Cys Gly Cys Gly  Ala Gly Ala Cys Cys  Cys Ala Cys
    4850                4855                4860

Gly Cys  Thr Cys Ala Cys Cys  Gly Gly Cys Thr Cys  Cys Ala Gly
    4865                4870                4875

Ala Thr  Thr Thr Ala Thr Cys  Ala Gly Cys Ala Ala  Thr Ala Ala
    4880                4885                4890

Ala Cys  Cys Ala Gly Cys Cys  Ala Gly Cys Cys Gly  Gly Ala Ala
    4895                4900                4905

Gly Gly  Gly Cys Cys Gly Ala  Gly Cys Gly Cys Ala  Gly Ala Ala
    4910                4915                4920
```

-continued

Gly Thr Gly Gly Thr Cys Cys Thr Gly Cys Ala Ala Cys Thr Thr
    4925                4930                4935

Thr Ala Thr Cys Cys Gly Cys Cys Thr Cys Ala Thr Cys Cys
    4940                4945                4950

Ala Gly Thr Cys Thr Ala Thr Thr Ala Thr Thr Gly Thr Thr
    4955                4960                4965

Gly Cys Cys Gly Gly Ala Ala Gly Cys Thr Ala Gly Ala Gly
    4970                4975                4980

Thr Ala Ala Gly Thr Ala Gly Thr Thr Cys Gly Cys Ala Gly
    4985                4990                4995

Thr Thr Ala Ala Thr Ala Gly Thr Thr Thr Gly Cys Gly Cys Ala
    5000                5005                5010

Ala Cys Gly Thr Thr Gly Thr Thr Gly Cys Cys Ala Thr Thr Gly
    5015                5020                5025

Cys Thr Ala Cys Ala Gly Gly Cys Ala Thr Cys Gly Thr Gly Gly
    5030                5035                5040

Thr Gly Thr Cys Ala Cys Gly Cys Thr Cys Gly Thr Cys Gly Thr
    5045                5050                5055

Thr Thr Gly Gly Thr Ala Thr Gly Gly Cys Thr Thr Cys Ala Thr
    5060                5065                5070

Thr Cys Ala Gly Cys Thr Cys Cys Gly Gly Thr Thr Cys Cys Cys
    5075                5080                5085

Ala Ala Cys Gly Ala Thr Cys Ala Ala Gly Gly Cys Gly Ala Gly
    5090                5095                5100

Thr Thr Ala Cys Ala Thr Gly Ala Thr Cys Cys Cys Cys Cys Ala
    5105                5110                5115

Thr Gly Thr Thr Gly Thr Gly Cys Ala Ala Ala Ala Ala Ala Gly
    5120                5125                5130

Cys Gly Gly Thr Thr Ala Gly Cys Thr Cys Cys Thr Thr Cys Gly
    5135                5140                5145

Gly Thr Cys Cys Thr Cys Cys Gly Ala Thr Cys Gly Thr Thr Gly
    5150                5155                5160

Thr Cys Ala Gly Ala Ala Gly Thr Ala Ala Gly Thr Thr Gly Gly
    5165                5170                5175

Cys Cys Gly Cys Ala Gly Thr Gly Thr Thr Ala Thr Cys Ala Cys
    5180                5185                5190

Thr Cys Ala Thr Gly Gly Thr Thr Ala Thr Gly Gly Cys Ala Gly
    5195                5200                5205

Cys Ala Cys Thr Gly Cys Ala Thr Ala Ala Thr Thr Cys Thr Cys
    5210                5215                5220

Thr Thr Ala Cys Thr Gly Thr Cys Ala Thr Gly Cys Cys Ala Thr
    5225                5230                5235

Cys Cys Gly Thr Ala Ala Gly Ala Thr Gly Cys Thr Thr Thr Thr
    5240                5245                5250

Cys Thr Gly Thr Gly Ala Cys Thr Gly Gly Thr Gly Ala Gly Thr
    5255                5260                5265

Ala Cys Thr Cys Ala Ala Cys Ala Ala Gly Thr Cys Ala Thr
    5270                5275                5280

Thr Cys Thr Gly Ala Gly Ala Ala Thr Ala Gly Thr Gly Thr Ala
    5285                5290                5295

Thr Gly Cys Gly Gly Cys Gly Ala Cys Cys Gly Ala Gly Thr Thr
    5300                5305                5310

```
Gly Cys Thr Cys Thr Thr Gly Cys Cys Cys Gly Gly Cys Gly Thr
    5315                5320                5325

Cys Ala Ala Thr Ala Cys Gly Gly Gly Ala Thr Ala Ala Thr Ala
    5330                5335                5340

Cys Cys Gly Cys Gly Cys Cys Ala Cys Ala Thr Ala Gly Cys Ala
    5345                5350                5355

Gly Ala Ala Cys Thr Thr Thr Ala Ala Ala Ala Gly Thr Gly Cys
    5360                5365                5370

Thr Cys Ala Thr Cys Ala Thr Thr Gly Gly Ala Ala Ala Ala Cys
    5375                5380                5385

Gly Thr Thr Cys Thr Thr Cys Gly Gly Gly Gly Cys Gly Ala Ala
    5390                5395                5400

Ala Ala Cys Thr Cys Thr Cys Ala Ala Gly Gly Ala Thr Cys Thr
    5405                5410                5415

Thr Ala Cys Cys Gly Cys Thr Gly Thr Thr Gly Ala Gly Ala Thr
    5420                5425                5430

Cys Cys Ala Gly Thr Thr Cys Gly Ala Thr Gly Thr Ala Ala Cys
    5435                5440                5445

Cys Cys Ala Cys Thr Cys Gly Thr Gly Cys Ala Cys Cys Cys Ala
    5450                5455                5460

Ala Cys Thr Gly Ala Thr Cys Thr Thr Cys Ala Gly Cys Ala Thr
    5465                5470                5475

Cys Thr Thr Thr Thr Ala Cys Thr Thr Thr Cys Ala Cys Cys Ala
    5480                5485                5490

Gly Cys Gly Thr Thr Thr Cys Thr Gly Gly Gly Thr Gly Ala Gly
    5495                5500                5505

Cys Ala Ala Ala Ala Ala Cys Ala Gly Gly Ala Ala Gly Gly Cys
    5510                5515                5520

Ala Ala Ala Ala Thr Gly Cys Cys Gly Cys Ala Ala Ala Ala Ala
    5525                5530                5535

Ala Gly Gly Gly Ala Ala Thr Ala Ala Gly Gly Gly Cys Gly Ala
    5540                5545                5550

Cys Ala Cys Gly Gly Ala Ala Ala Thr Gly Thr Thr Gly Ala Ala
    5555                5560                5565

Thr Ala Cys Thr Cys Ala Thr Ala Cys Thr Cys Thr Thr Cys Cys
    5570                5575                5580

Thr Thr Thr Thr Thr Cys Ala Ala Thr Ala Thr Thr Ala Thr Thr
    5585                5590                5595

Gly Ala Ala Gly Cys Ala Thr Thr Thr Ala Thr Cys Ala Gly Gly
    5600                5605                5610

Gly Thr Thr Ala Thr Thr Gly Thr Cys Thr Cys Ala Thr Gly Ala
    5615                5620                5625

Gly Cys Gly Gly Ala Thr Ala Cys Ala Thr Ala Thr Thr Thr Gly
    5630                5635                5640

Ala Ala Thr Gly Thr Ala Thr Thr Thr Ala Gly Ala Ala Ala Ala
    5645                5650                5655

Ala Thr Ala Ala Ala Cys Ala Ala Thr Ala Gly Gly Gly Gly Thr
    5660                5665                5670

Thr Thr Cys Cys Gly Cys Gly Cys Ala Cys Ala Thr Thr Thr Cys
    5675                5680                5685

Cys Cys Cys Gly Ala Ala Ala Ala Gly Thr Gly Cys Cys Ala Cys
    5690                5695                5700

Cys Thr Gly Ala Cys Gly Thr Cys Thr Ala Ala Gly Ala Ala Ala
```

-continued

```
    5705                5710                5715

Cys Cys  Ala Thr Thr Ala Thr  Thr Ala Thr Cys Ala  Thr Gly Ala
    5720                5725                5730

Cys Ala  Thr Thr Ala Ala Cys  Cys Thr Ala Thr Ala  Ala Ala Ala
    5735                5740                5745

Ala Thr  Ala Gly Gly Cys Gly  Thr Ala Thr Cys Ala  Cys Gly Ala
    5750                5755                5760

Gly Gly  Cys Cys Cys Thr Thr  Thr Cys Gly Thr Cys
    5765                5770                5775
```

VIRUS-LIKE PARTICLE COMPOSITIONS AND VACCINES AGAINST EPSTEIN-BARR VIRUS INFECTION AND DISEASE

This application claims priority to U.S. provisional Application Ser. No. 62/134,785, filed on Mar. 18, 2015, which is herein incorporated by reference in its entirety.

A sequence listing has been submitted in an ASCII text file named "18176.txt" created on Aug. 8, 2019, consisting of 417 KB, the entire content of which is herein incorporated by reference.

FIELD OF THE INVENTION

The present invention relates to prophylactic and/or therapeutic vaccines that contain Newcastle disease virus (NDV) virus-like particles (VLPs) comprising one or more Epstein-Barr Virus (EBV) antigens. The invention's prophylactic and/or therapeutic vaccines are useful for preventing and/or treating infection with EBV and/or disease associated Epstein-Barr Virus, such as cancer.

BACKGROUND OF THE INVENTION

Epstein-Barr virus (EBV), an oncogenic gammaherpesvirus, causes acute infectious mononucleosis (AIM) and is linked to the development of several human malignancies. Approaches for EBV vaccine development are limited due in part to the oncogenic potential of the EBV genome and lack of animal models to test vaccine candidates. The EBV envelope glycoprotein, gp350/220, has been proposed as a vaccine antigen. However, in small Phase I/II clinical trials, vaccination with either vector constructs expressing gp350/220, or with the purified recombinant gp350 protein, did not prevent EBV infection although it did reduce the incidence of acute infectious mononucleosis (AIM) in young adults. Importantly, recombinant EBVΔgp350/220 can infect both epithelial and primary B cells in vitro. While previous studies indicate that immunity to gp350/220 can limit infection, the poor success of using gp350/220 as a single vaccine antigen calls for innovative approaches utilizing multiple EBV proteins.

At least 4 EBVgp350/220 vaccine candidates have been tested in "clinical trials" such as Vaccinia vector expressing gp350/220 (Gu et al., 1995 (Phase I-Chinese population, EBV naïve 1-3 years old children), and Recombinant gp350 in CHO cells (Non-splicing variant) (3 dose regimen adjuvanted with ASO4) (Jackman et al. 1999; Moutchen et al, 2007. (Phase I/II) Safety and Immunogenicity in aged 18-37 years old EBV naïve Belgians; Sokal et al., 2007. Phase I randomized, double-blind placebo control in aged 16-25 years EBV naïve Belgians; Rees et al., 2009. Phase I chronic kidney disease kids awaiting organ transplants (UK)). However, none of these vaccine candidates achieved complete blockage of EBV infection.

Notably, EBNA1, LMP2 and gp350/220 antigens have been developed and independently tested in various clinical trials as vaccine candidates against EBV infection and EBV+ cells with promising results.

Candidate therapeutic vaccines in clinical trials include MVA-vector expressing EBNA-1 and LMP1 or LMP2 (Taylor et al, 2004 construction of the MVA vector expressing EBNA1 and or LMP2; Hui et al., 2013-EBNA1-LMP2 (Phase I targeting NPC patients in China); Taylor et al 2014 EBNA1-LMP2 (A Phase I Trial in UK Patients with EBV-Positive Cancer), as well as Adoptive transfer PBMCs for treatment of PTLDs and NPCs (Louis, et al., 2009, 2010, Heslop et al. 1996 T cells adoptive transfer; and Chia et al., 2012 Phase I targeting NPC patients in China. Dendritic cells are transduced with adenovirus vector expressing ΔLMP1-LMP2). A recent phase I clinical trial of recombinant modified vaccinia Ankara (MVA) vector encoding deletion of Gly-Ala regions from the EBNA1 sequence fused to LMP2 as a vaccine candidate elicited a robust EBV-specific CD4+ and CD8+ T cell response in humans. However, the strategy used to deliver these two important EBV antigens, known for their oncogenic potential, may pose major health risks, particularly in immunosuppressed individuals. Furthermore, these vaccine candidates cannot generate neutralizing antibodies to eliminate reactivation or new EBV infections. There is also a risk of vaccine tolerance since the protein is constantly produced.

Thus, there is an urgent need for EBV vaccines that are safe, prevent EBV infection and/or limit EBV disease symptoms.

BRIEF DESCRIPTION OF THE DRAWINGS

FIG. 1A-E. Schematic diagram showing construction and assembly of NDV NP as a carrier of EGFP, truncated EBNA1, LMP2 (full length) and/or tEBNA1-LMP2 incorporated into either gp350/220 or gH/gL VLPs. (FIG. 1A) Construction of NP-EGFP chimera plasmid. (FIG. 1B) Diagram of full-length NDV-F (top), full-length wild type NDV (middle) and chimeric gp350/220 NDV F (bottom). (FIG. 1C) Schematic illustration of cDNAs pCAGGS-NDV-M, -NP-EGFP and gp350/220-F (chimera) all cotransfected into CHO cells for VLPs assembly and release. (FIG. 1D) Construction of NP-tEBNA1, LMP2 and/or tEBNA1-LMP2. (FIG. 1E) Schematic illustration of cDNAs pCAGGS NDV-M, -NP-tEBNA1, LMP2 and/or tEBNA1-LMP2 and gH-F/gL-HN (chimeras) cotransfected into CHO cells for VLPs assembly and release.

FIG. 2A-B. Assembly and characterization of EBVgp350/220 VLPs incorporated with NDV-NP-EGFP. (FIG. 2A) Expression of EGFP in CHO cells transfected with pCAGGS-NDV-NP-EGFP detected by microscopy. (FIG. 2B) Immunolot detection of gp350/220 in VLPs purified from supernatant of transfected CHO cells mAb-2A1 (anti gp350/220). Lysates were separated in 4-12% gel. Purified EBV from B95-8 cells was used as positive control.

FIG. 3A-D. Immunoblot analysis of EBV-EBNA1, NDV-NP and gp350/220 incorporated into VLPs. (FIG. 3A) Detection of NDV NP-EBNA1 from purified VLPs from supernatant of CHO transfected cells using polyclonal anti-NDV Ab. (FIG. 3B) Detection of EBNA1 in gp350/220 VLPs using specific Ab to EBNA1 DNA binding domain. (FIG. 3C) Detection of gp350/220 incorporated into VLPs (FIG. 3D) anti-EBNA1 Gly-Arg rich repeat domain. 4-12% gel was used.

FIG. 4-47. Refer to each drawing for its description.

FIGS. 50-53. Refer to each drawing for its description.

FIG. 54. Terminal protein LMP2A [Human herpesvirus 4] (SEQ ID NO:01) NCB1 Reference Sequence: YP_401631.1.

FIG. 55. Glycoprotein gp110 precursor [Human herpesvirus 4] (SEQ ID NO:02) NCB1 Reference Sequence: YP_403713.1.

FIG. 56. gH, Glycoprotein gp85 precursor [Human herpesvirus 4] (SEQ ID NO:03) NCB1 Reference Sequence: YP_401700.1.

FIG. 57. gL (BKRF2) [Human herpesvirus 4 type 2] (SEQ ID NO:04) NCB1 Reference Sequence: YP_001129472.1.

FIG. 58. L1 [Human papillomavirus type 16) (SEQ ID NO:05) GenBank: AAD33259.1.

FIG. 59. L2 [Human papillomavirus type 16) (SEQ ID NO:06) GenBank: AAD33258.1.

FIG. 60. L2 protein [Human papillomavirus type 18] (SEQ ID NO:07) GenBank: AGG40790.1.

FIG. 61. EBNA-1 protein [Human herpesvirus 4] (SEQ ID NO:08) NCB1 Reference Sequence: YP_401677.1.

Figure 62A:
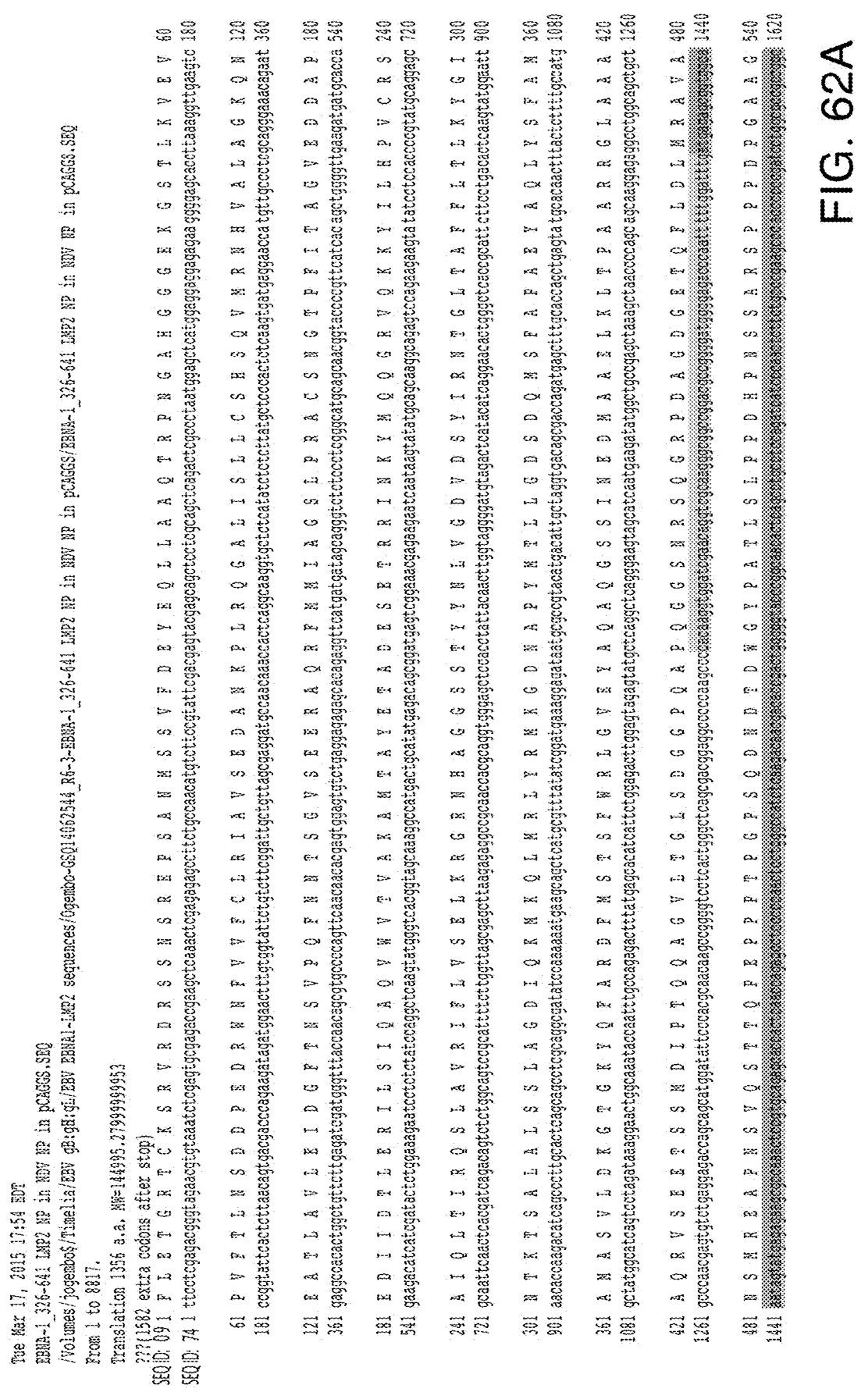
Figure 62B:
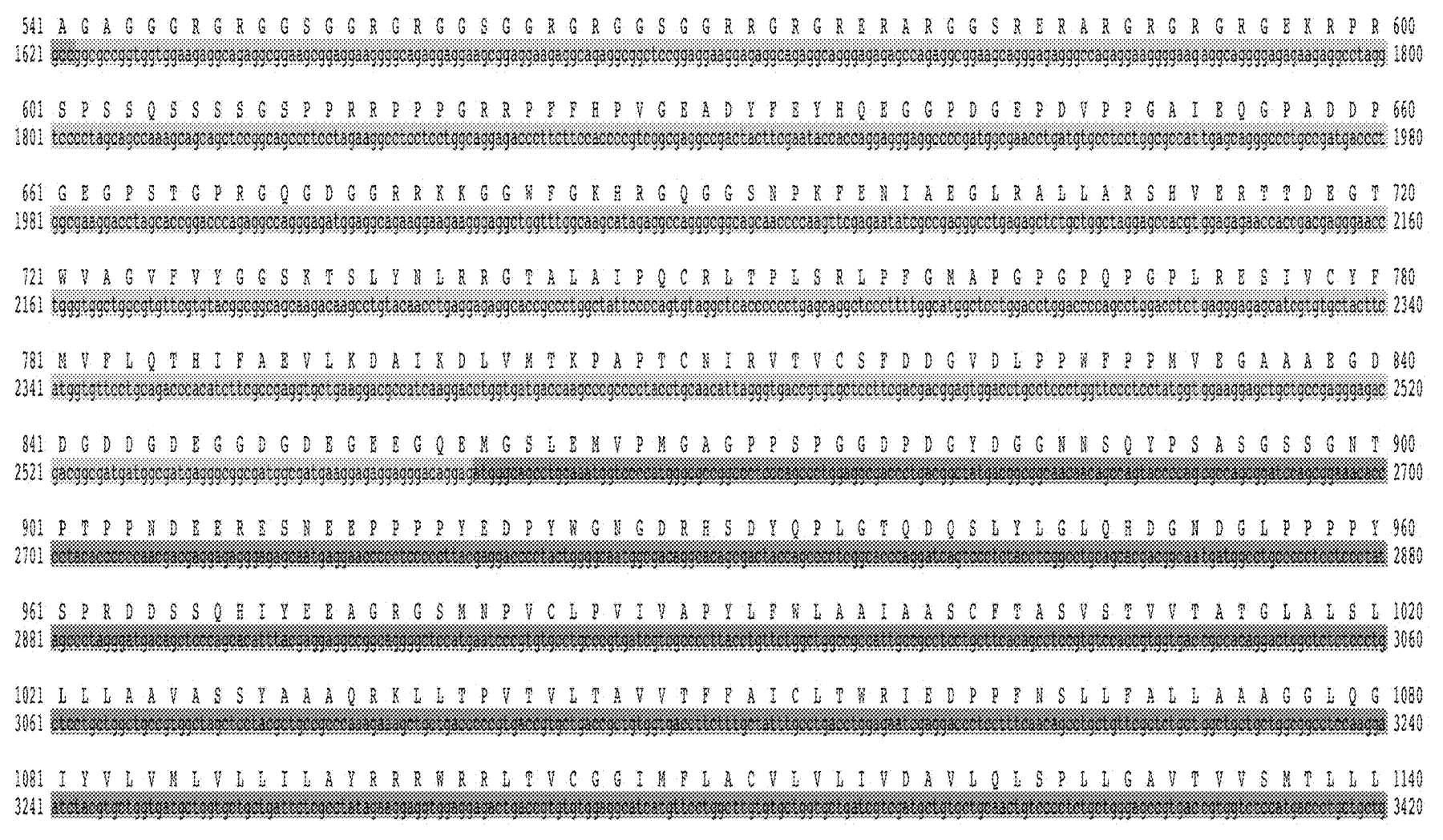
Figure 62C:
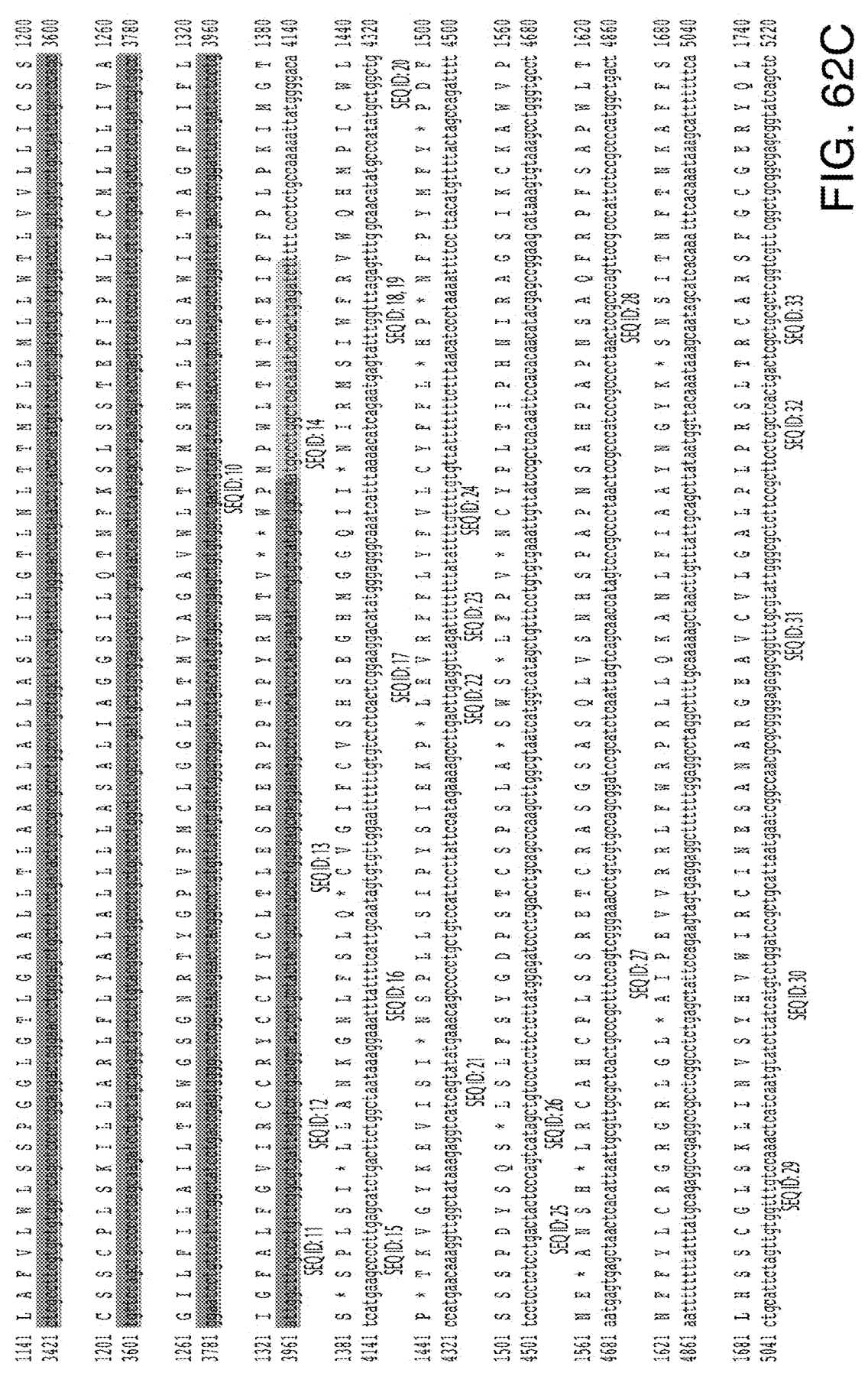
Figure 62D:
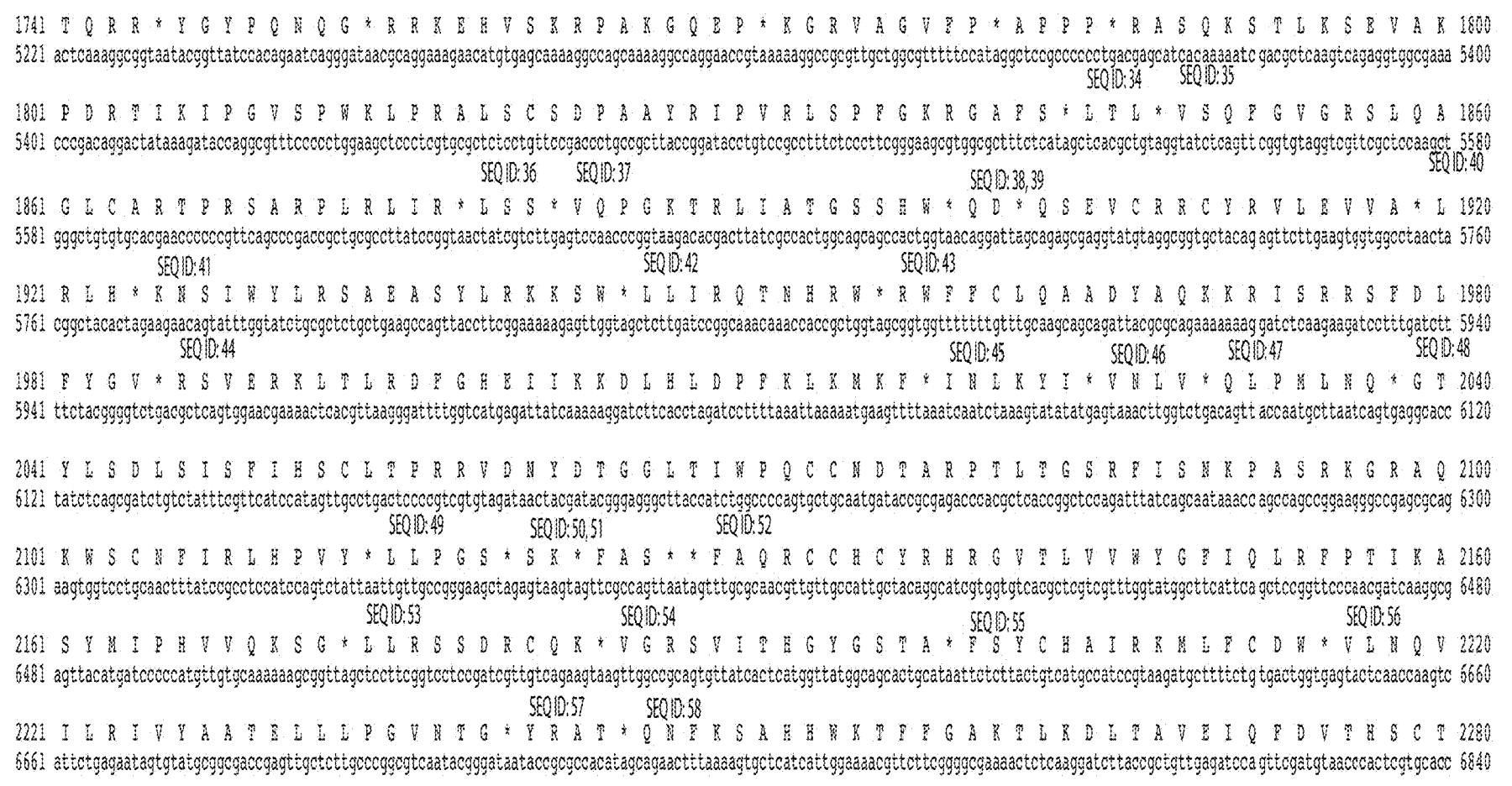

FIG. 62A-E. EBNA-1_326-641 LMP2 NP in NDV NP in pCAGGS.SEQ Translation.

Figure 63A:
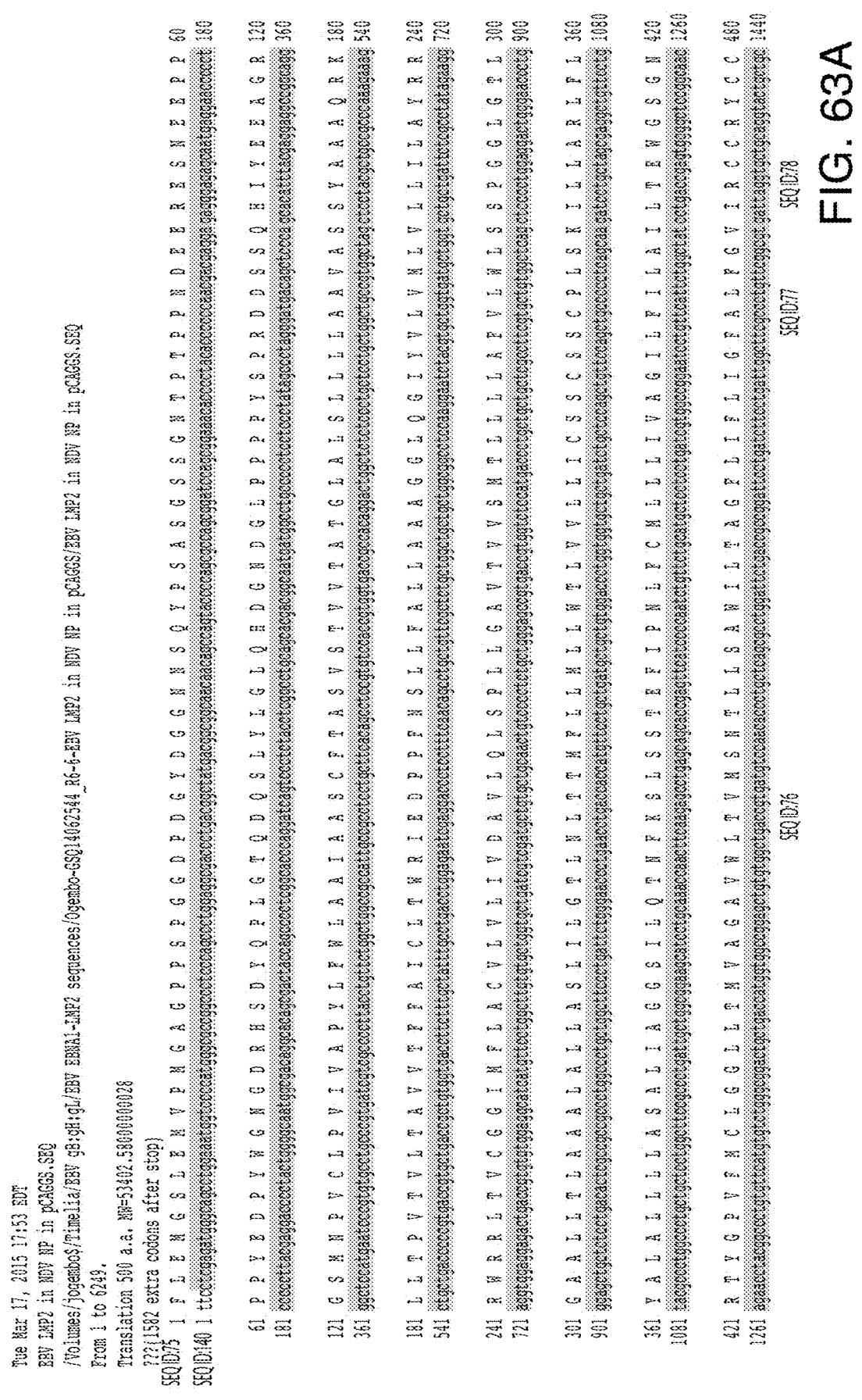
Figure 63B:
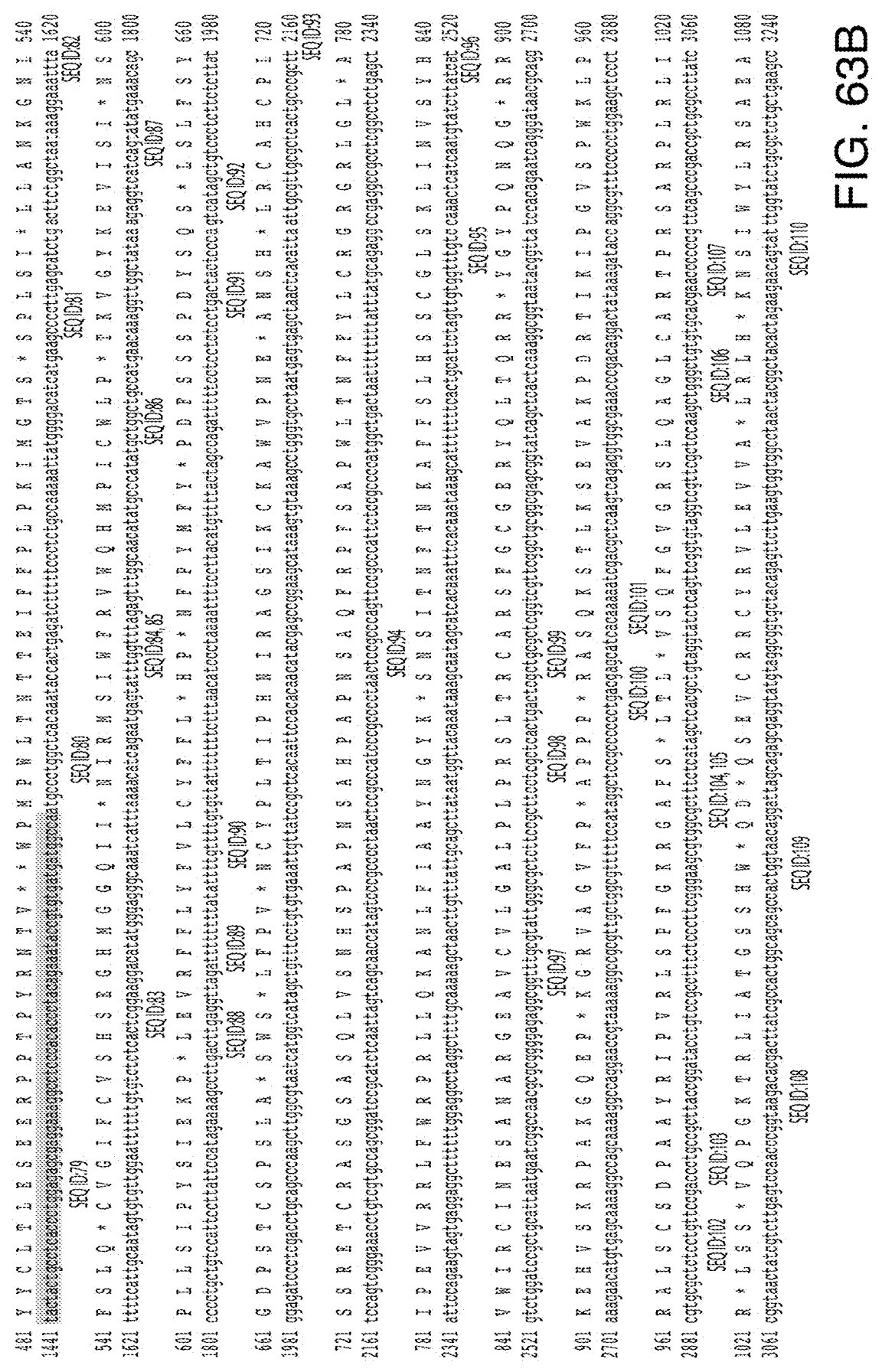
Figure 63C:
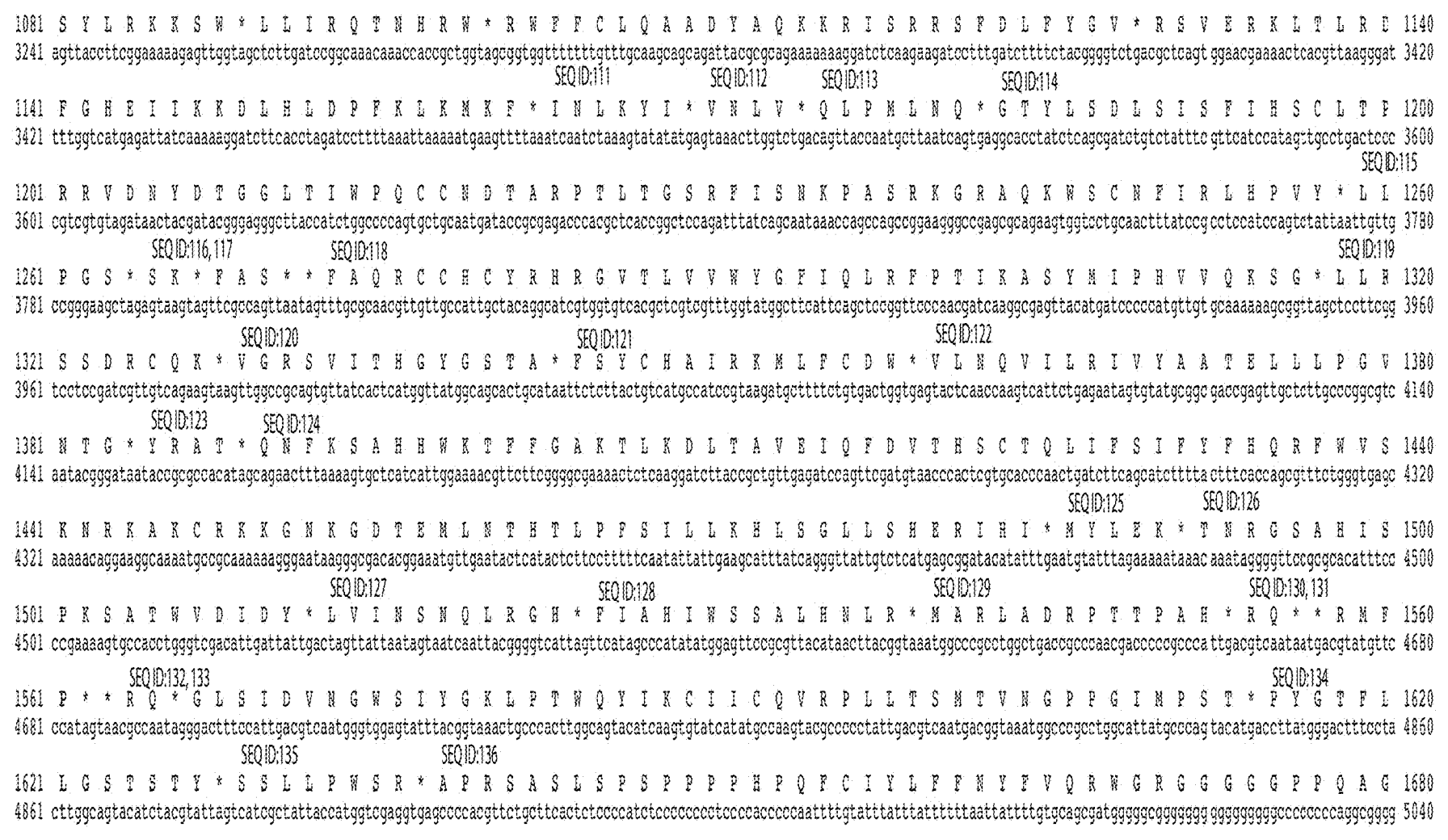
Figure 63D:
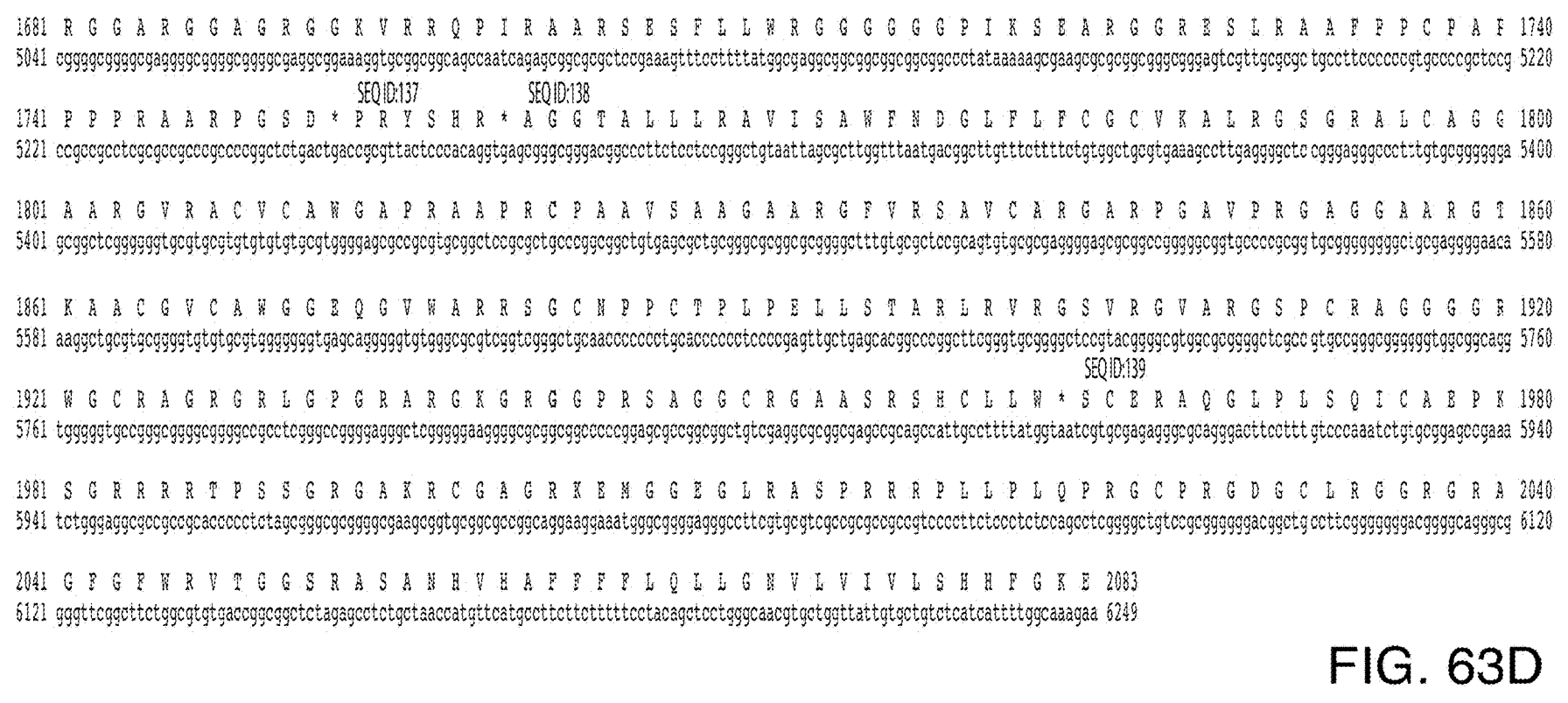

FIG. 63A-D. EBV LMP2 in NDV NP in pCAGGS.SEQ Translation.

Figure 64A:
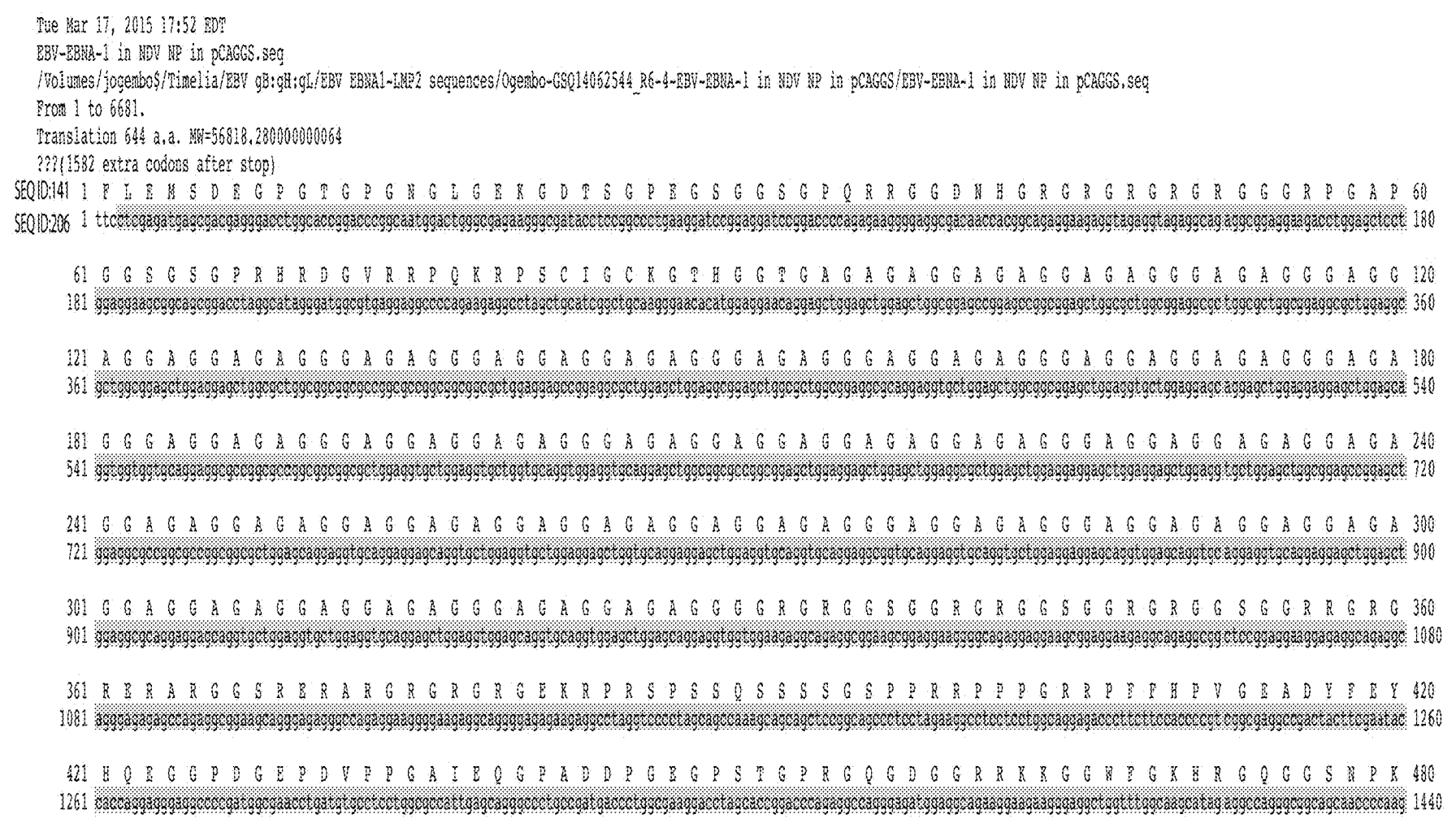
Figure 64B:
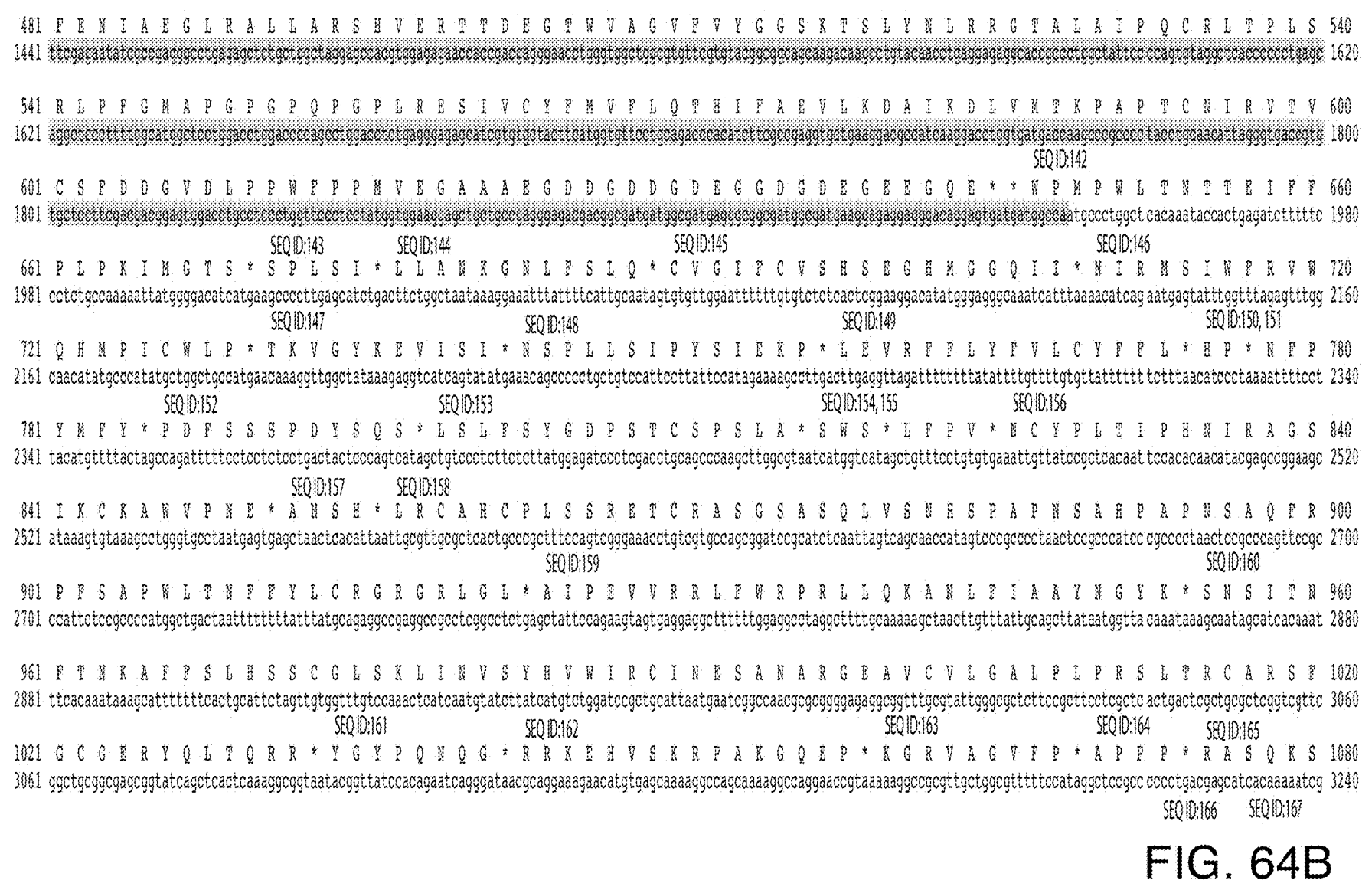
Figure 64C:
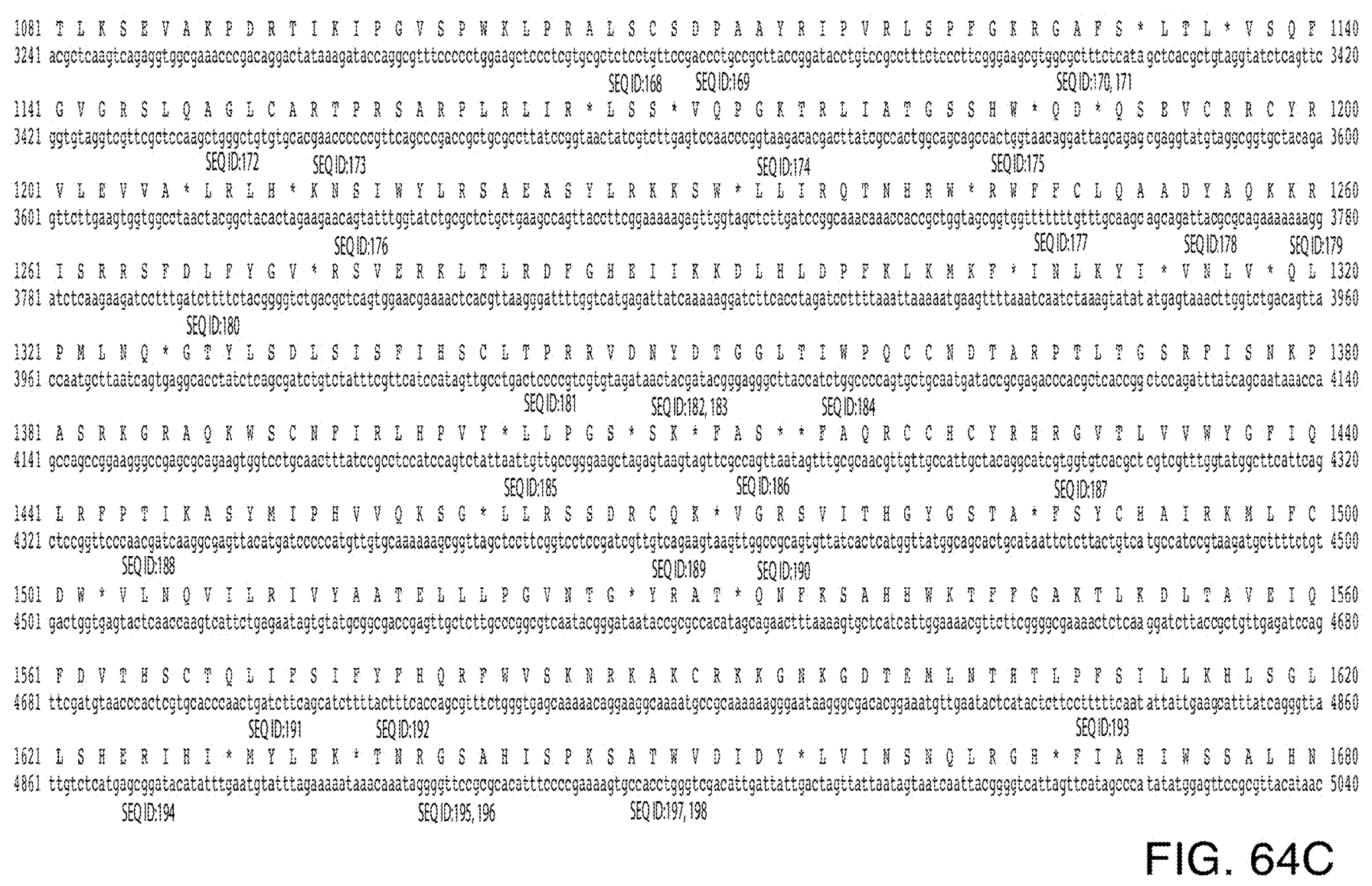
Figure 64D:
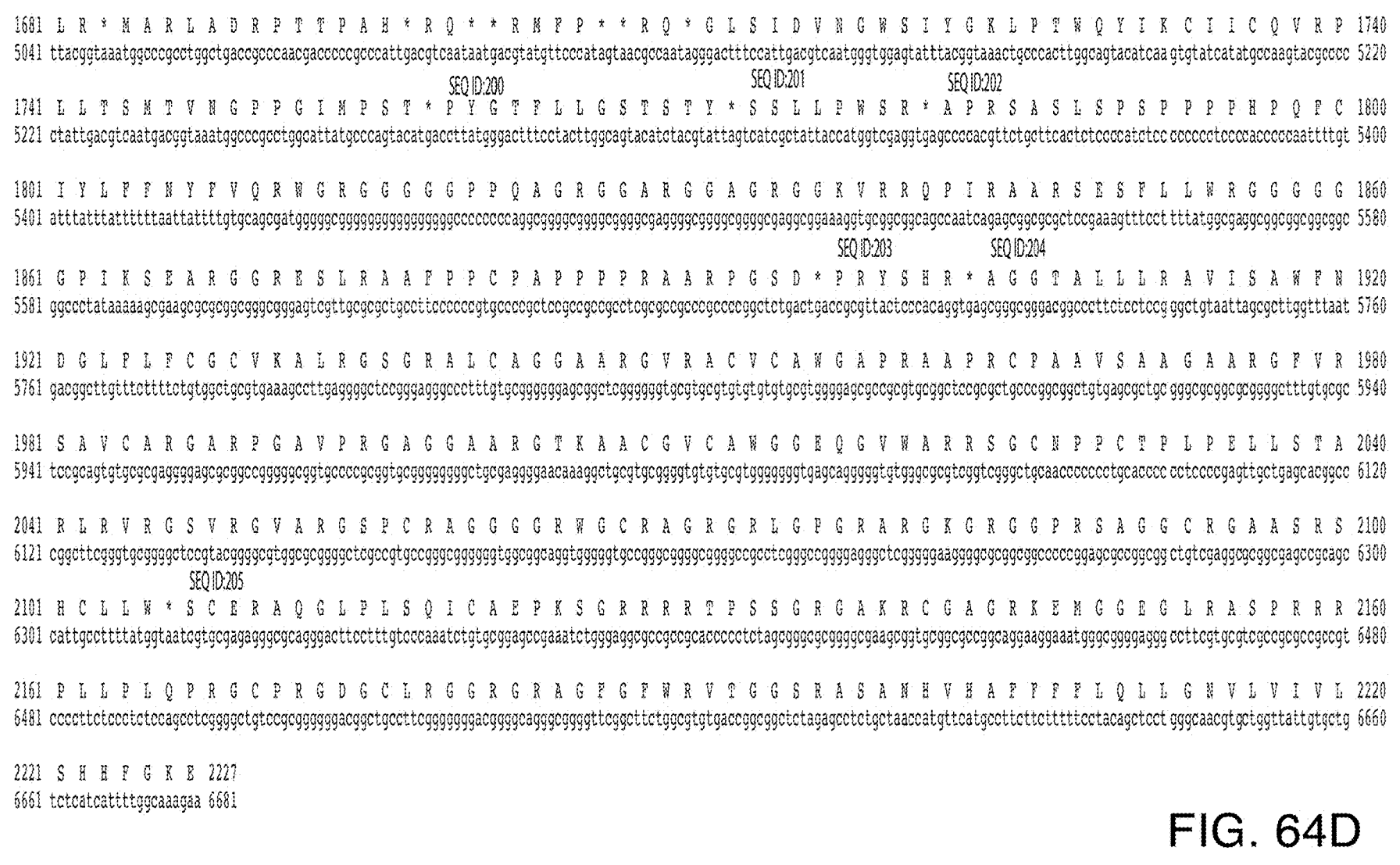

FIG. 64A-D. EBV-EBNA-1 in NDV NP in pCAGGS.seq Translation.

Figure 65A:
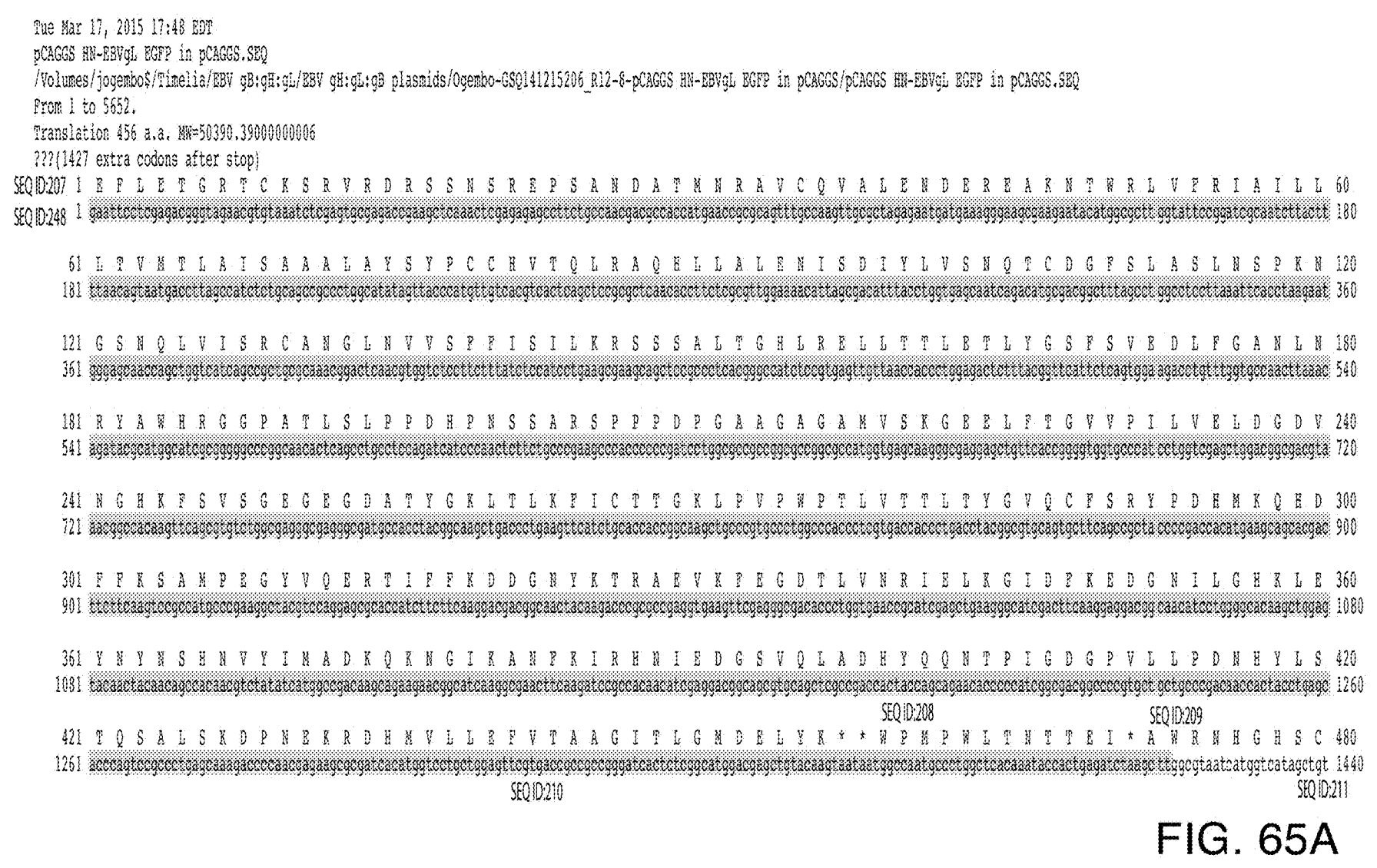
Figure 65B:
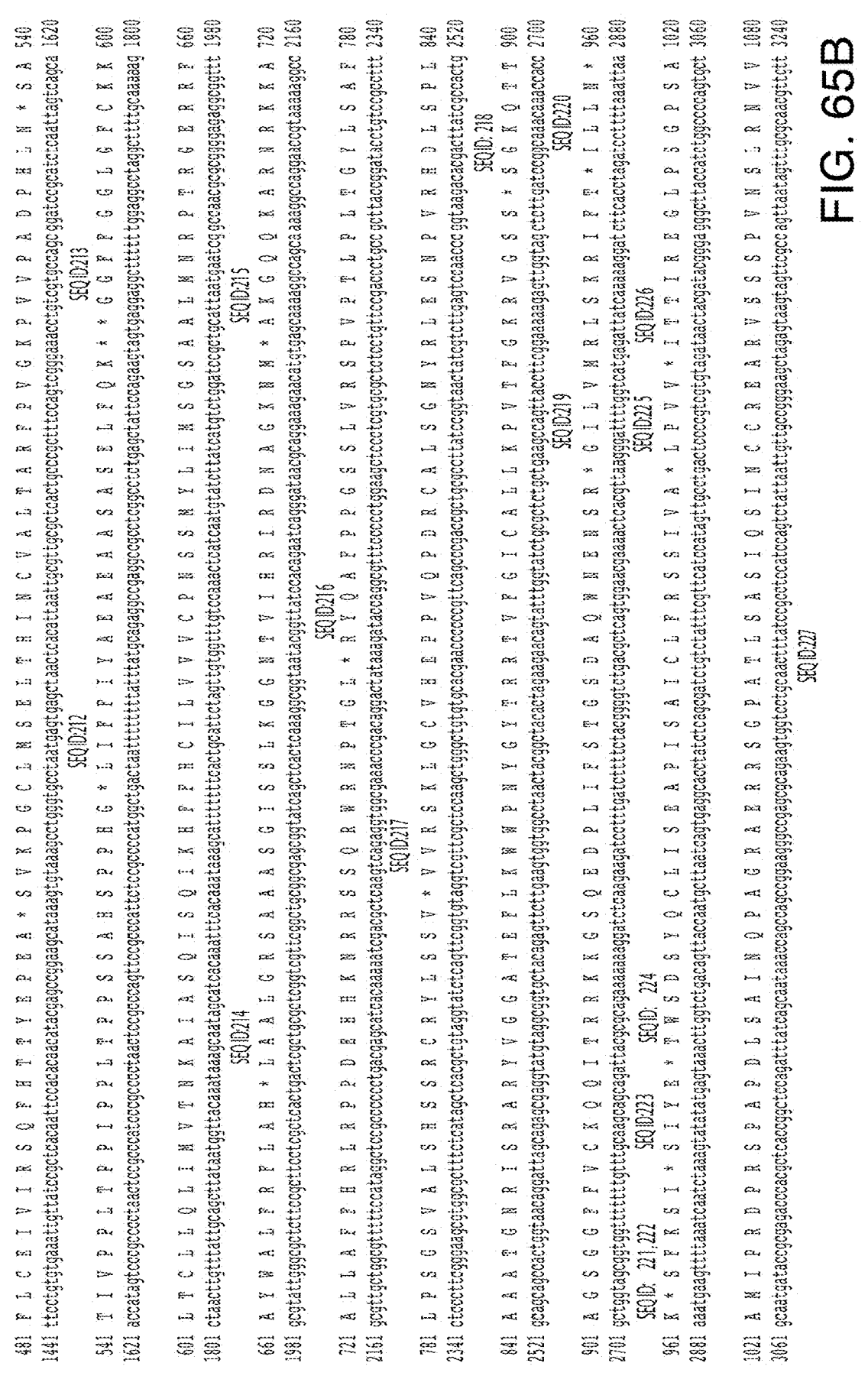
Figure 65C:
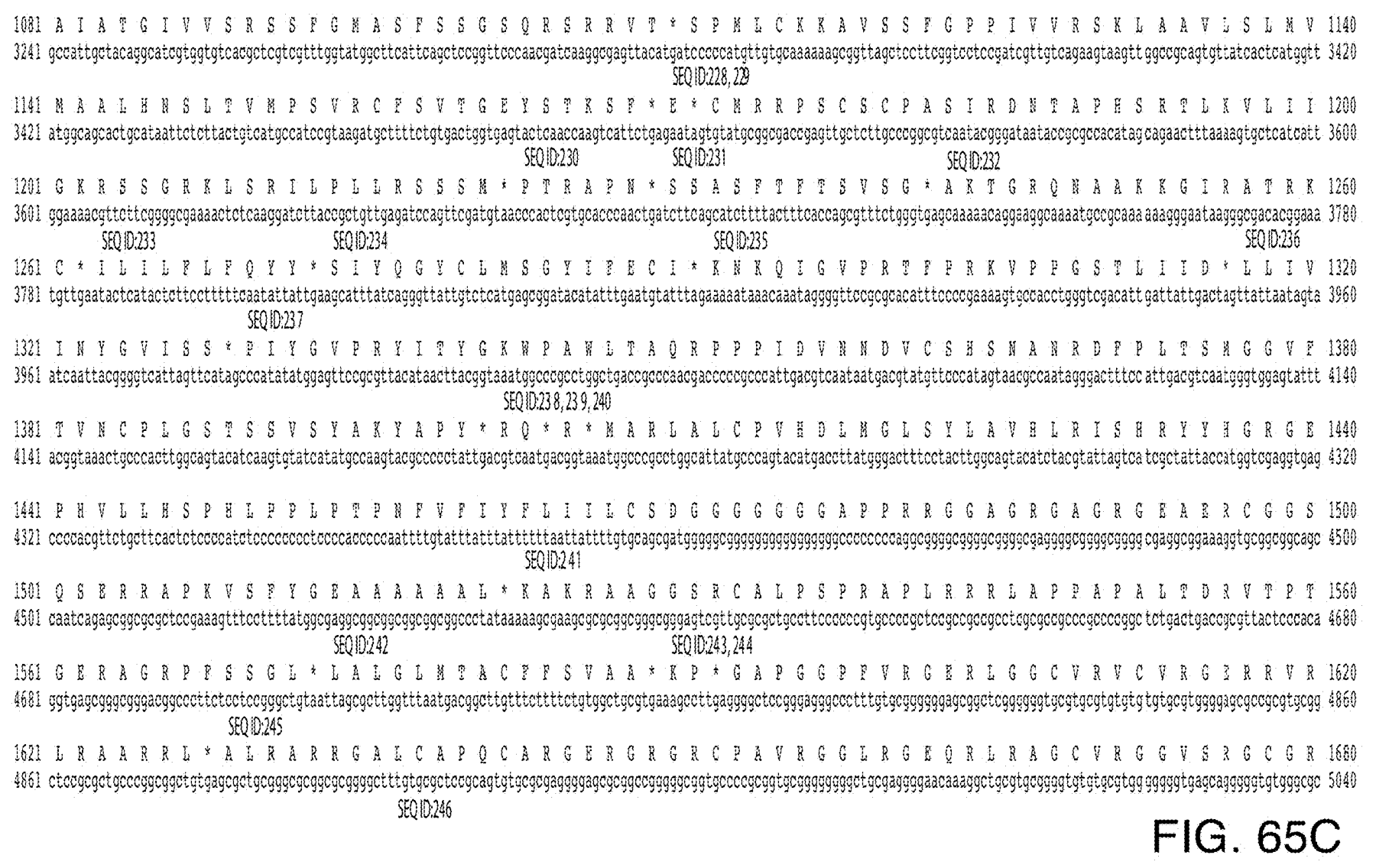
Figure 65D:
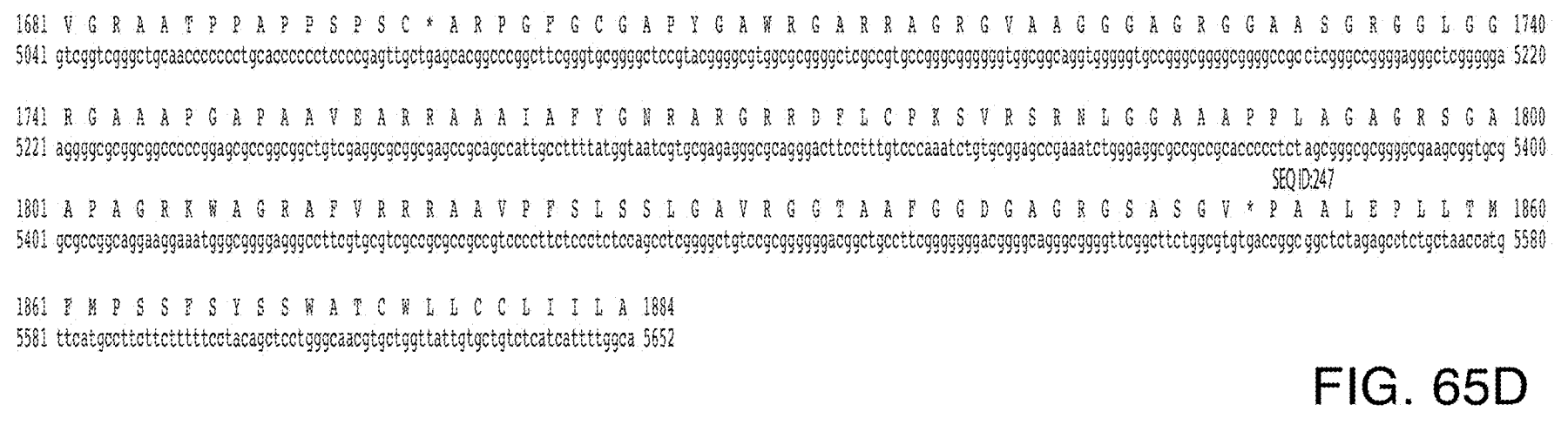

FIG. 65A-D. pCAGGS HN-EBVgL EGFP in pCAGGS.SEQ Translation.

Figure 66A:
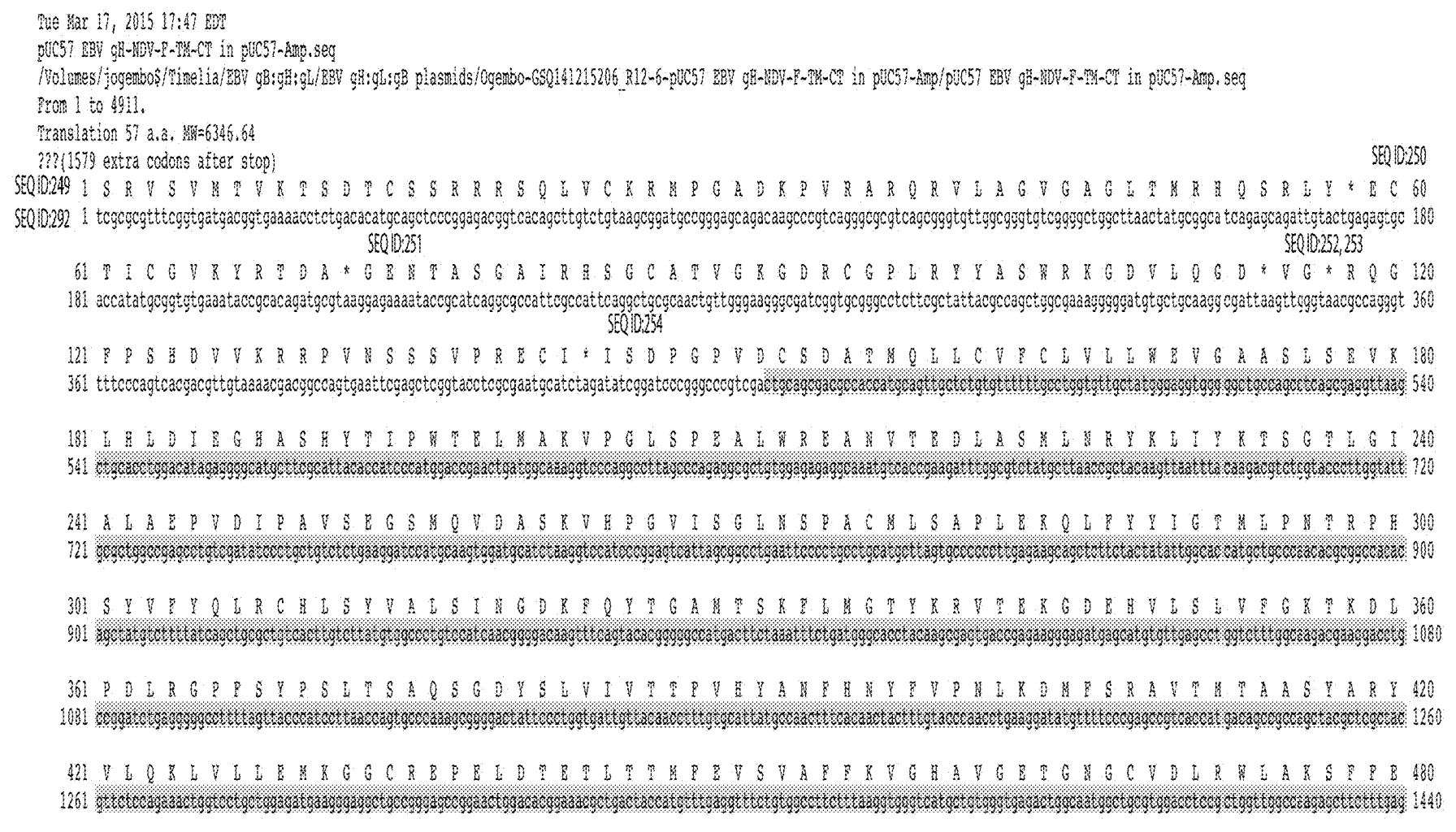
Figure 66B:
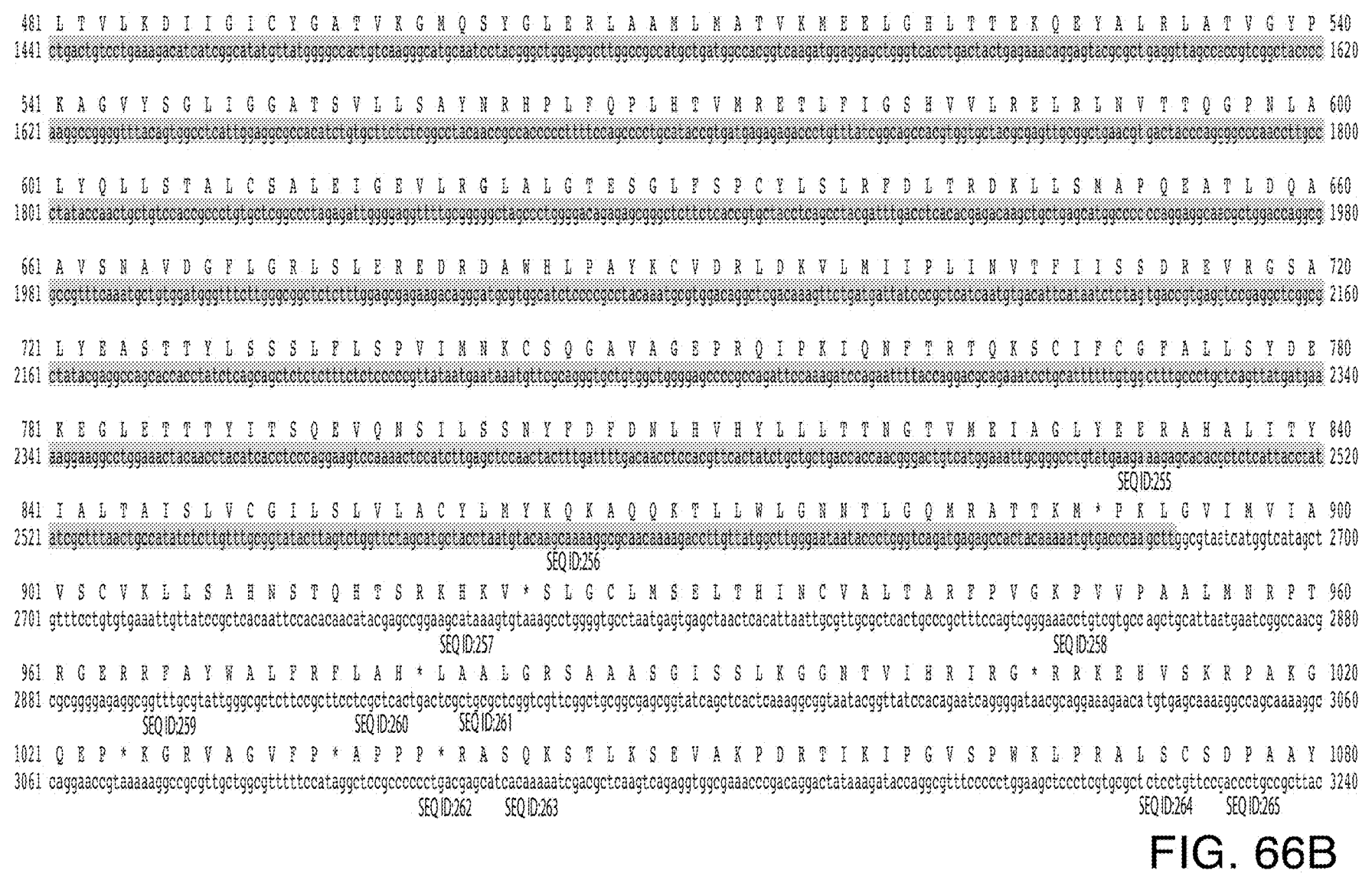
Figure 66C:
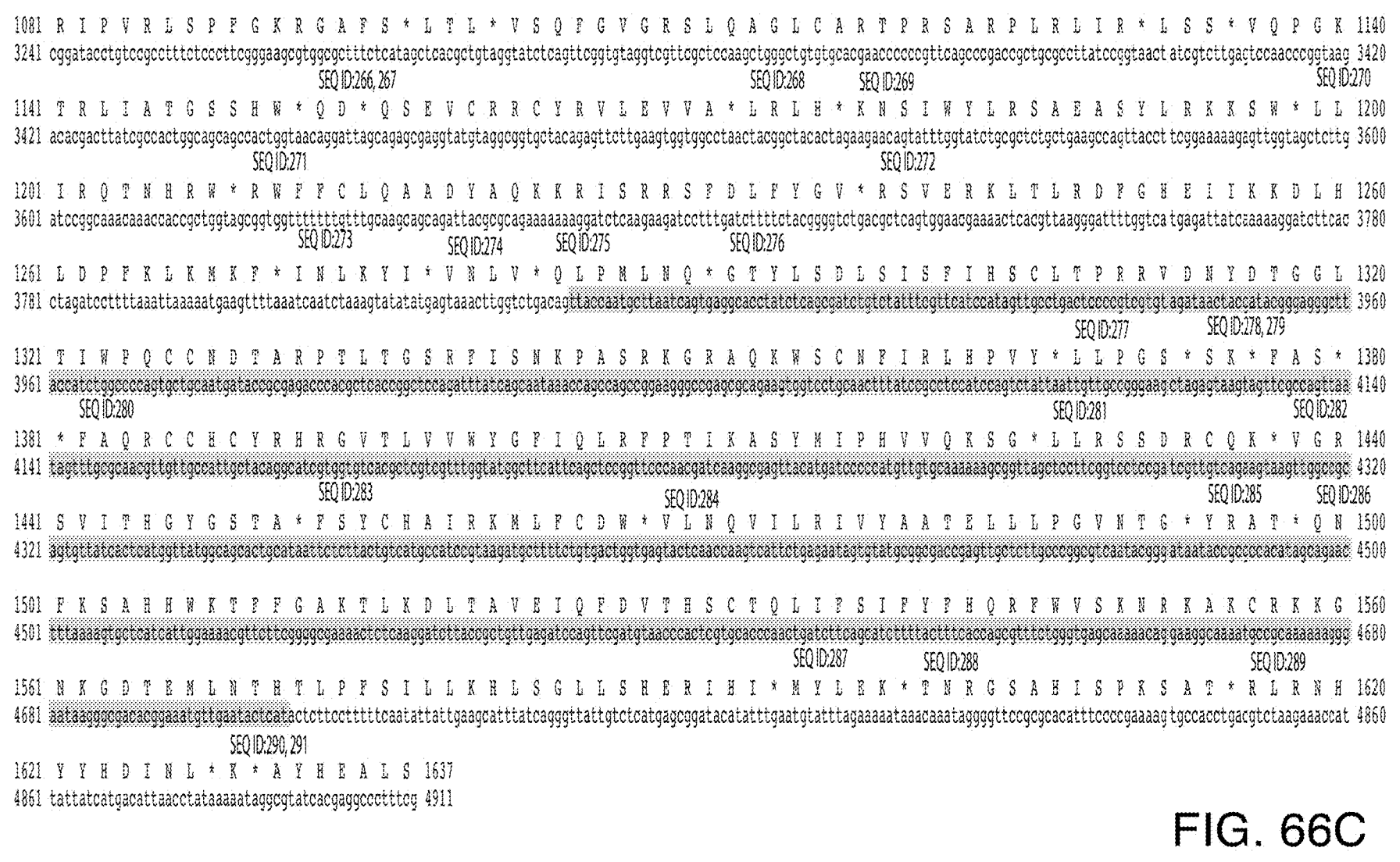

FIG. 66A-C. pUC57 EBV gH-NDV-F-TM-CT in pUC57-Amp.seq Translation.

Figure 67A:
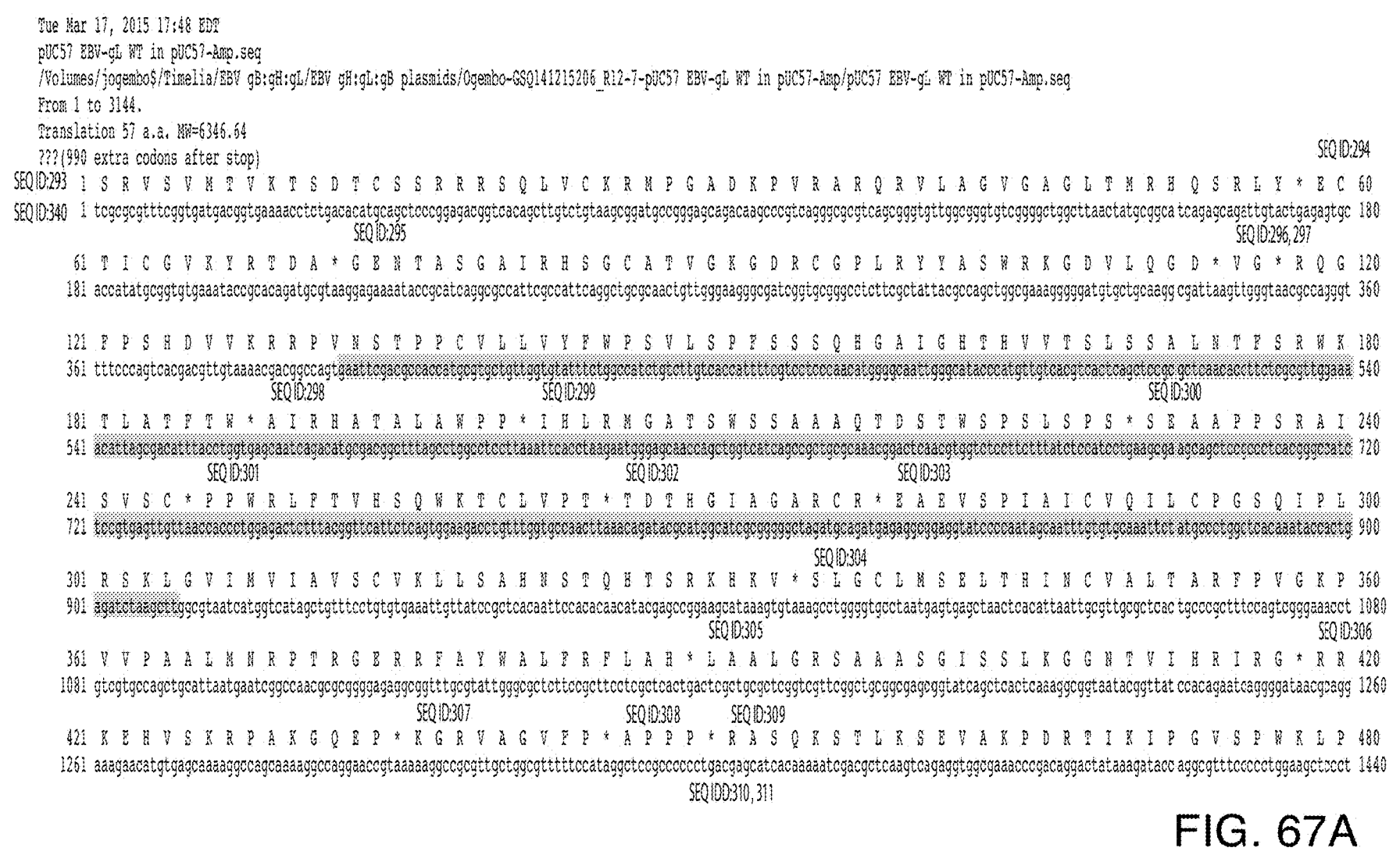

FIG. 67A-B. pUC57 EBV-gL WT in pUC57-Amp.seq Translation.

Figure 68A:
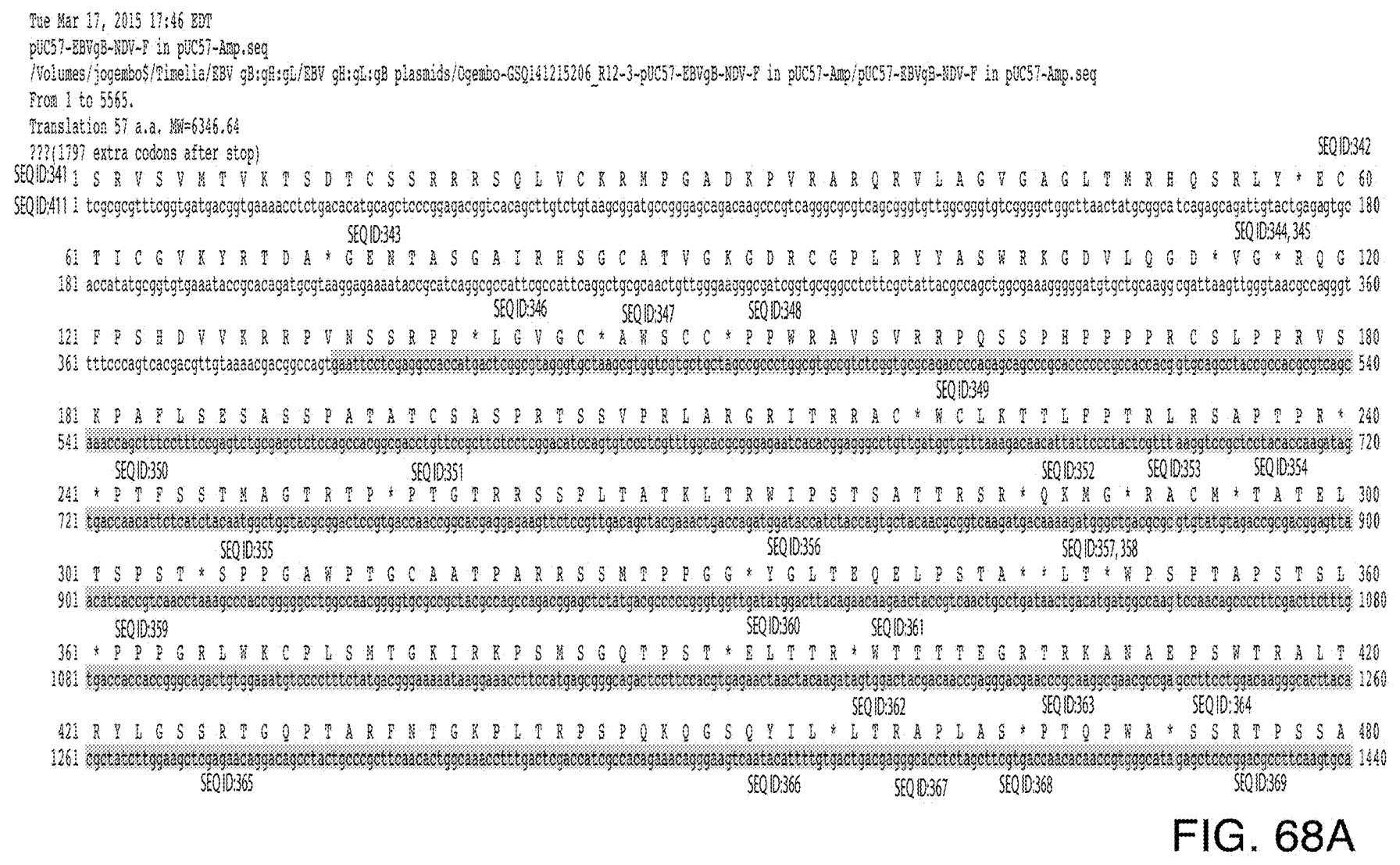
Figure 68B:
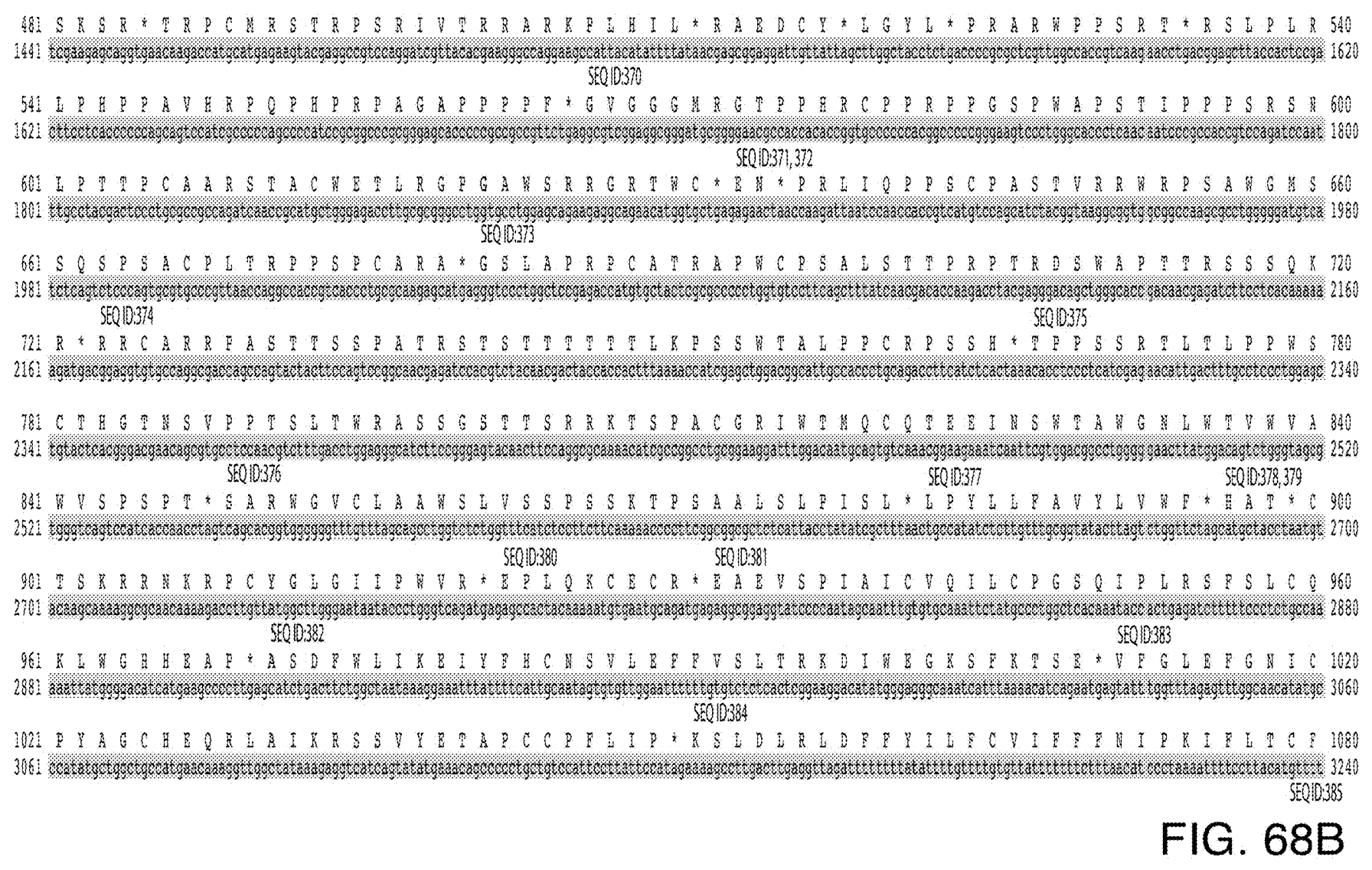
Figure 68C:
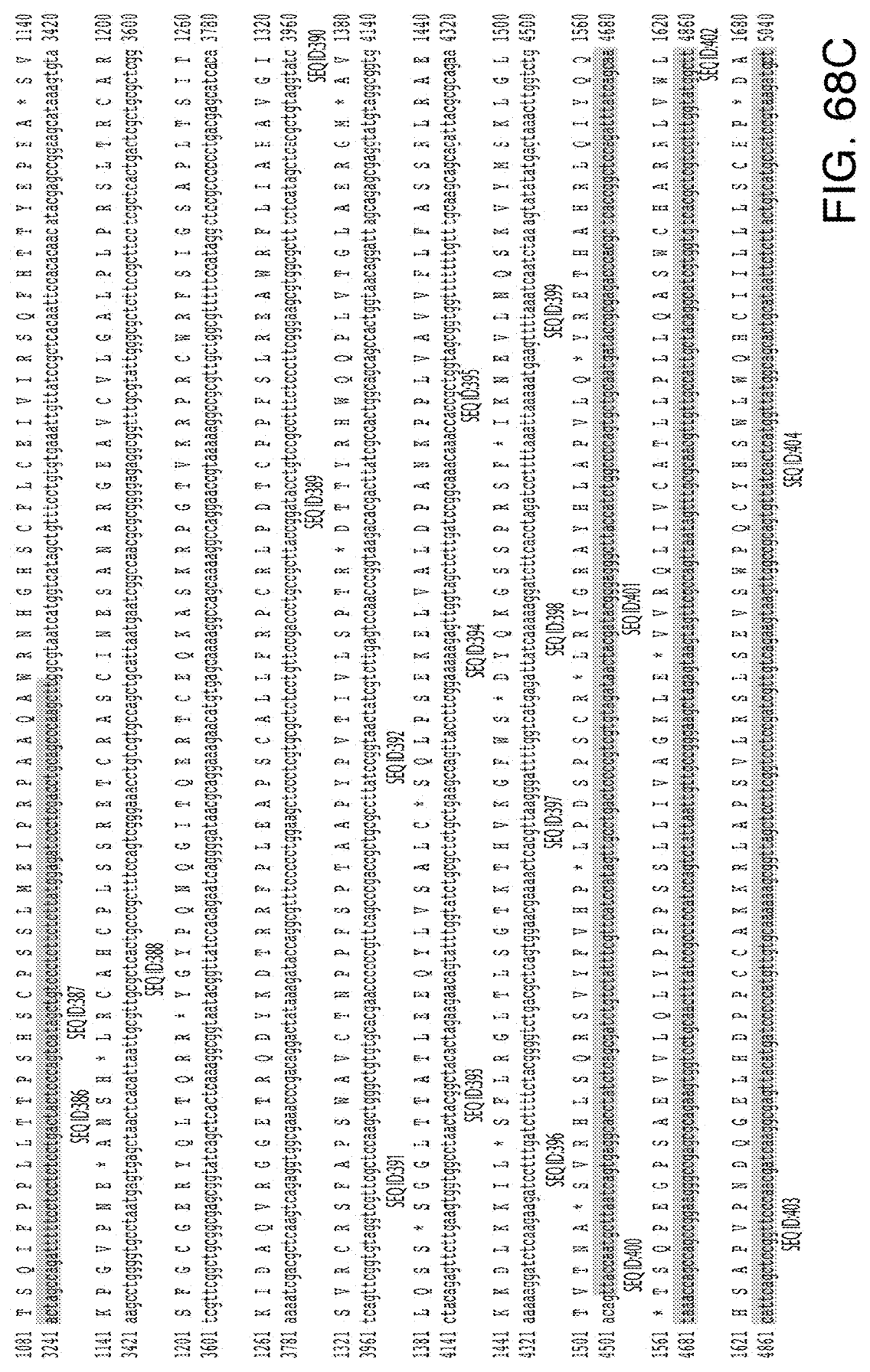
Figure 68D:
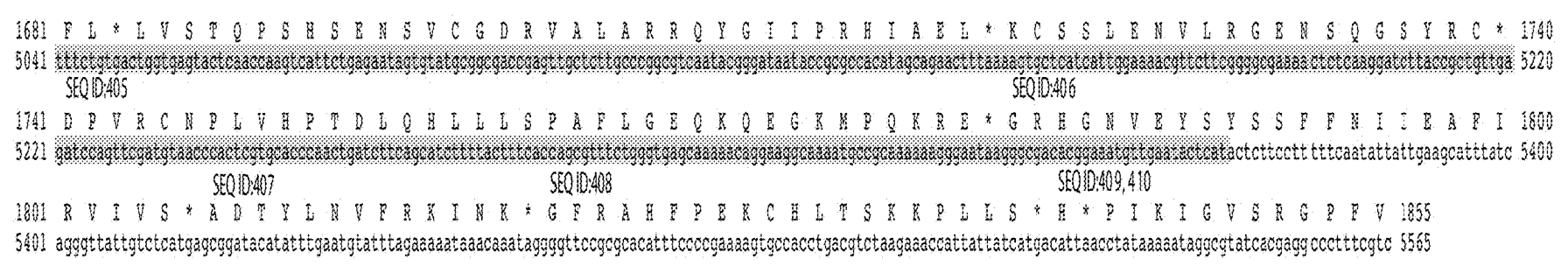

FIG. 68A-D. pUC57-EBVgB-NDV-F in pUC57-Amp.seq Translation.

Figure 69A:
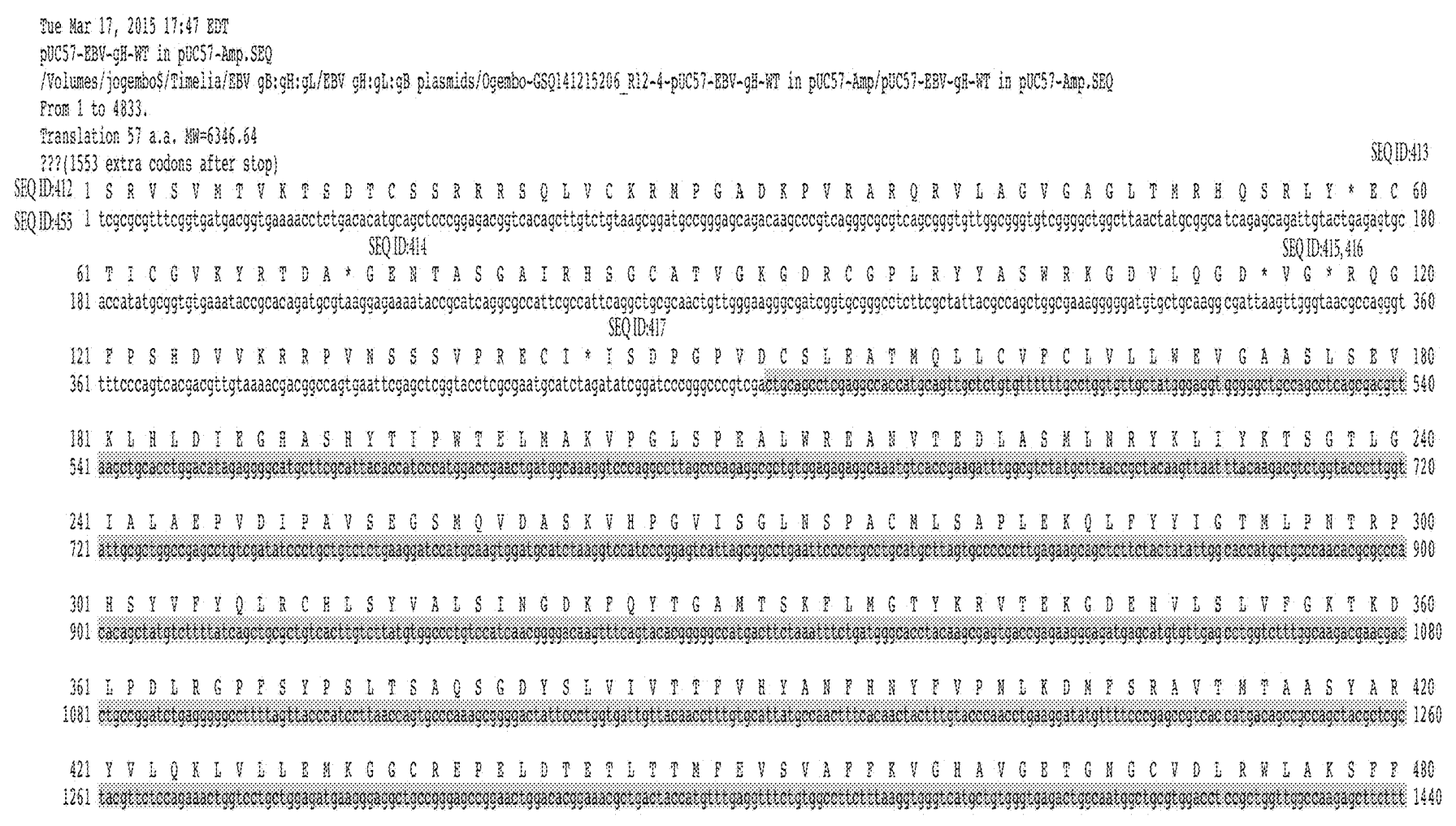
Figure 69B:
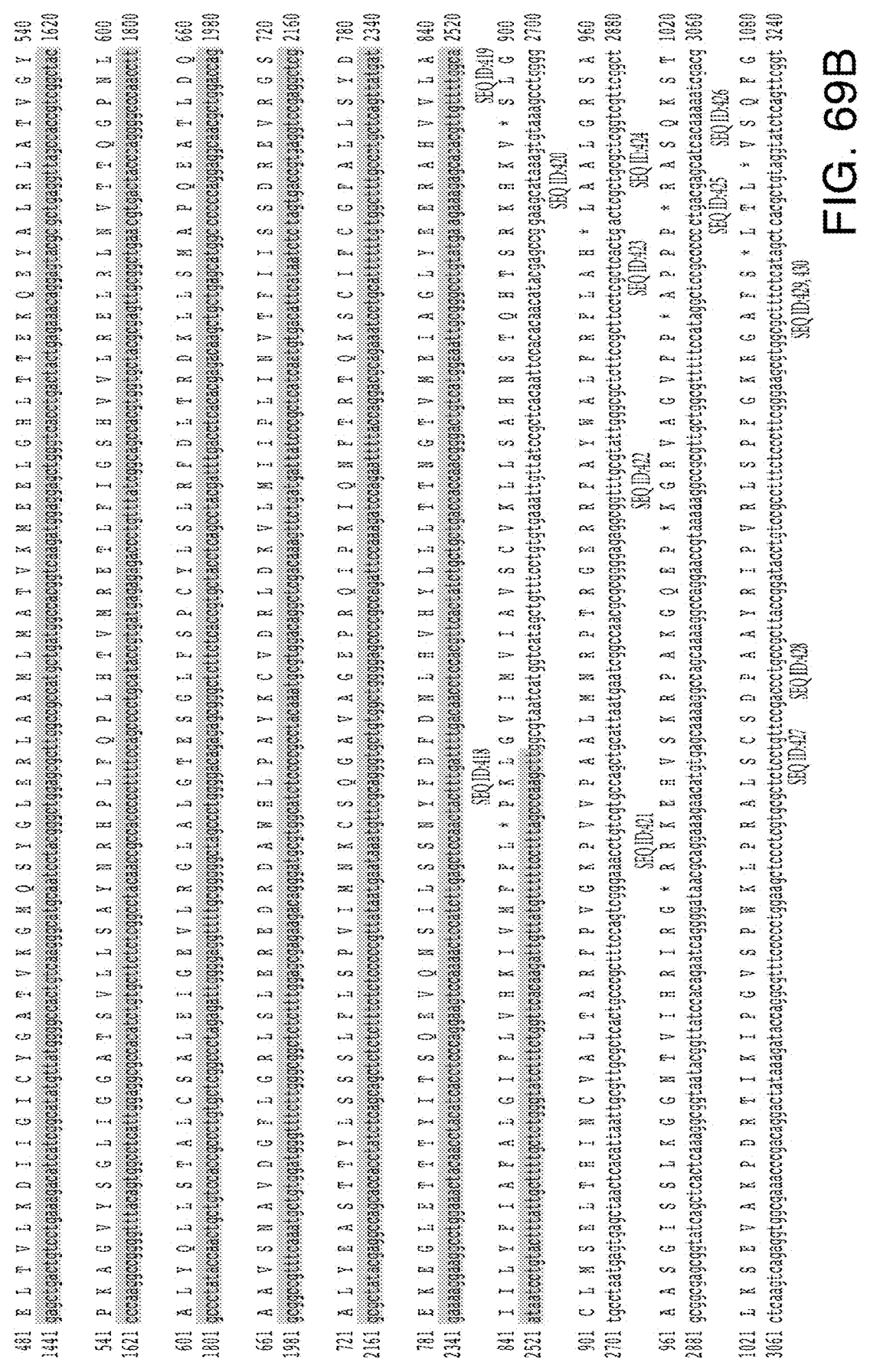
Figure 69C:
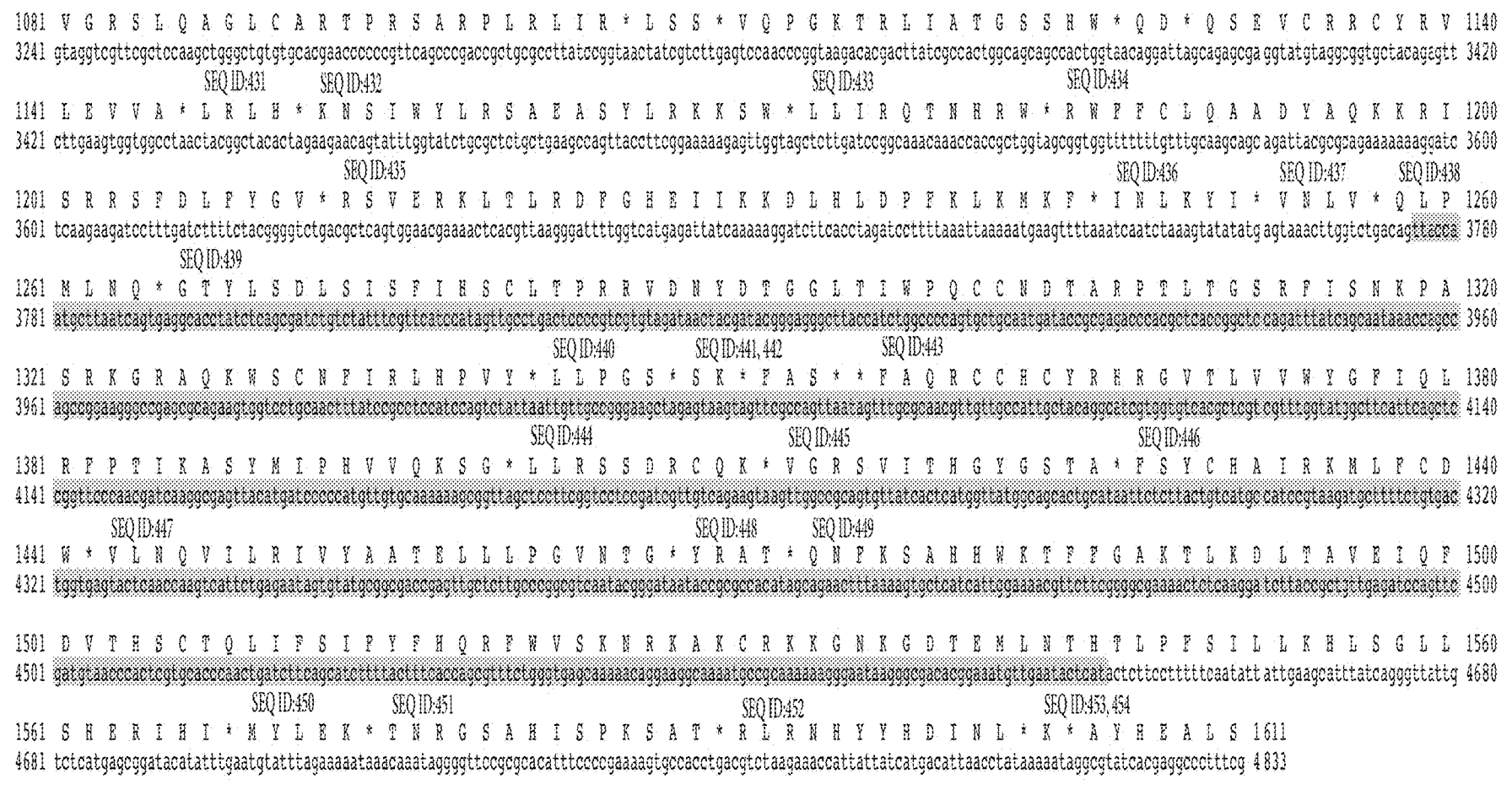

FIG. 69A-C. pUC57-EBV-gH-WT in pUC57-Amp.SEQ Translation.

Figure 70B:
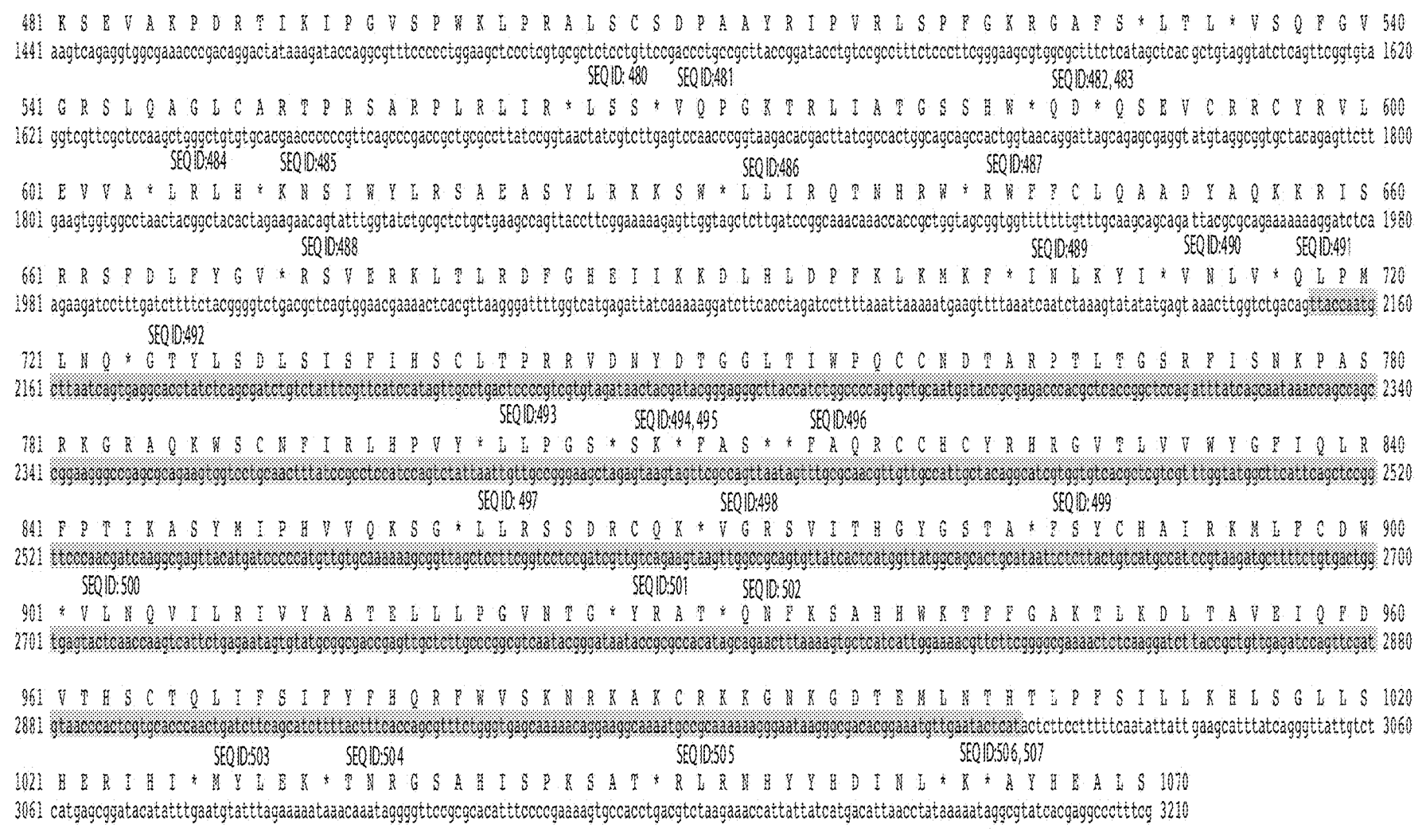

FIG. 70A-B. puC57-EBV-gL-NDV-HN in pUC57-Amp.SEQ Translation.

Figure 71A:
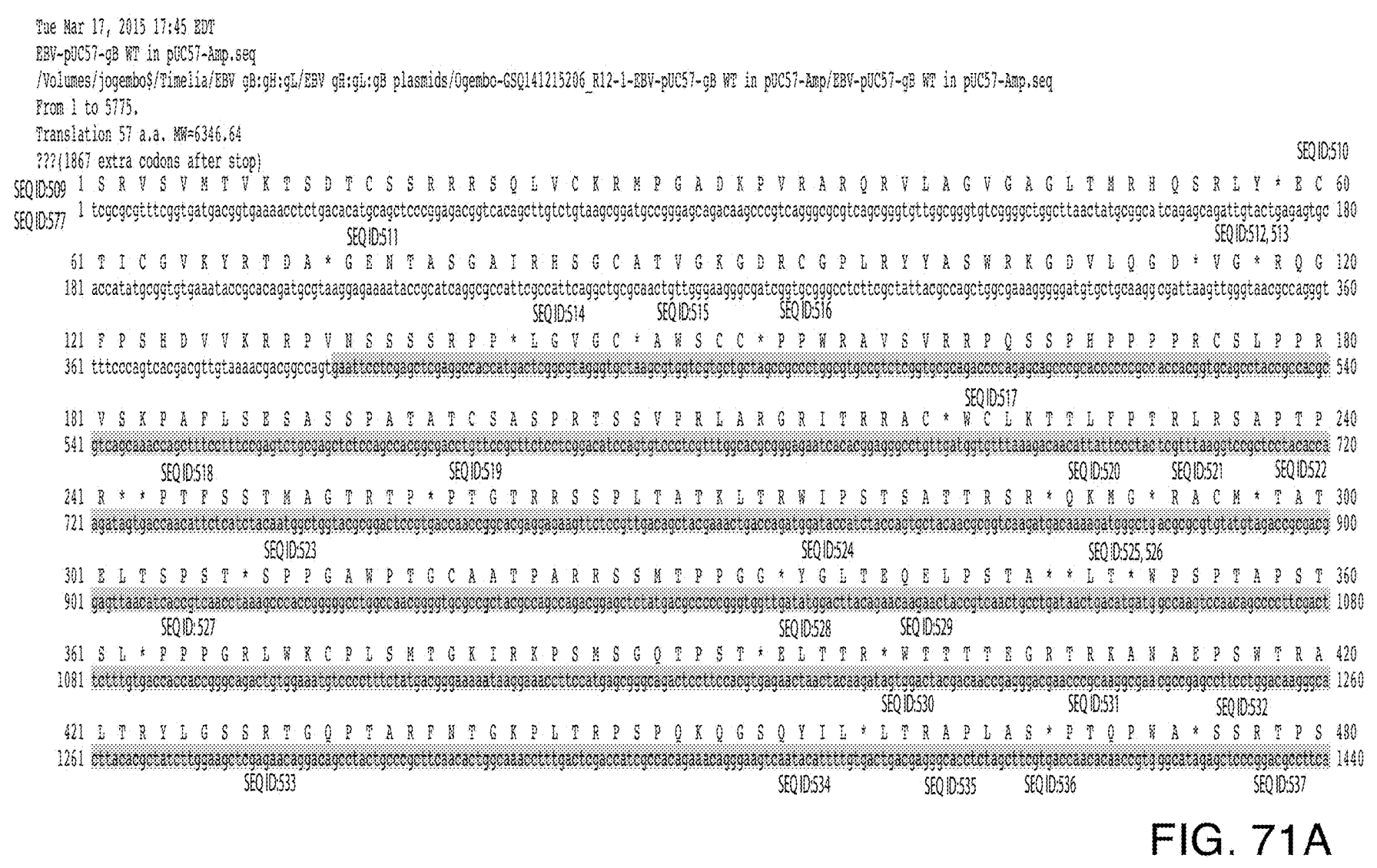
Figure 71B:
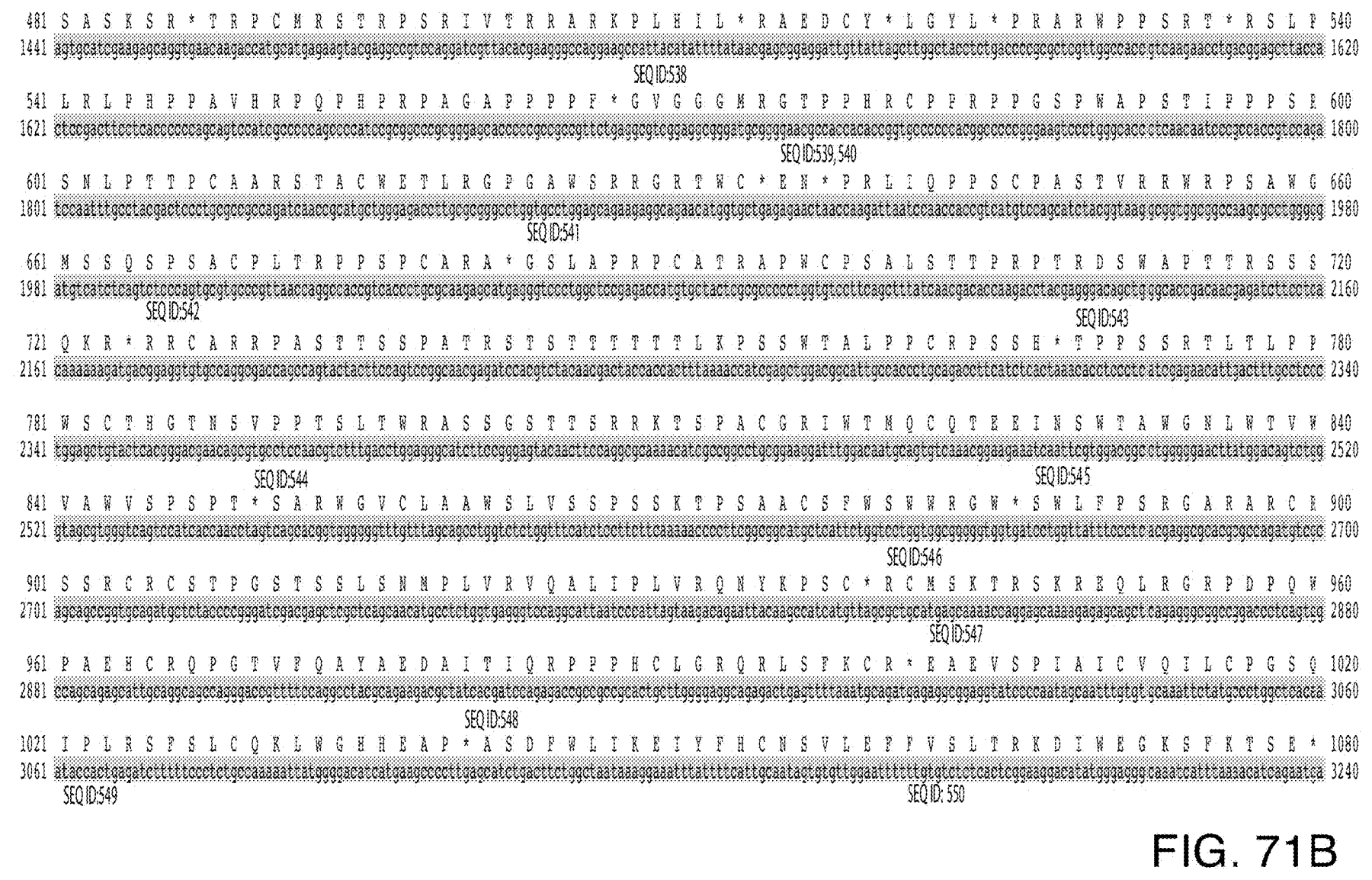
Figure 71C:
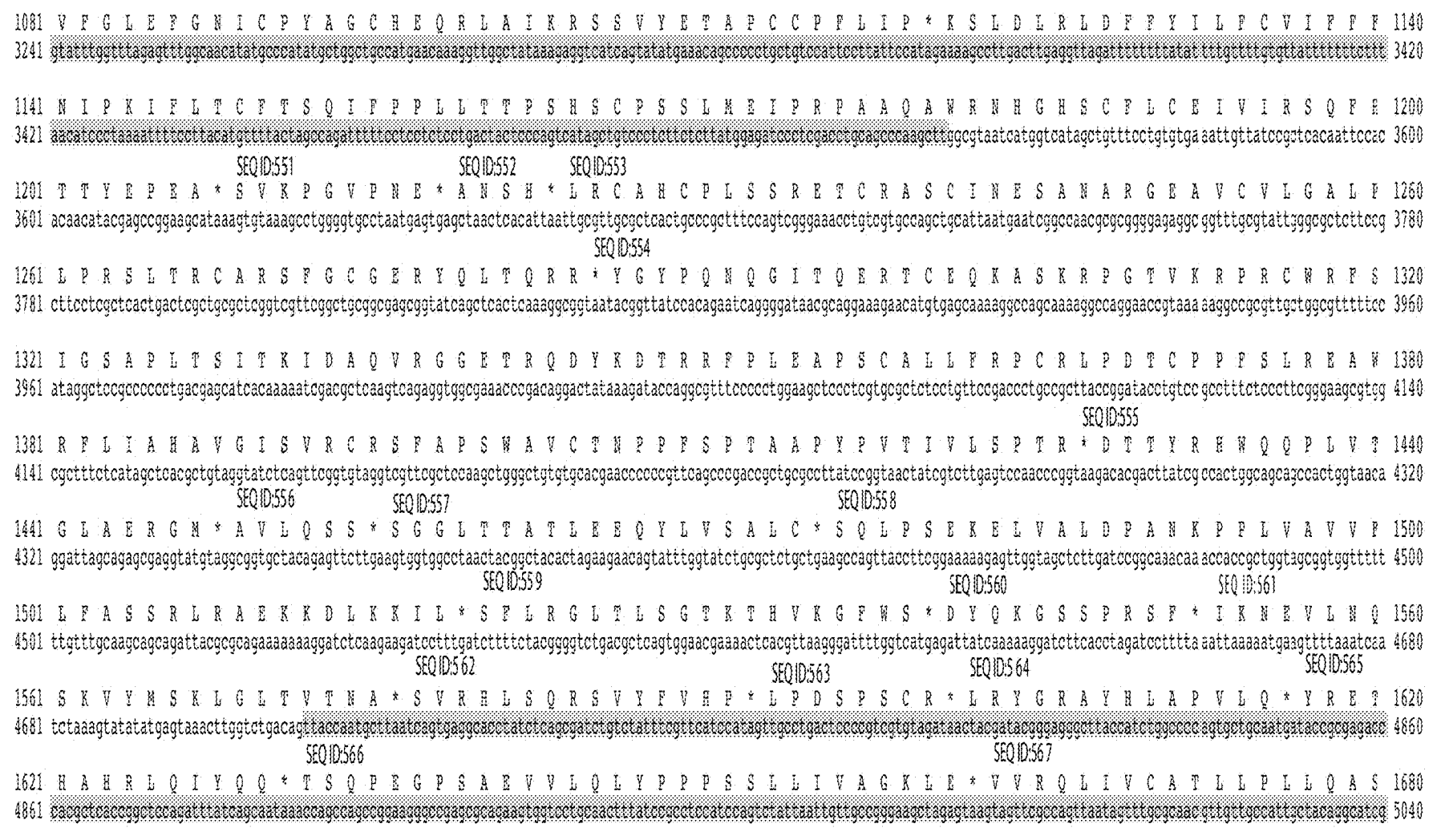

FIG. 71A-D. EBV-pUC57-gB WT in pUC57-Amp.seq Translation.

Figure 72:
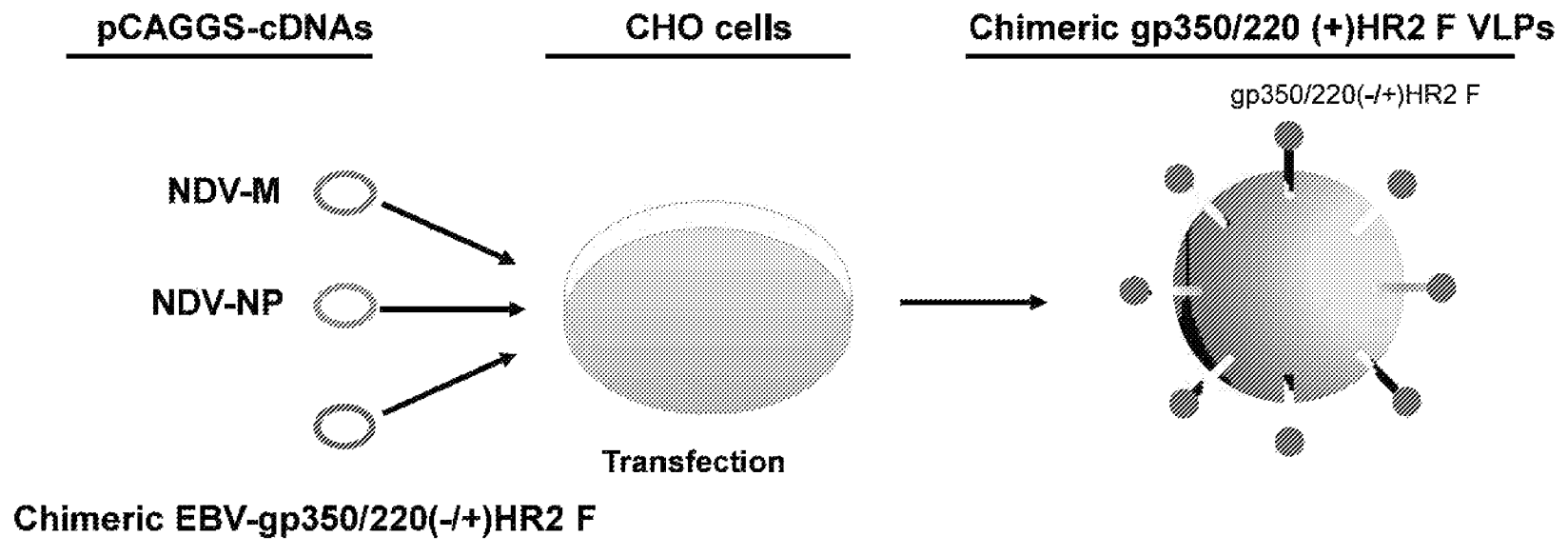

FIG. 72. A diagram showing the transfection process used in the production of chimeric EBVgp350/220(−/+)HR2 F VLPs. Ogembo et al., J. Trans. Med. 2015; 13:50. Pantua et al., J. Virol. 2006; 11062-73.

FIG. 75A-D. Characterization of EBV-gp350/220-F VLPs. Cell supernatants from independent EBV VLP preparations were harvested daily between 24-96 h, concentrated, and purified by sucrose-gradient centrifugation followed by particle lysis and immunoblot analysis. (FIG. 75A) Supernatants produced in CHO cells were pooled and purified, immunoblot indicating the presence of EBVgp350/220 ED, and NDV-F C-terminal peptides using mAb-72A1 anti-gp350/220 (left panel), polyclonal anti-HR2 (middle panel), and polyclonal anti-NDV (right panel), respectively. Each blot included lysates of purified EBV and ND, which served as controls. (FIG. 75B) Electron micrograph of negatively stained sucrose gradient purified EBVgp350-220-F VLPs prepared in CHO cells compared with native EBV using immunogold-coupled goat anti-mouse IgG binds the surface of a chimeric EBVgp350/220-F VLP and EBV (control). Image shows the structure and size of the chimeric VLP compared with EBV in the absence of antibody (top), and in the presence of mAb-72A1 anti-gp350/220 (middle), as well as a chimeric KSHV-derived VLP or KSHV. (FIG. 75C) Different combinations of pCAGGS plasmids encoding F, M, NP, gp350/220 and gp350/220-F as indicated were co-transfected into 293T cells. Material released into the supernatant was pelleted and analyzed by immunoblot using anti-gp350/220 and anti-HR2 antibodies. Lane 1: NDV-VLP (NP, M, F), lane 2: NP, M, lane 3: NP, M, gp350/220 WT, lane 4: EBV VLP (NP, M, EBVgp350/220-F), lane 5: M, EBVgp350/220-F, lane 6: pCAGGS. Bands of the expected molecular weight were detected by both antibodies in lane 4 alone, indicating a chimeric EBV VLP specifically assembled and was released. (FIG. 75D) Silver stain of increasing amounts of purified chimeric VLPs released from ELL-0 cells compared with NDV. The position of EBVgp350/220-F protein, NDV-NP and -M are indicated by arrows. Molecular weight markers are indicated at left.

(FIG. 78A) EBV infection assay. Because EBV does not plaque, the infectivity of EGFP-EBV from a frozen stock was directly quantitated by cytometry. Five microliters of stock virus in the absence of serum yielded ~50% infection (green fluorescence) 73 h after infection of Raji and was selected for neutralization experiments. (FIG. 78B) EBV neutralization assay. Pooled terminal bleed sera from groups of five BALB/c mice immunized with EBVgp350/220-F VLP, UV-EBV or soluble recombinant gp350/220 ED were pre-incubated with EGFP-EBV to assess neutralization (Methods). Infected cells were incubated at 37° C. for 72 h at which time EGFP positive Raji cells were enumerated by cytometry. X-axis indicates neutralizing antibody source. Y-axis displays percent of EGFP+ Raji cells post-infection. Terminal sera or mAb controls were pre-incubated 1:1 with EGFP-EBV resulting in further virus dilution such that ~25% of Raji cells were maximally infected (fluoresced green) in the presence of the non-blocking mAb-2L10 or TNE. Pre-incubation with mAb-72A1 (neutralizing) served as the positive control. Results are expressed as mean±standard deviations (SD). Horizontal black lines terminating in short vertical lines compare sets of neutralization experiments with p values indicated above the line. Ogembo et al., *J. Trans. Med.* 2015; 13:50.

FIG. 79A-C. Schematic of construction and assembly of NDV NP as a carrier of EGFP into gp350/220/HR2 F VLPs. Schematic of (FIG. 79A) NP-EGFP chimera plasmid construction; (FIG. 79B) gp350/220-HR2 F plasmid construction showing full-length NDV-F (top), full-length wild type gp350/220 with splicing sites (middle) and chimeric gp350/220 NDV F HR2 (bottom); and (FIG. 79C) co-transfection of plasmids into CHO cells for assembly and release of VLPs.

FIG. 80A-B. Characterization of EBVgp350/220 VLPs incorporated with NDV-NP-EGFP. (FIG. 80A) Expression of EGFP in CHO cells transfected with pCAGGS-NDV-NP-EGFP detected by microscopy. (FIG. 80B) Immunoblot of VLPs purified from the supernatant of transfected CHO cells using mAh-72A1 (anti-gp350:220) as the detection antibody. Lysates were separated on a 4-12% gel. Purified EBV from B95-8-EGFP cells was used as a positive control.

FIG. 81. EBVgp350/220-HR2 F EGFP VLPs binds CD21 on Raji cells. Raji cells expressing complement receptor type 2 (CD21) were incubated with purified EBV, EBVgp350/220 F, EBVgp350/220-HR2 F, or EBVgp350/220-HR2 F NP-EGFP VLPs. Attachment of EBVgp350/220 VLPs was next detected directly with AF488-coupled anti-gp350/220 (mAb-2L10) that recognizes an epitope distal to the attachment site. The results were measured by flow cytometry.

FIG. 82A-D. Characterization of EBVgp350/220-EBNA1 VLPs. Purified EBVgp350/220-tEBNA1 VLPs were lysed in non-reducing Laemmli buffer and run on 4-20% SDS-agarose gel and proteins were detected via immunoblot. (FIG. 82A) mAb-72A1anti-gp350/220, (FIG. 82B) mAb anti DNA binding domain EBV-EBNA1 (a gift from Dr. F. Grässer. Institut für Virologie, Germany), (FIG. 82C) polyclonal anti-NDV, and (FIG. 82D) anti-EBNA1 Gly-Arg regions Abs were used to detect respective proteins.

FIG. 83A-E. Construction and schematic illustration of EBVgH/gL-NP-VLP production and immunoblot detection of EBVgp350/220-NP-tEBNA1 VLPs. Construction and schematic of: (FIG. 83A) EBV gH-F, (FIG. 83B) EBV gL-HN, and (FIG. 83C) NP-tEBNA1 plasmids for VLP production. (FIG. 83D) EBVgp350/220-tEBNA1 VLPs were produced as outlined in FIG. 73. Purified EBVgp350/220-tEBNA1 VLPs were lysed on non-reducing Laemmli buffer and run on 4-20% SDS-agarose gel followed by silver stain (FIG. 83D) and immunoblot (FIG. 83E). Polyclonal anti-NDV (top panel), mAb anti DNA binding domain EBV-EBNA1 (a gift from Dr. F. Grässer, Institut für Virologie, Germany, second panel), mAb-72A1 anti-gp350/220 (third panel) and anti-EBNA1 Gly-Arg regions (bottom panel) Abs were used to detect respective proteins.

FIG. 84A-B. Construction and schematic illustration of EBVgB-NPLMP2 VLP or EBVgB-NP-fEBNA1-LMP2 VLP production. Schematic illustration of (FIG. 84A) NDV-F, EBVgB, EBVgB-F, NP-LMP2 and NO-tEBNA1-LMP2 plasmids for VLP production. (FIG. 84B) Schematic of cDNAs pCAGGS-NDV-M, -NP-tEBNA1-LMP2 or NP-LMP2, and -gB-F chimera co-transfected into CHO cells for VLP production.

FIG. 85. Chimeric EBVgB-NDV F is well expressed on the surface of CHO cells. High expression of EBVgB-WT, EBVgB His and EBVgB-F on the surface of CHO cells. $10^6$ cells were transfected with 1 μg of EBVgB-WT, EBVgB His and EBVgB-F or pCAGGS alone (vector control). At 72 h post-transfection, cells were stained with mAb anti-gB (clone CL55) followed by AF488-coupled goat anti-mouse IgG (H+L) and analyzed by flow cytometry.

FIG. 86A-C. Characterization of EBVgB-F NP-LMP2 and EBVgB-F NP-EBNA1 proteins were incorporated in VLPs. Characterization of EBVgp350/220-EBNA1 VLPs. Purified VLPs were lysed on non-reducing Laemmli buffer and run on 4-20% SDS-agarose gel followed by immunoblot. (FIG. 86A) mAb-CL55 and BA23 anti-B (top and middle panels), polyclonal anti-NDV bottom panel), (FIG. 86B)mAb anti EBV-LMP2 (top panel), and polyclonal anti-NDV (bottom panel) Abs were used to detect respective proteins. (FIG. 86C) Silver stain of increasing amounts of purified chimeric VLPs released from CHO cells compared with NDV. The position of EBVgB-F LMP2 protein, NDV-NP and -M are indicated by arrows. Molecular weight markers are indicated at left.

FIG. 87. Experimental layout and immunization of BALB/c mice with VLPs carrying EBV glycoproteins. BALB/c mice were immunized with 10 μg of EBVgH/gL-EBNA1 VLP, EBVgB-LMP2 VLP, or UV-inactivated EBV and boosted twice at days 26 and 56 without adjuvants. TNE served as a negative control for immunogen. At day 161 mice were sacrificed.

FIG. 88. Splenocytes from mice immunized with EBVgH/gL-EBNA1 VLPs and EBVgB-LMP2 VLPs generated significantly higher IFN-γ than mice immunized with UV-inactivated EBV and EBVgp350/220 VLPs. BALB/c mice were immunized with 10 μg of EBVgH/gL-EBNA1 VLP, EBVgB-LMP2 VLP, or UV-inactivated EBV and boosted twice at days 29 and 54 without adjuvants. TNE served as a negative control for immunogen. At day 161 mice were sacrificed and $5\times10^5$ splenocytes were stimulated in vitro with the corresponding as well as control peptides. 1 μg/mL of synthetic peptides derived from $EBNA1_{-(HPVGEADYFEY)}$, $LMP2_{-(CLGGLLTMV)}$ or Promix EBV peptide pool consisting of 26 peptides, each corresponding to a defined HLA class 1-restricted T cell epitope from EBV were used in the assay. After overnight culturing, the supernatants were tested for IFN-γ release by ELISA. SIINFEKL ovalbumin was used as a negative control and concavalin A and IL1B were used as model antigens.

DEFINITIONS

To facilitate understanding of the invention, a number of terms are defined below.

The term "recombinant" molecule refers to a molecule that is produced using molecular biological techniques. Thus, "recombinant DNA molecule" refers to a DNA molecule that is comprised of segments of DNA joined together by means of molecular biological techniques. A "recombinant protein" or "recombinant polypeptide" as used herein refers to a protein molecule that is expressed using a recombinant DNA molecule. A "recombinant" virus-like particle (VLP) refers to a VLP that is expressed using a recombinant DNA molecule.

Figure 4:
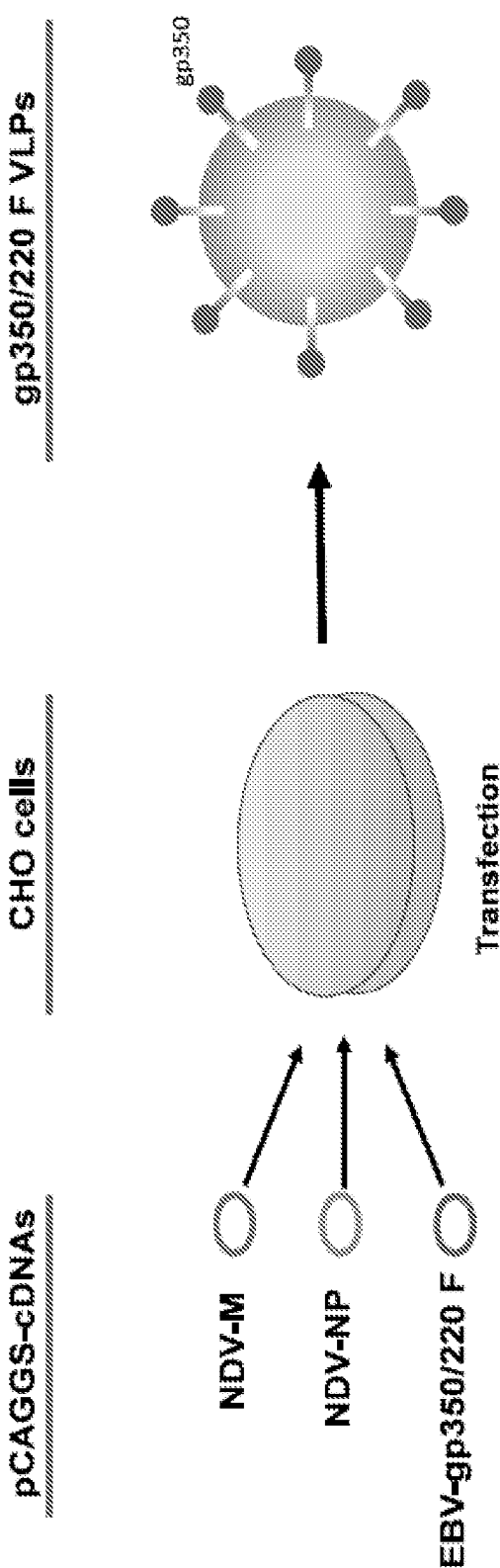
Figure 5:
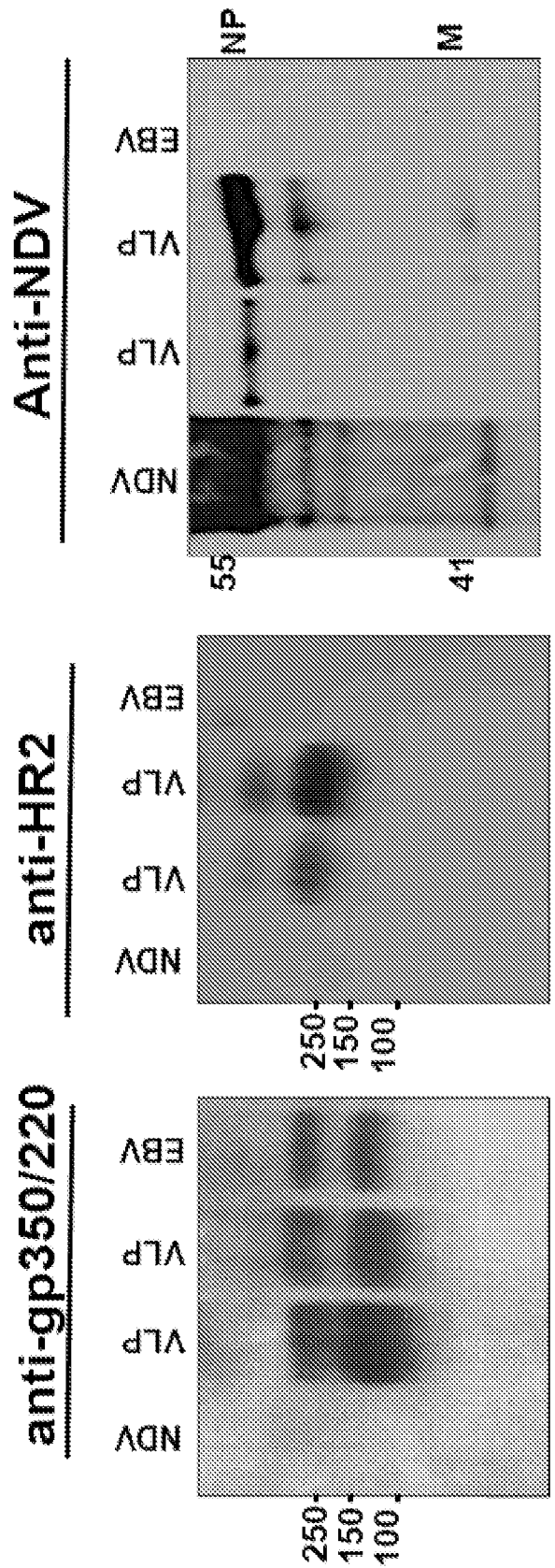
Figure 7:
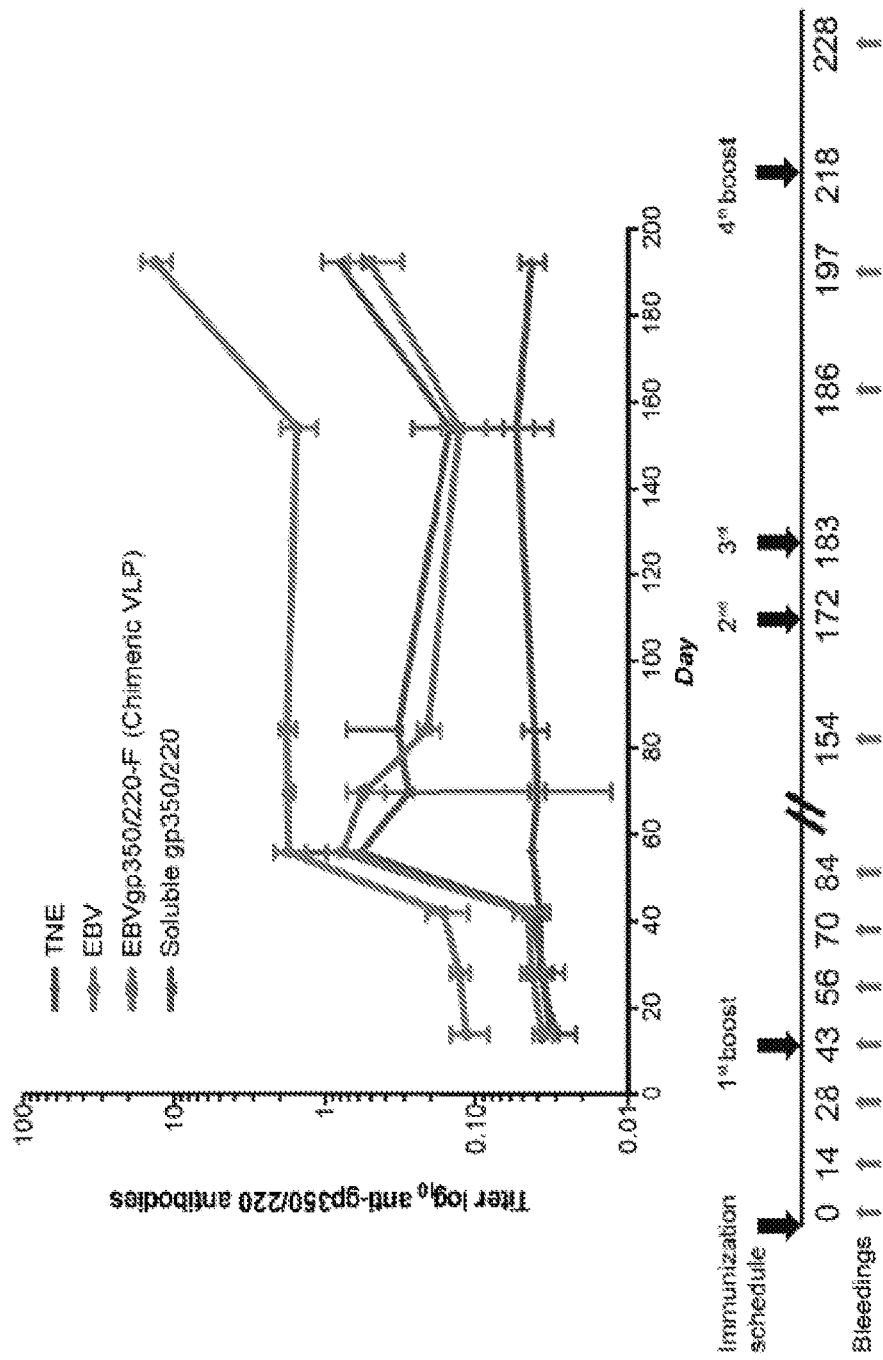

A "virus-like particle" and "VLP" interchangeably refer to a non-replicating, non-infectious particle shell that contains one or more virus proteins, lacks the viral RNA and/or DNA genome, and that approximately resembles live virus in external conformation. Methods for producing and characterizing recombinant VLPs containing Newcastle Disease Virus (NDV) proteins have been described (Pantua et al. (2006) J. Virol. 80:11062-11073; U.S. Pat. No. 7,951,384 issued to Morrison et al. on May 1, 2011; U.S. Pat. No. 8,974,797, issued to Morrison on Mar. 10, 2015, each of which is incorporated by reference). Further methods for producing NDV VLPs are disclosed herein.

The term "inside" a VLP when made in reference to the location of a polypeptide sequence means that the polypeptide sequence is located on the inner surface of the virus-like particle, and is encapsulated by the virus-like particle such that the polypeptide sequence is not exposed on the outside surface of the virus-like particle. Preferably, though not necessarily, the polypeptide that is inside the VLP is not accessible to binding with antibodies that are present outside the VLP.

"Operable combination" and "operably linked" when in reference to the relationship between nucleic acid sequences and/or amino acid sequences refers to linking (i.e., fusing) the sequences in frame such that they perform their intended function. For example, operably linking a promoter sequence to a nucleotide sequence of interest refers to linking the promoter sequence and the nucleotide sequence of interest in a manner such that the promoter sequence is capable of directing the transcription of the nucleotide sequence of interest and/or the synthesis of a polypeptide encoded by the nucleotide sequence of interest.

The term "matrix protein", "membrane protein", or "M protein" as used herein, means any protein localized between the envelope and the nucleocapsid core and facilitates the organization and maintenance of the virion structure and budding processes. Exemplary NDV M protein sequences include those described in U.S. Pat. No. 7,951,384 issued to Morrison et al. on May 1, 2011; U.S. Pat. No. 8,974,797, issued to Morrison on Mar. 10, 2015, each of which is incorporated by reference.

The term "nuclcocapsid protein" or "NP protein" as used herein, means any protein that associates with genomic RNA (i.e., for example, one molecule per hexamer) and protects the RNA from nuclease digestion. Exemplary NP protein sequences from NDV include those described in U.S. Pat. No. 7,951,384 issued to Morrison et al. on May 1,2011; U.S. Pat. No. 8,974,797, issued to Morrison on Mar. 10, 2015, each of which is incorporated by reference.

The term "fusion protein" or "F protein" as used herein, means any protein that projects from the envelope surface and mediates host cell entry by inducing fusion between the viral envelope and the cell membrane. However, it is not intended that the present invention be limited to functional F proteins. For example, an F protein may be encoded by a mutant F gene such as, but not limited to, F-K115Q. F-K115Q is believed to eliminate the normal cleavage and subsequent activation of the fusion protein. F-K115Q mimics naturally occurring F-protein mutations in avirulent NDV strains, and in cell culture, eliminates any potential side effects of cell-cell fusion on the release of VLPs. Exemplary NDV F protein sequences include those described in U.S. Pat. No. 7,951,384 issued to Morrison et al. on May 1, 2011; U.S. Pat. No. 8,974,797, issued to Morrison on Mar. 10, 2015, each of which is incorporated by reference.

"HR2 domain," "heptad repeat domain 2," "HR-B domain," and "heptad repeat domain B" interchangeably refer to a sequence that is present in the F protein of a Paramyxovirus, and that folds as an amphipathic alpha helix. The HR2 domain of NDV is exemplified by those described in U.S. Pat. No. 8,974,797, issued to Morrison on Mar. 10, 2015, incorporated by reference.

The term "haemagglutinin-neuraminidase protein", "HN protein", or G protein as used herein, means any protein that spans the viral envelope and projects from the surface as spikes to facilitate cell attachment and entry (i.e., for example, by binding to sialic acid on a cell surface). These proteins possess both haemagglutination and neuraminidase activity. Exemplary NDV HN protein sequences include those described in U.S. Pat. No. 7,951,384 issued to Morrison et al. on May 1, 2011; U.S. Pat. No. 8,974,797, issued to Morrison on Mar. 10, 2015, each of which is incorporated by reference.

The term "glycoprotein" as used herein, refers to any protein conjugated to a carbohydrate.

Figure 48:
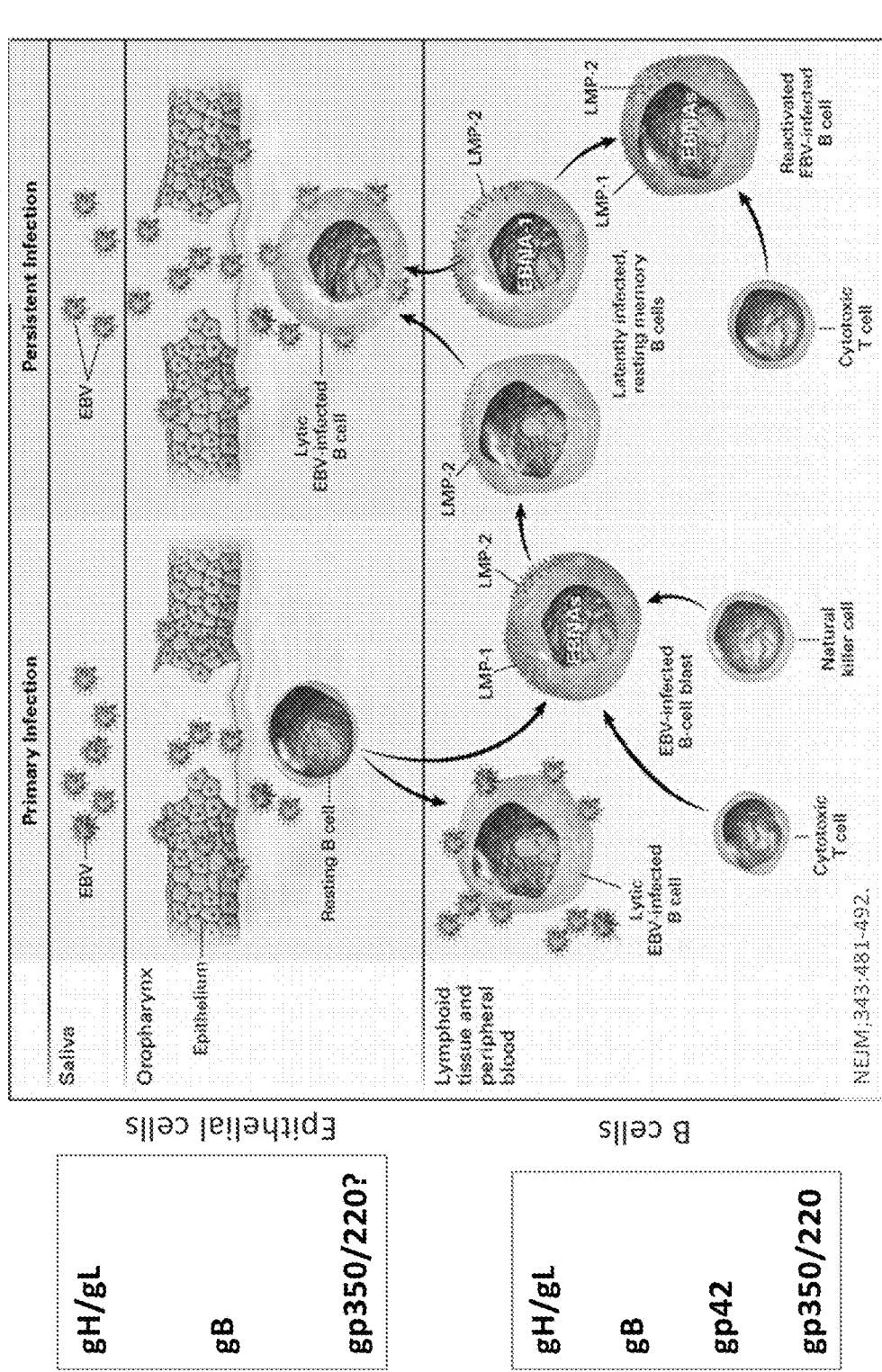
FIG. 48. EBV entry pathways.

"Epstein-Barr Virus," "EBV," "human herpesvirus 4" and "HHV-4" interchangeably refer to an oncogenic human herpesvirus. EBV is the cause of acute infectious mononucleosis (AIM, also known as glandular fever). It is also associated with particular forms of cancer, such as Hodgkin's lymphoma. Burkitt's lymphoma, nasopharyngeal carcinoma, and conditions associated with human immunodeficiency virus (HIV), such as hairy leukoplakia and central nervous system lymphomas. EBV infects B cells of the immune system and epithelial cells. Once the virus's initial lytic infection is brought under control, EBV latently persists in the individual's B cells for the rest of the individual's life due to a complex life cycle (FIG. 48) that includes alternate latent find lytic phases.

"Symptom of EBV infection" includes acute infectious mononucleosis (AIM, also known as glandular fever) and/or the presence of EBV-associated cancer. "EBV-associated cancer" refers to cancer that is caused and/or aggravated, at least in part, by infection with EBV, such as Hodgkin's lymphoma, Burkitt's lymphoma, nasopharyngeal carcinoma, cervical cancer, hairy leukoplakia and central nervous system lymphomas.

The terms "antigen," "immunogen," "antigenic," "immunogenic," "antigenically active," and "immunologically active" when made in reference to a molecule, refer to any substance that is capable of inducing a specific humoral and/or cell-mediated immune response. In a particular embodiment, the antigen comprises at least a portion or an ectodomain.

The term "ectodomain" when in reference to a membrane protein refers to the portion of the protein that is exposed on the extracellular side of a lipid bilayer of a cell, virus and the like.

"EBV antigen" refers to an antigen from EBV, such as "gB, gH, gL, and gp350/220" and tumor-associated EBV antigens.

The term "gB" refers to glycoprotein gp110 precursor of Human herpesvirus 4 and is exemplified in FIG. 55 (SEQ ID NO.02), NCBI Reference Sequence: YP_401713.1.

The term "gH" refers to glycoprotein gp85 precursor of human herpesvirus 4 and is exemplified by in FIG. 56 (SEQ ID NO:03), NCBI Reference Sequence: YP_401700.1.

The term "gL" and "BKRF2" are interchangeably used, and exemplified in FIG. 57 by BKRF2 protein of human herpesvirus 4 type 2 (SEQ ID NO:04), NCBI Reference Sequence: YP_001129472.1.

The term "gp350/220" is the predominant EBV envelope protein. Interactions between EBVgp350/220 and complement receptor type 2 (CR2)CD21 and/or (CR1)CD35 on B-cells is required for cellular attachment and initiation of latent infection.

"Tumor-associated EBV antigens" are EBV antigens that are associated with tumors in subjects who are infected with EBV. Exemplary tumor-associated EBV antigens include EBNA1, LMP1, LMP2, and BARF1, those described in Lin et al. "CD4 and CD8 T cell responses to tumor-associated Epstein-Barr virus antigens in nasopharyngeal carcinoma patients." Cancer Immunol Immunother. 2008 July; 57(7): 963-75; Kohrt et al. "Dynamic CD8 T-cell responses to tumor-associated Epstein-Barr virus antigens in patients with Epstein-Barr virus-negative Hodgkin's disease," Oncol Res. 2009; 18(5-6):287-92; Parmita et al., "Humoral immune responses to Epstein-Barr virus encoded tumor associated proteins and their putative extracellular domains in nasopharyngeal carcinoma patients and regional controls," J Med Virol. 2011 April; 83(4):665-78.

Figure 8:
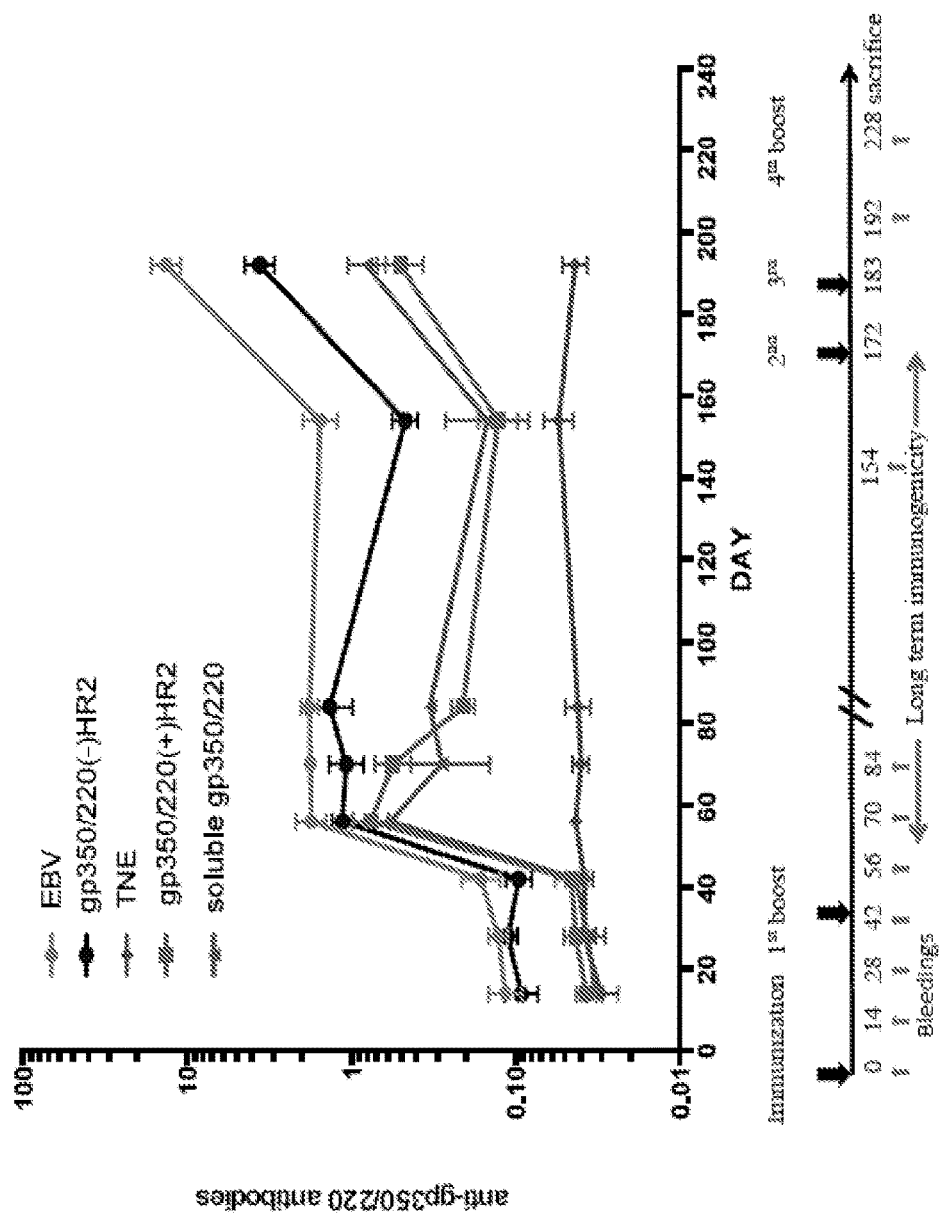
Figure 11:
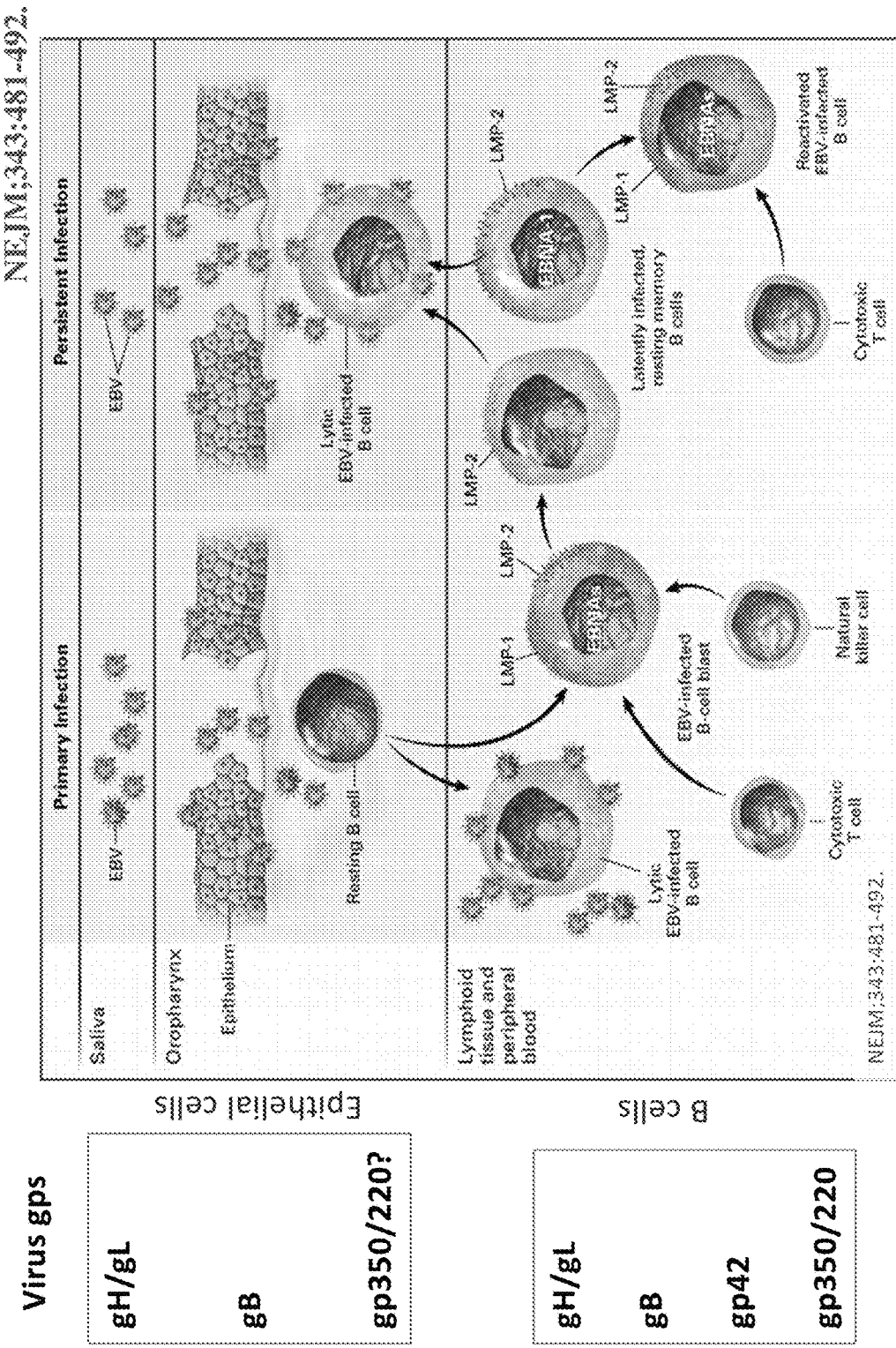
Figure 15:
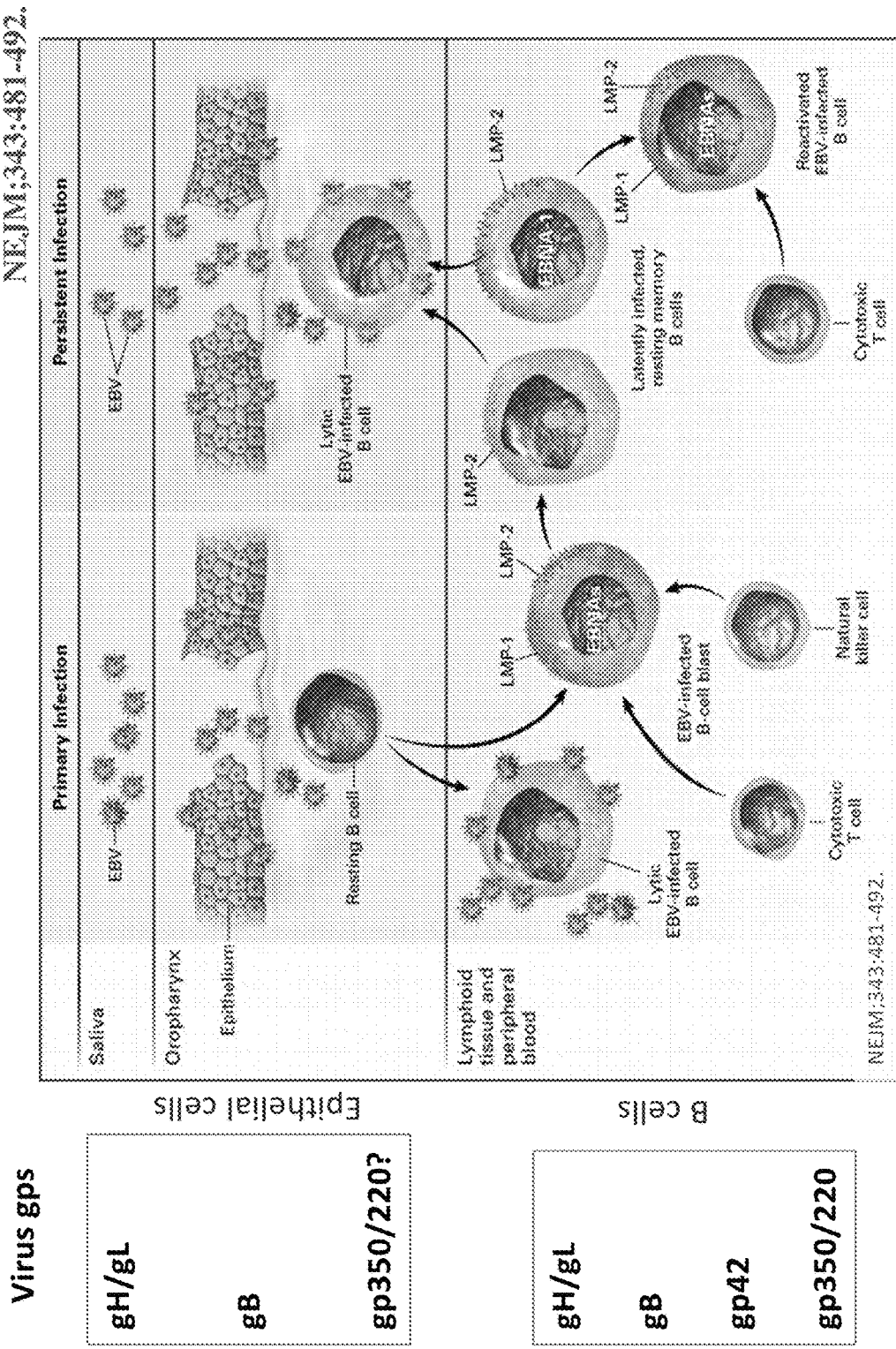
Figure 16:
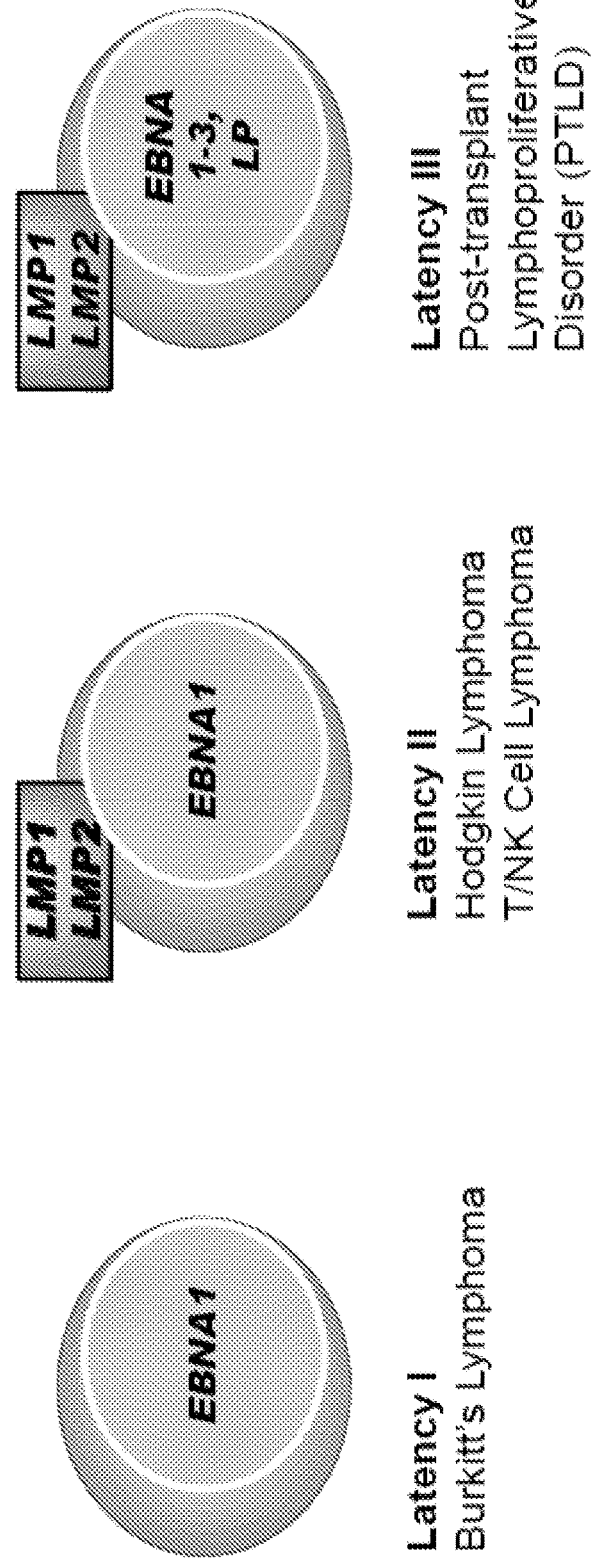
Figure 20:
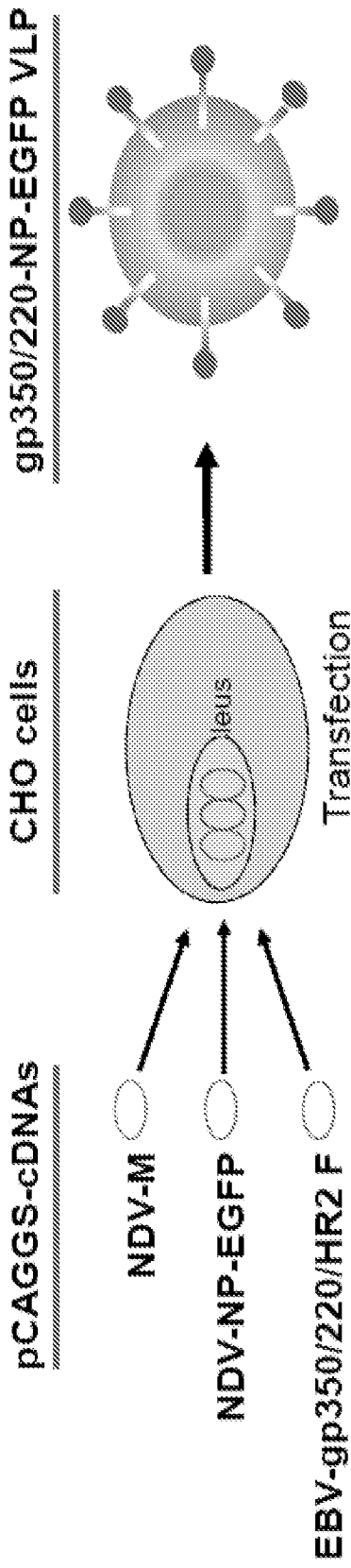
Figure 21:
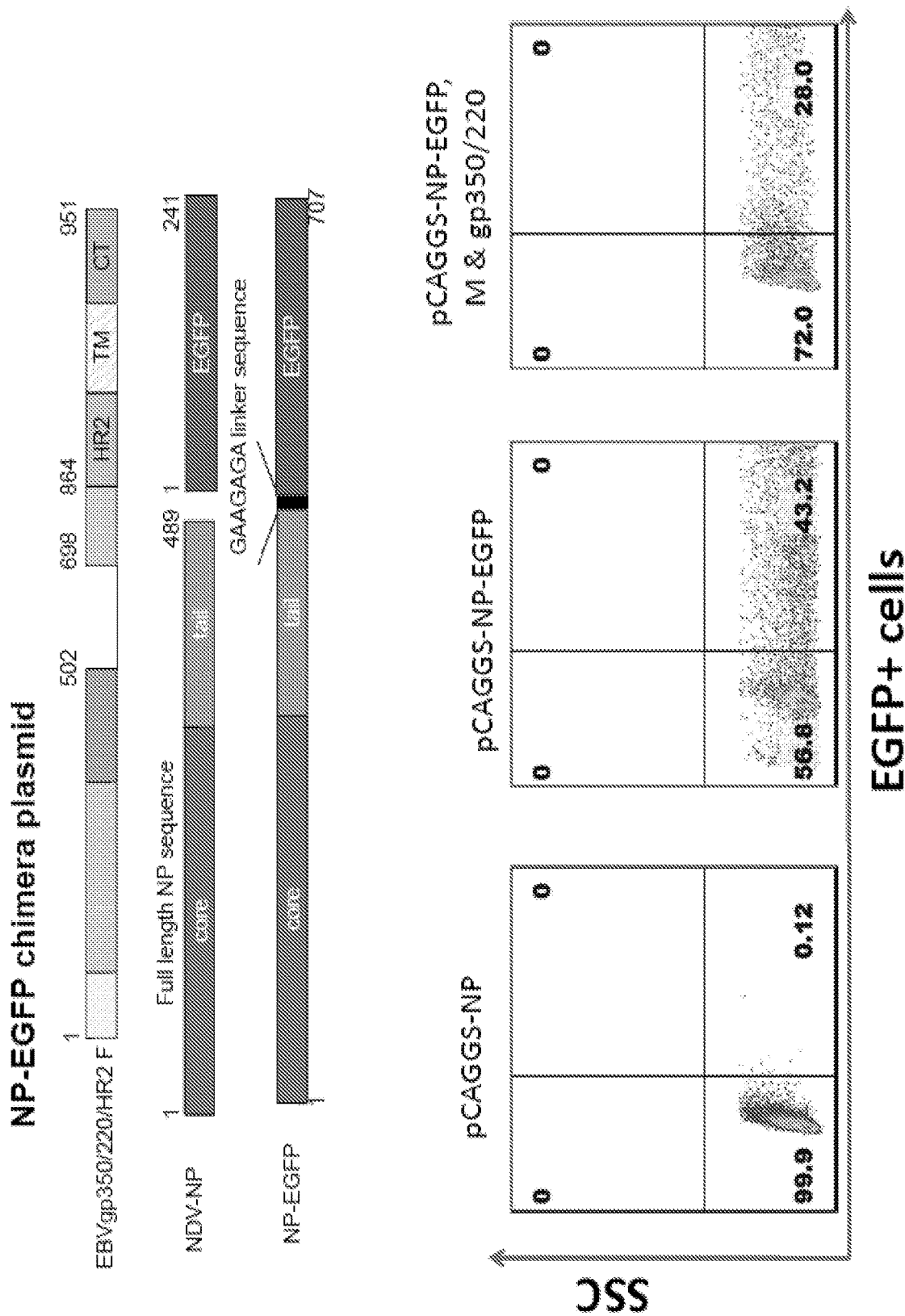
Figure 22:
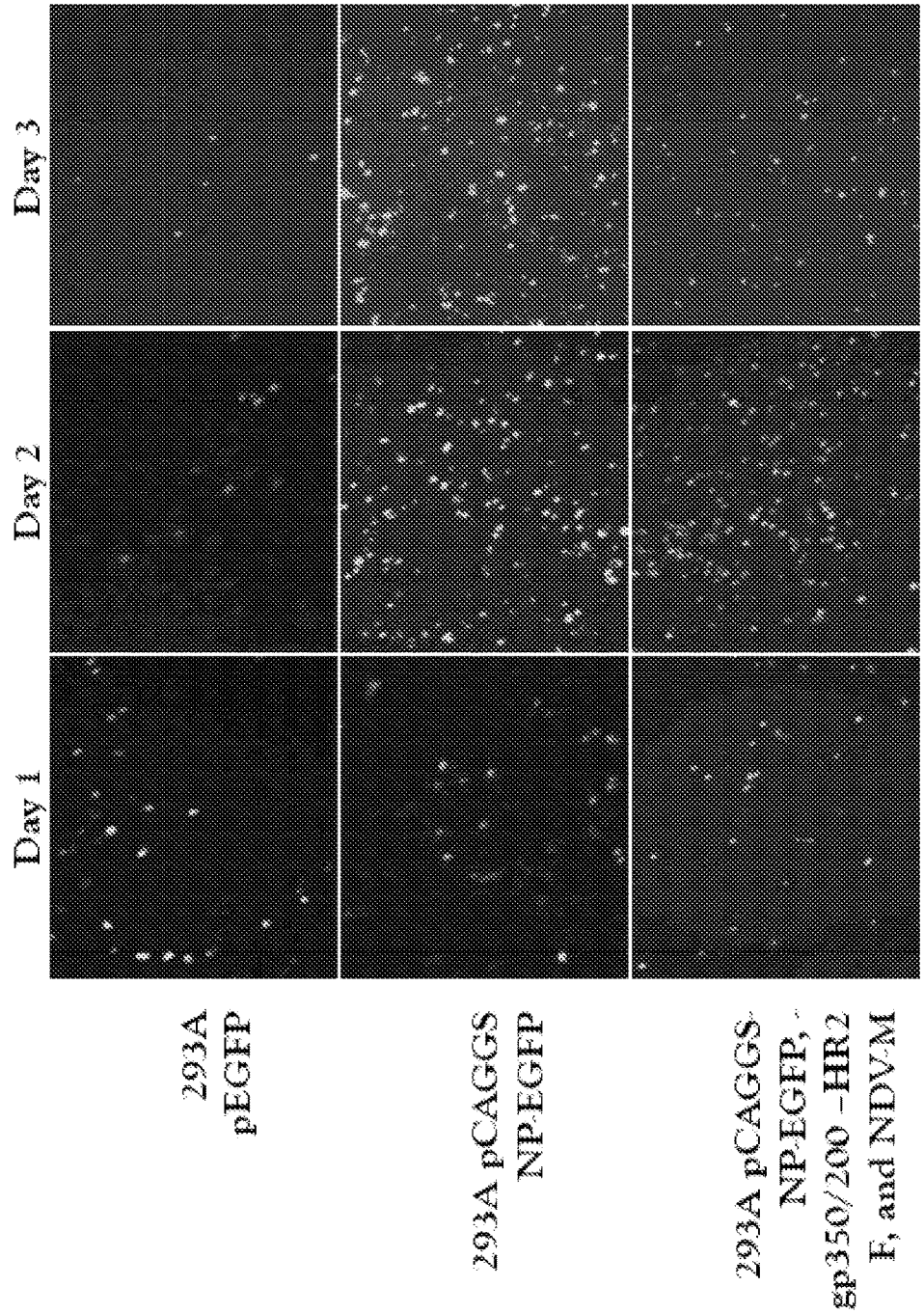
Figure 23:
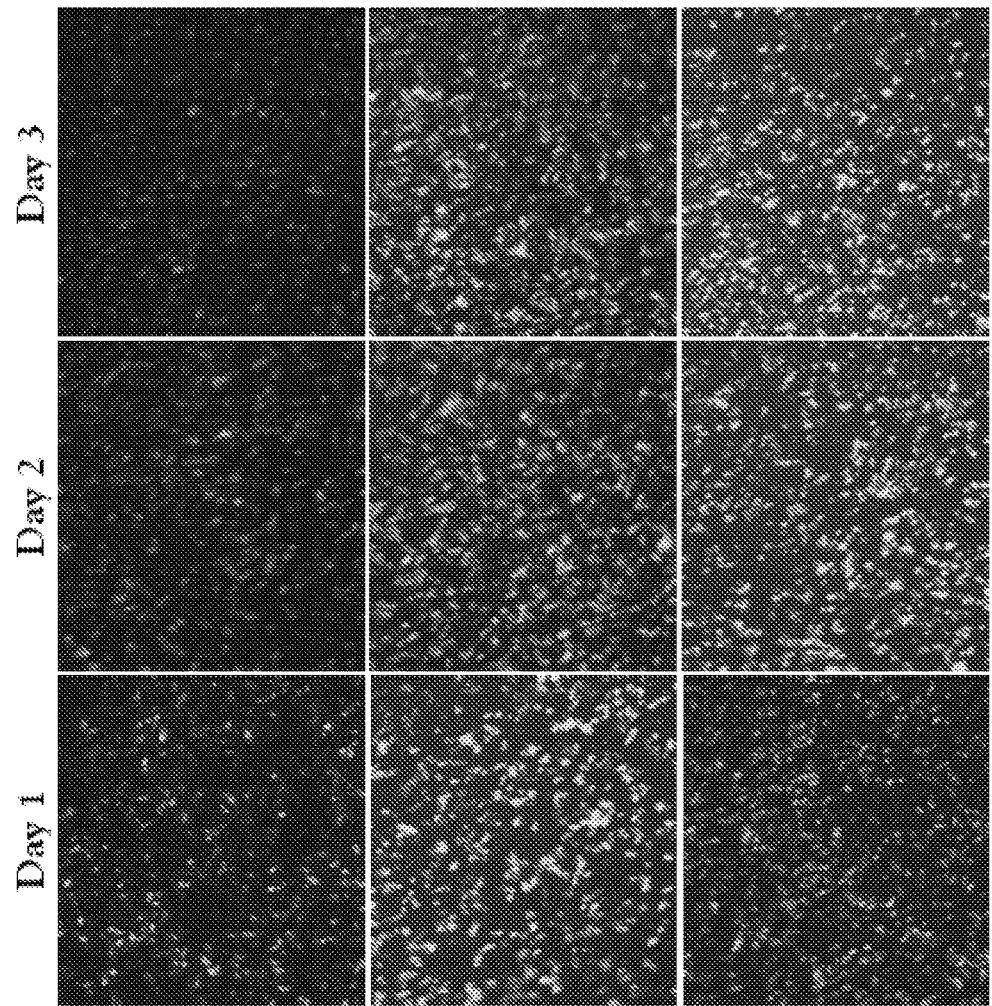
Figure 24:
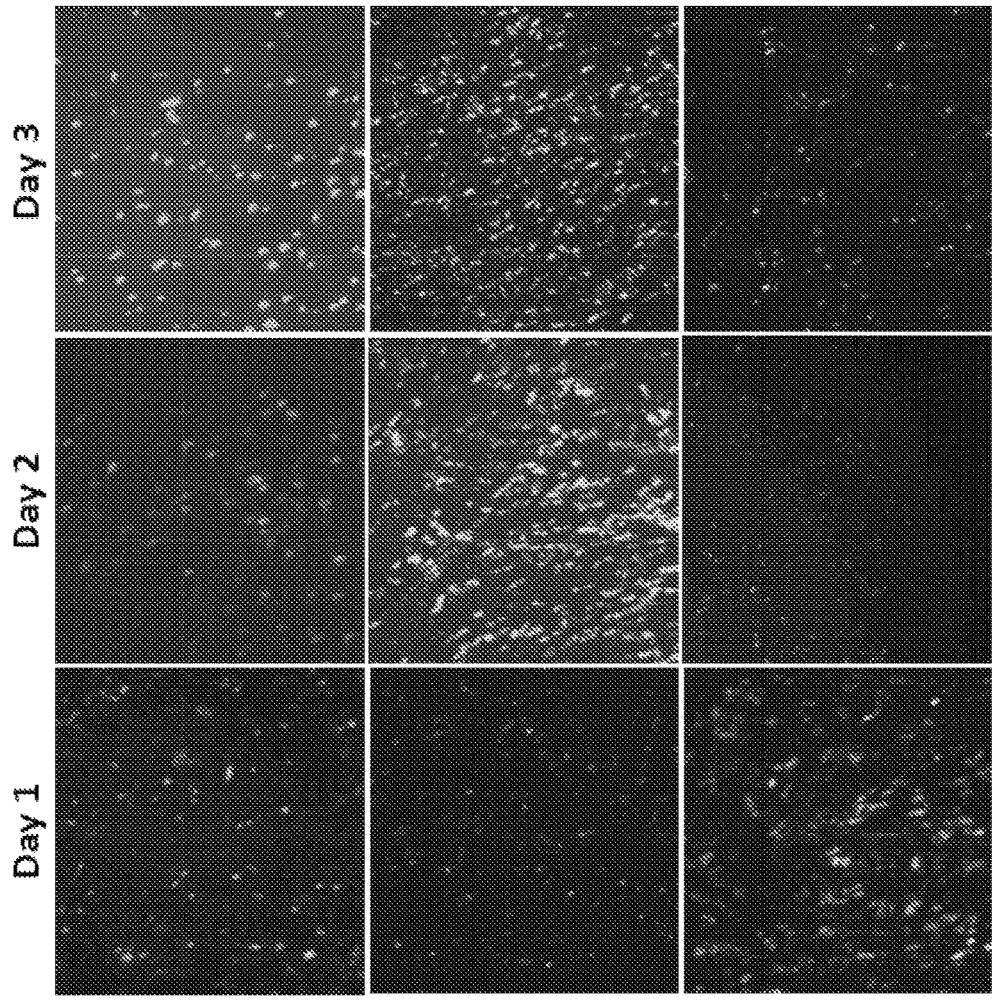
Figure 25:
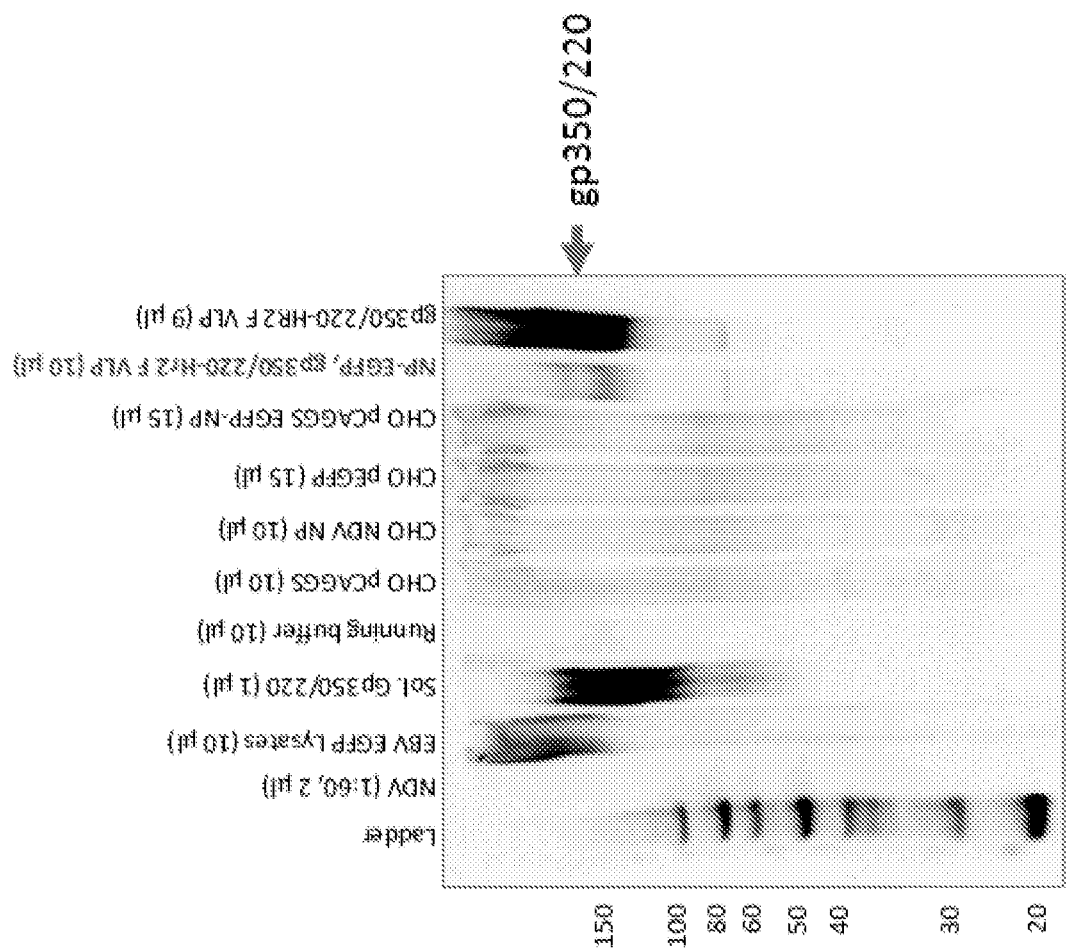
Figure 26:
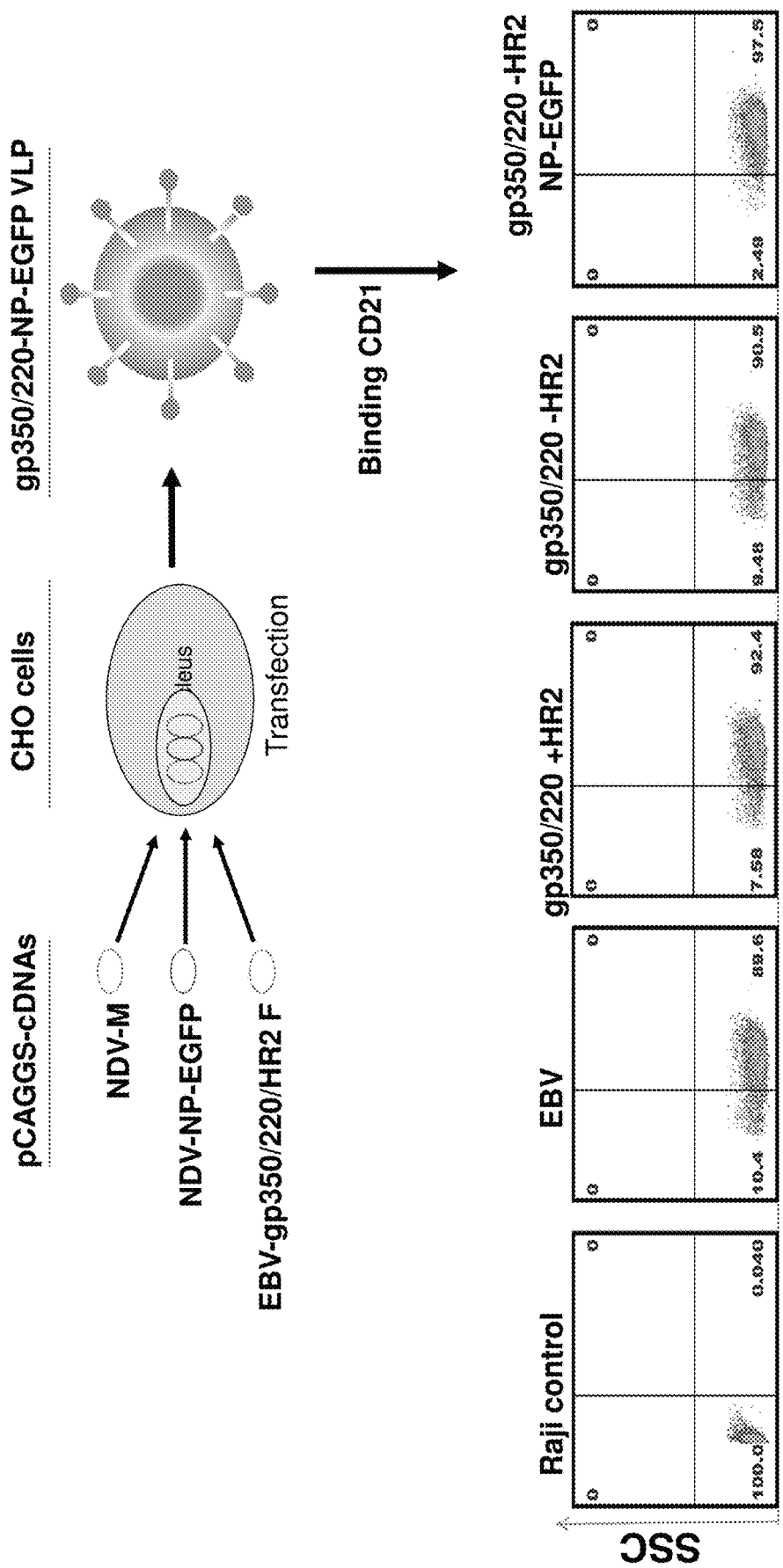
Figure 27:
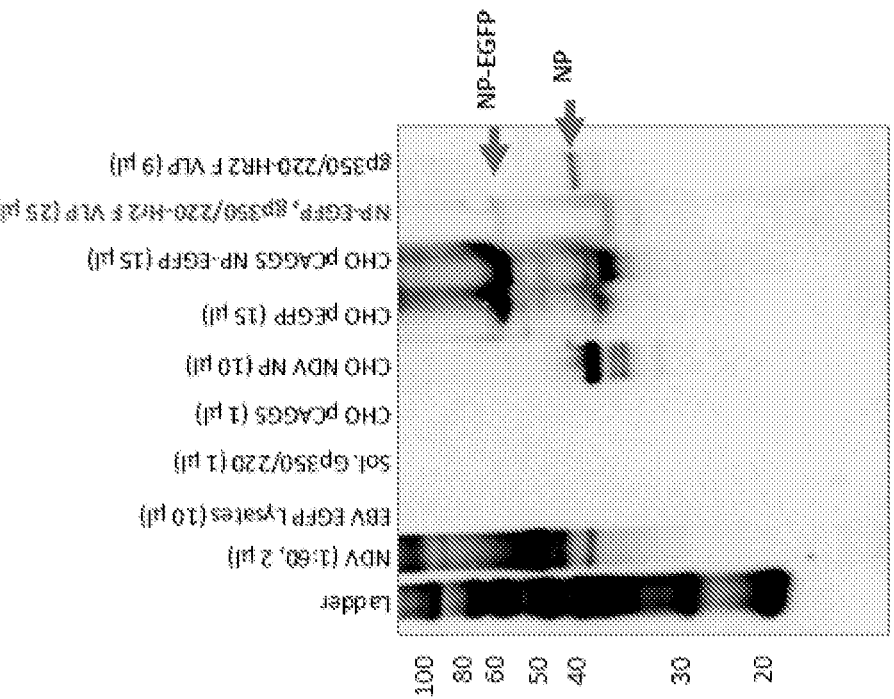
Figure 28:
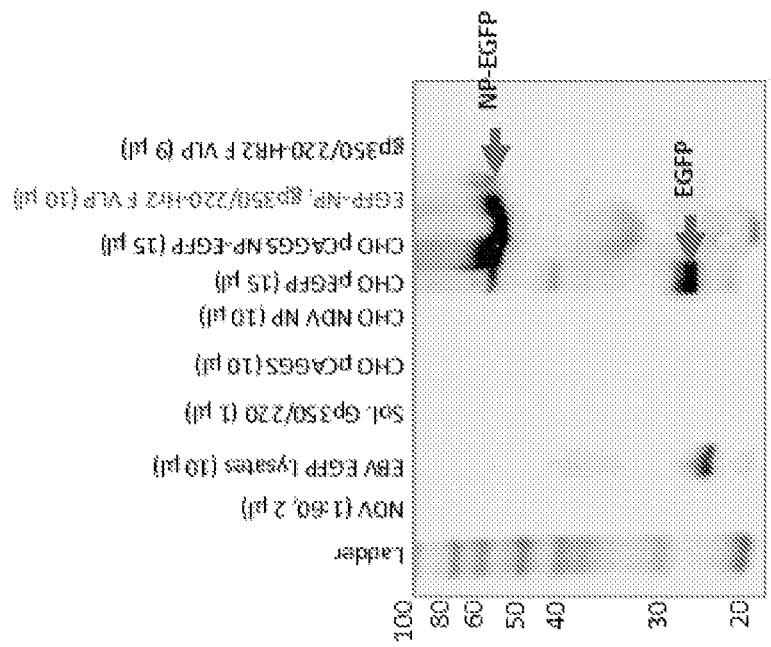
Figure 32:
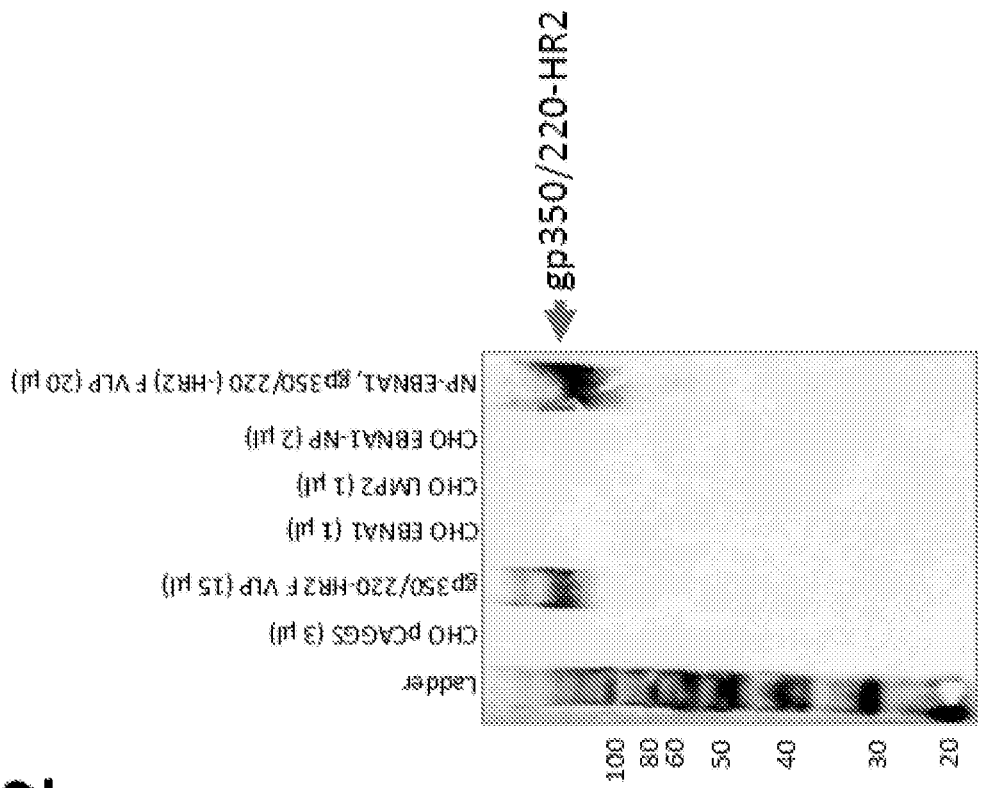
Figure 33:
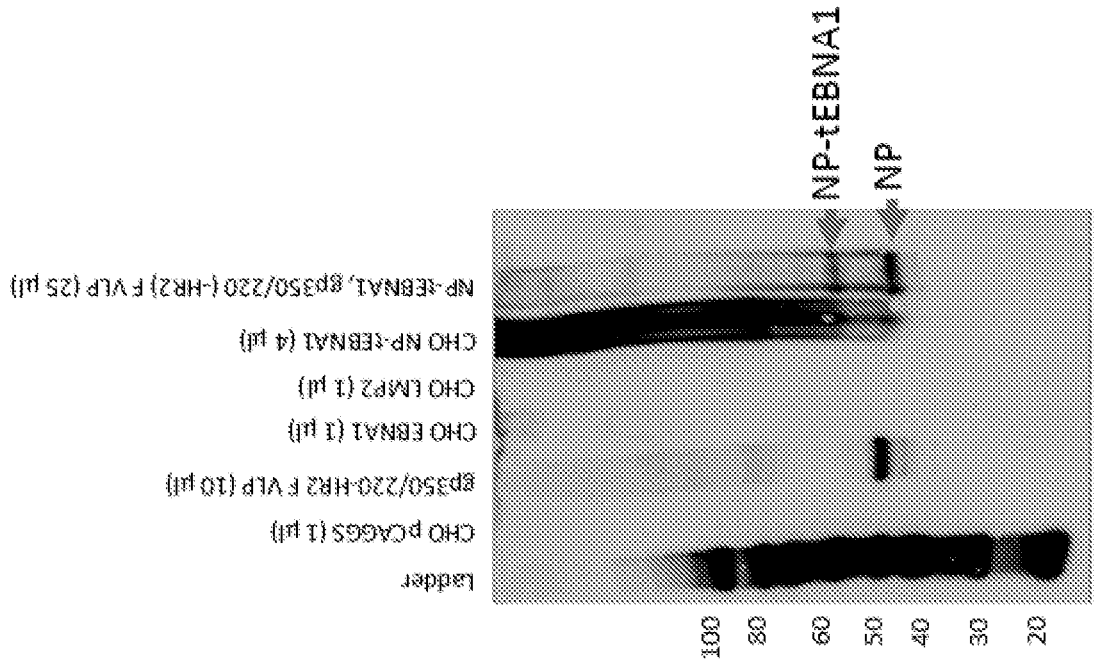
Figure 34:
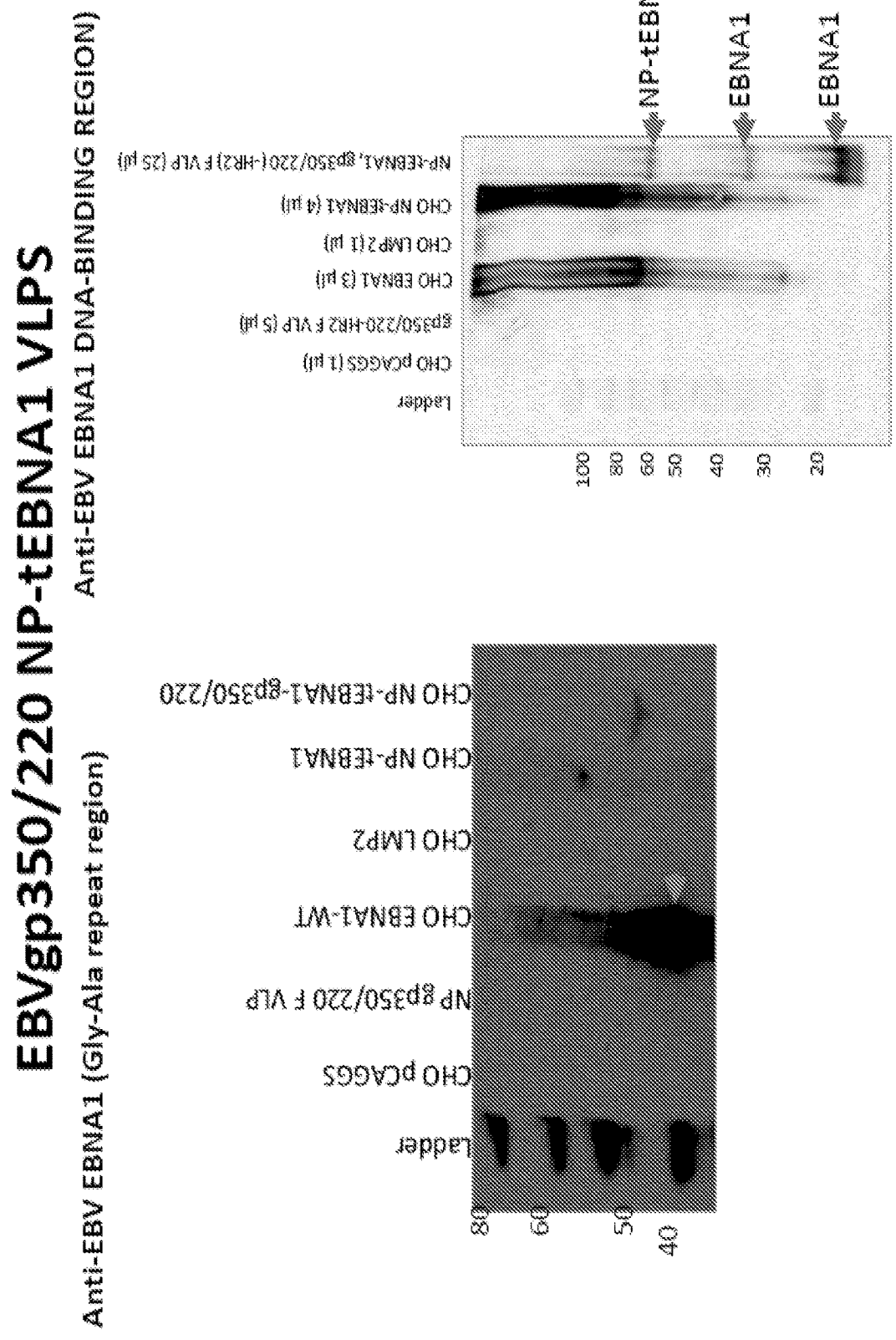
Figure 36:
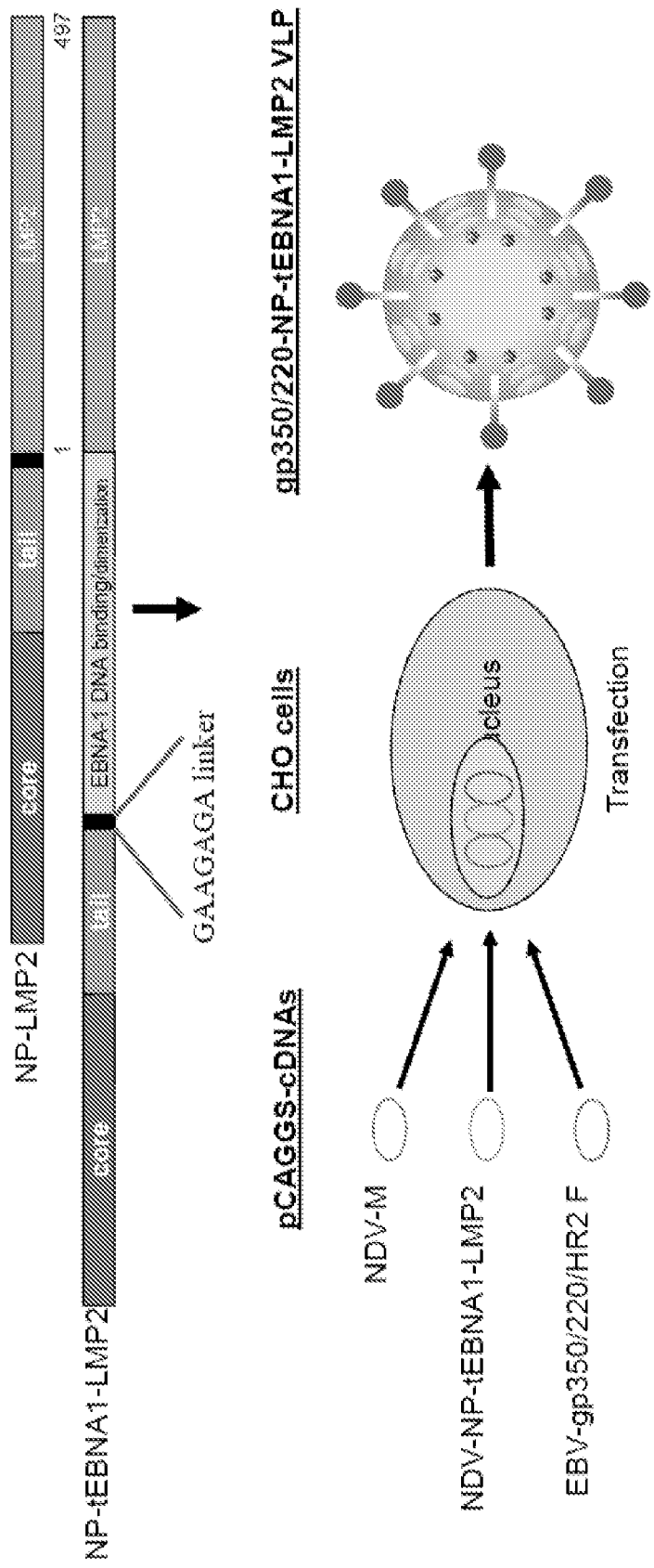
Figure 39:
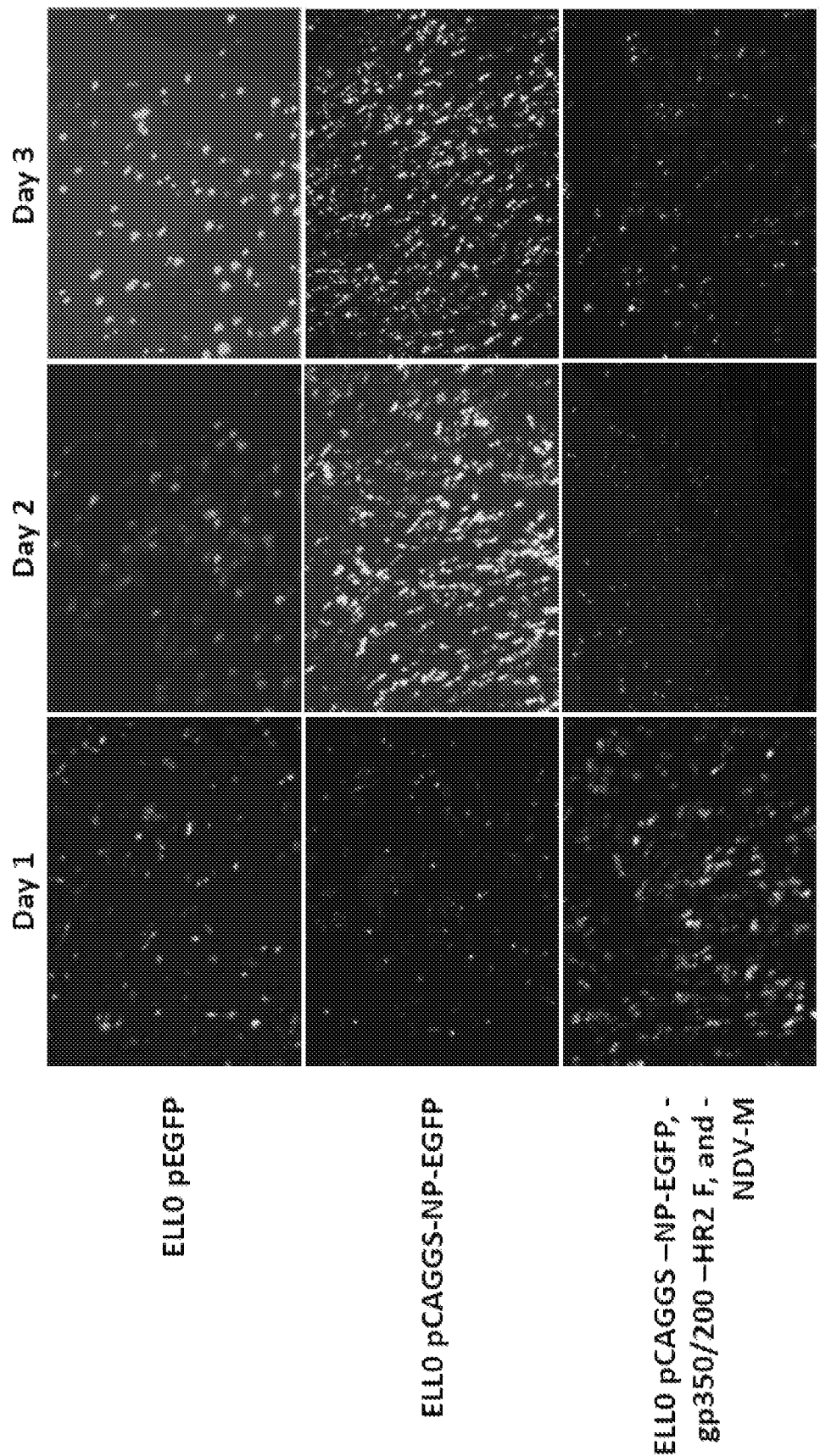
Figure 40:
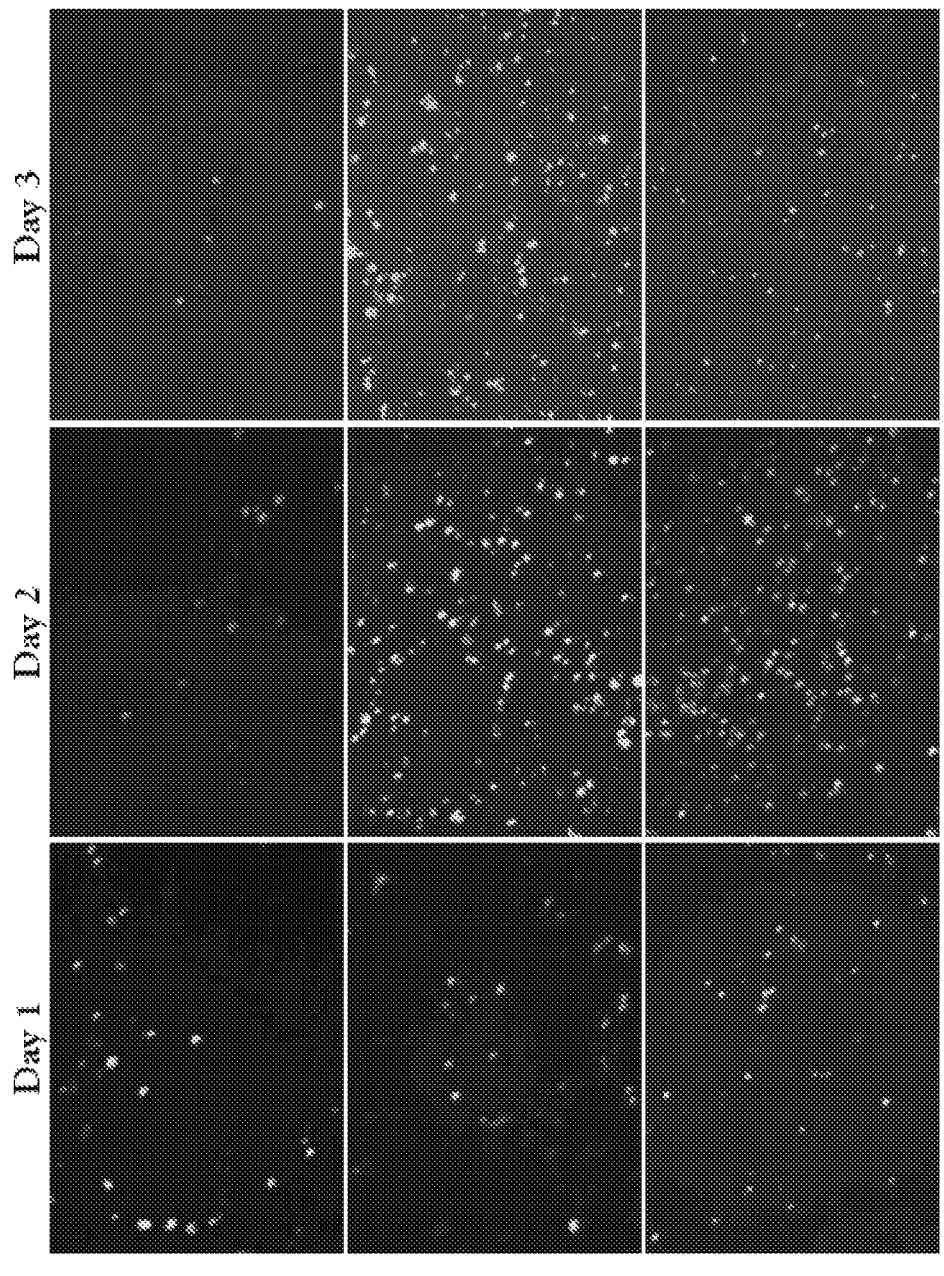
Figure 41:
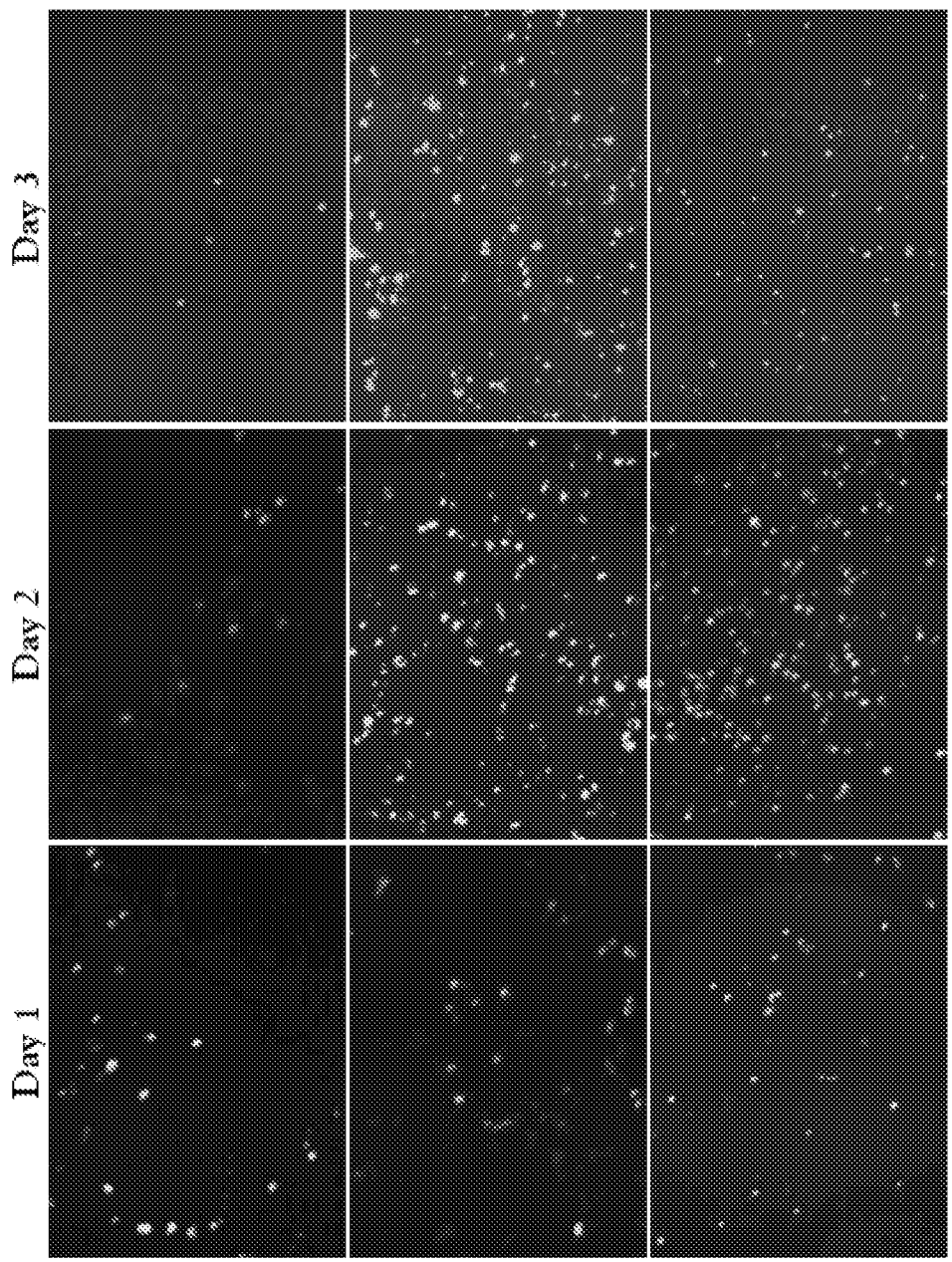
Figure 42:
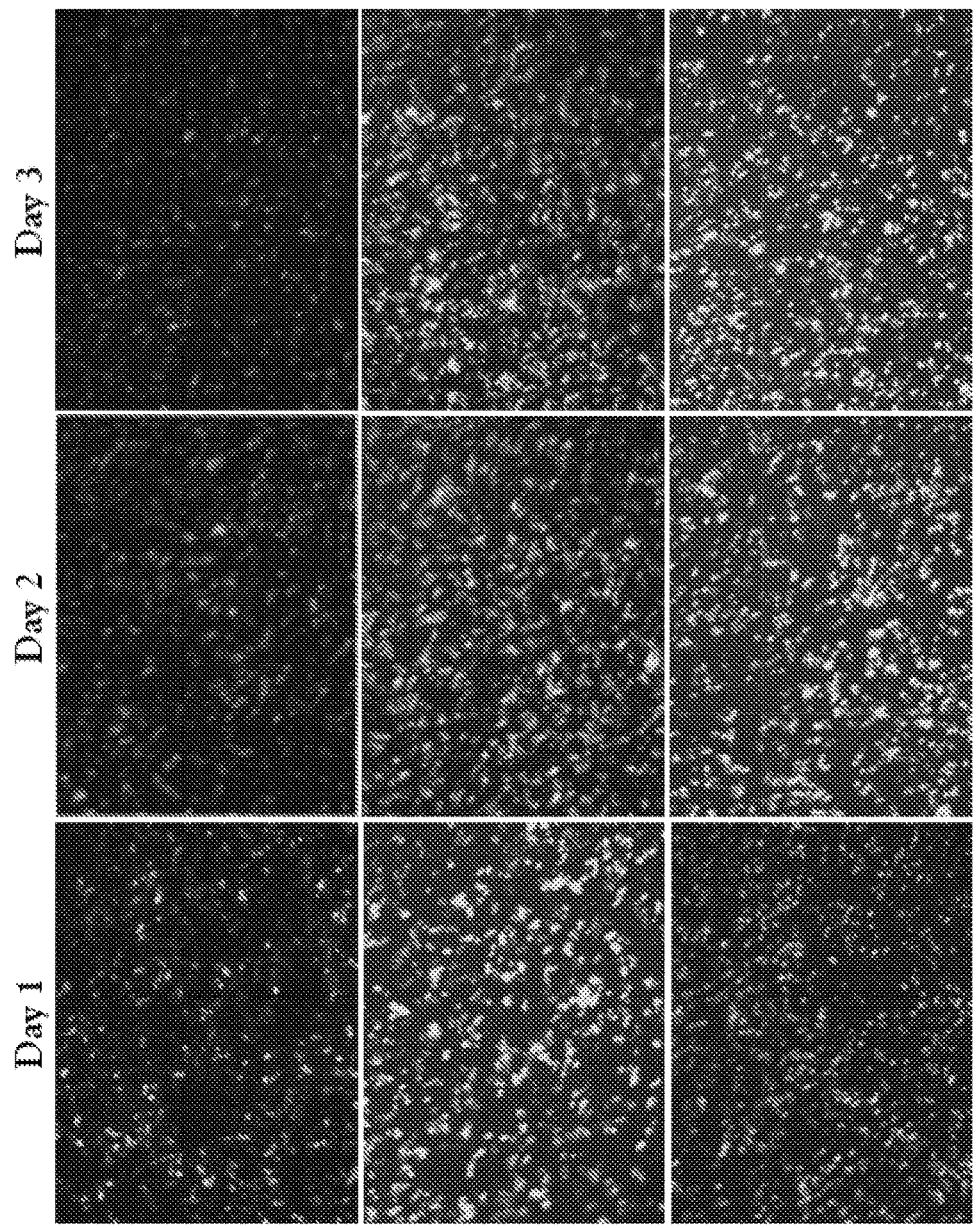
Figure 43:
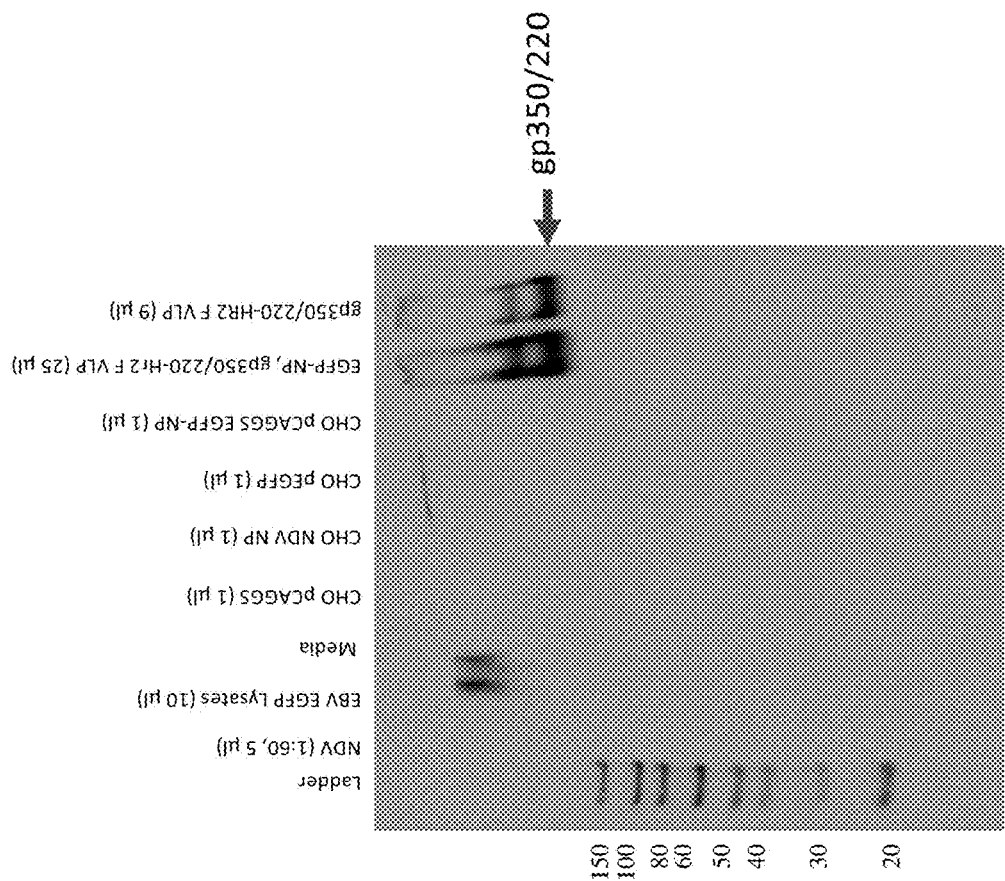
Figure 44:
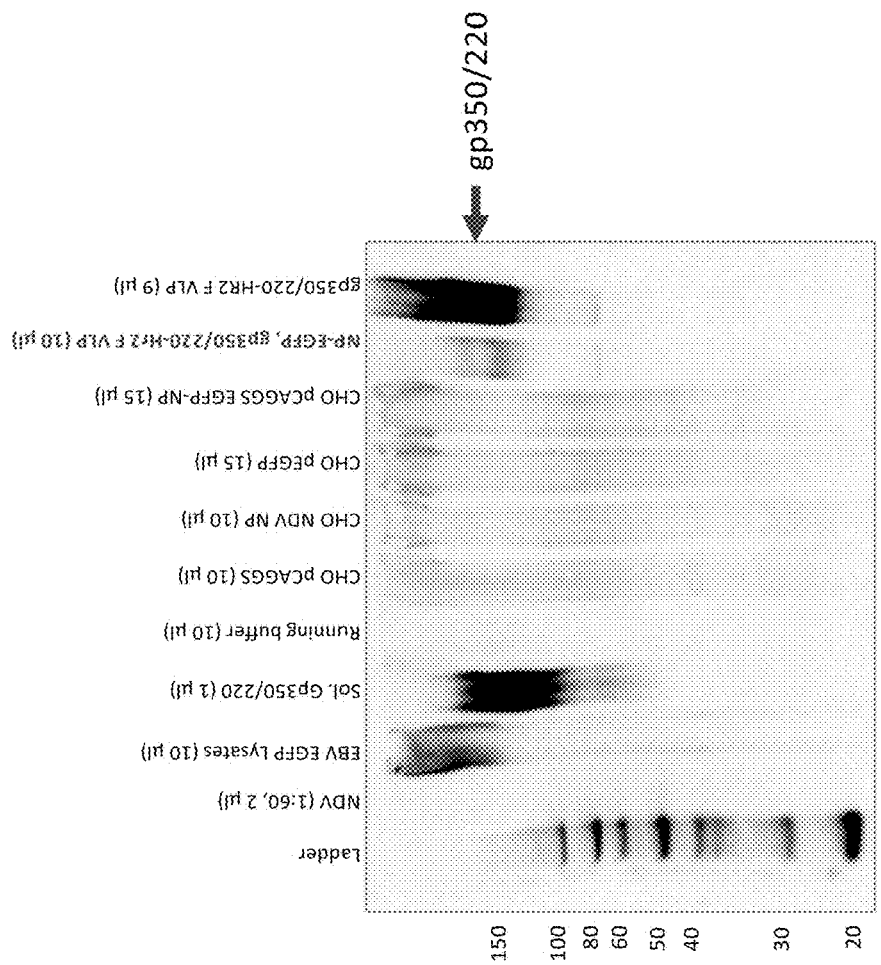
Figure 45:
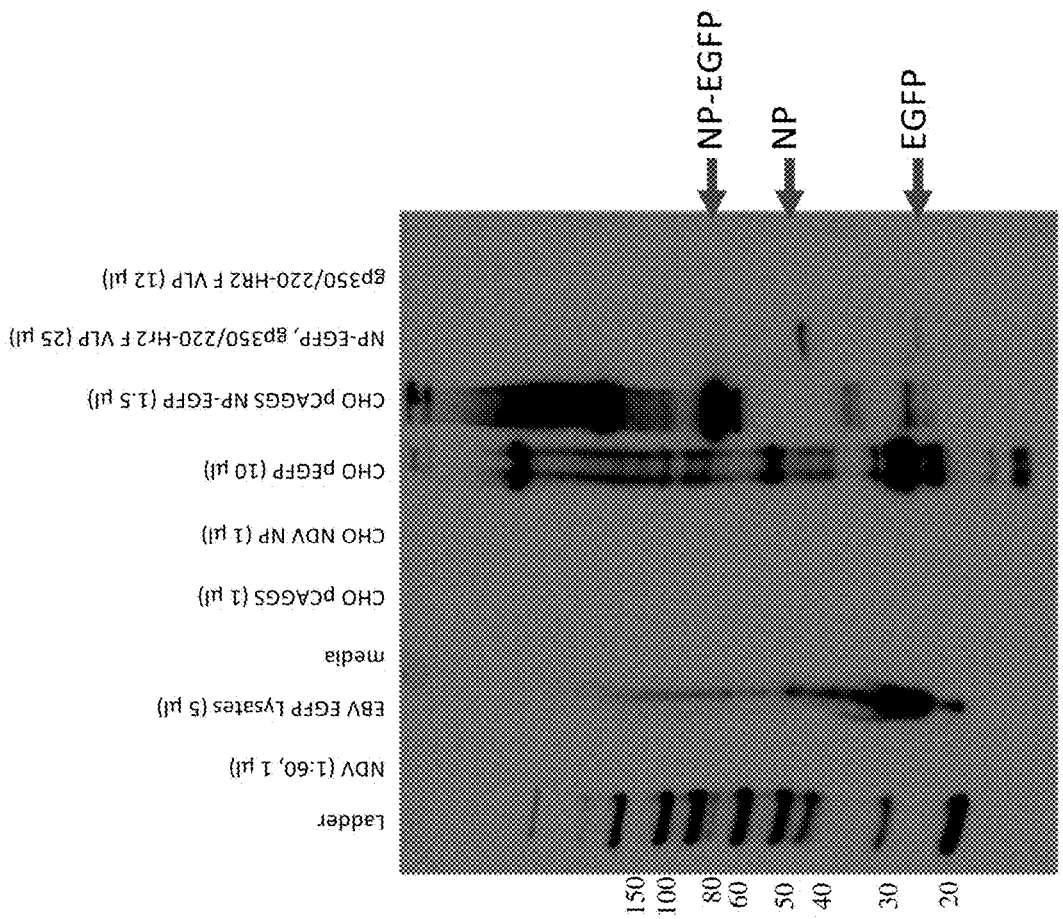
Figure 46:
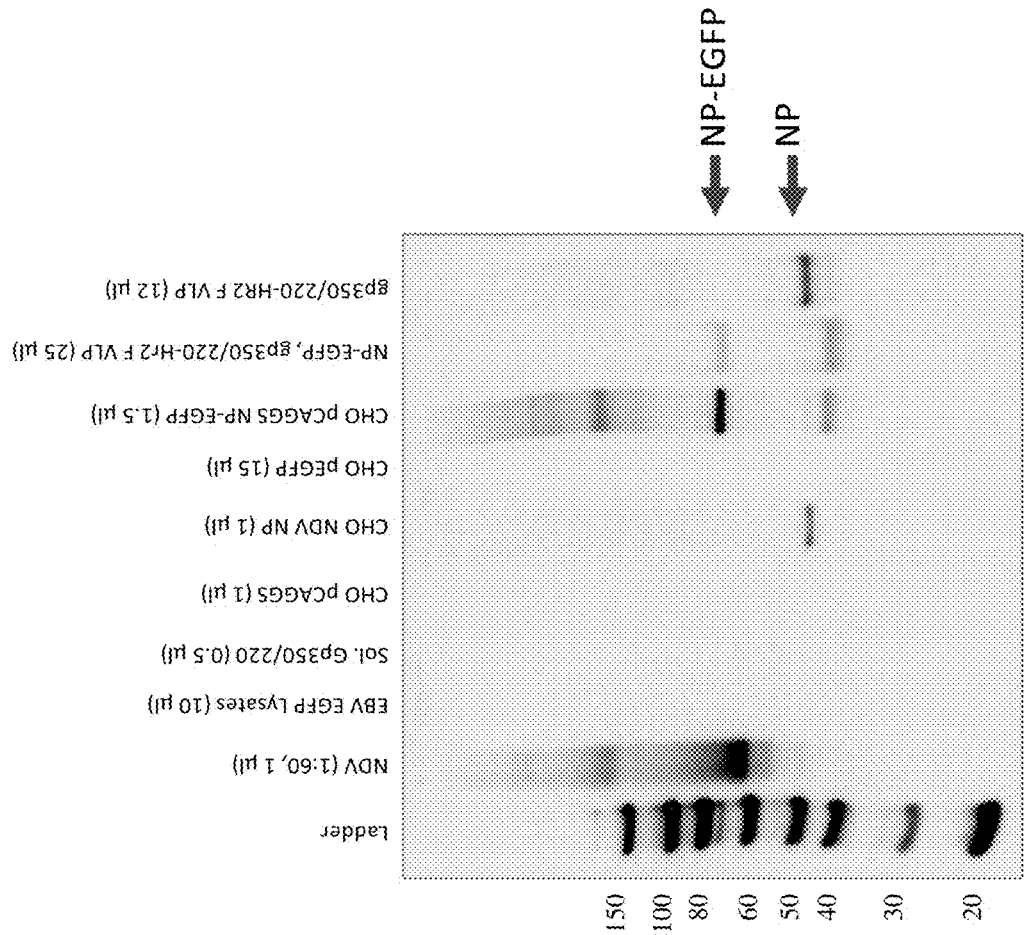
Figure 47:
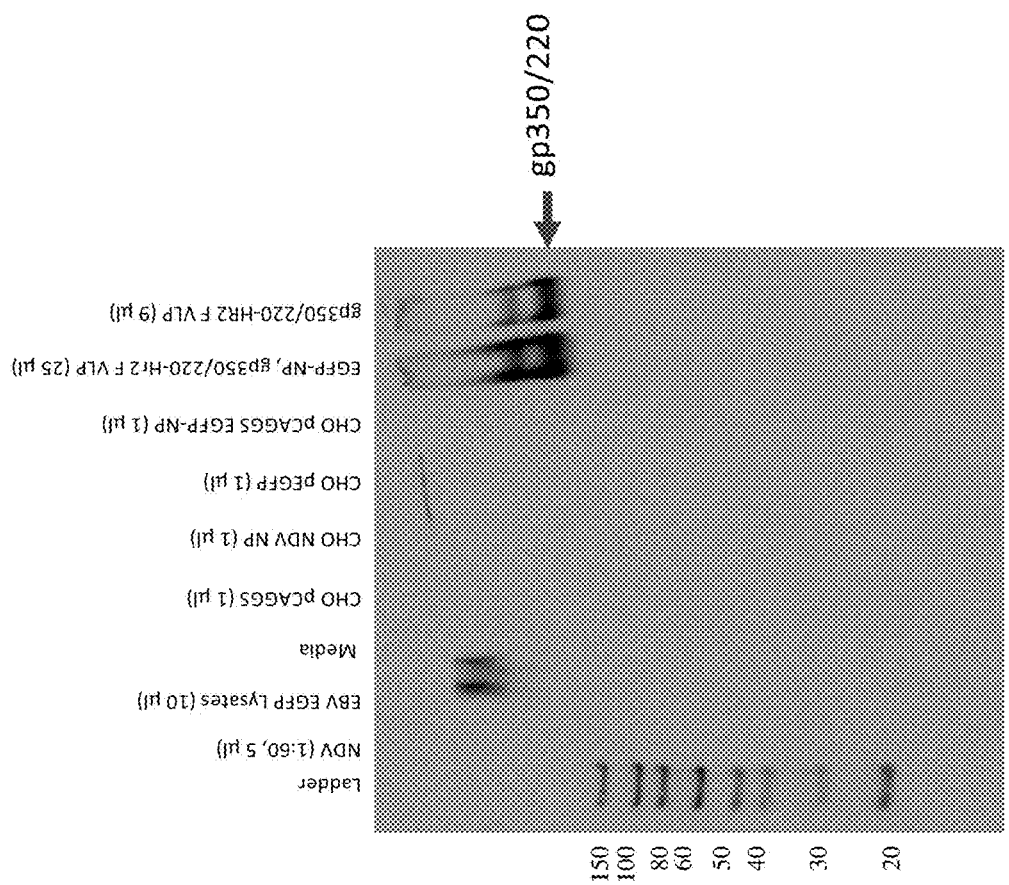

"EBNA1" is exemplified in FIG. 8 by human herpesvirus 4 SEQ ID NO:08, NCBI Reference Sequence: YP_401677.1.

Figure 52:
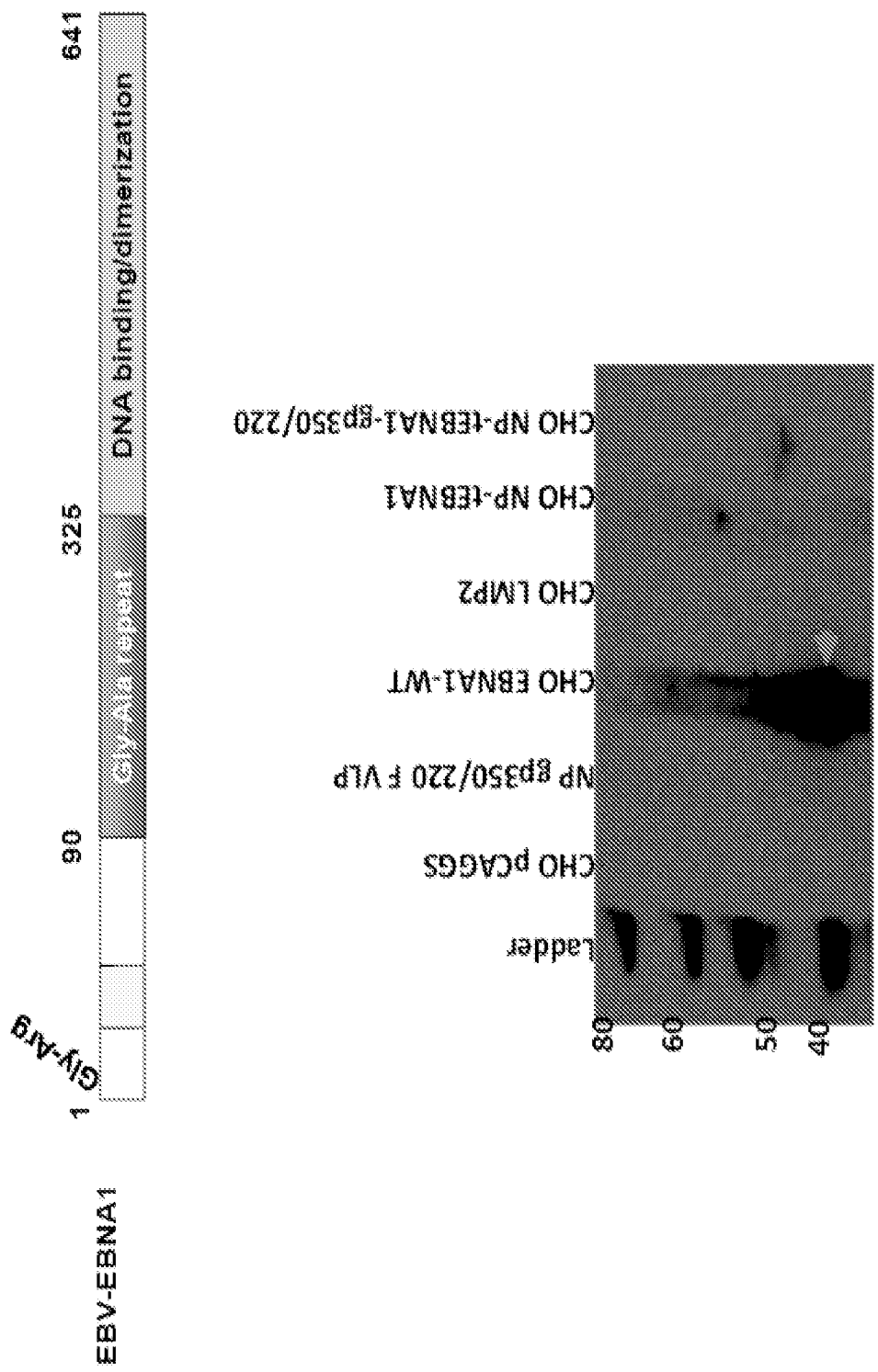
Figure 53:
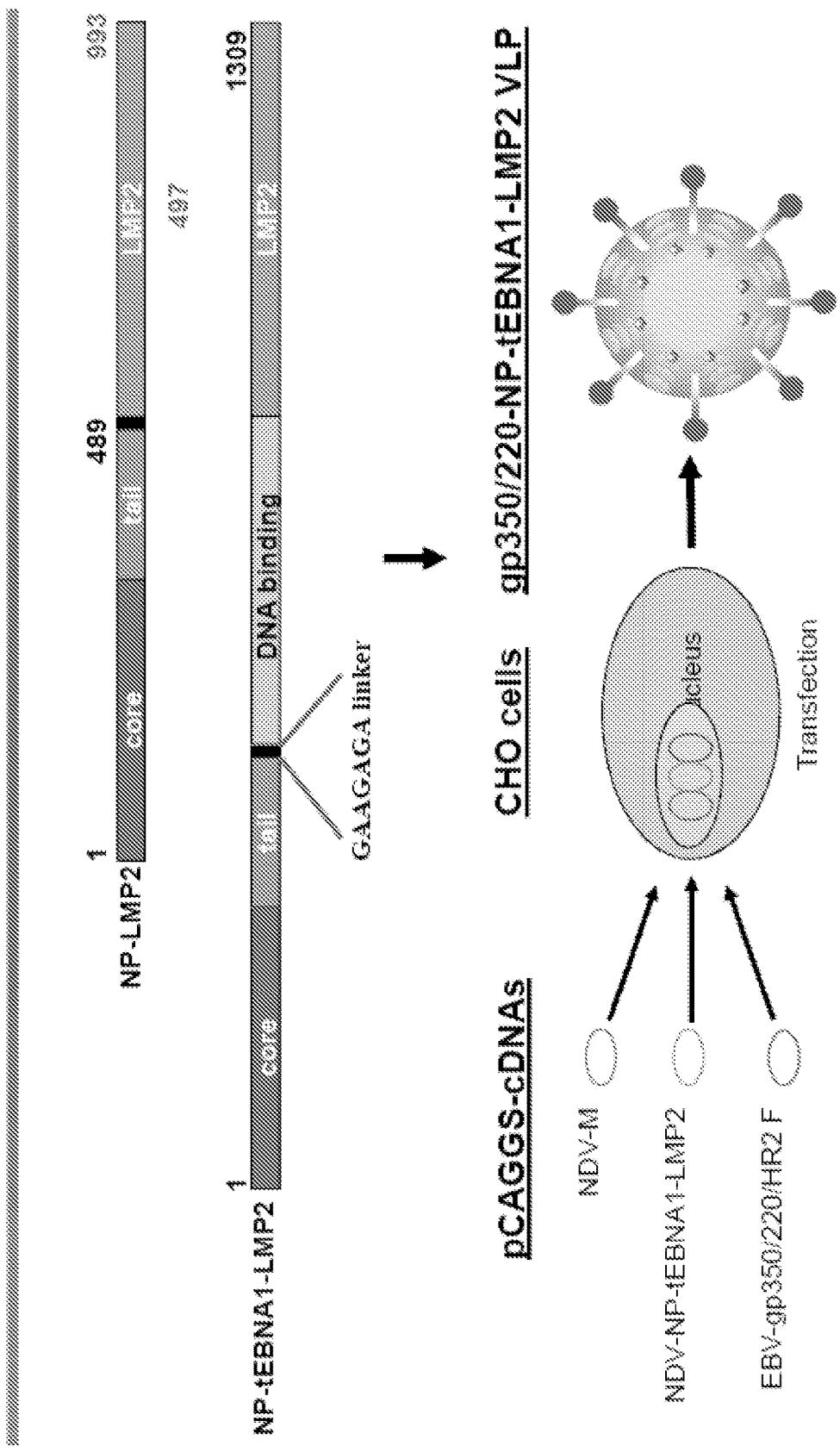
Figure 73:
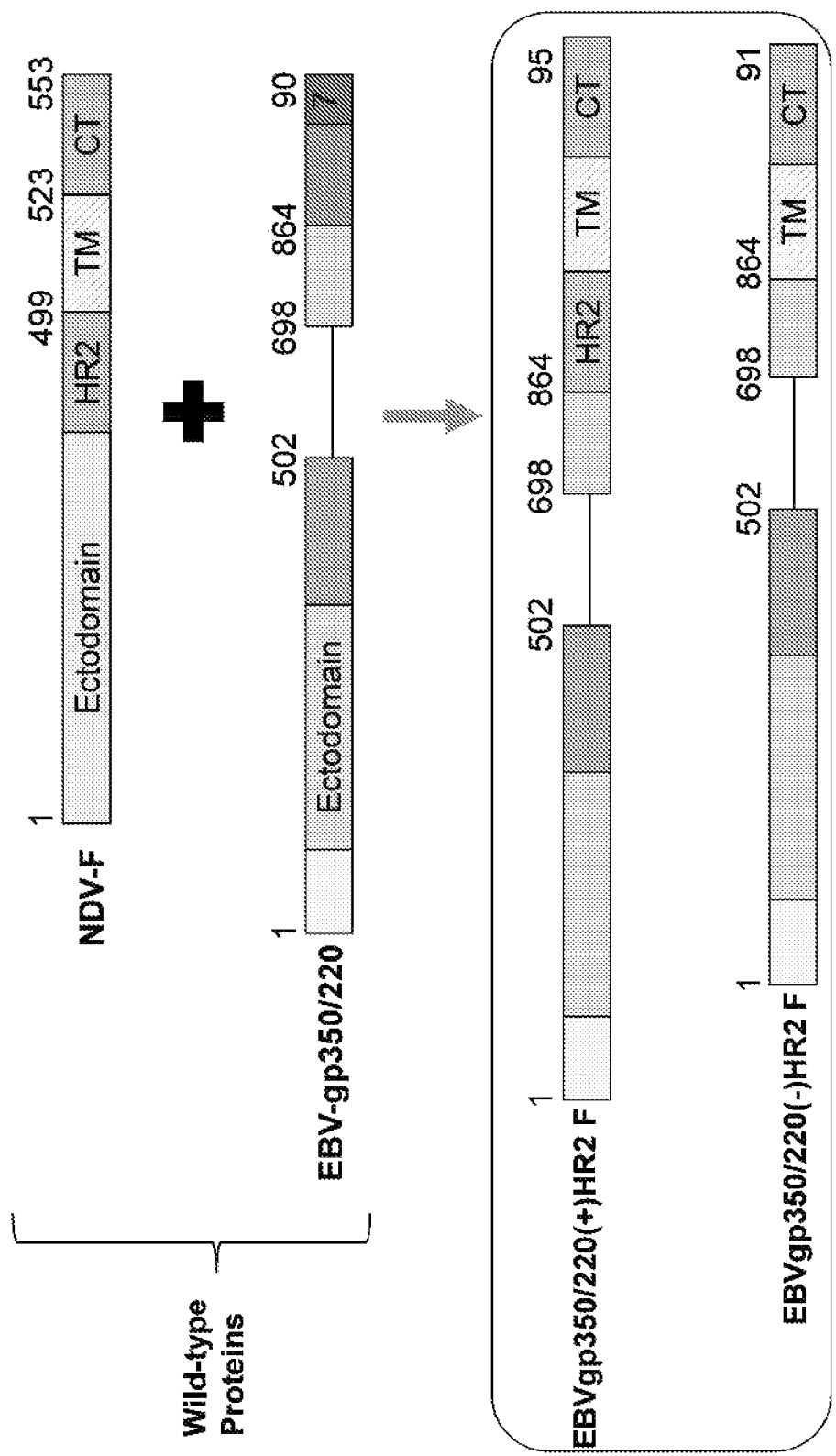
FIG. 73. Schematic of EBVgp350/220 F chimeric protein. A diagram of full length wild type NDV-F (top), full length EBVgp350/220-WT (center), and chimeric EBVgp350/220 (−/−)HR2 F contruct (bottom) (not to scale). C-terminal amino acid sequences comprising the gp350/220 ectodomain (ED) and N-terminal sequences from NDV-F HR2 at the point of fusion are indicated. The single line represents amino acid sequences deleted in frame in the gp220 isoform. Both isoforms contain the N-terminal B-cell attachment epitope. Ogembo et al., J. Trans. Med. 2015; 13:50.

"Truncated EBNA" and "tEBNA1" interchangeably refer to EBNA1 that lacks the Gly-Ala rich domain known to impair presentation of cis-linked sequences, and are exemplified by the sequence from amino acid 325-641 of FIG. 8's EBNA SEQ ID NO:08. Constructs containing tEBNA1 are exemplified in FIGS. 50 and 52.

"LMP2" is exemplified in FIG. 54 by the terminal protein LMP2A of human herpesvirus 4 (SEQ ID NO:01), NCBI Reference Sequence: YP_401631.1.

"L1" is exemplified in FIG. 58 by human papillomavirus type 16 SEQ ID NO.05, Gen Bank: AAD33259.1.

"L2" is exemplified in FIG. 59 by human papillomavirus type 16 SEQ ID NO:06, Gen Bank: AAD33258.1, and in FIG. 60 by human papillomavirus type 18 SEQ ID NO.07, Gen Bank: AGG40790.1.

Physiologically acceptable "carrier" and "diluents" for vaccine preparation include water, saline solution, human serum albumin, oils, polyethylene glycols, aqueous dextrose, glycerin, propylene glycol or other synthetic solvents. Carriers may be liquid carriers (such as water, saline, culture medium, saline, aqueous dextrose, and glycols) or solid carriers (such as carbohydrates exemplified by starch, glucose, lactose, sucrose, and dextrans, anti-oxidants exemplified by ascorbic acid and glutathione, and hydrolyzed proteins).

The term "expression vector" refers to a nucleotide sequence containing a desired coding sequence and appropriate nucleic acid sequences necessary for the expression (i.e., transcription into RNA and/or translation into a polypeptide) of the operably linked coding sequence in a particular host cell. Expression vectors are exemplified by, but not limited to, plasmid, phagemid, shuttle vector, cosmid, virus, chromosome, mitochondrial DNA, plastid DNA, and nucleic acid fragments thereof. Nucleic acid sequences used for expression in prokaryotes include a promoter, optionally an operator sequence, a ribosome binding site and possibly other sequences. Eukaryotic cells are known to utilize promoters, enhancers, and termination and polyadenylation signals.

"Mammalian subject" includes human, non-human primate, murine, ovine, bovine, ruminant, lagomorph, porcine, caprine, equine, canine, felines, avc, etc.).

A subject "in need" of reducing one or more symptoms of a disease, and/or "in need for a particular treatment (such as immunization) against a disease includes a subject that exhibits and/or is at risk of exhibiting one or more symptoms of the disease. For Example, subjects may be at risk based on family history, genetic factors, environmental factors, etc. This term includes animal models of the disease. Thus, administering a composition (which reduces a disease and/or which reduces one or more symptoms of a disease) to a subject in need of reducing the disease and/or of reducing one or more symptoms of the disease includes prophylactic administration of the composition (i.e., before the disease and/or one or more symptoms of the disease are detectable) and/or therapeutic administration of the composition (i.e., after the disease and/or one or more symptoms of the disease are detectable). The invention's compositions and methods are also useful for a subject "at risk" for disease refers to a subject that is predisposal to contracting and/or expressing one or more symptoms of the disease. This predisposition may be genetic (e.g., a particular genetic tendency to expressing one or more symptoms of the disease, such as heritable disorders, etc.), or due to other factors (e.g., environmental conditions, exposures to detrimental compounds, including carcinogens, present in the environment, etc.). The term subject "at risk" includes subjects "suffering from disease," i.e., a subject that is experiencing one or more symptoms of the disease. It is not intended that the present invention be limited to any particular signs or symptoms. Thus, it is intended that the present invention encompass subjects that are experiencing any range of disease, from sub-clinical symptoms to full-blown disease, wherein the subject exhibits at least one of the indicia (e.g., signs and symptoms) associated with the disease.

"Immunogenically effective amount" refers to that amount of a molecule that elicits and/or increases production of an "immune response" (i.e., production of specific antibodies and/or induction of a cytotoxic T lymphocyte (CTL) response) in a host upon vaccination with the molecule.

"Antibody" refers to an immunoglobulin (e.g., IgG, IgM, IgA, IgE, IgD, etc.) and/or portion thereof that contains a "variable domain" (also referred to as the "Fv region") that specifically binding to an antigen.

The term "specifically binds" and "specific binding" when made in reference to the binding of antibody to a molecule (e.g., peptide) or binding of a cell (e.g., T-cell) to a peptide, refer to an interaction of the antibody or cell with one or more epitopes on the molecule where the interaction is dependent upon the presence of a particular structure on the molecule. For example, if an antibody is specific for epitope "A" on the molecule, then the presence of a protein containing epitope A (or free, unlabeled A) in a reaction containing labeled "A" and the antibody will reduce the amount of labeled A bound to the antibody, in one embodiment, the level of binding of an antibody to a molecule is determined using the "IC50" i.e., "half maximal inhibitory concentration" that refer to the concentration of a substance (e.g., inhibitor, antagonist, etc.) that produces a 50% inhibition of a given biological process, or a component of a process (e.g., an enzyme, antibody, cell, cell receptor, microorganism, etc.). It is commonly used as a measure of an antagonist substance's potency.

SUMMARY OF THE INVENTION

The invention provides a recombinant virus-like particle (VLP) comprising, in operable combination, a) Newcastle disease virus (NDV) matrix (M) protein, b) NDV nucleocapsid (NP) protein, and c) one or more tumor-associated EBV antigen, wherein said one or more tumor-associated EBV antigen is inside said VLP. In one embodiment, said tumor-associated EBV antigen is selected from the group consisting of EBNA1, tEBNA1 and LMP2. In a further embodiment, said tumor-associated EBV antigen comprises tEBNA1 and LMP2. In another embodiment, the VLP further comprises, in operable combination, one or more Epstein-Barr Virus (EBV) antigens, wherein at least one of said one or more antigens is selected from the group consisting of gB, gH, and gL. In yet another embodiment, said VLP further comprises, in operable combination, EBV gp350/220. In one embodiment, said VLP further comprises, in operable combination, one or more NDV proteins. In a further embodiment, said one or more NDV proteins comprise NDV heptad repeat domain 2 (HR2) protein. In one embodiment, said one or more NDV proteins comprise NDV fusion (F) protein. In another embodiment, said one or more NDV proteins comprise NDV heamagglutinin-neuraminidase (HN) protein. In yet another embodiment, the VLP further comprises, in operable combination, one or more human papillomavirus antigens. In yet another embodiment, said one or more human papillomavirus antigens comprises one or more of L1 and L2.

The invention also provides a vaccine comprising any one or more of the VLPs described herein, and a physiologically acceptable carrier.

Also provided by the invention is an expression vector encoding any one or more of the recombinant VLPs described herein.

The invention additionally provides a method for immunizing a mammalian subject against cancer, comprising administering an immunologically effective amount of one or more vaccine of Claim 12 to a mammalian subject in need thereof to produce a treated subject, wherein said administering is under conditions to produce an immune response to one or more tumor-associated EBV antigen. In one embodiment, said cancer comprises an Epstein-Barr Virus (EBV)-associated cancer. In another embodiment, said EBV-associated cancer comprises cervical cancer. In one embodiment, said immune response comprises T lymphocytes that specifically bind to said one or more tumor-associated EBV antigen. In a further embodiment, said immune response lacks antibody that specifically binds to said one or more tumor-associated EBV antigen. In yet another embodiment, said T lymphocytes are selected from $CD4^+$ lymphocytes and $CD8^+$ lymphocytes. In a further embodiment, said method further comprises administering a recombinant VLP that contains, in operable combination, a) Newcastle disease virus (NDV) matrix (M) protein, and b) EBV gp350/220. In another embodiment, said method further comprises one or more of a) detecting said immune response to said one or more tumor-associated EBV antigen, and b) detecting a reduction in one or more symptoms of said cancer in said treated subject. In one particular embodiment, said administering is before manifestation of one or more symptoms of said cancer. In another embodiment, said administering is after manifestation of one or more symptoms of said cancer.

DESCRIPTION OF THE INVENTION

The present invention provides prophylactic and/or therapeutic vaccines that contain Newcastle disease virus (NDV) virus-like particles (VLPs) comprising one or more Epstein-Barr Virus (EBV) antigens. The invention's prophylactic and/or therapeutic vaccines are useful for preventing and/or treating infection with EBV and/or disease associated Epstein-Barr Virus, such as cancer.

In one embodiment, the invention relates to the use of virus-like particles (VLPs) as a multivalent vaccine for EBV, as well as the method of designing and producing these VLPs for this purpose. The VLPs stimulate both the production of nAbs (neutralizing antibodies) and EBV specific T-cells.

In one embodiment, the present invention involves the development of a safe and feasible method for generating VLPs to be used as a vaccine that targets both nAbs and to stimulate a T-cell response to viral antigens. Specifically, this invention uses the NDV platform to produce a multivalent vaccine to EBV, a worldwide virus associated with AIM and several cancers, in one embodiment, this process utilizes FDA-approved CHO cells to generate VLPs, mimic EBV on the surface, but do not contain viral DNA, avoiding safety concerns about the oncogenetic properties of the virus. Whereas past attempts have focused on inducing nAbs to gp350/220, which is required but not necessary for viral entry into the cell, in one embodiment, the invention's multivalent vaccine includes gH/gL and gB, both of which are necessary for the fusion and subsequent entry of EBV into both epithelial and B-cells (19,22). In addition to these surface proteins, the VLPs can be used as a vehicle for latent EBV antigens, EBNA1 and LMP2, which can be used to generate CD4+ T-cells that are specific for these antigens.

A) Epstein-Barr Virus (EBV) and Current Approaches

Epstein-Barr virus (EBV) is an oncogenic herpesvirus infecting over 95% of the adult population globally. It is implicated in the development of various types of lymphoproliferative diseases (LPDs) and carcinomas (1). Every year, EBV infection is estimated to be responsible for ~200,000 cancers globally (2). In low-income settings, primary EBV infection typically occurs during early childhood and is thought to be largely asymptomatic. However, in malaria endemic regions, childhood acquisition poses an increased risk of EBV positive Burkitt lymphoma (BL) (1, 3, 4). In high-income settings, primary EBV infection is often delayed until adolescence (4); and causes acute infectious mononucleosis (AIM) in 50-70% of adolescents (3). Although the disease is self-limiting, prolonged forms of AIM or chronic active EBV infection, may lead to fatal outcomes (5) or significantly increase the risk of developing EBV positive Hodgkin lymphoma (1). EBV is also highly associated with nasopharyngeal and gastric carcinomas, reflecting the epithelial tropism of the virus (3). Among infected individuals, EBV is controlled by T-cells and normally remains quiescent in memory B-cells (6). However, under conditions of immune suppression, the virus can reactivate, leading to an expansion of EBV-infected cells and increasing the likelihood of de novo infection, and transformation of infected B-cells as seen in BL, EBV positive post-transplant lymphoproliferative disorders (PTLDs), and AIDS-associated B-cell lymphomas (7-9). Management of EBV-associated diseases is problematic due to difficulties with diagnosis, surveillance, and treatment. In a meeting convened at the National Institutes of Health (NIH) in 2011, participants agreed that the need for a safe and effective vaccine to prevent and/or treat EBV-associated diseases is urgent (2). Several strategies to generate an EBV vaccine based on viral glycoprotein 350/220 (gp350/220), latent membrane proteins (LMP1-2), and EBV nuclear antigen 1 (EBNA-1) are currently in experimental stages and/or clinical trials (10, 11). However, most of these strategies have low safety profiles, and are designed to elicit the production of neutralizing antibodies (nAbs) to EBV envelope proteins (prophylactic), or a T-cell response to latent EBV antigens (therapeutic). None of the current proposed vaccines address both arms of immunity in a single candidate vaccine. Our vaccine utilizes a VLP platform which incorporate select multiple viral surface glycoproteins in addition to intracellular T-cell antigens to generate a polyvalent vaccine. These VLPs have high safety profiles and are efficiently produced in the FDA-approved Chinese hamster ovary (CHO) cell line.

Antibodies (Abs) provide the first line of defense against virus infection. Neutralizing Abs directed to EBV envelope glycoproteins are present in humans, maternal nAbs prevent neonatal infection, and it has been shown that they are induced in response to immunization both in humans and in other animals (12-14). However, persistent EBV infection and the limited evidence of immune selection of viral antigenic variants indicate that in vivo neutralization of EBV infection is suboptimal. This was observed in four independent phase I/II clinical trials, in which vaccination with either vector constructs expressing gp350/220, or with purified recombinant non-splicing variant gp350 soluble protein, did not prevent infection although incidence of AIM was reduced in young adults by more than 70% (14-17). Importantly, primary B-cells can be infected with recombinant EBV lacking gp350/220; suggesting that additional viral ligands may be mediating EBV infection in the absence of gp350/220 (18-22). These observations indicate that using gp350/220 as the only immunogen (monovalent vaccine) to target viral neutralization is too simplistic and may account for the variable success in using this protein in EBV vaccine development.

In EBV infection, EBVgp350/220, the attachment protein, binds to B-cell receptors CD21 and CD35, initiating the first contact of the virus and the host cells (23-26), and subsequently triggering endocytosis of the virions (27). This interaction enhances infection, but is not essential (18). Fusion between the viral envelope and the cellular membrane is a required step in the entry of all human herpesviruses (28). For EBV, the viral glycoproteins necessary for fusion of the viral envelope with the host cell receptors ore glycoprotein B (gB) (22), the complex of gH and gL (gH/gL), and gp42 (19). These complexes mediate infection and confer host cell specificity. EBV entry into B-cells is mediated by gB, gH/gL, and gp42; whereas entry into epithelial cells is facilitated by interaction between gB and gH/gL (22, 29, 30). It is important to note that co-expression of EBVgH and gL is required for transport of gH to the cell surface which results in the formation of a stable complex of gH/gL (29). Recently, integrins have been identified as the epithelial receptors for EBVgH/gL and this interaction initiates fusion in a two-step cascade (20). Recombinant EBV lacking gH docs not infect either epithelial or primary B-cells (31).

Although Abs to EBVgH/gL are not robustly produced in vivo during natural infection (perhaps due to masking by the immunodominant gp350/220), immunization of mice with recombinant gH can boost immunogenicity and generate Abs capable of blocking EBV infection (20, 21, 32). The ability of gH/gL Abs to neutralize infection is also well-conserved in herpes simplex virus-1 (33, 34), cytomegalovirus (35, 36) and Kaposi sarcoma herpesvirus (KSHV) (37). Monoclonal Abs to the gH protein or the gH/gL complex block EBV infection, indicating a critical role for gH/gL in EBV infection (38, 39). No specific nAbs to EBVgL or -gB have been reported so far (10). NAbs directed to EBVgp42, have been identified (40).

T-cell-mediated responses are effective in controlling persistent EBV infection, as evidenced by some form of immunosuppression usually preceding EBV-associated lymphomas and PTLDs (1, 41). Furthermore, adoptive transfer of EBV-specific T-cells can induce remission in transplant patients (42,43).

The current hypothesis is that protection against EBV relics on inducing $CD4^+$ and $CD8^+$ T-cell immune responses, and the development of EBV therapeutic vaccine candidates have focused on enhancing such responses (44). EBNA1-specific $CD4^+$ and $CD8^+$ T-cells are frequently detected in EBV-infected individuals (45, 46), and both T-cell subsets can be effective in controlling growth of EBV-immortalized B-cells (47). Notably. EBNA1, LMP2, and EBVgp350/220 antigens have been developed and independently tested in various clinical trials as vaccine candidates against EBV infection and $EBV^+$ cells with promising results (17, 48, 49). Recent phase I clinical trials of recombinant modified vaccinia Ankara vector encoding deletion of Gly-Ala regions from the EBNA1 sequence (known to impair presentation of cis-linked sequences) fused to LMP2 as a vaccine candidate elicited a robust EBV-specific $CD4^+$ and $CD8^+$ T-cell response in humans (44, 48, 50). However, the strategy used to deliver these two important EBV antigens (a DNA vaccine), known for their oncogenic potential, may pose major health risks, such as inducing an antibody response to DNA or integration of DNA in an undesired location in the host genome causing unchecked cell growth, particularly in immunosuppressed individuals. Furthermore, these vaccine candidates cannot elicit nAbs to eliminate reactivated or new EBV infections. There is also a risk of vaccine tolerance since the quantity of proteins produced and secreted in vivo is unregulated. EBV DNA packaging mutants (51), and disabled virions that lack the major oncoproteins have also been proposed as an alternative strategy (52).

However, incomplete knowledge of all the virion proteins functions, concerns about inadvertent association of oncogenic DNA/RNA fragments with the assembled VLPs, limited production and release of the virus, as well as current requirements for their propagation in transformed human cell lines suggest that such strategies may not meet the stringent FDA safety guidelines. Our strategy will address all these limitations by combining select multiple EBV antigens in a VLP platform which is efficiently produced in CHO cells, immunogenic, and safe to use in all populations, irrespective of immune status.

B) Compositions and Methods for Treating Cancer

The invention provides prophylactic and/or therapeutic vaccines that contain Newcastle disease virus (NDV) virus-like particles (VLPs) comprising one or more tumor-associated Epstein-Barr Virus (EBV) antigens.

In one embodiment, the invention's VLPs induce both nAbs and protective human T-cell responses will not only be an invaluable candidate vaccine in preventing EBV infection, but also of utmost importance in preventing BL in African children, acute infectious mononucleosis in 50-70% of US adolescents, nasopharyngeal carcinoma (endemic in Southeast Asia), post-transplant lymphoproliferative disorders, and non-Hodgkin lymphoma (in iatrogenic and AIDS-immunodeficient patients). The Newcastle virus disease vaccine platform is also invaluable for the development of candidate prophylactic and therapeutic vaccines against other human viruses, as it provides a safe and effective method of targeting both arms of the immune system.

In one embodiment the invention provides a recombinant virus-like particle (VLP) comprising, in operable combination, a) Newcastle disease virus (NDV) matrix (M) protein, b) NDV nucleocapsid (NP) protein, and c) one or more tumor-associated EBV antigen, wherein the one or more tumor-associated EBV antigen is inside the VLP. In one embodiment, the tumor-associated EBV antigen is selected from the group consisting of EBNA1, tEBNA1 and LMP2. In one embodiment, the tumor-associated EBV antigen comprises tEBNA1 and LMP2. In one embodiment, the VLP further comprises, in operable combination, one or more Epstein-Barr Virus (EBV) antigens, wherein at least one of the one or more antigens is selected from the group consisting of gB, gH, and gL. In one embodiment, the VLP further comprises, in operable combination, EBV gp350/220. In one embodiment, the VLP further comprises, in operable combination, one or more NDV proteins, exemplified by, NDV HR2 protein, NDV F protein, and NDV HN protein. In one embodiment, the VLP, further comprises, in operable combination, one or more human papillomavirus antigens. In one embodiment, the one or more human papillomavirus antigens comprises one or more of L1 and L2.

The invention also provides a vaccine comprising one or more of any of the VLPs described herein, and a physiologically acceptable carrier.

The invention also provides an expression vector encoding any one or more of the recombinant VLPs described herein.

The invention also provides a method for immunizing a mammalian subject against cancer, comprising administering an immunologically effective amount of any one or more of the vaccines described herein to a mammalian subject in need thereof to produce a treated subject, wherein the administering is under conditions to produce an immune response to one or more tumor-associated EBV antigen. In one embodiment, the cancer comprises an Epstein-Barr Virus (EBV) associated cancer, in one embodiment, the EBV-associated cancer comprises cervical cancer. In one embodiment, the immune response comprises T lymphocytes that specifically bind to the one or more tumor-associated EBV antigen. In one embodiment, the immune response lacks antibody that specifically binds to the one or more tumor-associated EBV antigen. In one embodiment, the T lymphocytes are selected from CD4+ lymphocytes and CD8+ lymphocytes. In one embodiment, the method further comprises administering a recombinant VLP that contains, in operable combination, a) Newcastle disease virus (NDV) matrix (M) protein, and b) EBV gp350/220. In one embodiment, the method further comprises one or more of a) detecting the immune response to the one or more tumor-associated EBV antigen, and b) detecting a reduction in one or more symptoms of the cancer in the treated subject. In one embodiment: administering the vaccine is prophylactic before manifestation of one or more symptoms of the cancer. In one embodiment, administering the vaccine is therapeutic after manifestation of one or more symptoms of the cancer. In one embodiment, the vaccine prevents cancer and/or the spread of cancer.

C) Compositions and Methods for Immunizing Against Epstein-Barr Virus (EBV)

The invention provides prophylactic and/or therapeutic vaccines that contain Newcastle disease virus (NDV) virus-like particles (VLPs) comprising one or more Epstein-Barr Virus (EBV) antigens. The invention provides evidence that viral antigens capable of eliciting T cells response can be incorporated into the virus-like particle by fusing NDV-nucleoprotein.

Approaches to EBV vaccine development are limited due in part to the oncogenic potential of the EBV genome and a lack of animal models for testing vaccine candidates. VLPs are safe, immunogenic and have been successfully used to prevent infections against other oncogenic viruses such as human papillomavirus and hepatitis B virus. The EBV envelope glycoprotein gp350/220 (EBVgp350/220) has been proposed as a potential vaccine antigen. However, in four independent phase I/II clinical trials, vaccination with EBVgp350/220 did not prevent EBV infection. Importantly, recombinant EBV lacking gp350/220 can infect both epithelial and primary B cells in vitro. These preliminary studies demonstrate that using pooled sera from mice immunized four times with EBVgp350/220 VLPs without adjuvants neutralized EBV infection in vitro, resulting in 46% inhibition. Whereas neutralization with sera from mice immunized with UV-inactivated EBV resulted in ~88% inhibition. This suggests that other envelope glycoproteins may have a role in virus entry, independent of gp350/220. The EBVgH/gL envelope glycoprotein complex is definitively required for EBV fusion and entry, and thus is a potential target for developing a prophylactic vaccine. Antibodies to the EBVgH/gL complex can neutralize virus infection, and recombinant EBV lacking gH cannot infect both epithelial and primary B cells. To our knowledge, these proteins have not yet been tested as part of candidate vaccines in any animal model or clinical trial.

Data herein provides evidence that generation of VLPs containing both EBVgH/gL and EBV EBNA1 and/or LMP2 consistently expressed in most EBV positive tumors is feasible. Recent phase I clinical trials of recombinant modified vaccinia Ankara vector encoding deletion of Gly-Ala regions from the EBNA1 sequence fused to LMP2 as a vaccine candidate elicited a robust EBV-specific CD4+ and CD8+ T-cell response. Because EBV is a human pathogen, the process described takes advantage of both human peripheral blood mononuclear cells (PBMCs) and immunodeficient mice (NOD-scidIL2r$\gamma^{null}$ mice, NSG) reconstituted with human immune system components (humanized BLT model, bone marrow/liver/thymus) as models to test EBNA1-specific CD4+ and CD8+ T-cell responses.

Figure 49:
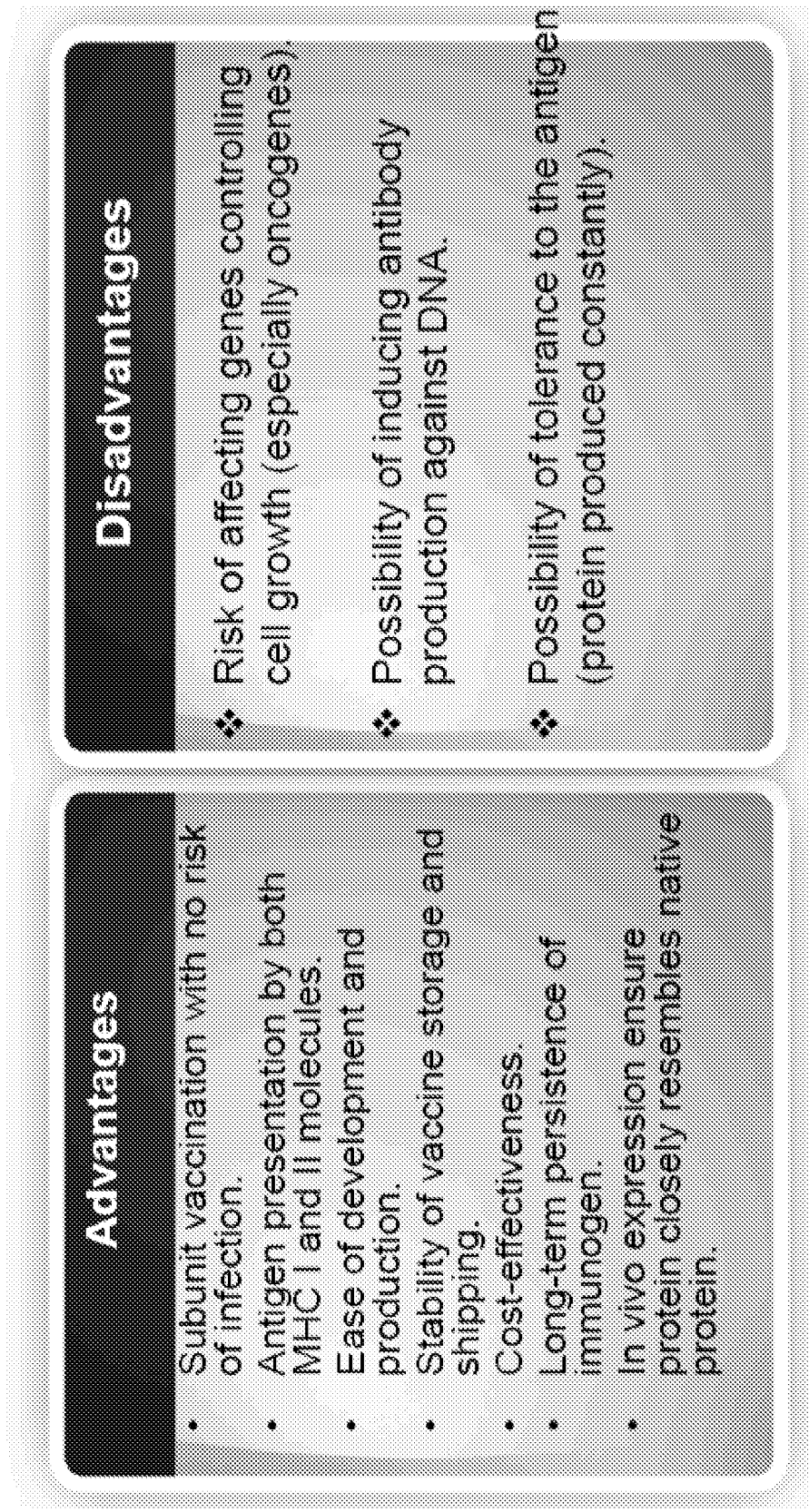
FIG. 49. Challenges of DNA based vaccines.

Current approaches to EBV vaccine development are limited due in part to the oncogenic potential of the EBV genome (FIG. 49). To generate a potent EBV vaccine candidate we included multiple vaccine antigens including tumor-associated antigens in our VLPs (exemplified in FIGS. 1A-E-3A-D).

Despite strong evidence that antibodies (Abs) to gH/gL can neutralize EBV infection, these proteins have not been used to generate an EBV vaccine. In one embodiment, the invention's VLP vaccines contain two tumor-associated antigens (EBNA1 and LMP2); EBNA 1 is consistently expressed in B cells of all BL patients and recognized by CD4+ T cells and LMP2 is primarily targeted by CD8+ T cells.

Data herein demonstrate that VLPs containing a functionally inactive truncated EBNA1 (tEBNA1, lacking the Gly-Ala rich domain known to impair presentation of cis-linked sequences), LMP2, and gH/gL, stimulate robust humoral and cellular responses against EBV. Thus, in one embodiment, the invention provides NDV VLPs containing tEBNA1, LMP2, gB and gH/gL for use as a vaccine to induce neutralizing antibodies (nAbs) and/or EBV specific CD4+ and CD8+ T cells responses. In a particular, embodiment, the invention provides EBVgH/gL:tEBNA1-LMP2 VLPs that can be used alone or together with EBVgp350/220 VLPs to prevent EBV infection and its associated diseases. In another embodiment, the invention's vaccines are therapeutic and/or prophylactic vaccines against infectious diseases and cancers, such as cervical cancer.

In one embodiment, the invention provides a recombinant virus-like particle (VLP) comprising, in operable combination, a) Newcastle disease virus (NDV) matrix (M) protein, and b) two or more Epstein-Barr Virus (EBV) antigens, wherein at least one of the two or more antigens is selected from the group consisting of gB, gH, and gL. In one embodiment, the two or more EBV antigens comprise a tumor-associated EBV antigen, wherein the tumor-associated EBV antigen is exemplified by, but not limited to, EBNA1 and LMP2. In a particular embodiment, EBNA1 is truncated (tEBNA1, i.e., EBNA1 that lacks the Gly-Ala rich domain). In a further embodiment the VLP comprises EBV gp350/220. In a particular embodiment, the VLP further comprises, in operable combination, one or more NDV proteins, exemplified by, but not limited to NDV nucleocapsid (NP) protein, NDV heptad repeat domain 2 (HR2) protein, NDV fusion (F) protein, and NDV heamagglutinin-neuraminidase (HN) protein.

The invention further provides a VLP that contains, in operable combination, a) Newcastle disease virus (NDV) matrix (M) protein, and b) EBV gp350/220 (Ogembo et al., "5A chimeric EBV gp350/220-based VLP replicates the virion B-cell attachment mechanism and elicits long-lasting neutralizing antibodies in mice," Journal of Translational Medicine (2015) 13:50). In a particular embodiment, the VLP further comprises, in operable combination, one or more NDV proteins, exemplified by, but not limited to NDV nucleocapsid (NP) protein, NDV heptad repeat domain 2 (HR2) protein, NDV fusion (F) protein, and NDV heamagglutinin-neuraminidase (HN) protein.

The invention further provides a vaccine comprising any one or more of the VLPs described herein, and a physiologically acceptable carrier.

Also provided is an expression vector encoding any one or more of the recombinant VLPs described herein.

The invention also provides a method for immunizing a mammalian subject against Epstein-Barr Virus (EBV), comprising administering an immunologically effective amount of one or more of the VLP vaccines described herein to a mammalian subject in need thereof to produce a treated subject, wherein the administering step is under conditions to produce an immune response to one or more EBV antigen. In one embodiment, the method comprises administering (A) a first recombinant VLP comprising, in operable combination, a) Newcastle disease virus (NDV) matrix (M) protein, and b) two or more Epstein-Barr Virus (EBV) antigens, wherein at least one of the two or more antigens is selected from the group consisting of gB, gH, and gL, and (B) a second recombinant VLP that contains, in operable combination, a) Newcastle disease virus (NDV) matrix (M) protein, and b) EBV gp350/220. In one preferred embodiment, administering the vaccine does not produce EBV-associated cancer. In another embodiment, the method further comprises one or more of a) detecting the immune response to the one or more EBV antigen, b) delecting a reduction in one or more symptoms of EBV infection in the treated subject, and c) determining the presence and/or absence of EBV-associated cancer in the treated subject. In one embodiment, the invention's vaccination method is used prophylactically by administering the vaccine before manifestation of one or more symptoms of infection of the subject with the EBV. In a further embodiment, the invention's vaccination method is used therapeutically by administering the vaccine after manifestation of one or more symptoms of infection of the subject with the EBV. In a particular embodiment, the immune response by the treated subject comprises antibody that specifically binds to the one or more EBV antigen. In a particular embodiment, immune response comprises T lymphocytes that specifically bind to the one or more EBV antigen. In a further embodiment, the T lymphocytes are selected from CD4$^+$ lymphocytes and CD8$^+$ lymphocytes.

EXPERIMENTAL

The following examples serve to illustrate certain preferred embodiments and aspects of the present invention and are not to be construed as limiting the scope thereof.

Example 1

Materials And Methods. The following is a brief description of the exemplary materials and methods used in the subsequent Examples.

Virus and Cell Lines

B95-8 strain harboring EBfaV-GFP was obtained from Dr. Richard Longnecker (Northwestern University, Chicago). EGFP-EBV was prepared as described (53). Purified Kaposi's sarcoma herpesvirus (KSHV) and EBV-EGFP from the AGS cell line were generous gifts from Dr. Christine King (SUNY Upstate Medical School) and Dr. Liisa Selin (University of Massachusetts Medical School), respectively.

Human embryonic kidney HEK-293A cell line, a cloned derivative of 293 was purchased from Life Science Technologies. HEK-293T, a 293 derivative expressing SV-40 T antigen, CHO, Vero (African green monkey kidney), ELL-0 (chicken embryo), K562 (human erythroleukemia), Raji (EBV+ Burkitt's lymphoma), HB168 (72A1 murine hybridoma) were all purchased from the American Type Culture Collection. Cell lines 293A, CHO, and ELL-0 were cultured in Dubelco's Modified Eagle's medium (DMEM). B95-3, K562, HB168 and Raji cell line were grown in RPMI media. All media contained 1% L-glutamine, 10% heat-inactivated fetal bovine serum (FBS) and 2% penicillin-streptomycin unless otherwise specified.

Antibodies

Primary monoclonal antibodies (mAb)-72A1 and -2L10 anti-gp350/220 were purchased from EMD Millipore. Polyclonal rabbit anti-Newcastle disease virus (NDV) and anti-HR2 have been previously described (54). MAb anti-CD35 (clone E11) and anti-CD21 (clone LT21) were purchased from BioLegend, mAb EBNA1 (clone 1H4-1) was a gift of Dr. F. Grässer, Institut für Virologie, Germany. Both goat polyclonal anti-EBNA1 Gly-Arg regions and rat monoclonal anti-EBV LMP2A (clone 14B7) were purchased from Abcam. Monoclonal anti-EGFP (clone GSN149) was purchased from Sigma. All the antibodies to EBVgH, EBVgH/gL and EBVgB were gifts of Dr. Lindsey Hutt-Fletcher (Louisiana State University Health Sciences Center, Shreveport, La.). mAh anti EBVgH/gL (clone CL59) recognizes gH alone and binds to an epitope between residues 501-628 which is part of the C-terminal flap structure in domain 1V; E1D1 recognizes only gH/gL complex and partially blocks binding to an integrin so probably binds somewhere on the domain 1/domain II interface. CL40 recognizes gH/gL complex. mAb anti-gB (clone CL55) recognizes the ectodomain of the glycoprotein, while rabbit polyclonal anti-gB (clone BA23) recognizes C-terminal domain.

Secondary: Horseradish peroxidase (HRP)-conjugated goat anti-mouse IgG (total and isotype specific) antibodies, goat anti-rabbit or goat anti-rat antibodies for immunoblot or ELISA were purchased from Sigma. Goat F(ab')2 anti-mouse IgG (H+L) AF488 or AF594 was used for cytometric and confocal analyses (Invitrogen). Goat anti-mouse IgG (H+L) immunogold was used for electron microscopy (EM) (Aurion).

Plasmid Vectors pCAGGS-EBVgp350/220-F or pCAGGS-EBVgp350/220-HR2 F

Full length EBVgp350/220 (BLLF1) from the BamHI L fragment of EBV genome strain B95-8 (55) was amplified by PCR and cloned into pCAGGS as described (56). A chimeric fragment consisting of amino acids 1-864 encoding the gp350/220 ectodomain (ED) fused to the amino acids 466-553 of the NDV-F heptad repeat 2 (HR2), transmembrane (TM) and cytoplasmic (CT) domains was constructed by three-way ligation to obtain EBVgp350/220-F as described (56). Full length chimeric EBVgp350-220-F lacking the heptad region of the NDV TM region was synthesized by Gencwiz, cloned into pCAGGS vector (pCAGGS-EBVgp350/220-HR2 F) and sequence fidelity verified. A full-length gp350/220 wild type (WT) were also synthesized and cloned into pCAGGS vector to be used as a control in various experiments. pCAGGS-F, pCAGGS-M and pCAGGS-NP derived from NDV (Avulavirus) have been described (57).

pCAGGS EBVgH/gL (gp85/gp25)

To construct chimeric EBVgH F and EBVgL-HN proteins, sequences encoding the TM domain lacking the heptad region and the cytoplasmic tail of the NDV F protein (amino acids 499-553) or hemagglutinin-neuraminidase (HN) protein (amino acids 1-46) were fused to the sequence encoding the ectodomain of gH, amino acids 1-679 and to amino acids 25-137 of gL, respectively. These chimera proteins were synthesized and cloned individually into the pCAGGS vector. cDNAs of full length gH WT (amino acids 1-707) and gL WT (amino acids 1-137) were also synthesized and individually cloned into pCAGGS vector as controls.

pCAGGS-EBVgB-F (gp110)

A chimeric fragment consisting of amino acids 1-736 encoding the EBVgB ectodomain fused to the NDV-F lacking HR2 region of the TM and CT domains (amino acids 466-553) was synthesized. The synthesized sequence was cloned into pCAGGS vector and sequence fidelity verified. A full-length EBVgB WT (amino acids 1-790) was also synthesized and cloned into pCAGGS vector as a control.

Generation of Fusion Protein Between NT and EGFP, Truncated EBNA1 or LMP2.

Fusion proteins between NP (amino acids 1-489) and EGFP (amino acids 1-241), truncated EBNA1 encoding deletion of Gly-Ala regions from the EBNA1 sequence known to impair presentation of cis-linked sequences (amino acids 326-641), or full length LMP2 (amino acids 1-497) were synthesized by Genesviz and fidelity of the sequences verified. The specific fusion sequences were individually cloned into pCAGGS vector. Full length EGFP, EBNA1 and LMP2 were also synthesized and cloned into pCAGGS vector as controls.

Transfection, Generation and Purification of EBVgp350/220-F, EBVgp359/220-EGFP, gp350/220-EBNA1, EBVgH/gL, EBVgH/gL-EBNA1 and EBVgB-LMP2 VLPs.

To determine surface expression of the EBV glycoproteins, 1.0 µg/well of pCAGGS, pCAGGS-gp350/220 WT, pCAGGS-EBVgp350/220-F, pCAGGS-EBVgp350/220-HR2 F, pCAGGS-EBVgH WT, pCAGGS-EBVgH-F, pCAGGS-EBVgL WT, pCAGGS-EBVgL-HN or pCAGGS-EGFP were individually transfected into 80% subconfluent CHO cells seeded in six-well tissue culture plates using Lipofectamine and Reagent Plus (Life Sciences Technologies) according to the manufacturer's direction. Both gH-F/gL-HN or gH WT/gL WT plasmids were also transfected into CHO cells to assess the formation of the gH/gL complex. Cells were harvested at 48 h post-transfection to assess surface expression of individual protein by cytmetry after staining with specific primary antibody followed by secondary antibody. In certain cases, surface expression of individual proteins were also assessed transfected 293A, Vero or ELL-0 cell lines. Cytometric analysis was performed on a LSRII benchtop FC (Becton-Dickinson, B-D) and data analyzed using CellQuest Pro Version 4.0.1 (B-D) and/or FlowJo Cytometry Analysis software (Tree Star Inc) as described (56).

For VLP preparation, equal amounts (8 µg/plasmid) of pCAGGS-NDV M, NP and pCAGGS-EBVgp350/220-F plasmids were co-transfected into cells seeded in T-175 $cm^2$ flasks. DNA-Lipofectamine complexes were incubated at 37° C. for 5 h with 293T and ELL-0 or overnight with CHO cells. Complexes were removed by washing and 20 ml of complete media with or without 4 mM of sodium butyrate (Millipore ED) and 20 ng/ml of TPA (12-O-tetradecanonylphorhol 13-acetate) (Sigma) were added. VLPs were isolated by sucrose gradient purification as described (58). Similar strategy was used to generate EBVgp350/220-HR2 F, EBVgp350/220-HR2 F-EGFP, EBVgp350/220-HR2 F-EBNA1, EBVgH/gL-EBNA 1 and EBVgB-LMP2 VLPs in CHO cells.

Silver Stain, Immunoblot Analysis, Electron Microscopy and Immunogold Staining

Purified EBV, VLPs or cells were lysed in RIPA buffer (Boston Bioproducts) containing complete protease inhibitor cocktail (Roche Applied Science). Cell lysates were incubated on ice for 15 min, and then centrifuged for 5 min at 14.000×rpm in microcentrifuge. The protein content of lysates was determined by Bradford assay using Coomassie Brilliant Blue (Sigma). Lysates were boiled for 5 min in Laemmli SDS-sample butter (Boston Bioproducts) under non-reducing or reducing conditions. A known quantity of protein lysate was loaded onto a 4-12% polyacrylamide gel for protein separation. Protein was detected by Pierce's silver stain kit following manufacturer's recommendation. For immunoblot analyses, separated proteins were transferred to a PVDF membrane (Life Sciences Tech.) using iblot (Life Sciences Tech.). Membranes were pre-incubated with 5% non-fat dry milk (LabSciemific) for 30 min and detected with specific antibodies as previously outlined (26,59).

Purified VLPs and viruses were analyzed by EM as described (60). Briefly, particles were dialyzed against 2 L of 1×TNE (100 mM Tris; 2.0M NaCl; 10 mM EDTA; pH 7.4) to remove residual sucrose. Purified KSHV, EBV and VLP gp350-220 HR2 F were incubated with 3% BSA in TNE for 45 min and embedded on the grid. Primary antibody (10 ug/ml) was diluted in 1% BSA/TNE and adsorbed to the grid for 1 hour at room temperature. Following three washes with 1×TNE, secondary gold-conjugated antibody was added for 1 hour at room temperature (RT). The grids were washed twice with TNE, and negatively stained with 12% phosphotungstic acid (pH 7) for 15 sec; air dried for 30 min and examined using a Tecnai transmission electron microscope.

Confocal Microscopy, Cell Binding Assays

Cells were washed three times with 1× phosphate buffer saline (PBS) and confocal microscopy performed as previously outlined (26). Briefly, $1 \times 10^6$ cells were seeded onto Labtek slides and incubated at RT for 1 hour with standard amounts of VLP predetermined based on silver stain and/or Bradford assay quantification of total protein. Mixture of cells and VLPs were stained with mAb Alexa-fluor (AF) 594 anti-CD21 or mAb AF488 anti-CD35 for 30 min on ice. Nuclei were stained with DAPI 33342 (Sigma) for 5 min at RT. Stained cells were washed three times, mounted (Mounting Medium, DakoCytomation) and imaged using an UPlanApo 60×1.42 NA objective on an Olympus BX62 microscope fitted with a cooled Hamamatsu Orca AG CCD camera. The microscope, filters, and camera were controlled as outlined (61). The deconvolution process is described (26).

Immunization, Enzyme-Linked Immunosorbent Assay (ELISA) for Antibodies and IFN-γ

Sera from terminal bleed of mice immunized with EBVgB-LMP2 VLP, EBVgH/gL VLP, EBVgp350/220-HR2 F VLP, EBVgp350/220-HR2 F VLP, or UV-inactivated EBV were used to determine IgG liters measured by ELISA (62). Soluble gp350-220 ED or lysates from ELL-0 cells transfected with gB or gH/gL were used as target antigens. Briefly, 96-well microtiter plates (Nunc-Immuno Plate Maxisorp) were coated with 50 ng/well of recombinant gp350/220 ED, gB or gH gL in a carbonate buffer (pH 6.2) at 4° C. overnight and blocked with 1% BSA. Serially diluted sera in PBS was added for 2 h at RT and washed. Antibody binding was detected with HRP-labeled goat anti-mouse IgG, secondary antibodies at RT for 1 h. Plates were washed 5× and the substrate tetramethylbenzidine (Life Science Technologies) was added. Reactions were stopped with 2M sulfuric acid. To determine antibody titer, optical density was read at 450 nm with an ELISA reader (Spectramax® Plus 384, Molecular Devices). The highest antibody dilution yielding an $OD_{45}$2× higher than that of TNE-treated mice was designated the endpoint titer. Anti-gp350/220 mAbs served as positive control for gp350/220.

Peptides corresponding to the immunization components, as well as control peptides were used to stimulate $5\times10^5$ splenocytes in. Synthetic peptides derived from $EBNA1_{-(HPVGEADYFEY)}$, $LMP2_{-(CLGGLLTMV)}$ or Promix EBV peptide pool consisting of 26 peptides, each corresponding to a defined HLA class I-restricted T cell epitope from EBV were used at concentration of 1 μg/mL in the assay. After overnight culturing, the supernatants were tested for IFN-γ release by ELISA. SIINFEKL ovalbumin was used as a negative control and concavalin A and IL1B were used as model antigens.

Serum EBY-Neutralization Studies and Statistical Analysis

Terminal bleed sera from mice serially immunized with UV-EBV, soluble gp350/220 ED, TNE, EBVgp350/220-F and EBVgp350/220-HR2 VLPs were heat-inactivated at 56° C. to remove complement. Sera were pre-incubated 1:1 with purified EGFP-EBV at different concentrations (typically a 1:5 virus dilution from a frozen stock) for 1 h at RT before infecting $10^5$ Raji or 293 cell lines seeded in 24-well tissue culture plates as previously outlined (53, 56, 63). Anti-gp350/220 mAb-72A1 (neutralizing), mAb-2L10 (non-neutralizing) and sera from TNE-treated mice (vehicle) served as controls. Experiments were repeated at least 3 times. Plates were incubated at 37° C. for 3 days and visualized daily to enumerate $GFP^+$ cells. Cytometry was performed on day 3 for end-point analysis. Neutralization data were analyzed using Graph Pad Prism 6 Software (GraphPad Software, Inc., San Diego) as described (56).

Example 2

Construction and Purification of Epstein-Barr Virus-Like Particle (EBV-VLP) gp350/220 Using Newcastle Disease Virus Platform as a Prophylactic Vaccine Candidate Against EBV Infection. See FIGS. 4-11.

Figure 74:
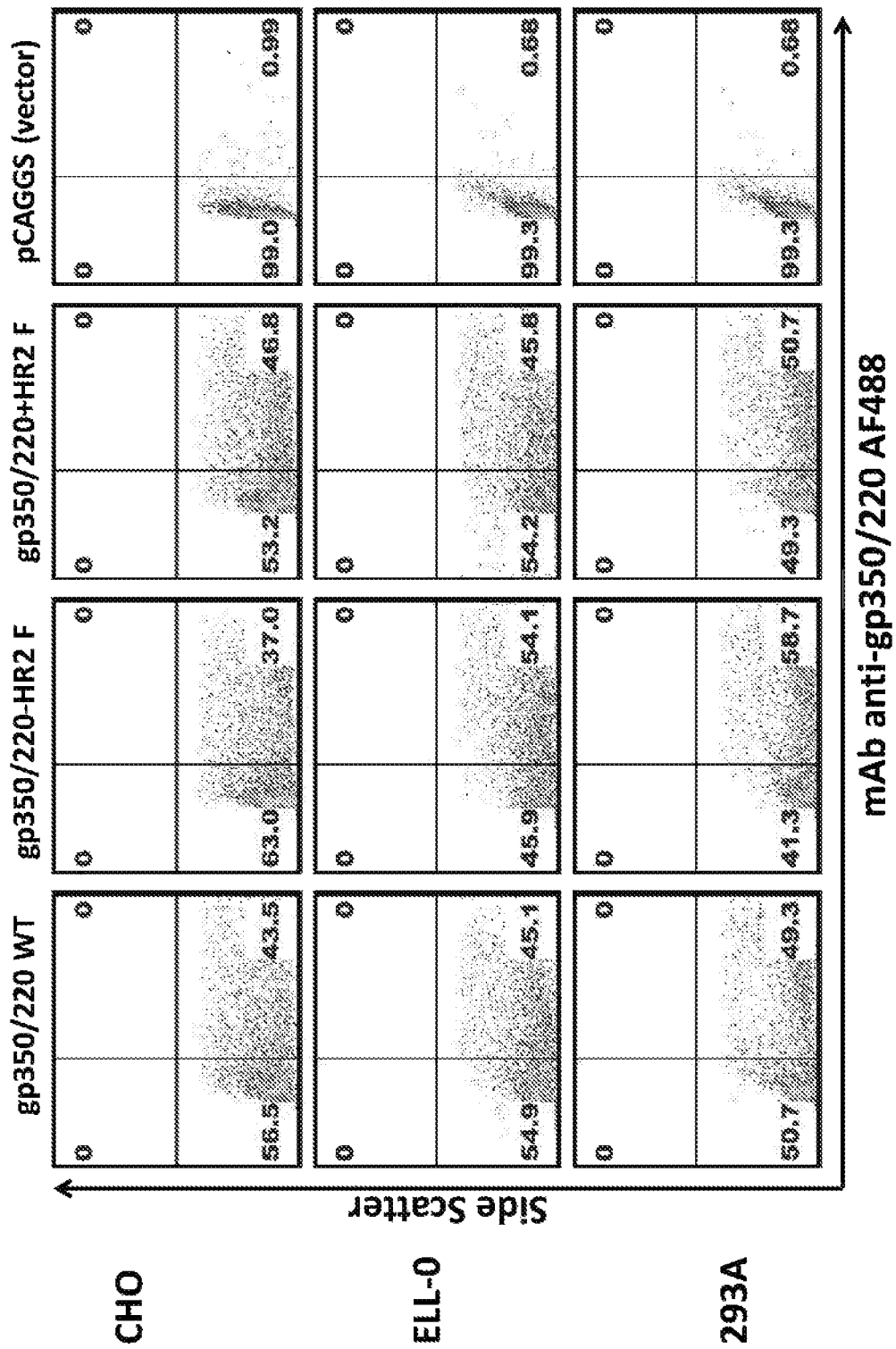
FIG. 74. Expression of EBVgp350/220-WT and EBVgp350/220-F was measured in three transfected cell lines (CHO, ELL-0, and 293A) compared to the vector control. One million cells from each cell line was transfected with 1 μg of either pCAGGS-EBVgp350/220 WT, pCAGGS-EBVgp350/220-HR2 F, pCAGCS-EBVgp350/220+HR2 F or pCAGGS alone (vector control). At 72 h post-transfection, cells were stained with anti-gp350/220 mAb-72A1 followed by AF488-coupled goat anti-mouse IgG (H+L) and analyzed by flow cytometry.

Example 3

Development of a Novel gH/gL VLPs. See FIGS. 12-16.

Example 4

Development of a Novel gH/gL-EBNA1-LMP2 VLPs. See FIGS. 17-29.

Example 5

NDVNP as a Carrier for EBNA1-LMP2 in EBVgp350/220 or gH/gL VLPs. See FIGS. 30-34.

Example 6

Generating NP-tEBNA1-LMP2 Chimera Protein. See FIGS. 35-37.

Example 7

NP-EGFP Blots. See FIGS. 38-47.

Example 8

Generating VLPS Containing NP-tEBNA1 Chimera Protein and Containing NP-tEBNA1-LMP2 Chimera Protein See FIGS. 50-53 and 62A-E-71A-D.

Example 9

Detection of Chimeric EBV-gp350/220-F, EBVgH-F/gL-HN and EBVgB-F on the Surface of Mammalian and Avian Cell Lines In this study, we generated novel VLPs known for their safety, adjuvanicity and efficacy; to present select EBV glycoproteins (gp350/220, gH/gL or gB) and/or latent genes expressed in EBV positive tumors (EBNA1 and/or LMP2) to elicit neutralizing antibodies and T-cell responses, respectively. These VLPs are devoid of EBV genomic DNA and are efficiently produced in CHO cell line; an FDA approved vehicle. Newcastle disease VLP-based platform has been shown to efficiently assemble from three or four virion proteins, the envelope glycoproteins, F (fusion, a type I glycoprotein) and/or HN (hemaglutinin-neuraminidase, a type 2 glycoprotein), together with core proteins M (matrix) and NP (nuclcocapsid protein) that drive assembly and release as described (58, 64); patent issued to Morrison et al., U.S. Pat. No. 7,951,384 issued to Morrison et al. on May 1, 2011; U.S. Pat. No. 8,974,797, issued to Morrison on Mar. 10, 2015, each of which is incorporated by reference and see also FIG. 72. Further novel methods for producing NDV-based VLPs are disclosed herein.

To generate EBVgp350/220 bearing VLPs; we first constructed an EBVgp350/220 F, EBVgp350/220-HR2 F, chimeric plasmids (FIG. 73). To assess whether the expressed chimera proteins appropriately localized to the plasma membrane, pCAGGS-EBVgp350/220-F. pCAGOS-EBVgp350/220-HR2 F and pCAGGS-EBVgp350/220 WT plasmids were individually transfected into CHO, ELL-0 and 293A cell lines from three different species. Membrane expression of the gp350/220 was analyzed by cytometry. MAb-72A1 directed to the N-terminal attachment protein binding epitope of gp350/220 (65) detected expression of both gp350/220 WT and chimeric EBVgp350/220 F proteins at the surface of all relevant transfectants (FIG. 74).

Example 10

Assembly and Characterization of Chimeric EBVgp350/220 F VLPs

Following confirmation of plasma membrane expression, as required for particle assembly, pCAGGS-EBVgp350/220-F was co-transfected with NDV core proteins M, NP into CHO, 293T or ELL-0 cell lines to generate chimeric VLPs as diagram in FIG. 75A. Particles from distinct preparations released into cell supernatants were purified, characterized by immunoblot (FIG. 75A, 75C; electron microscopy (FIG. 75B), and silver stain (FIG. 75D) as outlined (56). These analyses confirmed that proteins of correct sizes (350 and 220 kDa) were made and these VLPs are similar in size, shape and structure to the native virus, by negative staining and immunogold-conjugated antibody analysis.

Example 11

Visualization of EBVgp350/220-F VLP Attachment to CD21 and CD35 Bearing Cells

Figure 76:
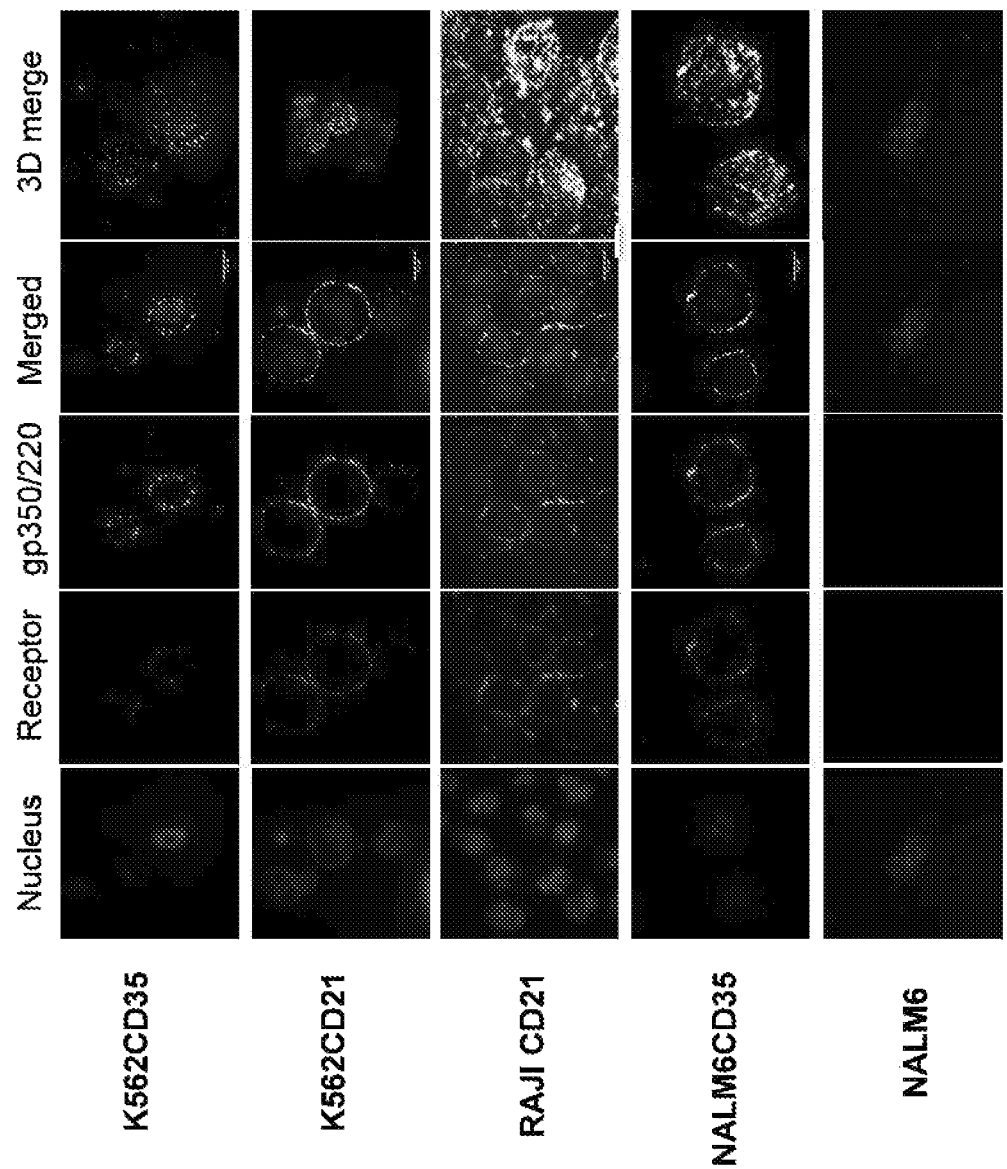
FIG. 76. Purified EBVgp350/220-F VLPs bind CD21 and CD35. Raji, Nalm6, and K562 cells lines transfected with either CD21 or CD35 were characterized and prepared as described (Ogembo et al., Cell Reports 2013; 371-385). Untransfected NALM6 cells were used as a control. The cells were stained with primary mAbs to either CD35 or CD21 depending on which complement receptor they had been transfected with followed by AF594-coupled goat Fab*2 anti-mouse IgG (red). Next, attachment of EBVgp350/220-F VLPs was detected directly with AF488-coupled anti-gp350/220 (mAb-2L10) (green) that recognizes an epitope distal to the attachment site. Cell content was documented by nuclear staining with DAP1. Sequential confocal images showed that the chimeric VLP binds to CD21 or CD35 bearing cells whereas no binding to receptor negative Nalm6 cells was seen. Visualization of 3D merged images confirmed extensive co-localization (yellow) of the chimeric VLPs with both CD21 and CD35. Ogembo et al., J. Trans. Med. 2015; 13:50.

EBVgp350/220 binds CD21 and/or CD35 on human cells (23, 26). To determine whether chimeric VLPs expressed from CHO cells retained the receptor-binding specificity of the virion envelope protein, we incubated EBVgp350/220-F VLPs with Raji, a latently EBV-infected B-cell line that naturally expresses high amounts of CD21 (23) and can be superinfected with EBV. In addition, a panel of receptor negative cell lines, Nalm6 and K562 (not shown), together with their CD21 or CD35 transfected sublines was investigated (26). Receptors (red) and VLPs (green) were visualized by indirect immunofluorescence using a confocal microscope for detection as shown in FIG. 76. EBVgp350/220 F VLPs abundantly bound Raji, no attachment to Nalm6 was detected. Nalm6CD21, Nalm6CD35 K562CD21 and K562CD35 all bound EBVgp350/220-F VLPs.

Example 12

Figure 77:
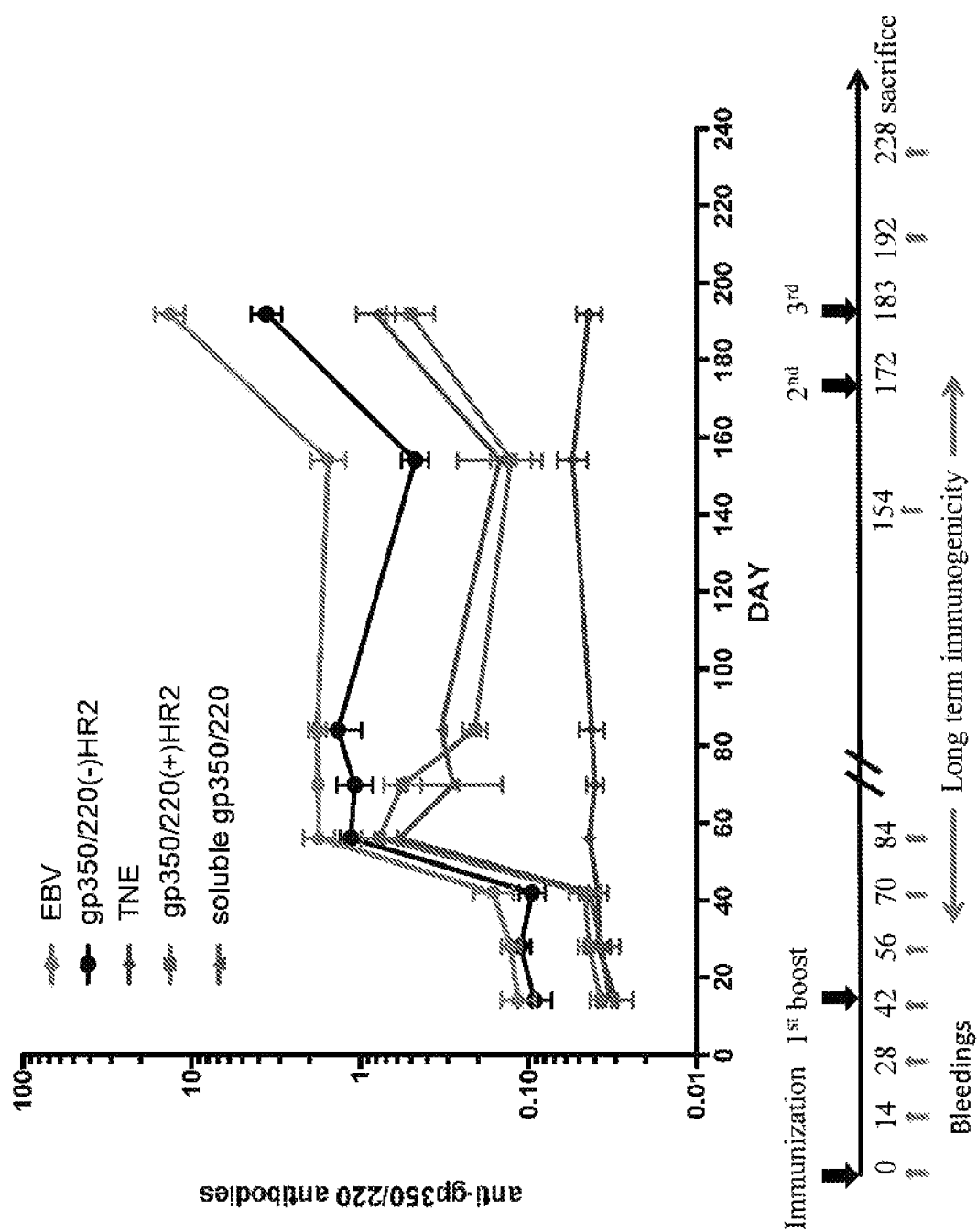
FIG. 77. Long-term IgG anti-gp350/220 antibodies are generated in mice immunized with EBVgp350/220-F VLPs, UV-EBV and soluble recombinant gp350/220 ED. Groups of Five mice were immunized intraperitoneally with either EBVgp350/220(+)HR2 VLPs (green), EBVgp350/220(−)HR2 VLPs (black), inactivated UV-EBV (red), soluble recombinant gp350/220 ED (purple) or TNE, which served as vehicle control (blue). Each immunogen contained equivalent amounts of gp350-220, and both primary and booster vaccinations contained equivalent immunogen. Booster immunizations were performed on days 43, 172, 183 and 218 as indicated on the time line (bottom). All immunizations were performed in the absence of adjuvant. Anti-gp350/220 IgG titers were determined for 8 time points during the immunization schedule using ELISA. Ogembo et al., J. Trans. Med. 2015; 13:50.

Development of Specific IgG Responses to EBVgp350/220 in BALB/c mice immunized with EBVgp350/220-F VLPs To determine whether chimeric VLPs elicit EBVgp350/220 specific antibody responses, a group of five mice were immunized intraperitoneally with 10 µg of EBVgp350/220-F VLP derived from CHO cells. UV-EBV and soluble gp350/220 ED served as positive controls and TNE as vehicle negative control. Equivalence of gp350/220 protein content among the different immunogens was determined by both silver stain and Bradford assay (not shown). All animals received booster immunizations on days 43, 172, 183 and 218. Sera were collected two weeks post-boost. None of the animals displayed signs of local or systemic inflammation or changes in feeding or body weight that would indicate toxicity. Soluble recombinant gp350/220 ED served as the target antigen in an IgG ELISA. Anti-gp350/220 specific total IgG antibody titers significantly increased among mice immunized with the chimeric VLP, UV-EBV and soluble recombinant gp350/220 ED compared with pre-vaccination and control titers (FIG. 77). Historical controls using NDV-F VLFs as immunogen were non-reactive in gp350/220-based ELISAs (not shown). The increase in EBV-gp350/220 specific antibody appeared to plateau on day 84 after the initial boost, but then further increased after the second and third boosts. There was a significant difference in antibody titers of mice immunized with UV-EBV, compared with soluble gp350/220 ED and EBVgp350/220-F VLP, although the slopes of the response curves were similar. Gp350/220 specific antibody was absent from TNE-immunized mice. All gp350/220-based immunogens produced long-term gp350/220-specific responses, though mice immunized with native EBV maintained significantly higher titers of gp350/220 antibody compared to mice immunized with VLP or soluble recombinant protein.

Example 12

Anti EBV-gp350/220 Antibodies Generated Following VLP Immunization Neutralize EBV Infection In Vitro.

Figure 78A:
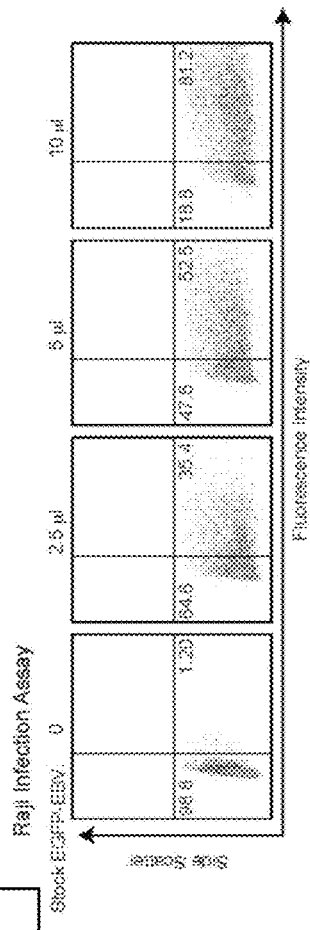
FIG. 78A-B. Neutralization of EBV (EGFP-EBV) infection of Raji cells by pre-incubation with antibodies generated in response to EBVgp350/220-F VLP immunization.
Figure 78B:
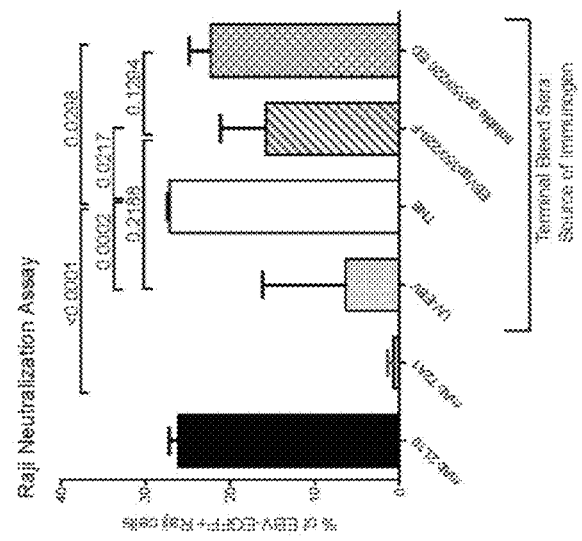

It is well known that titer is not the sole gauge of a protective antibody response, as certain immunogens can induce antibodies that promote, rather than block infection and high affinity blocking antibodies can be highly effective at low titers (66). To evaluate the protective efficacy of antibodies generated in response to chimeric EBV-VLP, UV-EBV and soluble recombinant gp350/220 ED, we assessed the in vitro neutralizing antibody titers of sera boosted four times (collected day 228) with the immunogens described above. Because EBV does not plaque and large virus quantities are difficult to obtain, EBV was titered by the Raji cell infection assay (FIG. 78A). As predicted, pre-incubation of EGFP-EBV 1:1 with serum from TNE treated mice (negative control) produced ~27% fluorescence of Raji (FIG. 78B) as did pre-treatment with the non-neutralizing anti-gp350/220 mAb-2L10. In contrast when terminal sera from mice immunized with EBVgp350/220-F VLPs or UV-EBV was pre-incubated with EGFP-EBV, infection was reduced in comparison with TNE-immunized sera: 15% (p=0.0217) and 5% fluorescent cells (p=0.0002), respectively. As expected, purified mAb-72A1 (positive control) containing only IgG1 antibody directed to the gp350/220 attachment epitope was most effective at neutralization (1% fluorescent cells, p=<0.0001 compared with TNE). Antibodies generated after immunization with soluble recombinant gp350/220 ED were least effective (22% fluorescent cells, p=0.0298 versus TNE). Though the numbers are small, the comparative ability of antibodies generated in response to immunization with chimeric VLP versus UV-EBV to neutralize EBV infection of Raji cells was not significant (p=0.2188).

Because of the inability of sera from mice immunized with gp350/220 VLPs to effectively neutralize EBV infection in vitro (sterile condition), we reasoned that incorporation of EBVgH/gL or EBVgB with tumor-associated EBV antigens EBNA-1 and/or LMP2 as components of VLPs will enhance and sustain both humoral and T-cell responses. Furthermore, adoptive transfer of antigen-specific cytotoxic T lymphocytes (CTLs) offers safe and effective therapy for eradication of EBV-associated cancers, however, they do not expand or persist long term (42, 67). Thus, vaccination strategies that induce a robust antibody response and enhance EBV specific T-cell immunity are crucial for an effective EBV vaccine.

Figure 81:
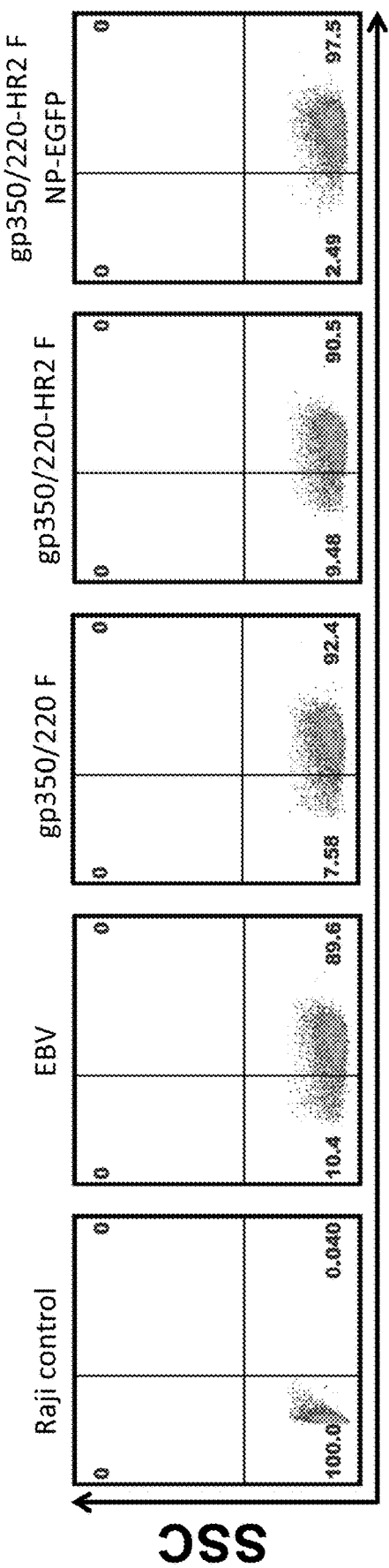
Figure 82A:
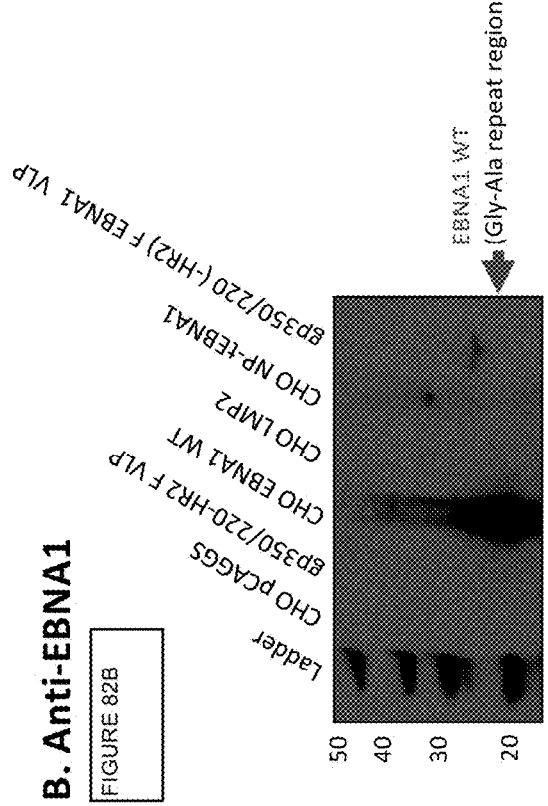
Figure 82B:
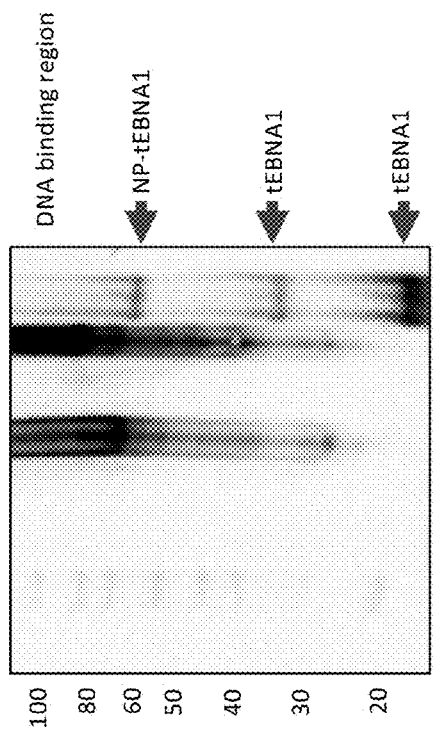
Figure 82C:
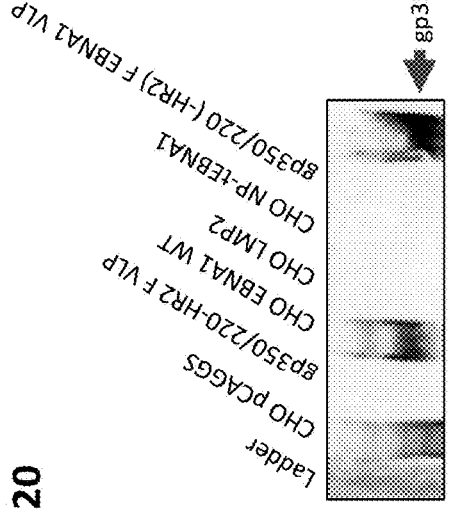
Figure 82D:
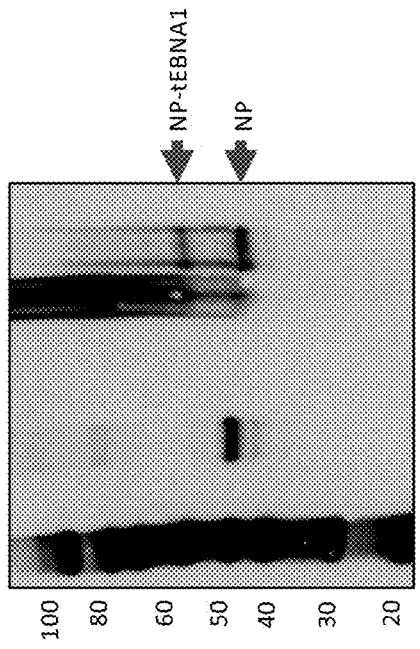

Immunization with inactivated virus particles or a subunit vaccine such as soluble recombinant proteins, in the absence of intracellular replication rarely induces robust CTL responses. An important reason for the poor immunogenicity is due to the difficulty of an exogenous antigen to activate the major histocompatibility complex (MHC) class I pathway (68, 69). Typically, antigens that cannot gain access to the cytosol of the host cell activate the MHC class II pathway while antigens that are endocytosed are processed through the MHC class I pathway. VLPs are an interesting exception, since they can be efficiently processed by the MHC class I pathway through receptor mediated binding and entry (52, 70-72). This attribute makes VLPs promising candidates for the development of subunit vaccines, particularly for oncogenic viruses such as EBV. In nature, EBV only infects humans, however, humanized mouse models harboring functional human immune system components are easily infected with EBV (73). Many aspects of human EBV biology, including EBV latent infection, EBV-associated diseases, and T-cell-mediated immune responses are reproducible in humanized mice (74). Antibody responses are also elicited in humanized mice, however, the generation of antigen-specific IgG has been challenging (73). As a proof of concept, we first generated a fusion protein between NP and EGFP as illustrated (FIG. 79A), NDV-F and EBVgp350/220 (FIG. 79B). The NP-EGFP fusion protein was transfected into CHO cells together with gp350/220 HR2 F chimera, and NDV-M as illustrated in FIG. 79C The transfected CHO cells expressed NP-EGFP protein (FIG. 80A), and efficiently assembled and released gp350/220-NP-EGFP VLPs into the supernatant when co-transfected with both pCAGGS-M and gp350/220. These gp350/220-NP-EGFP VLPs incorporated proteins of correct molecular sizes as confirmed by immunoblot (FIG. 80B) anti bound CD21 expressed on the surface of Raji cells (FIG. 81).

Using a similar strategy, we incorporated a truncated form of EBNA1 (tEBNA1) in which the Gly-Ala region known to impair presentation of cis-linked sequences is deleted into EBVgp350/220 (FIGS. 82A-D) and EBVgH gL-EBNA1 VLPs (FIGS. 83A-E). This confirmed that it is possible to generate VLPs containing antigens that are not expressed on the surface of the particles, in this case the latent EBV antigen EBNA1. The sequence of the antigen was present in detectable amounts in the supernatant of the transfected cells, and able to bind the antibody despite the deleted Gly-Ala region.

Figure 85:
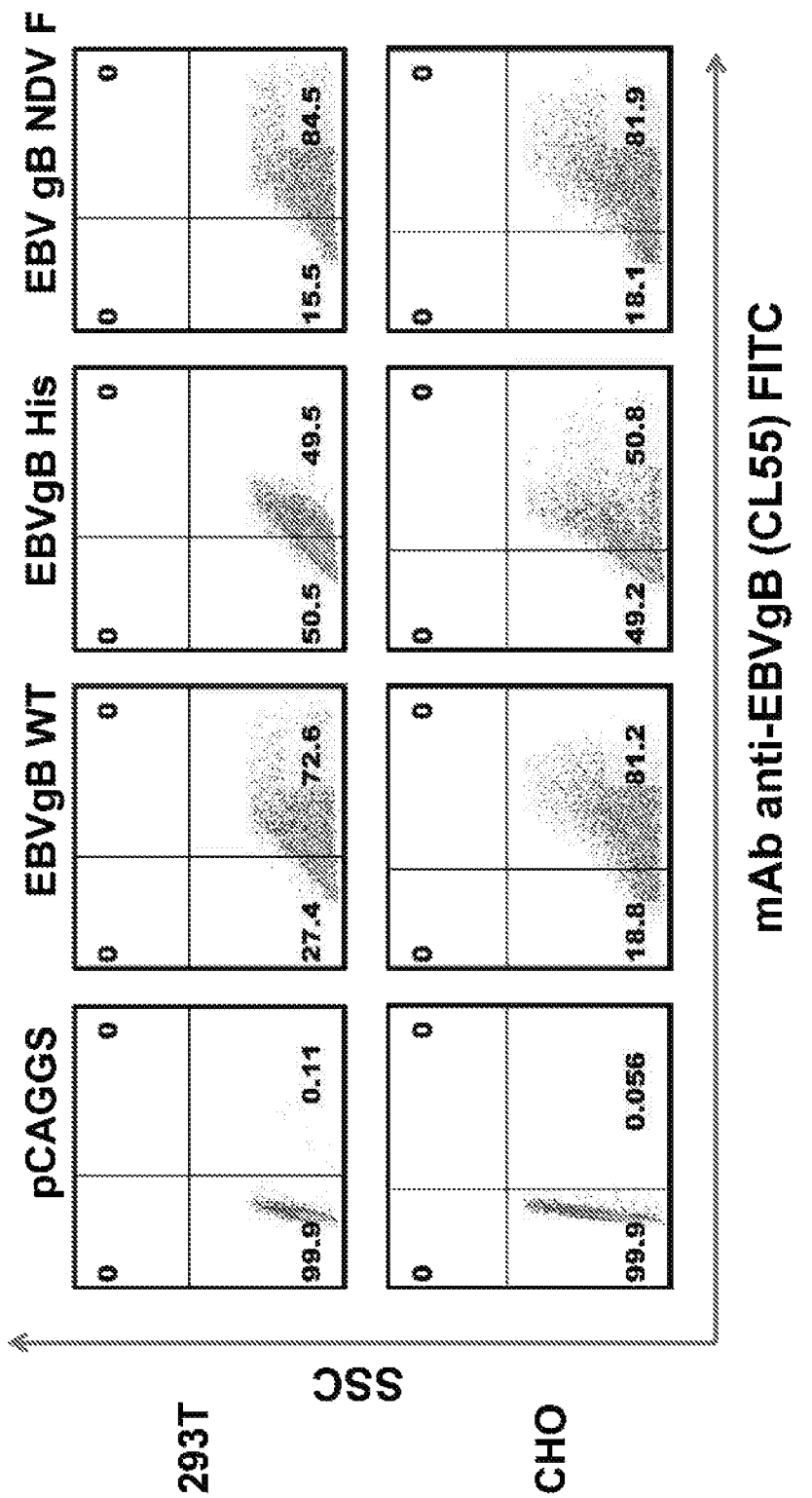
Figure 86:
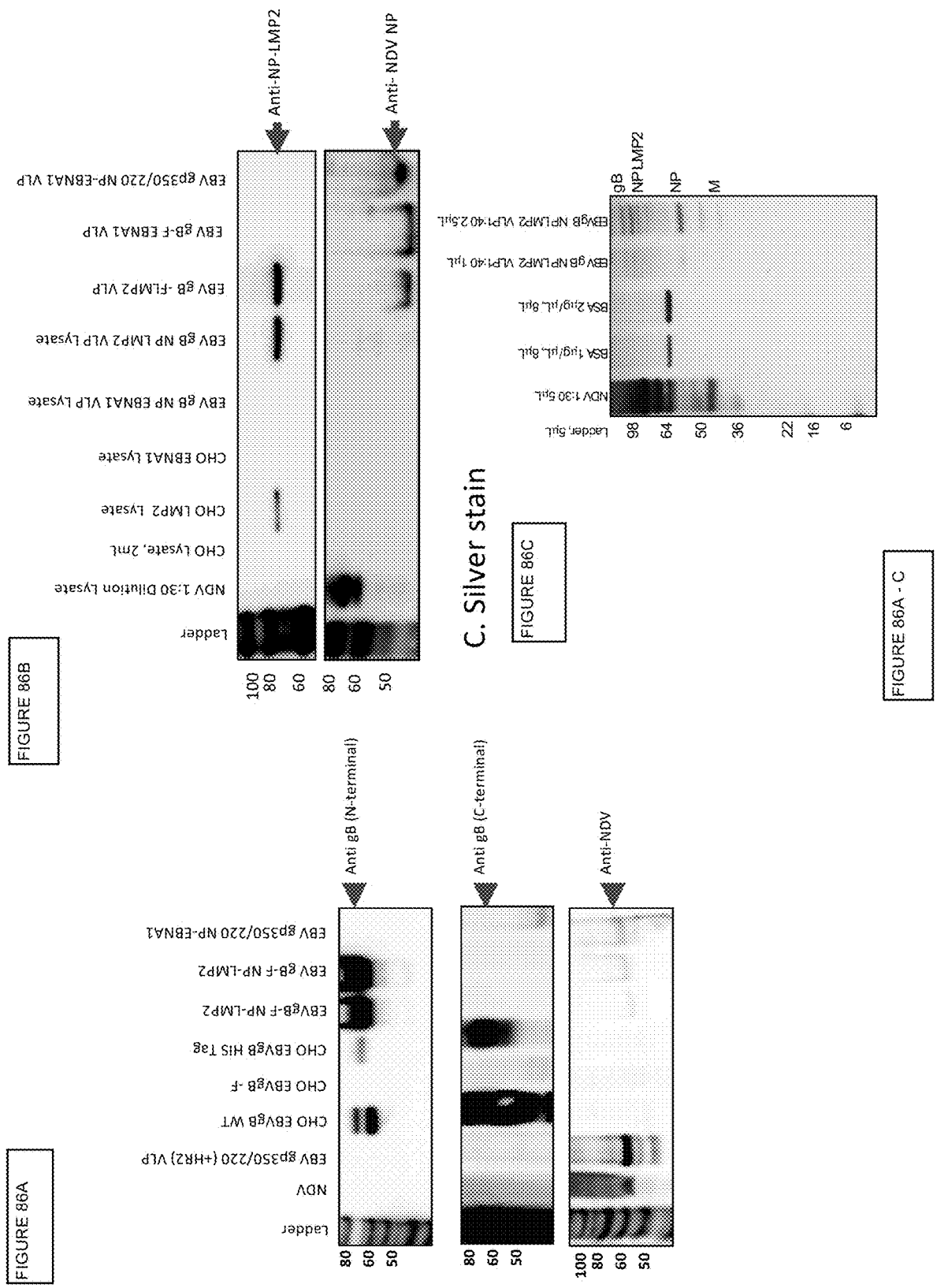

Construction and schematic illustration of pACGGS-EBVgB WT, chimeric pCAGSS-EBVgB-NDV F, chimeric pCAGGS-NP-LMP2 plasmids is outlined in FIG. 84A-B. These constructs were transfected into CHO cells to determine expression of EBVgB on the cell surface was determined by cytometry (FIG. 85). We further confirmed that proteins (gB, LMP2, NP) were made and were of the right sizes (FIG. 86A-C).

Figure 87:
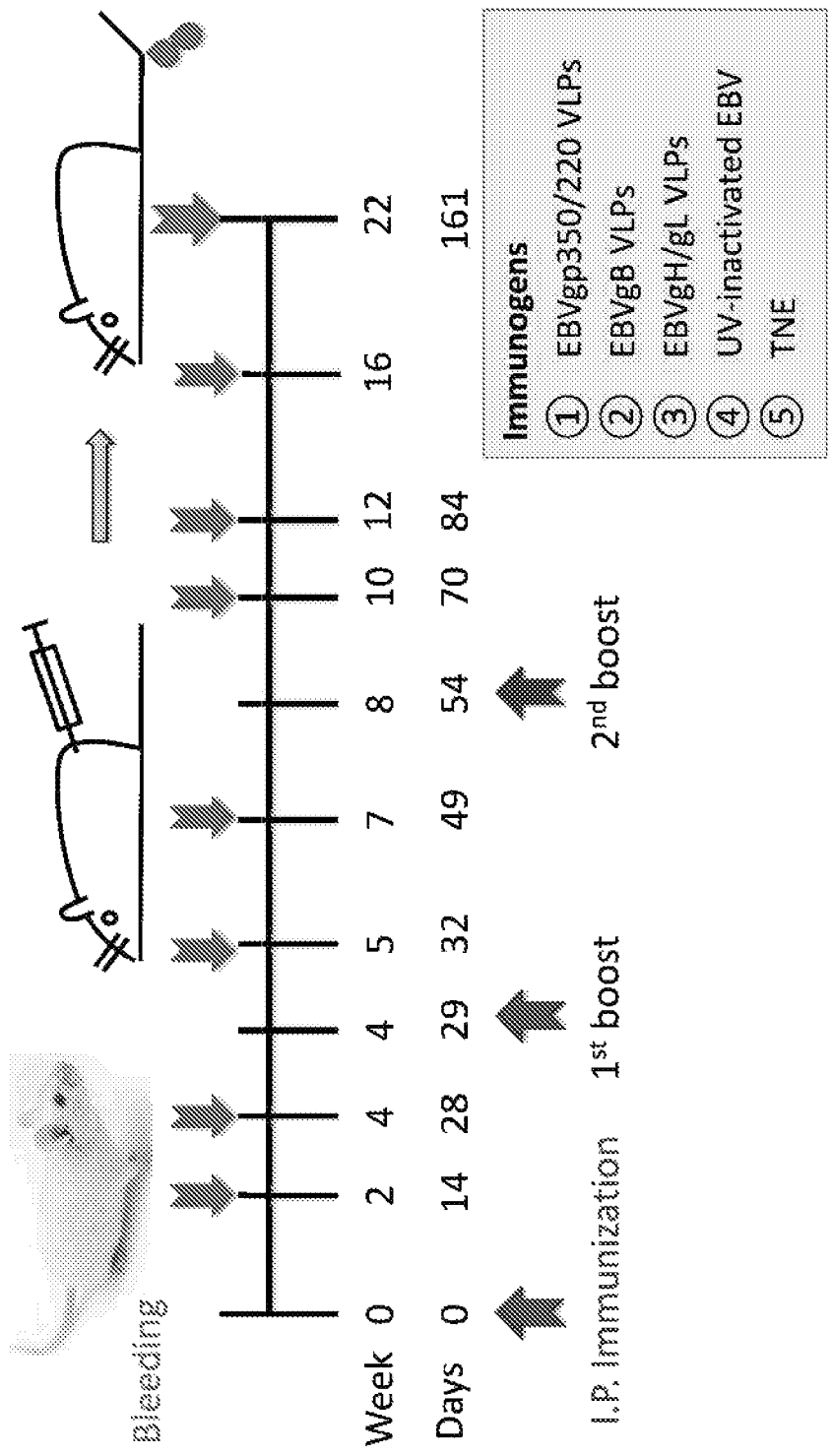
Figure 88:
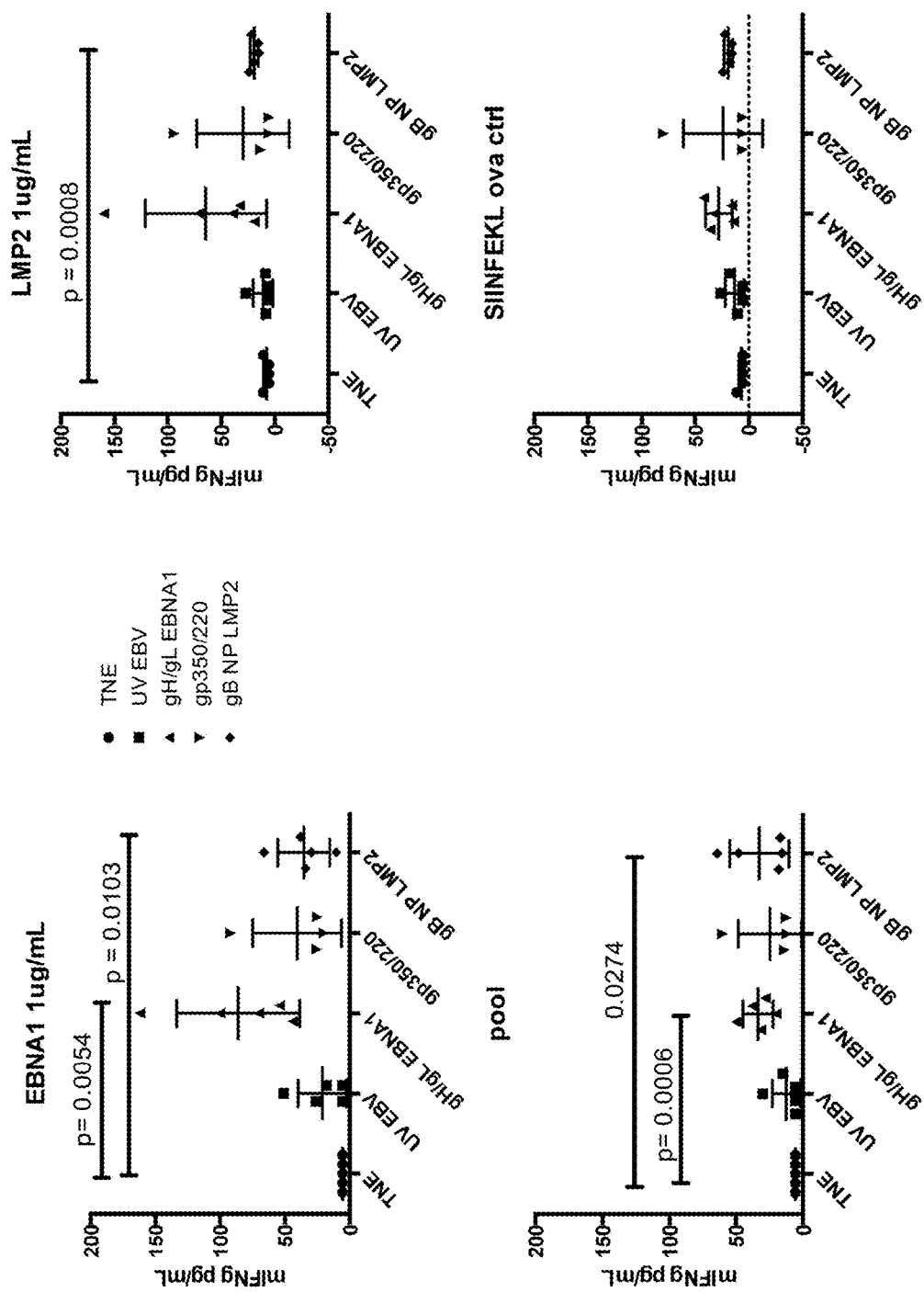

Several studies on host immune responses against EBV have suggested that both B and T-cells immunity play a critical role in the protection against EBV infection and control of EBV-associated diseases. We hypothesized that incorporation of tumor-associated EBV antigens tEBNA-1 and LMP2 as components of VLPs will enhance and sustain both humoral and T-cell responses in BALB/c mice. To test our hypothesis, groups of 5 mice were immunized thrice at day 0, 29 and 54 intraperitoneally with 10 μg of EBVgH/gL-tEBNA1 VLPs, EBVgB-LMP2 VLPs, EBVgp350/220 VLPs, or UV-inactivated EBV resuspended in 500 μl of TNE. The animals were boosted twice at day 29 and 54 without adjuvants as illustrated (FIG. 87). TNE served as control for immunogens. At day 161 mice were sacrificed and 5×10$^5$ splenocytes were stimulated in vitro with the corresponding as well as control peptides. 1 μg/mL of synthetic peptides derived from EBNA1$_{(HPVGEADYFEY)}$, LMP2$_{(CLGGLLTMV)}$ or Promix EBV peptide pool consisting of 26 peptides, each corresponding to a defined HLA class 1-restricted T cell epitope from EBV were used in the assay. After overnight culturing, the supernatants were tested for IFN-γ release by ELISA. SIINFEKL ovalbumin was used as a negative control and concavalin A and IL1B were used as model antigens. Splenocytes from mice immunized with EBVgH/gL-EBNA1 VLPs and EBVgB-LMP2 VLPs generated significantly higher IFN-γ than mice immunized with UV-inactivated EBV and EBVgp350/220 VLPs (FIG. 88). Experiments are ongoing to determine the ability of the mice, sera from specific time points (including terminal bleed) to neutralize EBV expressing EGFP in an in vitro system as outlined (56).

REFERENCES

1. Rickinson A B, Kieff E. Epstein-Barr Virus. In: Knipe D, Howley P, editors. Fields Virology. Fifth ed. Philadelphia: Lippincott Wilkins and Williams; 2007. p. 2680-700.
2. Cohen J I, Fauci A S, Varmus H, Nabel G J. Epstein-Barr Virus: An Important Vaccine Target for Cancer Prevention. Science Translational Medicine. 2011; 3(107): 107fs7-fs7.
3. Kutok J, Wang F. Spectrum of Epstein-Barr virus-associated diseases. Annu Rev Pathol Mech Dis. 2006; 1:375-404.
4. Hjalgrim H, Frihorg J, Melbye M. The epidemiology of EBV and its association with malignant disease. In: Arvin A, Campadelli-Fiume G, Mocarski E, Moore P S, Roizman B. Whitley R, et al., editors. Human Herpesviruses: Biology, Therapy, and Immunoprophylaxis. Cambridge2007.
5. Luzuriaga K, Sullivan J L. Infectious mononucleosis. New England Journal of Medecine 2010; 362:1993-2000.
6. Babcock G J, Decker L L, Volk M, Thorley-Lawson D A. EBV persistence in memory B cells in vivo, Immunity. 1998; 9(3):395-404.
7. Goedert J J, Cote T R, Virgo P, Scoppa S M, Kingma D W, Gail M H, et al. Spectrum of AIDS-associated malignant disorders. Lancet. 1998; 351(9119): 1833-9. Epub 1998/07/04. PubMed PMID: 9652666.
8. Coté T R, Biggar R J, Rosenberg P S, Devesa S S, Percy C, Yellin F J, et al. Non-Hodgkin's lymphoma among people with AIDS: Incidence, presentation and public health burden. International Journal of Cancer. 1998; 73(5):645-50.
9. Gottschalk S, Rooney C M, Heslop H E. Post-transplant lymphoproliferative disorders. Annu Rev Med. 2005; 56:29-44.
10. Cohen J I. Epstein-barr virus vaccines. Clinical & translational immunology. 2015; 4(1):e32. Epub Feb. 2, 2015. doi: 10.1038/cti.2014.27. PubMed PMID: 25671130; PubMed Central PMCID. PMC4318489.
11. Balfour H H, Jr. Progress, prospects, and problems in Epstein-Barr virus vaccine development. CurrOpin Virol. 2014; 6C:1-5. Epub Mar. 19, 2014. doi: 10.1016 j.coviro.2014.02.005. PubMed PMID: 24632197.
12. Biggar R J, Henle G, Böcker J. Lennette E T, Fleisher G, Henle W. Primary Epstein-Barr virus infections in African infants, II. Clinical and serological observations during seroconversion. International Journal of Cancer. 1978; 22(3):244-50.
13. Biggar R J, Henle W, Fleisher G, Bocker J, Lennette E T, Henle G. Primary Epstein-Barr virus infections in african infants. I. Decline of maternal antibodies and time of infection. International Journal of Cancer. 1978; 22(3): 239-43.
14. Gu S Y, Huang T M, Ruan L, Miao Y H, Lu H, Chu M, et al. First EBV vaccine trial in humans using recombinant vaccinia virus expressing the major membrane antigen. Dev Biol Stand. 1995; 84:171-7. Epub Jan. 1, 1995. PubMed PMID: 7796951.
15. Moutschen M, Leonard P, Sokal E M, Smets F, Haumont M, Mazzu P, et al. Phase I/II studies to evaluate safety and immunogenicity of a recombinant gp350 Epstein-Barr virus vaccine in healthy adults. Vaccine. 2007; 25(24): 4697-705. Epub May 5, 2007. doi: 10.1016/j.vaccine.2007.04.008. PubMed PMID: 17485150.
16. Rees L, Tizard E J, Morgan A J, Cubitt W D. Finerty S, Oyewole-Eletu T A, et al. A phase I trial of epstein-barr virus gp350 vaccine for children with chronic kidney disease awaiting transplantation. Transplantation. 2009; 88(8): 1025-9. Epub Oct. 27, 2009. doi: 10.1097/TP.0b0Bc318b9d918 00007890-200910270-00013 [pii]. PubMed PMID: 19855249.
17. Sokal E M, Hoppenbrouwers K. Vandermeulen C, Moutschen M, Léonard P, Moreels A, et al. Recombinant gp350 vaccine for infectious mononucleosis: a phase 2, randomized, double blind, placebo-controlled trial to evaluate the safety, immunogenicity, and efficacy of an Epstein-Barr virus vaccine in healthy young adults. Journal of Infectious Diseases. 2007; 196(12): 1749-53.
18. Janz A, Oezel M, Kurzeder C, Mautner J, Pich D, Kost M, et al. Infectious Epstein-Barr virus lacking major glycoprotein BLLF1 (gp350/220) demonstrates the existence of additional viral ligands. Journal of virology. 2000;74(21): 10142-52. Epub Oct. 12, 2000. PubMed PMID: 11024143; PubMed Central PMCID: PMC 102053.
19. Borza C M. Hutt-Fletcher L M. Alternate replication in B cells and epithelial cells switches tropism of Epstein-Barr virus. Nature medicine. 2002; 8(6):594-9. Epub Apr. 6, 2002. doi: 10.1038 nm0602-594. PubMed PMID: 12042810.
20. Chesnokova L S, Hutt-Fletcher L M. Fusion of Epstein-Barr virus with epithelial cells can be triggered by alphavbeta5 in addition to alphavbeta6 and alphavbeta8, and integrin binding triggers a conformational change in glycoproteins gHgL. Journal of virology. 2011;85(24): 13214-23. Epub Oct. 1, 2011. doi: 10.1128/JVI.05580-11. PubMed PMID: 21957301; PubMed Central PMCID: PMC3233123.
21. Miller N, Hutt-Fletcher L M. A monoclonal antibody to glycoprotein gp85 inhibits fusion but not attachment of Epstein-Barr virus. Journal of virology. 1988; 62(7):2366-72. Epub Jul. 1, 1988. PubMed PMID: 2836619; PubMed Central PMCID: PMC253393.
22. Wang H B, Zhang H, Zhang J P, Li Y, Zhao B, Feng O K, et al. Neuropilin 1 is ait entry factor that promotes EBV infection of nasopharyngeal epithelial cells. Nature communications. 2015; 6:6240. Epub Feb. 12, 2015. doi: 10.1038/ncomms7240. PubMed PMID: 25670642.
23. Fingeroth J D, Weis J J, Tedder T F, Strominger J L, Biro P A, Fearon D T. Epstein-Barr virus receptor of human B lymphocytes is the C3d receptor CR2. Proc Natl Acad Sci USA. 1984; 81(14):4510-4. Epub Jul. 1, 1984. PubMed PMID: 6087328; PubMed Central PMCID: PMC345620.
24. Nemerow G R, Cooper N R. Early events in the infection of human B lymphocytes by Epstein-Barr virus: the internalization process. Virology. 1984; 132(1): 186-98. Epub Jan. 15, 1984. PubMed PMID: 6320532.
25. Nemerow G R, Houghten R A, Moore M D, Cooper N R. Identification of an epitope in the major envelope protein of Epstein-Barr virus that mediates viral binding to the B lymphocyte EBV receptor (CR2). Cell. 1989; 56(3):369-77.
26. Ogembo J G, Kannan L, Ghiran I, Nicholson-Weller A, Finberg R W, Tsokos G C, et al. Human complement receptor type 1/CD35 is an Epstein-Barr Virus receptor. Cell Rep. 2013; 3(2):371-85. Epub Feb. 19, 2013. doi: 10.1016/j.celrep.2013.01.023. PubMed PMID: 23416052; PubMed Central PMCID: PMC3633082.
27. Tanner J, Weis J, Fearon D, Whang Y, Kieff E. Epstein-Barr virus gp350/220 binding to the B lymphocyte C3d receptor mediates adsorption, capping, and endocytosis. Cell. 1987; 50(2):203-13. Epub Jul. 17, 1987. doi: 0092-8674(87)90216-9 [pii]. PubMed PMID: 3036369.
28. Eisenberg R J, Atanasiu D, Cairns T M, Gallagher J R, Krummenacher C, Cohen G H. Herpes virus fusion and entry: a story with many characters. Viruses. 2012; 4(5): 800-32. Epub Jul. 4, 2012. doi: 10.3390 V4050800. PubMed PMID: 22754650; PubMed Central PMCID: PMC3386629.
29. Li Q. Turk S M, Hutt-Fletcher L M. The Epstein-Barr virus (EBV) BZLF2 gene product associates with the gH and gL homologs of EBV and carries an epitope critical to infection of B cells but not of epithelial cells. Journal of virology. 1995; 69(7):3987-94. Epub Jul. 1, 1995. PubMed PMID: 7539502; PubMed Central PMCID: PMC 189130.
30. Wang X, Hutt-Fletcher L M. Epstein-Barr virus lacking glycoprotein gp42 can bind to B cells but is not able to infect. Journal of virology. 1998;72(1):158-63.
31. Molesworth S J, Lake C M, Borza C M, Turk S M, Hutt-Fletcher L M. Epstein-Barr virus gH is essential for penetration of B cells but also plays a role in attachment of virus to epithelial cells. Journal of virology. 2000;74 (14):6324-32. Epub Jun. 23, 2000. PubMed PMID: 10864642; PubMed Central PMCID: PMC112138.
32. Wu L, Borza C M. Hutt-Fletcher L M. Mutations of Epstein-Barr virus gH that are differentially able to support fusion with B cells or epithelial cells. Journal of virology. 2005; 79(17): 10923-30. Epub Aug. 17, 2005. doi: 10.1128/JVI.79.17.10923-10930.2005. PubMed PMID: 16103144; PubMed Central PMCID: PMC1193614.
33. Fuller A O, Santos R E, Spear P G. Neutralizing antibodies specific for glycoprotein H of herpes simplex virus permit viral attachment to cells but prevent penetration. Journal of virology. 1989; 63(8):3435-43. Epub Aug. 1, 1989. PubMed PMID: 2545914; PubMed Central PMCID: PMC250919.
34. Compels U A, Carss A L, Saxby C, Hancock D C, Forrester A, Minson A C. Characterization and sequence analyses of antibody-selected antigenic variants of herpes simplex virus show a conformationally complex epitope on glycoprotein H. Journal of virology. 1991;65(5):2393-401. Epub May 1, 1991. PubMed PMID: 1707982; PubMed Central PMCID: PMC240591.
35. Nokta M, Tolpin M D, Nadler P J, Pollard R B. Human monoclonal anti-cytomegalovirus (CMV) antibody (MSL 109): enhancement of in vitro foscarnet- and ganciclovir-induced inhibition of CMV replication. Antiviral research. 1994; 24(1);17-26. Epub May 1, 1994. PubMed PMID: 7944310.
36. Wussow F, Chiuppesi F, Martinez J, Campo J, Johnson E, Flechsig C, et al. Human cytomegalovirus vaccine based on the envelope gH/gL pentamer complex2014.
37. Naranatt P P, Akula S M, Chandran B. Characterization of gamma2-human herpesvirus-8 glycoproteins gH and gL. Archives of virology. 2002; 147(7): 1349-70. Epub Jul. 12, 2002. doi: 10.1007/s00705-002-0813-7. PubMed PMID: 12111412.

38. Kirschner A N, Omerovic J, Popov B. Longnecker R, Jardetzky I S. Soluble Epstein Barr virus glycoproteins gH, gL, and gp42 form a 1:1:1 stable complex that acts like soluble gp42 in B-cell fusion but not in epithelial cell fusion. Journal of virology. 2006; 80(19):9444-54. Epub Sep. 16, 2006. doi: 10.1128/JVI.00572-06. PubMed PMID: 16973550; PubMed Central PMCID: PMC1617263.

39. Rowe C L, Connolly S A, Chen J, Jardetzky T S. Longnecker R. A soluble form of Epstein-Barr virus gH/gL inhibits EBV-induced membrane fusion and does not function in fusion. Virology. 2013; 436(1): 118-26. Epub Dec. 4, 2012. doi: 10.1016/j.virol.2012.10.039. PubMed PMID: 23200314; PubMed Central PMCID: PMC3545092.

40. Li Q, Spriggs M K, Kovals S, Turk S M, Comeau M R, Nepom B, et al. Epstein-Barr virus uses HLA class II as a cofactor for infection of B lymphocytes. Journal of virology. 1997; 71(6):4657-62.

41. Icheva V, Kayser S, Wolff D, Tuve S, Kyzirakos C, Bethge W, et al. Adoptive transfer of Epstein-Barr virus (EBV) nuclear antigen 1-specific T cells as treatment for EBV reactivation and lymphoproliferative disorders after allogeneic stem-cell transplantation. Journal of Clinical Oncology. 2012:JCO. 2011.39. 8495.

42. Heslop H E, Ng CY, Li C, Smith C A, Lottin S K. Krance R A, et al. Long term restoration of immunity against Epstein Barr virus infection by adoptive transfer of gene-modified virus specific T lymphocytes. Nature medicine. 1996; 2(5):551-5.

43. Icheva V, Kayser S, Wolff D, Tuve S. Kyzirakos C, Bethge W, et al. Adoptive transfer of epstein-barr virus (EBV) nuclear antigen 1-specific t cells as treatment for EBV reactivation and lymphoproliferative disorders after allogeneic stem-cell transplantation. J Clin Oncol. 2013; 31(1):39-48. Epub Nov. 22, 2012. doi: 10.1200/JCO.2011.39.8495. PubMed PMID: 23169501.

44. Taylor G S, Jia H, Harrington K. Lee L W, Turner J, Ladell K, et al. A Recombinant Modified Vaccinia Ankara Vaccine Encoding Epstein-Barr Virus (EBV) Target Antigens: A Phase 1 Trial in UK Patients with EBV-Positive Cancer. Clin Cancer Res. 2014; 20(19):5009-22, Epub Aug. 16, 2014. doi: 10.1158/1078-0432.CCR-14-1122-T. PubMed PMID: 25124688.

45. Fogg M H, Wirth L J, Posner M, Wang F. Decreased EBNA-1-specific CD8+ T cells in patients with Epstein-Barr virus-associated nasopharyngeal carcinoma. Proc Natl Acad Sci USA. 2009; 106(9):3318-23. Epub Feb. 13, 2009. doi: 10.1073/pnas.0813320106. PubMed PMID: 19211798; PubMed Central PMCID: PMC2651339.

46. Long H M, Chagoury O L, Leese A M, Ryan G B. James E, Morton L T, et al. MHC II tetramers visualize human CD4+ T cell responses to Epstein-Barr virus infection and demonstrate atypical kinetics of the nuclear antigen EBNA1 response. The Journal of experimental medicine. 2013; 210(5):933-49. Epub Apr. 10, 2013. doi: 10.1084/jem.20121437. PubMed PMID: 23569328; PubMed Central PMCID: PMC3646497.

47. Lee S P. Brooks J M, Al-Jarrah H. Thomas W A, Haigh T A, Taylor G S, et al. CD8 T cell recognition of endogenously expressed Epstein-Barr virus nuclear antigen 1. The Journal of experimental medicine. 2004; 199(10): 1409-20. Epub May 19, 2004. doi: 10.1084/jcm.20040121. PubMed PMID: 15148339; PubMed Central PMCID: PMC2211813.

48. Taylor G S. Haigh T A, Gudgeon N H, Phelps R J, Lee S P, Steven N M, et al. Dual stimulation of Epstein-Barr Virus (EBV)-specific CD4+- and CD8+-T-cell responses by a chimeric antigen construct: potential therapeutic vaccine for EBV-positive nasopharyngeal carcinoma. Journal of virology. 2004; 78(2):768-78. Epub Dec. 25, 2003. PubMed PMID: 14694109; PubMed Central PMCID: PMC368843.

49. Apcher S, Daskalogianni C, Manoury B, Fahraeus R. Epstein-Barr virus-encoded EBNA1 interference with MHC class I antigen presentation reveals a close correlation between mRNA translation initiation and antigen presentation. PLoS Pathog. 2010; 6(10):e1001151. Epub Oct. 27, 2010. doi: 10.137) journal.ppat. 1001151. PubMed PMID: 20976201; PubMed Central PMCID: PMC2954899.

50. Hui E P, Taylor G S, Jia H, Mo B B, Chan S L, Ho R, et al. Phase 1 trial of recombinant modified vaccinia ankara encoding Epstein-Barr viral tumor antigens in nasopharyngeal carcinoma patients. Cancer Res. 2013; 73(6); 1676-88. Epub Jan. 26, 2013. doi: 10.1158/0008-5472.CAN-12-2448. PubMed PMID: 23348421.

51. Pavlova S, Feederle R, Gartner K., Fuchs W, Granzow H. Delecluse H J. An Epstein-Barr virus mutant produces immunogenic defective particles devoid of viral DNA. Journal of virology. 2013; 87(4):2011-22. Epub Dec. 14, 2012. doi: 10.1128/JVI.02533-12. PubMed PMID: 23236073; PubMed Central PMCID: PMC3571473.

52. Ruiss R, Jochum S, Wanner G, Reisbach G, Hammerschmidt W, Zeidler R. A virus-like particle-based Epstein-Barr virus vaccine. Journal of virology. 2011; 85(24): 13105-13.

53. Speck P, Longnecker R. Epstein-Barr virus (EBV) infection visualized by EGFP expression demonstrates dependence on known mediators of EBV entry. Archive of Virology. 1999; 144(6): 1123-37. Epub Aug. 14, 1999. PubMed PMID: 10446648.

54. McGinnes L W, Reitter J N, Gravel K, Morrison T G. Evidence for mixod membrane topology of the newcastle disease virus fusion protein. Journal of Virolology. 2003; 77(3):1951-63. Epub Jan. 15, 2003. PubMed PMID: 12525629; PubMed Central PMCID: PMC140911.

55. Biggin M, Farrell P J, Burrell B G. Transcription and DNA sequence of the BamHI L fragment of B95-8 Epstein-Barr virus. EMBO J. 1984; 3(5): 1083-90. Epub May 1, 1984. PubMed PMID: 6203743; PubMed Central PMCID: PMC557477.

56. Ogembo J G, Muraswki M R, McGinnes L W, Parcharidou A, Sutiwisesak R, Tison T, et al. A chimeric EBV gp350/220-based VLP replicates the virion B-cell attachment mechanism and elicits long-lasting neutralizing antibodies in mice. Journal of Translational Medicine. 2015; 13(1):50.

57. Pantua H D, McGinnes L W, Peeples M E, Morrison T G. Requirements for the assembly and release of Newcastle disease virus-like particles. Journal of Virolology. 2006; 80(22):11062-73. Epub Sep. 15, 2006. doi: 10.1128/JVI.00726-06. PubMed PMID: 16971425; PubMed Central PMCID: PMC 1642154.

58. McGinnes L W. Morrison T G. Newcastle Disease Virus-Like Particles: Preparation, Purification, Quantification, and Incorporation of Foreign Glycoproteins. Current Protocols in Microbiology. 2013:18.2. 1-.2.21.

59. Laliberte J P, McGinnes L W, Peeples M E, Morrison T G. Integrity of membrane lipid rafts is necessary for the ordered assembly and release of infectious Newcastle disease virus particles. Journal of virology. 2006; 80(21):

10652-62. Epub Oct. 17, 2006. doi: 10.1128 JVI.0183-06. PubMed PMID: 17041223; PubMed Central PMCID; PMC1641742.
60. Battisti A J, Meng G, Winkler D C, McGinnes L W, Plevka P, Steven A C, et al. Structure and assembly of a paramyxovirus matrix protein. Proceedings of the National Academy of Sciences. 2012; 109(35); 13996-4000.
61. Ghiran I, Giodek A M, Weaver G, Klickstein L B, Nicholson-Weller A. Ligation of erythrocyte CR1 induces its clustering in complex with scaffolding protein FAP-1. Blood. 2008; 112(8):3465-73. Epub Aug. 8, 2008. doi: blood-2008-04-151845 [pii]10.1182/blood-2008-04-151845. PubMed PMID: 18684861; PubMed Central PMCID: PMC2569183.
62. Murawski M R, McGinnes L W, Finberg R W, Kurt-Jones E A, Massare M J, Smith G, et al. Newcastle disease virus-like particles containing respiratory syncytial virus G protein induced protection in BALB/c mice, with no evidence of immunopathology. Journal of virology. 2010; 84(2):1110-23. Epub Nov. 6, 2009. doi: 10.1128/JVI.01709-09. PubMed PMID: 19889768; PubMed Central PMCID: PMC2798376.
63. Sashihara J, Burbclo P D, Savoldo B, Pierson T C, Cohen J I. Human antibody titers to Epstein-Barr Virus (EBV) gp350 correlate with neutralization of infectivity better than antibody titers to EBV gp42 using a rapid flow cytometry-based EBV neutralization assay. Virology. 2009; 391(2):249-56. Epub Jul. 9, 2009. doi: S0042-6822(09)00358-4 [pii]10.1016/j.virol.2009.06.013. PubMed PMID: 19584018; PubMed Central PMCID: PMC2728425.
64. Pantua H, McGinnes L W, Leszyk J, Morrison T G. Characterization of an alternate form of Newcastle disease virus fusion protein. Journal of virology. 2005; 79(18): 11660-70. Epub Sep. 6, 2005. doi: 10.1128/JVI.79.18,11660-11670.2005. PubMed PMID; 16140743; PubMed Central PMCID: PMC1212644.
65. Tanner J, Whang Y, Sample J, Scars A, Kieff E. Soluble gp350/220 and deletion mutant glycoproteins block Epstein-Barr virus adsorption to lymphocytes. Journal of virology. 1988; 62(12):4452-64. Epub Dec. 1, 1988. PubMed PMID: 2460635; PubMed Central PMCID: PMC253554.
66. Civoli P, Kroenke M A, Reynhardt K, Zhuang Y, Kaliyaperumal A, Gupta S. Development and optimization of neutralizing antibody assays to monitor clinical immunogenicity. Bioanalysis. 2012; 4(22):2725-35, Epub Dec. 6, 2012. doi; 10.4155/bio. 12.239.PubMed PMID: 23210655.
67. Gallot G, Vollant S, Saïagh S, Clemenceau B, Vivien R, Cerato E, et al. T-cell Therapy Using a Bank of EBV-specific Cytotoxic T Cells: Lessons From a Phase I/II Feasibility and Safety Study. Journal of Immunotherapy. 2014;37(3):170-9.
68. Braciale T J, Morrison L A, Sweetser M T, Sambrook J, Gething M J, Braciale V L. Antigen presentation pathways to class I and class II MHC-restricted T lymphocytes. Immunological reviews. 1987; 98:95-114. PubMed PM ID: 2443444.
69. Germain R N. Immunology. The ins and outs of antigen processing and presentation. Nature. 1986; 322(6081): 687-9. doi: 10.1038/322687a0. PubMed PMID: 3489186.
70. Adhikary D, Behrends U, Feederle R, Delecluse H J, Mautner J. Standardized and highly efficient expansion of Epstein-Barr virus-specific CD4+ T cells by using virus-like particles. Journal of virology. 2008; 82(8):3903-11. Epub Feb. 15, 2008. doi: 10.1128/JVI.02227-07. PubMed PMID: 18272580; PubMed Central PMCID. PMC: 2293016.
71. Schirmbeck R, Böhm W, Reimann J. Virus-like particles induce MHC class I-restricted T-cell responses. Intervirology. 1996; 39(1-2):111-9.
72. Paliard X, Liu Y, Wagner R, Wolf H, Baenziger J, Walker C M. Priming of strong, broad, and long-lived HIV type 1 p55gag-specific CD8+ cytotoxic T cells after administration of a virus-like particle vaccine in rhesus macaques. AIDS research and human retroviruses. 2000; 16(3):273-82.
73. Yajima M, Imadome K, Nakagawa A, Watanabe S, Terasluma K, Nakamura H, et al. A new humanized mouse model of Epstein-Barr virus infection that reproduces persistent infection, lymphoproliferative disorder, and cell-mediated and humoral immune responses. The Journal of infectious diseases. 2008; 198(5):673-82. Epub Jul. 17, 2008. doi: 10.1086/590502. PubMed PMID: 18627269.
74. Chatterjee B, Leung C S, Munz C. Animal models of Epstein-Barr virus infection. Journal of immunological methods. 2014.

Each and every publication and patent mentioned in die above specification is herein incorporated by reference in its entirety for all purposes. Various modifications and variations of the described methods and system of the invention will be apparent to those skilled in the art without departing from the scope and spirit of the invention. Although the invention has been described in connection with specific embodiments, the invention as claimed should not be unduly limited to such specific embodiments. Indeed, various modifications of the described modes for carrying out the invention which are obvious to those skilled in the art and in fields related thereto are intended to be within the scope of the following claims.

We claim:

1. A recombinant virus-like particle (VLP) comprising, in operable combination, a) Newcastle disease virus (NDV) matrix (M) protein, b) NDV nucleocapsid (NP) protein, and c) one or more tumor-associated EBV antigen, wherein said one or more tumor-associated EBV antigen is operably linked to said NP protein and is inside said VLP.

2. The VLP of claim 1, wherein said tumor-associated EBV antigen is selected from the group consisting of EBNA1, tEBNA1 and LMP2.

3. The VLP of claim 1, wherein said tumor-associated EBV antigen comprises tEBNA1 and LMP2.

4. The VLP of claim 3, further comprising, in operable combination, one or more Epstein-Barr Virus (EBV) antigens, wherein at least one of said one or more antigens is selected from the group consisting of gB, gH, and gL.

5. The VLP of claim 3, wherein said VLP further comprises, in operable combination, EBV gp350/220.

6. The VLP of claim 3, wherein said VLP further comprises, in operable combination, one or more NDV proteins.

7. The VLP of claim 6, wherein said one or more NDV proteins comprise NDV heptad repeat domain 2 (HR2) protein.

8. The VLP of claim 7, wherein said one or more NDV proteins comprise NDV fusion (F) protein.

9. The VLP of claim 8, wherein said one or more NDV proteins comprise NDV heamagglutinin-neuraminidase (HN) protein.

10. The VLP of claim 1, further comprising, in operable combination, one or more human papillomavirus antigens.

11. The VLP of claim 10, wherein said one or more human papillomavirus antigens comprises one or more of L1 and L2.

12. A vaccine comprising the VLP of claim 1 and a physiologically acceptable carrier.

13. An expression vector encoding the recombinant VLP of claim 1.

14. A method for immunizing a mammalian subject against cancer, comprising administering an immunologically effective amount of one or more vaccine of claim 12 to a mammalian subject in need thereof to produce a treated subject, wherein said administering is under conditions to produce an immune response to one or more tumor-associated EBV antigen.

15. The method of claim 14, wherein said cancer comprises an Epstein-Barr Virus (EBV) -associated cancer.

16. The method of claim 14, wherein said EBV-associated cancer comprises cervical cancer.

17. The method of claim 14, wherein said immune response comprises T lymphocytes that specifically bind to said one or more tumor-associated EBV antigen.

18. The method of claim 17, wherein said immune response lacks antibody that specifically binds to said one or more tumor-associated EBV antigen.

19. The method of claim 17, wherein said T lymphocytes are selected from $CD4^+$ lymphocytes and $CD8^+$ lymphocytes.

20. The method of claim 14, wherein said method further comprises administering a recombinant VLP that contains, in operable combination, a) Newcastle disease virus (NDV) matrix (M) protein, and b) EBV gp350/220.

21. The method of claim 14, wherein said method further comprises one or more of a) detecting said immune response to said one or more tumor-associated EBV antigen, and b) detecting a reduction in one or more symptoms of said cancer in said treated subject.

22. The method of claim 14, wherein said administering is before manifestation of one or more symptoms of said cancer.

23. The method of claim 14, wherein said administering is after manifestation of one or more symptoms of said cancer.

* * * * *